(12) United States Patent
Szabo et al.

(10) Patent No.: US 9,434,919 B2
(45) Date of Patent: Sep. 6, 2016

(54) FUNGAL PROTEASES

(71) Applicant: Codexis, Inc., Redwood City, CA (US)

(72) Inventors: Lorand Szabo, Budapest (HU); Zsolt Molnar, Miskolc (HU); Attila Laszlo Nemeth, Budapest (HU)

(73) Assignee: Codexis, Inc., Redwood City, CA (US)

(*) Notice: Subject to any disclaimer, the term of this patent is extended or adjusted under 35 U.S.C. 154(b) by 0 days.

(21) Appl. No.: 14/950,712

(22) Filed: Nov. 24, 2015

(65) Prior Publication Data

US 2016/0075990 A1 Mar. 17, 2016

Related U.S. Application Data

(62) Division of application No. 13/598,051, filed on Aug. 29, 2012, now abandoned.

(60) Provisional application No. 61/541,327, filed on Sep. 30, 2011, provisional application No. 61/564,107, filed on Nov. 28, 2011.

(51) Int. Cl.
| | |
|---|---|
| *C12N 1/14* | (2006.01) |
| *C12N 9/20* | (2006.01) |
| *C12N 9/58* | (2006.01) |
| *C12N 9/24* | (2006.01) |
| *C12P 21/00* | (2006.01) |
| *C12P 21/02* | (2006.01) |
| *C12N 9/48* | (2006.01) |
| *C12R 1/645* | (2006.01) |
| *C12P 19/14* | (2006.01) |
| *C12P 19/02* | (2006.01) |

(52) U.S. Cl.
CPC . *C12N 1/14* (2013.01); *C12N 9/20* (2013.01); *C12N 9/24* (2013.01); *C12N 9/2482* (2013.01); *C12N 9/48* (2013.01); *C12N 9/58* (2013.01); *C12P 21/00* (2013.01); *C12P 21/02* (2013.01); *C12R 1/645* (2013.01); *C12Y 301/01008* (2013.01); *C12P 19/02* (2013.01); *C12P 19/14* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,356,196 A | 10/1982 | Hultquist | |
| 4,461,648 A | 7/1984 | Foody | |
| 4,556,430 A | 12/1985 | Converse et al. | |
| 4,600,590 A | 7/1986 | Dale | |
| 4,683,195 A | 7/1987 | Mullis et al. | |
| 4,683,202 A | 7/1987 | Mullis | |
| 4,965,188 A | 10/1990 | Mullis et al. | |
| 5,037,663 A | 8/1991 | Dale | |
| 5,171,592 A | 12/1992 | Holtzapple et al. | |
| 5,594,119 A | 1/1997 | Yaver et al. | |
| 5,605,793 A | 2/1997 | Stemmer | |
| 5,688,663 A | 11/1997 | Yaver et al. | |
| 5,811,238 A | 9/1998 | Stemmer et al. | |
| 5,811,381 A | 9/1998 | Emalfarb et al. | |
| 5,830,721 A | 11/1998 | Stemmer et al. | |
| 5,834,252 A | 11/1998 | Stemmer et al. | |
| 5,837,458 A | 11/1998 | Minshull et al. | |
| 5,928,905 A | 7/1999 | Stemmer et al. | |
| 5,939,544 A | 8/1999 | Karstens et al. | |
| 6,015,707 A | 1/2000 | Emalfarb et al. | |
| 6,096,548 A | 8/2000 | Stemmer | |
| 6,106,888 A | 8/2000 | Dale et al. | |
| 6,117,679 A | 9/2000 | Stemmer | |
| 6,132,970 A | 10/2000 | Stemmer | |
| 6,165,793 A | 12/2000 | Stemmer | |
| 6,176,176 B1 | 1/2001 | Dale et al. | |
| 6,180,406 B1 | 1/2001 | Stemmer | |
| 6,251,674 B1 | 6/2001 | Tobin et al. | |
| 6,277,638 B1 | 8/2001 | Stemmer | |
| 6,287,861 B1 | 9/2001 | Stemmer et al. | |
| 6,287,862 B1 | 9/2001 | delCardayre et al. | |
| 6,291,242 B1 | 9/2001 | Stemmer | |
| 6,297,053 B1 | 10/2001 | Stemmer | |
| 6,303,344 B1 | 10/2001 | Patten et al. | |
| 6,309,883 B1 | 10/2001 | Minshull et al. | |
| 6,319,713 B1 | 11/2001 | Patten et al. | |
| 6,319,714 B1 | 11/2001 | Crameri et al. | |
| 6,323,030 B1 | 11/2001 | Stemmer | |
| 6,326,204 B1 | 12/2001 | delCardayre et al. | |
| 6,335,160 B1 | 1/2002 | Patten et al. | |
| 6,335,198 B1 | 1/2002 | delCardayre et al. | |
| 6,344,356 B1 | 2/2002 | Stemmer | |
| 6,352,859 B1 | 3/2002 | delCardayre et al. | |
| 6,355,484 B1 | 3/2002 | Patten et al. | |
| 6,358,740 B1 | 3/2002 | Patten et al. | |

(Continued)

FOREIGN PATENT DOCUMENTS

| | | |
|---|---|---|
| WO | 95/22625 A1 | 8/1995 |
| WO | 97/00078 A1 | 1/1997 |

(Continued)

OTHER PUBLICATIONS

Upadhyay, J.M., et al., "A new variety of thermophilic mold, *Thermoascus aurantiacus* var. levisporus," Mycopathol., 87:71-80 [1984].

Van Tilbeurgh, H., et al., "Detection and differentiation of cellulase components using low molecular mass fluorogenic substrates," FEBS Lett., 187: 283-288 [1985].

Van Tilbeurgh, H., et al., "The use of 4-methylumbelliferyl and other chromophoric glycosides in the study of cellulolytic enxymes," FEBS Lett., 149: 152-156 [1982].

Venturi, L.L., et al., "Extracellular Beta-D-glucosidasefrom *Chaetomium thermophilum* var. coprophilum:production, purification and some biochemical properties," J. Basic Microbiol., 42: 55-66 [2002].

(Continued)

*Primary Examiner* — Manjunath Rao
*Assistant Examiner* — William W Moore
(74) *Attorney, Agent, or Firm* — Codexis, Inc.

(57) ABSTRACT

The present invention provides fungal proteases and improved fungal strains that are deficient in protease production.

9 Claims, 2 Drawing Sheets

(56) References Cited

U.S. PATENT DOCUMENTS

| | | |
|---|---|---|
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,509,171 B1 | 1/2003 | Berka et al. |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,573,086 B1 | 6/2003 | Emalfarb et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,933,133 B2 | 8/2005 | Tausif et al. |
| 6,946,296 B2 | 9/2005 | Patten et al. |
| 6,961,664 B2 | 11/2005 | Selifonov et al. |
| 6,995,017 B1 | 2/2006 | Stemmer |
| 7,024,312 B1 | 4/2006 | Selfinov et al. |
| 7,058,515 B1 | 6/2006 | Selfinov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,421,347 B2 | 9/2008 | Selfinov et al. |
| 7,430,477 B2 | 9/2008 | Selfinov et al. |
| 7,465,791 B1 | 12/2008 | Hallberg et al. |
| 7,527,927 B1 | 5/2009 | Ho et al. |
| 7,534,564 B2 | 5/2009 | Patten et al. |
| 7,620,500 B2 | 11/2009 | Mundorff et al. |
| 7,620,502 B2 | 11/2009 | Selfinov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,754,457 B2 | 7/2010 | Foody et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selfinov et al. |
| 7,868,138 B2 | 1/2011 | Stemmer et al. |
| 7,873,499 B2 | 1/2011 | Selfinov et al. |
| 7,904,249 B2 | 3/2011 | Selfinov et al. |
| 7,957,912 B2 | 6/2011 | Selfinov et al. |
| 8,236,551 B2 | 8/2012 | Dhawan et al. |
| 2003/0187243 A1 | 10/2003 | Emalfarb et al. |
| 2006/0246545 A1 | 11/2006 | Wang |
| 2007/0031953 A1 | 2/2007 | Dunson, Jr. et al. |
| 2007/0238155 A1 | 10/2007 | Gusakov et al. |
| 2008/0104724 A1 | 5/2008 | Sticklen et al. |
| 2008/0108105 A1 | 5/2008 | van Peij et al. |
| 2008/0194005 A1 | 8/2008 | Emalfarb et al. |
| 2008/0206816 A1 | 8/2008 | Idiris et al. |
| 2008/0220990 A1 | 9/2008 | Fox |
| 2008/0248530 A1 | 10/2008 | Hansen et al. |
| 2009/0099079 A1 | 4/2009 | Emalfarb et al. |
| 2009/0253173 A1 | 10/2009 | Wang |
| 2009/0312196 A1 | 12/2009 | Colbeck et al. |
| 2011/0124058 A1 | 5/2011 | Baidyaroy et al. |
| 2011/0129881 A1 | 6/2011 | Yang et al. |
| 2012/0003703 A1* | 1/2012 | Mitchell ............ C12N 9/2437 435/99 |
| 2012/0030839 A1 | 2/2012 | Embalfarb et al. |
| 2012/0190076 A1 | 7/2012 | Clark et al. |
| 2012/0208235 A1* | 8/2012 | Zhang ............... C12N 9/48 435/69.1 |
| 2012/0276594 A1* | 11/2012 | Voladri ............. C12N 9/2437 435/99 |
| 2012/0288892 A1* | 11/2012 | Maiyuran ............ C12N 9/58 435/68.1 |
| 2013/0084608 A1 | 4/2013 | Szabo et al. |
| 2013/0095532 A1* | 4/2013 | Schoonneveld-Bergmans .......................... C12N 9/18 435/105 |
| 2013/0145501 A1* | 6/2013 | Sagt ............... C12Y 302/01091 800/298 |
| 2013/0219571 A1* | 8/2013 | Schoonneveld-Bergmans .......................... C07K 14/37 800/306 |
| 2014/0033373 A1* | 1/2014 | Schooneveld-Bergmans .......................... C12N 9/2434 800/306 |

FOREIGN PATENT DOCUMENTS

| | | |
|---|---|---|
| WO | 97/35966 A1 | 10/1997 |
| WO | 98/15633 A1 | 4/1998 |
| WO | 98/27230 A1 | 6/1998 |
| WO | 00/42651 A1 | 7/2000 |
| WO | 00/46375 A2 | 8/2000 |
| WO | 01/75767 A2 | 10/2001 |
| WO | 2008/073914 A2 | 6/2008 |
| WO | 2009/045651 A2 | 4/2009 |
| WO | 2009/152336 A1 | 12/2009 |
| WO | 2010/022511 A1 | 3/2010 |
| WO | 2010/080532 A1 | 7/2010 |
| WO | 2010/107303 A2 | 9/2010 |
| WO | 2011/041594 A1 | 4/2011 |
| WO | 2011/098580 A1 | 8/2011 |
| WO | 2012/048334 A2 | 4/2012 |
| WO | 2012/061382 A1 | 5/2012 |
| WO | 2012/088159 A2 | 6/2012 |
| WO | 2013/048661 A1 | 4/2013 |

OTHER PUBLICATIONS

Von Klopotek, A., "Revision der thermophilen Sporotrichum-Arten: *Chlysosporittm thermophilum* (Apinis) comb. nov. und *Chrysosporium fergusii* spec. nov. = status conidialis yon Co~ynascus thermophilus (Fergus u_nd Sinden) comb. nov.," Arch. Microbiol., 98:365-369 [1974].

Wang, Y., et al., "Agrobacterium-meditated gene disruption using split-marker in Grosmannia clavigera, a mountain pine beetle associated pathogen," Curr. Genet., 56:297-307 [2010].

Weil, J., et al., "Pretreatment of Yellow Poplar Sawdust by Pressure Cooking in Water," Appl. Biochem. Biotechnol., 68(1-2): 21-40 [1997].

Wells, J.A., et al., "Cassette mutagenesis: an efficient method for generation of multiple mutations at defined sites," Gene, 34:315-323 [1985].

Zhang, Y.-H. P., et al., "Outlook for cellulase improvement: Screening and selection strategies," Biotechnol. Adv., 24: 452-481 [2006].

Zhang, J.-H., et al., "Directed evolution of a fucosidase from a galactosidase by DNA shuffling and screening" Proc. Nat. Acad. Sci. U.S.A., 94:4504-4509 [1997].

Zhu, T., et al., "Construction of two Gateway vectors for gene expression in fungi," Plasmid, 62:128-33 [2009].

(56) References Cited

OTHER PUBLICATIONS

Zrenner, R. et al., "Analysis of the expression of potato uridinediphosphate-glueose pyrophosphorylase and its inhibition by antisense RNA," Planta., 190(2):247-52 [1993].
GenBank accession No. AEO57290 dated Jul. 23, 2012.
GenBank accession No. AEO59424 dated Jul. 23, 2012.
GenBank accession No. AEO60458 dated Jul. 23, 2012.
NCBI Reference Sequence: XM_003664621 dated Jan. 4, 2012.
NCBI Reference Sequence: XM_003665655 dated Jan. 4, 2012.
UniProt Accession No. G2QGL4 dated Nov. 16, 2011.
UniProt Accession No. G2QJ92 dated Nov. 16, 2011.
UniProt Accession No. G2QCB5 dated Nov. 16, 2011.
Archer, D.B., et al., "Strategies for improving heterologous protein production from filamentous fungi," Antonie Van Leeuwenhoek, 65:245-250 [1994].
Wiebe, M.G., "Stable production of recombinant proteins in filamentous fungi-problems and improvements," Mycologist, 17(part3):140-144 [2003].
Naundorf, A., et al., "Influence of pH on the expression of a recombinant epoxide hydrolase in *Aspergillus niger*," Biotechnol J, 4(5): 756-65 [May 2009].
Adachi, K., et al., "Efficient gene identification and targeted gene disruption in the wheat blotch fungus *Mycosphaerella graminicola* using TAGKO," Curr. Genet, 42:123-7 [2002].
Awao, T., et al., "A new thermophilic species of Myceliophthora," Mycotaxon 16(2):436-440 [1983].
Bailey, M.J., et al., "Interlaboratory testing of methods for assay of xylanase activity," J. Biotechnol., 23(3): 257-270 [1992].
Biely, P., et al., "Recent progress in the assays ofxylanolytic enzymes," J. Sci. Food Agricul., 86: 1636-1647 [2006].
Botstein, D., et al., "Strategies and Applications ofin Vitro Mutagenesis," Science, 229(4719):1193-1201 [1985].
Cannon, P.F., "Name changes in fungi of microbiological, industrial and medical importance (Part4)," Mycopathol., 111:75-83 [1990].
Carter, P., "Site-directed mutagenesis," Biochem. J., 237:1-7 [1986].
Chang, X.-B., et al., "Modification of DNA ends can decrease end joining relative to homologous recombination in mammalian cells," Proc. Natl. Acad. Sci. USA, 84:4959-4963 [1987].
Christians, F.C., et al., "Directed evolution of thymidine kinase for AZT phosphorylation using DNA family shuffling," Nat. Biotechnol., 17:259-264 [1999].
Combier, J.-P., et al., "Agrobacterium tumefaciens-mediated transformation as a tool for insertional mutagenesis in the symbiotic ectomycorrhizal fungus *Hebeloma cylindrosporum*," FEMS Microbiol Lett., 220:141-8 [2003].
Crameri, A., et al., "DNA shuffling of a family of genes from diverse species accelerates directed evolution," Nature, 391:288-291 [1998].
Crameri, A., et al., "Improved green fluorescent protein by molecular evolution using DNA shuffling," Nat. Biotechnol., 14:315-319 [1996].
Crameri, A., et al., "Molecular evolution of an arsenate detoxification pathway by DNA shuffling," Nat. Biotechnol., 15:436-438 [1997].
Dale, S.J., et al., "Oligonucleotide-Directed Random Mutagenesis Using the Phosphorothioate Method," Meth. Mol. Biol., 57:369-74 [1996].
Davidson, R.C., et al., "Gene disiruption by biolistic transformation in serotype D strains of *Cryptococcus neoformans*," Fung. Genet. Biol., 29:38-48 [2000].
Davidson, R.C., et al., "A PCR-based strategy to generate integrative targeting alleles with large regions of homology," Microbiol., 148:2607-2615 [2002].
De Vries, et al., "aguA, the Gene Encoding an Extracellular alpha-Glucuronidase from *Aspergillus tubingensis*, Is Specifically Induced on Xylose and Not on Glucuronic Acid," J. Bacteriol., 180: 243-249 [1998].
Dynan, W.S., et al., "Control of eukaryotic messenger RNA synthesis by sequence-specific DNA-binding proteins," Nature 316:774-78 [1985].
Fab, S.H., et al., "Influence of Specific Signal Peptide Mutations on the Expression and Secretion of the alpha-Amylase Inhibitor Tendamistat in Streptomyces lividans," J. Biol. Chem., 271:15244-15252 [1996].
Fire, A., et al., "Potent and specific genetic interference by double-stranded RNA in Caenorhabditis elegans," Nature, 391:806-11 [1998].
Firon, A., et al., "Identification of Essential Genes in the Human Fungal Pathogen *Aspergillus fumigatus* by Transposon Mutagenesis," Eukaryot. Cell, 2(2):247-55 [2003].
Florea, S., et al., "Elimination of marker genes from transformed filamentous fungi by unselected transient transfection with a Cre-expressing plasmid," Fung. Genet. Biol., 46:721-730 [2009].
Garg. A.K., "An addition to the genus *Chrysosporium corda*," Mycopathologia, 30(3-4):221-224 (1966).
Georgieva, T.I., et al., "Evaluation of continuous ethanol fermentation of dilute-acid corn stover hydrolysate using thermophilic anaerobic bacterium Thermoanaerobacter BG1L1," Appl. Microbiol, Biotech., 77: 61-86 [2007].
Ghose, T.K., "Measurement of Cellulase Activities," Pure Appl. Chem., 59(2): 257-268 [1987].
Glenn, J.K., et al., "Mn(II) Oxidation Is the Principal Function of the Extracellular Mn-Peroxidase from *Phanerochaete chrysosporium*," Arch. Biochem. Biophys., 251(2):688-696 [1986].
Guarro, L.P., et al., "*Myceliophthora vellerea (Chrysosporium asperatum)* anamorph of Ctenomyces serratus," Mycotaxon, 23: 419-427 [1985].
Harris, P.V., et al., "Stimulation of Lignocellulosic Biomass Hydrolysis by Proteins of Glycoside Hydrolase Family 61: Structure and Function of a Large, Enigmatic Family," Biochem., 49:3305-3316 [2010].
Harvey, P.J., et al., "Veratryl alcohol as a mediator and the role of radical cations in lignin biodegradation by *Phanerochaete chrysosporium*," FEBS Lett., 195(1,2):242-246 [1986].
Herrmann, M.C., et al., "The Beta-D-xylosidase of Trichoderma reesei is a multifunctional Beta-D-xylan xylohydrolase", Biochem. J., 321: 375-381 [1997].
Igarashi, K., et al., "Cellobiose dehydrogenase enhances *Phanerochaete chrysosporium* cellobiohydrolase I activity by relieving product inhibition," Eur. J. Biochem., 253:101-106 [1998].
Kadotani, H., et al., "RNA Silencing in the Phytopathogenic Fungus *Magnaporthe oryzae*," Mol. Plant Microbe Interact., 16(9):769-76 [2003].
Kramer, B., et al., "Different base/base mismatches are corrected with different efficiencies by the methyl-directed DNA mismatch-repair system of *E. coli*," Cell, 38:879-887 [1984].
Lever, M., "A new reaction for colorimetric determination of carbohydrates," Anal. Biochem., 47: 273-279 [1972].
Ling, M.M., et al., "Approaches to DNA Mutagenesis: An Overview," Anal. Biochem., 254(2):157-78 [1997].
Mansfield, S.D., et al., "Cellobiose Dehydrogenase, an Active Agent in Cellulose Depolymerization," Appl. Environ. Microbiol., 63(10): 3804-3809 [1997].
Melander, C., et al., "New approaches to the analysis of enzymatically hydrolyzed methyl cellulose. Part 2. Comparison of various enzyme preparations," Biomacromol., 7(5):1410-1421 [2006].
Minshull, J., et al., "Protein evolution by molecular breeding," Curr. Op. Chem. Biol., 3:284-290 [1999].
Miyagishi, M., et al., "U6 promoter-driven siRNAs with four uridine 3' orverhangs efficiently supress targeted gene expression in mammalian cells," Nat. Biotechnol., 19:497-500 [2002].
Moustafa, A.F., et al., "Thielavia aegyptiaca, a new thermotolerant ascomycete from Egyptian soils," Persoonia 14:173-175 [1990].
Ngiam, C., et al., "Characterization of a Foldase, Protein Disulfide Isomerase A, in the Protein Secretory Pathway of *Aspergillus niger*," Appl Environ Microbiol., 66(2):775-82 [2000].
Paddison, P.J., et al., "Short hairpin RNAs (shRNAs) induce sequence-specific silencing in mammalian cells," Genes Dev. ,16:948-958 [2002].

(56) References Cited

OTHER PUBLICATIONS

Rothestein, R.J., "One-step gene disruption in Yeast," Meth. Enzymol., 101:202-211 [1983].

Smith, M., "In Vitro Mutagenesis," Ann. Rev. Genet., 19:423-462 [1985].

Spanikova, S., et al., "Glucuronoyl esterase—Novel carbohydrate esterase produced by Schizophyllum commune," FEBS Lett., 580: 4597-4601 [2006].

Stemmer, W.P.C., "DNA shuffling by random fragmentation and reassembly: In vitro recombination for molecular evolution," Proc. Nat. Acad. Sci. USA, 91:10747-10751 [1994].

Stemmer, W.P.C., "Rapid evolution of a protein in vitro by DNA shuffling," Nature, 370:389-391 [1994].

Teeri, T.T., et al., "Trichoderma reesei cellobiohydrolases: why so efficient on crystalline cellulose?" Biochem. Soc. Trans., 26: 173-178 [1998].

Teeri, T.T., "Crystalline cellulose degradation: new insight into the function of cellobiohydrolases," Trends Biotechnol., 15:160-167 [1997].

Thon, M.R., et al., "Restriction Enzyme-Mediated Integration Used to Produce Pathogenicity Mutants of Colletotrichum graminicola," Mol. Plant Microbe Interact., 13(12):1356-65 [2000].

\* cited by examiner

US 9,434,919 B2

FUNGAL PROTEASES

The present application is a Divisional of U.S. patent application Ser. No. 13/598,051, filed Aug. 29, 2012, which claims priority to U.S. Prov. Pat. Appln. Ser. No. 61/541,327, filed Sep. 30, 2011, and U.S. Prov. Pat. Appln. Ser. No. 61/564,107, filed Nov. 28, 2011, all of which are incorporated by reference in their entireties for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX35-108US1_ST25.TXT, created on Aug. 28, 2012, 461,224 bytes, machine format IBM-PC, MS-Windows operating system, is hereby incorporated by reference.

FIELD OF THE INVENTION

The present invention provides fungal proteases and improved fungal strains that are deficient in protease production.

BACKGROUND

Proteases find use in various settings where the degradation of protein compositions is desirable. Proteases, also referred to as "proteinases" and "proteolytic enzymes," catalyze the breakdown of peptide bonds within proteins. Different types of proteases hydrolyze different types of peptide bonds. Proteolytic enzymes play important roles in fungal development and physiology. Secreted proteases are required for survival and growth of various fungal species, and these enzymes play roles in accessing a variety of substrates during intracellular protein turnover, processing translocation, sporulation, germination, and differentiation. In addition, fungal proteases are widely used in biotechnology, mainly in areas such as food processing, leather processing, and in detergent compositions, as well as in bioremediation compositions and in the production of therapeutic peptides.

SUMMARY OF THE INVENTION

The present invention provides fungal proteases and improved fungal strains that are deficient in protease production.

The present invention provides proteases comprising the polypeptide sequences set forth in SEQ ID NOS:3, 6, 9, and/or 12, and biologically active fragments thereof. In some embodiments, the proteases are fungal proteases. The present invention also provides polynucleotide sequences encoding the proteases. In some embodiments, the present invention provides polynucleotide sequences encoding the fungal proteases provided herein. In some embodiments, the polynucleotide sequence is selected from SEQ ID NOS:1, 2, 4, 5, 7, 8, 10, and/or 11, and/or a fragment and/or fusion of SEQ ID NOS: 1, 2, 4, 5, 7, 8, 10, and/or 11. In some additional embodiments, the present invention provides isolated polynucleotide sequences encoding at least one protease, wherein the polynucleotide hybridizes to the full length complement of SEQ ID NO: 1, 2, 4, 5, 7, 8, 10, and/or 11, under stringent hybridization conditions. In some additional embodiments, the present invention provides isolated polynucleotides obtainable from a filamentous fungus. In some embodiments, the filamentous fungus is *Myceliophthora thermophila*.

The present invention also provides vectors comprising at least one polynucleotide sequence encoding at least one protease, as provided herein. In some embodiments, the polynucleotide sequence is operably linked to regulatory sequences suitable for expression of the polynucleotide sequence in a suitable host cell. In some embodiments, the host cell is a prokaryotic cell, while in some other embodiments, it is an eukaryotic cell. In some further embodiments, the host cell is a yeast or filamentous fungal cell. In some embodiments, the host cell is *Myceliophthora thermophila*. In some embodiments, the host cells comprising at least one vector as provided herein are prokaryotic or eukaryotic cells. In some embodiments, the host cell is a yeast or filamentous fungal cell. In some embodiments, the host cell is *Myceliophthora thermophila*.

The present invention also provides isolated *Myceliophthora* strains deficient in at least one protease native to *Myceliophthora*, wherein the protease comprises an amino acid sequence having at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity with a polypeptide sequence set forth in SEQ ID NO: 3, 6, 9, and/or 12. In some embodiments, the *Myceliophthora* is *Myceliophthora thermophila*. In some additional embodiments, the *Myceliophthora* produces at least one enzyme. In some further embodiments, the *Myceliophthora* produces at least one cellulase. In still some further embodiments, the *Myceliophthora* produces at least one enzyme selected from beta-glucosidases, endoglucanases, cellobiohydrolases, cellobiose dehydrogenases, endoxylanases, beta-xylosidases, xylanases, arabinofuranosidases, alpha-glucuronidases, acetylxylan esterases, feruloyl esterases, alpha-glucuronyl esterases, lipases, amylases, glucoamylases, and/or proteases. In some additional embodiments, the *Myceliophthora* produces at least one recombinant cellulase and/or non-cellulase, while in some other embodiments, the *Myceliophthora* produces at least two recombinant cellulases and/or non-cellulase, and in still some additional embodiments, the *Myceliophthora* produces at least three recombinant cellulases and/or non-cellulase. In some embodiments, the cellulase is a recombinant cellulase selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some embodiments, the cellulase is a recombinant *Myceliophthora* cellulase selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some additional embodiments, the cellulase is a recombinant cellulase selected from EG1b, EG2, EG3, EG4, EG5, EG6, CBH1a, CBH1b, CBH2a, CBH2b, GH61a, and/or BGL.

The present invention also provides compositions comprising the isolated *Myceliophthora* provided herein. The present invention also provides compositions comprising the isolated *Myceliophthora thermophila* provided herein. In some embodiments, the present invention provides compositions comprising at least one of the enzymes produced by at least one isolated *Myceliophthora* provided herein. In some embodiments, the present invention provides compositions comprising at least one of the enzymes produced by at least one isolated *Myceliophthora thermophila* provided herein.

The present invention also provides methods for producing the *Myceliophthora* described herein, comprising providing a *Myceliophthora* having protease activity, wherein the protease comprises an amino acid sequence having at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity with the polypeptide sequence set forth in SEQ ID NO: 3, 6, 9, and/or 12; and mutating the *Myceliophthora* under conditions such that the protease is mutated to produce a protease-deficient *Myceliophthora*. In some embodiments, the present invention provides methods for producing the *Myceliophthora thermophila* described herein, comprising providing a *Myceliophthora thermophila* having protease activity, wherein the protease comprises an amino acid sequence having at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity with the polypeptide sequence set forth in SEQ ID NO: 3, 6, 9, and/or 12; and mutating the *Myceliophthora thermophila* under conditions such that the protease is mutated to produce a protease-deficient *Myceliophthora thermophila*.

The present invention also provides methods for producing at least one enzyme, comprising providing *Myceliophthora*, under conditions such that at least one enzyme is produced by the *Myceliophthora*. In some embodiments, the at least one enzyme comprises at least one recombinant enzyme. In some further embodiments, the at least one enzyme comprises at least one recombinant cellulase, at least two recombinant cellulases, at least three recombinant cellulases, at least four recombinant cellulases, and/or at least five recombinant cellulases. In some embodiments, the cellulase is selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some additional embodiments, the cellulase is a *Myceliophthora* cellulase selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some further embodiments, the cellulase is selected from EG1b, EG2, EG3, EG4, EG5, EG6, CBH1a, CBH1b, CBH2a, CBH2b, GH61a, and/or BGL. In still some additional embodiments, the *Myceliophthora* further produces at least one additional enzyme (e.g., a non-cellulase enzyme). In some embodiments, at least one additional enzyme is a recombinant non-cellulase enzyme. In still additional embodiments, at least one non-cellulase enzyme is a *Myceliophthora* non-cellulase enzyme. In some embodiments, at least one non-cellulase enzyme comprises at least one endoxylanase, beta-xylosidase, xylanase, arabinofuranosidase, alpha-glucuronidase, acetylxylan esterase, feruloyl esterase, alpha-glucuronyl esterase, lipase, amylase, glucoamylase, and/or protease.

The present invention also provides methods for producing at least one enzyme, comprising providing *Myceliophthora thermophila*, under conditions such that at least one enzyme is produced by the *M. thermophila*. In some embodiments, the at least one enzyme comprises at least one recombinant enzyme. In some further embodiments, the at least one enzyme comprises at least one recombinant cellulase, at least two recombinant cellulases, at least three recombinant cellulases, at least four recombinant cellulases, and/or at least five recombinant cellulases. In some embodiments, the cellulase is selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some additional embodiments, the cellulase is a *M. thermophila* cellulase selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some further embodiments, the cellulase is selected from EG1b, EG2, EG3, EG4, EG5, EG6, CBH1a, CBH1b, CBH2a, CBH2b, GH61a, and/or BGL. In still some additional embodiments, the *M. thermophila* further produces at least one additional enzyme (e.g., a non-cellulase enzyme). In some embodiments, at least one non-cellulase enzyme is a recombinant non-cellulase enzyme. In still additional embodiments, at least one non-cellulase enzyme is a *M. thermophila* non-cellulase enzyme. In some embodiments, at least one non-cellulase enzyme comprises at least one endoxylanase, beta-xylosidase, xylanase, arabinofuranosidase, alpha-glucuronidase, acetylxylan esterase, feruloyl esterase, alpha-glucuronyl esterase, lipase, amylase, glucoamylase, and/or protease.

The present invention also provides compositions comprising at least one enzyme produced using at least one of the methods provided herein. In some embodiments the compositions further comprise at least one enzyme produced by *Myceliophthora*. In some embodiments, at least one enzyme is a *Myceliophthora* enzyme produced by a protease-deficient *Myceliophthora* strain. In some further embodiments, the at least one enzyme is a recombinant enzyme. In still some additional embodiments, the compositions comprise at least one enzyme selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some embodiments, the compositions comprise at least one enzyme, wherein the enzyme is a *Myceliophthora* cellulase selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some embodiments, the compositions comprise at least one cellulase selected from EG1b, EG2, EG3, EG4, EG5, EG6, CBH1a, CBH1b, CBH2a, CBH2b, GH61a, and/or BGL. In some additional embodiments, the compositions comprise at least one non-cellulase enzyme. In some embodiments, the cellulase-containing compositions further comprise at least one non-cellulase enzyme. In some embodiments, the non-cellulase enzyme is a recombinant non-cellulase enzyme. In some embodiments, the compositions comprise at least one non-cellulase enzyme selected from at least one lipase, amylase, glucoamylase, and/or protease.

The present invention also provides saccharification methods comprising (a) providing a biomass and *Myceliophthora*, (b) culturing the *Myceliophthora* provided herein under conditions in which at least one enzyme is secreted into a culture broth, and (c) combining the broth and biomass under conditions such that saccharification occurs, where (b) may take place before or simultaneously with (c). The present invention also provides saccharification methods comprising combining at least one composition provided herein and biomass under conditions such that saccharification occurs. The present invention further provides saccharification methods comprising combining any of enzymes produced as provided herein with biomass, under conditions such that saccharification occurs. In some embodiments, the *M. thermophila* does not produce at least one protease selected from Protease #1, Protease #2, Protease #3, and/or Protease #4, as provided herein. In some embodiments, the *Myceliophthora* does not produce at least one polypeptide selected from SEQ ID NOS: 3, 6, 9, and/or 12. In some embodiments, the gene encoding at least one protease selected from the genes encoding Protease #1, Protease #2, Protease #3, and/or Protease #4 has been deleted from the *Myceliophthora*. In some embodiments, at least one polynucleotide sequence selected from SEQ ID NOS: 1, 2, 4, 5, 7, 8, 10, and/or 11 is deleted from the genome of the *Myceliophthora*.

The present invention also provides saccharification methods comprising (a) providing a biomass and *Myceliophthora thermophila*, (b) culturing the *Myceliophthora thermophila* provided herein under conditions in which at least one enzyme is secreted into a culture broth, and (c) combining the broth and biomass under conditions such that saccharification occurs, where (b) may take place before or simultaneously with (c). The present invention also provides saccharification methods comprising combining at least one composition provided herein and biomass under conditions such that saccharification occurs. The present invention further provides saccharification methods comprising combining any of enzymes produced as provided herein with biomass, under conditions such that saccharification occurs. In some embodiments, the *Myceliophthora thermophila* does not produce at least one protease selected from Protease #1, Protease #2, Protease #3, and/or Protease #4, as provided herein. In some embodiments, the *Myceliophthora thermophila* does not produce at least one polypeptide selected from SEQ ID NOS: 3, 6, 9, and/or 12. In some embodiments, the gene encoding at least one protease selected from the genes encoding Protease #1, Protease #2, Protease #3, and/or Protease #4 has been deleted from the *Myceliophthora thermophila*. In some embodiments, at least one polynucleotide sequence selected from SEQ ID NOS: 1, 2, 4, 5, 7, 8, 10, and/or 11 is deleted from the genome of the *Myceliophthora thermophila*.

The present invention also provides saccharification methods comprising (a) providing a biomass and *Myceliophthora*, (b) culturing the *Myceliophthora* provided herein under conditions in which at least one enzyme is secreted into a culture broth, (c) recovering at least one cellulase and/or non-cellulase enzyme from the broth, (d) combining the recovered cellulase enzyme and/or at least one non-cellulase enzyme and biomass under conditions such that saccharification occurs. The present invention also provides saccharification methods comprising combining at least one composition provided herein and biomass under conditions such that saccharification occurs. The present invention further provides saccharification methods comprising combining any of enzymes produced as provided herein with biomass, under conditions such that saccharification occurs. In some embodiments, the *Myceliophthora* does not produce at least one protease selected from Protease #1, Protease #2, Protease #3, and/or Protease #4, as provided herein. In some embodiments, the *Myceliophthora* does not produce at least one protease selected from Protease #1, Protease #2, Protease #3, and/or Protease #4, as provided herein. In some embodiments, the *Myceliophthora* does not produce at least one polypeptide selected from SEQ ID NOS:3, 6, 9, and/or 12. In some embodiments, the gene encoding at least one protease selected from the genes encoding Protease #1, Protease #2, Protease #3, and/or Protease #4 has been deleted from the *Myceliophthora*. In some embodiments, at least one polynucleotide sequence selected from SEQ ID NOS: 1, 2, 4, 5, 7, 8, 10, and/or 11 have been deleted from the genome of the *Myceliophthora*.

The present invention also provides saccharification methods comprising (a) providing a biomass and *Myceliophthora thermophila*, (b) culturing the *Myceliophthora thermophila* provided herein under conditions in which at least one enzyme is secreted into a culture broth, (c) recovering at least one cellulase and/or non-cellulase enzyme from the broth, (d) combining the recovered cellulase enzyme and/or at least one non-cellulase enzyme and biomass under conditions such that saccharification occurs. The present invention also provides saccharification methods comprising combining at least one composition provided herein and biomass under conditions such that saccharification occurs. The present invention further provides saccharification methods comprising combining any of enzymes produced as provided herein with biomass, under conditions such that saccharification occurs. In some embodiments, the *Myceliophthora thermophila* does not produce at least one protease selected from Protease #1, Protease #2, Protease #3, and/or Protease #4, as provided herein. In some embodiments, the *Myceliophthora thermophila* does not produce at least one polypeptide selected from SEQ ID NOS: 3, 6, 9, and/or 12. In some embodiments, the gene encoding at least one protease selected from the genes encoding Protease #1, Protease #2, Protease #3, and/or Protease #4 has been deleted from the *Myceliophthora thermophila*. In some embodiments, at least one sequence selected from SEQ ID NOS: 1, 2, 4, 5, 7, 8, 10, and/or 11 has been deleted from the genome of the *Myceliophthora thermophila*.

The present invention also provides isolated fungal proteases comprising amino acid sequences that are at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to any of SEQ ID NOS:3, 6, 9, and/or 12 or a biologically active fragment of any of SEQ ID NOS:3, 6, 9, and/or 12, wherein the amino acid sequence of the protease is numbered with reference to SEQ ID NO:3. In some embodiments, the fungal proteases comprise the polypeptide sequence(s) set forth in SEQ ID NOS:3, 6, 9, and/or 12, or a biologically active fragment thereof.

The present invention also provides isolated polynucleotide sequences encoding the fungal proteases provided herein. In some embodiments, the isolated polynucleotide sequences comprise at least one sequence selected from SEQ ID NOS:1, 2, 4, 5, 7, 8, 10, and/or 11, and/or a fragment and/or fusion of SEQ ID NOS:1, 2, 4, 5, 7, 8, 10, and/or 11. In some additional embodiments, the polynucleotides hybridize to the full length complement of SEQ ID NO:1, 2, 4, 5, 7, 8, 10, and/or 11, under stringent hybridization conditions. In some additional embodiments, the isolated polynucleotides are obtainable from a filamentous fungus. In some further embodiments, the filamentous fungus is *Myce-

*liophthora*. In still some additional embodiments, the filamentous fungus is *Myceliophthora thermophila*.

The present invention also provides vectors comprising at least one polynucleotide sequence encoding at least one protease provided herein. In some embodiments, the isolated polynucleotide sequences comprise at least one sequence selected from SEQ ID NOS:1, 2, 4, 5, 7, 8, 10, and/or 11, and/or a fragment and/or fusion of SEQ ID NOS:1, 2, 4, 5, 7, 8, 10, and/or 11. In some additional embodiments, the polynucleotides hybridize to the full length complement of SEQ ID NO:1, 2, 4, 5, 7, 8, 10, and/or 11, under stringent hybridization conditions. In some additional embodiments, the isolated polynucleotides are obtainable from a filamentous fungus. In some further embodiments, the filamentous fungus is *Myceliophthora*. In still some additional embodiments, the filamentous fungus is *Myceliophthora thermophila*. In some embodiments, the polynucleotide sequence(s) comprising the vector is operably linked to regulatory sequences suitable for expression of the polynucleotide sequence in a suitable host cell. In some embodiments, the host cell is a prokaryotic or eukaryotic cell. In some further embodiments, the host cell is a eukaryotic cell. In some additional embodiments, the host cell is a yeast or filamentous fungal cell. In some embodiments, the host cell is *Myceliophthora*. In some further embodiments, the host cell is *Myceliophthora thermophila*.

The present invention further provides host cells comprising at least one vector as provided herein. In some embodiments the host cell is prokaryotic or eukaryotic cell. In some embodiments, the host cell is a prokaryotic or eukaryotic cell. In some further embodiments, the host cell is a eukaryotic cell. In some additional embodiments, the host cell is a yeast or filamentous fungal cell. In some embodiments, the host cell is *Myceliophthora*. In some further embodiments, the host cell is *Myceliophthora thermophila*. In some embodiments, the isolated polynucleotide sequences of the vectors comprise at least one sequence selected from SEQ ID NOS:1, 2, 4, 5, 7, 8, 10, and/or 11, and/or a fragment and/or fusion of SEQ ID NOS:1, 2, 4, 5, 7, 8, 10, and/or 11. In some additional embodiments, the polynucleotides hybridize to the full length complement of SEQ ID NO:1, 2, 4, 5, 7, 8, 10, and/or 11, under stringent hybridization conditions. In some additional embodiments, the isolated polynucleotides are obtainable from a filamentous fungus. In some further embodiments, the filamentous fungus is *Myceliophthora*. In still some additional embodiments, the filamentous fungus is *Myceliophthora thermophila*.

The present invention also provides isolated *Myceliophthora* deficient in at least one protease native to *Myceliophthora*, wherein the protease comprises an amino acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% identity with the polypeptide sequence set forth in SEQ ID NO:3, 6, 9, and/or 12. In some embodiments, the protease comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity with the polypeptide sequence set forth in SEQ ID NO:3, 6, 9, and/or 12. In some embodiments the *Myceliophthora* is *Myceliophthora thermophila*. In some additional embodiments, the *Myceliophthora* produces at least one enzyme. In some embodiments, the *Myceliophthora* provided herein produces at least one cellulase. In some further embodiments, the *Myceliophthora* produces at least one cellulase is selected from beta-glucosidases, endo-glucanases, cellobiohydrolases, cellobiose dehydrogenases, xylanases, beta-xylosidases, arabinofuranosidases, alpha-glucuronidases, acetylxylan esterases, feruloyl esterases, alpha-glucuronyl esterases, laccases, and/or peroxidases. In some embodiments, the *Myceliophthora* produces at least one recombinant cellulase, while in some alternative embodiments the *Myceliophthora* produces at least two recombinant cellulases, and in some further embodiments, the *Myceliophthora* produces at least three, four, five, or more recombinant cellulases. In some embodiments, the recombinant cellulase comprises a recombinant cellulase selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some additional embodiments, the cellulase comprises a recombinant *Myceliophthora* cellulase selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some further embodiments, the cellulase is a recombinant cellulase selected from EG1b, EG2, EG3, EG4, EG5, EG6, CBH1a, CBH1b, CBH2a, CBH2b, GH61a, and/or BGL. In some additional embodiments, the *Myceliophthora* further produces at least one non-cellulase enzyme. In some embodiments, the *Myceliophthora* produces at least one non-cellulase enzyme comprising at least one lipase, amylase, glucoamylase, protease, oxidase, and/or reductase. In some additional embodiments, the *Myceliophthora* produces two, three, four, or more non-cellulase enzymes.

The present invention also provides compositions comprising the *Myceliophthora* provided herein. The present invention also provides compositions comprising at least one enzyme produced by the *Myceliophthora* provided herein. In some embodiments, the *Myceliophthora* is *Myceliophthora thermophila*. The present invention also provides compositions comprising *Myceliophthora thermophila*. In some embodiments the compositions comprise at least one additional enzyme produced by at least one *Myceliophthora* provided herein. In some further embodiments, the compositions further comprise at least one additional enzyme produced by any suitable organism, including but not limited to any suitable eukaryotic and/or prokaryotic organisms. In some further embodiments, the compositions further comprise at least one additional suitable organism, including but not limited to eukaryotic and prokaryotic organisms. In some embodiments, the additional organism is selected from yeast, filamentous fungi, and bacteria.

The present invention further provides methods for producing the *Myceliophthora* provided herein, comprising providing a *Myceliophthora* having protease activity, wherein the protease comprises at least one amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity with at least one polypeptide sequence set forth in SEQ ID NO:3, 6, 9, and/or 12; and mutating the *Myceliophthora* under conditions such that a protease-deficient *Myceliophthora* is produced. The present invention further provides methods for producing the *Myceliophthora* provided herein, comprising providing a *Myceliophthora* having protease activity, wherein the protease comprises at least one amino acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identity with at least one polypeptide sequence set forth in SEQ ID NO:3, 6, 9, and/or 12; and mutating the *Myceliophthora* under conditions such that a protease-deficient *Myceliophthora* is produced. It is not intended that the protease-deficient *Myceliophthora* be produced using any particular methods, as it is intended that any suitable method for production of protease-deficient fungal organisms will find use in the present invention. In some embodiments, the *Myceliophthora* is *Myceliophthora thermophila*.

The present invention also provides methods for producing at least one enzyme, comprising providing the *Myceliophthora* provided herein, under conditions such that at least one enzyme is produced by the *Myceliophthora*. In some embodiments, at least one enzyme produced by the isolated *Myceliophthora* comprises at least one recombinant enzyme. In some embodiments, at least one enzyme comprises at least one recombinant cellulase, while in some alternative embodiments the methods provide at least two recombinant cellulases, and some further embodiments, the methods provide at least three, four, or five or more recombinant cellulases. In some embodiments, the cellulase is selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). IN some further embodiments, the cellulase is a *Myceliophthora* cellulase selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some additional embodiments, the cellulase is selected from EG1b, EG2, EG3, EG4, EG5, EG6, CBH1a, CBH1b, CBH2a, CBH2b, GH61a, and/or BGL. In some embodiments, the *Myceliophthora* further produces at least one non-cellulase enzyme. In some additional embodiments, the non-cellulase enzyme(s) is/are recombinant non-cellulase enzyme(s). In some further embodiments, the non-cellulase enzyme(s) comprise at least one lipase, amylase, glucoamylase, protease, oxidase, and/or reductase. In some additional embodiments, the *Myceliophthora* produces two, three, four, or more non-cellulase enzymes. In some embodiments, the *Myceliophthora* is *Myceliophthora thermophila*.

The present invention also provides compositions comprising at least one enzyme produced using at least one method provided herein. In some embodiments, the composition further comprises *Myceliophthora*. In some additional embodiments, the compositions comprise at least one *Myceliophthora* enzyme. In some further embodiments, at least one enzyme is a recombinant enzyme. In some additional embodiments, at least one enzyme is selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some embodiments, the compositions comprise at least one enzyme comprising at least one *Myceliophthora* cellulase selected from beta-glucosidases (BGLs), Type 1 cellobiohydrolases (CBH1s), Type 2 cellobiohydrolases (CBH2s), glycoside hydrolase 61s (GH61s), and/or endoglucanases (EGs). In some embodiments, the cellulase is selected from EG1b, EG2, EG3, EG4, EG5, EG6, CBH1a, CBH1b, CBH2a, CBH2b, GH61a, and/or BGL. In some additional embodiments, the *Myceliophthora* is *Myceliophthora thermophila*. In some further embodiments, the compositions further comprise at least one non-cellulase enzyme. In some embodiments, at least one non-cellulase enzyme is a recombinant non-cellulase enzyme. In some further embodiments, the non-cellulase enzyme(s) comprise at least one lipase, amylase, glucoamylase, protease, oxidase, and/or reductase. In some additional embodiments, the *Myceliophthora* produces two, three, four, or more non-cellulase enzymes. In some embodiments, the *Myceliophthora* is *Myceliophthora thermophila*.

The present invention also provides saccharification methods comprising (a) providing biomass and protease-deficient *Myceliophthora* as provided herein in a culture broth, (b) culturing the protease-deficient *Myceliophthora* under conditions in which at least one enzyme is secreted by the *Myceliophthora* into the culture broth to provide an enzyme-containing broth, and (c) combining the enzyme-containing broth and the biomass under conditions such that saccharification occurs, where (b) may take place before or simultaneously with (c). In some embodiments, the saccharification methods comprise combining at least one composition as provided herein and biomass under conditions such that saccharification occurs. In some further embodiments, fermentable sugars are produced during saccharification.

The present invention also provides methods for producing a fermentable sugar from at least one cellulosic substrate, comprising contacting the cellulosic substrate with at least one enzyme selected from beta-glucosidase (Bgl), at least one endoglucanase (EG), at least one type 2b cellobiohydrolase (CBH2b), at least one glycoside hydrolase 61(GH61), and/or at least one CBH1a produced by at least one protease-deficient *Myceliophthora* provided herein, under conditions in which the fermentable sugar is produced.

The present invention also provides methods of producing at least one end-product from at least one cellulosic substrate, the method comprising: (a) contacting the cellulosic substrate with at least one enzyme selected from beta-glucosidase (Bgl), at least one endoglucanase (EG), at least one type 2b cellobiohydrolase (CBH2b), at least one glycoside hydrolase 61(GH61), and/or at least one CBH1a produced by the protease-deficient *Myceliophthora* provided herein, under conditions in which fermentable sugars are produced; and (b) contacting the fermentable sugars with a microorganism in a fermentation to produce the end-product. In some embodiments, the cellulosic substrate is pretreated prior to step (a). In some embodiments, at least one end product comprises at least one fermentation end product. In some embodiments, the methods further comprise recovering at least one end product. In some additional embodiments, the fermentation end product is selected from alcohols, organic acids, diols, fatty acids, lactic acid, acetic acid, 3-hydroxypropionic acid, acrylic acid, succinic acid, citric acid, malic acid, fumaric acid, amino acids, 1,3-propanediol, ethylene, glycerol, fatty alcohols, butadiene, and beta-lactams. In some embodiments, the fermentation end product is at least one alcohol selected from ethanol and butanol. In some further embodiments, the alcohol is ethanol. In some additional embodiments, the microorganism is a yeast. In some embodiments, the yeast is *Saccharomyces*.

The present invention also provides use of at least one protease-deficient *Myceliophthora* provided herein and/or at least one composition as provided herein, to produce at least one fermentation end product. In some embodiments, the present invention also provides use of at least one protease-deficient *Myceliophthora* provided herein and/or at least one composition provided herein to produce at least one fermentation end product selected from alcohols, fatty acids, lactic acid, acetic acid, 3-hydroxypropionic acid, acrylic acid, citric acid, malic acid, fumaric acid, succinic acid, amino acids, 1,3-propanediol, ethylene, glycerol, butadiene, fatty alcohols, and beta-lactams. In some embodiments, the fermentation end product is an alcohol selected from ethanol and butanol. In some further embodiments, the alcohol is ethanol.

DESCRIPTION OF THE INVENTION

Figure 1:
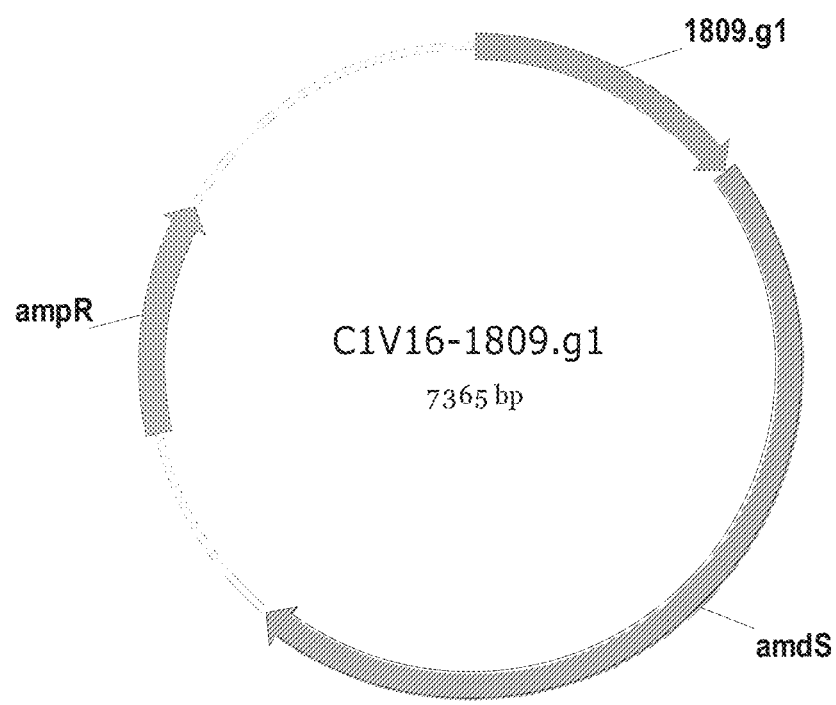
FIG. 1 provides a map of the construct C1V16-1809.g1.
Figure 2:
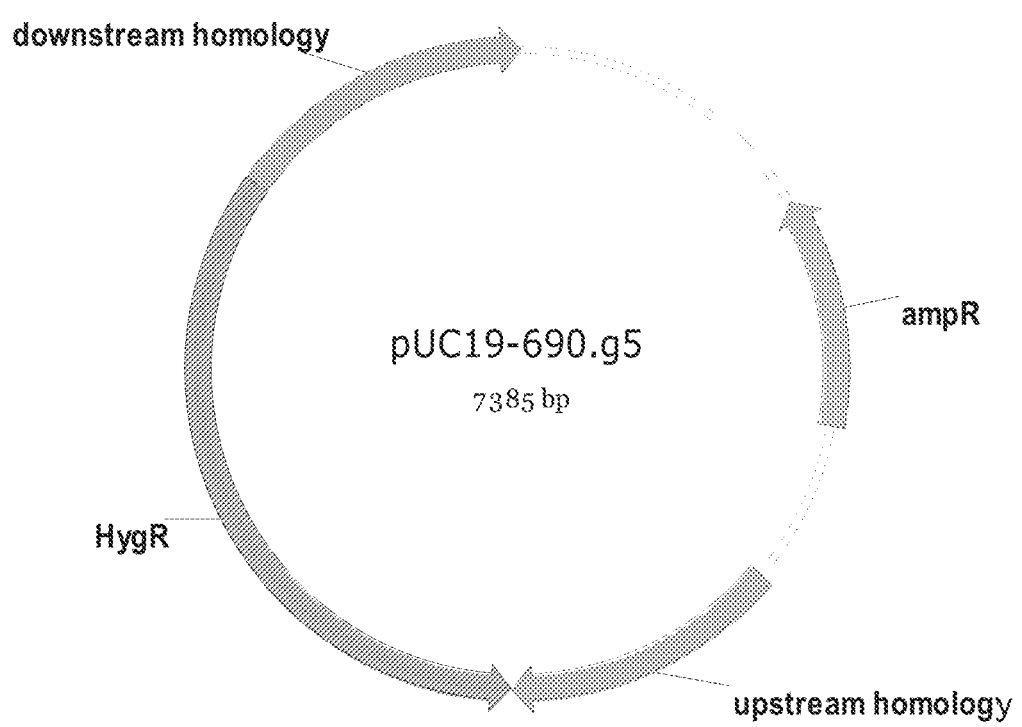
FIG. 2 provides a map of the construct pUC19-690.g5.

The present invention provides fungal proteases and improved fungal strains that are deficient in protease production.

In some embodiments, the improved fungal strains find use in hydrolyzing cellulosic material to glucose. In some embodiments, the improved fungal strains find use in hydrolyzing lignocellulose material. As indicated herein, the present invention provides improved fungal strains for the conversion of cellulose to fermentable sugars (e.g., glucose). In particular, the improved fungal strains provided herein are genetically modified to reduce the amount of endogenous protease activity secreted by the cells. The present invention also provides purified enzymes produced by the improved fungal strains provided herein.

Fungi are particularly suitable for large scale production of useful proteins, particularly proteins that are secreted from cells. Proteolytic enzymes play roles in these production processes, as they are generally required for proper processing of proteins and the metabolic health of the host organism. However, proteolytic degradation can sometimes result in decreased yields of secreted proteins. In addition, separation of intact from cleaved proteins, particularly on a large scale, is challenging and time-consuming Thus, in some situations it is desirable to attenuate protease production and/or activity. Means to achieve this attenuation include, but are not limited to deleting (i.e., knocking out) the genes encoding proteases that are problematic in protein production.

The present invention provides novel proteases obtained from *Myceliophthora thermophila*, as well as *M. thermophila* strains that are deficient in the production of at least one protease.

DEFINITIONS

Unless otherwise indicated, the practice of the present invention involves conventional techniques commonly used in molecular biology, protein engineering, microbiology, and fermentation science, which are within the skill of the art. Such techniques are well-known and described in numerous texts and reference works well known to those of skill in the art. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. Many technical dictionaries are known to those of skill in the art. Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole.

Also, as used herein, the singular "a", "an," and "the" include the plural references, unless the context clearly indicates otherwise. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein. Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below. Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates)

As used herein, "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the present invention. Some specific types of proteases include but are not limited to, cysteine proteases including pepsin, papain and serine proteases including chymotrypsins, carboxypeptidases and metalloendopeptidases.

As used herein, the term "protease-deficient" refers to microbial strains, in particular fungal strains (e.g., *M. thermophila*) that produce reduced levels or no endogenous or heterologous proteases. In some embodiments, the strains do not produce at least one protease selected from Protease #1, Protease #2, Protease #3, and/or Protease #4, as provided herein. In some embodiments, the *M. thermophila* does not produce at least one polypeptide selected from SEQ ID NOS:3, 6, 9, and/or 12. In some embodiments, the gene encoding at least one protease selected from the genes encoding Protease #1, Protease #2, Protease #3, and/or Protease #4 has been deleted from the *M. thermophila*. In some embodiments, at least one polynucleotide sequence selected from SEQ ID NOS:1, 2, 4, 5, 7, 8, 10, and/or 11 have been deleted from the genome of the *M. thermophila*. In some additional embodiments, at least one polynucleotide sequence selected from SEQ ID NOS: 1, 2, 4, 5, 7, 8, 10, and/or 11 have been mutated, such that the *M. thermophila* produces a reduced level of at least one protease (e.g., Protease #1, Protease #2, Protease #3, and/or Protease #4), as compared to a *M. thermophila* in which SEQ ID NOS: 1, 2, 4, 5, 7, 8, 10, and/or 11 have not been mutated. In some embodiments, at least one polynucleotide sequence or a portion thereof selected from SEQ ID NOS: 1, 2, 4, 5, 7, 8, 10, and/or 11 are expressed by *M thermophila*, but reduced levels or no detectable levels of at least one protease (e.g., Protease #1, Protease #2, Protease #3, and/or Protease #4) are produced. It is also intended that the term be used to indicate that a strain is deficient in the production of a specific protease but not other protease(s). Thus, in some embodiments, the strain is deficient in the production of at least one protease selected from Protease #1, Protease #2, Protease #3, and/or Protease #4, but is not deficient in production of at least one additional protease, including but not limited to endogenous and/or heterologous protease(s).

As used herein, "substrate" refers to a substance or compound that is converted or designated for conversion into another compound (e.g., a product) by the action of an enzyme. The term includes not only a single compound but also combinations of compounds, such as solutions, mixtures and other materials which contain at least one substrate.

As used herein, "conversion" refers to the enzymatic transformation of a substrate to the corresponding product. "Percent conversion" refers to the percent of the substrate that is converted to the product within a period of time under specified conditions.

The terms "polynucleotide" and "nucleic acid", used interchangeably herein, refer to a polymeric form of nucleotides of any length, either ribonucleotides or deoxyribonucleotides. These terms include, but are not limited to, single-, double- or triple-stranded DNA, genomic DNA, cDNA, RNA, DNA-RNA hybrid, polymers comprising purine and pyrimidine bases, and/or other natural, chemically, biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and/or nucleotide branches. In some alternative embodiments, the sequence of nucleotides is interrupted by non-nucleotide components.

As used herein, the terms "DNA construct" and "transforming DNA" are used interchangeably to refer to DNA that is used to introduce sequences into a host cell or organism. The DNA may be generated in vitro by PCR or any other suitable technique(s) known to those in the art. In some embodiments, the DNA construct comprises a sequence of interest (e.g., as an "incoming sequence"). In some embodiments, the sequence is operably linked to additional elements such as control elements (e.g., promoters, etc.). In some embodiments, the DNA construct further comprises at least one selectable marker. In some further embodiments, the DNA construct comprises an incoming sequence flanked by homology boxes. In some further embodiments, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In some other embodiments, the DNA construct comprises non-homologous sequences. Once the DNA construct is assembled in vitro, it may be used to: 1) insert heterologous sequences into a desired target sequence of a host cell; 2) mutagenize a region of the host cell chromosome (i.e., replace an endogenous sequence with a heterologous sequence); 3) delete target genes; and/or 4) introduce a replicating plasmid into the host. In some embodiments, the incoming sequence comprises at least one selectable marker. This sequence can code for one or more proteins of interest. It can have other biological functions. In many cases the incoming sequence comprises at least one selectable marker, such as a gene that confers antimicrobial resistance.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette/vector includes, among other sequences, a nucleic acid sequence to be transcribed and a promoter. In some embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "vector" refers to a polynucleotide construct designed to introduce nucleic acids into one or more cell types. Vectors include cloning vectors, expression vectors, shuttle vectors, plasmids, cassettes and the like. In some embodiments, the polynucleotide construct comprises a DNA sequence encoding the enzyme (e.g., precursor or mature enzyme) that is operably linked to a suitable prosequence capable of effecting the expression of the DNA in a suitable host.

As used herein, "a secretion signal peptide" can be a propeptide, a prepeptide or both. For example, the term "propeptide" refers to a protein precursor that is cleaved to yield a mature protein. The term "prepeptide" refers to a polypeptide synthesized with an N-terminal signal peptide that targets it for secretion. Accordingly, a "pre-pro-peptide" is a polypeptide that contains a signal peptide that targets the polypeptide for secretion and which is cleaved off to yield a mature polypeptide. Signal peptides are found at the N-terminus of the protein and are typically composed of between about 3 to about 136 basic and hydrophobic amino acids.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, transduction, and electroporation.

As used herein, the terms "transformed" and "stably transformed" refers to a cell that has a non-native (i.e., heterologous) polynucleotide sequence integrated into its genome or as an episomal plasmid that is maintained for at least two generations.

As used herein, the terms "control sequences" and "regulatory sequences" refer to nucleic acid sequences necessary and/or useful for expression of a polynucleotide encoding a polypeptide. In some embodiments, control sequences are native (i.e., from the same gene) or foreign (i.e., from a different gene) to the polynucleotide encoding the polypeptide. Control sequences include, but are not limited to leaders, polyadenylation sequences, propeptide sequences, promoters, signal peptide sequences, and transcription terminators. In some embodiments, at a minimum, control sequences include a promoter, and transcriptional and translational stop signals. In some embodiments, control sequences are provided with linkers for the purpose of introducing specific restriction sites facilitating ligation of the control sequences with the coding region of the polynucleotide encoding the polypeptide.

As used herein, "operably linked" refers to a configuration in which a control sequence is appropriately placed (i.e., in a functional relationship) at a position relative to a polynucleotide of interest such that the control sequence directs or regulates the expression of the polynucleotide and/or polypeptide of interest. Thus, a nucleic acid is "operably linked" to another nucleic acid sequence when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein the term "gene" refers to a polynucleotide (e.g., a DNA segment), that encodes a polypeptide and includes regions preceding and following the coding regions as well as intervening sequences (introns) between individual coding segments (exons).

Nucleic acids "hybridize" when they associate, typically in solution. There are numerous texts and other reference materials that provide details regarding hybridization methods for nucleic acids (See e.g., Tijssen, *Laboratory Techniques in Biochemistry and Molecular Biology-Hybridization with Nucleic Acid Probes*," Part 1, Chapter 2, Elsevier, New York, [1993], incorporated herein by reference). For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. ("low" stringency), at least at 55° C. ("medium" or "moderate" stringency), at least at 60° C. ("medium-high" stringency), at least at 65° C. ("high" stringency), and at least at 70° C. ("very high" stringency). In some embodiments, the stringency conditions include those that: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. In other embodiments, the stringency conditions include overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors to accomplish the desired stringency.

As used herein, an "endogenous" or "homologous" gene refers to a gene that is found in a parental strain of a cell (e.g., a fungal or bacterial cell). In some embodiments, endogenous genes are present in wild-type strains. As used herein in making comparisons between nucleic acid sequences, "homologous genes" (or "homologue" genes) refers to genes from different, but usually related species, that correspond to each other and are identical or very similar to each other. The term encompasses genes that are separated by speciation (i.e., the development of new species) (e.g., orthologous genes), as well as genes that have been separated by genetic duplication (e.g., paralogous genes).

As used herein, "heterologous" polynucleotides are any polynucleotides that are introduced into a host cell through the use of laboratory techniques/manipulation, and include polynucleotides that are removed from a host cell, subjected to laboratory manipulation, and then reintroduced into a host cell.

As used herein, when used with reference to a nucleic acid or polypeptide, the term "heterologous" refers to a sequence that is not normally expressed and secreted by an organism (e.g., a "wild-type" organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector).

As used herein, a "heterologous enzyme" is used in reference to an enzyme that is encoded by a heterologous gene. However, it is also contemplated herein that a heterologous gene can encode an endogenous or homologous enzyme. As used herein, the term "heterologous gene" refers to a gene that occurs in a form not found in a parental strain of the fungal cell. Thus, in some embodiments, a heterologous gene is a gene that is derived from a species that is different from the species of the fungal cell expressing the gene and recognized anamorphs, teleomorphs or taxonomic equivalents of the fungal cell expressing the gene. In some embodiments, a heterologous gene is a modified version of a gene that is endogenous to the host fungal cell (e.g., an endogenous gene subjected to manipulation and then introduced or transformed into the host cell). For example, in some embodiments, a heterologous gene has an endogenous coding sequence, but has modifications in the promoter sequence. Similarly, in other embodiments, a heterologous gene encodes the same amino acid sequence as an endogenous gene, but has modifications in codon usage and/or to noncoding regions (e.g., introns), and/or combinations thereof. For example, in some embodiments, a heterologous gene contains modifications to the coding sequence to encode a non-wild-type polypeptide. As another example, in some embodiments, a heterologous gene has the same promoter sequence, 5' and 3' untranslated regions and coding regions as a parental strain, but is located in another region of the same chromosome, or on an entirely different chromosome as compared to a parental strain of the host cell. In some embodiments, the heterologous gene is a gene that has been modified to overexpress a gene product of interest.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (i.e., non-recombinant) form of the cell or express native genes that are otherwise abnormally expressed, under-expressed or not expressed at all as a result of deliberate human intervention. "Recombinant" "engineered," and "non-naturally occurring," when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (i.e., non-recombinant) form of the cell or express native genes that are otherwise expressed at a different level. "Recombination," "recombining," and "generating a recombined" nucleic acid also encompass the assembly of two or more nucleic acid fragments wherein the assembly gives rise to a chimeric gene.

As used herein, a "genetically modified" or "genetically engineered" cell is a cell whose genetic material has been altered using genetic engineering techniques. A genetically modified cell also refers to a derivative of or the progeny of a cell whose genetic material has been altered using genetic engineering techniques. An example of a genetic modification as a result of genetic engineering techniques includes a modification to the genomic DNA. Another example of a genetic modification as a result of genetic engineering techniques includes introduction of a stable heterologous nucleic acid into the cell. For example, in some embodiments, the genetically modified fungal cell of the present invention secretes a reduced amount of at least one protease or the secreted enzyme has a reduced ability to oxidize cellobiose.

As used herein, the term "overexpression" refers to any state in which a gene is caused to be expressed at an elevated rate or level as compared to the endogenous expression rate or level for that gene. In some embodiments, "overexpression" includes an elevated translation rate or level of the gene compared to the endogenous translation rate or level for that gene. In some embodiments, overexpression includes an elevated transcription rate or level of the gene compared to the endogenous transcription rate or level for that gene. For example, in some embodiments, a heterologous gene is introduced into a fungal cell to express a gene encoding a heterologous enzyme such as a beta-glucosidase from another organism. In some other embodiments, a heterologous gene is introduced into a fungal cell to overexpress a gene encoding a homologous enzyme such as a beta-glucosidase.

In some embodiments, mutant DNA sequences are generated using site saturation mutagenesis in at least one codon. In some other embodiments, site saturation mutagenesis is performed for two or more codons. In some further embodiments, mutant DNA sequences have more than about 50%, more than about 55%, more than about 60%, more than about 65%, more than about 70%, more than about 75%, more than about 80%, more than about 81%, more than about 82%, more than about 83%, more than about 84%, more than about 85%, more than about 86%, more than about 87%, more than about 88%, more than about 89%, more than about 90%, more than about 91%, more than about 92%, more than about 93%, more than about 94%, more than about 95%, more than about 96%, more than about 97%, more than about 98%, or more than about 99% homology with the wild-type sequence. In some alternative embodiments, mutant DNA is generated in vivo using any suitable known mutagenic procedures including, but not limited to the use of radiation, nitrosoguanidine, etc. The desired DNA sequence is then isolated and used in the methods provided herein.

As used herein, the terms "amplification" and "gene amplification" refer to a method by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both. "Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, that is capable of acting as a synthesis initiation point when placed under conditions in which synthesis of a primer extension product which is complementary to a nucleic acid strand is induced (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. In some embodiments, the primer is an oligodeoxyribonucleotide. The primer must be sufficiently long to prime the synthesis of extension products in the presence of the inducing agent. As known in the art, the exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" (PCR) refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This method for amplifying the target sequence is well known in the art.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In some embodiments of the invention, restriction sites are engineered into the selective marker and into 5' and 3' ends of the DNA construct.

As used herein, "homologous recombination" means the exchange of DNA fragments between two DNA molecules or paired chromosomes at the site of identical or nearly identical nucleotide sequences. In some embodiments, chromosomal integration is homologous recombination.

As used herein "amino acid" refers to peptide or protein sequences or portions thereof. The terms "protein," "peptide," and "polypeptide" are used interchangeably in reference to a polymer of amino acid residues). The term "amino acid" refers to naturally occurring and synthetic amino acids, as well as amino acid analogs. Naturally occurring amino acids are those encoded by the genetic code, as well as those amino acids that are later modified (e.g., hydroxyproline, γ-carboxyglutamate, and O-phosphoserine). "The term amino acid analogs" refers to compounds that have the same basic chemical structure as a naturally occurring amino acid (i.e., an α-carbon that is bound to a hydrogen, a carboxyl group, an amino group, and an R group, such as homoserine, norleucine, methionine sulfoxide, or methionine methyl sulfonium). Such analogs have modified R groups (e.g., norleucine) or modified peptide backbones, but retain the same basic chemical structure as a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. It is also understood that a polypeptide may be encoded by more than one nucleotide sequence, due to the degeneracy of the genetic code.

A used herein, an amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

As used herein, the terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

As used herein, "conservative substitution," as used with respect to amino acids, refers to the substitution of an amino acid with a chemically similar amino acid. Amino acid substitutions that do not generally alter specific activity are well known in the art and are described in numerous textbooks. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, as well as these in reverse. As used herein, a conservative substitute for a residue is another residue in the same group as shown below.

| | |
|---|---|
| basic amino acids | arginine (R), lysine (K), histidine (H) |
| acidic amino acids | glutamic acid (E), aspartic acid (D) |
| polar amino acids | glutamine (Q), asparagine (N) |
| hydrophobic amino acids | leucine (L), isoleucine (I), valine (V) |
| aromatic amino acids | phenylalanine (F), tryptophan (W), tyrosine (Y) |
| small amino acids | glycine (G), alanine (A), serine (S), threonine (T), proline (P), cysteine (C), methionine (M) |

The following nomenclature may be used to describe substitutions in a reference sequence relative to a reference sequence or a variant polypeptide or nucleic acid sequence: "R-#-V," where "#" refers to the position in the reference sequence, "R" refers to the amino acid (or base) at that position in the reference sequence, and "V" refers to the amino acid (or base) at that position in the variant sequence.

The term "amino acid substitution set" or "substitution set" refers to a group of amino acid substitutions. A substitution set can have 1, 2, 3, 4, 5, 6, 7, 8, 9, 10, 11, 12, 13, 14, 15, or more amino acid substitutions.

As used herein, "deletion" when used in reference to a polypeptide, refers to modification of the polypeptide by removal of one or more amino acids from a reference polypeptide. Deletions can comprise removal of 1 or more amino acids, 2 or more amino acids, 3 or more amino acids, 4 or more amino acids, 5 or more amino acids, 6 or more amino acids, 7 or more amino acids, 8 or more amino acids, 9 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered at least one protease enzyme. Deletions may be present in the internal portions and/or terminal portions of the polypeptide. In some embodiments, the deletion comprises a continuous segment, while in other embodiments, it is discontinuous.

As used herein, a "gene deletion" or "deletion mutation" is a mutation in which at least part of a sequence of the DNA making up the gene is missing. Thus, a "deletion" in reference to nucleic acids is a loss or replacement of genetic material resulting in a complete or partial disruption of the sequence of the DNA making up the gene. Any number of nucleotides can be deleted, from a single base to an entire piece of a chromosome. Thus, in some embodiments, the term "deletion" refers to the removal of a gene necessary for encoding a specific protein (e.g., a protease). In this case, the strain having this deletion can be referred to as a "deletion strain." In some embodiments, the *Myceliophthora* (e.g., *M. thermophila*) is a deletion strain comprising deletion of at least one gene encoding at least one protease selected from Protease #1, Protease #2, Protease #3, and/or Protease #4. In some additional embodiments, the *Myceliophthora* (e.g., *M. thermophila*) is a strain described in U.S. Pat. No. 8,236,551 and/or WO 2012/061382 (both of which are incorporated herein by reference), comprising deletion and/or inactivation of at least one cdh gene, and further comprising deletion of at least one polynucleotide sequence selected from SEQ ID NOS:1, 3, 4, and/or 6. In some embodiments, the *Myceliophthora* (e.g., *M. thermophila*) is a deletion strain comprising deletion of at least one polynucleotide sequence selected from SEQ ID NOS:1, 3, 4, and/or 6. In some additional embodiments, the *Myceliophthora* (e.g., *M thermophila*) is a strain described in U.S. Pat. No. 8,236,551 and/or WO 2012/061382 (both of which are incorporated herein by reference), comprising deletion and/or inactivation of at least one cdh gene, and further comprising deletion of at least one polynucleotide sequence selected from SEQ ID NOS:1, 3, 4, and/or 6.

As used herein, "gene inactivation" refers to any alteration results in greatly reduced or the absence of gene expression. The term encompasses any embodiment in which at least one gene is inactivated by any means, including but not limited to deletion, alterations, promoter alterations, antisense RNA, dsRNA, etc. In some embodiments, the *Myceliophthora* (e.g., *M. thermophila*) comprises a strain comprising inactivation of at least one gene encoding at least one protease selected from Protease #1, Protease #2, Protease #3, and/or Protease #4. In some embodiments, the *Myceliophthora* (e.g., *M. thermophila*) is a strain comprising inactivation of at least one polynucleotide sequence selected from SEQ ID NOS:1, 3, 4, and/or 6. In some embodiments, the *Myceliophthora* (e.g., *M. thermophila*) comprises a strain described in U.S. Pat. No. 8,236,551 and/or WO 2012/061382, comprising deletion and/or inactivation of at least one cdh gene, and further comprising inactivation of at least one gene encoding at least one protease selected from Protease #1, Protease #2, Protease #3, and/or Protease #4. In some additional embodiments, the *Myceliophthora* (e.g., *M. thermophila*) is a strain described in U.S. Pat. No. 8,236,551 and/or WO 2012/061382 (both of which are incorporated herein by reference), comprising deletion and/or inactivation of at least one cdh gene, and further comprising inactivation of at least one polynucleotide sequence selected from SEQ ID NOS:1, 3, 4, and/or 6.

As used herein, "fragment" refers to a polypeptide that has an amino-terminal and/or carboxy-terminal and/or internal deletion, as compared to a reference polypeptide, but where the remaining amino acid sequence is identical to the corresponding positions in the reference sequence. Fragments can typically have about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, or about 99% of the full-length of at least one protease polypeptide, for example the polypeptide of SEQ ID NOS:2, 4 and/or 6. In some instances, the sequences of the non-naturally occurring and wild-type at least one protease polypeptide disclosed herein include an initiating methionine (M) residue (i.e., M at position 1). However, the skilled artisan will recognize that this initiating methionine residue can be removed during the course of biological processing of the enzyme, such as in a host cell or in vitro translation system, to generate a mature enzyme lacking the initiating methionine residue, but otherwise retaining the enzyme's properties. Thus, for each of the protease polypeptides disclosed herein having an amino acid sequence comprising an initiating methionine, the present disclosure also encompasses the polypeptide with the initiating methionine residue deleted (i.e., a fragment of the at least one protease polypeptide lacking a methionine at position 1).

As used herein, the term "biologically active fragment," refers to a polypeptide that has an amino-terminal and/or carboxy-terminal deletion(s) and/or internal deletion(s), but where the remaining amino acid sequence is identical to the corresponding positions in the sequence to which it is being compared (e.g., a full-length protease of the present invention) and that retains substantially all of the activity of the full-length polypeptide. In some embodiments, the biologically active fragment is a biologically active protease fragment. A biologically active fragment can comprise about 60%, about 65%, about 70%, about 75%, about 80%, about 85%, at about 90%, about 91%, about 92%, about 93%, about 94%, about 95%, about 96%, about 97%, about 98%, or about 99% of a full-length protease polypeptide As used herein, "protein of interest" and "polypeptide of interest" refer to a protein/polypeptide that is desired and/or being assessed. In some embodiments, the protein of interest is expressed intracellularly, while in other embodiments, it is a secreted polypeptide. In some embodiments, these protein of interest is an enzyme, including but not limited to the enzymes described herein (e.g., a protease). In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

A polynucleotide is said to "encode" an RNA or a polypeptide if, in its native state or when manipulated by methods known to those of skill in the art, it can be transcribed and/or translated to produce the RNA, the polypeptide or a fragment thereof. The anti-sense strand of such a nucleic acid is also said to encode the sequences. As is known in the art, DNA can be transcribed by an RNA polymerase to produce RNA, but RNA can be reverse transcribed by reverse transcriptase to produce a DNA. Thus, a DNA molecule can effectively encode an RNA molecule and vice versa.

As used herein, "host strain" and "host cell" refers to a suitable host for an expression vector comprising DNA. The "host cells" used in the present invention generally are prokaryotic or eukaryotic hosts which preferably have been manipulated by methods known to those skilled in the art. In some embodiments, host cells are transformed with vectors constructed using recombinant DNA techniques. Such transformed host cells are capable of either replicating vectors encoding protein variant(s) and/or expressing the desired protein variant(s). In the case of vectors which encode the pre- or prepro-form of the protein variant, such variants, when expressed, are typically secreted from the host cell into the host cell medium.

As used herein, "naturally-occurring enzyme" refers to an enzyme having the unmodified amino acid sequence identical to that found in nature (i.e., "wild-type"). Naturally occurring enzymes include native enzymes (i.e., those enzymes naturally expressed or found in the particular microorganism).

The terms "wild-type sequence" and "naturally-occurring sequence" are used interchangeably herein, to refer to a polypeptide or polynucleotide sequence that is native or naturally occurring in a host cell. In some embodiments, the wild-type sequence refers to a sequence of interest that is the starting point of a protein engineering project. The wild-type sequence may encode either a homologous or heterologous protein.

As used herein, the terms "isolated" and "purified" refer to a material that is removed from its original environment (e.g., the natural environment, if it is naturally occurring). For example, the material is said to be "purified" when it is present in a particular composition in a higher or lower concentration than exists in a naturally-occurring or wild-type organism or in combination with components not normally present upon expression from a naturally-occurring or wild-type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still considered to be isolated, in that such vector or composition is not part of its natural environment. In some embodiments, a nucleic acid or protein is said to be purified, for example, if it gives rise to essentially one band in an electrophoretic gel or blot. In some embodiments, the terms "isolated" and "purified" are used to refer to a molecule (e.g., an isolated nucleic acid, polypeptide, etc.) or other component that is removed from at least one other component with which it is naturally associated. In some embodiments, the term "isolated" refers to a nucleic acid, polypeptide, or other component that is partially or completely separated from components with which it is normally associated in nature. Thus, the term encompasses a substance in a form or environment that does not occur in nature. Non-limiting examples of isolated substances include, but are not limited to: any non-naturally occurring substance; any substance including, but not limited to, any enzyme, variant, polynucleotide, protein, peptide or cofactor, that is at least partially removed from one or more or all of the naturally occurring constituents with which it is associated in nature; any substance modified by the hand of man relative to that substance found in nature; and/or any substance modified by increasing the amount of the substance relative to other components with which it is naturally associated (e.g., multiple copies of a gene encoding the substance; and/or use of a stronger promoter than the promoter naturally associated with the gene encoding the substance). In some embodiments, a polypeptide of interest is used in industrial applications in the form of a fermentation broth product (i.e., the polypeptide is a component of a fermentation broth) used as a product in industrial applications such as ethanol production. In some embodiments, in addition to the polypeptide of interest (e.g., an EG1b polypeptide), the fermentation broth product further comprises ingredients used in the fermentation process (e.g., cells, including the host cells containing the gene encoding the polypeptide of interest and/or the polypeptide of interest), cell debris, biomass, fermentation media, and/or fermentation products. In some embodiments, the fermentation broth is optionally subjected to one or more purification steps (e.g., filtration) to remove or reduce at least one components of a fermentation process. Accordingly, in some embodiments, an isolated substance is present in such a fermentation broth product.

The terms "purification" and "isolation" when used in reference to an enzyme (e.g., at least one protease), mean that the enzyme is altered from its natural state by virtue of separating the enzyme from some or all of the naturally occurring constituents with which it is associated in nature. This may be accomplished by any suitable art-recognized separation technique, including but not limited to ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis, separation on a gradient or any other suitable methods, to remove whole cells, cell debris, impurities, extraneous proteins, or enzymes undesired in the final composition. It is further possible to then add constituents to an enzyme-containing composition which provide additional benefits, for example, activating agents, anti-inhibition agents, desirable ions, compounds to control pH, other enzymes, etc.

The term "isolated," when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions (e.g., promoters and terminators). The identification of associated regions will be evident to one of ordinary skill in the art (See e.g., Dynan and Tijan, Nature 316:774-78 [1985]). The term "an isolated DNA sequence" is alternatively referred to as "a cloned DNA sequence."

The term "isolated," when used in reference to a protein, refers to a protein that is found in a condition other than its native environment. In some embodiments, the isolated protein is substantially free of other proteins, particularly other homologous proteins. An isolated protein is more than about 10% pure, preferably more than about 20% pure, and even more preferably more than about 30% pure, as determined by SDS-PAGE. Further aspects of the invention encompass the protein in a highly purified form (i.e., more than about 40% pure, more than about 50% pure, more than about 55% pure, more than about 60% pure, more than about 65% pure, more than about 70% pure, more than about 75% pure, more than about 80% pure, more than about 85% pure, more than about 90% pure, more than about 95% pure, more than about 96% pure, more than about 97% pure, more than about 98% pure, or even more than about 99% pure), as determined by SDS-PAGE.

As used herein, the phrase "substantially pure polypeptide" refers to a composition in which the polypeptide species is the predominant species present (i.e., on a molar or weight basis, it is more abundant than any other individual macromolecular species in the composition), and is generally a substantially purified composition when the object species comprises at least about 50 percent of the macromolecular species present by mole or % weight. Generally, a substantially pure enzyme composition will comprise about 60% or more, about 65% or more, about 70% or more, about 75% or more, about 80% or more, about 85% or more, about 90% or more, about 95% or more, about 96% or more, about 97% or more, about 98%, or about 99% or more, or more of all macromolecular species by mole or percent weight present in the composition. Solvent species, small molecules (<500 Daltons), and elemental ion species are not considered macromolecular species.

As used herein, the term "starting gene" refers to a gene of interest that encodes a protein of interest that is to be improved, deleted, mutated, and/or otherwise changed using the present invention.

The term "property" and grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, and/or enhancer function), a property affecting RNA processing (e.g., RNA splicing, RNA stability, RNA conformation, and/or post-transcriptional modification), a property affecting translation (e.g., level, regulation, binding of mRNA to ribosomal proteins, and/or post-translational modification). For example, a binding site for a transcription factor, polymerase, regulatory factor, etc., of a nucleic acid may be altered to produce desired characteristics or to identify undesirable characteristics.

The term "property" and grammatical equivalents thereof in the context of a polypeptide (including proteins), as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, $k_m$, $k_{cat}$, $k_{cat}/k_m$ ratio, protein folding, inducing an immune response, not inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat disease, etc. Indeed, it is not intended that the present invention be limited to any particular property.

As used herein, the term "screening" has its usual meaning in the art and is, in general a multi-step process. In the first step, a mutant nucleic acid or variant polypeptide is provided. In the second step, a property of the mutant nucleic acid or variant polypeptide is determined. In the third step, the determined property is compared to a property of the corresponding precursor nucleic acid, to the property of the corresponding naturally occurring polypeptide or to the property of the starting material (e.g., the initial sequence) for the generation of the mutant nucleic acid. It will be apparent to the skilled artisan that the screening procedure for obtaining a nucleic acid or protein with an altered property depends upon the property of the starting material, and the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH optima, specificity, etc., before and after mutation, wherein a change indicates an alteration. In some embodiments, the screens are performed in a high-throughput manner, including multiple samples being screened simultaneously, including, but not limited to assays utilizing chips, phage display, multiple substrates and/or indicators, and/or any other suitable method known in the art. As used in some embodiments, screens encompass selection steps in which variants of interest are enriched from a population of variants. It is intended that the term encompass any suitable means for selection. Indeed, it is not intended that the present invention be limited to any particular method of screening.

As used herein, the term "targeted randomization" refers to a process that produces a plurality of sequences where one or several positions have been randomized. In some embodiments, randomization is complete (i.e., all four nucleotides, A, T, G, and C can occur at a randomized position). In some alternative embodiments, randomization of a nucleotide is limited to a subset of the four nucleotides. Targeted randomization can be applied to one or several codons of a sequence, coding for one or several proteins of interest. When expressed, the resulting libraries produce protein populations in which one or more amino acid positions can contain a mixture of all 20 amino acids or a subset of amino acids, as determined by the randomization scheme of the randomized codon. In some embodiments, the individual members of a population resulting from targeted randomization differ in the number of amino acids, due to targeted or random insertion or deletion of codons. In some further embodiments, synthetic amino acids are included in the protein populations produced. In some additional embodiments, the majority of members of a population resulting from targeted randomization show greater sequence homology to the consensus sequence than the starting gene. In some embodiments, the sequence encodes one or more proteins of interest. In some alternative embodiments, the proteins have differing biological functions.

The terms "modified nucleic acid sequence" and "modified genes" are used interchangeably herein to refer to a nucleic acid sequence that includes a deletion, insertion, substitution or any other change and/or interruption of the naturally occurring nucleic acid sequence. In some embodiments, the expression product of the modified sequence is a truncated protein (e.g., if the modification is a deletion or interruption in the sequence). In some embodiments, the truncated protein retains biological activity. In some alternative embodiments, the expression product of the modified sequence is an elongated protein (e.g., modifications comprising an insertion into the nucleic acid sequence). In some further embodiments, an insertion leads to a truncated protein (e.g., when the insertion results in the formation of a stop codon). Thus, an insertion may result in either a truncated protein or an elongated protein as an expression product.

As used herein, the terms "mutant nucleic acid sequence," "mutant nucleotide sequence," and "mutant gene" are used interchangeably in reference to a nucleotide sequence that has an alteration in at least one codon occurring in a host cell's wild-type nucleotide sequence. The expression product of the mutant sequence is a protein with an altered amino acid sequence relative to the wild-type. In some embodiments, the expression product has an altered functional capacity (e.g., enhanced enzymatic activity).

As used herein, the term "degenerate codon" refers to a codon used to represent a set of different codons (also referred to as an "ambiguous codon"). For example, the degenerate codon "NNT" represents a set of 16 codons having the base triplet sequence (A, C, T, or G)/(A, C, T, or G)/T.

As used herein, "coding sequence" refers to that portion of a polynucleotide that encodes an amino acid sequence of a protein (e.g., a gene).

As used herein, the term "antibodies" refers to immunoglobulins. Antibodies include but are not limited to immunoglobulins obtained directly from any species from which it is desirable to obtain antibodies. In addition, the present invention encompasses modified antibodies. The term also refers to antibody fragments that retain the ability to bind to the epitope that the intact antibody binds and includes polyclonal antibodies, monoclonal antibodies, chimeric antibodies, anti-idiotype (anti-ID) antibodies. Antibody fragments include, but are not limited to the complementarity-determining regions (CDRs), single-chain fragment variable regions (scFv), heavy chain variable region (VH), and light chain variable region (VL) fragments.

As used herein, the term "oxidation stable" refers to enzymes of the present invention that retain a specified amount of enzymatic activity over a given period of time under conditions prevailing during the use of the invention, for example while exposed to or contacted with oxidizing agents. In some embodiments, the enzymes retain at least about 50%, about 60%, about 70%, about 75%, about 80%, about 85%, about 90%, about 92%, about 95%, about 96%, about 97%, about 98%, or about 99% enzymatic activity after contact with an oxidizing agent over a given time period, for example, at least about 1 minute, about 3 minutes, about 5 minutes, about 8 minutes, about 12 minutes, about 16 minutes, about 20 minutes, etc.

As used herein, the terms "thermally stable" and "thermostable" refer to enzymes of the present invention that retain a specified amount of enzymatic activity after exposure to identified temperatures over a given period of time under conditions prevailing during the use of the enzyme, for example, when exposed to altered temperatures. "Altered temperatures" include increased or decreased temperatures. In some embodiments, the enzymes retain at least about 50%, about 60%, about 70%, about 75%, about 80%, about 85%, about 90%, about 92%, about 95%, about 96%, about 97%, about 98%, or about 99% enzymatic activity after exposure to altered temperatures over a given time period, for example, at least about 60 minutes, about 120 minutes, about 180 minutes, about 240 minutes, about 300 minutes, etc.

As used herein, the term "thermophilic fungus" refers to any fungus which exhibits optimum growth at a temperature of at least about 35° C., and generally below about 100° C., such as for example between about 35° C. to about 80° C., between about 35° C. to about 75° C., between about 40° C. to about 65° C., or between about 40° C. to about 60° C. Typically, the optimum growth is exhibited at a temperature of at least about 35° C. to about 60° C.

As used herein, "solvent stable" refers to a polypeptide that maintains similar activity (more than for example, about 60% to about 80%) after exposure to varying concentrations (e.g., about 5 to about 99%) of a non-aqueous solvent (e.g., isopropyl alcohol, tetrahydrofuran, 2-methyltetrahydrofuran, acetone, toluene, butylacetate, methyl tert-butylether, etc.) for a period of time (e.g., about 0.5 to about 24 hrs) compared to a reference polypeptide.

As used herein, "pH stable" refers to a polypeptide that maintains similar activity (more than for example, about 60% to about 80%) after exposure to low or high pH (e.g., about 4.5 to about 6, or about 8 to about 12) for a period of time (e.g., 0.5-24 hrs) compared to a reference polypeptide.

As used herein, the term "enhanced stability" in the context of an oxidation, chelator, thermal and/or pH stable enzyme refers to a higher retained enzymatic activity over time as compared to other enzymes and/or wild-type enzymes.

As used herein, the term "diminished stability" in the context of an oxidation, chelator, thermal and/or pH stable enzyme refers to a lower retained enzymatic activity over time as compared to other enzymes and/or wild-type enzymes.

As used herein, "secreted activity" refers to enzymatic activity of at least one protease enzymes produced by a fungal cell that is present in an extracellular environment. An extracellular environment can be, for example, an extracellular milieu such as a culture medium. The secreted activity is influenced by the total amount of at least one protease secreted, and also is influenced by the catalytic efficiency of the secreted at least one protease.

As used herein, a "protease that is secreted by a cell" is a protease produced by the cell in a manner such that the protease is exported across the cell membrane and then subsequently released into the extracellular milieu, such as into culture media.

As used herein, the term "culturing" refers to growing a population of microbial cells under suitable conditions in a liquid or solid medium.

The terms "biomass," and "biomass substrate," encompass any suitable materials for use in saccharification reactions. The terms encompass, but are not limited to materials that comprise cellulose (i.e., "cellulosic biomass," "cellulosic feedstock," and "cellulosic substrate"). Biomass can be derived from plants, animals, or microorganisms, and may include, but is not limited to agricultural, industrial, and forestry residues, industrial and municipal wastes, and terrestrial and aquatic crops grown for energy purposes. Examples of biomass substrates include, but are not limited to, wood, wood pulp, paper pulp, corn fiber, corn grain, corn cobs, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, switchgrass, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to cultivated crops (e.g., grasses, including C4 grasses, such as switch grass, cord grass, rye grass, *miscanthus*, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in some alternative embodiments, the biomass comprises a mixture of fibers that originate from different biomasses. In some embodiments, the biomass may also comprise transgenic plants that express ligninase and/or cellulase enzymes (See e.g., US 2008/0104724 A1).

A biomass substrate is said to be "pretreated" when it has been processed by some physical and/or chemical means to facilitate saccharification. As described further herein, in some embodiments, the biomass substrate is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis. Thus, the term "biomass" encompasses any living or dead biological material that contains a polysaccharide substrate, including but not limited to cellulose, starch, other forms of long-chain carbohydrate polymers, and mixtures of such sources. It may or may not be assembled entirely or primarily from glucose or xylose, and may optionally also contain various other pentose or hexose monomers. Xylose is an aldopentose containing five carbon atoms and an aldehyde group. It is the precursor to hemicellulose, and is often a main constituent of biomass. In some embodiments, the substrate is slurried prior to pretreatment. In some embodiments, the consistency of the slurry is between about 2% and about 30% and more typically between about 4% and about 15%. In some embodiments, the slurry is subjected to a water and/or acid soaking operation prior to pretreatment. In some embodiments, the slurry is dewatered using any suitable method to reduce steam and chemical usage prior to pretreatment. Examples of dewatering devices include, but are not limited to pressurized screw presses (See e.g., WO 2010/022511, incorporated herein by reference) pressurized filters and extruders.

In some embodiments, the pretreatment is carried out to hydrolyze hemicellulose, and/or a portion thereof present in the cellulosic substrate to monomeric pentose and hexose sugars (e.g., xylose, arabinose, mannose, galactose, and/or any combination thereof). In some embodiments, the pretreatment is carried out so that nearly complete hydrolysis of the hemicellulose and a small amount of conversion of cellulose to glucose occurs. In some embodiments, an acid concentration in the aqueous slurry from about 0.02% (w/w) to about 2% (w/w), or any amount therebetween, is typically used for the treatment of the cellulosic substrate. Any suitable acid finds use in these methods, including but not limited to, hydrochloric acid, nitric acid, and/or sulfuric acid. In some embodiments, the acid used during pretreatment is sulfuric acid. Steam explosion is one method of performing acid pretreatment of biomass substrates (See e.g., U.S. Pat. No. 4,461,648). Another method of pretreating the slurry involves continuous pretreatment (i.e., the cellulosic biomass is pumped though a reactor continuously). This methods are well-known to those skilled in the art (See e.g., U.S. Pat. No. 7,754,457).

In some embodiments, alkali is used in the pretreatment. In contrast to acid pretreatment, pretreatment with alkali may not hydrolyze the hemicellulose component of the biomass. Rather, the alkali reacts with acidic groups present on the hemicellulose to open up the surface of the substrate. In some embodiments, the addition of alkali alters the crystal structure of the cellulose so that it is more amenable to hydrolysis. Examples of alkali that find use in the pretreatment include, but are not limited to ammonia, ammonium hydroxide, potassium hydroxide, and sodium hydroxide. One method of alkali pretreatment is Ammonia Freeze Explosion, Ammonia Fiber Explosion or Ammonia Fiber Expansion ("AFEX" process; See e.g., U.S. Pat. Nos. 5,171,592; 5,037,663; 4,600,590; 6,106,888; 4,356,196; 5,939,544; 6,176,176; 5,037,663 and 5,171,592). During this process, the cellulosic substrate is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. In some embodiments, the flashed ammonia is then recovered using methods known in the art. In some alternative methods, dilute ammonia pretreatment is utilized. The dilute ammonia pretreatment method utilizes more dilute solutions of ammonia or ammonium hydroxide than AFEX (See e.g., WO2009/045651 and US 2007/0031953). This pretreatment process may or may not produce any monosaccharides.

An additional pretreatment process for use in the present invention includes chemical treatment of the cellulosic substrate with organic solvents, in methods such as those utilizing organic liquids in pretreatment systems (See e.g., U.S. Pat. No. 4,556,430; incorporated herein by reference). These methods have the advantage that the low boiling point liquids easily can be recovered and reused. Other pretreatments, such as the Organosolv™ process, also use organic liquids (See e.g., U.S. Pat. No. 7,465,791, which is also incorporated herein by reference). Subjecting the substrate to pressurized water may also be a suitable pretreatment method (See e.g., Weil et al. (1997) Appl. Biochem. Biotechnol., 68(1-2): 21-40 [1997], which is incorporated herein by reference). In some embodiments, the pretreated cellulosic biomass is processed after pretreatment by any of several steps, such as dilution with water, washing with water, buffering, filtration, or centrifugation, or any combination of these processes, prior to enzymatic hydrolysis, as is familiar to those skilled in the art. The pretreatment produces a pretreated feedstock composition (e.g., a "pretreated feedstock slurry") that contains a soluble component including the sugars resulting from hydrolysis of the hemicellulose, optionally acetic acid and other inhibitors, and solids including unhydrolyzed feedstock and lignin. In some embodiments, the soluble components of the pretreated feedstock composition are separated from the solids to produce a soluble fraction. In some embodiments, the soluble fraction, including the sugars released during pretreatment and other soluble components (e.g., inhibitors), is then sent to fermentation. However, in some embodiments in which the hemicellulose is not effectively hydrolyzed during the pretreatment one or more additional steps are included (e.g., a further hydrolysis step(s) and/or enzymatic treatment step(s) and/or further alkali and/or acid treatment) to produce fermentable sugars. In some embodiments, the separation is carried out by washing the pretreated feedstock composition with an aqueous solution to produce a wash stream and a solids stream comprising the unhydrolyzed, pretreated feedstock. Alternatively, the soluble component is separated from the solids by subjecting the pretreated feedstock composition to a solids-liquid separation, using any suitable method (e.g., centrifugation, microfiltration, plate and frame filtration, cross-flow filtration, pressure filtration, vacuum filtration, etc.). Optionally, in some embodiments, a washing step is incorporated into the solids-liquids separation. In some embodiments, the separated solids containing cellulose, then undergo enzymatic hydrolysis with cellulase enzymes in order to convert the cellulose to glucose. In some embodiments, the pretreated feedstock composition is fed into the fermentation process without separation of the solids contained therein. In some embodiments, the unhydrolyzed solids are subjected to enzymatic hydrolysis with cellulase enzymes to convert the cellulose to glucose after the fermentation process. In some embodiments, the pretreated cellulosic feedstock is subjected to enzymatic hydrolysis with cellulase enzymes.

Lignocellulose (also "lignocellulosic biomass") comprises a matrix of cellulose, hemicellulose and lignin. Economic production of biofuels from lignocellulosic biomass typically involves conversion of the cellulose and hemicellulose components to fermentable sugars, typically monosaccharides such as glucose (from the cellulose) and xylose and arabinose (from the hemicelluloses). Nearly complete conversion can be achieved by a chemical pretreatment of the lignocellulose followed by enzymatic hydrolysis with cellulase enzymes. The chemical pretreatment step renders the cellulose more susceptible to enzymatic hydrolysis and in some cases, also hydrolyzes the hemicellulose component. Numerous chemical pretreatment processes known in the art find use in the present invention, and include, but are not limited to, mild acid pretreatment at high temperatures and dilute acid, ammonium pretreatment and/or organic solvent extraction.

Lignin is a more complex and heterogeneous biopolymer than either cellulose or hemicellulose and comprises a variety of phenolic subunits. Enzymatic lignin depolymerization can be accomplished by lignin peroxidases, manganese peroxidases, laccases, esterases, and/or cellobiose dehydrogenases (CDH), often working in synergy. However, as the name suggests, CDH enzymes also oxidize cellobiose to cellobionolactone. Several reports indicate that the oxidation of cellobiose by CDH enhances the rate of cellulose hydrolysis by cellulases by virtue of reducing the concentrations of cellobiose, which is a potent inhibitor of some cellulase components (See e.g., Mansfield et al., Appl. Environ. Microbiol., 63: 3804-3809 [1997]; and Igarishi et al., Eur. J. Biochem., 253:101-106 [1998]). Recently, it has been reported that CDHs can enhance the activity of cellulolytic enhancing proteins from Glycosyl Hydrolase family 61 (See e.g., WO2010/080532A1).

Thus, as used herein, the term "lignocellulosic biomass" refers to any plant biomass comprising cellulose and hemicellulose, bound to lignin. In some embodiments, the biomass may optionally be pretreated to increase the susceptibility of cellulose to hydrolysis by chemical, physical and biological pretreatments (such as steam explosion, pulping, grinding, acid hydrolysis, solvent exposure, and the like, as well as combinations thereof). Various lignocellulosic feedstocks find use, including those that comprise fresh lignocellulosic feedstock, partially dried lignocellulosic feedstock, fully dried lignocellulosic feedstock, and/or any combination thereof. In some embodiments, lignocellulosic feedstocks comprise cellulose in an amount greater than about 20%, more preferably greater than about 30%, more preferably greater than about 40% (w/w). For example, in some embodiments, the lignocellulosic material comprises from about 20% to about 90% (w/w) cellulose, or any amount therebetween, although in some embodiments, the lignocellulosic material comprises less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5% cellulose (w/w). Furthermore, in some embodiments, the lignocellulosic feedstock comprises lignin in an amount greater than about 10%, more typically in an amount greater than about 15% (w/w). In some embodiments, the lignocellulosic feedstock comprises small amounts of sucrose, fructose and/or starch. The lignocellulosic feedstock is generally first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In some embodiments, at least 90% by weight of the particles produced from the size reduction have lengths less than between about 1/16 and about 4 in (the measurement may be a volume or a weight average length). In some embodiments, the equipment used to reduce the particle size reduction is a hammer mill or shredder. Subsequent to size reduction, the feedstock is typically slurried in water, as this facilitates pumping of the feedstock. In some embodiments, lignocellulosic feedstocks of particle size less than about 6 inches do not require size reduction.

As used herein, the term "lignocellulosic feedstock" refers to any type of lignocellulosic biomass that is suitable for use as feedstock in saccharification reactions.

As used herein, the term "pretreated lignocellulosic feedstock," refers to lignocellulosic feedstocks that have been subjected to physical and/or chemical processes to make the fiber more accessible and/or receptive to the actions of cellulolytic enzymes, as described above.

As used herein, the term "recovered" refers to the harvesting, isolating, collecting, or recovering of protein from a cell and/or culture medium. In the context of saccharification, it is used in reference to the harvesting the fermentable sugars produced during the saccharification reaction from the culture medium and/or cells. In the context of fermentation, it is used in reference to harvesting the fermentation product from the culture medium and/or cells. Thus, a process can be said to comprise "recovering" a product of a reaction (such as a soluble sugar recovered from saccharification) if the process includes separating the product from other components of a reaction mixture subsequent to at least some of the product being generated in the reaction.

As used herein, the term "slurry" refers to an aqueous solution in which are dispersed one or more solid components, such as a cellulosic substrate.

As used herein, the term "saccharification" refers to the process in which substrates (e.g., cellulosic biomass) are broken down via the action of cellulases to produce fermentable sugars (e.g. monosaccharides such as but not limited to glucose).

As used herein, the term "fermentable sugars" refers to simple sugars (e.g., monosaccharides, disaccharides and short oligosaccharides), including but not limited to glucose, xylose, galactose, arabinose, mannose and sucrose. Indeed, a fermentable sugar is any sugar that a microorganism can utilize or ferment.

As used herein the term "soluble sugars" refers to water-soluble hexose monomers and oligomers of up to about six monomer units.

As used herein, the term "fermentation" is used broadly to refer to the cultivation of a microorganism or a culture of microorganisms that use simple sugars, such as fermentable sugars, as an energy source to obtain a desired product.

As used herein, the term "fermenting organism" refers to any organism, including bacterial and fungal organisms such as yeast and filamentous fungi, suitable for producing at least one desired end product. Especially suitable fermenting organisms are able to ferment (i.e., convert) sugars, such as glucose, fructose, maltose, xylose, mannose and/or arabinose, directly or indirectly into a desired end product.

As used herein, the term "cellodextrin" refers to a glucose polymer of varying length (i.e., comprising at least two glucose monomers). Each glucose monomer is linked via a beta-1,4 glycosidic bond. A cellodextrin is classified by its degree of polymerization (DP), which indicates the number of glucose monomers the cellodextrin contains. The most common cellodextrins are: cellobiose (DP=2); cellotriose (DP=3); cellotetrose (DP=4); cellopentose (DP=5); and cellohexose (DP=6). In some embodiments, cellodextrins have a DP of 2-6 (i.e., cellobiose, cellotriose, cellotetrose, cellopentose, and/or cellohexose). In some embodiments, cellodextrins have a DP greater than 6. The degree of polymerization of cellodextin molecules can be measured (e.g., by mass spectrometry, including but not limited to matrix-assisted laser desorption/ionization (MALDI) mass spectrometry and electrospray ionization ion trap (ESI-IT) mass spectrometry). Methods of measuring the degree of polymerization of cellodextrin molecules are known in the art (See e.g., Melander et al., Biomacromol., 7:1410-1421 [2006]).

As used herein, the term "cellulase" refers to a category of enzymes capable of hydrolyzing cellulose (e.g., beta-1, 4-glucan or beta-D-glucosidic linkages) to shorter cellulose chains, oligosaccharides, cellobiose and/or glucose. Cellulases, as known in the art and as described herein, are typically found in a mixture of different types of cellulolytic enzymes. In some embodiments, "cellulase" includes hemicellulose-hydrolyzing enzymes such as endoxylanase, beta-xylosidase, arabinofuranosidase, alpha-glucuronidase, acetylxylan esterase, feruloyl esterase, alpha-glucuronyl esterase, etc. A "cellulase-producing fungal cell" is a fungal cell that expresses and secretes at least one cellulose hydrolyzing enzyme. In some embodiments, the cellulase-producing fungal cells express and secrete a mixture of cellulose hydrolyzing enzymes. "Cellulolytic," "cellulose hydrolyzing," "cellulose degrading," and similar terms refer to cellulase enzymes such as endoglucanases, cellobiohydrolases (the latter are also referred to as "exoglucanases"), and beta-glucosidases (also known as "cellobiases") that act synergistically to break down the cellulose first to soluble di- or oligosaccharides such as cellobiose, which are then further hydrolyzed to glucose by beta-glucosidase. "Cellulases" typically comprise a mixture of different types of cellulolytic enzymes (e.g., endoglucanases, beta-glucosidases and cellobiohydrolases, the latter are also referred to as "exoglucanases") that act synergistically to break down the cellulose to soluble di- or oligosaccharides such as cellobiose, which are then further hydrolyzed to glucose by beta-glucosidase. Cellulase enzymes are produced by a wide variety of microorganisms. Cellulases, as well as hemicellulases from filamentous fungi and some bacteria are widely exploited for many industrial applications that involve processing of natural fibers to sugars.

Among the cellulase-producing filamentous fungi, there are those that also produce a variety of enzymes involved in lignin degradation. For example, organisms of such genera as *Myceliophthora, Chrysosporium, Sporotrichum, Thielavia, Phanerochaete, Trichoderma* and *Trametes* produce and secrete a mixture of cellulases, hemicellulases and lignin degrading enzymes. These types of organisms are commonly called "white rot fungi" by virtue of their ability to digest lignin and to distinguish them from the "brown rot" fungi (such as *Trichoderma*) which typically cannot digest lignin.

As used herein, the terms "cellobiose dehydrogenase" and "CDH" refer to a cellobiose:acceptor 1-oxidoreductase that catalyzes the conversion of cellobiose in the presence of an acceptor to cellobiono-1,5-lactone and a reduced acceptor. Examples of cellobiose dehydrogenases are included in the enzyme classification (E.C. 1.1.99.18).

As used herein, the term "endoglucanase" or "EG" refers to a class of cellulases (E.C.3.2.1.4) that hydrolyze internal beta-1,4 glucosidic linkages in cellulose. The term "endoglucanase" refers to an endo-1,4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenan, beta-1,4 bonds in mixed beta-1,3 glucans such as cereal beta-D-glucans or xyloglucans, and other plant material containing cellulosic components. Endoglucanase activity can be determined based on a reduction in substrate viscosity or increase in reducing ends determined by a reducing sugar assay (See e.g., Zhang et al., Biotechnol. Adv., 24: 452-481 [2006]). In some embodiments, endoglucanase activity is determined using carboxymethyl cellulose (CMC) hydrolysis (See e.g., Ghose, Pure Appl. Chem., 59: 257-268 [1987]).

As used herein, "EG1" refers to a carbohydrate active enzyme expressed from a nucleic acid sequence coding for a glycohydrolase (GH) Family 7 catalytic domain classified under EC 3.2.1.4 or any protein, polypeptide or catalytically active fragment thereof. In some embodiments, the EG1 is functionally linked to a carbohydrate binding module (CBM), such as a Family 1 cellulose binding domain. In some embodiments, the EG1 enzyme is EG1b.

As used herein, the term "EG2" refers to a carbohydrate active enzyme expressed from a nucleic acid sequence coding for a glycohydrolase (GH) Family 5 catalytic domain classified under EC 3.2.1.4 or any protein, polypeptide or catalytically active fragment thereof. In some embodiments, the EG2 is functionally linked to a carbohydrate binding module (CBM), such as a Family 1 cellulose binding domain.

As used herein, the term "EG3" refers to a carbohydrate active enzyme expressed from a nucleic acid sequence coding for a glycohydrolase (GH) Family 12 catalytic domain classified under EC 3.2.1.4 or any protein, polypeptide or catalytically active fragment thereof. In some embodiments, the EG3 is functionally linked to a carbohydrate binding module (CBM), such as a Family 1 cellulose binding domain.

As used herein, the term "EG4" refers to a carbohydrate active enzyme expressed from a nucleic acid sequence coding for a glycohydrolase (GH) Family 61 catalytic domain classified under EC 3.2.1.4 or any protein, polypeptide or fragment thereof. In some embodiments, the EG4 is functionally linked to a carbohydrate binding module (CBM), such as a Family 1 cellulose binding domain.

As used herein, the term "EG5" refers to a carbohydrate active enzyme expressed from a nucleic acid sequence coding for a glycohydrolase (GH) Family 45 catalytic domain classified under EC 3.2.1.4 or any protein, polypeptide or fragment thereof. In some embodiments, the EG5 is functionally linked to a carbohydrate binding module (CBM), such as a Family 1 cellulose binding domain.

As used herein, the term "EG6" refers to a carbohydrate active enzyme expressed from a nucleic acid sequence coding for a glycohydrolase (GH) Family 6 catalytic domain classified under EC 3.2.1.4 or any protein, polypeptide or fragment thereof. In some embodiments, the EG6 is functionally linked to a carbohydrate binding module (CBM), such as a Family 1 cellulose binding domain.

As used herein, the terms "cellobiohydrolase" and "CBH" are defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (See e.g., Teeri, Trends Biotechnol., 15:160-167 [1997]; and Teeri et al., Biochem. Soc. Trans., 26: 173-178 [1998]). In some embodiments, cellobiohydrolase activity is determined using a fluorescent disaccharide derivative 4-methylumbelliferyl-.beta.-D-lactoside (See e.g., van Tilbeurgh et al., FEBS Left., 149: 152-156 [1982]; and van Tilbeurgh and Claeyssens, FEBS Lett., 187: 283-288 [1985]).

As used herein, the terms "CBH1" and "type 1 cellobiohydrolase" refer to a carbohydrate active enzyme expressed from a nucleic acid sequence coding for a glycohydrolase (GH) Family 7 catalytic domain classified under EC 3.2.1.91 or any protein, polypeptide or catalytically active fragment thereof. In some embodiments, the CBH1 is functionally linked to a carbohydrate binding module (CBM), such as a Family 1 cellulose binding domain.

As used herein, the terms "CBH2" and "type 2 cellobiohydrolase" refer to a carbohydrate active enzyme expressed from a nucleic sequence coding for a glycohydrolase (GH) Family 6 catalytic domain classified under EC 3.2.1.91 or any protein, polypeptide or catalytically active fragment thereof. Type 2 cellobiohydrolases are also commonly referred to as "the Cel6 family." The CBH2 may be functionally linked to a carbohydrate binding module (CBM), such as a Family 1 cellulose binding domain.

As used herein, the terms "beta-glucosidase," "cellobiase," and "BGL" refers to a category of cellulases (EC 3.2.1.21) that catalyze the hydrolysis of cellobiose to glucose. More particularly, the term "beta-glucosidase" refers to beta-D-glucoside glucohydrolases (E.C. 3.2.1.21), that catalyze the hydrolysis of terminal non-reducing beta-D-glucose residues with the release of beta-D-glucose. Beta-glucosidase activity can be determined using any suitable method (See e.g., Venturi et al., J. Basic Microbiol., 42: 55-66 [2002]). In some embodiments, one unit of beta-glucosidase activity is defined as 1.0 pmole of p-nitrophenol produced per minute at 40° C., at pH 5 from 1 mM p-nitrophenyl-beta-D-glucopyranoside as substrate in 100 mM sodium citrate containing 0.01% TWEEN®-20.

As used herein, the term "glycoside hydrolase 61" and "GH61" refers to a category of cellulases that enhance cellulose hydrolysis when used in conjunction with one or more additional cellulases. The GH61 family of cellulases is described, for example, in the Carbohydrate Active Enzymes (CAZY) database (See e.g., Harris et al., Biochem., 49(15): 3305-16 [2010]).

A "hemicellulase" as used herein, refers to a polypeptide that can catalyze hydrolysis of hemicellulose into small polysaccharides such as oligosaccharides, or monomeric saccharides. Hemicellulloses include xylan, glucuonoxylan, arabinoxylan, glucomannan and xyloglucan. Hemicellulases include, for example, the following: endoxylanases, b-xylosidases, a-L-arabinofuranosidases, a-D-glucuronidases, feruloyl esterases, coumaroyl esterases, a-galactosidases, b-galactosidases, b-mannanases, and b-mannosidases. In some embodiments, the present invention provides enzyme mixtures that comprise one or more hemicellulases.

As used herein, the terms "xylan degrading activity" and "xylanolytic activity" are defined as biological activities that hydrolyze xylan-containing material. The two basic approaches for measuring xylanolytic activity include: (1) measuring the total xylanolytic activity, and (2) measuring the individual xylanolytic activities (endoxylanases, beta-xylosidases, arabinofuranosidases, alpha-glucuronidases, acetylxylan esterases, feruloyl esterases, and alpha-glucuronyl esterases) (See e.g., Biely and Puchard, J. Sci. Food Agricul., 86: 1636-1647 [2006]; Spanikova and Biely, FEBS Lett., 580: 4597-4601 [2006]; and Herrmann et al., Biochem. J., 321: 375-381 [1997]). Total xylan degrading activity can be measured by determining the reducing sugars formed from various types of xylan, including oat spelt, beechwood, and larchwood xylans, or by photometric determination of dyed xylan fragments released from various covalently dyed xylans. A commonly used total xylanolytic activity assay is based on production of reducing sugars from polymeric 4-O-methyl glucuronoxylan (See e.g., Bailey et al., J. Biotechnol., 23(3): 257-270 [1992]). In some embodiments, xylan degrading activity is determined by measuring the increase in hydrolysis of birchwood xylan (Sigma) by xylan-degrading enzyme(s) under the following typical conditions: 1 mL reactions, 5 mg/mL substrate (total solids), 5 mg of xylanolytic protein/g of substrate, 50 mM sodium acetate at pH 5, 50° C., for 24 hours, and sugar analysis using p-hydroxybenzoic acid hydrazide (PHBAH) assay (See e.g., Lever, Anal. Biochem., 47: 273-279 [1972]).

As used herein, the term "xylanase activity" is defined herein as a 1,4-beta-D-xylan-xylohydrolase activity (E.C. 3.2.1.8) that catalyzes the endo-hydrolysis of 1,4-beta-D-xylosidic linkages in xylans. In some embodiments, xylanase activity is determined using birchwood xylan as substrate. One unit of xylanase activity is defined as 1.0 µmole of reducing sugar measured in glucose equivalents produced per minute during the initial period of hydrolysis at 50° C., at pH 5 from 2 g of birchwood xylan per liter as substrate in 50 mM sodium acetate containing 0.01% TWEEN®-20 (See e.g., Lever, Anal. Biochem., 47: 273-279 [1972]).

As used herein, the term "beta-xylosidase activity" is defined herein as a beta-D-xyloside xylohydrolase (E.C. 3.2.1.37) that catalyzes the exo-hydrolysis of short beta (1→4)-xylooligosaccharides, to remove successive D-xylose residues from the non-reducing termini. In some embodiments, one unit of beta-xylosidase activity is defined as 1.0 µmole of p-nitrophenol produced per minute at 40° C., at pH 5 from 1 mM p-nitrophenyl-beta-D-xyloside as substrate in 100 mM sodium citrate containing 0.01% TWEEN®-20.

As used herein, the term "acetylxylan esterase activity" is defined herein as a carboxylesterase activity (EC 3.1.1.72) that catalyses the hydrolysis of acetyl groups from polymeric xylan, acetylated xylose, acetylated glucose, alpha-napthyl acetate, and p-nitrophenyl acetate. In some embodiments, acetylxylan esterase activity is determined using 0.5 mM p-nitrophenylacetate as substrate in 50 mM sodium acetate containing 0.01% TWEEN®-20, at pH 5.0. One unit of acetylxylan esterase activity is defined as the amount of enzyme capable of releasing 1 pmole of p-nitrophenolate anion per minute at pH 5, and 25° C.

As used herein, the term "feruloyl esterase activity" is defined herein as a 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. In some embodiments, feruloyl esterase activity is determined using 0.5 mM p-nitrophenylferulate as substrate in 50 mM sodium acetate, at pH 5.0. One unit of feruloyl esterase activity equals the amount of enzyme capable of releasing 1 µmole of p-nitrophenolate anion per minute at pH 5, and 25° C.

As used herein, the term "alpha-glucuronidase activity" is defined herein as an alpha-D-glucosiduronate glucuronohydrolase activity (EC 3.2.1.139) that catalyzes the hydrolysis of an alpha-D-glucuronoside to D-glucuronate and an alcohol (See e.g., de Vries, J. Bacteriol., 180: 243-249 [1998]). One unit of alpha-glucuronidase activity equals the amount of enzyme capable of releasing 1 pmole of glucuronic or 4-O-methylglucuronic acid per minute at pH 5, 40° C.

As used herein, the term "alpha-L-arabinofuranosidase activity" is defined as an alpha-L-arabinofuranoside arabinofuranohydrolase activity (EC 3.2.1.55) that catalyzes the hydrolysis of terminal non-reducing alpha-L-arabinofuranoside residues in alpha-L-arabinosides. The enzyme activity acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase. In some embodiments, alpha-L-arabinofuranosidase activity is determined using 5 mg of medium viscosity wheat arabinoxylan (Megazyme International Ireland, Ltd., Wicklow, Ireland) per mL of 100 mM sodium acetate pH 5 in a total volume of 200 µL for 30 minutes at 40° C., followed by arabinose analysis by AMINEX®. HPX-87H column chromatography (Bio-Rad Laboratories, Inc., Hercules, Calif.).

Enzymatic lignin depolymerization can be accomplished by lignin peroxidases, manganese peroxidases, laccases, and/or cellobiose dehydrogenases (CDH), often working in synergy. These extracellular enzymes, essential for lignin degradation, are often referred to as "lignin-modifying enzymes" or "LMEs." Three of these enzymes comprise two glycosylated heme-containing peroxidases:lignin peroxidase (LIP); Mn-dependent peroxidase (MNP); and, a copper-containing phenoloxidase laccase (LCC).

As used herein, the "total available cellulose" is the amount (wt %) of cellulose that is accessible to enzymatic hydrolysis. Total available cellulose is typically equal to, or very close to being equal to, the amount of initial cellulose present in a hydrolysis reaction.

As used herein, the "residual cellulose" is the portion (wt %) of the total available cellulose in the hydrolysis mixture that remains unhydrolyzed. Residual cellulose can be measured directly by, for example, IR spectroscopy, or can be measured by, for example, measuring the amount of glucose generated by concentrated acid hydrolysis of the residual solids.

As used herein, the "total hydrolyzed cellulose" is the portion of the total available cellulose that is hydrolyzed in the hydrolysis mixture. For example, the total hydrolyzed cellulose can be calculated as the difference between the "total available cellulose" and the "residual cellulose." The "theoretical maximum glucose yield" is the maximum amount (wt %) of glucose that could be produced under a given condition from the total available cellulose.

As used herein, "Gmax" refers to the maximum amount (wt %) of glucose that could be produced from the total hydrolyzed cellulose. Gmax can be calculated, for example, by directly measuring the amount of residual cellulose remaining at the end of a reaction under a given reaction conditions, subtracting the amount of residual cellulose from the total available cellulose to determine the total hydrolyzed cellulose, and then calculating the amount of glucose that could be produced from the total hydrolyzed cellulose.

As used herein, "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

As used herein, the term "C1" refers to a *Chrysosporium lucknowense* fungal strain described by Garg (See, Garg, Mycopathol., 30: 3-4 [1966]). "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophilia*. Other C1 strains include organisms deposited under accession numbers ATCC 44006, CBS (Centraalbureau voor Schimmelcultures) 122188, CBS 251.72, CBS 143.77, CBS 272.77, and VKM F-3500D. Exemplary C1 derivatives include modified organisms in which one or more endogenous genes or sequences have been deleted or modified and/or one or more heterologous genes or sequences have been introduced. Derivatives include UV18#100f Δalp1, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δpyr5 Δalp1 Δpep4 Δalp2, as described in WO2008073914, incorporated herein by reference.

Methods for recombinant expression of proteins in fungi and other organisms are well known in the art, and a number of suitable expression vectors are available or can be constructed using routine methods. Protocols for cloning and expression in fungal hosts and other organisms are well known in the art (See e.g., Zhu et al., Plasmid 6:128-33 [2009]). Standard references for techniques and protocols are widely available and known to those in the art (See e.g., U.S. Pat. Nos. 6,015,707, 5,811,381 and 6,573,086; US Pat. Pub. Nos. US 2003/0187243, US 2007/0238155, US 2008/0194005, US 2009/0099079; WO 2008/073914 and WO 98/15633, each of which is incorporated by reference herein for all purposes).

Mutagenesis may be performed in accordance with any of the techniques known in the art, including random and site-specific mutagenesis. Directed evolution can be performed with any of the techniques known in the art to screen for improved promoter variants including shuffling. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

DETAILED DESCRIPTION OF THE INVENTION

In some embodiments, the improved fungal strains find use in hydrolyzing cellulosic material to glucose. In some embodiments, the improved fungal strains find use in hydrolyzing lignocellulose material. As indicated herein, the present invention provides improved fungal strains for the conversion of cellulose to fermentable sugars (e.g., glucose). In particular, the improved fungal strains provided herein are genetically modified to reduce the amount of endogenous protease activity secreted by the cells. The present invention also provides purified enzymes produced by the improved fungal strains provided herein.

Genetically Modified Fungal Cells

The genetically modified fungal cells provided herein exhibit a reduction in the amount of at least one endogenous protease activity that is secreted by the cell. It will be readily appreciated that any suitable genetic modification known in the art can be employed to reduce the secreted activity of at least one endogenous protease. For example, as described below, modifications contemplated herein include modifications that reduce the amount of at least one protease secreted by the cell. Modifications that reduce the amount of at least one protease expressed by the cell are also contemplated. Additional embodiments include modifications that reduce the transcription level of at least one protease. Still further embodiments include the complete or partial deletion of a gene encoding at least one protease. Other embodiments include modifications that reduce the catalytic efficiency of at least one protease.

In some genetically modified fungal cells provided herein, at least one protease activity secreted by the cell is reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the level of at least one protease activity secreted by the unmodified parental fungal cell grown or cultured under essentially the same culture conditions. In some embodiments, the genetically modified fungal cells are *Myceliophthora*. In some embodiments, the genetically modified fungal cells are *M. thermophila* that do not produce at least one polypeptide selected from SEQ ID NOS:3, 6, 9, and/or 12. In some embodiments, the gene encoding at least one protease selected from the genes encoding Protease #1, Protease #2, Protease #3, and/or Protease #4 has been deleted from the *Myceliophthora* (e.g., *M. thermophila*). In some embodiments, at least one polynucleotide sequence selected from SEQ ID NOS:1, 2, 4, 5, 7, 8, 10, and/or 11 have been deleted from the genome of the *Myceliophthora*.

In some embodiments, the fungal cells of the present invention have been genetically modified to reduce the amount of at least one endogenous protease secreted by the cell. A reduction in the amount of secreted protease(s) can be a complete or partial reduction of the protease(s) secreted to the extracellular milieu. Reduction in the amount of secreted protease(s) can be accomplished by reducing the amount of at least one protease produced by the cell and/or by reducing the ability of the cell to secrete at least one protease produced by the cell. Methods for reducing the ability of the cell to secrete a polypeptide can be performed according to any of a variety of suitable methods known in the art (See e.g., Fass and Engels J. Biol. Chem., 271:15244-15252 [1996], which is incorporated by reference herein in its entirety). For example, the gene encoding a secreted polypeptide can be modified to delete or inactivate a secretion signal peptide. In some embodiments, the fungal cells have been genetically modified to disrupt the N-terminal secretion signal peptide of at least one protease. In some embodiments, the amount of at least one protease secreted by the cell is reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the secretion of at least one protease in an unmodified organism grown or cultured under essentially the same culture conditions.

Furthermore, in some embodiments, the total amount of at least one protease activity is reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the total amount of at least one protease secreted in an unmodified organism grown or cultured under essentially the same culture conditions.

Decreased secretion of at least one protease can be determined by any of a variety of suitable methods known in the art for detection of protein or enzyme levels. For example, the levels of at least one protease in the supernatant of a fungal culture can be detected using Western blotting techniques, two-dimensional (2D) gels, or any other suitable protein detection techniques. Similarly, secreted protease activity in the supernatant of a fungal culture can be measured using any suitable activity assay as known in the art.

In some embodiments, the fungal cells have been genetically modified to reduce the amount of at least one endogenous protease expressed by the cell. As used herein, expression refers to conversion of the information encoded in a gene to the protein encoded by that gene. Thus, a reduction of the amount of an expressed protease represents a reduction in the amount of the protease that is eventually translated by the cell. In some such embodiments, the reduction in the expression is accomplished by reducing the amount of mRNA that is transcribed from a gene encoding protease. In some other embodiments, the reduction in the expression is accomplished by reducing the amount of protein that is translated from a mRNA encoding protease.

The amount of protease expressed by the cell can be reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the expression of protease in an unmodified fungal cell. In some such embodiments, the reduction in the expression is accomplished by reducing the amount of mRNA that is transcribed from a gene encoding protease in an unmodified organism grown or cultured under essentially the same culture conditions.

Furthermore, in some embodiments, a reduction in the expression level of a protease results in at least about 5%, about 10%, about 15%, about 20%, about 25%, about 30%, about 35%, about 40%, about 45%, about 50%, about 55%, about 60%, about 65%, about 70%, about 75%, about 80%, 85% about, 90%, about 91%, about 92%, about 93%, about 94%, about 95%, about 96%, about 97%, about 98%, or about a 99% reduction in the total expression level of protease activity by the fungal cell relative to an unmodified fungal cell grown or cultured under essentially the same culture conditions.

Decreased expression of a protease can be determined by any of a variety of methods known in the art for detection of protein or enzyme levels. For example, the levels of protease in the supernatant of a fungal culture can be detected using chromatographic methods, Western blotting techniques or any other suitable protein detection techniques that use an antibody specific to protease. Indeed, it is not intended that the present invention be limited to any particular method.

Methods for reducing production of a polypeptide are well known and can be performed using any of a variety of suitable methods known in the art. For example, the gene encoding a secreted polypeptide can be modified to disrupt a translation initiation sequence such as a Shine-Delgarno sequence or a Kozak consensus sequence. Furthermore, the gene encoding a secreted polypeptide can be modified to introduce a frameshift mutation in the transcript encoding the endogenous protease. It will also be recognized that usage of uncommon codons can result in reduced expression of a polypeptide. It will be appreciated that in some embodiments, the gene encoding the protease has at least one nonsense mutation that results in the translation of a truncated protein.

Other methods of reducing the amount of expressed polypeptide include post-transcriptional RNA silencing methodologies such as antisense RNA and RNA interference. Antisense techniques are well-established, and include using a nucleotide sequence complementary to the nucleic acid sequence of the gene. More specifically, expression of at least one protease-encoding gene by a fungal cell may be reduced or eliminated by introducing a nucleotide sequence complementary to the nucleic acid sequence, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. Methods for expressing antisense RNA are known in the art (See e.g., Ngiam et al., Appl Environ Microbiol., 66(2):775-82 [2000]; and Zrenner et al., Planta., 190(2):247-52 [1993]), both of which are hereby incorporated by reference herein in their entirety). In some embodiments, the mRNA is destabilized though secondary structure changes (e.g., altered introns). In some embodiments, destabilization occurs due to alterations in terminators.

Furthermore, modification, downregulation or inactivation of at least one protease encoding gene provided herein may be obtained via RNA interference (RNAi) techniques (See e.g., Kadotani et al. Mol. Plant Microbe Interact., 16:769-76 [2003], which is incorporated by reference herein in its entirety). RNA interference methodologies include double stranded RNA (dsRNA), short hairpin RNAs (shRNAs) and small interfering RNAs (siRNAs). Potent silencing using dsRNA may be obtained using any suitable technique (See e.g., Fire et al., Nature 391:806-11 [1998]). Silencing using shRNAs is also well-established (See e.g., Paddison et al., Genes Dev., 16:948-958 [2002]). Silencing using siRNA techniques are also known (See e.g., Miyagishi et al., Nat. Biotechnol., 20:497-500 [2002]). The content of each of the above-cited references is incorporated by reference herein in its entirety.

In some embodiments, the fungal cells of the present invention have been genetically modified to reduce the transcription level of a gene encoding at least one endogenous protease. As used herein, transcription and similar terms refer to the conversion of the information encoded in a gene to an RNA transcript. Accordingly, a reduction of the transcription level of a protease is a reduction in the amount of RNA transcript of an RNA coding for a protease. In some embodiments, the transcription level is reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the transcription level of a protease in an unmodified organism grown or cultured under essentially the same culture conditions.

Furthermore, in some embodiments, a reduction in the transcription level of a protease results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the total protease secreted by the fungal cell relative to an unmodified organism grown or cultured under essentially the same culture conditions. Decreased transcription can be determined by any of a variety of methods known in the art for detection of transcription levels. For example, the levels of transcription of a particular mRNA in a fungal cell can be detected using quantitative RT-PCR techniques or other RNA detection techniques that specifically detect a particular mRNA. Methods for reducing transcription level of a gene can be performed according to any suitable method known in the art, and include partial or complete deletion of the gene, and disruption or replacement of the promoter of the gene such that transcription of the gene is greatly reduced or even inhibited. For example, the promoter of the gene can be replaced with a weak promoter (See e.g., U.S. Pat. No. 6,933,133, which is incorporated by reference herein in its entirety). Thus, where the weak promoter is operably linked with the coding sequence of an endogenous polypeptide, transcription of that gene is greatly reduced or inhibited.

In some embodiments, the fungal cells of the present invention have been genetically modified to at least partially delete a gene encoding the endogenous protease. Typically, this deletion reduces or eliminates the total amount of endogenous protease secreted by the fungal cell. In some embodiments, complete or near-complete deletion of the gene sequence is contemplated. However, a deletion mutation need not completely remove the entire gene sequence encoding protease, in order to reduce the amount of endogenous protease secreted by the fungal cell. For example, in some embodiments, there is a partial deletion that removes one or more nucleotides encoding an amino acid in a protease active site, encoding a secretion signal, or encoding another portion of the protease that plays a role in endogenous protease activity being secreted by the fungal cell.

A deletion in a gene encoding protease in accordance with the embodiments provided herein includes a deletion of one or more nucleotides in the gene encoding the protease. In some embodiments, there is a deletion of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100%, of the gene encoding the protease, wherein the amount of protease secreted by the cell is reduced.

Thus, in some embodiments, the deletion results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the activity of the protease secreted by the fungal cell, relative to the activity of protease secreted by an unmodified organism grown or cultured under essentially the same culture conditions.

Furthermore, in some embodiments, the deletion results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the total protease secreted by the fungal cell relative to an unmodified fungal cell grown or cultured under essentially the same culture conditions.

Deletion of a protease gene can be detected and confirmed by any of a variety of methods known in the art for detection of gene deletions, including the methods provided herein. For example, gene deletion can be confirmed using PCR amplification of the modified genomic region. It will be appreciated that additional suitable techniques for confirming deletion can be used and are well known, including Southern blot techniques, DNA sequencing of the modified genomic region, and screening for positive or negative markers incorporated during recombination events. Indeed, any suitable method known in the art finds use in the present invention.

Methods for complete and/or partial deletion of a gene are well-known and the genetically modified fungal cells described herein can be generated using any of a variety of deletion methods known in the art that result in a reduction in the amount of at least one endogenous protease secreted by the cells. Such methods may advantageously include standard gene disruption using homologous flanking markers (See e.g., Rothstein, Meth. Enzymol., 101:202-211 [1983], incorporated herein by reference in its entirety). Additional techniques for gene deletion include PCR-based methods for standard deletion (See e.g., Davidson et al., Microbiol., 148:2607-2615 [2002], incorporated herein by reference in its entirety).

Additional gene deletion techniques include, but are not limited to "positive-negative" cassettes (See e.g., Chang et al., Proc. Natl. Acad. Sci. USA 84:4959-4963 [1987]), cre/lox based deletion (See e.g., Florea et al., Fung. Genet. Biol., 46:721-730 [2009]), biolistic transformation to increase homologous recombination, and *Agrobacterium*-mediated gene disruption.

Methods to introduce DNA or RNA into fungal cells are known to those of skill in the art and include, but are not limited to PEG-mediated transformation of protoplasts, electroporation, biolistic transformation (See e.g., Davidson et al., Fung. Genet. Biol., 29:38-48 [2000]), and *Agrobacterium*-mediated transformation (See e.g., Wang et al., Curr. Genet., 56:297-307 [2010]).

Further methods for complete or partial gene deletion include disruption of the gene. Such gene disruption techniques are known to those of skill in the art, including, but not limited to insertional mutagenesis, the use of transposons, and marked integration. However, it will be appreciated that any suitable technique that provides for disruption of the coding sequence or any other functional aspect of a gene finds use in generating the genetically modified fungal cells provided herein. Methods of insertional mutagenesis can be performed according to any suitable method known in the art (See e.g., Combier et al., FEMS Microbiol Lett., 220:141-8 [2003], which is incorporated by reference herein in its entirety). In addition, *Agrobacterium*-mediated insertional mutagenesis can be used to insert a sequence that disrupts the function of the encoded gene, such as disruption of the coding sequence or any other functional aspect of the gene.

Transposon mutagenesis methodologies provide another means for gene disruption. Transposon mutagenesis is well known in the art, and can be performed using in vivo techniques (See e.g., Firon et al., Eukaryot. Cell 2:247-55 [2003]); or by the use of in vitro techniques (See e.g., Adachi et al., Curr. Genet., 42:123-7 [2002]); both of these references are incorporated by reference in their entireties. Thus, targeted gene disruption using transposon mutagenesis can be used to insert a sequence that disrupts the function of the encoded gene, such as disruption of the coding sequence or any other functional aspect of the gene.

Restriction enzyme-mediated integration (REMI) is another methodology for gene disruption, and is well known in the art (See e.g., Thon et al., Mol. Plant Microbe Interact., 13:1356-65 [2000], which is incorporated by reference herein in its entirety). REMI generates insertions into genomic restriction sites in an apparently random manner, some of which cause mutations. Thus, insertional mutants that demonstrate a disruption in the gene encoding the endogenous protease can be selected and utilized as provided herein.

In some other embodiments, the fungal cell has been genetically modified to reduce the catalytic efficiency of the protease. A reduction in catalytic efficiency refers to a reduction in the activity of protease, relative to unmodified protease, as measured using standard techniques known in the art. Thus, a genetic modification that reduces catalytic efficiency can result in, for example, a translated protein product that has a reduction in enzymatic activity.

A reduction in catalytic efficiency is a reduction of protease activity of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to unmodified protease, as measured using standard techniques.

In some further embodiments, the genetic modification results in a reduction of protease activity of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% in the total protease activity secreted by the fungal cell, as compared to unmodified protease, as measured using standard techniques.

Methods for reducing catalytic efficiency of proteases are well known, and as such, any of a variety of suitable methods known in the art for reducing catalytic efficiency find use in genetically modifying the fungal cells provided herein. Thus, for example, the fungal cell can be genetically modified to inactivate one or more residues in an active site of the protease. For example, one or more residues can be modified to decrease substrate binding, and/or one or more residues can be modified to decrease the catalytic activity of the protease. Similarly, it will be apparent that mutation of residues outside an active site can result in allosteric change in the shape or activity of the protease, such that the catalytic efficient of the enzyme is reduced. In some embodiments, other domains are targeted for at least one mutation which results in a reduced catalytic efficiency of at least one endogenous protease.

As provided herein, a fungal cell that has been genetically modified to reduce the activity of at least one protease typically has reduced secreted activity of an endogenous protease. Accordingly, one or more protease enzymes from each of the fungal species described herein can be targeted for genetic modification. In some embodiments, the protease is from a fungal species in the family Chaetomiaceae. In some embodiments, the protease is from a fungal species selected from *Sporotrichum cellulophilum, Thielavia heterothallica, Corynascus heterothallicus, Thielavia terrestris, Chaetomium globosum*, and *Myceliophthora thermophila*.

Certain amino acid sequences encoding protease are provided herein. For example, in one embodiment, the nucleotide sequences (gDNA and cDNA) encoding one *Myceliophthora thermophila* protease ("Protease #1") are set forth herein as SEQ ID NOS:1 and 2, and the encoded amino acid sequence is set forth as SEQ ID NO:3. In another embodiment, nucleotide sequences (gDNA and cDNA) encoding another *Myceliophthora thermophila* protease ("Protease #2) are set forth herein as SEQ ID NOS:4 and 5, and the encoded amino acid sequence is set forth as SEQ ID NO:6. In yet another embodiment, the nucleotide sequences (gDNA and cDNA) of another *Myceliophthora thermophila* protease ("Protease #3) are set forth herein as SEQ ID NOS:7 and 8, and the encoded amino acid sequence is set forth as SEQ ID NO:9. In yet another embodiment, the nucleotide sequences (gDNA and cDNA) of another *Myceliophthora thermophila* protease ("Protease #4) are set forth herein as SEQ ID NOS:10 and 11, and the encoded amino acid sequence is set forth as SEQ ID NO:12.

In some embodiments, the protease is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NOS:1, 2, 4, 5, 7, 8, 10, and/or 11. In some embodiments, the protease is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to a nucleic acid sequence encoding the amino acid sequence set forth as SEQ ID NOS:3, 6, 9, and/or 12. In some embodiments, the protease is encoded by a nucleic acid sequence that can selectively hybridize to SEQ ID NOS:1, 2, 4, 5, 7, 8, 10, and/or 11, under moderately stringent or stringent conditions, as described hereinabove. In some embodiments, the protease is encoded by a nucleic acid sequence that can selectively hybridize under moderately stringent or stringent conditions to a nucleic acid sequence that encodes SEQ ID NOS:3, 6, 9, and/or 12. In some embodiments, the protease comprises an amino acid sequence with at least about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85% about 86%, about 87%, about 88%, about 89%, about 90%, about 91%, about 92%, about 93%, about 94%, about 95%, about 96%, about 97%, about 98%, about 99%, or about 100% similarity to the amino acid sequence set forth as SEQ ID NOS:3, 6, 9, and/or 12. Protease sequences can be identified by any of a variety of methods known in the art. For example, a sequence alignment can be conducted against a database, for example against the NCBI database, and sequences with the lowest HMM E-value can be selected.

In some embodiments, the fungal cells of the present invention have been genetically modified to reduce the amount of protease activity from two or more endogenous protease enzymes secreted by the cell. In some embodiments, a first of the two or more proteases comprises an amino acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO:3, 6, 9, or 12, and a second of the two or more protease enzymes comprises an amino acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO:3, 6, 9, or 12.

As indicated herein, the present invention provides fungal cells from the family Chaetomiaceae that have been genetically modified to reduce the amount of endogenous protease activity that is secreted by the cell, where the fungal cell is capable of secreting a cellulase-containing enzyme mixture. The Chaetomiaceae are a family of fungi in the Ascomycota, class Sordariomycetes. The family Chaetomiaceae includes the genera *Achaetomium, Aporothielavia, Chaetomidium, Chaetomium, Corylomyces, Corynascus, Farrowia, Thielavia, Zopfiella*, and *Myceliophthora*. In some embodiments, the genetically modified fungal cell provided herein is a Chaetomiaceae family member selected from *Myceliophthora, Thielavia, Corynascus*, and *Chaetomium*.

In some embodiments, the genetically modified fungal cell is an anamorph or teleomorph of a Chaetomiaceae family member selected from *Myceliophthora, Thielavia, Corynascus*, and *Chaetomium*. In some embodiments, the genetically modified fungal cell is selected from *Sporotrichum, Chrysosporium, Paecilomyces, Talaromyces* and *Acremonium*. It is also contemplated that the genetically modified fungal cell can also be selected from the genera *Ctenomyces, Thermoascus*, and *Scytalidium*, including anamorphs and teleomorphs of fungal cells of these genera. In some embodiments, the genetically modified fungal cell is selected from strains of *Sporotrichum cellulophilum, Thielavia heterothallica, Corynascus heterothallicus, Thielavia terrestris*, and *Myceliophthora thermophila*, including anamorphs and teleomorphs thereof. It is not intended that the present invention be limited to any particular genus within the Chaetomiaceae family. In some further embodiments, the genetically modified fungal cell is a thermophilic species of *Acremonium, Arthroderma, Corynascus, Thielavia, Myceliophthora, Thermoascus, Chromocleista, Byssochlamys, Sporotrichum, Chaetomium, Chrysosporium, Scytalidium, Ctenomyces, Paecilomyces*, or *Talaromyces*. It will be understood that for all of the aforementioned species, the genetically modified fungal cell presented herein encompasses both the perfect and imperfect states, and other taxonomic equivalents (e.g., anamorphs), regardless of the species name by which they are known (See e.g., Cannon, Mycopathol., 111:75-83 [1990]; Moustafa et al., Persoonia 14:173-175 [1990]; Upadhyay et al., Mycopathol., 87:71-80 [1984]; Guano et al., Mycotaxon 23: 419-427 [1985]; Awao et al., Mycotaxon 16:436-440 [1983]; and von Klopotek, Arch. Microbiol., 98:365-369 [1974]). Those skilled in the art will readily recognize the identity of appropriate equivalents. Accordingly, it will be understood that, unless otherwise stated, the use of a particular species designation in the present disclosure also refers to species that are related by anamorphic or teleomorphic relationship.

In some embodiments provided herein, the fungal cell is further genetically modified to increase its production of one or more saccharide hydrolyzing enzymes. For example, in some embodiments, the fungal cell overexpresses a homologous or heterologous gene encoding a saccharide hydrolysis enzyme such as beta-glucosidase. In some embodiments, the one or more saccharide hydrolysis enzyme is a cellulase enzyme described herein. For example, in some embodiments, the enzyme is any one of a variety of endoglucanases, cellobiohydrolases, beta-glucosidases, endoxylanases, beta-xylosidases, arabinofuranosidases, alpha-glucuronidases, acetylxylan esterases, feruloyl esterases, and alpha-glucuronyl esterases, and/or any other enzyme involved in saccharide hydrolysis. In some embodiments, the fungal cell is genetically modified to increase expression of beta-glucosidase. Thus, in some embodiments, the fungal cell comprises a polynucleotide sequence for increased expression of beta-glucosidase-encoding polynucleotide. In some embodiments, the fungal cell is further genetically modified to delete polynucleotides encoding one or more endogenous protease enzymes.

In some embodiments, the saccharide hydrolyzing enzyme is endogenous to the fungal cell, while in other embodiments, the saccharide hydrolyzing enzyme is exogenous to the fungal cell. In some additional embodiments, the enzyme mixture further comprises a saccharide hydrolyzing enzyme that is heterologous to the fungal cell. Still further, in some embodiments, the methods for generating glucose comprise contacting cellulose with an enzyme mixture that comprises a saccharide hydrolyzing enzyme that is heterologous to the fungal cell.

In some embodiments, a fungal cell is genetically modified to increase the expression of a saccharide hydrolysis enzyme using any of a variety of suitable methods known to those of skill in the art. In some embodiments, the hydrolyzing enzyme-encoding polynucleotide sequence is adapted for increased expression in a host fungal cell. As used herein, a polynucleotide sequence that has been adapted for expression is a polynucleotide sequence that has been inserted into an expression vector or otherwise modified to contain regulatory elements necessary for expression of the polynucleotide in the host cell, positioned in such a manner as to permit expression of the polynucleotide in the host cell. Such regulatory elements required for expression include promoter sequences, transcription initiation sequences and, optionally, enhancer sequences. For example, in some embodiments, a polynucleotide sequence is inserted into a plasmid vector adapted for expression in the fungal host cell.

In some embodiments, the genetically modified fungal cells provided herein are cellulase-producing fungal cells. In some embodiments, the cellulase-producing fungal cells express and secrete a mixture of cellulose hydrolyzing enzymes. In some embodiments, the genetically modified fungal cells provided herein are fungal cells from the family Chaetomiaceae that secrete two or more cellulose hydrolyzing enzymes (e.g., endoglucanase, cellobiohydrolase, and/or beta-glucosidase). In some additional embodiments, the cellulase-producing fungal cells produce two or more of these enzymes, in any combination. Additionally, in some embodiments, the genetically modified fungal cell is derived from a lignocellulose-competent parental fungal cell.

The present invention also provides a fungal culture in a vessel comprising a genetically modified fungal cell as described hereinabove. In some embodiments, the vessel comprises a liquid medium, such as fermentation medium. For example, the vessel can be a flask, bioprocess reactor, or any suitable container. In some embodiments, the vessel comprises a solid growth medium. For example, the solid medium can be an agar medium such as potato dextrose agar, carboxymethylcellulose, cornmeal agar, and any other suitable medium. In some embodiments, the fungal cell described hereinabove is an isolated fungal cell.

Enzyme Mixtures

Also provided herein are enzyme mixtures that comprise at least one or more cellulose hydrolyzing enzymes expressed by a fungal cell that has been genetically modified to reduce the amount of endogenous protease activity secreted by the cell, as described herein. Cellulase enzymes are produced by a wide variety of microorganisms. Cellulases (and hemicellulases) from filamentous fungi and some bacteria are widely exploited for many industrial applications that involve processing of natural fibers to sugars. It is contemplated that mixtures of any enzymes set forth herein will find use in the present invention.

As a further guide to the reader, yet without implying any limitation in the practice of the present invention, exemplary mixtures of components that may be used as catalysts in a saccharification reaction to generate fermentable sugars from a cellulosic substrate are provided herein. Concentrations are given in wt/vol of each component in the final reaction volume with the cellulose substrate. Also provided are percentages of each component (wt/wt) in relation to the total mass of the components that are listed for addition into each mixture (the "total protein"). This may be a mixture of purified enzymes and/or enzymes in a culture supernatant.

By way of example, the invention embodies mixtures that comprise at least four, at least five, or all six of the following components. In some embodiments, cellobiohydrolase 1 (CBH1) finds use; in some embodiments CBH1 is present at a concentration of about 0.14 to about 0.23 g/L (about 15% to about 25% of total protein). Exemplary CBH1 enzymes include, but are not limited to *T. emersonii* CBH1(wild-type) (e.g., SEQ ID NO:137), wild-type *M. thermophila* CBH1a (e.g., SEQ ID NO:140), and the variants CBH1a-983 (e.g., SEQ ID NO:146) and CBH1a-145 (e.g., SEQ ID NO:143). In some embodiments, cellobiohydrolase 2 (CBH2) finds use; in some embodiments, CBH2 is present at a concentration of about 0.14 to about 0.23 g/L (about 15% to about 25% of total protein). Exemplary CBH2 enzymes include, but are not limited to wild-type CBH2b from *M. thermophila* (wild-type) (e.g., SEQ ID NO:149), and/or variants CHB2b var. 196 (e.g., SEQ ID NO: 152), CBH2b var. 287 (e.g., SEQ ID NO:155), and CBH2b var. 962 (e.g., SEQ ID NO:158). In some embodiments, endoglucanase 2 (EG2) finds use; in some embodiments, EG2 is present at a concentration of 0 to about 0.05 g/L (0 to about 5% of total protein). Exemplary EGs include, but are not limited to wild-type *M. thermophila* EG2 (e.g., SEQ ID NO:125). In some further embodiments, endoglucanase 1 (EG1) finds use; in some embodiments, EG1 is present at a concentration of about 0.05 to about 0.14 g/L (about 5% to about 15% of total protein). Exemplary EG1s include, but are not limited to wild-type *M. thermophila* EG1b (e.g., SEQ ID NO:122). In some embodiments, beta-glucosidase (BGL) finds use in the present invention; in some embodiments, BGL is present at a concentration of about 0.05 to about 0.09 g/L (about 5% to about 10% of total protein). Exemplary beta-glucosidases include, but are not limited to wild-type *M. thermophila* BGL1 (e.g., SEQ ID NO:128), as well as variant BGL-900 (e.g., SEQ ID NO:134), and variant BGL-883 (e.g., SEQ ID NO:131). In some further embodiments, GH61 protein and/or protein variants find use; in some embodiments, GH61 enzymes are present at a concentration of about 0.23 to about 0.33 g/L (about 25% to about 35% of total protein). Exemplary GH61s include, but are not limited to wild-type *M. thermophila* GH61a (e.g., SEQ ID NO:14), GH61a Variant 1 (e.g., SEQ ID NO:17), GH61a Variant 5 (e.g., SEQ ID NO:20), and/or GH61a Variant 9 (e.g., SEQ ID NO:23), and/or any other GH61a variant proteins, as well as any of the other GH61 enzymes (e.g., GH61b, GH61c, GH61d, GH61e, GH61f, GH61g, GH61h, GH61i, GH61j, GH61k, GH61l, GH61m, GH61n, GH61o, GH61p, GH61q, GH61r, GH61s, GH61t, GH61u, GH61v, GH61w, GH61x, and/or GH61y) as provided herein (e.g., polynucleotide and polypeptide sequences including, but not limited to SEQ ID NOS:25-120).

In some embodiments, one, two or more than two enzymes are present in the mixtures of the present invention. In some embodiments, GH61p is present at a concentration of about 0.05 to about 0.14 g/L (e.g., about 1% to about 15% of total protein). Exemplary *M. thermophila* GH61p enzymes include, but are not limited to those set forth in SEQ ID NOS:82 and 85. In some embodiments, GH61f is present at a concentration of about 0.05 to about 0.14 g/L (about 1% to about 15% of total protein). An exemplary *M. thermophila* GH61f is set forth in SEQ ID NO:41. In some additional embodiments, at least one additional GH61 enzyme provided herein (e.g., GH61b, GH61c, GH61d, GH61e, GH61g, GH61h, GH61i, GH61j, GH61k, GH61l, GH61m, GH61n, GH61n, GH61o, GH61q, GH61r, GH61s, GH61t, GH61u, GH61v, GH61w, GH61x, and/or GH61y, finds use at an appropriate concentration (e.g., about 0.05 to about 0.14 g/L [about 1% to about 15% of total protein]).

In some embodiments, at least one xylanase at a concentration of about 0.05 to about 0.14 g/L (about 1% to about 15% of total protein) finds use in the present invention. Exemplary xylanases include but are not limited to the *M. thermophila* xylanase-3 (SEQ ID NO:161), xylanase-2 (SEQ ID NO:164), xylanase-1 (SEQ ID NO:167), xylanase-6 (SEQ ID NO:170), and xylanase-5 (SEQ ID NO:173).

In some additional embodiments, at least one beta-xylosidase at a concentration of about 0.05 to about 0.14 g/L (e.g., about 1% to about 15% of total protein) finds use in the present invention. Exemplary beta-xylosidases include but are not limited to the *M. thermophila* beta-xylosidase (SEQ ID NO:176).

In still some additional embodiments, at least one acetyl xylan esterase at a concentration of about 0.05 to about 0.14 g/L (e.g., about 1% to about 15% of total protein) finds use in the present invention. Exemplary acetylxylan esterases include but are not limited to the *M. thermophila* acetylxylan esterase (SEQ ID NO:179).

In some further additional embodiments, at least one ferulic acid esterase at a concentration of about 0.05 to about 0.14 g/L (e.g., about 1% to about 15% of total protein) finds use in the present invention. Exemplary ferulic esterases include but are not limited to the *M. thermophila* ferulic acid esterase (SEQ ID NO:182).

In some embodiments, the enzyme mixtures comprise at least one GH61 variant protein as provided herein and at least one cellulase, including but not limited to any of the enzymes described herein. In some embodiments, the enzyme mixtures comprise at least one GH61 variant protein and at least one wild-type GH61 protein. In some embodiments, the enzyme mixtures comprise at least one GH61 variant protein and at least one non-cellulase enzyme. Indeed, it is intended that any combination of enzymes will find use in the enzyme compositions comprising at least one GH61 variant of the present invention.

The concentrations listed above are appropriate for a final reaction volume with the biomass substrate in which all of the components listed (the "total protein") is about 0.75 g/L, and the amount of glucan is about 93 g/L, subject to routine optimization. The user may empirically adjust the amount of each component and total protein for cellulosic substrates that have different characteristics and/or are processed at a different concentration. Any one or more of the components may be supplemented or substituted with variants with common structural and functional characteristics, as described below.

Without implying any limitation, the following mixtures further describe some embodiments of the present invention.

Some mixtures comprise CBH1a within a range of about 15% to about 30% total protein, typically about 20% to about 25%; CBH2 within a range of about 15% to about 30%, typically about 17% to about 22%; EG2 within a range of about 1% to about 10%, typically about 2% to about 5%; BGL1 within a range of about 5% to about 15%, typically about 8% to about 12%; GH61a within a range of about 10% to about 40%, typically about 20% to about 30%; EG1b within a range of about 5% to about 25%, typically about 10% to about 18%; and GH61f within a range of 0% to about 30%; typically about 5% to about 20%.

In some mixtures, exemplary BGL1s include the BGL1 variant 900 (SEQ ID NO:134) and/or variant 883 (SEQ ID NO:131). In some embodiments, other enzymes are *M. thermophila* wild-type: CBH1a (SEQ ID NO:140), CBH2b (SEQ ID NO:149), EG2 (SEQ ID NO:125), GH61a (SEQ ID NO:14), EG1b (SEQ ID NO:122) and GH61f (SEQ ID NO:41). Any one or more of the components may be supplemented or substituted with variants having common structural and functional characteristics with the component being substituted or supplemented, as described below. In a saccharification reaction, the amount of glucan is generally about 50 to about 300 g/L, typically about 75 to about 150 g/L. The total protein is about 0.1 to about 10 g/L, typically about 0.5 to about 2 g/L, or about 0.75 g/L.

Some mixtures comprise CBH1 within a range of about 10% to about 30%, typically about 15% to about 25%; CBH2b within a range of about 10% to about 25%, typically about 15% to about 20%; EG2 within a range of about 1% to about 10%, typically about 2% to about 5%; EG1b within a range of about 2% to about 25%, typically about 6% to about 14%; GH61a within a range of about 5% to about 50%, typically about 10% to about 35%; and BGL1 within a range of about 2% to about 15%, typically about 5% to about 12%. Also included is copper sulfate to generate a final concentration of $Cu^{++}$ of about 4 µM to about 200 µM, typically about 25 µM to about 60 µM. However, it is not intended that the added copper be limited to any particular concentration, as any suitable concentration finds use in the present invention and will be determined based on the reaction conditions.

In an additional mixture, an exemplary CBH1 is wild-type CBH1 from *T. emersonii* (SEQ ID NO:137), as well as wild-type *M. thermophila* CBH1a (SEQ ID NO:140), Variant 983 (SEQ ID NO:146), and Variant 145 (SEQ ID NO:143); exemplary CBH2 enzymes include the wild-type (SEQ ID NO:149), Variant 962 (SEQ ID NO:158), Variant 196 (SEQ ID NO:152), and Variant 287 (SEQ ID NO:155); an exemplary EG2 is the wild-type *M. thermophila* (SEQ ID NO:125); an exemplary EG1b is the wild-type (SEQ ID NO:122); exemplary GH61a enzymes include wild-type *M. thermophila* (SEQ ID NO:14), Variant 1 (SEQ ID NO:17), Variant 5 (SEQ ID NO:20), and Variant 9 (SEQ ID NO:23); and exemplary BGLs include wild-type *M. thermophila* BGL (SEQ ID NO:128), Variant 883 (SEQ ID NO:131), and Variant 900 (SEQ ID NO:134). Any one or more of the components may be supplemented or substituted with other variants having common structural and functional characteristics with the component being substituted or supplemented, as described below. In a saccharification reaction, the amount of glucan is generally about 50 to about 300 g/L, typically about 75 to about 150 g/L. The total protein is about 0.1 to about 10 g/L, typically about 0.5 to about 2 g/L, or about 0.75 g/L.

Any or all of the components listed in the mixtures referred to above may be supplemented or substituted with variant proteins that are structurally and functionally related, as described herein.

In some embodiments, the CBH1 cellobiohydrolase used in mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to either SEQ ID NO:140 (*M. thermophila*), SEQ ID NO:137 (*T. emersonii*), or a fragment of either SEQ ID NO:140 or SEQ ID NO:137 having cellobiohydrolase activity, as well as variants of *M. thermophila* CBH1a (e.g., SEQ ID NO:143 and/or SEQ ID NO:146), and/or variant fragment(s) having cellobiohydrolase activity. Exemplary CBH1 enzymes include, but are not limited to those described in US Pat. Appln. Publn. No. 2012/0003703 A1, which is hereby incorporated herein by reference in its entirety for all purposes.

In some embodiments, the CBH2b cellobiohydrolase used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:149 and/or a fragment of SEQ ID NO:149, as well as at least one variant *M. thermophila* CBH2b enzyme (e.g., SEQ ID NO:152, 155, and/or 158) and/or variant fragment(s) having cellobiohydrolase activity. Exemplary CBH2b enzymes are described in U.S. Pat. Appln. Ser. Nos. 61/479,800, and 13/459,038, both of which are hereby incorporated herein by reference in their entirety for all purposes.

In some embodiments, the EG2 endoglucanase used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:125 and/or a fragment of SEQ ID NO:125 having endoglucanase activity. Exemplary EG2 enzymes are described in U.S. patent application Ser. No. 13/332,114, and WO 2012/088159, both of which are hereby incorporated herein by reference in their entirety for all purposes.

In some embodiments, the EG1b endoglucanase used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:122 and/or a fragment of SEQ ID NO:122 having endoglucanase activity.

In some embodiments, the BGL1 beta-glucosidase used the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NOS:128, 131, and/or 134, or a fragment of SEQ ID NOS:128, 131, and/or 134 having beta-glucosidase activity. Exemplary BGL1 enzymes include, but are not limited to those described in US Pat. Appln. Publ. No. 2011/0129881, WO 2011/041594, and US Pat. Appln. Publ. No. 2011/0124058 A1, all of which are hereby incorporated herein by reference in their entireties for all purposes.

In some embodiments, the GH61f protein used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:41, and/or a fragment of SEQ ID NO:41 having GH61 activity, assayed as described elsewhere in this disclosure.

In some embodiments, the GH61p protein used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:82, SEQ ID NO:85, and/or a fragment of such sequence having GH61p activity.

In some embodiments, the xylanase used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:161, SEQ ID NO:164, SEQ ID NO:167, SEQ ID NO:170, and/or SEQ ID NO:173, and/or a fragment of such sequence having xylanase activity.

In some embodiments, the xylosidase used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:176 and/or a fragment of such sequence having xylosidase activity.

In still some additional embodiments, at least one acetyl xylan esterase at a concentration of about 0.05 to about 0.14 g/L (e.g., about 1% to about 15% of total protein) finds use in the present invention. Exemplary acetylxylan esterases include but are not limited to the *M. thermophila* acetylxylan esterase (SEQ ID NO:179).

In some further additional embodiments, at least one ferulic acid esterase at a concentration of about 0.05 to about 0.14 g/L (e.g., about 1% to about 15% of total protein) finds use in the present invention. Exemplary ferulic esterases include but are not limited to the *M. thermophila* ferulic acid esterase (SEQ ID NO:182).

In some embodiments, the enzyme mixture comprises at least one or more cellulose hydrolyzing enzymes expressed by a fungal cell that has been genetically modified to reduce the amount of endogenous protease activity that is secreted by the cell, as described herein. In some embodiments, the fungal cell is a lignocellulose-utilizing cell from the family Chaetomiaceae. In some embodiments, the genetically modified fungal cell provided herein is a Chaetomiaceae family member selected from *Myceliophthora, Thielavia, Corynascus*, or *Chaetomium*. In some other embodiments, the genetically modified fungal cell can also be an anamorph or teleomorph of a Chaetomiaceae family member selected from *Myceliophthora, Thielavia, Corynascus*, or *Chaetomium*. In addition, the genetically modified fungal cell can also be selected from *Sporotrichum* or *Acremonium* or *Talaromyces*. It is also contemplated that the genetically modified fungal cell be selected from *Ctenomyces, Thermoascus*, and *Scytalidium*, including anamorphs and teleomorphs of fungal cells from those genera. In some embodiments, the fungal cell is a species selected from *Sporotrichum cellulophilum, Thielavia heterothallica, Corynascus heterothallicus, Thielavia terrestris, Chaetomium globosum, Talaromyces stipitatus, Talaromyces emersonii,* and *Myceliophthora thermophila*, including anamorphs and teleomorphs thereof.

In some embodiments, at least one cellulase in the mixtures of the present invention is produced by any suitable organism. In some embodiments, at least one cellulase in the mixtures is produced by *Acidothermus cellulolyticus, Thermobifida fusca, Humicola grisea, Myceliophthora thermophila, Chaetomium thermophilum, Acremonium* sp., *Thielavia* sp, *Trichoderma reesei, Aspergillus* sp., or *Chrysosporium* sp., and/or at least one enzyme produced in a heterologous organism. Indeed, it is not intended that the present invention be limited to enzymes produced by protease-deficient *Myceliophthora*. The present invention encompasses enzyme mixtures comprising enzymes produced by *Myceliophthora* in combination with at least one cellulase and/or other enzymes produced by any other suitable organisms, wherein at least one cellulase and/or enzyme is either homologous or heterologous to the cell producing the cellulase(s) and/or other enzyme(s). In some embodiments, the enzyme mixtures comprise bacterial, as well as fungal enzymes. In some embodiments, bacterial enzymes produced by and/or from organisms such as *Bacillus* find use. However, it is not intended that the present invention be limited to any particular bacterial organism and/or any particular bacterial enzyme, as any suitable organisms and/or enzymes find use in the present invention. In some embodiments, cellulase enzymes of the cellulase mixture work together, resulting in decrystallization and hydrolysis of the cellulose from a biomass substrate to yield fermentable sugars, such as but not limited to glucose.

In some embodiments, the enzyme mixture is contained in a vessel comprising a genetically modified fungal cell as described herein. In some embodiments, the vessel comprises a liquid medium. In some embodiments, the vessel is a flask, bioprocess reactor, or any other suitable container. In some embodiments, the enzyme mixture is in a liquid volume. In some embodiments, the liquid volume can be greater than about 0.01 mL, about 0.1 mL, about 1 mL, about 10 mL, about 100 mL, about 1000 mL, or greater than about 10 L, about 50 L, about 100 L, about 200 L, about 300 L, about 400 L, about 500 L, about 600 L, about 700 L, about 800 L, about 900 L, about 1000 L, about 10,000 L, about 50,000 L, about 100,000 L, about 250,000 L, about 500,000 L or greater than about 1,000,000 L.

In addition to the enzymes described above, other enzymes such as laccases find use in the mixtures of the present invention. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

Mn-dependent peroxidases also find use in the mixtures of the present invention. The enzymatic activity of Mn-dependent peroxidase (MnP) in is dependent on $Mn^{2+}$. Without being bound by theory, it has been suggested that the main role of this enzyme is to oxidize $Mn^{2+}$ to $Mn^{3+}$ (See e.g., Glenn et al. Arch. Biochem. Biophys., 251:688-696 [1986]). Subsequently, phenolic substrates are oxidized by the $Mn^{3+}$ generated.

Lignin peroxidases also find use in the mixtures of the present invention. Lignin peroxidase is an extracellular heme that catalyzes the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalysed oxidation of lignin in vivo (See e.g., Harvey et al., FEBS Lett., 195:242-246 [1986]).

In some embodiments, it may be advantageous to utilize an enzyme mixture that is cell-free. A cell-free enzyme mixture typically comprises enzymes that have been separated from any cells, including the cells that secreted the enzymes. Cell-free enzyme mixtures can be prepared using any of a variety of suitable methodologies that are known in the art (e.g., filtration or centrifugation). In some embodiments, the enzyme mixture is partially cell-free, substantially cell-free, or entirely cell-free.

In some embodiments, two or more cellulases and any additional enzymes present in the cellulase enzyme mixture are secreted from a single genetically modified fungal cell or by different microbes in combined or separate fermentations. Similarly, two or more cellulases and any additional enzymes present in the cellulase enzyme mixture may be expressed individually or in sub-groups from different strains of different organisms and the enzymes combined in vitro to make the cellulase enzyme mixture. It is also contemplated that the cellulases and any additional enzymes in the enzyme mixture are expressed individually or in sub-groups from different strains of a single organism, and the enzymes combined to make the cellulase enzyme mixture.

In some embodiments, the enzyme mixture comprises at least one or more cellulose hydrolyzing enzymes expressed by a fungal cell that has been genetically modified to reduce the amount of endogenous protease activity that is secreted by the cell, as described herein. In some embodiments, the fungal cell is a lignocellulose-utilizing cell from the family Chaetomiaceae. In some embodiments, the genetically modified fungal cell provided herein is a Chaetomiaceae family member selected from *Myceliophthora, Thielavia, Corynascus,* and *Chaetomium*. The genetically modified fungal cell can also be an anamorph or teleomorph of a Chaetomiaceae family member selected from *Myceliophthora, Thielavia, Corynascus,* and *Chaetomium*. In addition, the genetically modified fungal cell can also be selected from *Sporotrichum, Acremonium, Ctenomyces, Scytalidium* and *Thermoascus*, including anamorphs and teleomorphs of fungal cells from these genera. In some embodiments, the fungal cell is a species selected from *Sporotrichum cellulophilum, Thielavia heterothallica, Corynascus heterothallicus, Thielavia terrestris, Chaetomium globosum, Talaromyces stipitatus, Talaromyces emersonii,* and *Myceliophthora thermophila*, including anamorphs and teleomorphs thereof.

In some embodiments, the cellulase enzyme mixture of the present invention is produced in a fermentation process in which the fungal cells described herein are grown in submerged liquid culture fermentation. In some embodiments, submerged liquid fermentations of fungal cells are incubated using batch, fed-batch or continuous processing. In a batch process, all the necessary materials, with the exception of oxygen for aerobic processes, are placed in a reactor at the start of the operation and the fermentation is allowed to proceed until completion, at which point the product is harvested. In some embodiments, batch processes for producing the enzyme mixture of the present invention are carried out in a shake-flask or a bioreactor. In some embodiments in which a fed-batch process is used, the culture is fed continuously or sequentially with one or more media components without the removal of the culture fluid. In continuous processes, fresh medium is supplied and culture fluid is removed continuously at volumetrically equal rates to maintain the culture at a steady growth rate. Those of skill in the art will appreciate that fermentation medium is typically liquid, and comprises a carbon source, a nitrogen source as well as other nutrients, vitamins and minerals which can be added to the fermentation media to improve growth and enzyme production of the fungal cells. These other media components may be added prior to, simultaneously with or after inoculation of the culture with the fungal cells.

In some embodiments of the process for producing the enzyme mixture of the present invention, the carbon source comprises a carbohydrate that will induce the expression of the cellulase enzymes from the fungal cell. For example, in some embodiments, the carbon source comprises one or more of cellulose, cellobiose, sophorose, xylan, xylose, xylobiose, and/or related oligo- or poly-saccharides known to induce expression of cellulases and beta-glucosidase in such fungal cells. In some embodiments utilizing batch fermentation, the carbon source is added to the fermentation medium prior to or simultaneously with inoculation. In some embodiments utilizing fed-batch or continuous operations, the carbon source is supplied continuously or intermittently during the fermentation process. For example, in some embodiments, the carbon source is supplied at a carbon feed rate of between about 0.2 and about 2.5 g carbon/L of culture/h, or any suitable amount therebetween.

The methods for producing and/or utilizing the enzyme mixture(s) of the present invention may be carried at any suitable temperature, typically from about 20° C. to about 100° C., or any suitable temperature therebetween, for example from about 20° C. to about 80° C., 25° C. to about 65° C., or any suitable temperature therebetween, or from about 20° C., about 22° C., about 25° C., about 26° C., about 27° C., about 28° C., about 29° C., about 30° C., about 32° C., about 35° C., about 37° C., about 40° C., about 45° C., about 50° C., about 55° C., about 60° C., about 65° C., about 70° C., about 75° C., about 80° C., about 85° C. C, about 90° C., about 95° C., and/or any suitable temperature therebetween.

The methods for producing and/or utilizing the enzyme mixture(s) of the present invention may be carried out at any suitable pH, typically from about 3.0 to 8.0, or any suitable pH therebetween, for example from about pH 3.5 to pH 6.8, or any suitable pH therebetween, for example from about pH 3.0, about 3.2, about 3.4, about 3.5, about 3.7, about 3.8, about 4.0, about 4.1, about 4.2, about 4.3, about 4.4, about 4.5, about 4.6, about 4.7, about 4.8, about 4.9, about 5.0, about 5.2, about 5.4, about 5.5, about 5.7, about 5.8, about 6.0, about 6.2, about 6.5, about 6.8, about 7.0, about 7.2, about 7.5, about 8.0, or any suitable pH therebetween.

In some embodiments, following fermentation, the fermentation medium containing the fungal cells is used, or the fermentation medium containing the fungal cells and an exogenously supplied enzyme mixture is used, or the enzyme mixture is separated from the fungal cells, for example by filtration or centrifugation, and the enzyme mixture in the fermentation medium is used. In some embodiments, low molecular solutes such as unconsumed components of the fermentation medium are removed by ultrafiltration. In some embodiments, the enzyme mixture is concentrated by evaporation, precipitation, sedimentation, filtration, or any suitable means. In some embodiments, chemicals such as glycerol, sucrose, sorbitol, etc., are added to stabilize the enzyme mixture. In some embodiments, other chemicals, such as sodium benzoate or potassium sorbate, are added to the enzyme mixture to prevent growth of microbial contaminants.

The present invention also provides processes for generating glucose, comprising contacting cellulose with the enzyme mixture described herein. For example, in some embodiments, the process comprises contacting cellulose with an enzyme mixture comprising two or more cellulose hydrolyzing enzymes, wherein at least one of the two or more cellulose hydrolyzing enzymes is expressed by a fungal cell as described herein. In some embodiments, the method for generating glucose from cellulose using the enzyme mixture is batch hydrolysis, continuous hydrolysis, or a combination thereof. In some embodiments, the hydrolysis is agitated, unmixed, or a combination thereof.

Fermentation

In some embodiments, methods for generating sugar(s) described herein further comprise fermentation of the resultant sugar(s) to an end product. Fermentation involves the conversion of a sugar source (e.g., a soluble sugar) to an end product through the use of a fermenting organism. Any suitable organism finds use in the present invention, including bacterial and fungal organisms (e.g., yeast and filamentous fungi), suitable for producing a desired end product. Especially suitable fermenting organisms are able to ferment (i.e., convert), sugars, such as glucose, fructose, maltose, xylose, mannose and/or arabinose, directly or indirectly into a desired end product. Examples of fermenting organisms include fungal organisms such as yeast. In some embodiments, yeast strains, including but not limited to the following genera find use: the genus *Saccharomyces* (e.g., *S. cerevisiae* and *S. uvarum*); *Pichia* (e.g., *P. stipitis* and *P. pastoris*); *Candida* (e.g., *C. utilis*, *C. arabinofermentans*, *C. diddensii*, *C. sonorensis*, *C. shehatae*, *C. tropicalis*, and *C. boidinii*). Other fermenting organisms include, but are not limited to strains of *Zymomonas*, *Hansenula* (e.g., *H. polymorpha* and *H. anomala*), *Kluyveromyces* (e.g., *K. fragilis*), and *Schizosaccharomyces* (e.g., *S. pombe*).

In some embodiments, the fermenting organisms are strains of *Escherichia* (e.g., *E. coli*), *Zymomonas* (e.g., *Z. mobilis*), *Zymobacter* (e.g., *Z. palmae*), *Klebsiella* (e.g., *K. oxytoca*), *Leuconostoc* (e.g., *L. mesenteroides*), *Clostridium* (e.g., *C. butyricum*), *Enterobacter* (e.g., *E. aerogenes*) and *Thermoanaerobacter* (e.g., *Thermoanaerobacter* BG1L1 [See e.g., Georgieva and Ahring, Appl. Microbiol, Biotech., 77: 61-86] *T. ethanolicus*, *T. thermosaccharolyticum*, or *T. mathranii*), *Lactobacillus*, *Corynebacterium glutamicum* strain R, *Bacillus* thermoglucosidaisus, and *Geobacillus thermoglucosidasius*. It is not intended that the fermenting organism be limited to these particular strains, as any suitable organism finds use in the present invention.

The fermentation conditions depend on the desired fermentation product and can easily be determined by one of ordinary skill in the art. In some embodiments involving ethanol fermentation by yeast, fermentation is typically ongoing for between about 1 hour to about 120 hours, or about 12 to about 96 hours. In some embodiments, the fermentation is carried out at a temperature between about 20° C. to about 40° C., or between about 26° C. and about 34° C., or about 32° C. In some embodiments, the fermentation pH is from about pH 3 to about pH 7, while in some other embodiments, the pH is about 4 to about 6.

In some embodiments, enzymatic hydrolysis and fermentation are conducted in separate vessels, so that each biological reaction can occur under its respective optimal conditions (e.g., temperature). In some other embodiments, the methods for producing glucose from cellulose are conducted simultaneously with fermentation in a simultaneous saccharification and fermentation (i.e., "SSF") reaction. In some embodiments, SSF is typically carried out at temperatures of about 28° C. to about 50° C., or about 30° C. to about 40° C., or about 35° C. to about 38° C., which is a compromise between the about 50° C. optimum for most cellulase enzyme mixtures and the about 28° C. to about 30° C. optimum for most yeast.

In some embodiments, the methods for generating glucose further comprise fermentation of the glucose to a desired end product. It is not intended that the methods provided herein be limited to the production of any specific end product. In some embodiments, end products include fuel alcohols or precursor industrial chemicals. For example, in some embodiments, fermentation products include precursor industrial chemicals such as alcohols (e.g., ethanol, methanol and/or butanol); organic acids (e.g., butyric acid, citric acid, acetic acid, itaconic acid, lactic acid, and/or gluconic acid); ketones (e.g., acetone); amino acids (e.g., glutamic acid); gases (e.g., $H_2$ and/or $CO_2$); antimicrobials (e.g., penicillin and/or tetracycline); enzymes; vitamins (e.g., riboflavin, $B_{12}$, and/or beta-carotene); and/or hormones. In some embodiments, the end product is a fuel alcohol. Suitable fuel alcohols are known in the art and include, but are not limited to lower alcohols such as methanol, ethanol, butanol and propyl alcohols.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar), uM and µM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) (hour(s)); U (units); MW (molecular weight); rpm (rotations per minute); ° C. (degrees Centigrade); wt % (weight percent); w.r.t. (with regard to); DNA (deoxyribonucleic acid); RNA (ribonucleic acid); gDNA (genomic DNA); cDNA (complementary DNA); HPLC (high pressure liquid chromatography); MS (mass spectroscopy); LC (liquid chromatography); LC/MS (liquid charomatography/mass spectroscopy); LC/MS/MS (liquid chromatography/multi-stage mass spectroscopy); HMF (hydroxymethylfurfural); YPD (Yeast extract 10 g/L; Peptone 20 g/L; Dextrose 20 g/L); DCPIP (2,6-dichlorophenolindophenol); CV (column volume); NREL (National Renewable Energy Laboratory, Golden, Colo.); ARS (ARS Culture Collection or NRRL Culture Collection, Peoria, Ill.); Lallemand (Lallemand Ethanol Technology, Milwaukee, Wis.); Cayla (Cayla-InvivoGen, Toulouse, France); Agilent New Brunswick (New Brunswick Scientific Co., Edison, N.J.); Agilent Technologies (Agilent Technologies, Inc., Santa Clara, Calif.); Sigma (Sigma Aldrich, St. Louis, Mo.); Qiagen (Qiagen, Inc., Valencia, Calif.); Eppendorf (Eppendorf AG, Hamburg, Germany); GE Healthcare (GE Healthcare, Waukesha, Wis.); Bruker Optics (Bruker Optics, Inc., Billerica, Mass.); Specac (Specac, Inc., Cranston, R.I.); Invitrogen (Invitrogen, Corp., Carlsbad, Calif.); Alphalyse (Alphalyse, Inc., Palo Alto, Calif.); Promega (Promega, Corp., Madison, Wis.); Sartorius (Sartorius-Stedim Biotech, SA, Aubagne, France); Finnzymes (Finnzymes Oy, Espoo, FI [part of Thermo Fisher Scientific]), CalBiochem (CalBiochem, EMD Chemicals, Inc., Gibbstown, N.J.); and Bio-Rad (Bio-Rad Laboratories, Hercules, Calif.).

Genomic, cDNA, and amino acid sequences of the three proteases of the present invention including Protease #1 (SEQ ID NOS:1-3), Protease #2 (SEQ ID NOS:4-6), Protease #3 (SEQ ID NOS:7-9) and Protease #4 (SEQ ID NOS:10-12) are provided below. Protease #1 comprises contig_1809, Protease #2 comprises contig_690, and Protease #3 comprises contig_1086 as described in the Examples.

```
Protease #1:
gDNA:
                                          (SEQ ID NO: 1)
ATGCAGCTCCTTAGTCTCGCCGCTCTCCTCCCCCTTGCCCTTGCGGCACC

GGTGATCAAGCCTCAGGGGCTCCAGCTGATTCCGGGCGACTACATCGTGA

AGCTGAAGGACGGTGCGTCCGAGAGCACTCTCCAGGACACCATCCGGCAC

CTCCAGGCAGGCGAGGCCAAGCATGTCTACCGCGCACGCCGGTTCAAGGG

CTTCGCGGCCAAGCTGAGCCCGCAGGTGGTCGATACCCTGAGCAAGCTGC

CCGAGGTTCGTTCGTCGTCTCATGTGTAATTATGTCACAAAAAGGGATAT

GTAGGATGCTAATTCAGACCCGCAGGTCGAATACATTGAGCAGGACGCCG

TCGTCACCATCCAGGCGCTGGTCACCCAGGAGGACGTGCCCTGGGGTCTG

GCCCGCATCTCGCACCACGAACTGGGTCCCACGTCGTACGTATACGACGA

CAGCGCCGGCGAGGTACCTGCGCCTATGTCATCGACACGGGCATCTATG

TGGCCCACTCTGTAAGTCTGGCCGTCAATTCACCCACTCTCCCGCTGCTG

CCACCGAATCTCTATTAGTATCTTGACGACTTTGTTGCGGAGACAACGAC

GCTGACTCTTTTGACTCCAGCAGTTCGAAGGCGCGCGACGTGGCTGGCC

AACTTTATCGACAGCAGCGATAGCGAGTCAGTTTAGCATCCCCCACCCCC

TGGTTGTTGCACTTGAATGAGCTGACCTTTCATAAATAAACAGCGGCGCG
```

```
GGCCACGGCACGCACGTGTCGGGCACGATCGGCGGCGTGACGTACGGCGT

GGCCAAGAAGACCAAGCTGTTCGCGGTCAAGGTGCTCAACGCGAGCGGGT

CGGGGACGGTGTCGTCGGTGCTGGCGGGGCTCGAGTTCGTCGCGTCGGAC

GCGCCGGCGCGCGTCGCCTCGGGCGAGTGCGCCAACGGCGCGGTCGCCAA

CCTGAGCCTCGGCGGCGGCCGGTCCACCGCCATCAACGCCGCCGCCGCCG

CCGCCGTCGACGCGGGCGTCTTCGTCGCCGTCGCGGCCGGCAACAGCAAC

ACCGACGCCCAGTCCACCTCCCCCGCCAGCGAGCCCAGCGTCTGCACCGT

CGGCGCCACCGACGACAGCGACGCCCGCGCCTACTTCTCCAACTACGGCA

GCGTCGTCGACGTCTTTGCTCCCGGCGTCGACGTCCTCAGCAGCTGGATC

GGCGGTGTCGATGCCACTGTGAGTTTTTTTTTTTCCTTTTCCCGTTTCTT

TTTGCTTCTTGTTTTCTCCCCATTTTGATGTTTTACATTACTTTCCTTCT

TCGTTGGCCGGATTCGTTTTCATCCTTTTTTTCTTCTTTCTTCTGTCAAA

AGGCGATAACAAGGGATGATGCGGAAAGAGAAGAGGAATAAAAACGGG

GAACCAGAACAAGAACATACCAGGCTGACTGGAAAACAAACAGAACACCA

TCTCGGGCACCTCGATGGCGACCCCGCATATCGCCGGCCTCGGGGCCTAT

CTCCTCGCTCTGCTGGGCCCCAGGTCGCCCGAGGAACTGTGCGAGTACAT

CAAGCAGACGGCCACCATCGGCACCATCACCAGCCTCCCCAGCGGCACCA

TCAACGCCATTGCCTACAACGGTGCTACAGCCTAA cDNA:
                                          (SEQ ID NO: 2)
ATGCAGCTCCTTAGTCTCGCCGCTCTCCTCCCCCTTGCCCTTGCGGCACC

GGTGATCAAGCCTCAGGGGCTCCAGCTGATTCCGGGCGACTACATCGTGA

AGCTGAAGGACGGTGCGTCCGAGAGCACTCTCCAGGACACCATCCGGCAC

CTCCAGGCAGGCGAGGCCAAGCATGTCTACCGCGCACGCCGGTTCAAGGG

CTTCGCGGCCAAGCTGAGCCCGCAGGTGGTCGATACCCTGAGCAAGCTGC

CCGAGGTCGAATACATTGAGCAGGACGCCGTCGTCACCATCCAGGCGCTG

GTCACCCAGGAGGACGTGCCCTGGGGTCTGGCCCGCATCTCGCACCACGA

ACTGGGTCCCACGTCGTACGTATACGACGACAGCGCCGGCGAGGGTACCT

GCGCCTATGTCATCGACACGGGCATCTATGTGGCCCACTCTCAGTTCGAA

GGCCGCGCGACGTGGCTGGCCAACTTTATCGACAGCAGCGATAGCGACGG

CGCGGGCCACGGCACGCACGTGTCGGGCACGATCGGCGGCGTGACGTACG

GCGTGGCCAAGAAGACCAAGCTGTTCGCGGTCAAGGTGCTCAACGCGAGC

GGGTCGGGGACGGTGTCGTCGGTGCTGGCGGGGCTCGAGTTCGTCGCGTC

GGACGCGCCGGCGCGCGTCGCCTCGGGCGAGTGCGCCAACGGCGCGGTCG

CCAACCTGAGCCTCGGCGGCGGCCGGTCCACCGCCATCAACGCCGCCGCC

GCCGCCGCCGTCGACGCGGGCGTCTTCGTCGCCGTCGCGGCCGGCAACAG

CAACACCGACGCCCAGTCCACCTCCCCCGCCAGCGAGCCCAGCGTCTGCA

CCGTCGGCGCCACCGACGACAGCGACGCCCGCGCCTACTTCTCCAACTAC

GGCAGCGTCGTCGACGTCTTTGCTCCCGGCGTCGACGTCCTCAGCAGCTG

GATCGGCGGTGTCGATGCCACTAACACCATCTCGGGCACCTCGATGGCGA

CCCCGCATATCGCCGGCCTCGGGGCCTATCTCCTCGCTCTGCTGGGCCCC
```

-continued
AGGTCGCCCGAGGAACTGTGCGAGTACATCAAGCAGACGGCCACCATCGG
CACCATCACCAGCCTCCCCAGCGGCACCATCAACGCCATTGCCTACAACG
GTGCTACAGCCTAA Polypeptide:
(SEQ ID NO: 3)
MQLLSLAALLPLALAAPVIKPQGLQLIPGDYIVKLKDGASESTLQDTIRH
LQAGEAKHVYRARRFKGFAAKLSPQVVDTLSKLPEVEYIEQDAVVTIQAL
VTQEDVPWGLARISHHELGPTSYVYDDSAGEGTCAYVIDTGIYVAHSQFE
GRATWLANFIDSSDSDGAGHGTHVSGTIGGVTYGVAKKTKLFAVKVLNAS
GSGTVSSVLAGLEFVASDAPARVASGECANGAVANLSLGGGRSTAINAAA
AAAVDAGVFVAVAAGNSNTDAQSTSPASEPSVCTVGATDDSDARAYFSNY
GSVVDVFAPGVDVLSSWIGGVDATNTISGTSMATPHIAGLGAYLLALLGP
RSPEELCEYIKQTATIGTITSLPSGTINAIAYNGATA Protease #2:
gDNA:
(SEQ ID NO: 4)
ATGAGGTTACTCCGCACCGCGGGAGCGGCAACTCTCTTCCTGTCGCCCGC
CACTTTTGCGACCAACAACCCTCTGACCCCAGGCAAACTTGAGGCGGACA
TTAGAACCGAAGAGTATGAGAAGCAACAGTGCCAAACCTTTGATCCCTC
TCATTCGTTAACGAATATTGCCAAACCAGGTTGCAAAATGTCCTCTGGAA
CCTCAATCACATTGCGGTCACCCACGGCGGCAACCGAGCCTTTGGCGAGC
CTGGGTACAAAGCCTCGCTCGACTTTATTCTCGAGCGCGCCCAGACACGC
TTCCACAATGAGTTTGACACTGTCGTTCAGCCCTTCAACCACACCTACGG
CAAGACGAACCAGATCAAGGTGACTGGACCAGAGGGCGAGGATGTCTTTG
TCATCAGCCCATTGTACAATCCCGCCACGCCGCTGCCTGATGGTATCACC
GCTCCCTTGGTAGATACACCGGTCGATGACGAGCGCGGATCGGCGTGCTT
TCCGGACCAGTGGGAGGGGGTCGATGTGAAGGGGAAGCTGGTACTAGTAA
AGAGAGGCATTTGTGCTGTGGCAGATAAGTCGGCCCTTGCTAAGGAGCGC
GGGGCACTGGGTGAGCTACGTCCTGGCTGACGGGGGAAGCAAACGTTGAC
GTCGCTCTAGGGGTGATCTTGTATAACGAACAGCCGGGTACGAACATCGT
CGTCCCGACTCTGGGTGCAGAGAGCATCGGCAAGACTGTTCCTATCGGAA
TTATTCCCTTGGAAGTAGGACAGAGCTGGAAGTCCCGGTTGGCAGATGGC
GAGGAGGTGACTGTGCACCTGCTGGTCGATTCCATATCCGATACGCGCGA
GACGTGGAACATTATTGCCGAGACCAAACAGGGCGACCCCGACAAAGTTA
TCATGCTCGGTGCACATCTCGACAGCGTGCAGGCGGGAGCAGGCATCAAT
GACGACGGCAGCGGCACGGCAGCTCTCCTGGAGATCTTGACCGCGGTCCG
GCGCTACGATGGATTCCCACATAAGATTCGGTTCGCCTGGTGGGCAGCAG
AAGAGAGTGGTCTGGTCGGATCCCTCTACTACACCTCCCACTTGACCGAG
GAGGAAGCCGACCGCATCAAGTATTACTTCAACTACGACATGATTGGCTC
TCCCCATCCCGACTTTGAAATTGCAAGCGATGGCAACAGCGGAGTCGGGC
CGCAGCTTCTGGAGGAATACCTCGTCGAGCAGGGGAAGGAGATTGTCCAC
GGGTAAGTAGATCCCACTCCAGCTCCACATCTATTTTGCGTACCTGGTAC
CTCTATGATATGTGCAGGTTCCGCTGACCTTGGGATGCAAGCGGCTTCGG -continued
TTCTGGCTCCGATTTTGTGGGCTTCCTCGAGCTTGGCATCCCGAGTACCG
CGCTACATACCGGTGCAGGAGCTCCATTCGACGAATGCTACCACCAGGCG
TGTGATGACCTCGACAATATCAACTGGGAGGCGCTGACCGTCAATGCCAA
AGCGGCCGCTCGGGCGGCTGCCCGGCTGGCCAACTCGCTCGAGGGCGTGC
CGCCCCGCAAGAAAACTAGCCTGAATCTTCACACGCGCCGTGGAGTGGTG
CAAAACTTCCGAAAGTGGGCTTCATTGGCCGAGGAAGCGAGCCACGGGCA
CACGTGCTCGCACACGGGAAGAGGGTCGTAGTGTAA cDNA:
(SEQ ID NO: 5)
ATGAGGTTACTCCGCACCGCGGGAGCGGCAACTCTCTTCCTGTCGCCCGC
CACTTTTGCGACCAACAACCCTCTGACCCCAGGCAAACTTGAGGCGGACA
TTAGAACCGAAGAGTTGCAAAATGTCCTCTGGAACCTCAATCACATTGCG
GTCACCCACGGCGGCAACCGAGCCTTTGGCGAGCCTGGGTACAAAGCCTC
GCTCGACTTTATTCTCGAGCGCGCCCAGACACGCTTCCACAATGAGTTTG
ACACTGTCGTTCAGCCCTTCAACCACACCTACGGCAAGACGAACCAGATC
AAGGTGACTGGACCAGAGGGCGAGGATGTCTTTGTCATCAGCCCATTGTA
CAATCCCGCCACGCCGCTGCCTGATGGTATCACCGCTCCCTTGGTAGATA
CACCGGTCGATGACGAGCGCGGATCGGCGTGCTTTCCGGACCAGTGGGAG
GGGGTCGATGTGAAGGGGAAGCTGGTACTAGTAAAGAGAGGCATTTGTGC
TGTGGCAGATAAGTCGGCCCTTGCTAAGGAGCGCGGGGCACTGGGGGTGA
TCTTGTATAACGAACAGCCGGGTACGAACATCGTCGTCCCGACTCTGGGT
GCAGAGAGCATCGGCAAGACTGTTCCTATCGGAATTATTCCCTTGGAAGT
AGGACAGAGCTGGAAGTCCCGGTTGGCAGATGGCGAGGAGGTGACTGTGC
ACCTGCTGGTCGATTCCATATCCGATACGCGCGAGACGTGGAACATTATT
GCCGAGACCAAACAGGGCGACCCCGACAAAGTTATCATGCTCGGTGCACA
TCTCGACAGCGTGCAGGCGGGAGCAGGCATCAATGACGACGGCAGCGGCA
CGGCAGCTCTCCTGGAGATCTTGACCGCGGTCCGGCGCTACGATGGATTC
CCACATAAGATTCGGTTCGCCTGGTGGGCAGCAGAAGAGAGTGGTCTGGT
CGGATCCCTCTACTACACCTCCCACTTGACCGAGGAGGAAGCCGACCGCA
TCAAGTATTACTTCAACTACGACATGATTGGCTCTCCCCATCCCGACTTT
GAAATTGCAAGCGATGGCAACAGCGGAGTCGGGCCGCAGCTTCTGGAGGA
ATACCTCGTCGAGCAGGGGAAGGAGATTGTCCACGCGGGCTTCGGTTCTG
GCTCCGATTTTGTGGGCTTCCTCGAGCTTGGCATCCCGAGTACCGCGCTA
CATACCGGTGCAGGAGCTCCATTCGACGAATGCTACCACCAGGCGTGTGA
TGACCTCGACAATATCAACTGGGAGGCGCTGACCGTCAATGCCAAAGCGG
CCGCTCGGGCGGCTGCCCGGCTGGCCAACTCGCTCGAGGGCGTGCCGCCC
CGCAAGAAAACTAGCCTGAATCTTCACACGCGCCGTGGAGTGGTGCAAAA
CTTCCGAAAGTGGGCTTCATTGGCCGAGGAAGCGAGCCACGGGCACACGT
GCTCGCACACGGGAAGAGGGTCGTAGTGTAA Polypeptide:
(SEQ ID NO: 6)
MRLLRTAGAATLFLSPATFATNNPLTPGKLEADIRTEELQNVLWNLNHIA
VTHGGNRAFGEPGYKASLDFILERAQTRFHNEFDTVVQPFNHTYGKTNQI KVTGPEGEDVFVISPLYNPATPLPDGITAPLVDTPVDDERGSACFPDQWE
GVDVKGKLVLVKRGICAVADKSALAKERGALGVILYNEQPGTNIVVPTLG
AESIGKTVPIGIIPLEVGQSWKSRLADGEEVTVHLLVDSISDTRETWNII
AETKQGDPDKVIMLGAHLDSVQAGAGINDDGSGTAALLEILTAVRRYDGF
PHKIRFAWWAAEESGLVGSLYYTSHLTEEEADRIKYYFNYDMIGSPHPDF
EIASDGNSGVGPQLLEEYLVEQGKEIVHGGFGSGSDFVGFLELGIPSTAL
HTGAGAPFDECYHQACDDLDNINWEALTVNAKAAARAAARLANSLEGVPP
RKKTSLNLHTRRGVVQNFRKWASLAEEASHGHTCSHTGKRVVV Protease #3:
gDNA:
(SEQ ID NO: 7)
ATGTGTTGGCTGTGGGAGCGATCAGTGGCAATATTACTGGCGGCCGGCGT
GATCGCCAACCCGCTCCGCCCGCGCCGGATCCCCTGGCCGGAGCCGGTTC
CGGCATCTTCCATCGGGCCCATTGACTGGTCTTCAATACCGCCTTCTCCC
TACAAACACGCCTTGCGGCAGACCAACACCACCACGACCAGCAGCAGTAG
CAGCAGCAGCAGCAGCAAATATGACAATCAAGTCTACTCGGTACAGGTCT
CGGGATCTTCCTCCTCCCCGCCAGCATCCGTCGACTGGCGCAACCGCGAC
GGCCAGAACTACATCACGACACCGCAGGACCAGGGCGCCTGTAACAGCTG
CTGGGCGTTCGCCGTGGCGGCGCTGATCGAGTCCATGATGCGCATCGAGC
ACGGGGTCTGGGGCAAGCGCAGCGAGGCCGACGTGCACGACGGGGTGGGC
GCGGCGTGCGAGAGCGTGGGCAACGCCGAGGACACGCTGGCCTGGGTGGC
CGGGCAGGGGCCCGAATTCGTCGCCGACCCGACCCGGCCCGCCCCGGGCA
TCGCCGACTGGGCCTGCGACCCCTACGAGGCGACGGCGCACGCCTACGAG
CACTGCGACGACCGCTCCGGGCGCACGACGCACATTCCCTACTACCAGGC
CCTCGGCCTGGTCGAGGACCAGAAGCGGTGGCTGGACGAGTACGGGCCCA
TCATCGCCACCTTTGTCCTCTACGACGACTTTGGCTCGTGGAAGCCGACC
GCGGCCGGCGGAAGCGGCGGTGACGTGTACCGGTGGGACGGCGTTTCCGG
CTCGGACGGCAACCACCTCGCCATCGTGATCGGCTACGACGACGAGAAGC
AGGCCTGGCTTATGAAGAACTCATGGGATCCGGATGGGGGACGAGGGA
TTTGTCTACTTTGCGTAAGTCAGGGGTTCCACTGCTTTTTTTTTTTCCC
CTCCAAAATCGTTTGCCTCTCGGTAATTTTATCCGCATCCAGGGAACTGA
CAACAGATACAGGTACGGCGAGGCCAACATCGACAACTGGACCAAGTATG
GGCTCGTCAATGTCAACCCGGACCCGTGGACACGCAGGAAGCACCAGAGC
GGAAGCATGATGCAATCCGGCAACGGCGAGACGCACCGAAACTTTGAGCT
GCTCGTCAGCGAGGCCGGGGGTTCCGGCTTCACGCACGTCTCCCGCGATG
GGAACAGTACCCAATGGAGCAAGGTGCTGGAGGTCTCGGGCAGCGGCAGC
GGCAGCGGCCTCGTGGGCCAGCCTGCCATTCTCGGCACCTCCTTCAACCG
GGACTTCCACGCGGTGAGCCTGGATGAGAACCAGGTGGTCCAACAGTGGG
CATACAGACAGTCGGAGATGCGCTGGTCCCGGGTCTCGGCCATCGAGGGC
ACTAAGATCGACGGCTTTCCCGGTCTCGCCCAGAGCGACGGCTCAACTCT
GGTCATGGTGGTCAAGCACGCCGACGGCACCCTGAACGAGGTAAGCATAT
CTTGCCGGAAGTCATAATTAACGAAGGAAGATCTTCCGTAAAAGAAAAGG AAAAGATGAAAAAAAAAAGGTACACGTGCTAACGGCGGATCGCACAAGTG
GCAACAAGCACCCAACAGCACAACCTGGACCCTGGCCAACTCACCCATCG
CAAGCGGCATCGCCCAGAGCGGGCCGGCGCTCGTGCAGTCCAACGCCGGA
CTCAACCTCTACGACCGGCAGCAGGGCGCCTCGCGGGGCAACATCTACAC
CGTCGCGGTCCGCGAGGACGGCAAGCTGCAGCTCTTCTGGCGCCCCGGCG
CGGACGCGGCCGGGTGGTCGGCCGGGGAGGTGTTCGGCGGCTCCGGCGTC
GTGGACCCCGGCTCGCCGCCCGTCATGATTCAGGACTACTCGGGGACGGC
CAACGAGACGAGCGTCGGCCGGTTCCAGCTGGCCGTCGCCGTCGGGGGGA
GCGTCCAACACTGGGAGCGGGCCAACGACGACCTCGAGGCCGGGCAGGCC
CCGCCCGCGGGGGCAGAAGGGGGGTCCCCGGCGGGCAGGTGGGAACTGGT
CGAGACGGCGGGCACCGGGGTGAAGCGCGTCTGGGCGCTGCTCCAGGGGA
GCTTTGGTGGGAGGCTGCACATGATCACGGAGGGCACGGACGGCCGGCTG
TCGTACTGGGAGCGCGATGAGAAGTGGGTTGAGGTCGAGAAGCTGCCGGC
GTTGAGCGACGCCGCTTGGACGAGATCGGGCCCGGTGAGTGGTGGTTGAG
GGTAGTCCCAAGTACCTGATTATAATTATATGAAAGAGATGTCCCCCGAA
TAATTATATGAGTGAACCAACGACCATGAAGACATGCGGCTTTATCAGCA
TACCGACGCGACTTGTCCTGGTTGCATCTGCTACGACCCCTGATTAATTA
CAACACCGCACAGCGGCAGAGACGGGGCCAGAAGCTGCACATAGAAAGAA
GGCTGGACAACTTCCCCGAGACGCTATAA cDNA:
(SEQ ID NO: 8)
ATGTGTTGGC TGTGGGAGCG ATCAGTGGCA ATATTACTGG
CGGCCGGCGT GATCGCCAAC CCGCTCCGCC CGCGCCGGAT
CCCCTGGCCG GAGCCGGTTC CGGCATCTTC CATCGGGCCC
ATTGACTGGT CTTCAATACC GCCTTCTCCC TACAAACACG
CCTTGCGGCA GACCAACACC ACCACGACCA GCAGCAGTAG
CAGCAGCAGC AGCAGCAAAT ATGACAATCA AGTCTACTCG
GTACAGGTCT CGGGATCTTC CTCCTCCCCG CCAGCATCCG
TCGACTGGCG CAACCGCGAC GGCCAGAACT ACATCACGAC
ACCGCAGGAC CAGGGCGCCT GTAACAGCTG CTGGGCGTTC
GCCGTGGCGG CGCTGATCGA GTCCATGATG CGCATCGAGC
ACGGGGTCTG GGGCAAGCGC AGCGAGGCCG ACGTGCACGA
CGGGGTGGGC GCGGCGTGCG AGAGCGTGGG CAACGCCGAG
GACACGCTGG CCTGGGTGGC CGGGCAGGGG CCCGAATTCG
TCGCCGACCC GACCCGGCCC GCCCCGGGCA TCGCCGACTG
GGCCTGCGAC CCCTACGAGG CGACGGCGCA CGCCTACGAG
CACTGCGACG ACCGCTCCGG GCGCACGACG CACATTCCCT
ACTACCAGGC CCTCGGCCTG GTCGAGGACC AGAAGCGGTG
GCTGGACGAG TACGGGCCCA TCATCGCCAC CTTTGTCCTC
TACGACGACT TTGGCTCGTG GAAGCCGACC GCGGCCGGCG
GAAGCGGCGG TGACGTGTAC CGGTGGGACG GCGTTTCCGG

```
CTCGGACGGC AACCACCTCG CCATCGTGAT CGGCTACGAC
GACGAGAAGC AGGCCTGGCT TATGAAGAACT CATGGGGATCCGGATGG
GGGGACGAGGGA TTTGTCTACT TTGCGTACGG CGAGGCCAAC
ATCGACAACT GGACCAAGTA TGGGCTCGTC AATGTCAACC
CGGACCCGTG GACACGCAGG AAGCACCAGAGCGGAAGCATGATGCAAT
CC GGCAACGGCG AGACGCACCG AAACTTTGAG CTGCTCGTCA
GCGAGGCCGGGGGTTCCGGC TTCACGCACG TCTCCCGCGA
TGGGAACAGT ACCCAATGGA GCAAGGTGCT GGAGGTCTCG
GGCAGCGGCA GCGGCAGCGG CCTCGTGGGC CAGCCTGCCA
TTCTCGGCAC CTCCTTCAACCGGGACTTCC ACGCGGTGAG
CCTGGATGAG AACCAGGTGG TCCAACAGTGGCATACAGA
CAGTCGGAGA TGCGCTGGTC CCGGGTCTCG GCCATCGAGG
GCACTAAGAT CGACGGCTTTCCCGGTCTCG CCCAGAGCGA
CGGCTCAACT CTGGTCATGG TGGTCAAGCA CGCCGACGGC
ACCCTGAACG AGTGGCAACA AGCACCCAAC AGCACAACCT
GGACCCTGGCCAACTCACCC ATCGCAAGCG GCATCGCCCA
GAGCGGGCCG GCGCTCGTGC AGTCCAACGCGGACTCAAC
CTCTACGACC GGCAGCAGGG CGCCTCGCGG GGCAACATCT
ACACCGTCGC GGTCCGCGAGGACGGCAAGC TGCAGCTCTT
CTGGCGCCCC GGCGCGGACG CGGCCGGGTGGTCGGCCGGG
GAGGTGTTCG GCGGCTCCGG CGTCGTGGAC CCCGGCTCGC
CGCCCGTCAT GATTCAGGAC TACTCGGGGA CGGCCAACGA
GACGAGCGTC GGCCGGTTCC AGCTGGCCGTCGCCGTCGGG
GGGAGCGTCC AACACTGGGA GCGGGCCAAC GACGACCTCGAGGCCGG
GCAGGCCCCGCCC GCGGGGGCAG AAGGGGGGTC CCGGCGGGCAGGTG
GGAACTGGTCGAGACGGCGGGCACC GGGGTGAAGC GCGTCTGGGC
GCTGCTCCAG GGGAGCTTTG GTGGGAGGCT GCACATGATC
ACGGAGGGCA CGGACGGCCG GCTGTCGTAC TGGGAGCGCGATGAGAA
GTGGGTTGAGGTC GAGAAGCTGC CGGCGTTGAG CGACGCCGCT
TGGACGAGAT CGGGCCCGGTGAGTGGTGGTTGA

Polypeptide:
                                        (SEQ ID NO: 9)
MCWLWERSVA ILLAAGVIAN PLRPRRIPWP EPVPASSIGP
IDWSSIPPSP YKHALRQTNT TTTSSSSSSS SSKYDNQVYS
VQVSGSSSSP PASVDWRNRD GQNYITTPQD QGACNSCWAF
AVAALIESMM RIEHGVWGKR SEADVHDGVG AACESVGNAE
DTLAWVAGQG PEFVADPTRP APGIADWACD PYEATAHAYE
HCDDRSGRTT HIPIYYQALGL VEDQKRWLDE YGPIIATFVL
YDDFGSWKPT AAGGSGGDVY RWDGVSGSDGNHLAIVIGYDDEKQAWLM
KNSWGSGWGDEG FVYFAYGEAN IDNWTKYGLV NVNPDPWTRR
KHQSGSMMQS GNGETHRNFE LLVSEAGGSG FTHVSRDGNS
TQWSKVLEVS GSGSGSGLVG QPAILGTSFN RDFHAVSLDE
NQVVQQWAYR QSEMRWSRVS AIEGTKIDGF PGLAQSDGST
LVMVVKHADG TLNEWQQAPN STTWTLANSP IASGIAQSGP
ALVQSNAGLN LYDRQQGASR GNIYTVAVRE DGKLQLFWRP
GADAAGWSAG EVFGGSGVVD PGSPPVMIQD YSGTANETSV
GRFQLAVAVG GSVQHWERAN DDLEAGQAPP AGAEGGSPAG
RWELVETAGT GVKRVWALLQ GSFGGRLHMI TEGTDGRLSY
WERDEKWVEV EKLPALSDAA WTRSGPVSGG Protease #4:
gDNA:
                                        (SEQ ID NO: 10)
ATGTGTTGGCTGTGGGAGCGATCAGTGGCAATATTACTGGCGGCCGGCGT
GATCGCCAACCCGCTCCGCCCGCGCCGGATCCCCTGGCCGGAGCCGGTTC
CGGCATCTTCCATCGGGCCCATTGACTGGTCTTCAATACCGCCTTCTCCC
TACAAACACGCCTTGCGGCAGACCAACACCACCACGACCAGCAGCAGTAG
CAGCAGCAGCAGCAAATATGACAATCAAGTCTACTCGGTACAGGTCT
CGGGATCTTCCTCCTCCCCGCCAGCATCCGTCGACTGGCGCAACCGCGAC
GGCCAGAACTACATCACGACACCGCAGGACCAGGGCGCCTGTAACAGCTG
CTGGGCGTTCGCCGTGGCGGCGCTGATCGAGTCCATGATGCGCATCGAGC
ACGGGGTCTGGGGCAAGCGCAGCGAGGCCGACGTGCACGACGGGGTGGGC
GCGGCGTGCGAGAGCGTGGGCAACGCCGAGGACACGCTGGCCTGGGTGGC
CGGGCAGGGGCCCGAATTCGTCGCCGACCCGACCCGGCCCGCCCCGGGCA
TCGCCGACTGGGCCTGCGACCCCTACGAGGCGACGGCGCACGCCTACGAG
CACTGCGACGACCGCTCCGGGCGCACGACGCACATTCCCTACTACCAGGC
CCTCGGCCTGGTCGAGGACCAGAAGCGGTGGCTGGACGAGTACGGGCCCA
TCATCGCCACCTTTGTCCTCTACGACGACTTTGGCTCGTGGAAGCCGACC
GCGGCCGGCGGAAGCGGCGGTGACGTGTACCGGTGGGACGGCGTTTCCGG
CTCGGACGGCAACCACCTCGCCATCGTGATCGGCTACGACGACGAGAAGC
AGGCCTGGCTTATGAAGAACTCATGGGGATCCGGATGGGGGACGAGGGA
TTTGTCTACTTTGCGTAAGTCAGGGGTTCCACTGCTTTTTTTTTTCCC
CTCCAAAATCGTTTGCCTCTCGGTAATTTTATCCGCATCCAGGGAACTGA
CAACAGATACAGGTACGGCGAGGCCAACATCGACAACTGGACCAAGTATG
GGCTCGTCAATGTCAACCCGGACCCGTGGACACGCAGGAAGCACCAGAGC
GGAAGCATGATGCAATCCGGCAACGGCGAGACGCACCGAAACTTTGAGCT
GCTCGTCAGCGAGGCCGGGGGTTCCGGCTTCACGCACGTCTCCCGCGATG
GGAACAGTACCCAATGGAGCAAGGTGCTGGAGGTCTCGGGCAGCGGCAGC
GGCAGCGGCCTCGTGGGCCAGCCTGCCATTCTCGGCACCTCCTTCAACCG
GGACTTCCACGCGGTGAGCCTGGATGAGAACCAGGTGGTCCAACAGTGGG
CATACAGACAGTCGGAGATGCGCTGGTCCCGGGTCTCGGCCATCGAGGGC
ACTAAGATCGACGGCTTTCCCGGTCTCGCCCAGAGCGACGGCTCAACTCT
GGTCATGGTGGTCAAGCACGCCGACGGCACCCTGAACGAGGTAAGCATAT
CTTGCCGGAAGTCATAATTAACGAAGGAAGATCTTCCGTAAAAGAAAAGG
AAAAGATGAAAAAAAAAAGGTACACGTGCTAACGGCGGATCGCACAAGTG
```

-continued

```
GCAACAAGCACCCAACAGCACAACCTGGACCCTGGCCAACTCACCCATCG
CAAGCGGCATCGCCCAGAGCGGGCCGGCGCTCGTGCAGTCCAACGCCGGA
CTCAACCTCTACGACCGGCAGCAGGGCGCCTCGCGGGGCAACATCTACAC
CGTCGCGGTCCGCGAGGACGGCAAGCTGCAGCTCTTCTGGCGCCCCGGCG
CGGACGCGGCCGGGTGGTCGGCCGGGGAGGTGTTCGGCGGCTCCGGCGTC
GTGGACCCCGGCTCGCCGCCCGTCATGATTCAGGACTACTCGGGGACGGC
CAACGAGACGAGCGTCGGCCGGTTCCAGCTGGCCGTCGCCGTCGGGGGGA
GCGTCCAACACTGGGAGCGGGCCAACGACGACCTCGAGGCCGGGCAGGCC
CCGCCCGCGGGGCAGAAGGGGGGTCCCCGGCGGGCAGGTGGGAACTGGT
CGAGACGGCGGGCACCGGGGTGAAGCGCGTCTGGGCGCTGCTCCAGGGGA
GCTTTGGTGGAGGCTGCACATGATCACGGAGGGCACGGACGGCCGGCTG
TCGTACTGGGAGCGCGATGAGAAGTGGGTTGAGGTCGAGAAGCTGCCGGC
GTTGAGCGACGCCGCTTGGACGAGATCGGGCCCGGTGAGTGGTGGTTGAG
GGTAGTCCCAAGTACCTGATTATAATTATATGAAAGAGATGTCCCCCGAA
TAATTATATGAGTGAACCAACGACCATGAAGACATGCGGCTTTATCAGCA
TACCGACGCGACTTGTCCTGGTTGCATCTGCTACGACCCCTGATTAATTA
CAACACCGCACAGCGGCAGAGACGGGGCCAGAAGCTGCACATAGAAAGAA
GGCTGGACAACTTCCCCGAGACGCTA
``` cDNA:

(SEQ ID NO: 11)
```
ATGTGTTGGCTGTGGGAGCGATCAGTGGCAATATTACTGGCGGCCGGCGT
GATCGCCAACCCGCTCCGCCCGCGCCGGATCCCCTGGCCGGAGCCGGTTC
CGGCATCTTCCATCGGGCCCATTGACTGGTCTTCAATACCGCCTTCTCCC
TACAAACACGCCTTGCGGCAGACCAACACCACCACGACCAGCAGCAGTAG
CAGCAGCAGCAGCAGCAAATATGACAATCAAGTCTACTCGGTACAGGTCT
CGGGATCTTCCTCCTCCCCGCCAGCATCCGTCGACTGGCGCAACCGCGAC
GGCCAGAACTACATCACGACACCGCAGGACCAGGGCGCCTGTAACAGCTG
CTGGGCGTTCGCCGTGGCGGCGCTGATCGAGTCCATGATGCGCATCGAGC
ACGGGGTCTGGGGCAAGCGCAGCGAGGCCGACGTGCACGACGGGGTGGGC
GCGGCGTGCGAGAGCGTGGGCAACGCCGAGGACACGCTGGCCTGGGTGGC
CGGGCAGGGGCCCGAATTCGTCGCCGACCCGACCCGGCCCGCCCCGGGCA
TCGCCGACTGGGCCTGCGACCCCTACGAGGCGACGGCGCACGCCTACGAG
CACTGCGACGACCGCTCCGGGCGCACGACGCACATTCCCTACTACCAGGC
CCTCGGCCTGGTCGAGGACCAGAAGCGGTGGCTGGACGAGTACGGGCCCA
TCATCGCCACCTTTGTCCTCTACGACGACTTTGGCTCGTGGAAGCCGACC
GCGGCCGGCGGAAGCGGCGGTGACGTGTACCGGTGGGACGGCGTTTCCGG
CTCGGACGGCAACCACCTCGCCATCGTGATCGGCTACGACGACGAGAAGC
AGGCCTGGCTTATGAAGAACTCATGGGGATCCGGATGGGGGACGAGGGA
TTTGTCTACTTTGCGTACGGCGAGGCCAACATCGACAACTGGACCAAGTA
TGGGCTCGTCAATGTCAACCCGGACCCGTGGACACGCAGGAAGCACCAGA
GCGGAAGCATGATGCAATCCGGCAACGGCGAGACGCACCGAAACTTTGAG
```

-continued

```
CTGCTCGTCAGCGAGGCCGGGGGTTCCGGCTTCACGCACGTCTCCCGCGA
TGGGAACAGTACCCAATGGAGCAAGGTGCTGGAGGTCTCGGGCAGCGGCA
GCGGCAGCGGCCTCGTGGGCCAGCCTGCCATTCTCGGCACCTCCTTCAAC
CGGGACTTCCACGCGGTGAGCCTGGATGAGAACCAGGTGGTCCAACAGTG
GGCATACAGACAGTCGGAGATGCGCTGGTCCCGGGTCTCGGCCATCGAGG
GCACTAAGATCGACGGCTTTCCCGGTCTCGCCCAGAGCGACGGCTCAACT
CTGGTCATGGTGGTCAAGCACGCCGACGGCACCCTGAACGAGTGGCAACA
AGCACCCAACAGCACAACCTGGACCCTGGCCAACTCACCCATCGCAAGCG
GCATCGCCCAGAGCGGGCCGGCGCTCGTGCAGTCCAACGCCGGACTCAAC
CTCTACGACCGGCAGCAGGGCGCCTCGCGGGGCAACATCTACACCGTCGC
GGTCCGCGAGGACGGCAAGCTGCAGCTCTTCTGGCGCCCCGGCGCGGACG
CGGCCGGGTGGTCGGCCGGGGAGGTGTTCGGCGGCTCCGGCGTCGTGGAC
CCCGGCTCGCCGCCCGTCATGATTCAGGACTACTCGGGGACGGCCAACGA
GACGAGCGTCGGCCGGTTCCAGCTGGCCGTCGCCGTCGGGGGGAGCGTCC
AACACTGGGAGCGGGCCAACGACGCCTCGAGGCCGGGCAGGCCCCGCCCG
CGGGGGCAGAAGGGGGGTCCCCGGCGGGCAGGTGGGAACTGGTCGAGACG
GCGGGCACCGGGGTGAAGCGCGTCTGGGCGCTGCTCCAGGGGAGCTTTGG
TGGGAGGCTGCACATGATCACGGAGGGCACGGACGGCCGGCTGTCGTACT
GGGAGCGCGATGAGAAGTGGGTTGAGGTCGAGAAGCTGCCGGCGTTGAGC
GACGCCGCTTGGACGAGATCGGGCCCGGTGAGTGGTGGTTGA
```

Polypeptide:

(SEQ ID NO: 12)
MCWLWERSVAILLAAGVIANPLRPRRIPWPEPVPASSIGPIDWSSIPPSP
YKHALRQTNTTTTSSSSSSSSSSKYDNQVYSVQVSGSSSSPPASVDWRNRD
GQNYITTPQDQGACNSCWAFAVAALIESMMRIEHGVWGKRSEADVHDGVG
AACESVGNAEDTLAWVAGQGPEFVADPTRPAPGIADWACDPYEATAHAYE
HCDDRSGRTTHIPYYQALGLVEDQKRWLDEYGPIIATFVLYDDFGSWKPT
AAGGSGGDVYRWDGVSGSDGNHLAIVIGYDDEKQAWLMKNSWGSGWGDEG
FVYFAYGEANIDNWTKYGLVNVNPDPWTRRKHQSGSMMQSGNGETHRNFE
LLVSEAGGSGFTHVSRDGNSTQWSKVLEVSGSGSGSGLVGQPAILGTSFN
RDFHAVSLDENQVVQQWAYRQSEMRWSRVSAIEGTKIDGFPGLAQSDGST
LVMVVKHADGTLNEWQQAPNSTTWTLANSPIASGIAQSGPALVQSNAGLN
LYDRQQGASRGNIYTVAVREDGKLQLFWRPGADAAGWSAGEVFGGSGVVD
PGSPPVMIQDYSGTANETSVGRFQLAVAVGGSVQHWERANDDLEAGQAPP
AGAEGGSPAGRWELVETAGTGVKRVWALLQGSFGGRLHMITEGTDGRLSY
WERDEKWVEVEKLPALSDAAWTRSGPRQRRGQKLHIERRLDNFPETL

The wild-type *M. thermophila* C1 GH61a cDNA (SEQ ID NO:13) and amino acid (SEQ ID NO:14) sequences are provided below. The signal sequence is underlined in SEQ ID NO:14. SEQ ID NO:15 provides the GH61a sequence without the signal sequence.

(SEQ ID NO: 13)
```
ATGTCCAAGGCCTCTGCTCTCCTCGCTGGCCTGACGGGCGCGGCCCTCGT
CGCTGCACATGGCCACGTCAGCCACATCGTCGTCAACGGCGTCTACTACA
```

-continued

```
GGAACTACGACCCCACGACAGACTGGTACCAGCCCAACCCGCCAACAGTC
ATCGGCTGGACGGCAGCCGATCAGGATAATGGCTTCGTTGAACCCAACAG
CTTTGGCACGCCAGATATCATCTGCCACAAGAGCGCCACCCCCGGCGGCG
GCCACGCTACCGTTGCTGCCGGAGACAAGATCAACATCGTCTGGACCCCC
GAGTGGCCCGAATCCCACATCGGCCCCGTCATTGACTACCTAGCCGCCTG
CAACGGTGACTGCGAGACCGTCGACAAGTCGTCGCTGCGCTGGTTCAAGA
TTGACGGCGCCGGCTACGACAAGGCCGCCGGCCGCTGGGCCGCCGACGCT
CTGCGCGCCAACGGCAACAGCTGGCTCGTCCAGATCCCGTCGGATCTCAA
GGCCGGCAACTACGTCCTCCGCCACGAGATCATCGCCCTCCACGGTGCTC
AGAGCCCCAACGGCGCCCAGGCCTACCCGCAGTGCATCAACCTCCGCGTC
ACCGGCGGCGGCAGCAACCTGCCCAGCGGCGTCGCCGGCACCTCGCTGTA
CAAGGCGACCGACCCGGGCATCCTCTTCAACCCCTACGTCTCCTCCCCGG
ATTACACCGTCCCCGGCCCGGCCCTCATTGCCGGCGCCGCCAGCTCGATC
GCCCAGAGCACGTCGGTCGCCACTGCCACCGGCACGGCCACCGTTCCCGG
CGGCGGCGGCGCCAACCCTACCGCCACCACCACCGCCGCCACCTCCGCCG
CCCCGAGCACCACCCTGAGGACGACCACTACCTCGGCCGCGCAGACTACC
GCCCCGCCCTCCGGCGATGTGCAGACCAAGTACGGCCAGTGTGGTGGCAA
CGGATGGACGGGCCCGACGGTGTGCGCCCCCGGCTCGAGCTGCTCCGTCC
TCAACGAGTGGTACTCCCAGTGTTTGTAA
```

(SEQ ID NO: 14)
MSKASALLAGLTGAALVAAHGHVSHIVVNGVYYRNYDPTTDWYQPNPPTV
IGWTAADQDNGFVEPNSFGTPDIICHKSATPGGGHATVAAGDKINIVWTP
EWPESHIGPVIDYLAACNGDCETVDKSSLRWFKIDGAGYDKAAGRWAADA
LRANGNSWLVQIPSDLKAGNYVLRHEIIALHGAQSPNGAQAYPQCINLRV
TGGGSNLPSGVAGTSLYKATDPGILFNPYVSSPDYTVPGPALIAGAASSI
AQSTSVATATGTATVPGGGGANPTATTTAATSAAPSTTLRTTTTSAAQTT
APPSGDVQTKYGQCGGNGWTGPTVCAPGSSCSVLNEWYSQCL (SEQ ID NO: 15)
HGHVSHIVVNGVYYRNYDPTTDWYQPNPPTVIGWTAADQDNGFVEPNSFG
TPDIICHKSATPGGGHATVAAGDKINIVWTPEWPESHIGPVIDYLAACNG
DCETVDKSSLRWFKIDGAGYDKAAGRWAADALRANGNSWLVQIPSDLKAG
NYVLRHEIIALHGAQSPNGAQAYPQCINLRVTGGGSNLPSGVAGTSLYKA
TDPGILFNPYVSSPDYTVPGPALIAGAASSIAQSTSVATATGTATVPGGG
GANPTATTTAATSAAPSTTLRTTTTSAAQTTAPPSGDVQTKYGQCGGNGW
TGPTVCAPGSSCSVLNEWYSQCL

The cDNA sequence of a *M. thermophila* GH61a variant ("Variant 1") (SEQ ID NO:16) and amino acid (SEQ ID NO:17) sequence are provided below. The signal sequence is underlined in SEQ ID NO:17. SEQ ID NO:18 provides the GH61a Variant 1 sequence without the signal sequence.

(SEQ ID NO: 16)
ATGTCCAAGGCCTCTGCTCTCCTCGCTGGCCTGACGGGCGCGGCCCTCGT
CGCTGCACACGGCCACGTCAGCCACATCGTCGTCAACGGCGTCTACTACA

-continued

```
GGGGCTACGACCCCACGACAGACTGGTACCAGCCCAACCCGCCAACAGTC
ATCGGCTGGACGGCAGCCGATCAGGATAATGGCTTCGTTGAACCCAACAG
CTTTGGCACGCCAGATATCATCTGCCACAAGAGCGCCACCCCCGGCGGCG
GCCACGCTACCGTTGCTGCCGGAGACAAGATCAACATCGTCTGGACCCCC
GAGTGGCCCCACTCCCACATCGGCCCCGTCATTGACTACCTAGCCGCCTG
CAACGGTGACTGCGAGACCGTCGACAAGTCGTCGCTGCGCTGGTTCAAGA
TTGACGGCGCCGGCTACGACAAGGCCGCCGGCCGCTGGGCCGCCGACGCT
CTGCGCGCCAACGGCAACAGCTGGCTCGTCCAGATCCCGTCGGATCTCAA
GCCCGGCAACTACGTCCTCCGCCACGAGATCATCGCCCTCCACGGTGCTC
AGAGCCCCAACGGCGCCCAGGCGTACCCGCAGTGCATCAACCTCCGCGTC
ACCGGCGGCGGCAGCAACCTGCCCAGCGGCGTCGCCGGCACCTCGCTGTA
CAAGGCGACCGACCCGGGCATCCTCTTCAACCCCTACGTCTCCTCCCCGG
ATTACACCGTCCCCGGCCCGGCCCTCATTGCCGGCGCCGCCAGCTCGATC
GCCCAGAGCACGTCGGTCGCCACTGCCACCGGCACGGCCACCGTTCCCGG
CGGCGGCGGCGCCAACCCTACCGCCACCACCACCGCCGCCACCTCCGCCG
CCCCGAGCACCACCCTGAGGACGACCACTACCTCGGCCGCGCAGACTACC
GCCCCGCCCTCCGGCGATGTGCAGACCAAGTACGGCCAGTGTGGTGGCAA
CGGATGGACGGGCCCGACGGTGTGCGCCCCCGGCTCGAGCTGCTCCGTCC
TCAACGAGTGGTACTCCCAGTGTTTGTAA
```

(SEQ ID NO: 17)
MSKASALLAGLTGAALVAAHGHVSHIVVNGVYYRGYDPTTDWYQPNPPTV
IGWTAADQDNGFVEPNSFGTPDIICHKSATPGGGHATVAAGDKINIVWTP
EWPHSHIGPVIDYLAACNGDCETVDKSSLRWFKIDGAGYDKAAGRWAADA
LRANGNSWLVQIPSDLKPGNYVLRHEIIALHGAQSPNGAQAYPQCINLRV
TGGGSNLPSGVAGTSLYKATDPGILFNPYVSSPDYTVPGPALIAGAASSI
AQSTSVATATGTATVPGGGGANPTATTTAATSAAPSTTLRTTTTSAAQTT
APPSGDVQTKYGQCGGNGWTGPTVCAPGSSCSVLNEWYSQCL (SEQ ID NO: 18)
HGHVSHIVVNGVYYRGYDPTTDWYQPNPPTVIGWTAADQDNGFVEPNSFG
TPDIICHKSATPGGGHATVAAGDKINIVWTPEWPHSHIGPVIDYLAACNG
DCETVDKSSLRWFKIDGAGYDKAAGRWAADALRANGNSWLVQIPSDLKPG
NYVLRHEIIALHGAQSPNGAQAYPQCINLRVTGGGSNLPSGVAGTSLYKA
TDPGILFNPYVSSPDYTVPGPALIAGAASSIAQSTSVATATGTATVPGGG
GANPTATTTAATSAAPSTTLRTTTTSAAQTTAPPSGDVQTKYGQCGGNGW
TGPTVCAPGSSCSVLNEWYSQCL

The cDNA sequence of a *M. thermophila* GH61a variant ("Variant 5") (SEQ ID NO:19) and amino acid (SEQ ID NO:20) sequence are provided below. The signal sequence is underlined in SEQ ID NO:20. SEQ ID NO:21 provides the GH61a Variant 5 sequence without the signal sequence.

(SEQ ID NO: 19)
ACACAAATGTCCAAGGCCTCTGCTCTCCTCGCTGGCCTGACGGGCGCGGC
CCTCGTCGCTGCACACGGCCACGTCAGCCACATCGTCGTCAACGGCGTCT
ACTACAGGAACTACGACCCCACGACAGACTGGTACCAGCCCAACCCGCCA

```
ACAGTCATCGGCTGGACGGCAGCCGATCAGGATAATGGCTTCGTTGAACC

CAACAGCTTTGGCACGCCAGATATCATCTGCCACAAGAGCGCCACCCCCG

GCGGCGGCCACGCTACCGTTGCTGCCGGAGACAAGATCAACATCGTATGG

ACCCCCGAGTGGCCCCACTCCCACATCGGCCCCGTCATTGACTACCTAGC

CGCCTGCAACGGTGACTGCGAGACCGTCGACAAGTCGTCGCTGCGCTGGT

TCAAGATTGACGGCGCCGGCTACGACAAGGCCGCCGGCCGCTGGGCCGCC

GACGCTCTGCGCGCCAACGGCAACAGCTGGCTCGTCCAGATCCCGTCGGA

TCTCGCGGCCGGCAACTACGTCCTCCGCCACGAGATCATCGCCCTCCACG

GTGCTCAGAGCCCCAACGGCGCCCAGGCGTACCCGCAGTGCATCAACCTC

CGCGTCACCGGCGGCGGCAGCAACCTGCCCAGCGGCGTCGCCGGCACCTC

GCTGTACAAGGCGACCGACCCGGGCATCCTCTTCAACCCCTACGTCTCCT

CCCCGGATTACACCGTCCCCGGCCCGGCCCTCATTGCCGGCGCCGCCAGC

TCGATCGCCCAGAGCACGTCGGTCGCCACTGCCACCGGCACGGCCACCGT

TCCCGGCGGCGGCGGCGCCAACCCTACCGCCACCACCACCGCCGCCACCT

CCGCCGCCCCGAGCACCACCCTGAGGACGACCACTACCTCGGCCGCGCAG

ACTACCGCCCCGCCCTCCGGCGATGTGCAGACCAAGTACGGCCAGTGTGG

TGGCAACGGATGGACGGGCCCGACGGTGTGCGCCCCCGGCTCGAGCTGCT

CCGTCCTCAACGAGTGGTACTCCCAGTGTTTGTAA
```

(SEQ ID NO: 20)
MSKASALLAGLTGAALVAAHGHVSHIVVNGVYYRNYDPTTDWYQPNPPTV

IGWTAADQDNGFVEPNSFGTPDIICHKSATPGGGHATVAAGDKINIVWTP

EWPHSHIGPVIDYLAACNGDCETVDKSSLRWFKIDGAGYDKAAGRWAADA

LRANGNSWLVQIPSDLAAGNYVLRHEIIALHGAQSPNGAQAYPQCINLRV

TGGGSNLPSGVAGTSLYKATDPGILFNPYVSSPDYTVPGPALIAGAASSI

AQSTSVATATGTATVPGGGGANPTATTTAATSAAPSTTLRTTTTSAAQTT

APPSGDVQTKYGQCGGNGWTGPTVCAPGSSCSVLNEWYSQCL (SEQ ID NO: 21)
HGHVSHIVVNGVYYRNYDPTTDWYQPNPPTVIGWTAADQDNGFVEPNSFG

TPDIICHKSATPGGGHATVAAGDKINIVWTPEWPHSHIGPVIDYLAACNG

DCETVDKSSLRWFKIDGAGYDKAAGRWAADALRANGNSWLVQIPSDLAAG

NYVLRHEIIALHGAQSPNGAQAYPQCINLRVTGGGSNLPSGVAGTSLYKA

TDPGILFNPYVSSPDYTVPGPALIAGAASSIAQSTSVATATGTATVPGGG

GANPTATTTAATSAAPSTTLRTTTTSAAQTTAPPSGDVQTKYGQCGGNGW

TGPTVCAPGSSCSVLNEWYSQCL

The cDNA sequence of a *M. thermophila* GH61a variant ("Variant 9") (SEQ ID NO:22) and amino acid (SEQ ID NO:23) sequence are provided below. The signal sequence is underlined in SEQ ID NO:23. SEQ ID NO:24 provides Variant 9 sequence without the signal sequence.

(SEQ ID NO: 22)
ACAAACATGTCCAAGGCCTCTGCTCTCCTCGCTGGCCTGACGGGCGCGGC

CCTCGTCGCTGCACATGGCCACGTCAGCCACATCGTCGTCAACGGCGTCT

```
ACTACAGGAACTACGACCCCACGACAGACTGGTACCAGCCCAACCCGCCA

ACAGTCATCGGCTGGACGGCAGCCGATCAGGATAATGGCTTCGTTGAACC

CAACAGCTTTGGCACGCCAGATATCATCTGCCACAAGAGCGCCACCCCCG

GCGGCGGCCACGCTACCGTTGCTGCCGGAGACAAGATCAACATCCAGTGG

ACCCCCGAGTGGCCCGAATCCCACATCGGCCCCGTCATTGACTACCTAGC

CGCCTGCAACGGTGACTGCGAGACCGTCGACAAGTCGTCGCTGCGCTGGT

TCAAGATTGACGGCGCCGGCTACGACAAGGCCGCCGGCCGCTGGGCCGCC

GACGCTCTGCGCGCCAACGGCAACAGCTGGCTCGTCCAGATCCCGTCGGA

TCTCAAGGCCGGCAACTACGTCCTCCGCCACGAGATCATCGCCCTCCACG

GTGCTCAGAGCCCCAACGGCGCCCAGAACTACCCGCAGTGCATCAACCTC

CGCGTCACCGGCGGCGGCAGCAACCTGCCCAGCGGCGTCGCCGGCACCTC

GCTGTACAAGGCGACCGACCCGGGCATCCTCTTCAACCCCTACGTCTCCT

CCCCGGATTACACCGTCCCCGGCCCGGCCCTCATTGCCGGCGCCGCCAGC

TCGATCGCCCAGAGCACGTCGGTCGCCACTGCCACCGGCACGGCCACCGT

TCCCGGCGGCGGCGGCGCCAACCCTACCGCCACCACCACCGCCGCCACCT

CCGCCGCCCCGAGCACCACCCTGAGGACGACCACTACCTCGGCCGCGCAG

ACTACCGCCCCGCCCTCCGGCGATGTGCAGACCAAGTACGGCCAGTGTGG

TGGCAACGGATGGACGGGCCCGACGGTGTGCGCCCCCGGCTCGAGCTGCT

CCGTCCTCAACGAGTGGTACTCCCAGTGTTTGTAA
```

(SEQ ID NO: 23)
MSKASALLAGLTGAALVAAHGHVSHIVVNGVYYRNYDPTTDWYQPNPPTV

IGWTAADQDNGFVEPNSFGTPDIICHKSATPGGGHATVAAGDKINIQWTP

EWPESHIGPVIDYLAACNGDCETVDKSSLRWFKIDGAGYDKAAGRWAADA

LRANGNSWLVQIPSDLKAGNYVLRHEIIALHGAQSPNGAQNYPQCINLRV

TGGGSNLPSGVAGTSLYKATDPGILFNPYVSSPDYTVPGPALIAGAASSI

AQSTSVATATGTATVPGGGGANPTATTTAATSAAPSTTLRTTTTSAAQTT

APPSGDVQTKYGQCGGNGWTGPTVCAPGSSCSVLNEWYSQCL (SEQ ID NO: 24)
HGHVSHIVVNGVYYRNYDPTTDWYQPNPPTVIGWTAADQDNGFVEPNSFG

TPDIICHKSATPGGGHATVAAGDKINIQWTPEWPESHIGPVIDYLAACNG

DCETVDKSSLRWFKIDGAGYDKAAGRWAADALRANGNSWLVQIPSDLKAG

NYVLRHEIIALHGAQSPNGAQNYPQCINLRVTGGGSNLPSGVAGTSLYKA

TDPGILFNPYVSSPDYTVPGPALIAGAASSIAQSTSVATATGTATVPGGG

GANPTATTTAATSAAPSTTLRTTTTSAAQTTAPPSGDVQTKYGQCGGNGW

TGPTVCAPGSSCSVLNEWYSQCL

The polynucleotide (SEQ ID NO:25) and amino acid (SEQ ID NO:26) sequences of an *M. thermophila* GH61b are provided below. The signal sequence is shown underlined in SEQ ID NO:26. SEQ ID NO:27 provides the sequence of this GH61b without the signal sequence.

(SEQ ID NO: 25)
ATGAAGCTCTCCCTCTTTTCCGTCCTGGCCACTGCCCTCACCGTCGAGG

GGCATGCCATCTTCCAGAAGGTCTCCGTCAACGGAGCGGACCAGGGCTCC

```
CTCACCGGCCTCCGCGCTCCCAACAACAACAACCCCGTGCAGAATGTCAA

CAGCCAGGACATGATCTGCGGCCAGTCGGGATCGACGTCAACACTATCA

TCGAGGTCAAGGCCGGCGATAGGATCGGTGCCTGGTATCAGCATGTCATC

GGCGGTGCCCAGTTCCCCAACGACCCAGACAACCCGATTGCCAAGTCGCA

CAAGGGCCCCGTCATGGCCTACCTCGCCAAGGTTGACAATGCCGCAACCG

CCAGCAAGACGGGCCTGAAGTGGTTCAAGATTTGGGAGGATACCTTTAAT

CCCAGCACCAAGACCTGGGGTGTCGACAACCTCATCAACAACAACGGCTG

GGTGTACTTCAACCTCCCGCAGTGCATCGCCGACGGCAACTACCTCCTCC

GCGTCGAGGTCCTCGCTCTGCACTCGGCCTACTCCCAGGGCCAGGCTCAG

TTCTACCAGTCCTGCGCCCAGATCAACGTATCCGGCGGCGGCTCCTTCAC

GCCGGCGTCGACTGTCAGCTTCCCGGGTGCCTACAGCGCCAGCGACCCCG

GTATCCTGATCAACATCTACGGCGCCACCGGCCAGCCCGACAACAACGGC

CAGCCGTACACTGCCCCTGGGCCCGCGCCCATCTCCTGC
```
                                                (SEQ ID NO: 26)
<u>MKLSLFSVLATALTVEGHA</u>IFQKVSVNGADQGSLTGLRAPNNNNPVQNVN

SQDMICGQSGSTSNTIIEVKAGDRIGAWYQHVIGGAQFPNDPDNPIAKSH

KGPVMAYLAKVDNAATASKTGLKWFKIWEDTFNPSTKTWGVDNLINNNGW

VYFNLPQCIADGNYLLRVEVLALHSAYSQGQAQFYQSCAQINVSGGGSFT

PASTVSFPGAYSASDPGILINIYGATGQPDNNGQPYTAPGPAPISC (SEQ ID NO: 27)
IFQKVSVNGADQGSLTGLRAPNNNNPVQNVNSQDMICGQSGSTSNTIIEV

KAGDRIGAWYQHVIGGAQFPNDPDNPIAKSHKGPVMAYLAKVDNAATASK

TGLKWFKIWEDTFNPSTKTWGVDNLINNNGWVYFNLPQCIADGNYLLRVE

VLALHSAYSQGQAQFYQSCAQINVSGGGSFTPASTVSFPGAYSASDPGIL

INIYGATGQPDNNGQPYTAPGPAPISC

The polynucleotide (SEQ ID NO:28) and amino acid (SEQ ID NO:29) sequences of an *M. thermophila* GH61c are provided below. The signal sequence is shown underlined in SEQ ID NO:29. SEQ ID NO:30 provides the sequence of this GH61c without the signal sequence.

```
                                                (SEQ ID NO: 28)
ATGGCCCTCCAGCTCTTGGCGAGCTTGGCCCTCCTCTCAGTGCCGGCCCT

TGCCCACGGTGGCTTGGCCAACTACACCGTCGGTGATACTTGGTACAGAG

GCTACGACCCAAACCTGCCGCCGGAGACGCAGCTCAACCAGACCTGGATG

ATCCAGCGGCAATGGGCCACCATCGACCCCGTCTTCACCGTGTCGGAGCC

GTACCTGGCCTGCAACAACCCGGGCGCGCCGCCGCCCTCGTACATCCCCA

TCCGCGCCGGTGACAAGATCACGGCCGTGTACTGGTACTGGCTGCACGCC

ATCGGGCCCATGAGCGTCTGGCTCGCGCGTGCGGCGACACGCCCGCGGC

CGACTGCCGCGACGTCGACGTCAACCGGGTCGGCTGGTTCAAGATCTGGG

AGGGCGGCCTGCTGGAGGGTCCCAACCTGGCCGAGGGGCTCTGGTACCAA

AAGGACTTCCAGCGCTGGGACGGCTCCCCGTCCCTCTGGCCCGTCACGAT

CCCCAAGGGGCTCAAGAGCGGGACCTACATCATCCGGCACGAGATCCTGT

CGCTTCACGTCGCCCTCAAGCCCCAGTTTTACCCGGAGTGTGCGCATCTG

AATATTACTGGGGGCGGAGACTTGCTGCCACCCGAAGAGACTCTGGTGCG

GTTTCCGGGGGTTTACAAAGAGGACGATCCCTCTATCTTCATCGATGTCT

ACTCGGAGGAGAACGCGAACCGGACAGATTATACGGTTCCGGGAGGGCCA

ATCTGGGAAGGG
```
                                                (SEQ ID NO: 29)
<u>MALQLLASLALLSVPALAHGGLA</u>NYTVGDTWYRGYDPNLPPETQLNQTWM

IQRQWATIDPVFTVSEPYLACNNPGAPPPSYIPIRAGDKITAVYWYWLHA

IGPMSVWLARCGDTPAADCRDVDVNRVGWFKIWEGGLLEGPNLAEGLWYQ

KDFQRWDGSPSLWPVTIPKGLKSGTYIIRHEILSLHVALKPQFYPECAHL

NITGGGDLLPPEETLVRFPGVYKEDDPSIFIDVYSEENANRTDYTVPGGP

IWEG (SEQ ID NO: 30)
NYTVGDTWYRGYDPNLPPETQLNQTWMIQRQWATIDPVFTVSEPYLACNN

PGAPPPSYIPIRAGDKITAVYWYWLHAIGPMSVWLARCGDTPAADCRDVD

VNRVGWFKIWEGGLLEGPNLAEGLWYQKDFQRWDGSPSLWPVTIPKGLKS

GTYIIRHEILSLHVALKPQFYPECAHLNITGGGDLLPPEETLVRFPGVYK

EDDPSIFIDVYSEENANRTDYTVPGGPIWEG

The polynucleotide (SEQ ID NO:31) and amino acid (SEQ ID NO:32) sequences of an *M. thermophila* GH61d are provided below. The signal sequence is shown underlined in SEQ ID NO:32. SEQ ID NO:33 provides the sequence of this GH61d without the signal sequence.

```
                                                (SEQ ID NO: 31)
ATGAAGGCCCTCTCTCTCCTTGCGGCTGCCGGGGCAGTCTCTGCGCATAC

CATCTTCGTCCAGCTCGAAGCAGACGGCACGAGGTACCCGGTTTCGTACG

GGATCCGGGACCCAACCTACGACGGCCCCATCACCGACGTCACATCCAAC

GACGTTGCTTGCAACGGCGGTCCGAACCCGACGACCCCCTCCAGCGACGT

CATCACCGTCACCGCGGGCACCACCGTCAAGGCCATCTGGAGGCACACCC

TCCAATCCGGCCCGGACGATGTCATGGACGCCAGCCACAAGGGCCCGACC

CTGGCCTACATCAAGAAGGTCGGCGATGCCACCAAGGACTCGGGCGTCGG

CGGTGGCTGGTTCAAGATCCAGGAGGACGGTTACAACAACGGCCAGTGGG

GCACCAGCACCGTTATCTCCAACGGCGGCGAGCACTACATTGACATCCCG

GCCTGCATCCCCGAGGGTCAGTACCTCCTCCGCGCCGAGATGATCGCCCT

CCACGCGGCCGGGTCCCCGGCGGCGCTCAGCTCTACATGGAATGTGCCC

AGATCAACATCGTCGGCGGCTCCGGCTCGGTGCCCAGCTCGACGGTCAGC

TTCCCCGGCGCGTATAGCCCCAACGACCCGGGTCTCCTCATCAACATCTA

TTCCATGTCGCCCTCGAGCTCGTACACCATCCCGGGCCCGCCCGTTTTCA

AGTGC
```
                                                (SEQ ID NO: 32)
<u>MKALSLLAAAGAVSA</u>HTIFVQLEADGTRYPVSYGIRDPTYDGPITDVTSN

DVACNGGPNPTTPSSDVITVTAGTTVKAIWRHTLQSGPDDVMDASHKGPT

LAYIKKVGDATKDSGVGGGWFKIQEDGYNNGQWGTSTVISNGGEHYIDIP

```
ACIPEGQYLLRAEMIALHAAGSPGGAQLYMECAQINIVGGSGSVPSSTVS

FPGAYSPNDPGLLINIYSMSPSSSYTIPGPPVFKC
```

(SEQ ID NO: 33)
```
HTIFVQLEADGTRYPVSYGIRDPTYDGPITDVTSNDVACNGGPNPTTPSS

DVITVTAGTTVKAIWRHTLQSGPDDVMDASHKGPTLAYIKKVGDATKDSG

VGGGWFKIQEDGYNNGQWGTSTVISNGGEHYIDIPACIPEGQYLLRAEMI

ALHAAGSPGGAQLYMECAQINIVGGSGSVPSSTVSFPGAYSPNDPGLLIN

IYSMSPSSSYTIPGPPVFKC
```

The polynucleotide (SEQ ID NO:34) and amino acid (SEQ ID NO:35) sequences of an *M. thermophila* GH61e are provided below. The signal sequence is shown underlined in SEQ ID NO:35. SEQ ID NO:36 provides the sequence of this GH61d without the signal sequence.

(SEQ ID NO: 34)
```
ATGAAGTCGTCTACCCCGGCCTTGTTCGCCGCTGGGCTCCTTGCTCAGCA

TGCTGCGGCCCACTCCATCTTCCAGCAGGCGAGCAGCGGCTCGACCGACT

TTGATACGCTGTGCACCCGGATGCCGCCCAACAATAGCCCCGTCACTAGT

GTGACCAGCGGCGACATGACCTGCAAAGTCGGCGGCACCAAGGGGGTGTC

CGGCTTCTGCGAGGTGAACGCCGGCGACGAGTTCACGGTTGAGATGCACG

CGCAGCCCGGCGACCGCTCGTGCGCCAACGAGGCCATCGGCGGGAACCAC

TTCGGCCCGGTCCTCATCTACATGAGCAAGGTCGACGACGCCTCCACCGC

CGACGGGTCCGGCGACTGGTTCAAGGTGGACGAGTTCGGCTACGACGCAA

GCACCAAGACCTGGGGCACCGACAAGCTCAACGAGAACTGCGGCAAGCGC

ACCTTCAACATCCCCAGCCACATCCCCGCGGGCGACTATCTCGTCCGGGC

CGAGGCTATCGCGCTACACACTGCCAACCAGCCAGGCGGCGCGCAGTTCT

ACATGAGCTGCTATCAAGTCAGGATTTCCGGCGGCGAAGGGGCCAGCTG

CCTGCCGGAGTCAAGATCCCGGGCGCGTACAGTGCCAACGACCCCGGCAT

CCTTGTCGACATCTGGGGTAACGATTTCAACGACCCTCCAGGACACTCGG

CCCGTCACGCCATCATCATCATCAGCAGCAGCAGCAACAACAGCGGCGCC

AAGATGACCAAGAAGATCCAGGAGCCCACCATCACATCGGTCACGGACCT

CCCCACCGACGAGGCCAAGTGGATCGCGCTCCAAAAGATCTCGTACGTGG

ACCAGACGGGCACGGCGCGGACATACGAGCCGGCGTCGCGCAAGACGCGG

TCGCCAAGAGTCTAG
```

(SEQ ID NO: 35)
<u>MKSSTPALFAAGLLAQHAAAH</u>SIFQQASSGSTDFDTLCTRMPPNNSPVTS
VTSGDMTCKVGGTKGVSGFCEVNAGDEFTVEMHAQPGDRSCANEAIGGNH
FGPVLIYMSKVDDASTADGSGDWFKVDEFGYDASTKTWGTDKLNENCGKR
TFNIPSHIPAGDYLVRAEAIALHTANQPGGAQFYMSCYQVRISGGEGGQL
PAGVKIPGAYSANDPGILVDIWGNDFNDPPGHSARHAIIIISSSSNNSGA
KMTKKIQEPTITSVTDLPTDEAKWIALQKISYVDQTGTARTYEPASRKTR
SPRV (SEQ ID NO: 36)
HSIFQQASSGSTDFDTLCTRMPPNNSPVTSVTSGDMTCKVGGTKGVSGFC
EVNAGDEFTVEMHAQPGDRSCANEAIGGNHFGPVLIYMSKVDDASTADGS
GDWFKVDEFGYDASTKTWGTDKLNENCGKRTFNIPSHIPAGDYLVRAEAI
ALHTANQPGGAQFYMSCYQVRISGGEGGQLPAGVKIPGAYSANDPGILVD
IWGNDFNDPPGHSARHAIIIISSSSNNSGAKMTKKIQEPTITSVTDLPTD
EAKWIALQKISYVDQTGTARTYEPASRKTRSPRV

The polynucleotide (SEQ ID NO:37) and amino acid (SEQ ID NO:38) sequences of an alternative *M. thermophila* GH61e are provided below. The signal sequence is shown underlined in SEQ ID NO:38. SEQ ID NO:39 provides the sequence of this GH61e without the signal sequence.

(SEQ ID NO: 37)
```
ATGAAGTCGTCTACCCCGGCCTTGTTCGCCGCTGGGCTCCTTGCTCAGCA

TGCTGCGGCCCACTCCATCTTCCAGCAGGCGAGCAGCGGCTCGACCGACT

TTGATACGCTGTGCACCCGGATGCCGCCCAACAATAGCCCCGTCACTAGT

GTGACCAGCGGCGACATGACCTGCAACGTCGGCGGCACCAAGGGGGTGTC

GGGCTTCTGCGAGGTGAACGCCGGCGACGAGTTCACGGTTGAGATGCACG

CGCAGCCCGGCGACCGCTCGTGCGCCAACGAGGCCATCGGCGGGAACCAC

TTCGGCCCGGTCCTCATCTACATGAGCAAGGTCGACGACGCCTCCACTGC

CGACGGGTCCGGCGACTGGTTCAAGGTGGACGAGTTCGGCTACGACGCAA

GCACCAAGACCTGGGGCACCGACAAGCTCAACGAGAACTGCGGCAAGCGC

ACCTTCAACATCCCCAGCCACATCCCCGCGGGCGACTATCTCGTCCGGGC

CGAGGCTATCGCGCTACACACTGCCAACCAGCCAGGCGGCGCGCAGTTCT

ACATGAGCTGCTATCAAGTCAGGATTTCCGGCGGCGAAGGGGCCAGCTG

CCTGCCGGAGTCAAGATCCCGGGCGCGTACAGTGCCAACGACCCCGGCAT

CCTTGTCGACATCTGGGGTAACGATTTCAACGAGTACGTTATTCCGGGCC

CCCCGGTCATCGACAGCAGCTACTTC
```

(SEQ ID NO: 38)
<u>MKSSTPALFAAGLLAQHAAAH</u>SIFQQASSGSTDFDTLCTRMPPNNSPVTS
VTSGDMTCNVGGTKGVSGFCEVNAGDEFTVEMHAQPGDRSCANEAIGGNH
FGPVLIYMSKVDDASTADGSGDWFKVDEFGYDASTKTWGTDKLNENCGKR
TFNIPSHIPAGDYLVRAEAIALHTANQPGGAQFYMSCYQVRISGGEGGQL
PAGVKIPGAYSANDPGILVDIWGNDFNEYVIPGPPVIDSSYF (SEQ ID NO: 39)
HSIFQQASSGSTDFDTLCTRMPPNNSPVTSVTSGDMTCNVGGTKGVSGFC
EVNAGDEFTVEMHAQPGDRSCANEAIGGNHFGPVLIYMSKVDDASTADGS
GDWFKVDEFGYDASTKTWGTDKLNENCGKRTFNIPSHIPAGDYLVRAEAI
ALHTANQPGGAQFYMSCYQVRISGGEGGQLPAGVKIPGAYSANDPGILVD
IWGNDFNEYVIPGPPVIDSSYF

The polynucleotide (SEQ ID NO:40) and amino acid (SEQ ID NO:41) sequences of a *M. thermophila* GH61f are provided below. The signal sequence is shown underlined in SEQ ID NO:41. SEQ ID NO:42 provides the sequence of this GH61f without the signal sequence.

(SEQ ID NO: 40)
```
ATGAAGTCCTTCACCCTCACCACTCTGGCCGCCCTGGCTGGCAACGCCGC

CGCTCACGCGACCTTCCAGGCCCTCTGGGTCGACGGCGTCGACTACGGCG
```

```
CGCAGTGTGCCCGTCTGCCCGCGTCCAACTCGCCGGTCACCGACGTGACC
TCCAACGCGATCCGCTGCAACGCCAACCCCTCGCCCGCTCGGGGCAAGTG
CCCGGTCAAGGCCGGCTCGACCGTTACGGTCGAGATGCATCAGCAACCCG
GTGACCGCTCGTGCAGCAGCGAGGCGATCGGCGGGGCGCACTACGGCCCC
GTGATGGTGTACATGTCCAAGGTGTCGGACGCGGCGTCGGCGGACGGGTC
GTCGGGCTGGTTCAAGGTGTTCGAGGACGGCTGGGCCAAGAACCCGTCCG
GCGGGTCGGGCGACGACGACTACTGGGGCACCAAGGACCTGAACTCGTGC
TGCGGGAAGATGAACGTCAAGATCCCCGCCGACCTGCCCTCGGGCGACTA
CCTGCTCCGGGCCGAGGCCCTCGCGCTGCACACGGCCGGCAGCGCGGGCG
GCGCCCAGTTCTACATGACCTGCTACCAGCTCACCGTGACCGGCTCCGGC
AGCGCCAGCCCGCCCACCGTCTCCTTCCCGGGCGCCTACAAGGCCACCGA
CCCGGGCATCCTCGTCAACATCCACGCCCCGCTGTCCGGCTACACCGTGC
CCGGCCCGGCCGTCTACTCGGGCGGCTCCACCAAGAAGGCCGGCAGCGCC
TGCACCGGCTGCGAGTCCACTTGCGCCGTCGGCTCCGGCCCCACCGCCAC
CGTCTCCCAGTCGCCCGGTTCCACCGCCACCTCGGCCCCCGGCGGCGGCG
GCGGCTGCACCGTCCAGAAGTACCAGCAGTGCGGCGGCCAGGGCTACACC
GGCTGCACCAACTGCGCGTCCGGCTCCACCTGCAGCGCGGTCTCGCCGCC
CTACTACTCGCAGTGCGTC
```
(SEQ ID NO: 41)
<u>MKSFTLTTLAALAGNAAAH</u>ATFQALWVDGVDYGAQCARLPASNSPVTDVT
SNAIRCNANPSPARGKCPVKAGSTVTVEMHQQPGDRSCSSEAIGGAHYGP
VMVYMSKVSDAASADGSSGWFKVFEDGWAKNPSGGSGDDDYWGTKDLNSC
CGKMNVKIPADLPSGDYLLRAEALALHTAGSAGGAQFYMTCYQLTVTGSG
SASPPTVSFPGAYKATDPGILVNIHAPLSGYTVPGPAVYSGGSTKKAGSA
CTGCESTCAVGSGPTATVSQSPGSTATSAPGGGGGCTVQKYQQCGGQGYT
GCTNCASGSTCSAVSPPYYSQCV (SEQ ID NO: 42)
HATFQALWVDGVDYGAQCARLPASNSPVTDVTSNAIRCNANPSPARGKCP
VKAGSTVTVEMHQQPGDRSCSSEAIGGAHYGPVMVYMSKVSDAASADGSS
GWFKVFEDGWAKNPSGGSGDDDYWGTKDLNSCCGKMNVKIPADLPSGDYL
LRAEALALHTAGSAGGAQFYMTCYQLTVTGSGSASPPTVSFPGAYKATDP
GILVNIHAPLSGYTVPGPAVYSGGSTKKAGSACTGCESTCAVGSGPTATV
SQSPGSTATSAPGGGGGCTVQKYQQCGGQGYTGCTNCASGSTCSAVSPPY
YSQCV

The polynucleotide (SEQ ID NO:43) and amino acid (SEQ ID NO:44) sequences of an *M. thermophila* GH61g are provided below. The signal sequence is shown underlined in SEQ ID NO:44. SEQ ID NO:45 provides the sequence of this GH61g without the signal sequence.

(SEQ ID NO: 43)
```
ATGAAGGGACTCCTCGGCGCCGCCGCCCTCTCGCTGGCCGTCAGCGATGT
CTCGGCCCACTACATCTTTCAGCAGCTGACGACGGGCGGCGTCAAGCACG
CTGTGTACCAGTACATCCGCAAGAACACCAACTATAACTCGCCCGTGACC
GATCTGACGTCCAACGACCTCCGCTGCAATGTGGGTGCTACCGGTGCGGG
CACCGATACCGTCACGGTGCGCGCCGGCGATTCGTTCACCTTCACGACCG
ATACGCCCGTTTACCACCAGGGCCCGACCTCGATCTACATGTCCAAGGCC
CCCGGCAGCGCGTCCGACTACGACGGCAGCGGCGGCTGGTTCAAGATCAA
GGACTGGGCTGACTACACCGCCACGATTCCGGAATGTATTCCCCCCGGCG
ACTACCTGCTTCGCATCCAGCAACTCGGCATCCACAACCCTTGGCCCGCG
GGCATCCCCCAGTTCTACATCTCTTGTGCCCAGATCACCGTGACTGGTGG
CGGCAGTGCCAACCCCGGCCCGACCGTCTCCATCCCAGGCGCCTTCAAGG
AGACCGACCCGGGCTACACTGTCAACATCTACAACAACTTCCACAACTAC
ACCGTCCCTGGCCCAGCCGTCTTCACCTGCAACGGTAGCGGCGGCAACAA
CGGCGGCGGCTCCAACCCAGTCACCACCACCACCACCACCACCACCAGGC
CGTCCACCAGCACCGCCCAGTCCCAGCCGTCGTCGAGCCCGACCAGCCCC
TCCAGCTGCACCGTCGCGAAGTGGGGCCAGTGCGGAGGACAGGGTTACAG
CGGCTGCACCGTGTGCGCGGCCGGGTCGACCTGCCAGAAGACCAACGACT
ACTACAGCCAGTGCTTGTAG
```
(SEQ ID NO: 44)
<u>MKGLLGAAALSLAVSDVSAHY</u>IFQQLTTGGVKHAVYQYIRKNTNYNSPVT
DLTSNDLRCNVGATGAGTDTVTVRAGDSFTFTTDTPVYHQGPTSIYMSKA
PGSASDYDGSGGWFKIKDWADYTATIPECIPPGDYLLRIQQLGIHNPWPA
GIPQFYISCAQITVTGGGSANPGPTVSIPGAFKETDPGYTVNIYNNFHNY
TVPGPAVFTCNGSGGNNGGGSNPVTTTTTTTRPSTSTAQSQPSSSPTSP
SSCTVAKWGQCGGQGYSGCTVCAAGSTCQKTNDYYSQCL (SEQ ID NO: 45)
HYIFQQLTTGGVKHAVYQYIRKNTNYNSPVTDLTSNDLRCNVGATGAGTD
TVTVRAGDSFTFTTDTPVYHQGPTSIYMSKAPGSASDYDGSGGWFKIKDW
ADYTATIPECIPPGDYLLRIQQLGIHNPWPAGIPQFYISCAQITVTGGGS
ANPGPTVSIPGAFKETDPGYTVNIYNNFHNYTVPGPAVFTCNGSGGNNGG
GSNPVTTTTTTTRPSTSTAQSQPSSSPTSPSSCTVAKWGQCGGQGYSGC
TVCAAGSTCQKTNDYYSQCL

The polynucleotide (SEQ ID NO:46) and amino acid (SEQ ID NO:47) sequences of an alternative *M. thermophila* GH61g are provided below. The signal sequence is shown underlined in SEQ ID NO:47. SEQ ID NO:48 provides the sequence of this GH61g without the signal sequence.

(SEQ ID NO: 46)
```
CTGACGACGGGCGGCGTCAAGCACGCTGTGTACCAGTACATCCGCAAGAA
CACCAACTATAACTCGCCCGTGACCGATCTGACGTCCAACGACCTCCGCT
GCAATGTGGGTGCTACCGGTGCGGGCACCGATACCGTCACGGTGCGCGCC
GGCGATTCGTTCACCTTCACGACCGATACGCCCGTTTACCACCAGGGCCC
GACCTCGATCTACATGTCCAAGGCCCCCGGCAGCGCGTCCGACTACGACG
GCAGCGGCGGCTGGTTCAAGATCAAGGACTGGGGTGCCGACTTTAGCAGC
GGCCAGGCCACCTGGACCTTGGCGTCTGACTACACCGCCACGATTCCGGA
```

```
ATGTATTCCCCCGGCGACTACCTGCTTCGCATCCAGCAACTCGGCATCC

ACAACCCTTGGCCCGCGGGCATCCCCCAGTTCTACATCTCTTGTGCCCAG

ATCACCGTGACTGGTGGCGGCAGTGCCAACCCCGGCCCGACCGTCTCCAT

CCCAGGCGCCTTCAAGGAGACCGACCCGGGCTACACTGTCAACATCTACA

ACAACTTCCACAACTACACCGTCCCTGGCCCAGCCGTCTTCACCTGCAAC

GGTAGCGGCGGCAACAACGGCGGCGGCTCCAACCCAGTCACCACCACCAC

CACCACCACCACCAGGCCGTCCACCAGCACCGCCCAGTCCCAGCCGTCGT

CGAGCCCGACCAGCCCCTCCAGCTGCACCGTCGCGAAGTGGGGCCAGTGC

GGAGGACAGGGTTACAGCGGCTGCACCGTGTGCGCGGCCGGGTCGACCTG

CCAGAAGACCAACGACTACTACAGCCAGTGCTTG (SEQ ID NO: 47)
MKGLLGAAALSLAVSDVSAHYIFQQLTTGGVKHAVYQYIRKNTNYNSPVT

DLTSNDLRCNVGATGAGTDTVTVRAGDSFTFTTDTPVYHQGPTSIYMSKA

PGSASDYDGSGGWFKIKDWGADFSSGQATWTLASDYTATIPECIPPGDYL

LRIQQLGIHNPWPAGIPQFYISCAQITVTGGGSANPGPTVSIPGAFKETD

PGYTVNIYNNFHNYTVPGPAVFTCNGSGGNNGGGSNPVTTTTTTTRPST

STAQSQPSSSPTSPSSCTVAKWGQCGGQGYSGCTVCAAGSTCQKTNDYYS

QCL (SEQ ID NO: 48)
HYIFQQLTTGGVKHAVYQYIRKNTNYNSPVTDLTSNDLRCNVGATGAGTD

TVTVRAGDSFTFTTDTPVYHQGPTSIYMSKAPGSASDYDGSGGWFKIKDW

GADFSSGQATWTLASDYTATIPECIPPGDYLLRIQQLGIHNPWPAGIPQF

YISCAQITVTGGGSANPGPTVSIPGAFKETDPGYTVNIYNNFHNYTVPGP

AVFTCNGSGGNNGGGSNPVTTTTTTTRPSTSTAQSQPSSSPTSPSSCTV

AKWGQCGGQGYSGCTVCAAGSTCQKTNDYYSQCL
```

The polynucleotide (SEQ ID NO:49) and amino acid (SEQ ID NO:50) sequences of an *M. thermophila* GH61h are provided below. The signal sequence is shown underlined in SEQ ID NO:50. SEQ ID NO:51 provides the sequence of this GH61h without the signal sequence.

```
                                            (SEQ ID NO: 49)
ATGTCTTCCTTCACCTCCAAGGGTCTCCTTTCCGCCCTCATGGGCGCGGC

AACGGTTGCCGCCCACGGTCACGTCACCAACATCGTCATCAACGGCGTCT

CATACCAGAACTTCGACCCATTCACGCACCCTTATATGCAGAACCCTCCG

ACGGTTGTCGGCTGGACCGCGAGCAACACGGACAACGGCTTCGTCGGCCC

CGAGTCCTTCTCTAGCCCGGACATCATCTGCCACAAGTCCGCCACCAACG

CTGGCGGCCATGCCGTCGTCGCGGCCGGCGATAAGGTCTTCATCCAGTGG

GACACCTGGCCCGAGTCGCACCACGGTCCGGTCATCGACTATCTCGCCGA

CTGCGGCGACGCGGGCTGCGAGAAGGTCGACAAGACCACGCTCAAGTTCT

TCAAGATCAGCGAGTCCGGCCTGCTCGACGGCACTAACGCCCCCGGCAAG

TGGGCGTCCGACACGCTGATCGCCAACAACAACTCGTGGCTGGTCCAGAT

CCCGCCCAACATCGCCCCGGGCAACTACGTCCTGCGCCACGAGATCATCG

CCCTGCACAGCGCCGGCCAGCAGAACGGCGCCCAGAACTACCCTCAGTGC

TTCAACCTGCAGGTCACCGGCTCCGGCACTCAGAAGCCCTCCGGCGTCCT

CGGCACCGAGCTCTACAAGGCCACCGACGCCGGCATCCTGGCCAACATCT

ACACCTCGCCCGTCACCTACCAGATCCCCGGCCCGGCCATCATCTCGGGC

GCCTCCGCCGTCCAGCAGACCACCTCGGCCATCACCGCCTCTGCTAGCGC

CATCACCGGCTCCGCTACCGCCGCGCCCACGGCTGCCACCACCACCGCCG

CCGCCGCCGCCACCACTACCACCACCGCTGGCTCCGGTGCTACCGCCACG

CCCTCGACCGGCGGCTCTCCTTCTTCCGCCCAGCCTGCTCCTACCACCGC

TGCCGCTACCTCCAGCCCTGCTCGCCCGACCCGCTGCGCTGGTCTGAAGA

AGCGCCGTCGCCACGCCCGTGACGTCAAGGTTGCCCTC (SEQ ID NO: 50)
MSSFTSKGLLSALMGAATVAAHGHVTNIVINGVSYQNFDPFTHPYMQNPP

TVVGWTASNTDNGFVGPESFSSPDIICHKSATNAGGHAVVAAGDKVFIQW

DTWPESHHGPVIDYLADCGDAGCEKVDKTTLKFFKISESGLLDGTNAPGK

WASDTLIANNNSWLVQIPPNIAPGNYVLRHEIIALHSAGQQNGAQNYPQC

FNLQVTGSGTQKPSGVLGTELYKATDAGILANIYTSPVTYQIPGPAIISG

ASAVQQTTSAITASASAITGSATAAPTAATTTAAAAATTTTTAGSGATAT

PSTGGSPSSAQPAPTTAAATSSPARPTRCAGLKKRRRHARDVKVAL (SEQ ID NO: 51)
AHGHVTNIVINGVSYQNFDPFTHPYMQNPPTVVGWTASNTDNGFVGPESF

SSPDIICHKSATNAGGHAVVAAGDKVFIQWDTWPESHHGPVIDYLADCGD

AGCEKVDKTTLKFFKISESGLLDGTNAPGKWASDTLIANNNSWLVQIPPN

IAPGNYVLRHEIIALHSAGQQNGAQNYPQCFNLQVTGSGTQKPSGVLGTE

LYKATDAGILANIYTSPVTYQIPGPAIISGASAVQQTTSAITASASAITG

SATAAPTAATTTAAAAATTTTTAGSGATATPSTGGSPSSAQPAPTTAAAT

SSPARPTRCAGLKKRRRHARDVKVAL
```

The polynucleotide (SEQ ID NO:52) and amino acid (SEQ ID NO:53) sequences of an *M. thermophila* GH61i are provided below. The signal sequence is shown underlined in SEQ ID NO:53. SEQ ID NO:54 provides the sequence of this GH61i without the signal sequence.

```
                                            (SEQ ID NO: 52)
ATGAAGACGCTCGCCGCCCTCGTGGTCTCGGCCGCCCTCGTGGCCGCGCA

CGGCTATGTTGACCACGCCACGATCGGTGGCAAGGATTATCAGTTCTACC

AGCCGTACCAGGACCCTTACATGGGCGACAACAAGCCCGATAGGGTTTCC

CGCTCCATCCCGGGCAACGGCCCCGTGGAGGACGTCAACTCCATCGACCT

CCAGTGCCACGCCGGTGCCGAACCGGCCAAGCTCCACGCCCCCGCCGCCG

CCGGCTCGACCGTGACGCTCTACTGGACCCTCTGGCCCGACTCCCACGTC

GGCCCCGTCATCACCTACATGGCTCGCTGCCCCGACACCGGCTGCCAGGA

CTGGTCCCGGGAACTAAGCCCGTTTGGTTCAAGATCAAGGAAGGCGGCC

GTGAGGGCACCTCCAATACCCGCTCATGACGGCCCCCTCCGCCTACACC

TACACGATCCCGTCCTGCCTCAAGAGCGGCTACTACCTCGTCCGCCACGA

GATCATCGCCCTGCACTCGGCCTGGCAGTACCCCGGCGCCCAGTTCTACC
```

CGGGCTGCCACCAGCTCCAGGTCACCGGCGGCGGCTCCACCGTGCCCTCT

ACCAACCTGGTCTCCTTCCCCGGCGCCTACAAGGGGAGCGACCCCGGCAT

CACCTACGACGCTTACAAGGCGCAACCTTACACCATCCCTGGCCCGGCCG

TGTTTACCTGCTGA (SEQ ID NO: 53)
<u>MKTLAALVVSAALVAAHG</u>YVDHATIGGKDYQFYQPYQDPYMGDNKPDRVS

RSIPGNGPVEDVNSIDLQCHAGAEPAKLHAPAAAGSTVTLYWTLWPDSHV

GPVITYMARCPDTGCQDWSPGTKPVWFKIKEGGREGTSNTPLMTAPSAYT

YTIPSCLKSGYYLVRHEIIALHSAWQYPGAQFYPGCHQLQVTGGGSTVPS

TNLVSFPGAYKGSDPGITYDAYKAQPYTIPGPAVFTC (SEQ ID NO: 54)
YVDHATIGGKDYQFYQPYQDPYMGDNKPDRVSRSIPGNGPVEDVNSIDLQ

CHAGAEPAKLHAPAAAGSTVTLYWTLWPDSHVGPVITYMARCPDTGCQDW

SPGTKPVWFKIKEGGREGTSNTPLMTAPSAYTYTIPSCLKSGYYLVRHEI

IALHSAWQYPGAQFYPGCHQLQVTGGGSTVPSTNLVSFPGAYKGSDPGIT

YDAYKAQPYTIPGPAVFTC

The polynucleotide (SEQ ID NO:55) and amino acid (SEQ ID NO:56) sequences of an alternative *M. thermophila* GH61i are provided below. The signal sequence is shown underlined in SEQ ID NO:56. SEQ ID NO:57 provides the sequence of this GH61i without the signal sequence.

(SEQ ID NO: 55)
ATGAAGACGCTCGCCGCCCTCGTGGTCTCGGCCGCCCTCGTGGCCGCGCA

CGGCTATGTTGACCACGCCACGATCGGTGGCAAGGATTATCAGTTCTACC

AGCCGTACCAGGACCCTTACATGGGCGACAACAAGCCCGATAGGGTTTCC

CGCTCCATCCCGGGCAACGGCCCCGTGGAGGACGTCAACTCCATCGACCT

CCAGTGCCACGCCGGTGCCGAACCGGCCAAGCTCCACGCCCCCGCCGCCG

CCGGCTCGACCGTGACGCTCTACTGGACCCTCTGGCCCGACTCCCACGTC

GGCCCCGTCATCACCTACATGGCTCGCTGCCCCGACACCGGCTGCCAGGA

CTGGTCCCCGGGAACTAAGCCCGTTTGGTTCAAGATCAAGGAAGGCGGCC

GTGAGGGCACCTCCAATGTCTGGGCTGCTACCCCGCTCATGACGGCCCCC

TCCGCCTACACCTACACGATCCCGTCCTGCCTCAAGAGCGGCTACTACCT

CGTCCGCCACGAGATCATCGCCCTGCACTCGGCCTGGCAGTACCCCGGCG

CCCAGTTCTACCCGGGCTGCCACCAGCTCCAGGTCACCGGCGGCGGCTCC

ACCGTGCCCTCTACCAACCTGGTCTCCTTCCCCGGCGCCTACAAGGGGAG

CGACCCCGGCATCACCTACGACGCTTACAAGGCGCAACCTTACACCATCC

CTGGCCCGGCCGTGTTTACCTGC (SEQ ID NO: 56)
<u>MKTLAALVVSAALVAAHG</u>YVDHATIGGKDYQFYQPYQDPYMGDNKPDRVS

RSIPGNGPVEDVNSIDLQCHAGAEPAKLHAPAAAGSTVTLYWTLWPDSHV

GPVITYMARCPDTGCQDWSPGTKPVWFKIKEGGREGTSNVWAATPLMTAP

SAYTYTIPSCLKSGYYLVRHEIIALHSAWQYPGAQFYPGCHQLQVTGGGS

TVPSTNLVSFPGAYKGSDPGITYDAYKAQPYTIPGPAVFTC (SEQ ID NO: 57)
YVDHATIGGKDYQFYQPYQDPYMGDNKPDRVSRSIPGNGPVEDVNSIDLQ

CHAGAEPAKLHAPAAAGSTVTLYWTLWPDSHVGPVITYMARCPDTGCQDW

SPGTKPVWFKIKEGGREGTSNVWAATPLMTAPSAYTYTIPSCLKSGYYLV

RHEIIALHSAWQYPGAQFYPGCHQLQVTGGGSTVPSTNLVSFPGAYKGSD

PGITYDAYKAQPYTIPGPAVFTC

The polynucleotide (SEQ ID NO:58) and amino acid (SEQ ID NO:59) sequences of an *M. thermophila* GH61j are provided below. The signal sequence is shown underlined in SEQ ID NO:59. SEQ ID NO:60 provides the sequence of this GH61j without the signal sequence.

(SEQ ID NO: 58)
ATGAGATACTTCCTCCAGCTCGCTGCGGCCGCGGCCTTTGCCGTGAACAG

CGCGGCGGGTCACTACATCTTCCAGCAGTTCGCGACGGGCGGGTCCAAGT

ACCCGCCCTGGAAGTACATCCGGCGCAACACCAACCCGGACTGGCTGCAG

AACGGGCCGGTGACGGACCTGTCGTCGACCGACCTGCGCTGCAACGTGGG

CGGGCAGGTCAGCAACGGGACCGAGACCATCACCTTGAACGCCGGCGACG

AGTTCAGCTTCATCCTCGACACGCCCGTCTACCATGCCGGCCCCACCTCG

CTCTACATGTCCAAGGCGCCCGGAGCTGTGGCCGACTACGACGGCGGCGG

GGCCTGGTTCAAGATCTACGACTGGGGTCCGTCGGGGACGAGCTGGACGT

TGAGTGGCACGTACACTCAGAGAATTCCCAAGTGCATCCCTGACGGCGAG

TACCTCCTCCGCATCCAGCAGATCGGGCTCCACAACCCCGGCGCCGCGCC

ACAGTTCTACATCAGCTGCGCTCAAGTCAAGGTCGTCGATGGCGGCAGCA

CCAATCCGACCCCGACCGCCCAGATTCCGGGAGCCTTCCACAGCAACGAC

CCTGGCTTGACTGTCAATATCTACAACGACCCTCTCACCAACTACGTCGT

CCCGGGACCTAGAGTTTCGCACTGG (SEQ ID NO: 59)
<u>MRYFLQLAAAAAFAVNSAAGH</u>YIFQQFATGGSKYPPWKYIRRNTNPDWLQ

NGPVTDLSSTDLRCNVGGQVSNGTETITLNAGDEFSFILDTPVYHAGPTS

LYMSKAPGAVADYDGGGAWFKIYDWGPSGTSWTLSGTYTQRIPKCIPDGE

YLLRIQQIGLHNPGAAPQFYISCAQVKVVDGGSTNPTPTAQIPGAFHSND

PGLTVNIYNDPLTNYVVPGPRVSHW (SEQ ID NO: 60)
HYIFQQFATGGSKYPPWKYIRRNTNPDWLQNGPVTDLSSTDLRCNVGGQV

SNGTETITLNAGDEFSFILDTPVYHAGPTSLYMSKAPGAVADYDGGGAWF

KIYDWGPSGTSWTLSGTYTQRIPKCIPDGEYLLRIQQIGLHNPGAAPQFY

ISCAQVKVVDGGSTNPTPTAQIPGAFHSNDPGLTVNIYNDPLTNYVVPGP

RVSHW

The polynucleotide (SEQ ID NO:61) and amino acid (SEQ ID NO:62) sequences of an *M. thermophila* GH61k are provided below. The signal sequence is shown underlined in SEQ ID NO:62. SEQ ID NO:63 provides the sequence of this GH61k without the signal sequence.

(SEQ ID NO: 61)
ATGCACCCCTCCCTTCTTTTCACGCTTGGGCTGGCGAGCGTGCTTGTCCC

CCTCTCGTCTGCACACACTACCTTCACGACCCTCTTCGTCAACGATGTCA

-continued

```
ACCAAGGTGATGGTACCTGCATTCGCATGGCGAAGAAGGGCAATGTCGCC
ACCCATCCTCTCGCAGGCGGTCTCGACTCCGAAGACATGGCCTGTGGTCG
GGATGGTCAAGAACCCGTGGCATTTACGTGTCCGGCCCCAGCTGGTGCCA
AGTTGACTCTCGAGTTTCGCATGTGGGCCGATGCTTCGCAGTCCGGATCG
ATCGATCCATCCCACCTTGGCGTCATGGCCATCTACCTCAAGAAGGTTTC
CGACATGAAATCTGACGCGGCCGCTGGCCCGGGCTGGTTCAAGATTTGG
ACCAAGGCTACGACTTGGCGGCCAAGAAGTGGGCCACCGAGAAGCTCATC
GACAACAACGGCCTCCTGAGCGTCAACCTTCCAACCGGCTTACCAACCGG
CTACTACCTCGCCCGCCAGGAGATCATCACGCTCCAAAACGTTACCAATG
ACAGGCCAGAGCCCCAGTTCTACGTCGGCTGCGCACAGCTCTACGTCGAG
GGCACCTCGGACTCACCCATCCCCTCGGACAAGACGGTCTCCATTCCCGG
CCACATCAGCGACCCGGCCGACCCGGGCCTGACCTTCAACGTCTACACGG
GCGACGCATCCACCTACAAGCCGCCCGGCCCCGAGGTTTACTTCCCCACC
ACCACCACCACCACCTCCTCCTCCTCCCGGAAGCAGCGACAACAAGGG
AGCCAGGCGCCAGCAAACCCCGACGACAAGCAGGCCGACGGCCTCGTTC
CAGCCGACTGCCTCGTCAAGAACGCGAACTGGTGCGCCGCTGCCCTGCCG
CCGTACACCGACGAGGCCGGCTGCTGGGCCGCCGCCGAGGACTGCAACAA
GCAGCTGGACGCGTGCTACACCAGCGCACCCCCCTCGGGCAGCAAGGGGT
GCAAGGTCTGGGAGGAGCAGGTGTGCACCGTCGTCTCGCAGAAGTGCGAG
GCCGGGGATTTCAAGGGGCCCCGCAGCTCGGGAAGGAGCTCGGCGAGGG
GATCGATGAGCCTATTCCGGGGGGAAAGCTGCCCCGGCGGTCAACGCGG
GAGAGAACGGGAATCATGCGGAGGTGGTGGTGATGATGGTGATGATGAT
AATGATGAGGCCGGGCTGGGGCAGCGTCGACTCCGACTTTTGCTGCTCC
TGGTGCGGCCAAGACTCCCCAACCAAACTCCGAGAGGGCCCGGCGCCGTG
AGGCGCATTGGCGGCGACTGGAATCTGCTGAG
```

(SEQ ID NO: 62)
<u>MHPSLLFTLGLASVLVPLSSA</u>HTTFTTLFVNDVNQGDGTCIRMAKKGNVA
THPLAGGLDSEDMACGRDGQEPVAFTCPAPAGAKLTLEFRMWADASQSGS
IDPSHLGVMAIYLKKVSDMKSDAAAGPGWFKIWDQGYDLAAKKWATEKLI
DNNGLLSVNLPTGLPTGYYLARQEIITLQNVTNDRPEPQFYVGCAQLYVE
GTSDSPIPSDKTVSIPGHISDPADPGLTFNVYTGDASTYKPPGPEVYFPT
TTTTTSSSSSGSSDNKGARRQQTPDDKQADGLVPADCLVKNANWCAAALP
PYTDEAGCWAAAEDCNKQLDACYTSAPPSGSKGCKVWEEQVCTVVSQKCE
AGDFKGPPQLGKELGEGIDEPIPGGKLPPAVNAGENGNHGGGGGDDGDDD
NDEAGAGAASTPTFAAPGAAKTPQPNSERARRREAHWRRLESAE (SEQ ID NO: 63)
HTTFTTLFVNDVNQGDGTCIRMAKKGNVATHPLAGGLDSEDMACGRDGQE
PVAFTCPAPAGAKLTLEFRMWADASQSGSIDPSHLGVMAIYLKKVSDMKS
DAAAGPGWFKIWDQGYDLAAKKWATEKLIDNNGLLSVNLPTGLPTGYYLA
RQEIITLQNVTNDRPEPQFYVGCAQLYVEGTSDSPIPSDKTVSIPGHISD
PADPGLTFNVYTGDASTYKPPGPEVYFPTTTTTTSSSSSGSSDNKGARRQ
QTPDDKQADGLVPADCLVKNANWCAAALPPYTDEAGCWAAAEDCNKQLDA
CYTSAPPSGSKGCKVWEEQVCTVVSQKCEAGDFKGPPQLGKELGEGIDEP
IPGGKLPPAVNAGENGNHGGGGGDDGDDDNDEAGAGAASTPTFAAPGAAK
TPQPNSERARRREAHWRRLESAE

The polynucleotide (SEQ ID NO:64) and amino acid (SEQ ID NO:65) sequences of a *M. thermophila* GH61l are provided below. The signal sequence is shown underlined in SEQ ID NO:65. SEQ ID NO:66 provides the sequence of this GH61l without the signal sequence.

(SEQ ID NO: 64)
```
ATGTTTTCTCTCAAGTTCTTTATCTTGGCCGGTGGGCTTGCTGTCCTCAC
CGAGGCTCACATAAGACTAGTGTCGCCCGCCCCTTTTACCAACCCTGACC
AGGGCCCCAGCCCACTCCTAGAGGCTGGCAGCGACTATCCCTGCCACAAC
GGCAATGGGGGCGGTTATCAGGGAACGCCAACCCAGATGGCAAAGGGTTC
TAAGCAGCAGCTAGCCTTCCAGGGGTCTGCCGTTCATGGGGGTGGCTCCT
GCCAAGTGTCCATCACCTACGACGAAAACCCGACCGCTCAGAGCTCCTTC
AAGGTCATTCACTCGATTCAAGGTGGCTGCCCCGCCAGGGCCGAGACGAT
CCCGGATTGCAGCGCACAAAATATCAACGCCTGCAATATAAAGCCCGATA
ATGCCCAGATGGACACCCCGGATAAGTATGAGTTCACGATCCCGGAGGAT
CTCCCCAGTGGCAAGGCCACCCTCGCCTGGACATGGATCAACACTATCGG
CAACCGCGAGTTTTATATGGCATGCGCCCCGGTTGAGATCACCGGCGACG
GCGGTAGCGAGTCGGCTCTGGCTGCGCTGCCCGACATGGTCATTGCCAAC
ATCCCGTCCATCGGAGGAACCTGCGCGACCGAGGAGGGGAAGTACTACGA
ATATCCCAACCCCGGTAAGTCGGTCGAAACCATCCCGGGCTGGACCGATT
TGGTTCCCCTGCAAGGCGAATGCGGTGCTGCCTCCGGTGTCTCGGGCTCC
GGCGGAAACGCCAGCAGTGCTACCCCTGCCGCAGGGGCCGCCCCGACTCC
TGCTGTCCGCGGCCGCCGTCCCACCTGGAACGCC
```

(SEQ ID NO: 65)
<u>MFSLKFFILAGGLAVLTEAH</u>IRLVSPAPFTNPDQGPSPLLEAGSDYPCHN
GNGGGYQGTPTQMAKGSKQQLAFQGSAVHGGGSCQVSITYDENPTAQSSF
KVIHSIQGGCPARAETIPDCSAQNINACNIKPDNAQMDTPDKYEFTIPED
LPSGKATLAWTWINTIGNREFYMACAPVEITGDGGSESALAALPDMVIAN
IPSIGGTCATEEGKYYEYPNPGKSVETIPGWTDLVPLQGECGAASGVSGS
GGNASSATPAAGAAPTPAVRGRRPTWNA (SEQ ID NO: 66)
HIRLVSPAPFTNPDQGPSPLLEAGSDYPCHNGNGGGYQGTPTQMAKGSKQ
QLAFQGSAVHGGGSCQVSITYDENPTAQSSFKVIHSIQGGCPARAETIPD
CSAQNINACNIKPDNAQMDTPDKYEFTIPEDLPSGKATLAWTWINTIGNR
EFYMACAPVEITGDGGSESALAALPDMVIANIPSIGGTCATEEGKYYEYP
NPGKSVETIPGWTDLVPLQGECGAASGVSGSGGNASSATPAAGAAPTPAV
RGRRPTWNA

The polynucleotide (SEQ ID NO:67) and amino acid (SEQ ID NO:68) sequences of a *M. thermophila* GH61m are provided below. The signal sequence is shown underlined in SEQ ID NO:68. SEQ ID NO:69 provides the sequence of this GH61m without the signal sequence.

(SEQ ID NO: 67)
ATGAAGCTCGCCACGCTCCTCGCCGCCCTCACCCTCGGGGTGGCCGACCA

GCTCAGCGTCGGGTCCAGAAAGTTTGGCGTGTACGAGCACATTCGCAAGA

ACACGAACTACAACTCGCCCGTTACCGACCTGTCGGACACCAACCTGCGC

TGCAACGTCGGCGGGGGCTCGGGCACCAGCACCACCGTGCTCGACGTCAA

GGCCGGAGACTCGTTCACCTTCTTCAGCGACGTTGCCGTCTACCACCAGG

GGCCCATCTCGCTGTGCGTGGACCGGACCAGTGCAGAGAGCATGGATGGA

CGGGAACCGGACATGCGCTGCCGAACTGGCTCACAAGCTGGCTACCTGGC

GGTGACTGACTACGACGGGTCCGGTGACTGTTTCAAGATCTATGACTGGG

GACCGACGTTCAACGGGGGCCAGGCGTCGTGGCCGACGAGGAATTCGTAC

GAGTACAGCATCCTCAAGTGCATCAGGGACGGCGAATACCTACTGCGGAT

TCAGTCCCTGGCCATCCATAACCCAGGTGCCCTTCCGCAGTTCTACATCA

GCTGCGCCCAGGTGAATGTGACGGGCGGAGGCACCGTCACCCCCGAGATCA

AGGCGACCGATCCTGATCTATTTCAACTTCCACTCGTATATCGTCCCTGG

GCCGGCAGTGTTCAAGTGCTAG (SEQ ID NO: 68)
MKLATLLAALTLGVADQLSVGSRKFGVYEHIRKNTNYNSPVTDLSDTNLR

CNVGGGSGTSTTVLDVKAGDSFTFFSDVAVYHQGPISLCVDRTSAESMDG

REPDMRCRTGSQAGYLAVTDYDGSGDCFKIYDWGPTFNGGQASWPTRNSY

EYSILKCIRDGEYLLRIQSLAIHNPGALPQFYISCAQVNVTGGGTVTPRS

RRPILIYFNFHSYIVPGPAVFKC (SEQ ID NO: 69)
DQLSVGSRKFGVYEHIRKNTNYNSPVTDLSDTNLRCNVGGGSGTSTTVLD

VKAGDSFTFFSDVAVYHQGPISLCVDRTSAESMDGREPDMRCRTGSQAGY

LAVTDYDGSGDCFKIYDWGPTFNGGQASWPTRNSYEYSILKCIRDGEYLL

RIQSLAIHNPGALPQFYISCAQVNVTGGGTVTPRSRRPILIYFNFHSYIV

PGPAVFKC

The polynucleotide (SEQ ID NO:70) and amino acid (SEQ ID NO:71) sequences of an alternative *M. thermophila* GH61m are provided below. The signal sequence is shown underlined in SEQ ID NO:71. SEQ ID NO:72 provides the sequence of this GH61m without the signal sequence.

(SEQ ID NO: 70)
ATGAAGCTCGCCACGCTCCTCGCCGCCCTCACCCTCGGGCTCAGCGTCGG

GTCCAGAAAGTTTGGCGTGTACGAGCACATTCGCAAGAACACGAACTACA

ACTCGCCCGTTACCGACCTGTCGGACACCAACCTGCGCTGCAACGTCGGC

GGGGGCTCGGGCACCAGCACCACCGTGCTCGACGTCAAGGCCGGAGACTC

GTTCACCTTCTTCAGCGACGTTGCCGTCTACCACCAGGGGCCCATCTCGC

TGTGCGTGGACCGGACCAGTGCAGAGAGCATGGATGGACGGGAACCGGAC

ATGCGCTGCCGAACTGGCTCACAAGCTGGCTACCTGGCGGTGACTGTGAT

GACTGTGACTGACTACGACGGGTCCGGTGACTGTTTCAAGATCTATGACT

GGGGACCGACGTTCAACGGGGGCCAGGCGTCGTGGCCGACGAGGAATTCG

TACGAGTACAGCATCCTCAAGTGCATCAGGGACGGCGAATACCTACTGCG

GATTCAGTCCCTGGCCATCCATAACCCAGGTGCCCTTCCGCAGTTCTACA

TCAGCTGCGCCCAGGTGAATGTGACGGGCGGAGGCACCATCTATTTCAAC

TTCCACTCGTATATCGTCCCTGGGCCGGCAGTGTTCAAGTGC (SEQ ID NO: 71)
MKLATLLAALTLGLSVGSRKFGVYEHIRKNTNYNSPVTDLSDTNLRCNVG

GGSGTSTTVLDVKAGDSFTFFSDVAVYHQGPISLCVDRTSAESMDGREPD

MRCRTGSQAGYLAVTVMTVTDYDGSGDCFKIYDWGPTFNGGQASWPTRNS

YEYSILKCIRDGEYLLRIQSLAIHNPGALPQFYISCAQVNVTGGGTIYFN

FHSYIVPGPAVFKC (SEQ ID NO: 72)
RKFGVYEHIRKNTNYNSPVTDLSDTNLRCNVGGGSGTSTTVLDVKAGDSF

TFFSDVAVYHQGPISLCVDRTSAESMDGREPDMRCRTGSQAGYLAVTVMT

VTDYDGSGDCFKIYDWGPTFNGGQASWPTRNSYEYSILKCIRDGEYLLRI

QSLAIHNPGALPQFYISCAQVNVTGGGTIYFNFHSYIVPGPAVFKC

The polynucleotide (SEQ ID NO:73) and amino acid (SEQ ID NO:74) sequences of a *M. thermophila* GH61n are provided below.

(SEQ ID NO: 73)
ATGACCAAGAATGCGCAGAGCAAGCAGGGCGTTGAGAACCCAACAAGCGG

CGACATCCGCTGCTACACCTCGCAGACGGCGGCCAACGTCGTGACCGTGC

CGGCCGGCTCGACCATTCACTACATCTCGACCCAGCAGATCAACCACCCC

GGCCCGACTCAGTACTACCTGGCCAAGGTACCCCCCGGCTCGTCGGCCAA

GACCTTTGACGGGTCCGGCGCCGTCTGGTTCAAGATCTCGACCACGATGC

CTACCGTGGACAGCAACAAGCAGATGTTCTGGCCAGGGCAGAACACTTAT

GAGACCTCAAACACCACCATTCCCGCCAACACCCCGGACGGCGAGTACCT

CCTTCGCGTCAAGCAGATCGCCCTCCACATGGCGTCTCAGCCCAACAAGG

TCCAGTTCTACCTCGCCTGCACCCAGATCAAGATCACCGGTGGTCGCAAC

GGCACCCCCAGCCCGCTGGTCGCGCTGCCCGGAGCCTACAAGAGCACCGA

CCCCGGCATCCTGGTCGACATCTACTCCATGAAGCCCGAATCGTACCAGC

CTCCCGGGCCGCCCGTCTGGCGCGGCTAA (SEQ ID NO: 74)
MTKNAQSKQGVENPTSGDIRCYTSQTAANVVTVPAGSTIHYISTQQINHP

GPTQYYLAKVPPGSSAKTFDGSGAVWFKISTTMPTVDSNKQMFWPGQNTY

ETSNTTIPANTPDGEYLLRVKQIALHMASQPNKVQFYLACTQIKITGGRN

GTPSPLVALPGAYKSTDPGILVDIYSMKPESYQPPGPPVWRG

The polynucleotide (SEQ ID NO:75) and amino acid (SEQ ID NO:76) sequences of an alternative *M. thermophila* GH61n are provided below. The signal sequence is shown underlined in SEQ ID NO:76. SEQ ID NO:77 provides the sequence of this GH61n without the signal sequence.

(SEQ ID NO: 75)
ATGAGGCTTCTCGCAAGCTTGTTGCTCGCAGCTACGGCTGTTCAAGCTCA

CTTTGTTAACGGACAGCCCGAAGAGAGTGACTGGTCAGCCACGCGCATGA

-continued

```
CCAAGAATGCGCAGAGCAAGCAGGGCGTTGAGAACCCAACAAGCGGCGAC
ATCCGCTGCTACACCTCGCAGACGGCGGCCAACGTCGTGACCGTGCCGGC
CGGCTCGACCATTCACTACATCTCGACCCAGCAGATCAACCACCCCGGCC
CGACTCAGTACTACCTGGCCAAGGTACCCCCCGGCTCGTCGGCCAAGACC
TTTGACGGGTCCGGCGCCGTCTGGTTCAAGATCTCGACCACGATGCCTAC
CGTGGACAGCAACAAGCAGATGTTCTGGCCAGGGCAGAACACTTATGAGA
CCTCAAACACCACCATTCCCGCCAACACCCCGGACGGCGAGTACCTCCTT
CGCGTCAAGCAGATCGCCCTCCACATGGCGTCTCAGCCCAACAAGGTCCA
GTTCTACCTCGCCTGCACCCAGATCAAGATCACCGGTGGTCGCAACGGCA
CCCCCAGCCCGCTGGTCGCGCTGCCCGGAGCCTACAAGAGCACCGACCCC
GGCATCCTGGTCGACATCTACTCCATGAAGCCCGAATCGTACCAGCCTCC
CGGGCCGCCCGTCTGGCGCGGC
```

(SEQ ID NO: 76)
<u>MRLLASLLLAATAVQAH</u>FVNGQPEESDWSATRMTKNAQSKQGVENPTSGD
IRCYTSQTAANVVTVPAGSTIHYISTQQINHPGPTQYYLAKVPPGSSAKT
FDGSGAVWFKISTTMPTVDSNKQMFWPGQNTYETSNTTIPANTPDGEYLL
RVKQIALHMASQPNKVQFYLACTQIKITGGRNGTPSPLVALPGAYKSTDP
GILVDIYSMKPESYQPPGPPVWRG (SEQ ID NO: 77)
HFVNGQPEESDWSATRMTKNAQSKQGVENPTSGDIRCYTSQTAANVVTVP
AGSTIHYISTQQINHPGPTQYYLAKVPPGSSAKTFDGSGAVWFKISTTMP
TVDSNKQMFWPGQNTYETSNTTIPANTPDGEYLLRVKQIALHMASQPNKV
QFYLACTQIKITGGRNGTPSPLVALPGAYKSTDPGILVDIYSMKPESYQP
PGPPVWRG

The polynucleotide (SEQ ID NO:78) and amino acid (SEQ ID NO:79) sequences of an alternative *M. thermophila* GH61O are provided below. The signal sequence is shown underlined in SEQ ID NO:79. SEQ ID NO:80 provides the sequence of this GH61o without the signal sequence.

(SEQ ID NO: 78)
```
ATGAAGCCCTTTAGCCTCGTCGCCCTGGCGACTGCCGTGAGCGGCCATGC
CATCTTCCAGCGGGTGTCGGTCAACGGGCAGGACCAGGGCCAGCTCAAGG
GGGTGCGGGCGCCGTCGAGCAACTCCCCGATCCAGAACGTCAACGATGCC
AACATGGCCTGCAACGCCAACATTGTGTACCACGACAACACCATCATCAA
GGTGCCCGCGGGAGCCCGCGTCGGCGCGTGGTGGCAGCACGTCATCGGCG
GGCCGCAGGGCGCCAACGACCCGGACAACCCGATCGCCGCCTCCCACAAG
GGCCCCATCCAGGTCTACCTGGCCAAGGTGGACAACGCGGCGACGGCGTC
GCCGTCGGGCCTCAAGTGGTTCAAGGTGGCCGAGCGCGGCCTGAACAACG
GCGTGTGGGCCTACCTGATGCGCGTCGAGCTGCTCGCCCTGCACAGCGCC
TCGAGCCCCGGCGGCGCCCAGTTCTACATGGGCTGTGCACAGATCGAAGT
CACTGGCTCCGGCACCAACTCGGGCTCCGACTTTGTCTCGTTCCCCGGCG
CCTACTCGGCCAACGACCCGGGCATCTTGCTGAGCATCTACGACAGCTCG
GGCAAGCCCAACAATGGCGGGCGCTCGTACCCGATCCCCGGCCCGCGCCC
CATCTCCTGCTCCGGCAGCGGCGGCGGCGGCAACAACGGCGGCGACGGCG
GCGACGACAACAACGGTGGTGGCAACAACAACGGCGGCGGCAGCGTCCCC
CTGTACGGGCAGTGCGGCGGCATCGGCTACACGGGCCCGACCACCTGTGC
CCAGGGAACTTGCAAGGTGTCGAACGAATACTACAGCCAGTGCCTCCCC
```

(SEQ ID NO: 79)
<u>MKPFSLVALATAVSG</u>HAIFQRVSVNGQDQGQLKGVRAPSSNSPIQNVNDA
NMACNANIVYHDNTIIKVPAGARVGAWWQHVIGGPQGANDPDNPIAASHK
GPIQVYLAKVDNAATASPSGLKWFKVAERGLNNGVWAYLMRVELLALHSA
SSPGGAQFYMGCAQIEVTGSGTNSGSDFVSFPGAYSANDPGILLSIYDSS
GKPNNGGRSYPIPGPRPISCSGSGGGGNNGGDGGDDNNGGGNNNGGGSVP
LYGQCGGIGYTGPTTCAQGTCKVSNEYYSQCLP (SEQ ID NO: 80)
HAIFQRVSVNGQDQGQLKGVRAPSSNSPIQNVNDANMACNANIVYHDNTI
IKVPAGARVGAWWQHVIGGPQGANDPDNPIAASHKGPIQVYLAKVDNAAT
ASPSGLKWFKVAERGLNNGVWAYLMRVELLALHSASSPGGAQFYMGCAQI
EVTGSGTNSGSDFVSFPGAYSANDPGILLSIYDSSGKPNNGGRSYPIPGP
RPISCSGSGGGGNNGGDGGDDNNGGGNNNGGGSVPLYGQCGGIGYTGPTT
CAQGTCKVSNEYYSQCLP

The polynucleotide (SEQ ID NO:81) and amino acid (SEQ ID NO:82) sequences of a *M. thermophila* GH61p are provided below. The signal sequence is shown underlined in SEQ ID NO:82. SEQ ID NO:83 provides the sequence of this GH61p without the signal sequence.

(SEQ ID NO: 81)
```
ATGAAGCTCACCTCGTCCCTCGCTGTCCTGGCCGCTGCCGGCGCCCAGGC
TCACTATACCTTCCCTAGGGCCGGCACTGGTGGTTCGCTCTCTGGCGAGT
GGGAGGTGGTCCGCATGACCGAGAACCATTACTCGCACGGCCCGGTCACC
GATGTCACCAGCCCCGAGATGACCTGCTATCAGTCCGGCGTGCAGGGTGC
GCCCCAGACCGTCCAGGTCAAGGCGGGCTCCCAATTCACCTTCAGCGTGG
ATCCCTCCATCGGCCACCCCGGCCCTCTCCAGTTCTACATGGCTAAGGTG
CCGTCGGGCCAGACGGCCGCCACCTTTGACGGCACGGGAGCCGTGTGGTT
CAAGATCTACCAAGACGGCCCGAACGGCCTCGGCACCGACAGCATTACCT
GGCCCAGCGCCGGCAAAACCGAGGTCTCGGTCACCATCCCCAGCTGCATC
GAGGATGGCGAGTACCTGCTCCGGGTCGAGCACACCCCCCTCCCTACAGC
GCCAGCAGCGCAAAACCGAGCTCGCTCGTCACCATCCCCAGCTGCATACA
AGGCCACCGACCCGGGCATCCTCTTCCAGCTCTACTGGCCCATCCCGACC
GAGTACATCAACCCCGGCCCGGCCCCGTCTCTTGCTAA
```

(SEQ ID NO: 82)
<u>MKLTSSLAVLAAAGAQA</u>HYTFPRAGTGGSLSGEWEVVRMTENHYSHGPVT
DVTSPEMTCYQSGVQGAPQTVQVKAGSQFTFSVDPSIGHPGPLQFYMAKV
PSGQTAATFDGTGAVWFKIYQDGPNGLGTDSITWPSAGKTEVSVTIPSCI
EDGEYLLRVEHTPLPTAPAAQNRARSSPSPAAYKATDPGILFQLYWPIPT
EYINPGPAPVSC (SEQ ID NO: 83)
HYTFPRAGTGGSLSGEWEVVRMTENHYSHGPVTDVTSPEMTCYQSGVQGA

PQTVQVKAGSQFTFSVDPSIGHPGPLQFYMAKVPSGQTAATFDGTGAVWF

KIYQDGPNGLGTDSITWPSAGKTEVSVTIPSCIEDGEYLLRVEHTPLPTA

PAAQNRARSSPSPAAYKATDPGILFQLYWPIPTEYINPGPAPVSC

The polynucleotide (SEQ ID NO:84) and amino acid (SEQ ID NO:85) sequences of an alternative *M. thermophila* GH61p are provided below. The signal sequence is shown underlined in SEQ ID NO:85. SEQ ID NO:86 provides the sequence of this GH61p without the signal sequence.

(SEQ ID NO: 84)
ATGAAGCTCACCTCGTCCCTCGCTGTCCTGGCCGCTGCCGGCGCCCAGGC

TCACTATACCTTCCCTAGGGCCGGCACTGGTGGTTCGCTCTCTGGCGAGT

GGGAGGTGGTCCGCATGACCGAGACCATTACTCGCACGGCCCGGTCACCG

ATGTCACCAGCCCCGAGATGACCTGCTATCAGTCCGGCGTGCAGGGTGCG

CCCCAGACCGTCCAGGTCAAGGCGGGCTCCCAATTCACCTTCAGCGTGGA

TCCCTCCATCGGCCACCCCGGCCCTCTCCAGTTCTACATGGCTAAGGTGC

CGTCGGGCCAGACGGCCGCCACCTTTGACGGCACGGGAGCCGTGTGGTTC

AAGATCTACCAAGACGGCCCGAACGGCCTCGGCACCGACAGCATTACCTG

GCCCAGCGCCGGCAAAACCGAGGTCTCGGTCACCATCCCCAGCTGCATCG

AGGATGGCGAGTACCTGCTCCGGGTCGAGCACATCGCGCTCCACAGCGCC

AGCAGCGTGGGCGGCGCCCAGTTCTACATCGCCTGCGCCCAGCTCTCCGT

CACCGGCGGCTCCGGCACCCTCAACACGGGCTCGCTCGTCTCCCTGCCCG

GCGCCTACAAGGCCACCGACCCGGGCATCCTCTTCCAGCTCTACTGGCCC

ATCCCGACCGAGTACATCAACCCCGGCCCGGCCCCCGTCTCTTGC (SEQ ID NO: 85)
MKLTSSLAVLAAAGAQAHYTFPRAGTGGSLSGEWEVVRMTENHYSHGPVT

DVTSPEMTCYQSGVQGAPQTVQVKAGSQFTFSVDPSIGHPGPLQFYMAKV

PSGQTAATFDGTGAVWFKIYQDGPNGLGTDSITWPSAGKTEVSVTIPSCI

EDGEYLLRVEHIALHSASSVGGAQFYIACAQLSVTGGSGTLNTGSLVSLP

GAYKATDPGILFQLYWPIPTEYINPGPAPVSC (SEQ ID NO: 86)
HYTFPRAGTGGSLSGEWEVVRMTENHYSHGPVTDVTSPEMTCYQSGVQGA

PQTVQVKAGSQFTFSVDPSIGHPGPLQFYMAKVPSGQTAATFDGTGAVWF

KIYQDGPNGLGTDSITWPSAGKTEVSVTIPSCIEDGEYLLRVEHIALHSA

SSVGGAQFYIACAQLSVTGGSGTLNTGSLVSLPGAYKATDPGILFQLYWP

IPTEYINPGPAPVSC

The polynucleotide (SEQ ID NO:87) and amino acid (SEQ ID NO:88) sequences of an alternative *M. thermophila* GH61q are provided below. The signal sequence is shown underlined in SEQ ID NO:88. SEQ ID NO:89 provides the sequence of this GH61q without the signal sequence.

(SEQ ID NO: 87)
ATGCCGCCACCACGACTGAGCACCCTCCTTCCCCTCCTAGCCTTAATAGC

CCCCACCGCCCTGGGGCACTCCCACCTCGGGTACATCATCATCAACGGCG

AGGTATACCAAGGATTCGACCCGCGGCCGGAGCAGGCGAACTCGCCGTTG

CGCGTGGGCTGGTCGACGGGGGCAATCGACGACGGGTTCGTGGCGCCGGC

CAACTACTCGTCGCCCGACATCATCTGCCACATCGAGGGGGCCAGCCCGC

CGGCGCACGCGCCCGTCCGGGCGGGCGACCGGGTGCACGTGCAATGGAAC

GGCTGGCCGCTCGGACACGTGGGGCCGGTGCTGTCGTACCTGGCGCCCTG

CGGCGGGCTGGAGGGGTCCGAGAGCGGGTGCGCCGGGGTGGACAAGCGGC

AGCTGCGGTGGACCAAGGTGGACGACTCGCTGCCGGCGATGGAGCTG (SEQ ID NO: 88)
MPPPRLSTLLPLLALIAPTALGHSHLGYIIINGEVYQGFDPRPEQANSPL

RVGWSTGAIDDGFVAPANYSSPDIICHIEGASPPAHAPVRAGDRVHVQWN

GWPLGHVGPVLSYLAPCGGLEGSESGCAGVDKRQLRWTKVDDSLPAMEL (SEQ ID NO: 89)
HSHLGYIIINGEVYQGFDPRPEQANSPLRVGWSTGAIDDGFVAPANYSSP

DIICHIEGASPPAHAPVRAGDRVHVQWNGWPLGHVGPVLSYLAPCGGLEG

SESGCAGVDKRQLRWTKVDDSLPAMEL

The polynucleotide (SEQ ID NO:90) and amino acid (SEQ ID NO:91) sequences of an alternative *M. thermophila* GH61q are provided below. The signal sequence is shown underlined in SEQ ID NO:91. SEQ ID NO:92 provides the sequence of this GH61q without the signal sequence.

(SEQ ID NO: 90)
ATGCCGCCACCACGACTGAGCACCCTCCTTCCCCTCCTAGCCTTAATAGC

CCCCACCGCCCTGGGGCACTCCCACCTCGGGTACATCATCATCAACGGCG

AGGTATACCAAGGATTCGACCCGCGGCCGGAGCAGGCGAACTCGCCGTTG

CGCGTGGGCTGGTCGACGGGGGCAATCGACGACGGGTTCGTGGCGCCGGC

CAACTACTCGTCGCCCGACATCATCTGCCACATCGAGGGGGCCAGCCCGC

CGGCGCACGCGCCCGTCCGGGCGGGCGACCGGGTGCACGTGCAATGGAAA

CGGCTGGCCGCTCGGACACGTGGGGCCGGTGCTGTCGTACCTGGCGCCCT

GCGGCGGGCTGGAGGGGTCCGAGAGCGGGTGGACGACTCGCTGCCGGCGA

TGGAGCTGGTCGGGGCCGCGGGGGGCGCGGGGGGCGAGGACGACGGCAGC

GGCAGCGACGGCAGCGGCAGCGGCGGCAGCGGACGCGTCGGCGTGCCCGG

GCAGCGCTGGGCCACCGACGTGTTGATCGCGGCCAACAACAGCTGGCAGG

TCGAGATCCCGCGCGGGCTGCGGGACGGGCCGTACGTGCTGCGCCACGAG

ATCGTCGCGCTGCACTACGCGGCCGAGCCCGGCGGCGCGCAGAACTACCC

GCTCTGCGTCAACCTGTGGGTCGAGGGCGGCGACGGCAGCATGGAGCTGG

ACCACTTCGACGCCACCCAGTTCTACCGGCCCGACGACCCGGGCATCCTG

CTCAACGTGACGGCCGGCCTGCGCTCATACGCCGTGCCGGGCCCGACGCT

GGCCGCGGGGGCGACGCCGGTGCCGTACGCGCAGCAGAACATCAGCTCGG

CGAGGGCGGATGGAACCCCGTGATTGTCACCAGGAGCACGGAGACGGTG

CCCTTCACCGCGGCACCCACGCCAGCCGAGACGGCAGAAGCCAAAGGGGG

GAGGTATGATGACCAAACCCGAACTAAAGACCTAAATGAACGCTTCTTTT

ATAGTAGCCGGCCAGAACAGAAGAGGCTGACAGCGACCTCAAGAAGGGAA

CTAGTTGATCATCGTACCCGGTACCTCTCCGTAGCTGTCTGCGCAGATTT

-continued
CGGCGCTCATAAGGCAGCAGAAACCAACCACGAAGCTTTGAGAGGCGGCA

ATAAGCACCATGGCGGTGTTTCAGAG (SEQ ID NO: 91)
MPPPRLSTLLPLLALIAPTALGHSHLGYIIINGEVYQGFDPRPEQANSPL

RVGWSTGAIDDGFVAPANYSSPDIICHIEGASPPAHAPVRAGDRVHVQWK

RLAARTRGAGAVVPGALRRAGGVRERVDDSLPAMELVGAAGGAGGEDDGS

GSDGSGSGGSGRVGVPGQRWATDVLIAANNSWQVEIPRGLRDGPYVLRHE

IVALHYAAEPGGAQNYPLCVNLWVEGGDGSMELDHFDATQFYRPDDPGIL

LNVTAGLRSYAVPGPTLAAGATPVPYAQQNISSARADGTPVIVTRSTETV

PFTAAPTPAETAEAKGGRYDDQTRTKDLNERFFYSSRPEQKRLTATSRRE

LVDHRTRYLSVAVCADFGAHKAAETNHEALRGGNKHHGGVSE (SEQ ID NO: 92)
HSHLGYIIINGEVYQGFDPRPEQANSPLRVGWSTGAIDDGFVAPANYSSP

DIICHIEGASPPAHAPVRAGDRVHVQWKRLAARTRGAGAVVPGALRRAGG

VRERVDDSLPAMELVGAAGGAGGEDDGSGSDGSGSGGSGRVGVPGQRWAT

DVLIAANNSWQVEIPRGLRDGPYVLRHEIVALHYAAEPGGAQNYPLCVNL

WVEGGDGSMELDHFDATQFYRPDDPGILLNVTAGLRSYAVPGPTLAAGAT

PVPYAQQNISSARADGTPVIVTRSTETVPFTAAPTPAETAEAKGGRYDDQ

TRTKDLNERFFYSSRPEQKRLTATSRRELVDHRTRYLSVAVCADFGAHKA

AETNHEALRGGNKHHGGVSE

The polynucleotide (SEQ ID NO:93) and amino acid (SEQ ID NO:94) sequences of an M. thermophila GH61r are provided below. The signal sequence is shown underlined in SEQ ID NO:94. SEQ ID NO:95 provides the sequence of this GH61r without the signal sequence.

(SEQ ID NO: 93)
ATGAGGTCGACATTGGCCGGTGCCCTGGCAGCCATCGCTGCTCAGAAAGT

AGCCGGCCACGCCACGTTTCAGCAGCTCTGGCACGGCTCCTCCTGTGTCC

GCCTTCCGGCTAGCAACTCACCCGTCACCAATGTGGGAAGCAGAGACTTC

GTCTGCAACGCTGGCACCCGCCCCGTCAGTGGCAAGTGCCCCGTGAAGGC

TGGCGGCACCGTCACCATCGAGATGCACCAGCAACCCGGCGACCGCAGCT

GCAACAACGAAGCCATCGGAGGGGCGCATTGGGGCCCCGTCCAGGTGTAC

CTGACCAAGGTTCAGGACGCCGCGACGGCCGACGGCTCGACGGGCTGGTT

CAAGATCTTCTCCGACTCGTGGTCCAAGAAGCCCGGGGGCAACTTGGGCG

ACGACGACAACTGGGGCACGCGCGACCTGAACGCCTGCTGCGGGAAGATG

GAC (SEQ ID NO: 94)
MRSTLAGALAAIAAQKVAGHATFQQLWHGSSCVRLPASNSPVTNVGSRDF

VCNAGTRPVSGKCPVKAGGTVTIEMHQQPGDRSCNNEAIGGAHWGPVQVY

LTKVQDAATADGSTGWFKIFSDSWSKKPGGNLGDDDNWGTRDLNACCGKM

D (SEQ ID NO: 95)
HATFQQLWHGSSCVRLPASNSPVTNVGSRDFVCNAGTRPVSGKCPVKAGG

TVTIEMHQQPGDRSCNNEAIGGAHWGPVQVYLTKVQDAATADGSTGWFKI

FSDSWSKKPGGNLGDDDNWGTRDLNACCGKMD

The polynucleotide (SEQ ID NO:96) and amino acid (SEQ ID NO:97) sequences of an alternative M. thermophila GH61r are provided below. The signal sequence is shown underlined in SEQ ID NO:97. SEQ ID NO:98 provides the sequence of this GH61r without the signal sequence.

(SEQ ID NO: 96)
ATGAGGTCGACATTGGCCGGTGCCCTGGCAGCCATCGCTGCTCAGAAAGT

AGCCGGCCACGCCACGTTTCAGCAGCTCTGGCACGGCTCCTCCTGTGTCC

GCCTTCCGGCTAGCAACTCACCCGTCACCAATGTGGGAAGCAGAGACTTC

GTCTGCAACGCTGGCACCCGCCCCGTCAGTGGCAAGTGCCCCGTGAAGGC

TGGCGGCACCGTCACCATCGAGATGCACCAGCAACCCGGCGACCGCAGCT

GCAACAACGAAGCCATCGGAGGGGCGCATTGGGGCCCCGTCCAGGTGTAC

CTGACCAAGGTTCAGGACGCCGCGACGGCCGACGGCTCGACGGGCTGGTT

CAAGATCTTCTCCGACTCGTGGTCCAAGAAGCCCGGGGGCAACTCGGGCG

ACGACGACAACTGGGGCACGCGCGACCTGAACGCCTGCTGCGGGAAGATG

GACGTGGCCATCCCGGCCGACATCGCGTCGGGCGACTACCTGCTGCGGGC

CGAGGCGCTGGCCCTGCACACAGGCCGGACAGGCCGGCGGCGCCCAGTTCT

ACATGAGCTGCTACCAGATGACGGTCGAGGGCGGCTCCGGGACCGCCAAC

CCGCCCACCGTCAAGTTCCCGGGCGCCTACAGCGCCAACGACCCGGGCAT

CCTCGTCAACATCCACGCCCCCCTTTCCAGCTACACCGCGCCCGGCCCGG

CCGTCTACGCGGGCGGCACCATCCGCGAGGCCGGCTCCGCCTGCACCGGC

TGCGCGCAGACCTGCAAGGTCGGGTCGTCCCCGAGCGCCGTTGCCCCCGG

CAGCGGCGCGGGCAACGGCGGCGGGTTCCAACCCCGA (SEQ ID NO: 97)
MRSTLAGALAAIAAQKVAGHATFQQLWHGSSCVRLPASNSPVTNVGSRDF

VCNAGTRPVSGKCPVKAGGTVTIEMHQQPGDRSCNNEAIGGAHWGPVQVY

LTKVQDAATADGSTGWFKIFSDSWSKKPGGNSGDDDNWGTRDLNACCGKM

DVAIPADIASGDYLLRAEALALHTAGQAGGAQFYMSCYQMTVEGGSGTAN

PPTVKFPGAYSANDPGILVNIHAPLSSYTAPGPAVYAGGTIREAGSACTG

CAQTCKVGSSPSAVAPGSGAGNGGGFQPR (SEQ ID NO: 98)
HATFQQLWHGSSCVRLPASNSPVTNVGSRDFVCNAGTRPVSGKCPVKAGG

TVTIEMHQQPGDRSCNNEAIGGAHWGPVQVYLTKVQDAATADGSTGWFKI

FSDSWSKKPGGNSGDDDNWGTRDLNACCGKMDVAIPADIASGDYLLRAEA

LALHTAGQAGGAQFYMSCYQMTVEGGSGTANPPTVKFPGAYSANDPGILV

NIHAPLSSYTAPGPAVYAGGTIREAGSACTGCAQTCKVGSSPSAVAPGSG

AGNGGGFQPR

The polynucleotide (SEQ ID NO:99) and amino acid (SEQ ID NO:100) sequences of an M. thermophila GH61s are provided below. The signal sequence is shown underlined in SEQ ID NO:100. SEQ ID NO:101 provides the sequence of this GH61s without the signal sequence.

(SEQ ID NO: 99)
ATGCTCCTCCTCACCCTAGCCACACTCGTCACCCTCCTGGCGCGCCACGT

CTCGGCTCACGCCCGGCTGTTCCGCGTCTCTGTCGACGGGAAAGACCAGG

```
GCGACGGGCTGAACAAGTACATCCGCTCGCCGGCGACCAACGACCCCGTG

CGCGACCTCTCGAGCGCCGCCATCGTGTGCAACACCCAGGGGTCCAAGGC

CGCCCCGGACTTCGTCAGGGCCGCGGCCGGCGACAAGCTGACCTTCCTCT

GGGCGCACGACAACCCGGACGACCCGGTCGACTACGTCCTCGACCCGTCC

CACAAGGGCGCCATCCTGACCTACGTCGCCGCCTACCCCTCCGGGGACCC

GACCGGCCCCATCTGGAGCAAGCTTGCCGAGGAAGGATTCACCGGCGGGC

AGTGGGCGACCATCAAGATGATCGACAACGGCGGCAAGGTCGACGTGACG

CTGCCCGAGGCCCTTGCGCCGGGAAAGTACCTGATCCGCCAGGAGCTGCT

GGCCCTGCACCGGGCCGACTTTGCCTGCGACGACCCGGCCCACCCCAACC

GCGGCGCCGAGTCGTACCCCAACTGCGTCCAGGTGGAGGTGTCGGGCAGC

GGCGACAAGAAGCCGGACCAGAACTTTGACTTCAACAAGGGCTATACCTG

CGATAACAAAGGACTCCACTTTAAGATCTACATCGGTCAGGACAGCCAGT

ATGTGGCCCCGGGGCCGCGGCCTTGGAATGGGAGC (SEQ ID NO: 100)
MLLLTLATLVTLLARHVSAHARLFRVSVDGKDQGDGLNKYIRSPATNDPV

RDLSSAAIVCNTQGSKAAPDFVRAAAGDKLTFLWAHDNPDDPVDYVLDPS

HKGAILTYVAAYPSGDPTGPIWSKLAEEGFTGGQWATIKMIDNGGKVDVT

LPEALAPGKYLIRQELLALHRADFACDDPAHPNRGAESYPNCVQVEVSGS

GDKKPDQNFDFNKGYTCDNKGLHFKIYIGQDSQYVAPGPRPWNGS (SEQ ID NO: 101)
HARLFRVSVDGKDQGDGLNKYIRSPATNDPVRDLSSAAIVCNTQGSKAAP

DFVRAAAGDKLTFLWAHDNPDDPVDYVLDPSHKGAILTYVAAYPSGDPTG

PIWSKLAEEGFTGGQWATIKMIDNGGKVDVTLPEALAPGKYLIRQELLAL

HRADFACDDPAHPNRGAESYPNCVQVEVSGSGDKKPDQNFDFNKGYTCDN

KGLHFKIYIGQDSQYVAPGPRPWNGS
```

The polynucleotide (SEQ ID NO:102) and amino acid (SEQ ID NO:103) sequences of an *M. thermophila* GH61t are provided below.

```
                                                  (SEQ ID NO: 102)
ATGTTCACTTCGCTTTGCATCACAGATCATTGGAGGACTCTTAGCAGCCA

CTCTGGGCCAGTCATGAACTATCTCGCCCATTGCACCAATGACGACTGCA

AGTCTTTCAAGGGCGACAGCGGCAACGTCTGGGTCAAGATCGAGCAGCTC

GCGTACAACCCGTCAGCCAACCCCCCTGGGCGTCTGACCTCCTCCGTGA

GCACGGTGCCAAGTGGAAGGTGACGATCCCGCCCAGTCTTGTCCCCGGCG

AATATCTGCTGCGGCACGAGATCCTGGGGTTGCACGTCGCAGGAACCGTG

ATGGGCGCCCAGTTCTACCCCGGCTGCACCCAGATCAGGGTCACCGAAGG

CGGGAGCACGCAGCTGCCCTCGGGTATTGCGCTCCCAGGCGCTTACGGCC

CACAAGACGAGGGTATCTTGGTCGACTTGTGGAGGGTTAACCAGGGCCAG

GTCAACTACACGGCGCCTGGAGGACCCGTTTGGAGCGAAGCGTGGGACAC

CGAGTTTGGCGGGTCCAACACGACCGAGTGCGCCACCATGCTCGACGACC

TGCTCGACTACATGGCGGCCAACGACGAGTGGATCGGCTGGACGGCCTAG
```

```
                                                  (SEQ ID NO: 103)
MFTSLCITDHWRTLSSHSGPVMNYLAHCTNDDCKSFKGDSGNVWVKIEQL

AYNPSANPPWASDLLREHGAKWKVTIPPSLVPGEYLLRHEILGLHVAGTV

MGAQFYPGCTQIRVTEGGSTQLPSGIALPGAYGPQDEGILVDLWRVNQGQ

VNYTAPGGPVWSEAWDTEFGGSNTTECATMLDDLLDYMAANDEWIGWTA
```

The polynucleotide (SEQ ID NO:104) and amino acid (SEQ ID NO:105) sequences of an alternative *M. thermophila* GH61t are provided below.

```
                                                  (SEQ ID NO: 104)
ATGAACTATCTCGCCCATTGCACCAATGACGACTGCAAGTCTTTCAAGGG

CGACAGCGGCAACGTCTGGGTCAAGATCGAGCAGCTCGCGTACAACCCGT

CAGCCAACCCCCCTGGGCGTCTGACCTCCTCCGTGAGCACGGTGCCAAG

TGGAAGGTGACGATCCCGCCCAGTCTTGTCCCCGGCGAATATCTGCTGCG

GCACGAGATCCTGGGGTTGCACGTCGCAGGAACCGTGATGGGCGCCCAGT

TCTACCCCGGCTGCACCCAGATCAGGGTCACCGAAGGCGGGAGCACGCAG

CTGCCCTCGGGTATTGCGCTCCCAGGCGCTTACGGCCCACAAGACGAGGG

TATCTTGGTCGACTTGTGGAGGGTTAACCAGGGCCAGGTCAACTACACGG

CGCCTGGAGGACCCGTTTGGAGCGAAGCGTGGGACACCGAGTTTGGCGGG

TCCAACACGACCGAGTGCGCCACCATGCTCGACGACCTGCTCGACTACAT

GGCGGCCAACGACGACCCATGCTGCACCGACCAGAACCAGTTCGGGAGTC

TCGAGCCGGGGAGCAAGGCGGCCGGCGGCTCGCCGAGCCTGTACGATACC

GTCTTGGTCCCCGTTCTCCAGAAGAAAGTGCCGACAAAGCTGCAGTGGAG

CGGACCGGCGAGCGTCAACGGGGATGAGTTGACAGAGAGGCCC
```

```
                                                  (SEQ ID NO: 105)
MNYLAHCTNDDCKSFKGDSGNVWVKIEQLAYNPSANPPWASDLLREHGAK

WKVTIPPSLVPGEYLLRHEILGLHVAGTVMGAQFYPGCTQIRVTEGGSTQ

LPSGIALPGAYGPQDEGILVDLWRVNQGQVNYTAPGGPVWSEAWDTEFGG

SNTTECATMLDDLLDYMAANDDPCCTDQNQFGSLEPGSKAAGGSPSLYDT

VLVPVLQKKVPTKLQWSGPASVNGDELTERP
```

The polynucleotide (SEQ ID NO:106) and amino acid (SEQ ID NO:107) sequences of an *M. thermophila* GH61u are provided below. The signal sequence is shown underlined in SEQ ID NO:107. SEQ ID NO:108 provides the sequence of this GH61u without the signal sequence.

```
                                                  (SEQ ID NO: 106)
ATGAAGCTGAGCGCTGCCATCGCCGTGCTCGCGGCCGCCCTTGCCGAGGG

GCACTATACCTTCCCCAGCATCGCCAACACGGCCGACTGGCAATATGGCG

CATCACGACCAACTTCCAGAGCAACGGCCCCGTGACGGACGTCAACTCGG

ACCAGATCCGGTGCTACGAGCGCAACCCGGGCACCGGCGCCCCCGGCATC

TACAACGTCACGGCCGGCACAACCATCAACTACAACGCCAAGTCGTCCAT

CTCCCACCCGGGACCCATGGCCTTCTACATTGCCAAGGTTCCCGCCGGCC

AGTCGGCCGCCACCTGGGACGGTAAGGGCGCCGTCTGGTCCAAGATCCAC

CAGGAGATGCCGCACTTTGGCACCAGCCTCACCTGGGACTCCAACGGCCG
```

```
CACCTCCATGCCCGTCACCATCCCCCGCTGTCTGCAGGACGGCGAGTATC

TGCTGCGTGCAGAGCACATTGCCCTCCACAGCGCCGGCAGCCCCGGCGGC

GCCCAGTTCTACATTTCTTGTGCCCAGCTCTCAGTCACCGGCGGCAGCGG

GACCTGGAACCCCAGGAACAAGGTGTCGTTCCCCGGCGCCTACAAGGCCA

CTGACCCGGGCATCCTGATCAACATCTACTACCCCGTCCCGACTAGCTAC

ACTCCCGCTGGTCCCCCCGTCGACACCTGC
```

(SEQ ID NO: 107)
MKLSAAIAVLAAALAEGHYTFPSIANTADWQYVRITTNFQSNGPVTDVNS
DQIRCYERNPGTGAPGIYNVTAGTTINYNAKSSISHPGPMAFYIAKVPAG
QSAATWDGKGAVWSKIHQEMPHFGTSLTWDSNGRTSMPVTIPRCLQDGEY
LLRAEHIALHSAGSPGGAQFYISCAQLSVTGGSGTWNPRNKVSFPGAYKA
TDPGILINIYYPVPTSYTPAGPPVDTC (SEQ ID NO: 108)
HYTFPSIANTADWQYVRITTNFQSNGPVTDVNSDQIRCYERNPGTGAPGI
YNVTAGTTINYNAKSSISHPGPMAFYIAKVPAGQSAATWDGKGAVWSKIH
QEMPHFGTSLTWDSNGRTSMPVTIPRCLQDGEYLLRAEHIALHSAGSPGG
AQFYISCAQLSVTGGSGTWNPRNKVSFPGAYKATDPGILINIYYPVPTSY
TPAGPPVDTC

The polynucleotide (SEQ ID NO:109) and amino acid (SEQ ID NO:110) sequences of an *M. thermophila* GH61v are provided below. The signal sequence is shown underlined in SEQ ID NO:110. SEQ ID NO:111 provides the sequence of this GH61v without the signal sequence.

```
                                         (SEQ ID NO: 109)
ATGTACCGCACGCTCGGTTCCATTGCCCTGCTCGCGGGGGCGCTGCCGC

CCACGGCGCCGTGACCAGCTACAACATTGCGGGCAAGGACTACCCTGGAT

ACTCGGGCTTCGCCCCTACCGGCCAGGATGTCATCCAGTGGCAATGGCCC

GACTATAACCCCGTGCTGTCCGCCAGCGACCCCAAGCTCCGCTGCAACGG

CGGCACCGGGGCGGCGTGTATGCCGAGGCGGCCCCCGGCGACACCATCA

CGGCCACCTGGGCCCAGTGGACGCACTCCCAGGGCCCGATCCTGGTGTGG

ATGTACAAGTGCCCCGGCGACTTCAGCTCCTGCGACGGCTCCGGCGCGGG

TTGGTTCAAGATCGACGAGGCCGGCTTCCACGGCGACGGCACGACCGTCT

TCCTCGACACCGAGACCCCCTCGGGCTGGGACATTGCCAAGCTGGTCGGC

GGCAACAAGTCGTGGAGCAGCAAGATCCCTGACGGCCTCGCCCCGGGCAA

TTACCTGGTCCGCCACGAGCTCATCGCCCTGCACCAGGCCAACAACCCGC

AATTCTACCCCGAGTGCGCCCAGATCAAGGTCACCGGCTCTGGCACCGCC

GAGCCCGCCGCCTCCTACAAGGCCGCCATCCCCGGCTACTGCCAGCAGAG

CGACCCCAACATTTCGTTCAACATCAACGACCACTCCCTCCCGCAGGAGT

ACAAGATCCCCGGTCCCCCGGTCTTCAAGGGCACCGCCTCCGCCAAGGCT

CGCGCTTTCCAGGCC
```

(SEQ ID NO: 110)
MYRTLGSIALLAGGAAAHGAVTSYNIAGKDYPGYSGFAPTGQDVIQWQWP
DYNPVLSASDPKLRCNGGTGAALYAEAAPGDTITATWAQWTHSQGPILVW

MYKCPGDFSSCDGSGAGWFKIDEAGFHGDGTTVFLDTETPSGWDIAKLVG
GNKSWSSKIPDGLAPGNYLVRHELIALHQANNPQFYPECAQIKVTGSGTA
EPAASYKAAIPGYCQQSDPNISFNINDHSLPQEYKIPGPPVFKGTASAKA
RAFQA (SEQ ID NO: 111)
AVTSYNIAGKDYPGYSGFAPTGQDVIQWQWPDYNPVLSASDPKLRCNGGT
GAALYAEAAPGDTITATWAQWTHSQGPILVWMYKCPGDFSSCDGSGAGWF
KIDEAGFHGDGTTVFLDTETPSGWDIAKLVGGNKSWSSKIPDGLAPGNYL
VRHELIALHQANNPQFYPECAQIKVTGSGTAEPAASYKAAIPGYCQQSDP
NISFNINDHSLPQEYKIPGPPVFKGTASAKARAFQA

The polynucleotide (SEQ ID NO:112) and amino acid (SEQ ID NO:113) sequences of an *M. thermophila* GH61w are provided below. The signal sequence is shown underlined in SEQ ID NO:113. SEQ ID NO:114 provides the sequence of this GH61w without the signal sequence.

```
                                         (SEQ ID NO: 112)
ATGCTGACAACAACCTTCGCCCTCCTGACGGCCGCTCTCGGCGTCAGCGC

CCATTATACCCTCCCCAGGGTCGGGACCGGTTCCGACTGGCAGCACGTGC

GGCGGGCTGACAACTGGCAAAACAACGGCTTCGTCGGCGACGTCAACTCG

GAGCAGATCAGGTGCTTCCAGGCGACCCCTGCCGGCGCCCAAGACGTCTA

CACTGTTCAGGCGGGATCGACCGTGACCTACCACGCCAACCCCAGTATCT

ACCACCCCGGCCCCATGCAGTTCTACCTGGCCCGCGTTCCGGACGGACAG

GACGTCAAGTCGTGGACCGGCGAGGGTGCCGTGTGGTTCAAGGTGTACGA

GGAGCAGCCTCAATTTGGCGCCCAGCTGACCTGGCCTAGCAACGGCAAGA

GCTCGTTCGAGGTTCCTATCCCCAGCTGCATTCGGGCGGGCAACTACCTC

CTCCGCGCTGAGCACATCGCCCTGCACGTTGCCCAAAGCCAGGGCGGCGC

CCAGTTCTACATCTCGTGCGCCCAGCTCCAGGTCACTGGTGGCGGCAGCA

CCGAGCCTTCTCAGAAGGTTTCCTTCCCGGGTGCCTACAAGTCCACCGAC

CCCGGCATTCTTATCAACATCAACTACCCCGTCCCTACCTCGTACCAGAA

TCCGGGTCCGGCTGTCTTCCGTTGC
```

(SEQ ID NO: 113)
MLTTTFALLTAALGVSAHYTLPRVGTGSDWQHVRRADNWQNNGFVGDVNS
EQIRCFQATPAGAQDVYTVQAGSTVTYHANPSIYHPGPMQFYLARVPDGQ
DVKSWTGEGAVWFKVYEEQPQFGAQLTWPSNGKSSFEVPIPSCIRAGNYL
LRAEHIALHVAQSQGGAQFYISCAQLQVTGGGSTEPSQKVSFPGAYKSTD
PGILININYPVPTSYQNPGPAVFRC (SEQ ID NO: 114)
HYTLPRVGTGSDWQHVRRADNWQNNGFVGDVNSEQIRCFQATPAGAQDVY
TVQAGSTVTYHANPSIYHPGPMQFYLARVPDGQDVKSWTGEGAVWFKVYE
EQPQFGAQLTWPSNGKSSFEVPIPSCIRAGNYLLRAEHIALHVAQSQGGA
QFYISCAQLQVTGGGSTEPSQKVSFPGAYKSTDPGILININYPVPTSYQN
PGPAVFRC

The polynucleotide (SEQ ID NO:115) and amino acid (SEQ ID NO:116) sequences of a *M. thermophila* GH61x are provided below. The signal sequence is shown underlined in SEQ ID NO:116. SEQ ID NO:117 provides the sequence of this GH61x without the signal sequence.

(SEQ ID NO: 115)
ATGAAGGTTCTCGCGCCCCTGATTCTGGCCGGTGCCGCCAGCGCCCACAC

CATCTTCTCATCCCTCGAGGTGGGCGGCGTCAACCAGGGCATCGGGCAGG

GTGTCCGCGTGCCGTCGTACAACGGTCCGATCGAGGACGTGACGTCCAAC

TCGATCGCCTGCAACGGGCCCCCCAACCCGACGACGCCGACCAACAAGGT

CATCACGGTCCGGGCCGGCGAGACGGTGACGGCCGTCTGGCGGTACATGC

TGAGCACCACCGGCTCGGCCCCCAACGACATCATGGACAGCAGCCACAAG

GGCCCGACCATGGCCTACCTCAAGAAGGTCGACAACGCCACCACCGACTC

GGGCGTCGGCGGCGGCTGGTTCAAGATCCAGGAGGACGGCCTTACCAACG

GCGTCTGGGGCACCGAGCGCGTCATCAACGGCCAGGGCCGCCACAACATC

AAGATCCCCGAGTGCATCGCCCCCGGCCAGTACCTCCTCCGCGCCGAGAT

GCTTGCCCTGCACGGAGCTTCCAACTACCCCGGCGCTCAGTTCTACATGG

AGTGCGCCCAGCTCAATATCGTCGGCGGCACCGGCAGCAAGACGCCGTCC

ACCGTCAGCTTCCCGGGCGCTTACAAGGGTACCGACCCCGGAGTCAAGAT

CAACATCTACTGGCCCCCCGTCACCAGCTACCAGATTCCCGGCCCCGGCG

TGTTCACCTGC (SEQ ID NO: 116)
<u>MKVLAPLILAGAASA</u>HTIFSSLEVGGVNQGIGQGVRVPSYNGPIEDVTSN

SIACNGPPNPTTPTNKVITVRAGETVTAVWRYMLSTTGSAPNDIMDSSHK

GPTMAYLKKVDNATTDSGVGGGWFKIQEDGLTNGVWGTERVINGQGRHNI

KIPECIAPGQYLLRAEMLALHGASNYPGAQFYMECAQLNIVGGTGSKTPS

TVSFPGAYKGTDPGVKINIYWPPVTSYQIPGPGVFTC (SEQ ID NO: 117)
HTIFSSLEVGGVNQGIGQGVRVPSYNGPIEDVTSNSIACNGPPNPTTPTN

KVITVRAGETVTAVWRYMLSTTGSAPNDIMDSSHKGPTMAYLKKVDNATT

DSGVGGGWFKIQEDGLTNGVWGTERVINGQGRHNIKIPECIAPGQYLLRA

EMLALHGASNYPGAQFYMECAQLNIVGGTGSKTPSTVSFPGAYKGTDPGV

KINIYWPPVTSYQIPGPGVFTC

The polynucleotide (SEQ ID NO:118) and amino acid (SEQ ID NO:119) sequences of an *M. thermophila* GH61y are provided below. The signal sequence is underlined in SEQ ID NO:119. SEQ ID NO:120 provides the sequence of GH61y, without the signal sequence.

(SEQ ID NO: 118)
ATGATCGACAACCTCCCTGATGACTCCCTACAACCCGCCTGCCTCCGCCC

GGGCCACTACCTCGTCCGCCACGAGATCATCGCGCTGCACTCGGCCTGGG

CCGAGGGCGAGGCCCAGTTCTACCCCTTCCCCCTTTTTCCTTTTTTTCCC

TCCCTTCTTTTGTCCGGTAACTACACGATTCCCGGTCCCGCGATCTGGAA

GTGCCCAGAGGCACAGCAGAACGAG (SEQ ID NO: 119)
MIDNLPDDSLQPACLRPGHYLVRHEIIALHSAWAEGEAQFYPFPLFPFFP

SLLLSGNYTIPGPAIWKCPEAQQNE (SEQ ID NO: 120)
HYLVRHEIIALHSAWAEGEAQFYPFPLFPFFPSLLLSGNYTIPGPAIWKC

PEAQQNE

Wild-type EG1b cDNA (SEQ ID NO:121) and amino acid (SEQ ID NO:122) sequences are provided below. The signal sequence is underlined in SEQ ID NO:122. SEQ ID NO:123 provides the sequence of EG1b, without the signal sequence.

(SEQ ID NO: 121)
ATGGGGCAGAAGACTCTCCAGGGGCTGGTGGCGGCGGCGGCACTGGCAGC

CTCGGTGGCGAACGCGCAGCAACCGGGCACCTTCACGCCCGAGGTGCATC

CGACGCTGCCCGACGTGGAAGTGCACGACGAGCGGCGGGTGCGTCCAGCAG

GACACGTCGGTGGTGCTCGACTGGAACTACCGCTGGTTCCACACCGAGGA

CGGTAGCAAGTCGTGCATCACCTCTAGCGGCGTCGACCGGACCCTGTGCC

CGGACGAGGCGACGTGCGCCAAGAACTGCTTCGTCGAGGGCGTCAACTAC

ACGAGCAGCGGGGTCGAGACGTCCGGCAGCTCCCTCACCCTCCGCCAGTT

CTTCAAGGGCTCCGACGGCGCCATCAACAGCGTCTCCCCGCGCGTCTACC

TGCTCGGGGGAGACGGCAACTATGTCGTGCTCAAGCTCCTCGGCCAGGAG

CTGAGCTTCGACGTGGACGTATCGTCGCTCCCGTGCGGCGAGAACGCGGC

CCTGTACCTGTCCGAGATGGACGCGACGGGAGGACGGAACGAGTACAACA

CGGGCGGGGCCGAGTACGGGTCGGGCTACTGTGACGCCCAGTGCCCCGTG

CAGAACTGGAACAACGGGACGCTCAACACGGGCCGGGTGGGCTCGTGCTG

CAACGAGATGGACATCCTCGAGGCCAACTCCAAGGCCGAGGCCTTCACGC

CGCACCCCTGCATCGGCAACTCGTGCGACAAGAGCGGGTGCGGCTTCAAC

GCGTACGCGCGCGGTTACCACAACTACTGGGCCCCCGGCGGCACGCTCGA

CACGTCCCGGCCTTTCACCATGATCACCCGCTTCGTCACCGACGACGGCA

CCACCTCGGGCAAGCTCGCCCGCATCGAGCGCGTCTACGTCCAGGACGGC

AAGAAGGTGCCCAGCGCGGCGCCCGGGGGGGACGTCATCACGGCCGACGG

GTGCACCTCCGCGCAGCCCTACGCGGCCTTTCCGGCATGGGCGACGCCC

TCGGCCGCGGCATGGTCCTGGCCCTGAGCATCTGGAACGACGCGTCCGGG

TACATGAACTGGCTCGACGCCGGCAGCAACGGCCCCTGCAGCGACACCGA

GGGTAACCCGTCCAACATCCTGGCCAACCACCCGGACGCCCACGTCGTGC

TCTCCAACATCCGCTGGGGCGACATCGGCTCCACCGTCGACACCGGCGAT

GGCGACAACAACGGCGGCGGCCCCAACCCGTCATCCACCACCACCGCTAC

CGCTACCACCACCTCCTCCGGCCCGGCCGAGCCTACCCAGACCCACTACG

GCCAGTGTGGAGGGAAAGGATGGACGGGCCCTACCCGCTGCAGACGCCC

TACACCTGCAAGTACCAGAACGACTGGTACTCGCAGTGCCTGTAG (SEQ ID NO: 122)
<u>MGQKTLQGLVAAAALAASVANA</u>QQPGTFTPEVHPTLPTWKCTTSGGCVQQ

DTSVVLDWNYRWFHTEDGSKSCITSSGVDRTLCPDEATCAKNCFVEGVNY

TSSGVETSGSSLTLRQFFKGSDGAINSVSPRVYLLGGDGNYVVLKLLGQE

LSFDVDVSSLPCGENAALYLSEMDATGGRNEYNTGGAEYGSGYCDAQCPV

QNWNNGTLNTGRVGSCCNEMDILEANSKAEAFTPHPCIGNSCDKSGCGFN

AYARGYHNYWAPGGTLDTSRPFTMITRFVTDDGTTSGKLARIERVYVQDG

```
KKVPSAAPGGDVITADGCTSAQPYGGLSGMGDALGRGMVLALSIWNDASG
YMNWLDAGSNGPCSDTEGNPSNILANHPDAHVVLSNIRWGDIGSTVDTGD
GDNNGGGPNPSSTTTATATTTSSGPAEPTQTHYGQCGGKGWTGPTRCETP
YTCKYQNDWYSQCL (SEQ ID NO: 123)
QQPGTFTPEVHPTLPTWKCTTSGGCVQQDTSVVLDWNYRWFHTEDGSKSC
ITSSGVDRTLCPDEATCAKNCFVEGVNYTSSGVETSGSSLTLRQFFKGSD
GAINSVSPRVYLLGGDGNYVVLKLLGQELSFDVDVSSLPCGENAALYLSE
MDATGGRNEYNTGGAEYGSGYCDAQCPVQNWNNGTLNTGRVGSCCNEMDI
LEANSKAEAFTPHPCIGNSCDKSGCGFNAYARGYHNYWAPGGTLDTSRPF
TMITRFVTDDGTTSGKLARIERVYVQDGKKVPSAAPGGDVITADGCTSAQ
PYGGLSGMGDALGRGMVLALSIWNDASGYMNWLDAGSNGPCSDTEGNPSN
ILANHPDAHVVLSNIRWGDIGSTVDTGDGDNNGGGPNPSSTTTATATTTS
SGPAEPTQTHYGQCGGKGWTGPTRCETPYTCKYQNDWYSQCL
```

Wild-type *M. thermophila* EG2 polynucleotide (SEQ ID NO:124) and amino acid (SEQ ID NO:125) sequences are provided below. The signal sequence is underlined in SEQ ID NO:125. SEQ ID NO:126 provides the sequence of EG2, without the signal sequence.

```
                                        (SEQ ID NO: 124)
ATGAAGTCCTCCATCCTCGCCAGCGTCTTCGCCACGGGCGCCGTGGCTCA
AAGTGGTCCGTGGCAGCAATGTGGTGGCATCGGATGGCAAGGATCGACCG
ACTGTGTGTCGGGTTACCACTGCGTCTACCAGAACGATTGGTACAGCCAG
TGCGTGCCTGGCGCGGCGTCGACAACGCTCCAGACATCTACCACGTCCAG
GCCCACCGCCACCAGCACCGCCCCTCCGTCGTCCACCACCTCGCCTAGCA
AGGGCAAGCTCAAGTGGCTCGGCAGCAACGAGTCGGGCGCCGAGTTCGGG
GAGGGCAACTACCCCGGCCTCTGGGGCAAGCACTTCATCTTCCCGTCGAC
TTCGGCGATTCAGACGCTCATCAATGATGGATACAACATCTTCCGGATCG
ACTTCTCGATGGAGCGTCTGGTGCCCAACCAGTTGACGTCGTCCTTCGAC
GAGGGCTACCTCCGCAACCTGACCGAGGTGGTCAACTTCGTGACGAACGC
GGGCAAGTACGCCGTCCTGGACCCGCACAACTACGGCCGGTACTACGGCA
ACGTCATCACGGACACGAACGCGTTCCGGACCTTCTGGACCAACCTGGCC
AAGCAGTTCGCCTCCAACTCGCTCGTCATCTTCGACACCAACAACGAGTA
CAACACGATGGACCAGACCCTGGTGCTCAACCTCAACCAGGCCGCCATCG
ACGGCATCCGGGCCGCCGGCGCGACCTCGCAGTACATCTTCGTCGAGGGC
AACGCGTGGAGCGGGGCCTGGAGCTGGAACACGACCAACACCAACATGGC
CGCCCTGACGGACCCGCAGAACAAGATCGTGTACGAGATGCACCAGTACC
TCGACTCGGACAGCTCGGGCACCCACGCCGAGTGCGTCAGCAGCAACATC
GGCGCCCAGCGCGTCGTCGGAGCCACCCAGTGGCTCCGCGCCAACGGCAA
GCTCGGCGTCCTCGGCGAGTTCGCCGGCGGCGCCAACGCCGTCTGCCAGC
AGGCCGTCACCGGCCTCCTCGACCACCTCCAGGACAACAGCGACGTCTGG
CTGGGTGCCCTCTGGTGGGCCGCCGGTCCCTGGTGGGGCGACTACATGTA
CTCGTTCGAGCCTCCTTCGGGCACCGGCTATGTCAACTACAACTCGATCC
TAAAGAAGTACTTGCCGTAA (SEQ ID NO: 125)
MKSSILASVFATGAVAQSGPWQQCGGIGWQGSTDCVSGYHCVYQNDWYSQ
CVPGAASTTLQTSTTSRPTATSTAPPSSTTSPSKGKLKWLGSNESGAEFG
EGNYPGLWGKHFIFPSTSAIQTLINDGYNIFRIDFSMERLVPNQLTSSFD
EGYLRNLTEVVNFVTNAGKYAVLDPHNYGRYYGNVITDTNAFRTFWTNLA
KQFASNSLVIFDTNNEYNTMDQTLVLNLNQAAIDGIRAAGATSQYIFVEG
NAWSGAWSWNTTNTNMAALTDPQNKIVYEMHQYLDSDSSGTHAECVSSNI
GAQRVVGATQWLRANGKLGVLGEFAGGANAVCQQAVTGLLDHLQDNSEVW
LGALWWAAGPWWGDYMYSFEPPSGTGYVNYNSILKKYLP (SEQ ID NO: 126)
QSGPWQQCGGIGWQGSTDCVSGYHCVYQNDWYSQCVPGAASTTLQTSTTS
RPTATSTAPPSSTTSPSKGKLKWLGSNESGAEFGEGNYPGLWGKHFIFPS
TSAIQTLINDGYNIFRIDFSMERLVPNQLTSSFDEGYLRNLTEVVNFVTN
AGKYAVLDPHNYGRYYGNVITDTNAFRTFWTNLAKQFASNSLVIFDTNNE
YNTMDQTLVLNLNQAAIDGIRAAGATSQYIFVEGNAWSGAWSWNTTNTNM
AALTDPQNKIVYEMHQYLDSDSSGTHAECVSSNIGAQRVVGATQWLRANG
KLGVLGEFAGGANAVCQQAVTGLLDHLQDNSEVWLGALWWAAGPWWGDYM
YSFEPPSGTGYVNYNSILKKYLP
```

The polynucleotide (SEQ ID NO:127) and amino acid (SEQ ID NO:128) sequences of a wild-type BGL are provided below. The signal sequence is underlined in SEQ ID NO:128. SEQ ID NO:129 provides the polypeptide sequence without the signal sequence.

```
                                        (SEQ ID NO: 127)
ATGAAGGCTGCTGCGCTTTCCTGCCTCTTCGGCAGTACCCTTGCCGTTGC
AGGCGCCATTGAATCGAGAAAGGTTCACCAGAAGCCCCTCGCGAGATCTG
AACCTTTTTACCCGTCGCCATGGATGAATCCCAACGCCGACGGCTGGGCG
GAGGCCTATGCCCAGGCCAAGTCCTTTGTCTCCCAAATGACTCTGCTAGA
GAAGGTCAACTTGACCACGGGAGTCGGCTGGGGGGCTGAGCAGTGCGTCG
GCCAAGTGGGCGCGATCCCTCGCCTTGGACTTCGCAGTCTGTGCATGCAT
GACTCCCCTCTCGGCATCCGAGGAGCCGACTACAACTCAGCGTTCCCCTC
TGGCCAGACCGTTGCTGCTACCTGGGATCGCGGTCTGATGTACCGTCGCG
GCTACGCAATGGGCCAGGAGGCCAAAGGCAAGGGCATCAATGTCCTTCTC
GGACCAGTCGCCGGCCCCTTGGCCGCATGCCCGAGGGCGGTCGTAACTG
GGAAGGCTTCGCTCCGGATCCCGTCCTTACCGGCATCGGCATGTCCGAGA
CGATCAAGGGCATTCAGGATGCTGGCGTCATCGCTTGTGCGAAGCACTTT
ATTGGAAACGAGCAGGAGCACTTCAGACAGGTGCCAGAAGCCCAGGGATA
CGGTTACAACATCAGCGAAACCCTCTCCTCCAACATTGACGACAAGACCA
TGCACGAGCTCTACCTTTGGCCGTTTGCCGATGCCGTCCGGGCCGGCGTC
GGCTCTGTCATGTGCTCGTACCAGCAGGTCAACAACTCGTACGCCTGCCA
```

```
GAACTCGAAGCTGCTGAACGACCTCCTCAAGAACGAGCTTGGGTTTCAGG
GCTTCGTCATGAGCGACTGGCAGGCACAGCACACTGGCGCAGCAAGCGCC
GTGGCTGGTCTCGATATGTCCATGCCGGGCGACACCCAGTTCAACACTGG
CGTCAGTTTCTGGGGCGCCAATCTCACCCTCGCCGTCCTCAACGGCACAG
TCCCTGCCTACCGTCTCGACGACATGGCCATGCGCATCATGGCCGCCCTC
TTCAAGGTCACCAAGACCACCGACCTGGAACCGATCAACTTCTCCTTCTG
GACCGACGACACTTATGGCCCGATCCACTGGGCCGCCAAGCAGGGCTACC
AGGAGATTAATTCCCACGTTGACGTCCGCGCCGACCACGGCAACCTCATC
CGGGAGATTGCCGCCAAGGGTACGGTGCTGCTGAAGAATACCGGCTCTCT
ACCCCTGAACAAGCCAAAGTTCGTGGCCGTCATCGGCGAGGATGCTGGGT
CGAGCCCCAACGGGCCCAACGGCTGCAGCGACCGCGGCTGTAACGAAGGC
ACGCTCGCCATGGGCTGGGGATCCGGCACAGCCAACTATCCGTACCTCGT
TTCCCCCGACGCCGCGCTCCAGGCCCGGGCCATCCAGGACGGCACGAGGT
ACGAGAGCGTCCTGTCCAACTACGCCGAGGAAAAGACAAAGGCTCTGGTC
TCGCAGGCCAATGCAACCGCCATCGTCTTCGTCAATGCCGACTCAGGCGA
GGGCTACATCAACGTGGACGGTAACGAGGGCGACCGTAAGAACCTGACTC
TCTGGAACAACGGTGATACTCTGGTCAAGAACGTCTCGAGCTGGTGCAGC
AACACCATCGTCGTCATCCACTCGGTCGGCCCGGTCCTCCTGACCGATTG
GTACGACAACCCCAACATCACGGCCATTCTCTGGGCTGGTCTTCCGGGCC
AGGAGTCGGGCAACTCCATCACCGACGTGCTTTACGGCAAGGTCAACCCC
GCCGCCCGCTCGCCCTTCACTTGGGGCAAGACCCGCGAAAGCTATGGCGC
GGACGTCCTGTACAAGCCGAATAATGGCAATGGTGCGCCCCAACAGGACT
TCACCGAGGGCGTCTTCATCGACTACCGCTACTTCGACAAGGTTGACGAT
GACTCGGTCATCTACGAGTTCGGCCACGGCCTGAGCTACACCACCTTCGA
GTACAGCAACATCCGCGTCGTCAAGTCCAACGTCAGCGAGTACCGGCCCA
CGACGGGCACCACGGCCCAGGCCCCGACGTTTGGCAACTTCTCCACCGAC
CTCGAGGACTATCTCTTCCCCAAGGACGAGTTCCCCTACATCTACCAGTA
CATCTACCCGTACCTCAACACGACCGACCCCCGGAGGGCCTCGGCCGATC
CCCACTACGGCCAGACCGCCGAGGAGTTCCTCCCGCCCCACGCCACCGAT
GACGACCCCCAGCCGCTCCTCCGGTCCTCGGGCGGAAACTCCCCCGGCGG
CAACCGCCAGCTGTACGACATTGTCTACACAATCACGGCCGACATCACGA
ATACGGGCTCCGTTGTAGGCGAGGAGGTACCGCAGCTCTACGTCTCGCTG
GGCGGTCCCGAGGATCCCAAGGTGCAGCTGCGCGACTTTGACAGGATGCG
GATCGAACCCGGCGAGACGAGGCAGTTCACCGGCCGCCTGACGCGCAGAG
ATCTGAGCAACTGGGACGTCACGGTGCAGGACTGGGTCATCAGCAGGTAT
CCCAAGACGGCATATGTTGGGAGGAGCAGCCGGAAGTTGGATCTCAAGAT
TGAGCTTCCTTGA
```

(SEQ ID NO: 128)
MKAAALSCLFGSTLAVAGAIESRKVHQKPLARSEPFYPSPWMNPNADGWA
EAYAQAKSFVSQMTLLEKVNLTTGVGWGAEQCVGQVGAIPRLGLRSLCMH
DSPLGIRGADYNSAFPSGQTVAATWDRGLMYRRGYAMGQEAKGKGINVLL
GPVAGPLGRMPEGGRNWEGFAPDPVLTGIGMSETIKGIQDAGVIACAKHF
IGNEQEHFRQVPEAQGYGYNISETLSSNIDDKTMHELYLWPFADAVRAGV
GSVMCSYQQVNNSYACQNSKLLNDLLKNELGFQGFVMSDWQAHTGAASA
VAGLDMSMPGDTQFNTGVSFWGANLTLAVLNGTVPAYRLDDMAMRIMAAL
FKVTKTTDLEPINFSFWTDDTYGPIHWAAKQGYQEINSHVDVRADHGNLI
REIAAKGTVLLKNTGSLPLNKPKFVAVIGEDAGSSPNGPNGCSDRGCNEG
TLAMGWGSGTANYPYLVSPDAALQARAIQDGTRYESVLSNYAEEKTKALV
SQANATAIVFVNADSGEGYINVDGNEGDRKNLTLWNNGDTLVKNVSSWCS
NTIVVIHSVGPVLLTDWYDNPNITAILWAGLPGQESGNSITDVLYGKVNP
AARSPFTWGKTRESYGADVLYKPNNGNGAPQQDFTEGVFIDYRYFDKVDD
DSVIYEFGHGLSYTTFEYSNIRVVKSNVSEYRPTTGTTAQAPTFGNFSTD
LEDYLFPKDEFPYIYQYIYPYLNTTDPRRASADPHYGQTAEEFLPPHATD
DDPQPLLRSSGGNSPGGNRQLYDIVYTITADITNTGSVVGEEVPQLYVSL
GGPEDPKVQLRDFDRMRIEPGETRQFTGRLTRRDLSNWDVTVQDWVISRY
PKTAYVGRSSRKLDLKIELP (SEQ ID NO: 129)
IESRKVHQKPLARSEPFYPSPWMNPNADGWAEAYAQAKSFVSQMTLLEKV
NLTTGVGWGAEQCVGQVGAIPRLGLRSLCMHDSPLGIRGADYNSAFPSGQ
TVAATWDRGLMYRRGYAMGQEAKGKGINVLLGPVAGPLGRMPEGGRNWEG
FAPDPVLTGIGMSETIKGIQDAGVIACAKHFIGNEQEHFRQVPEAQGYGY
NISETLSSNIDDKTMHELYLWPFADAVRAGVGSVMCSYQQVNNSYACQNS
KLLNDLLKNELGFQGFVMSDWQAHTGAASAVAGLDMSMPGDTQFNTGVS
FWGANLTLAVLNGTVPAYRLDDMAMRIMAALFKVTKTTDLEPINFSFWTD
DTYGPIHWAAKQGYQEINSHVDVRADHGNLIREIAAKGTVLLKNTGSLPL
NKPKFVAVIGEDAGSSPNGPNGCSDRGCNEGTLAMGWGSGTANYPYLVSP
DAALQARAIQDGTRYESVLSNYAEEKTKALVSQANATAIVFVNADSGEGY
INVDGNEGDRKNLTLWNNGDTLVKNVSSWCSNTIVVIHSVGPVLLTDWYD
NPNITAILWAGLPGQESGNSITDVLYGKVNPAARSPFTWGKTRESYGADV
LYKPNNGNGAPQQDFTEGVFIDYRYFDKVDDDSVIYEFGHGLSYTTFEYS
NIRVVKSNVSEYRPTTGTTAQAPTFGNFSTDLEDYLFPKDEFPYIYQYIY
PYLNTTDPRRASADPHYGQTAEEFLPPHATDDDPQPLLRSSGGNSPGGNR
QLYDIVYTITADITNTGSVVGEEVPQLYVSLGGPEDPKVQLRDFDRMRIE
PGETRQFTGRLTRRDLSNWDVTVQDWVISRYPKTAYVGRSSRKLDLKIEL
P

The polynucleotide (SEQ ID NO:130) and amino acid (SEQ ID NO:131) sequences of a BGL variant ("Variant 883") are provided below. The signal sequence is underlined in SEQ ID NO:131. SEQ ID NO:132 provides the sequence of this BGL variant, without the signal sequence.

(SEQ ID NO: 130)
ATGAAGGCTGCTGCGCTTTCCTGCCTCTTCGGCAGTACCCTTGCCGTTGC
AGGCGCCATTGAATCGAGAAAGGTTCACCAGAAGCCCCTCGCGAGATCTG

AACCTTTTTACCCGTCGCCATGGATGAATCCCAACGCCGACGGCTGGGCG
GAGGCCTATGCCCAGGCCAAGTCCTTTGTCTCCCAAATGACTCTGCTAGA
GAAGGTCAACTTGACCACGGGAGTCGGCTGGGGGGCTGAGCAGTGCGTCG
GCCAAGTGGGCGCGATCCCTCGCCTTGGACTTCGCAGTCTGTGCATGCAT
GACTCCCCTCTCGGCATCCGAGGAGCCGACTACAACTCAGCGTTCCCCTC
TGGCCAGACCGTTGCTGCTACCTGGGATCGCGGTCTGATGTACCGTCGCG
GCTACGCAATGGGCCAGGAGGCCAAAGGCAAGGGCATCAATGTCCTTCTC
GGACCAGTCGCCGGCCCCCTTGGCCGCATGCCCGAGGGCGGTCGTAACTG
GGAAGGCTTCGCTCCGGATCCCGTCCTTACCGGCATCGGCATGTCCGAGA
CGATCAAGGGCATTCAGGATGCTGGCGTCATCGCTTGTGCGAAGCACTTT
ATTGGAAACGAGCAGGAGCACTTCAGACAGGTGCCAGAAGCCCAGGGATA
CGGTTACAACATCAGCGAAACCCTCTCCTCCAACATTGACGACAAGACCA
TGCACGAGCTCTACCTTTGGCCGTTTGCCGATGCCGTCCGGGCCGGCGTC
GGCTCTGTCATGTGCTCGTACAACCAGGTCAACAACTCGTACGCCTGCCA
GAACTCGAAGCTGCTGAACGACCTCCTCAAGAACGAGCTTGGGTTTCAGG
GCTTCGTCATGAGCGACTGGTGGGCACAGCACACTGGCGCAGCAAGCGCC
GTGGCTGGTCTCGATATGTCCATGCCGGGCGACACCATGTTCAACACTGG
CGTCAGTTTCTGGGGCGCCAATCTCACCCTCGCCGTCCTCAACGGCACAG
TCCCTGCCTACCGTCTCGACGACATGGCCATGCGCATCATGGCCGCCCTC
TTCAAGGTCACCAAGACCACCGACCTGGAACCGATCAACTTCTCCTTCTG
GACCCGCGACACTTATGGCCCGATCCACTGGGCCGCCAAGCAGGGCTACC
AGGAGATTAATTCCCACGTTGACGTCCGCGCCGACCACGGCAACCTCATC
CGGAACATTGCCGCCAAGGGTACGGTGCTGCTGAAGAATACCGGCTCTCT
ACCCCTGAACAAGCCAAAGTTCGTGGCCGTCATCGGCGAGGATGCTGGGC
CGAGCCCCAACGGGCCCAACGGCTGCAGCGACCGCGGCTGTAACGAAGGC
ACGCTCGCCATGGGCTGGGGATCCGGCACAGCCAACTATCCGTACCTCGT
TTCCCCCGACGCCGCGCTCCAGTTGCGGGCCATCCAGGACGGCACGAGGT
ACGAGAGCGTCCTGTCCAACTACGCCGAGGAAAATACAAAGGCTCTGGTC
TCGCAGGCCAATGCAACCGCCATCGTCTTCGTCAATGCCGACTCAGGCGA
GGGCTACATCAACGTGGACGGTAACGAGGGCGACCGTAAGAACCTGACTC
TCTGGAACAACGGTGATACTCTGGTCAAGAACGTCTCGAGCTGGTGCAGC
AACACCATCGTCGTCATCCACTCGGTCGGCCCGGTCCTCCTGACCGATTG
GTACGACAACCCCAACATCACGGCCATTCTCTGGGCTGGTCTTCCGGGCC
AGGAGTCGGGCAACTCCATCACCGACGTGCTTTACGGCAAGGTCAACCCC
GCCGCCCGCTCGCCCTTCACTTGGGGCAAGACCCGCGAAAGCTATGGCGC
GGACGTCCTGTACAAGCCGAATAATGGCAATTGGGCGCCCCAACAGGACT
TCACCGAGGGCGTCTTCATCGACTACCGCTACTTCGACAAGGTTGACAT
GACTCGGTCATCTACGAGTTCGGCCACGGCCTGAGCTACACCACCTTCGA
GTACAGCAACATCCGCGTCGTCAAGTCCAACGTCAGCGAGTACCGGCCCA
CGACGGGCACCACGATTCAGGCCCCGACGTTTGGCAACTTCTCCACCGAC
CTCGAGGACTATCTCTTCCCCAAGGACGAGTTCCCCTACATCCCGCAGTA

CATCTACCCGTACCTCAACACGACCGACCCCCGGAGGGCCTCGGCCGATC
CCCACTACGGCCAGACCGCCGAGGAGTTCCTCCCGCCCCACGCCACCGAT
GACGACCCCCAGCCGCTCCTCCGGTCCTCGGGCGGAAACTCCCCCGGCGG
CAACCGCCAGCTGTACGACATTGTCTACACAATCACGGCCGACATCACGA
ATACGGGCTCCGTTGTAGGCGAGGAGGTACCGCAGCTCTACGTCTCGCTG
GGCGGTCCCGAGGATCCCAAGGTGCAGCTGCGCGACTTTGACAGGATGCG
GATCGAACCCGGCGAGACGAGGCAGTTCACCGGCCGCCTGACGCGCAGAG
ATCTGAGCAACTGGGACGTCACGGTGCAGGACTGGGTCATCAGCAGGTAT
CCCAAGACGGCATATGTTGGGAGGAGCAGCCGGAAGTTGGATCTCAAGAT
TGAGCTTCCTTGA (SEQ ID NO: 131)
<u>MKAAALSCLFGSTLAVAGA</u>IESRKVHQKPLARSEPFYPSPWMNPNADGWA
EAYAQAKSFVSQMTLLEKVNLTTGVGWGAEQCVGQVGAIPRLGLRSLCMH
DSPLGIRGADYNSAFPSGQTVAATWDRGLMYRRGYAMGQEAKGKGINVLL
GPVAGPLGRMPEGGRNWEGFAPDPVLTGIGMSETIKGIQDAGVIACAKHF
IGNEQEHFRQVPEAQGYGYNISETLSSNIDDKTMHELYLWPFADAVRAGV
GSVMCSYNQVNNSYACQNSKLLNDLLKNELGFQGFVMSDWWAQHTGAASA
VAGLDMSMPGDTMFNTGVSFWGANLTLAVLNGTVPAYRLDDMAMRIMAAL
FKVTKTTDLEPINFSFWTRDTYGPIHWAAKQGYQEINSHVDVRADHGNLI
RNIAAKGTVLLKNTGSLPLNKPKFVAVIGEDAGPSPNGPNGCSDRGCNEG
TLAMGWGSGTANYPYLVSPDAALQLRAIQDGTRYESVLSNYAEENTKALV
SQANATAIVFVNADSGEGYINVDGNEGDRKNLTWNNGDTLVKNVSSWCS
NTIVVIHSVGPVLLTDWYDNPNITAILWAGLPGQESGNSITDVLYGKVNP
AARSPFTWGKTRESYGADVLYKPNNGNWAPQQDFTEGVFIDYRYFDKVDD
DSVIYEFGHGLSYTTFEYSNIRVVKSNVSEYRPTTGTTIQAPTFGNFSTD
LEDYLFPKDEFPYIPQYIYPYLNTTDPRRASADPHYGQTAEEFLPPHATD
DDPQPLLRSSGGNSPGGNRQLYDIVYTITADITNTGSVVGEEVPQLYVSL
GGPEDPKVQLRDFDRMRIEPGETRQFTGRLTRRDLSNWDVTVQDWVISRY
PKTAYVGRSSRKLDLKIELP (SEQ ID NO: 132)
IESRKVHQKPLARSEPFYPSPWMNPNADGWAEAYAQAKSFVSQMTLLEKV
NLTTGVGWGAEQCVGQVGAIPRLGLRSLCMHDSPLGIRGADYNSAFPSGQ
TVAATWDRGLMYRRGYAMGQEAKGKGINVLLGPVAGPLGRMPEGGRNWEG
FAPDPVLTGIGMSETIKGIQDAGVIACAKHFIGNEQEHFRQVPEAQGYGY
NISETLSSNIDDKTMHELYLWPFADAVRAGVGSVMCSYNQVNNSYACQNS
KLLNDLLKNELGFQGFVMSDWWAQHTGAASAVAGLDMSMPGDTMFNTGVS
FWGANLTLAVLNGTVPAYRLDDMAMRIMAALFKVTKTTDLEPINFSFWTR
DTYGPIHWAAKQGYQEINSHVDVRADHGNLRNIAAKGTVLLKNTGSLPL
NKPKFVAVIGEDAGPSPNGPNGCSDRGCNEGTLAMGWGSGTANYPYLVSP
DAALQLRAIQDGTRYESVLSNYAEENTKALVSQANATAIVFVNADSGEGY
INVDGNEGDRKNLTWNNGDTLVKNVSSWCSNTIVVIHSVGPVLLTDWYD

-continued

NPNITAILWAGLPGQESGNSITDVLYGKVNPAARSPFTWGKTRESYGADV
LYKPNNGNWAPQQDFTEGVFIDYRYFDKVDDDSVIYEFGHGLSYTTFEYS
NIRVVKSNVSEYRPTTGTTIQAPTFGNFSTDLEDYLFPKDEFPYIPQYIY
PYLNTTDPRRASADPHYGQTAEEFLPPHATDDDPQPLLRSSGGNSPGGNR
QLYDIVYTITADITNTGSVVGEEVPQLYVSLGGPEDPKVQLRDFDRMRIE
PGETRQFTGRLTRRDLSNWDVTVQDWVISRYPKTAYVGRSSRKLDLKIEL
P

The polynucleotide (SEQ ID NO:133) and amino acid (SEQ ID NO:134) sequences of a BGL variant ("Variant 900") are provided below. The signal sequence is underlined in SEQ ID NO:134. SEQ ID NO:135 provides the sequence of this BGL variant, without the signal sequence.

(SEQ ID NO: 133)
ATGAAGGCTGCTGCGCTTTCCTGCCTCTTCGGCAGTACCCTTGCCGTTGC
AGGCGCCATTGAATCGAGAAAGGTTCACCAGAAGCCCCTCGCGAGATCTG
AACCTTTTTACCCGTCGCCATGGATGAATCCCAACGCCATCGGCTGGGCG
GAGGCCTATGCCCAGGCCAAGTCCTTTGTCTCCCAAATGACTCTGCTAGA
GAAGGTCAACTTGACCACGGGAGTCGGCTGGGGGGAGGAGCAGTGCGTCG
GCAACGTGGGCGCGATCCCTCGCCTTGGACTTCGCAGTCTGTGCATGCAT
GACTCCCCTCTCGGCGTGCGAGGAACCGACTACAACTCAGCGTTCCCCTC
TGGCCAGACCGTTGCTGCTACCTGGGATCGCGGTCTGATGTACCGTCGCG
GCTACGCAATGGGCCAGGAGGCCAAAGGCAAGGGCATCAATGTCCTTCTC
GGACCAGTCGCCGGCCCCTTGGCCGCATGCCCGAGGGCGGTCGTAACTG
GGAAGGCTTCGCTCCGGATCCCGTCCTTACCGGCATCGGCATGTCCGAGA
CGATCAAGGGCATTCAGGATGCTGGCGTCATCGCTTGTGCGAAGCACTTT
ATTGGAAACGAGCAGGAGCACTTCAGACAGGTGCCAGAAGCCCAGGGATA
CGGTTACAACATCAGCGAAACCCTCTCCTCCAACATTGACGACAAGACCA
TGCACGAGCTCTACCTTTGGCCGTTTGCCGATGCCGTCCGGGCCGGCGTC
GGCTCTGTCATGTGCTCGTACAACCAGGGCAACAACTCGTACGCCTGCCA
GAACTCGAAGCTGCTGAACGACCTCCTCAAGAACGAGCTTGGGTTTCAGG
GCTTCGTCATGAGCGACTGGTGGGCACAGCACACTGGCGCAGCAAGCGCC
GTGGCTGGTCTCGATATGTCCATGCCGGGCGACACCATGGTCAACACTGG
CGTCAGTTTCTGGGGCGCCAATCTCACCCTCGCCGTCCTCAACGGCACAG
TCCCTGCCTACCGTCTCGACGACATGTGCATGCGCATCATGGCCGCCCTC
TTCAAGGTCACCAAGACCACCGACCTGGAACCGATCAACTTCTCCTTCTG
GACCCGCGACACTTATGGCCCGATCCACTGGGCCGCCAAGCAGGGCTACC
AGGAGATTAATTCCCACGTTGACGTCCGCGCCGACCACGGCAACCTCATC
CGGAACATTGCCGCCAAGGGTACGGTGCTGCTGAAGAATACCGGCTCTCT
ACCCCTGAACAAGCCAAAGTTCGTGGCCGTCATCGGCGAGGATGCTGGGC
CGAGCCCCAACGGGCCCAACGGCTGCAGCGACCGCGGCTGTAACGAAGGC
ACGCTCGCCATGGGCTGGGGATCCGGCACAGCCAACTATCCGTACCTCGT
TTCCCCCGACGCCGCGCTCCAGGCGCGGGCCATCCAGGACGGCACGAGGT

-continued

ACGAGAGCGTCCTGTCCAACTACGCCGAGGAAAATACAAAGGCTCTGGTC
TCGCAGGCCAATGCAACCGCCATCGTCTTCGTCAATGCCGACTCAGGCGA
GGGCTACATCAACGTGGACGGTAACGAGGGCGACCGTAAGAACCTGACTC
TCTGGAACAACGGTGATACTCTGGTCAAGAACGTCTCGAGCTGGTGCAGC
AACACCATCGTCGTCATCCACTCGGTCGGCCCGGTCCTCCTGACCGATTG
GTACGACAACCCCAACATCACGGCCATTCTCTGGGCTGGTCTTCCGGGCC
AGGAGTCGGGCAACTCCATCACCGACGTGCTTTACGGCAAGGTCAACCCC
GCCGCCCGCTCGCCCTTCACTTGGGGCAAGACCCGCGAAAGCTATGGCGC
GGACGTCCTGTACAAGCCGAATAATGGCAATTGGGCGCCCCAACAGGACT
TCACCGAGGGCGTCTTCATCGACTACCGCTACTTCGACAAGGTTGACGAT
GACTCGGTCATCTACGAGTTCGGCCACGGCCTGAGCTACACCACCTTCGA
GTACAGCAACATCCGCGTCGTCAAGTCCAACGTCAGCGAGTACCGGCCCA
CGACGGGCACCACGATTCAGGCCCCGACGTTTGGCAACTTCTCCACCGAC
CTCGAGGACTATCTCTTCCCCAAGGACGAGTTCCCCTACATCCCGCAGTA
CATCTACCCGTACCTCAACACGACCGACCCCCGGAGGGCCTCGGGCGATC
CCCACTACGGCCAGACCGCCGAGGAGTTCCTCCCGCCCCACGCCACCGAT
GACGACCCCCAGCCGCTCCTCCGGTCCTCGGGCGGAAACTCCCCCGGCGG
CAACCGCCAGCTGTACGACATTGTCTACACAATCACGGCCGACATCACGA
ATACGGGCTCCGTTGTAGGCGAGGAGGTACCGCAGCTCTACGTCTCGCTG
GGCGGTCCCGAGGATCCCAAGGTGCAGCTGCGCGACTTTGACAGGATGCG
GATCGAACCCGGCGAGACGAGGCAGTTCACCGGCCGCCTGACGCGCAGAG
ATCTGAGCAACTGGGACGTCACGGTGCAGGACTGGGTCATCAGCAGGTAT
CCCAAGACGGCATATGTTGGGAGGAGCAGCCGGAAGTTGGATCTCAAGAT
TGAGCTTCCTTGA (SEQ ID NO: 134)
<u>MKAAALSCLFGSTLAVAGA</u>IESRKVHQKPLARSEPFYPSPWMNPNAIGWA
EAYAQAKSFVSQMTLLEKVNLTTGVGWGEEQCVGNVGAIPRLGLRSLCMH
DSPLGVRGTDYNSAFPSGQTVAATWDRGLMYRRGYAMGQEAKGKGINVLL
GPVAGPLGRMPEGGRNWEGFAPDPVLTGIGMSETIKGIQDAGVIACAKHF
IGNEQEHFRQVPEAQGYGYNISETLSSNIDDKTMHELYLWPFADAVRAGV
GSVMCSYNQGNNSYACQNSKLLNDLLKNELGFQGFVMSDWWAQHTGAASA
VAGLDMSMPGDTMVNTGVSFWGANLTLAVLNGTVPAYRLDDMCMRIMAAL
FKVTKTTDLEPINFSFWTRDTYGPIHWAAKQGYQEINSHVDVRADHGNLI
RNIAAKGTVLLKNTGSLPLNKPKFVAVIGEDAGPSPNGPNGCSDRGCNEG
TLAMGWGSGTANYPYLVSPDAALQARAIQDGTRYESVLSNYAEENTKALV
SQANATAIVFVNADSGEGYINVDGNEGDRKNLTLWNNGDTLVKNVSSWCS
NTIVVIHSVGPVLLTDWYDNPNITAILWAGLPGQESGNSITDVLYGKVNP
AARSPFTWGKTRESYGADVLYKPNNGNWAPQQDFTEGVFIDYRYFDKVDD
DSVIYEFGHGLSYTTFEYSNIRVVKSNVSEYRPTTGTTIQAPTFGNFSTD
LEDYLFPKDEFPYIPQYIYPYLNTTDPRRASGDPHYGQTAEEFLPPHATD
DDPQPLLRSSGGNSPGGNRQLYDIVYTITADITNTGSVVGEEVPQLYVSL

GGPEDPKVQLRDFDRMRIEPGETRQFTGRLTRRDLSNWDVTVQDWVISRY

PKTAYVGRSSRKLDLKIELP (SEQ ID NO: 135)
IESRKVHQKPLARSEPFYPSPWMNPNAIGWAEAYAQAKSFVSQMTLLEKV

NLTTGVGWGEEQCVGNVGAIPRLGLRSLCMHDSPLGVRGTDYNSAFPSGQ

TVAATWDRGLMYRRGYAMGQEAKGKGINVLLGPVAGPLGRMPEGGRNWEG

FAPDPVLTGIGMSETIKGIQDAGVIACAKHFIGNEQEHFRQVPEAQGYGY

NISETLSSNIDDKTMHELYLWPFADAVRAGVGSVMCSYNQGNNSYACQNS

KLLNDLLKNELGFQGFVMSDWWAQHTGAASAVAGLDMSMPGDTMVNTGVS

FWGANLTLAVLNGTVPAYRLDDMCMRIMAALFKVTKTTDLEPINFSFWTR

DTYGPIHWAAKQGYQEINSHVDVRADHGNLIRNIAAKGTVLLKNTGSLPL

NKPKFVAVIGEDAGPSPNGPNGCSDRGCNEGTLAMGWGSGTANYPYLVSP

DAALQARAIQDGTRYESVLSNYAEENTKALVSQANATAIVFVNADSGEGY

INVDGNEGDRKNLTLWNNGDTLVKNVSSWCSNTIVVIHSVGPVLLTDWYD

NPNITAILWAGLPGQESGNSITDVLYGKVNPAARSPFTWGKTRESYGADV

LYKPNNGNWAPQQDFTEGVFIDYRYFDKVDDDSVIYEFGHGLSYTTFEYS

NIRVVKSNVSEYRPTTGTTIQAPTFGNFSTDLEDYLFPKDEFPYIPQYIY

PYLNTTDPRRASGDPHYGQTAEEFLPPHATDDDPQPLLRSSGGNSPGGNR

QLYDIVYTITADITNTGSVVGEEVPQLYVSLGGPEDPKVQLRDFDRMRIE

PGETRQFTGRLTRRDLSNWDVTVQDWVISRYPKTAYVGRSSRKLDLKIEL

P

The polynucleotide (SEQ ID NO:136) and amino acid (SEQ ID NO:137) sequences of wild-type *Talaromyces emersonii* CBH1 are provided below. The signal sequence is shown underlined in SEQ ID NO:137. SEQ ID NO:138 provides the sequence of this CBH1, without the signal sequence.

(SEQ ID NO: 136)
ATGCTTCGACGGGCTCTTCTTCTATCCTCTTCCGCCATCCTTGCTGTCAA

GGCACAGCAGGCCGGCACGGCGACGGCAGAGAACCACCCGCCCCTGACAT

GGCAGGAATGCACCGCCCCTGGGAGCTGCACCACCCAGAACGGGCGGTC

GTTCTTGATGCGAACTGGCGTTGGGTGCACGATGTGAACGGATACACCAA

CTGCTACACGGGCAATACCTGGGACCCCACGTACTGCCCTGACGACGAA

CCTGCGCCCAGAACTGTGCGCTGGACGGCGCGGATTACGAGGGCACCTAC

GGCGTGACTTCGTCGGGCAGCTCCTTGAAACTCAATTTCGTCACCGGGTC

GAACGTCGGATCCCGTCTCTACCTGCTGCAGGACGACTCGACCTATCAGA

TCTTCAAGCTTCTGAACCGCGAGTTCAGCTTTGACGTCGATGTCTCCAAT

CTTCCGTGCGGATTGAACGCGCTCTGTACTTTGTCGCCATGGACGCCGA

CGGCGGCGTGTCCAAGTACCCGAACAACAAGGCTGGTGCCAAGTACGAA

CCGGGTATTGCGACTCCCAATGCCCACGGGACCTCAAGTTCATCGACGGC

GAGGCCAACGTCGAGGGCTGGCAGCCGTCTTCGAACAACGCCAACACCGG

AATTGGCGACCACGGCTCCTGCTGTGCGGAGATGGATGTCTGGGAAGCAA

ACAGCATCTCCAATGCGGTCACTCCGCACCCGTGCGACACGCCAGGCCAG

ACGATGTGCTCTGGAGATGACTGCGGTGGCACATACTCTAACGATCGCTA

CGCGGGAACCTGCGATCCTGACGGCTGTGACTTCAACCCTTACCGCATGG

GCAACACTTCTTTCTACGGGCCTGGCAAGATCATCGATACCACCAAGCCC

TTCACTGTCGTGACGCAGTTCCTCACTGATGATGGTACGGATACTGGAAC

TCTCAGCGAGATCAAGCGCTTCTACATCCAGAACAGCAACGTCATTCCGC

AGCCCAACTCGGACATCAGTGGCGTGACCGGCAACTCGATCACGACGGAG

TTCTGCACTGCTCAGAAGCAGGCCTTTGGCGACACGGACGACTTCTCTCA

GCACGGTGGCCTGGCCAAGATGGGAGCGGCCATGCAGCAGGGTATGGTCC

TGGTGATGAGTTTGTGGGACGACTACGCCGCGCAGATGCTGTGGTTGGAT

TCCGACTACCCGACGGATGCGGACCCCACGACCCCTGGTATTGCCCGTGG

AACGTGTCCGACGGACTCGGGCGTCCCATCGGATGTCGAGTCGCAGAGCC

CCAACTCCTACGTGACCTACTCGAACATTAAGTTTGGTCCGATCAACTCG

ACCTTCACCGCTTCGTGA (SEQ ID NO: 137)
<u>MLRRALLLSSSAILAVKA</u>QQAGTATAENHPPLTWQECTAPGSCTTQNGAV

VLDANWRWVHDVNGYTNCYTGNTWDPTYCPDDETCAQNCALDGADYEGTY

GVTSSGSSLKLNFVTGSNVGSRLYLLQDDSTYQIFKLLNREFSFDVDVSN

LPCGLNGALYFVAMDADGGVSKYPNNKAGAKYGTGYCDSQCPRDLKFIDG

EANVEGWQPSSNNANTGIGDHGSCCAEMDVWEANSISNAVTPHPCDTPGQ

TMCSGDDCGGTYSNDRYAGTCDPDGCDFNPYRMGNTSFYGPGKIIDTTKP

FTVVTQFLTDDGTDTGTLSEIKRFYIQNSNVIPQPNSDISGVTGNSITTE

FCTAQKQAFGDTDDFSQHGGLAKMGAAMQQGMVLVMSLWDDYAAQMLWLD

SDYPTDADPTTPGIARGTCPTDSGVPSDVESQSPNSYVTYSNIKFGPINS

TFTAS (SEQ ID NO: 138)
QQAGTATAENHPPLTWQECTAPGSCTTQNGAVVLDANWRWVHDVNGYTNC

YTGNTWDPTYCPDDETCAQNCALDGADYEGTYGVTSSGSSLKLNFVTGSN

VGSRLYLLQDDSTYQIFKLLNREFSFDVDVSNLPCGLNGALYFVAMDADG

GVSKYPNNKAGAKYGTGYCDSQCPRDLKFIDGEANVEGWQPSSNNANTGI

GDHGSCCAEMDVWEANSISNAVTPHPCDTPGQTMCSGDDCGGTYSNDRYA

GTCDPDGCDFNPYRMGNTSFYGPGKIIDTTKPFTVVTQFLTDDGTDTGTL

SEIKRFYIQNSNVIPQPNSDISGVTGNSITTEFCTAQKQAFGDTDDFSQH

GGLAKMGAAMQQGMVLVMSLWDDYAAQMLWLDSDYPTDADPTTPGIARGT

CPTDSGVPSDVESQSPNSYVTYSNIKFGPINSTFTAS

The polynucleotide (SEQ ID NO:139) and amino acid (SEQ ID NO:140) sequences of wild-type *M. thermophila* CBH1a are provided below. The signal sequence is shown underlined in SEQ ID NO:140. SEQ ID NO:141 provides the sequence of this CBH1a, without the signal sequence.

(SEQ ID NO: 139)
ATGTACGCCAAGTTCGCGACCCTCGCCGCCCTTGTGGCTGGCGCCGCTGC

TCAGAACGCCTGCACTCTGACCGCTGAGAACCACCCCTCGCTGACGTGGT

```
CCAAGTGCACGTCTGGCGGCAGCTGCACCAGCGTCCAGGGTTCCATCACC
ATCGACGCCAACTGGCGGTGGACTCACCGGACCGATAGCGCCACCAACTG
CTACGAGGGCAACAAGTGGGATACTTCGTACTGCAGCGATGGTCCTTCTT
GCGCCTCCAAGTGCTGCATCGACGGCGCTGACTACTCGAGCACCTATGGC
ATCACCACGAGCGGTAACTCCCTGAACCTCAAGTTCGTCACCAAGGGCCA
GTACTCGACCAACATCGGCTCGCGTACCTACCTGATGGAGAGCGACACCA
AGTACCAGATGTTCCAGCTCCTCGGCAACGAGTTCACCTTCGATGTCGAC
GTCTCCAACCTCGGCTGCGGCCTCAATGGCGCCCTCTACTTCGTGTCCAT
GGATGCCGATGGTGGCATGTCCAAGTACTCGGGCAACAAGGCAGGTGCCA
AGTACGGTACCGGCTACTGTGATTCTCAGTGCCCCCGCGACCTCAAGTTC
ATCAACGGCGAGGCCAACGTAGAGAACTGGCAGAGCTCGACCAACGATGC
CAACGCCGGCACGGGCAAGTACGGCAGCTGCTGCTCCGAGATGGACGTCT
GGGAGGCCAACAACATGGCCGCCGCCTTCACTCCCCACCCTTGCACCGTG
ATCGGCCAGTCGCGCTGCGAGGGCGACTCGTGCGGCGGTACCTACAGCAC
CGACCGCTATGCCGGCATCTGCGACCCCGACGGATGCGACTTCAACTCGT
ACCGCCAGGGCAACAAGACCTTCTACGGCAAGGGCATGACGGTCGACACG
ACCAAGAAGATCACGGTCGTCACCCAGTTCCTCAAGAACTCGGCCGGCGA
GCTCTCCGAGATCAAGCGGTTCTACGTCCAGAACGGCAAGGTCATCCCCA
ACTCCGAGTCCACCATCCCGGGCGTCGAGGGCAACTCCATCACCCAGGAC
TGGTGCGACCGCCAGAAGGCCGCCTTCGGCGACGTGACCGACTTCCAGGA
CAAGGGCGGCATGGTCCAGATGGGCAAGGCCCTCGCGGGGCCCATGGTCC
TCGTCATGTCCATCTGGGACGACCACGCCGTCAACATGCTCTGGCTCGAC
TCCACCTGGCCCATCGACGGCGCCGGCAAGCCGGGCGCCGAGCGCGGTGC
CTGCCCCACCACCTCGGGCGTCCCCGCTGAGGTCGAGGCCGAGGCCCCA
ACTCCAACGTCATCTTCTCCAACATCCGCTTCGGCCCCATCGGCTCCACC
GTCTCCGGCCTGCCCGACGGCGGCAGCGGCAACCCCAACCCGCCCGTCAG
CTCGTCCACCCCGGTCCCCTCCTCGTCCACCACATCCTCCGGTTCCTCCG
GCCCGACTGGCGGCACGGGTGTCGCTAAGCACTATGAGCAATGCGGAGGA
ATCGGGTTCACTGGCCCTACCCAGTGCGAGAGCCCCTACACTTGCACCAA
GCTGAATGACTGGTACTCGCAGTGCCTGTAA (SEQ ID NO: 140)
MYAKFATLAALVAGAAAQNACTLTAENHPSLTYSKCTSGGSCTSVQGSIT
IDANWRWTHRTDSATNCYEGNKWDTSWCSDGPSCASKCCIDGADYSSTYG
ITTSGNSLNLKFVTKGQYSTNIGSRTYLMESDTKYQMFQLLGNEFTFDVD
VSNLGCGLNGALYFVSMDADGGMSKYSGNKAGAKYGTGYCDSQCPRDLKF
INGEANVENWQSSTNDANAGTGKYGSCCSEMDVWEANNMAAAFTPHPCTV
IGQSRCEGDSCGGTYSTDRYAGICDPDGCDFNSYRQGNKTFYGKGMTVDT
TKKITVVTQFLKNSAGELSEIKRFYVQNGKVIPNSESTIPGVEGNSITQD
WCDRQKAAFGDVTDFQDKGGMVQMGKALAGPMVLVMSIWDDHAVNMLWLD
STWPIDGAGKPGAERGACPTTSGVPAEVEAEAPNSNVIFSNIRFGPIGST

VSGLPDGGSGNPNPPVSSSTPVPSSSTTSSGSSGPTGGTGVAKHYEQCGG
IGFTGPTQCESPYTCTKLNDWYSQCL (SEQ ID NO: 141)
QNACTLTAENHPSLTYSKCTSGGSCTSVQGSITIDANWRWTHRTDSATNC
YEGNKWDTSWCSDGPSCASKCCIDGADYSSTYGITTSGNSLNLKFVTKGQ
YSTNIGSRTYLMESDTKYQMFQLLGNEFTFDVDVSNLGCGLNGALYFVSM
DADGGMSKYSGNKAGAKYGTGYCDSQCPRDLKFINGEANVENWQSSTNDA
NAGTGKYGSCCSEMDVWEANNMAAAFTPHPCTVIGQSRCEGDSCGGTYST
DRYAGICDPDGCDFNSYRQGNKTFYGKGMTVDTTKKITVVTQFLKNSAGE
LSEIKRFYVQNGKVIPNSESTIPGVEGNSITQDWCDRQKAAFGDVTDFQD
KGGMVQMGKALAGPMVLVMSIWDDHAVNMLWLDSTWPIDGAGKPGAERGA
CPTTSGVPAEVEAEAPNSNVIFSNIRFGPIGSTVSGLPDGGSGNPNPPVS
SSTPVPSSSTTSSGSSGPTGGTGVAKHYEQCGGIGFTGPTQCESPYTCTK
LNDWYSQCL
```

The polynucleotide (SEQ ID NO:142) and amino acid (SEQ ID NO:143) sequences of a *M. thermophila* CBH1a variant ("Variant 145") are provided below. The signal sequence is shown underlined in SEQ ID NO:143. SEQ ID NO:144 provides the sequence of this CBH1a, without the signal sequence.

```
                        (SEQ ID NO: 142)
ATGTACGCCAAGTTCGCGACCCTCGCCGCCCTTGTGGCTGGCGCCGCTGC
TCAGAACGCCTGCACTCTGACCGCTGAGAACCACCCCTCGCTGACGTGGT
CCAAGTGCACGTCTGGCGGCAGCTGCACCAGCGTCCAGGGTTCCATCACC
ATCGACGCCAACTGGCGGTGGACTCACCGGACCGATAGCGCCACCAACTG
CTACGAGGGCAACAAGTGGGATACTTCGTGGTGCAGCGATGGTCCTTCTT
GCGCCTCCAAGTGCTGCATCGACGGCGCTGACTACTCGAGCACCTATGGC
ATCACCACGAGCGGTAACTCCCTGAACCTCAAGTTCGTCACCAAGGGCCA
GTACTCGACCAACATCGGCTCGCGTACCTACCTGATGGAGAGCGACACCA
AGTACCAGATGTTCCAGCTCCTCGGCAACGAGTTCACCTTCGATGTCGAC
GTCTCCAACCTCGGCTGCGGCCTCAATGGCGCCCTCTACTTCGTGTCCAT
GGATGCCGATGGTGGCATGTCCAAGTACTCGGGCAACAAGGCAGGTGCCA
AGTACGGTACCGGCTACTGTGATTCTCAGTGCCCCCGCGACCTCAAGTTC
ATCAACGGCGAGGCCAACGTAGAGAACTGGCAGAGCTCGACCAACGATGC
CAACGCCGGCACGGGCAAGTACGGCAGCTGCTGCTCCGAGATGGACGTCT
GGGAGGCCAACAACATGGCCGCCGCCTTCACTCCCCACCCTTGCACCGTG
ATCGGCCAGTCGCGCTGCGAGGGCGACTCGTGCGGCGGTACCTACAGCAC
CGACCGCTATGCCGGCATCTGCGACCCCGACGGATGCGACTTCAACTCGT
ACCGCCAGGGCAACAAGACCTTCTACGGCAAGGGCATGACGGTCGACACG
ACCAAGAAGATCACGGTCGTCACCCAGTTCCTCAAGAACTCGGCCGGCGA
GCTCTCCGAGATCAAGCGGTTCTACGTCCAGAACGGCAAGGTCATCCCCA
ACTCCGAGTCCACCATCCCGGGCGTCGAGGGCAACTCCATCACCCAGGAC
```

```
TGGTGCGACCGCCAGAAGGCCGCCTTCGGCGACGTGACCGACTTCCAGGA

CAAGGGCGGCATGGTCCAGATGGGCAAGGCCCTCGCGGGGCCCATGGTCC

TCGTCATGTCCATCTGGGACGACCACGCCGTCAACATGCTCTGGCTCGAC

TCCACCTGGCCCATCGACGGCGCCGGCAAGCCGGGCGCCGAGCGCGGTGC

CTGCCCCACCACCTCGGGCGTCCCCGCTGAGGTCGAGGCCGAGGCCCCCA

ACTCCAACGTCATCTTCTCCAACATCCGCTTCGGCCCCATCGGCTCCACC

GTCTCCGGCCTGCCCGACGGCGGCAGCGGCAACCCCAACCCGCCCGTCAG

CTCGTCCACCCCGGTCCCCTCCTCGTCCACCACATCCTCCGGTTCCTCCG

GCCCGACTGGCGGCACGGGTGTCGCTAAGCACTATGAGCAATGCGGAGGA

ATCGGGTTCACTGGCCCTACCCAGTGCGAGAGCCCCTACACTTGCACCAA

GCTGAATGACTGGTACTCGCAGTGCCTGTAA
```

(SEQ ID NO: 143)
<u>MYAKFATLAALVAGAAAQ</u>NACTLTAENHPSLTWSKCTSGGSCTSVQGSIT
IDANWRWTHRTDSATNCYEGNKWDTSWCSDGPSCASKCCIDGADYSSTYG
ITTSGNSLNLKFVTKGQYSTNIGSRTYLMESDTKYQMFQLLGNEFTFDVD
VSNLGCGLNGALYFVSMDADGGMSKYSGNKAGAKYGTYCDSQCPRDLKF
INGEANVENWQSSTNDANAGTGKYGSCCSEMDVWEANNMAAAFTPHPCTV
IGQSRCEGDSCGGTYSTDRYAGICDPDGCDFNSYRQGNKTFYGKGMTVDT
TKKITVVTQFLKNSAGELSEIKRFYVQNGKVIPNSESTIPGVEGNSITQD
WCDRQKAAFGDVTDFQDKGGMVQMGKALAGPMVLVMSIWDDHAVNMLWLD
STWPIDGAGKPGAERGACPTTSGVPAEVEAEAPNSNVIFSNIRFGPIGST
VSGLPDGGSGNPNPPVSSSTPVPSSSTTSSGSSGPTGGTGVAKHYEQCGG
IGFTGPTQCESPYTCTKLNDWYSQCL (SEQ ID NO: 144)
QNACTLTAENHPSLTWSKCTSGGSCTSVQGSITIDANWRWTHRTDSATNC
YEGNKWDTSWCSDGPSCASKCCIDGADYSSTYGITTSGNSLNLKFVTKGQ
YSTNIGSRTYLMESDTKYQMFQLLGNEFTFDVDVSNLGCGLNGALYFVSM
DADGGMSKYSGNKAGAKYGTYCDSQCPRDLKFINGEANVENWQSSTNDA
NAGTGKYGSCCSEMDVWEANNMAAAFTPHPCTVIGQSRCEGDSCGGTYST
DRYAGICDPDGCDFNSYRQGNKTFYGKGMTVDTTKKITVVTQFLKNSAGE
LSEIKRFYVQNGKVIPNSESTIPGVEGNSITQDWCDRQKAAFGDVTDFQD
KGGMVQMGKALAGPMVLVMSIWDDHAVNMLWLDSTWPIDGAGKPGAERGA
CPTTSGVPAEVEAEAPNSNVIFSNIRFGPIGSTVSGLPDGGSGNPNPPVS
SSTPVPSSSTTSSGSSGPTGGTGVAKHYEQCGGIGFTGPTQCESPYTCTK
LNDWYSQCL

The polynucleotide (SEQ ID NO:145) and amino acid (SEQ ID NO:146) sequences of a *M. thermophila* CBH1a variant ("Variant 983") are provided below. The signal sequence is shown underlined in SEQ ID NO:146. SEQ ID NO:147 provides the sequence of this CBH1a variant, without the signal sequence.

(SEQ ID NO: 145)
```
ATGTACGCCAAGTTCGCGACCCTCGCCGCCCTTGTGGCTGGCGCCGCTGC

TCAGAACGCCTGCACTCTGAACGCTGAGAACCACCCCTCGCTGACGTGGT

CCAAGTGCACGTCTGGCGGCAGCTGCACCAGCGTCCAGGGTTCCATCACC

ATCGACGCCAACTGGCGGTGGACTCACCGGACCGATAGCGCCACCAACTG

CTACGAGGGCAACAAGTGGGATACTTCGTACTGCAGCGATGGTCCTTCTT

GCGCCTCCAAGTGCTGCATCGACGGCGCTGACTACTCGAGCACCTATGGC

ATCACCACGAGCGGTAACTCCCTGAACCTCAAGTTCGTCACCAAGGGCCA

GTACTCGACCAACATCGGCTCGCGTACCTACCTGATGGAGAGCGACACCA

AGTACCAGATGTTCCAGCTCCTCGGCAACGAGTTCACCTTCGATGTCGAC

GTCTCCAACCTCGGCTGCGGCCTCAATGGCGCCCTCTACTTCGTGTCCAT

GGATGCCGATGGTGGCATGTCCAAGTACTCGGGCAACAAGGCAGGTGCCA

AGTACGGTACCGGCTACTGTGATTCTCAGTGCCCCCGCGACCTCAAGTTC

ATCAACGGCGAGGCCAACGTAGAGAACTGGCAGAGCTCGACCAACGATGC

CAACGCCGGCACGGGCAAGTACGGCAGCTGCTGCTCCGAGATGGACGTCT

GGGAGGCCAACAACATGGCCGCCGCCTTCACTCCCCACCCTTGCACCGTG

ATCGGCCAGTCGCGCTGCGAGGGCGACTCGTGCGGCGGTACCTACAGCAC

CGACCGCTATGCCGGCATCTGCGACCCCGACGGATGCGACTTCAACTCGT

ACCGCCAGGGCAACAAGACCTTCTACGGCAAGGGCATGACGGTCGACACG

ACCAAGAAGATCACGGTCGTCACCCAGTTCCTCAAGAACTCGGCCGGCGA

GCTCTCCGAGATCAAGCGGTTCTACGTCCAGAACGGCAAGGTCATCCCCA

ACTCCGAGTCCACCATCCCGGGCGTCGAGGGCAACTCCATCACCCAGGAG

TACTGCGACCGCCAGAAGGCCGCCTTCGGCGACGTGACCGACTTCCAGGA

CAAGGGCGGCATGGTCCAGATGGGCAAGGCCCTCGCGGGGCCCATGGTCC

TCGTCATGTCCATCTGGGACGACCACGCCGACAACATGCTCTGGCTCGAC

TCCACCTGGCCCATCGACGGCGCCGGCAAGCCGGGCGCCGAGCGCGGTGC

CTGCCCCACCACCTCGGGCGTCCCCGCTGAGGTCGAGGCCGAGGCCCCCA

ACTCCAACGTCATCTTCTCCAACATCCGCTTCGGCCCCATCGGCTCCACC

GTCTCCGGCCTGCCCGACGGCGGCAGCGGCAACCCCAACCCGCCCGTCAG

CTCGTCCACCCCGGTCCCCTCCTCGTCCACCACATCCTCCGGTTCCTCCG

GCCCGACTGGCGGCACGGGTGTCGCTAAGCACTATGAGCAATGCGGAGGA

ATCGGGTTCACTGGCCCTACCCAGTGCGAGAGCCCCTACACTTGCACCAA

GCTGAATGACTGGTACTCGCAGTGCCTGTAA
```

(SEQ ID NO: 146)
<u>MYAKFATLAALVAGAAAQ</u>NACTLNAENHPSLTWSKCTSGGSCTSVQGSIT
IDANWRWTHRTDSATNCYEGNKWDTSYCSDGPSCASKCCIDGADYSSTYG
ITTSGNSLNLKFVTKGQYSTNIGSRTYLMESDTKYQMFQLLGNEFTFDVD
VSNLGCGLNGALYFVSMDADGGMSKYSGNKAGAKYGTYCDSQCPRDLKF
INGEANVENWQSSTNDANAGTGKYGSCCSEMDVWEANNMAAAFTPHPCTV
IGQSRCEGDSCGGTYSTDRYAGICDPDGCDFNSYRQGNKTFYGKGMTVDT
TKKITVVTQFLKNSAGELSEIKRFYVQNGKVIPNSESTIPGVEGNSITQE
YCDRQKAAFGDVTDFQDKGGMVQMGKALAGPMVLVMSIWDDHADNMLWLD
STWPIDGAGKPGAERGACPTTSGVPAEVEAEAPNSNVIFSNIRFGPIGST

VSGLPDGGSGNPNPPVSSSTPVPSSSTTSSGSSGPTGGTGVAKHYEQCGG

IGFTGPTQCESPYTCTKLNDWYSQCL (SEQ ID NO: 147)
QNACTLNAENHPSLTWSKCTSGGSCTSVQGSITIDANWRWTHRTDSATNC

YEGNKWDTSYCSDGPSCASKCCIDGADYSSTYGITTSGNSLNLKFVTKGQ

YSTNIGSRTYLMESDTKYQMFQLLGNEFTFDVDVSNLGCGLNGALYFVSM

DADGGMSKYSGNKAGAKYGTGYCDSQCPRDLKFINGEANVENWQSSTNDA

NAGTGKYGSCCSEMDVWEANNMAAAFTPHPCTVIGQSRCEGDSCGGTYST

DRYAGICDPDGCDFNSYRQGNKTFYGKGMTVDTTKKITVVTQFLKNSAGE

LSEIKRFYVQNGKVIPNSESTIPGVEGNSITQEYCDRQKAAFGDVTDFQD

KGGMVQMGKALAGPMVLVMSIWDDHADNMLWLDSTWPIDGAGKPGAERGA

CPTTSGVPAEVEAEAPNSNVIFSNIRFGPIGSTVSGLPDGGSGNPNPPVS

SSTPVPSSSTTSSGSSGPTGGTGVAKHYEQCGGIGFTGPTQCESPYTCTK

LNDWYSQCL

The polynucleotide (SEQ ID NO:148) and amino acid (SEQ ID NO:149) sequences of wild-type *M. thermophila* CBH2b are provided below. The signal sequence is shown underlined in SEQ ID NO:149. SEQ ID NO:150 provides the sequence of this CBH2b, without the signal sequence.

(SEQ ID NO: 148)
ATGGCCAAGAAGCTTTTCATCACCGCCGCGCTTGCGGCTGCCGTGTTGGC

GGCCCCCGTCATTGAGGAGCGCCAGAACTGCGGCGCTGTGTGGACTCAAT

GCGGCGGTAACGGGTGGCAAGGTCCCACATGCTGCGCCTCGGGCTCGACC

TGCGTTGCGCAGAACGAGTGGTACTCTCAGTGCCTGCCCAACAGCCAGGT

GACGAGTTCCACCACTCCGTCGTCGACTTCCACCTCGCAGCGCAGCACCA

GCACCTCCAGCAGCACCACCAGGAGCGGCAGCTCCTCCTCCTCCTCCACC

ACGCCCCCGCCCGTCTCCAGCCCCGTGACCAGCATTCCCGGCGGTGCGAC

CTCCACGGCGAGCTACTCTGGCAACCCCTTCTCGGGCGTCCGGCTCTTCG

CCAACGACTACTACAGGTCCGAGGTCCACAATCTCGCCATTCCTAGCATG

ACTGGTACTCTGGCGGCCAAGGCTTCCGCCGTCGCCGAAGTCCCTAGCTT

CCAGTGGCTCGACCGGAACGTCACCATCGACACCCTGATGGTCCAGACTC

TGTCCCAGGTCCGGGCTCTCAATAAGGCCGGTGCCAATCCTCCCTATGCT

GCCCAACTCGTCGTCTACGACCTCCCCGACCGTGACTGTGCCGCCGCTGC

GTCCAACGGCGAGTTTTCGATTGCAAACGGCGGCGCCGCCAACTACAGGA

GCTACATCGACGCTATCCGCAAGCACATCATTGAGTACTCGGACATCCGG

ATCATCCTGGTTATCGAGCCCGACTCGATGGCCAACATGGTGACCAACAT

GAACGTGGCCAAGTGCAGCAACGCCGCGTCGACGTACCACGAGTTGACCG

TGTACGCGCTCAAGCAGCTGAACCTGCCCAACGTCGCCATGTATCTCGAC

GCCGGCCACGCCGGCTGGCTCGGCTGGCCCGCCAACATCCAGCCCGCCGC

CGAGCTGTTTGCCGGCATCTACAATGATGCCGGCAAGCCGGCTGCCGTCC

GCGGCCTGGCCACTAACGTCGCCAACTACAACGCCTGGAGCATCGCTTCG

GCCCCGTCGTACACGTCGCCTAACCCTAACTACGACGAGAAGCACTACAT

CGAGGCCTTCAGCCCGCTCTTGAACTCGGCCGGCTTCCCCGCACGCTTCA

TTGTCGACACTGGCCGCAACGGCAAACAACCTACCGGCCAACAACAGTGG

GGTGACTGGTGCAATGTCAAGGGCACCGGCTTTGGCGTGCGCCCGACGGC

CAACACGGGCCACGAGCTGGTCGATGCCTTTGTCTGGGTCAAGCCCGGCG

GCGAGTCCGACGGCACAAGCGACACCAGCGCCGCCCGCTACGACTACCAC

TGCGGCCTGTCCGATGCCCTGCAGCCTGCCCCCGAGGCTGGACAGTGGTT

CCAGGCCTACTTCGAGCAGCTGCTCACCAACGCCAACCCGCCCTTCTAA (SEQ ID NO: 149)
MAKKLFITAALAAAVLAAPVIEERQNCGAVWTQCGGNGWQGPTCCASGST

CVAQNEWYSQCLPNSQVTSSTTPSSTSTSQRSTSTSSSTTRSGSSSSSST

TPPPVSSPVTSIPGGATSTASYSGNPFSGVRLFANDYYRSEVHNLAIPSM

TGTLAAKASAVAEVPSFQWLDRNVTIDTLMVQTLSQVRALNKAGANPPYA

AQLVVYDLPDRDCAAAASNGEFSIANGGAANYRSYIDAIRKHIIEYSDIR

IILVIEPDSMANMVTNMNVAKCSNAASTYHELTVYALKQLNLPNVAMYLD

AGHAGWLGWPANIQPAAELFAGIYNDAGKPAAVRGLATNVANYNAWSIAS

APSYTSPNPNYDEKHYIEAFSPLLNSAGFPARFIVDTGRNGKQPTGQQQW

GDWCNVKGTGFGVRPTANTGHELVDAFVWVKPGGESDGTSDTSAARYDYH

CGLSDALQPAPEAGQWFQAYFEQLLTNANPPF (SEQ ID NO: 150)
APVIEERQNCGAVWTQCGGNGWQGPTCCASGSTCVAQNEWYSQCLPNSQV

TSSTTPSSTSTSQRSTSTSSSTTRSGSSSSSSTTPPPVSSPVTSIPGGAT

STASYSGNPFSGVRLFANDYYRSEVHNLAIPSMTGTLAAKASAVAEVPSF

QWLDRNVTIDTLMVQTLSQVRALNKAGANPPYAAQLVVYDLPDRDCAAAA

SNGEFSIANGGAANYRSYIDAIRKHIIEYSDIRIILVIEPDSMANMVTNM

NVAKCSNAASTYHELTVYALKQLNLPNVAMYLDAGHAGWLGWPANIQPAA

ELFAGIYNDAGKPAAVRGLATNVANYNAWSIASAPSYTSPNPNYDEKHYI

EAFSPLLNSAGFPARFIVDTGRNGKQPTGQQQWGDWCNVKGTGFGVRPTA

NTGHELVDAFVWVKPGGESDGTSDTSAARYDYHCGLSDALQPAPEAGQWF

QAYFEQLLTNANPPF

The polynucleotide (SEQ ID NO:151) and amino acid (SEQ ID NO:152) sequences of a *M. thermophila* CBH2b variant ("Variant 196") are provided below. The signal sequence is shown underlined in SEQ ID NO:152. SEQ ID NO:153 provides the sequence of this CBH2b variant, without the signal sequence.

(SEQ ID NO: 151)
ATGGCCAAGAAGCTTTTCATCACCGCCGCGCTTGCGGCTGCCGTGTTGGC

GGCCCCCGTCATTGAGGAGCGCCAGAACTGCGGCGCTGTGTGGACTCAAT

GCGGCGGTAACGGGTGGCAAGGTCCCACATGCTGCGCCTCGGGCTCGACC

TGCGTTGCGCAGAACGAGTGGTACTCTCAGTGCCTGCCCAACAGCCAGGT

GACGAGTTCCACCACTCCGTCGTCGACTTCCACCTCGCAGCGCAGCACCA

GCACCTCCAGCAGCACCACCAGGAGCGGCAGCTCCTCCTCCTCCTCCACC

ACGCCCACCCCGTCTCCAGCCCCGTGACCAGCATTCCCGGCGGTGCGAC

```
CTCCACGGCGAGCTACTCTGGCAACCCCTTCTCGGGCGTCCGGCTCTTCG

CCAACGACTACTACAGGTCCGAGGTCCACAATCTCGCCATTCCTAGCATG

ACTGGTACTCTGGCGGCCAAGGCTTCCGCCGTCGCCGAAGTCCCTAGCTT

CCAGTGGCTCGACCGGAACGTCACCATCGACACCCTGATGGTCCCGACTC

TGTCCCGCGTCCGGGCTCTCAATAAGGCCGGTGCCAATCCTCCCTATGCT

GCCCAACTCGTCGTCTACGACCTCCCCGACCGTGACTGTGCCGCCGCTGC

GTCCAACGGCGAGTTTTCGATTGCAAACGGCGGCGCCGCCAACTACAGGA

GCTACATCGACGCTATCCGCAAGCACATCATTGAGTACTCGGACATCCGG

ATCATCCTGGTTATCGAGCCCGACTCGATGGCCAACATGGTGACCAACAT

GAACGTGGCCAAGTGCAGCAACGCCGCGTCGACGTACCACGAGTTGACCG

TGTACGCGCTCAAGCAGCTGAACCTGCCCAACGTCGCCATGTATCTCGAC

GCCGGCCACGCCGGCTGGCTCGGCTGGCCCGCCAACATCCAGCCCGCCGC

CGAGCTGTTTGCCGGCATCTACAATGATGCCGGCAAGCCGGCTGCCGTCC

GCGGCCTGGCCACTAACGTCGCCAACTACAACGCCTGGAGCATCGCTTCG

GCCCCGTCGTACACGTCGCCTAACCCTAACTACGACGAGAAGCACTACAT

CGAGGCCTTCAGCCCGCTCTTGAACTCGGCCGGCTTCCCCGCACGCTTCA

TTGTCGACACTGGCCGCAACGGCAAACAACCTACCGGCCAACAACAGTGG

GGTGACTGGTGCAATGTCAAGGGCACCGGCTTTGGCGTGCGCCCGACGGC

CAACACGGGCCACGAGCTGGTCGATGCCTTTGTCTGGGTCAAGCCCGGCG

GCGAGTCCGACGGCACAAGCGACACCAGCGCCGCCCGCTACGACTACCAC

TGCGGCCTGTCCGATGCCCTGCAGCCTGCCCCCGAGGCTGGACAGTGGTT

CCAGGCCTACTTCGAGCAGCTGCTCACCAACGCCAACCCGCCCTTCTAA (SEQ ID NO: 152)
MAKKLFITAALAAAVLAAPVIEERQNCGAVWTQCGGNGWQGPTCCASGST

CVAQNEWYSQCLPNSQVTSSTTPSSTSTSQRSTSTSSSTTRSGSSSSSST

TPTPVSSPVTSIPGGATSTASYSGNPFSGVRLFANDYYRSEVHNLAIPSM

TGTLAAKASAVAEVPSFQWLDRNVTIDTLMVPTLSRVRALNKAGANPPYA

AQLVVYDLPDRDCAAAASNGEFSIANGGAANYRSYIDAIRKHIIEYSDIR

IILVIEPDSMANMVTNMNVAKCSNAASTYHELTVYALKQLNLPNVAMYLD

AGHAGWLGWPANIQPAAELFAGIYNDAGKPAAVRGLATNVANYNAWSIAS

APSYTSPNPNYDEKHYIEAFSPLLNSAGFPARFIVDTGRNGKQPTGQQQW

GDWCNVKGTGFGVRPTANTGHELVDAFVWVKPGGESDGTSDTSAARYDYH

CGLSDALQPAPEAGQWFQAYFEQLLTNANPPF (SEQ ID NO: 153)
APVIEERQNCGAVWTQCGGNGWQGPTCCASGSTCVAQNEWYSQCLPNSQV

TSSTTPSSTSTSQRSTSTSSSTTRSGSSSSSSTTPTPVSSPVTSIPGGAT

STASYSGNPFSGVRLFANDYYRSEVHNLAIPSMTGTLAAKASAVAEVPSF

QWLDRNVTIDTLMVPTLSRVRALNKAGANPPYAAQLVVYDLPDRDCAAAA

SNGEFSIANGGAANYRSYIDAIRKHIIEYSDIRIILVIEPDSMANMVTNM

NVAKCSNAASTYHELTVYALKQLNLPNVAMYLDAGHAGWLGWPANIQPAA

ELFAGIYNDAGKPAAVRGLATNVANYNAWSIASAPSYTSPNPNYDEKHYI

EAFSPLLNSAGFPARFIVDTGRNGKQPTGQQQWGDWCNVKGTGFGVRPTA

NTGHELVDAFVWVKPGGESDGTSDTSAARYDYHCGLSDALQPAPEAGQWF

QAYFEQLLTNANPPF
```

The polynucleotide (SEQ ID NO:154) and amino acid (SEQ ID NO:155) sequences of a *M. thermophila* CBH2b variant ("Variant 287") are provided below. The signal sequence is shown underlined in SEQ ID NO:155. SEQ ID NO:156 provides the sequence of this CBH2b variant, without the signal sequence.

```
                                    (SEQ ID NO: 154)
ATGGCCAAGAAGCTTTTCATCACCGCCGCGCTTGCGGCTGCCGTGTTGGC

GGCCCCCGTCATTGAGGAGCGCCAGAACTGCGGCGCTGTGTGGACTCAAT

GCGGCGGTAACGGGTGGCAAGGTCCCACATGCTGCGCCTCGGGCTCGACC

TGCGTTGCGCAGAACGAGTGGTACTCTCAGTGCCTGCCCAACAGCCAGGT

GACGAGTTCCACCACTCCGTCGTCGACTTCCACCTCGCAGCGCAGCACCA

GCACCTCCAGCAGCACCACCAGGAGCGGCAGCTCCTCCTCCTCCTCCACC

ACGCCCCCGCCCGTCTCCAGCCCCGTGACCAGCATTCCCGGCGGTGCGAC

CTCCACGGCGAGCTACTCTGGCAACCCCTTCTCGGGCGTCCGGCTCTTCG

CCAACGACTACTACAGGTCCGAGGTCCACAATCTCGCCATTCCTAGCATG

ACTGGTACTCTGGCGGCCAAGGCTTCCGCCGTCGCCGAAGTCCCTAGCTT

CCAGTGGCTCGACCGGAACGTCACCATCGACACCCTGATGGTCCCGACTC

TGTCCCGCGTCCGGGCTCTCAATAAGGCCGGTGCCAATCCTCCCTATGCT

GCCCAACTCGTCGTCTACGACCTCCCCGACCGTGACTGTGCCGCCGCTGC

GTCCAACGGCGAGTTTTCGATTGCAAACGGCGGCGCCGCCAACTACAGGA

GCTACATCGACGCTATCCGCAAGCACATCAAGGAGTACTCGGACATCCGG

ATCATCCTGGTTATCGAGCCCGACTCGATGGCCAACATGGTGACCAACAT

GAACGTGGCCAAGTGCAGCAACGCCGCGTCGACGTACCACGAGTTGACCG

TGTACGCGCTCAAGCAGCTGAACCTGCCCAACGTCGCCATGTATCTCGAC

GCCGGCCACGCCGGCTGGCTCGGCTGGCCCGCCAACATCCAGCCCGCCGC

CGAGCTGTTTGCCGGCATCTACAATGATGCCGGCAAGCCGGCTGCCGTCC

GCGGCCTGGCCACTAACGTCGCCAACTACAACGCCTGGAGCATCGCTTCG

GCCCCGTCGTACACGTCGCCTAACCCTAACTACGACGAGAAGCACTACAT

CGAGGCCTTCAGCCCGCTCTTGAACGACGCCGGCTTCCCCGCACGCTTCA

TTGTCGACACTGGCCGCAACGGCAAACAACCTACCGGCCAACAACAGTGG

GGTGACTGGTGCAATGTCAAGGGCACCGGCTTTGGCGTGCGCCCGACGGC

CAACACGGGCCACGAGCTGGTCGATGCCTTTGTCTGGGTCAAGCCCGGCG

GCGAGTCCGACGGCACAAGCGACACCAGCGCCGCCCGCTACGACTACCAC

TGCGGCCTGTCCGATGCCCTGCAGCCTGCCCCCGAGGCTGGACAGTGGTT

CCAGGCCTACTTCGAGCAGCTGCTCACCAACGCCAACCCGCCCTTCTAA (SEQ ID NO: 155)
MAKKLFITAALAAAVLAAPVIEERQNCGAVWTQCGGNGWQGPTCCASGST

CVAQNEWYSQCLPNSQVTSSTTPSSTSTSQRSTSTSSSTTRSGSSSSSST

TPPPVSSPVTSIPGGATSTASYSGNPFSGVRLFANDYYRSEVHNLAIPSM
```

-continued

TGTLAAKASAVAEVPSFQWLDRNVTIDTLMVPTLSRVRALNKAGANPPYA

AQLVVYDLPDRDCAAAASNGEFSIANGGAANYRSYIDAIRKHIKEYSDIR

IILVIEPDSMANMVTNMNVAKCSNAASTYHELTVYALKQLNLPNVAMYLD

AGHAGWLGWPANIQPAAELFAGIYNDAGKPAAVRGLATNVANYNAWSIAS

APSYTSPNPNYDEKHYIEAFSPLLNDAGFPARFIVDTGRNGKQPTGQQQW

GDWCNVKGTGFGVRPTANTGHELVDAFVWVKPGGESDGTSDTSAARYDYH

CGLSDALQPAPEAGQWFQAYFEQLLTNANPPF (SEQ ID NO: 156)
APVIEERQNCGAVWTQCGGNGWQGPTCCASGSTCVAQNEWYSQCLPNSQV

TSSTTPSSTSTSQRSTSTSSSTTRSGSSSSSSTTPPPVSSPVTSIPGGAT

STASYSGNPFSGVRLFANDYYRSEVHNLAIPSMTGTLAAKASAVAEVPSF

QWLDRNVTIDTLMVPTLSRVRALNKAGANPPYAAQLVVYDLPDRDCAAAA

SNGEFSIANGGAANYRSYIDAIRKHIKEYSDIRIILVIEPDSMANMVTNM

NVAKCSNAASTYHELTVYALKQLNLPNVAMYLDAGHAGWLGWPANIQPAA

ELFAGIYNDAGKPAAVRGLATNVANYNAWSIASAPSYTSPNPNYDEKHYI

EAFSPLLNDAGFPARFIVDTGRNGKQPTGQQQWGDWCNVKGTGFGVRPTA

NTGHELVDAFVWVKPGGESDGTSDTSAARYDYHCGLSDALQPAPEAGQWF

QAYFEQLLTNANPPF

The polynucleotide (SEQ ID NO:157) and amino acid (SEQ ID NO:158) sequences of a *M. thermophila* CBH2b variant ("Variant 962") are provided below. The signal sequence is shown underlined in SEQ ID NO:158. SEQ ID NO:159 provides the sequence of this CBH2b variant, without the signal sequence.

(SEQ ID NO: 157)
ATGGCCAAGAAGCTTTTCATCACCGCCGCGCTTGCGGCTGCCGTGTTGGC

GGCCCCCGTCATTGAGGAGCGCCAGAACTGCGGCGCTGTGTGGACTCAAT

GCGGCGGTAACGGGTGGCAAGGTCCCACATGCTGCGCCTCGGGCTCGACC

TGCGTTGCGCAGAACGAGTGGTACTCTCAGTGCCTGCCCAACAGCCAGGT

GACGAGTTCCACCACTCCGTCGTCGACTTCCACCTCGCAGCGCAGCACCA

GCACCTCCAGCAGCACCACCAGGAGCGGCAGCTCCTCCTCCTCCTCCACC

ACGCCCACCCCCGTCTCCAGCCCCGTGACCAGCATTCCCGGCGGTGCGAC

CTCCACGGCGAGCTACTCTGGCAACCCCTTCTCGGGCGTCCGGCTCTTCG

CCAACGACTACTACAGGTCCGAGGTCATGAATCTCGCCATTCCTAGCATG

ACTGGTACTCTGGCGGCCAAGGCTTCCGCCGTCGCCGAAGTCCCTAGCTT

CCAGTGGCTCGACCGGAACGTCACCATCGACACCCTGATGGTCACCACTC

TGTCCCAGGTCCGGGCTCTCAATAAGGCCGGTGCCAATCCTCCCTATGCT

GCCCAACTCGTCGTCTACGACCTCCCCGACCGTGACTGTGCCGCCGCTGC

GTCCAACGGCGAGTTTTCGATTGCAAACGGCGGCAGCGCCAACTACAGGA

GCTACATCGACGCTATCCGCAAGCACATCATTGAGTACTCGGACATCCGG

ATCATCCTGGTTATCGAGCCCGACTCGATGGCCAACATGGTGACCAACAT

GAACGTGGCCAAGTGCAGCAACGCCGCGTCGACGTACCACGAGTTGACCG

TGTACGCGCTCAAGCAGCTGAACCTGCCCAACGTCGCCATGTATCTCGAC

GCCGGCCACGCCGGCTGGCTCGGCTGGCCCGCCAACATCCAGCCCGCCGC

CGAGCTGTTTGCCGGCATCTACAATGATGCCGGCAAGCCGGCTGCCGTCC

GCGGCCTGGCCACTAACGTCGCCAACTACAACGCCTGGAGCATCGCTTCG

GCCCCGTCGTACACGCAGCCTAACCCTAACTACGACGAGAAGCACTACAT

CGAGGCCTTCAGCCCGCTCTTGAACTCGGCCGGCTTCCCCGCACGCTTCA

TTGTCGACACTGGCCGAACGGCAAACAACCTACCGGCCAACAACAGTGG

GGTGACTGGTGCAATGTCAAGGGCACCGGCTTTGGCGTGCGCCCGACGGC

CAACACGGGCCACGAGCTGGTCGATGCCTTTGTCTGGGTCAAGCCCGGCG

GCGAGTCCGACGGCACAAGCGACACCAGCGCCGCCCGCTACGACTACCAC

TGCGGCCTGTCCGATGCCCTGCAGCCTGCCCCCGAGGCTGGACAGTGGTT

CCAGGCCTACTTCGAGCAGCTGCTCACCAACGCCAACCCGCCCTTCTAA (SEQ ID NO: 158)
<u>MAKKLFITAALAAAVLAA</u>PVIEERQNCGAVWTQCGGNGWQGPTCCASGST

CVAQNEWYSQCLPNSQVTSSTTPSSTSTSQRSTSTSSSTTRSGSSSSSST

TPTPVSSPVTSIPGGATSTASYSGNPFSGVRLFANDYYRSEVMNLAIPSM

TGTLAAKASAVAEVPSFQWLDRNVTIDTLMVTTLSQVRALNKAGANPPYA

AQLVVYDLPDRDCAAAASNGEFSIANGGSANYRSYIDAIRKHIIEYSDIR

IILVIEPDSMANMVTNMNVAKCSNAASTYHELTVYALKQLNLPNVAMYLD

AGHAGWLGWPANIQPAAELFAGIYNDAGKPAAVRGLATNVANYNAWSIAS

APSYTQPNPNYDEKHYIEAFSPLLNSAGFPARFIVDTGRNGKQPTGQQQW

GDWCNVKGTGFGVRPTANTGHELVDAFVWVKPGGESDGTSDTSAARYDYH

CGLSDALQPAPEAGQWFQAYFEQLLTNANPPF (SEQ ID NO: 159)
APVIEERQNCGAVWTQCGGNGWQGPTCCASGSTCVAQNEWYSQCLPNSQV

TSSTTPSSTSTSQRSTSTSSSTTRSGSSSSSSTTPTPVSSPVTSIPGGAT

STASYSGNPFSGVRLFANDYYRSEVMNLAIPSMTGTLAAKASAVAEVPSF

QWLDRNVTIDTLMVTTLSQVRALNKAGANPPYAAQLVVYDLPDRDCAAAA

SNGEFSIANGGSANYRSYIDAIRKHIIEYSDIRIILVIEPDSMANMVTNM

NVAKCSNAASTYHELTVYALKQLNLPNVAMYLDAGHAGWLGWPANIQPAA

ELFAGIYNDAGKPAAVRGLATNVANYNAWSIASAPSYTQPNPNYDEKHYIE

AFSPLLNSAGFPARFIVDTGRNGKQPTGQQQWGDWCNVKGTGFGVRPTAN

TGHELVDAFVWVKPGGESDGTSDTSAARYDYHCGLSDALQPAPEAGQWFQ

AYFEQLLTNANPPF

The polynucleotide (SEQ ID NO:160) and amino acid (SEQ ID NO:161) sequences of another wild-type *M. thermophila* xylanase ("Xyl3") are provided below. The signal sequence is shown underlined in SEQ ID NO:161. SEQ ID NO:162 provides the sequence of this xylanase without the signal sequence.

(SEQ ID NO: 160)
ATGCACTCCAAAGCTTTCTTGGCAGCGCTTCTTGCGCCTGCCGTCTCAGG

GCAACTGAACGACCTCGCCGTCAGGGCTGGACTCAAGTACTTTGGTACTG

-continued

```
CTCTTAGCGAGAGCGTCATCAACAGTGATACTCGGTATGCTGCCATCCTC
AGCGACAAGAGCATGTTCGGCCAGCTCGTCCCCGAGAATGGCATGAAGTG
GGATGCTACTGAGCCGTCCCGTGGCCAGTTCAACTACGCCTCGGGCGACA
TCACGGCCAACACGGCCAAGAAGAATGGCCAGGGCATGCGTTGCCACACC
ATGGTCTGGTACAGCCAGCTCCCGAGCTGGGTCTCCTCGGGCTCGTGGAC
CAGGGACTCGCTCACCTCGGTCATCGAGACGCACATGAACAACGTCATGG
GCCACTACAAGGGCCAATGCTACGCCTGGGATGTCATCAACGAGGCCATC
AATGACGACGGCAACTCCTGGCGCGACAACGTCTTTCTCCGGACCTTTGG
GACCGACTACTTCGCCCTGTCCTTCAACCTAGCCAAGAAGGCCGATCCCG
ATACCAAGCTGTACTACAACGACTACAACCTCGAGTACAACCAGGCCAAG
ACGGACCGCGCTGTTGAGCTCGTCAAGATGGTCCAGGCCGCCGGCGCGCC
CATCGACGGTGTCGGCTTCCAGGGCCACCTCATTGTCGGCTCGACCCCGA
CGCGCTCGCAGCTGGCCACCGCCCTCCAGCGCTTCACCGCGCTCGGCCTC
GAGGTCGCCTACACCGAGCTCGACATCCGCCACTCGAGCCTGCCGGCCTC
TTCGTCGGCGCTCGCGACCCAGGGCAACGACTTCGCCAACGTGGTCGGCT
CTTGCCTCGACACCGCCGGCTGCGTCGGCGTCACCGTCTGGGGCTTCACC
GATGCGCACTCGTGGATCCCGAACACGTTCCCCGGCCAGGGCGACGCCCT
GATCTACGACAGCAACTACAACAAGAAGCCCGCGTGGACCTCGATCTCGT
CCGTCCTGGCCGCCAAGGCCACCGGCGCCCCGCCCGCCTCGTCCTCCACC
ACCCTCGTCACCATCACCACCCCTCCGCCGGCATCCACCACCGCCTCCTC
CTCCTCCAGTGCCACGCCCACGAGCGTCCCGACGCAGACGAGGTGGGGAC
AGTGCGGCGGCATCGGATGGACGGGGCCGACCCAGTGCGAGAGCCCATGG
ACCTGCCAGAAGCTGAACGACTGGTACTGGCAGTGCCTG
```

(SEQ ID NO: 161)

MHSKAFLAALLAPAVSGQLNDLAVRAGLKYFGTALSESVINSDTRYAAIL

SDKSMFGQLVPENGMKWDATEPSRGQFNYASGDITANTAKKNGQGMRCHT

MVWYSQLPSWVSSGSWTRDSLTSVIETHMNNVMGHYKGQCYAWDVINEAI

NDDGNSWRDNVFLRTFGTDYFALSFNLAKKADPDTKLYYNDYNLEYNQAK

TDRAVELVKMVQAAGAPIDGVGFQGHLIVGSTPTRSQLATALQRFTALGL

EVAYTELDIRHSSLPASSSALATQGNDFANVVGSCLDTAGCVGVTVWGFT

DAHSWIPNTFPGQGDALIYDSNYNKKPAWTSISSVLAAKATGAPPASSST

TLVTITTPPPASTTASSSSSATPTSVPTQTRWGQCGGIGWTGPTQCESPW

TCQKLNDWYWQCL (SEQ ID NO: 162)

QLNDLAVRAGLKYFGTALSESVINSDTRYAAILSDKSMFGQLVPENGMKW

DATEPSRGQFNYASGDITANTAKKNGQGMRCHTMVWYSQLPSWVSSGSWT

RDSLTSVIETHMNNVMGHYKGQCYAWDVINEAINDDGNSWRDNVFLRTFG

TDYFALSFNLAKKADPDTKLYYNDYNLEYNQAKTDRAVELVKMVQAAGAP

IDGVGFQGHLIVGSTPTRSQLATALQRFTALGLEVAYTELDIRHSSLPAS

SSALATQGNDFANVVGSCLDTAGCVGVTVWGFTDAHSWIPNTFPGQGDAL

IYDSNYNKKPAWTSISSVLAAKATGAPPASSSTTLVTITTPPPASTTASS

SSSATPTSVPTQTRWGQCGGIGWTGPTQCESPWTCQKLNDWYWQCL

The polynucleotide (SEQ ID NO:163) and amino acid (SEQ ID NO:164) sequences of a wild-type *M. thermophila* xylanase ("Xyl 2") are provided below. The signal sequence is shown underlined in SEQ ID NO:164. SEQ ID NO:165 provides the sequence of this xylanase without the signal sequence.

(SEQ ID NO: 163)

```
ATGGTCTCGTTCACTCTCCTCCTCACGGTCATCGCCGCTGCGGTGACGAC
GGCCAGCCCTCTCGAGGTGGTCAAGCGCGGCATCCAGCCGGGCACGGGCA
CCCACGAGGGGTACTTCTACTCGTTCTGGACCGACGGCCGTGGCTCGGTC
GACTTCAACCCCGGGCCCCGCGGCTCGTACAGCGTCACCTGGAACAACGT
CAACAACTGGGTTGGCGGCAAGGGCTGGAACCCGGGCCCGCCGCGCAAGA
TTGCGTACAACGGCACCTGGAACAACTACAACGTGAACAGCTACCTCGCC
CTGTACGGCTGGACTCGCAACCCGCTGGTCGAGTATTACATCGTGGAGGC
ATACGGCACGTACAACCCCTCGTCGGGCACGGCGCGGCTGGGCACCATCG
AGGACGACGGCGGCGTGTACGACATCTACAAGACGACGCGGTACAACCAG
CCGTCCATCGAGGGGACCTCCACCTTCGACCAGTACTGGTCCGTCCGCCG
CCAGAAGCGCGTCGGCGGCACTATCGACACGGGCAAGCACTTTGACGAGT
GGAAGCGCCAGGGCAACCTCCAGCTCGGCACCTGGAACTACATGATCATG
GCCACCGAGGGCTACCAGAGCTCTGGTTCGGCCACTATCGAGGTCCGGGA
GGCC
```

(SEQ ID NO: 164)

<u>MVSFTLLLTVIAAAVTTA</u>SPLEVVKRGIQPGTGTHEGYFYSFWTDGRGSV

DFNPGPRGSYSVTWNNVNNWVGGKGWNPGPPRKIAYNGTWNNYNVNSYLA

LYGWTRNPLVEYYIVEAYGTYNPSSGTARLGTIEDDGGVYDIYKTTRYNQ

PSIEGTSTFDQYWSVRRQKRVGGTIDTGKHFDEWKRQGNLQLGTWNYMIM

ATEGYQSSGSATIEVREA (SEQ ID NO: 165)

<u>MVSFTLLLTVIAAAVTTA</u>SPLEVVKRGIQPGTGTHEGYFYSFWTDGRGSV

DFNPGPRGSYSVTWNNVNNWVGGKGWNPGPPRKIAYNGTWNNYNVNSYLA

LYGWTRNPLVEYYIVEAYGTYNPSSGTARLGTIEDDGGVYDIYKTTRYNQ

PSIEGTSTFDQYWSVRRQKRVGGTIDTGKHFDEWKRQGNLQLGTWNYMIM

ATEGYQSSGSATIEVREA

The polynucleotide (SEQ ID NO:166) and amino acid (SEQ ID NO:167) sequences of another wild-type *M. thermophila* xylanase ("Xyl1") are provided below. The signal sequence is shown underlined in SEQ ID NO:167. SEQ ID NO:168 provides the sequence of this xylanase without the signal sequence.

(SEQ ID NO: 166)

```
ATGCGTACTCTTACGTTCGTGCTGGCAGCCGCCCCGGTGGCTGTGCTTGC
CCAATCTCCTCTGTGGGGCCAGTGCGGCGGTCAAGGCTGGACAGGTCCCA
CGACCTGCGTTTCTGGCGCAGTATGCCAATTCGTCAATGACTGGTACTCC
CAATGCGTGCCCGGATCGAGCAACCCTCCTACGGGCACCACCAGCAGCAC
CACTGGAAGCACCCCGGCTCCTACTGGCGGCGGCGGCAGCGGAACCGGCC
TCCACGACAAATTCAAGGCCAAGGGCAAGCTCTACTTCGGAACCGAGATC
```

```
GATCACTACCATCTCAACAACAATGCCTTGACCAACATTGTCAAGAAAGA
CTTTGGTCAAGTCACTCACGAGAACAGCTTGAAGTGGGATGCTACTGAGC
CGAGCCGCAATCAATTCAACTTTGCCAACGCCGACGCGGTTGTCAACTTT
GCCCAGGCCAACGGCAAGCTCATCCGCGGCCACACCCTCCTCTGGCACTC
TCAGCTGCCGCAGTGGGTGCAGAACATCAACGACCGCAACACCTTGACCC
AGGTCATCGAGAACCACGTCACCACCCTTGTCACTCGCTACAAGGGCAAG
ATCCTCCACTGGGACGTCGTTAACGAGATCTTTGCCGAGGACGGCTCGCT
CCGCGACAGCGTCTTCAGCCGCGTCCTCGGCGAGGACTTTGTCGGCATCG
CCTTCCGCGCCGCCCGCGCCGCCGATCCCAACGCCAAGCTCTACATCAAC
GACTACAACCTCGACATTGCCAACTACGCCAAGGTGACCCGGGGCATGGT
CGAGAAGGTCAACAAGTGGATCGCCCAGGGCATCCCGATCGACGGCATCG
GCACCCAGTGCCACCTGGCCGGGCCCGGCGGGTGGAACACGGCCGCCGGC
GTCCCCGACGCCCTCAAGGCCCTCGCCGCGGCCAACGTCAAGGAGATCGC
CATCACCGAGCTCGACATCGCCGGCGCCTCCGCCAACGACTACCTCACCG
TCATGAACGCCTGCCTCCAGGTCTCCAAGTGCGTCGGCATCACCGTCTGG
GGCGTCTCTGACAAGGACAGCTGGAGGTCGAGCAGCAACCCGCTCCTCTT
CGACAGCAACTACCAGCCAAAGGCGGCATACAATGCTCTGATTAATGCCT
TGTAA
```
                                (SEQ ID NO: 167)
MRTLTFVLAAAPVAVLAQSPLWGQCGGQGWTGPTTCVSGAVCQFVNDWYS

QCVPGSSNPPTGTTSSTTGSTPAPTGGGGSGTGLHDKFKAKGKLYFGTEI

DHYHLNNNALTNIVKKDFGQVTHENSLKWDATEPSRNQFNFANADAVVNF

AQANGKLIRGHTLLWHSQLPQWVQNINDRNTLTQVIENHVTTLVTRYKGK

ILHWDVVNEIFAEDGSLRDSVFSRVLGEDFVGIAFRAARAADPNAKLYIN

DYNLDIANYAKVTRGMVEKVNKWIAQGIPIDGIGTQCHLAGPGGWNTAAG

VPDALKALAAANVKEIAITELDIAGASANDYLTVMNACLQVSKCVGITVW

GVSDKDSWRSSSNPLLFDSNYQPKAAYNALINAL (SEQ ID NO: 168)
QSPLWGQCGGQGWTGPTTCVSGAVCQFVNDWYSQCVPGSSNPPTGTTSST

TGSTPAPTGGGGSGTGLHDKFKAKGKLYFGTEIDHYHLNNNALTNIVKKD

FGQVTHENSLKWDATEPSRNQFNFANADAVVNFAQANGKLIRGHTLLWHS

QLPQWVQNINDRNTLTQVIENHVTTLVTRYKGKILHWDVVNEIFAEDGSL

RDSVFSRVLGEDFVGIAFRAARAADPNAKLYINDYNLDIANYAKVTRGMV

EKVNKWIAQGIPIDGIGTQCHLAGPGGWNTAAGVPDALKALAAANVKEIA

ITELDIAGASANDYLTVMNACLQVSKCVGITVWGVSDKDSWRSSSNPLLF

DSNYQPKAAYNALINAL

The polynucleotide (SEQ ID NO:169) and amino acid (SEQ ID NO:170) sequences of another wild-type *M. thermophila* xylanase ("Xyl6") are provided below. The signal sequence is shown underlined in SEQ ID NO:170. SEQ ID NO:171 provides the sequence of this xylanase without the signal sequence.

(SEQ ID NO: 169)
ATGGTCTCGCTCAAGTCCCTCCTCCTCGCCGCGGCGGCGACGTTGACGGC

GGTGACGGCGCGCCCGTTCGACTTTGACGACGGCAACTCGACCGAGGCGC

TGGCCAAGCGCCAGGTCACGCCCAACGCGCAGGGCTACCACTCGGGCTAC

TTCTACTCGTGGTGGTCCGACGGCGGCGGCCAGGCCACCTTCACCCTGCT

CGAGGGCAGCCACTACCAGGTCAACTGGAGGAACACGGGCAACTTTGTCG

GTGGCAAGGGCTGGAACCCGGGTACCGGCCGGACCATCAACTACGGCGGC

TCGTTCAACCCGAGCGGCAACGGCTACCTGGCCGTCTACGGCTGGACGCA

CAACCCGCTGATCGAGTACTACGTGGTCGAGTCGTACGGGACCTACAACC

CGGGCAGCCAGGCCCAGTACAAGGGCAGCTTCCAGAGCGACGGCGGCACC

TACAACATCTACGTCTCGACCCGCTACAACGCGCCCTCGATCGAGGGCAC

CCGCACCTTCCAGCAGTACTGGTCCATCCGCACCTCCAAGCGCGTCGGCG

GCTCCGTCACCATGCAGAACCACTTCAACGCCTGGGCCCAGCACGGCATG

CCCCTCGGCTCCCACGACTACCAGATCGTCGCCACCGAGGGCTACCAGAG

CAGCGGCTCCTCCGACATCTACGTCCAGACTCACTAG (SEQ ID NO: 170)
MVSLKSLLLAAAATLTAVTARPFDFDDGNSTEALAKRQVTPNAQGYHSGY

FYSWWSDGGGQATFTLLEGSHYQVNWRNTGNFVGGKGWNPGTGRTINYGG

SFNPSGNGYLAVYGWTHNPLIEYYVVESYGTYNPGSQAQYKGSFQSDGGT

YNIYVSTRYNAPSIEGTRTFQQYWSIRTSKRVGGSVTMQNHFNAWAQHGM

PLGSHDYQIVATEGYQSSGSSDIYVQTH (SEQ ID NO: 171)
RPFDFDDGNSTEALAKRQVTPNAQGYHSGYFYSWWSDGGGQATFTLLEGS

HYQVNWRNTGNFVGGKGWNPGTGRTINYGGSFNPSGNGYLAVYGWTHNPL

IEYYVVESYGTYNPGSQAQYKGSFQSDGGTYNIYVSTRYNAPSIEGTRTF

QQYWSIRTSKRVGGSVTMQNHFNAWAQHGMPLGSHDYQIVATEGYQSSGS

SDIYVQTH

The polynucleotide (SEQ ID NO:172) and amino acid (SEQ ID NO:173) sequences of another wild-type *M. thermophila* xylanase ("Xyl5") are provided below. The signal sequence is shown underlined in SEQ ID NO:173. SEQ ID NO:174 provides the sequence of this xylanase, without the signal sequence.

(SEQ ID NO: 172)
ATGGTTACCCTCACTCGCCTGGCGGTCGCCGCGGCGGCCATGATCTCCAG

CACTGGCCTGGCTGCCCCGACGCCCGAAGCTGGCCCCGACCTTCCCGACT

TTGAGCTCGGGGTCAACAACCTCGCCCGCCGCGCTGGACTACAACCAG

AACTACAGGACCAGCGGCAACGTCAACTACTCGCCCACCGACAACGGCTA

CTCGGTCAGCTTCTCCAACGCGGGAGATTTTGTCGTCGGGAAGGGCTGGA

GGACGGGAGCCACCAGAAACATCACCTTCTCGGGATCGACACAGCATACC

TCGGGCACCGTGCTCGTCTCCGTCTACGGCTGGACCCGGAACCCGCTGAT

CGAGTACTACGTGCAGGAGTACACGTCCAACGGGGCCGGCTCCGCTCAGG

GCGAGAAGCTGGGCACGGTCGAGAGCGACGGGGGCACGTACGAGATCTGG

CGGCACCAGCAGGTCAACCAGCCGTCGATCGAGGGCACCTCGACCTTCTG

GCAGTACATCTCGAACCGCGTGTCCGGCCAGCGGCCCAACGGCGGCACCG
TCACCCTCGCCAACCACTTCGCCGCCTGGCAGAAGCTCGGCCTGAACCTG
GGCCAGCACGACTACCAGGTCCTGGCCACCGAGGGCTGGGGCAACGCCGG
CGGCAGCTCCCAGTACACCGTCAGCGGCTGA (SEQ ID NO: 173)
MVTLTRLAVAAAAMISSTGLAAPTPEAGPDLPDFELGVNNLARRALDYNQ
NYRTSGNVNYSPTDNGYSVSFSNAGDFVVGKGWRTGATRNITFSGSTQHT
SGTVLVSVYGWTRNPLIEYYVQEYTSNGAGSAQGEKLGTVESDGGTYEIW
RHQQVNQPSIEGTSTFWQYISNRVSGQRPNGGTVTLANHFAAWQKLGLNL
GQHDYQVLATEGWGNAGGSSQYTVSG (SEQ ID NO: 174)
APTPEAGPDLPDFELGVNNLARRALDYNQNYRTSGNVNYSPTDNGYSVSF
SNAGDFVVGKGWRTGATRNITFSGSTQHTSGTVLVSVYGWTRNPLIEYYV
QEYTSNGAGSAQGEKLGTVESDGGTYEIWRHQQVNQPSIEGTSTFWQYIS
NRVSGQRPNGGTVTLANHFAAWQKLGLNLGQHDYQVLATEGWGNAGGSSQ
YTVSG

The polynucleotide (SEQ ID NO:175) and amino acid (SEQ ID NO:176) sequences of a wild-type *M. thermophila* beta-xylosidase are provided below. The signal sequence is shown underlined in SEQ ID NO:176. SEQ ID NO:177 provides the sequence of this xylanase without the signal sequence.

(SEQ ID NO: 175)
ATGTTCTTCGCTTCTCTGCTGCTCGGTCTCCTGGCGGGCGTGTCCGCTTC
ACCGGGACACGGGCGGAATTCCACCTTCTACAACCCCATCTTCCCCGGCT
TCTACCCCGATCCGAGCTGCATCTACGTGCCCGAGCGTGACCACACCTTC
TTCTGTGCCTCGTCGAGCTTCAACGCCTTCCCGGGCATCCCGATTCATGC
CAGCAAGGACCTGCAGAACTGGAAGTTGATCGGCCATGTGCTGAATCGCA
AGGAACAGCTTCCCCGGCTCGCTGAGACCAACCGGTCGACCAGCGGCATC
TGGGCACCCACCCTCCGGTTCCATGACGACACCTTCTGGTTGGTCACCAC
ACTAGTGGACGACGACCGGCCGCAGGAGGACGCTTCCAGATGGGACAATA
TTATCTTCAAGGCAAAGAATCCGTATGATCCGAGGTCCTGGTCCAAGGCC
GTCCACTTCAACTTCACTGGCTACGACACGGAGCCTTTCTGGGACGAAGA
TGGAAAGGTGTACATCACCGGCGCCCATGCTTGGCATGTTGGCCCATACA
TCCAGCAGGCCGAAGTCGATCTCGACACGGGGGCCGTCGGCGAGTGGCGC
ATCATCTGGAACGGAACGGGCGGCATGGCTCCTGAAGGGCCGCACATCTA
CCGCAAAGATGGGTGGTACTACTTGCTGGCTGCTGAAGGGGGGACCGGCA
TCGACCATATGGTGACCATGGCCCGGTCGAGAAAAATCTCCAGTCCTTAC
GAGTCCAACCCAAACAACCCCGTGTTGACCAACGCCAACACGACCAGTTA
CTTTCAAACCGTCGGGCATTCAGACCTGTTCCATGACAGACATGGGAACT
GGTGGGCAGTCGCCCTCTCCACCCGCTCCGGTCCAGAATATCTTCACTAC
CCCATGGGCCGCGAGACCGTCATGACAGCCGTGAGCTGGCCGAAGGACGA
GTGGCCAACCTTCACCCCCATATCTGGCAAGATGAGCGGCTGGCCGATGC

CTCCTTCGCAGAAGGACATTCGCGGAGTCGGCCCCTACGTCAACTCCCCC
GACCCGGAACACCTGACCTTCCCCCGCTCGGCGCCCTGCCGGCCCACCT
CACCTACTGGCGATACCCGAACCCGTCCTCCTACACGCCGTCCCCGCCCG
GGCACCCCAACACCCTCCGCCTGACCCCGTCCCGCCTGAACCTGACCGCC
CTCAACGGCAACTACGCGGGGGCCGACCAGACCTTCGTCTCGCGCCGGCA
GCAGCACACCCTCTTCACCTACAGCGTCACGCTCGACTACGCGCCGCGGA
CCGCCGGGGAGGAGGCCGGCGTGACCGCCTTCCTGACGCAGAACCACCAC
CTCGACCTGGGCGTCGTCCTGCTCCCTCGCGGCTCCGCCACCGCGCCCTC
GCTGCCGGGCCTGAGTAGTAGTACAACTACTACTAGTAGTAGTAGTAGTC
GTCCGGACGAGGAGGAGGAGCGCGAGGCGGGCGAAGAGGAAGAAGAGGGC
GGACAAGACTTGATGATCCCGCATGTGCGGTTCAGGGGCGAGTCGTACGT
GCCCGTCCCGGCGCCCGTCGTGTACCCGATACCCCGGGCCTGGAGAGGCG
GGAAGCTTGTGTTAGAGATCCGGGCTTGTAATTCGACTCACTTCTCGTTC
CGTGTCGGGCCGGACGGGAGACGGTCTGAGCGGACGGTGGTCATGGAGGC
TTCGAACGAGGCCGTTAGCTGGGGCTTTACTGGAACGCTGCTGGGCATCT
ATGCGACCAGTAATGGTGGCAACGGAACCACGCCGGCGTATTTTTCGGAT
TGGAGGTACACACCATTGGAGCAGTTTAGGGAT (SEQ ID NO: 176)
MFFASLLLGLLAGVSAPGHGRNSTFYNPIFPGFYDPSCIYVPERDHTF
FCASSSFNAFPGIPIHASKDLQNWKLIGHVLNRKEQLPRLAETNRSTSGI
WAPTLRFHDDTFWLVTTLVDDDRPQEDASRWDNIIFKAKNPYDPRSWSKA
VHFNFTGYDTEPFWDEDGKVYITGAHAWHVGPYIQQAEVDLDTGAVGEWR
IIWNGTGGMAPEGPHIYRKDGWYYLLAAEGGTGIDHMVTMARSRKISSPY
ESNPNNPVLTNANTTSYFQTVGHSDLFHDRHGNWWAVALSTRSGPEYLHY
PMGRETVMTAVSWPKDEWPTFTPISGKMSGWPMPPSQKDIRGVGPYVNSP
DPEHLTFPRSAPLPAHLTYWRYPNPSSYTPSPPGHPNTLRLTPSRLNLTA
LNGNYAGADQTFVSRRQQHTLFTYSVTLDYAPRTAGEEAGVTAFLTQNHH
LDLGVVLLPRGSATAPSLPGLSSSTTTTSSSSSRPDEEEEREAGEEEEG
GQDLMIPHVRFRGESYVPVPAPVVYPIPRAWRGGKLVLEIRACNSTHFSF
RVGPDGRRSERTVVMEASNEAVSWGFTGTLLGIYATSNGGNGTTPAYFSD
WRYTPLEQFRD (SEQ ID NO: 177)
SPGHGRNSTFYNPIFPGFYDPSCIYVPERDHTFFCASSSFNAFPGIPIH
ASKDLQNWKLIGHVLNRKEQLPRLAETNRSTSGIWAPTLRFHDDTFWLVT
TLVDDDRPQEDASRWDNIIFKAKNPYDPRSWSKAVHFNFTGYDTEPFWDE
DGKVYITGAHAWHVGPYIQQAEVDLDTGAVGEWRIIWNGTGGMAPEGPHI
YRKDGWYYLLAAEGGTGIDHMVTMARSRKISSPYESNPNNPVLTNANTTS
YFQTVGHSDLFHDRHGNWWAVALSTRSGPEYLHYPMGRETVMTAVSWPKD
EWPTFTPISGKMSGWPMPPSQKDIRGVGPYVNSPDPEHLTFPRSAPLPAH
LTYWRYPNPSSYTPSPPGHPNTLRLTPSRLNLTALNGNYAGADQTFVSRR
QQHTLFTYSVTLDYAPRTAGEEAGVTAFLTQNHHLDLGVVLLPRGSATAP

-continued

SLPGLSSSTTTTSSSSSRPDEEEEREAGEEEEEGGQDLMIPHVRFRGESY

VPVPAPVVYPIPRAWRGGKLVLEIRACNSTHFSFRVGPDGRRSERTVVME

ASNEAVSWGFTGTLLGIYATSNGGNGTTPAYFSDWRYTPLEQFRD

The polynucleotide (SEQ ID NO:178) and amino acid (SEQ ID NO:179) sequences of a wild-type *M. thermophila* acetylxylan esterase ("Axe3") are provided below. The signal sequence is shown underlined in SEQ ID NO:179. SEQ ID NO:180 provides the sequence of this acetylxylan esterase without the signal sequence.

(SEQ ID NO: 178)
ATGAAGCTCCTGGGCAAACTCTCGGCGGCACTCGCCCTCGCGGGCAGCAG

GCTGGCTGCCGCGCACCCGGTCTTCGACGAGCTGATGCGGCCGACGGCGC

CGCTGGTGCGCCCGCGGGCGGCCCTGCAGCAGGTGACCAACTTTGGCAGC

AACCCGTCCAACACGAAGATGTTCATCTACGTGCCCGACAAGCTGGCCCC

CAACCCGCCCATCATAGTGGCCATCCACTACTGCACCGGCACCGCCCAGG

CCTACTACTCGGGCTCCCCTTACGCCCGCCTCGCCGACCAGAAGGGCTTC

ATCGTCATCTACCCGGAGTCCCCCTACAGCGGCACCTGTTGGGACGTCTC

GTCGCGCGCCGCCCTGACCCACAACGGCGGCGGCGACAGCAACTCGATCG

CCAACATGGTCACCTACACCCTCGAAAAGTACAATGGCGACGCCAGCAAG

GTCTTTGTCACCGGCTCCTCGTCCGGCGCCATGATGACGAACGTGATGGC

CGCCGCGTACCCGGAACTGTTCGCGGCAGGAATCGCCTACTCGGCGTGC

CCGCCGGCTGCTTCTACAGCCAGTCCGGAGGCACCAACGCGTGGAACAGC

TCGTGCGCCAACGGGCAGATCAACTCGACGCCCCAGGTGTGGGCCAAGAT

GGTCTTCGACATGTACCCGGAATACGACGGCCCGCGCCCCAAGATGCAGA

TCTACCACGGCTCGGCCGACGGCACGCTCAGACCCAGCAACTACAACGAG

ACCATCAAGCAGTGGTGCGGCGTCTTCGGCTTCGACTACACCCGCCCCGA

CACCACCCAGGCCAACTCCCCGCAGGCCGGCTACACCACCTACACCTGGG

GCGAGCAGCAGCTCGTCGGCATCTACGCCCAGGGCGTCGGACACACGGTC

CCCATCCGCGGCAGCGACGACATGGCCTTCTTTGGCCTGTGA (SEQ ID NO: 179)
MKLLGKLSAALALAGSRLAAAHPVFDELMRPTAPLVRPRAALQQVTNFGS

NPSNTKMFIYVPDKLAPNPPIIVAIHYCTGTAQAYYSGSPYARLADQKGF

IVIYPESPYSGTCWDVSSRAALTHNGGGDSNSIANMVTYTLEKYNGDASK

VFVTGSSSGAMMTNVMAAAYPELFAAGIAYSGVPAGCFYSQSGGTNAWNS

SCANGQINSTPQVWAKMVFDMYPEYDGPRPKMQIYHGSADGTLRPSNYNE

TIKQWCGVFGFDYTRPDTTQANSPQAGYTTYTWGEQQLVGIYAQGVGHTV

PIRGSDDMAFFGL (SEQ ID NO: 180)
HPVFDELMRPTAPLVRPRAALQQVTNFGSNPSNTKMFIYVPDKLAPNPPI

IVAIHYCTGTAQAYYSGSPYARLADQKGFIVIYPESPYSGTCWDVSSRAA

LTHNGGGDSNSIANMVTYTLEKYNGDASKVFVTGSSSGAMMTNVMAAAYP

ELFAAGIAYSGVPAGCFYSQSGGTNAWNSSCANGQINSTPQVWAKMVFDM

YPEYDGPRPKMQIYHGSADGTLRPSNYNETIKQWCGVFGFDYTRPDTTQA

NSPQAGYTTYTWGEQQLVGIYAQGVGHTVPIRGSDDMAFFGL

The polynucleotide (SEQ ID NO:181) and amino acid (SEQ ID NO:182) sequences of a wild-type *M. thermophila* ferulic acid esterase ("FAE") are provided below. The signal sequence is shown underlined in SEQ ID NO:182. SEQ ID NO:183 provides the sequence of this xylanase without the signal sequence (SEQ ID NO: 181)
ATGATCTCGGTTCCTGCTCTCGCTCTGGCCCTTCTGGCCGCCGTCCAGGT

CGTCGAGTCTGCCTCGGCTGGCTGTGGCAAGGCGCCCCCTTCCTCGGGCA

CCAAGTCGATGACGGTCAACGGCAAGCAGCGCCAGTACATTCTCCAGCTG

CCCAACAACTACGACGCCAACAAGGCCCACAGGGTGGTGATCGGGTACCA

CTGGCGCGACGGATCCATGAACGACGTGGCCAACGGCGGCTTCTACGATC

TGCGGTCCCGGGCGGGCGACAGCACCATCTTCGTTGCCCCCAACGGCCTC

AATGCCGGATGGGCCAACGTGGGCGGCGAGGACATCACCTTTACGGACCA

GATCGTAGACATGCTCAAGAACGACCTCTGCGTGGACGAGACCCAGTTCT

TTGCTACGGGCTGGAGCTATGGCGGTGCCATGAGCCATAGCGTGGCTTGT

TCTCGGCCAGACGTCTTCAAGGCCGTCGCGGTCATCGCCGGGGCCCAGCT

GTCCGGCTGCGCCGGCGGCACGACGCCCGTGGCGTACCTAGGCATCCACG

GAGCCGCCGACAACGTCCTGCCCATCGACCTCGGCCGCCAGCTGCGCGAC

AAGTGGCTGCAGACCAACGGCTGCAACTACCAGGGCGCCCAGGACCCCGC

GCCGGGCCAGCAGGCCCACATCAAGACCACCTACAGCTGCTCCCGCGCGC

CCGTCACCTGGATCGGCCACGGGGGCGGCCACGTCCCCGACCCCACGGGC

AACAACGGCGTCAAGTTTGCGCCCCAGGAGACCTGGGACTTCTTTGATGC

CGCCGTCGGAGCGGCCGGCGCGCAGAGCCCGATGACATAA (SEQ ID NO: 182)
MISVPALALALLAAVQVVESASAGCGKAPPSSGTKSMTVNGKQRQYILQL

PNNYDANKAHRVVIGYHWRDGSMNDVANGGFYDLRSRAGDSTIFVAPNGL

NAGWANVGGEDITFTDQIVDMLKNDLCVDETQFFATGWSYGGAMSHSVAC

SRPDVFKAVAVIAGAQLSGCAGGTTPVAYLGIHGAADNVLPIDLGRQLRD

KWLQTNGCNYQGAQDPAPGQQAHIKTTYSCSRAPVTWIGHGGGHVPDPTG

NNGVKFAPQETWDFFDAAVGAAGAQSPMT (SEQ ID NO: 183)
ASAGCGKAPPSSGTKSMTVNGKQRQYILQLPNNYDANKAHRVVIGYHWRD

GSMNDVANGGFYDLRSRAGDSTIFVAPNGLNAGWANVGGEDITFTDQIVD

MLKNDLCVDETQFFATGWSYGGAMSHSVACSRPDVFKAVAVIAGAQLSGC

AGGTTPVAYLGIHGAADNVLPIDLGRQLRDKWLQTNGCNYQGAQDPAPGQ

QAHIKTTYSCSRAPVTWIGHGGGHVPDPTGNNGVKFAPQETWDFFDAAVG

AAGAQSPMT

EXAMPLE 1

Protease Deletion Strain Production and Testing

In this Example, methods used to produce *M. thermophila* strains deficient in protease production are described.

Method One:

Genomic DNA was isolated from a *M. thermophila* strain ("CF-409") that contained a deletion of the alp1 gene. The DNA was isolated using the following method: hyphal inoculum was seeded into a standard fungal growth medium and allowed to grow for 72 hours at 35° C. The mycelial mat was collected and genomic DNA was extracted using standard methods known in the art.

A DNA fragment of the 1 kb internal region of gene "contig_1809. g1" from genomic *M. thermophila* DNA was amplified by primers cdxp001 (SEQ ID NO:184) and cdxp002 (SEQ ID NO:185), shown below. The PCR reaction was performed by using the PHUSION® polymerase (NEB) using PHUSION® GC buffer (NEB) at 98'C for 30 sec., followed by 35 cycles of 98'C for 10 sec., 72° C. for 1 min., and final extension at 72° C. for 5 min. The resultant DNA fragment was cloned into plasmid C1V16.1809.g1 (See, FIG. 1) using the IN-FUSION® cloning technique (IN-FUSION® Advantage PCR cloning kit with cloning enhancer, Clontech, Cat. No 639617), using the manufacturer's protocol.

| Primer Name | Sequence (5'-3') |
|---|---|
| cdxp001 | ACCGCGGTGGCGGCCAGGTTCGTTCGTCGTCTCATGTGT (SEQ ID NO: 184) |
| cdxp002 | CAATAGACATCAGCATCCGGCCAACGAAGAAGGAAAGTA (SEQ ID NO: 185) |

Protoplast Preparation

First, $10^6$ spores/ml of *M. thermophila* cells (W1L100LΔAlp1Δchi1Δpyr5Δbgl1::pyr5Δku70::Hyg) were inoculated into 100 ml standard fungal growth medium. The culture was incubated for 24 hours at 35° C., 250 rpm. To harvest the mycelium, the culture was filtered through a sterile Myracloth filter (Calbiochem) and washed with 100 ml 1700 mosmol NaCl/CaCl$_2$ solution (0.6 M NaCl, 0.27 M CaCl$_2$*H$_2$O). The washed mycelia were transferred into a clean tube and weighed. Caylase (20 mg/g mycelia) was dissolved in 1700 mosmol NaCl/CaCl$_2$ and UV-sterilized for 90 sec. Then, 3 ml of sterile Caylase solution was added to the washed mycelia and mixed. Then, 15 ml of 1700 mosmol NaCl/CaCl$_2$ solution was added into the tube and mixed. The mycelia/Caylase suspension was incubated at 30° C., 70 rpm for 2 hours. Protoplasts were harvested by filtering through a sterile Myracloth filter into a sterile 50 ml tube. Then, 25 ml cold STC (1.2 M sorbitol, 50 mM CaCl$_2$*H$_2$O, 35 mM NaCl, 10 mM Tris-HCl) was added to the flow through and the protoplasts were spun down at 2720 rpm for 10 min at 4° C. The pellet was re-suspended in 50 ml STC and centrifuged again. After the washing steps, the pellet was resuspended in 1 ml STC.

Transformation

Transformation was carried out in *M. thermophila* strain (W1L100LΔAlp1Δchi1Δpyr5Δbgl1::pyr5Δku70::Hyg) protoplasts, where homologous integration of the construct would disrupt contig_1809. g1, as described below. First, 5 μg plasmid DNA, 1 μl aurintricarboxylic acid, and 100 μl of the protoplast suspension were mixed together and incubated at room temperature for 25 min. Then, 1.7 ml PEG4000 solution (60% PEG4000 [polyethylene glycol, average molecular weight 4000 daltons], 50 mM CaCl$_2$*H$_2$O, 35 mM NaCl, 10 mM Tris-HCl) was added and mixed thoroughly. The solution was kept at room temperature for 20 min. The tube was filled with STC, mixed and centrifuged at 2500 rpm for 10 min at 4° C. The STC was poured off and the pellet was re-suspended in the remaining STC and plated on acetamide selective media plates, as known in the art. The plates were incubated for 5 days at 35° C. Colonies were re-streaked and checked by PCR for the presence of the integrated plasmid disrupting the protease coding region.

Testing the Effect of Protease Deletion

The protease-deleted strain was grown in fungal growth medium and incubated at 35° C., 250 rpm, 85% humidity for 2 days. An aliquot (10%) of this culture was then used to inoculate fungal growth medium comprising glucose, amino acids, minerals, and pen/strep, and incubated at 35° C., 300 rpm, 85% humidity for 4 days.

The proteolytic activity present in the fermentation medium was determined in microtiter plate assays. In order to determine whether there was protease activity capable of clipping purified *M. thermophila* CBH1a in the fermentation medium, purified CBH1a was diluted to 1 gain 50 mM Na acetate buffer, pH5.0 and mixed with fermentation medium supernatant, at a ratio of 1:3 (enzyme:fermentation medium). The control was fermentation medium obtained from a culture of unmodified *M. thermophila* strain at the same ratio of enzyme to fermentation medium (i.e., 1:3; enzyme:fermentation broth).

In order to determine whether there was protease activity capable of clipping purified *M. thermophila* GH61a in the fermentation medium, purified GH61a was diluted to 0.5 g/l in 50 mM Na acetate buffer, pH5.0 and mixed with fermentation medium at a ratio of 1:4 (enzyme:fermentation medium). The control was fermentation medium obtained from a culture of unmodified *M. thermophila* strain at the same ratio of enzyme to fermentation medium (i.e., 1:4; enzyme:fermentation broth).

Additional controls included 4 fold diluted pure 1 g/l CBH1a in 50 mM Na acetate buffer (pH5.0), and 5 fold diluted pure 0.5g/1 GH61a in 50 mM Na acetate buffer (pH5.0). In these experiments, 0.25 volume 50 mM Na acetate buffer (pH5.0) was added to each sample.

Samples were taken from time 0 and after 72 h shaking at 38° C., 900 rpm. The 0 time point and 72 h time point samples were run on SDS-PAGE and the proteolytic activity of the fermentation supernatants were assessed based on the level of CBH1a or GH61a lysis in comparison to the controls. The SDS-PAGE results showed that the deletion of the protease encoded by contig_1809. g1 eliminated GH61a and CBH1a clipping, in contrast to the fermentation medium from the unmodified *M. thermophila* strain.

EXAMPLE 2

Protease Deletion Strain Development and Testing

In this Example, methods used to produce *M. thermophila* strains deficient in protease production are described.

Genomic DNA was isolated from the CF-409 strain using standard methods known in the art. Genomic DNA fragments flanking the contig_690. g5 gene were cloned using primers cdxp003 and cdxp004 (upstream homology) and primers cdxp003 and cdxp004 (downstream homology). The PCR reaction was performed by using the GOTAQ® polymerase (Promega) at 95° C. for 2 min., followed by 35 cycles of 95'C for 30 sec., 53'C for 30 sec., 72° C. for 1 min., and final extension at 72° C. for 5 min. The resultant DNA fragments were cloned into plasmid pUC19, along with a HygR selection marker using the GeneArt cloning technique (GENEART® Seamless Cloning and Assembly Kit, Invitrogen Cat. No. A13288), according to the manufacturer's protocol to create "pUC19-690.g5." For gene contig_690. g5 knock-out, the split-marker method was employed, as known in the art. The two DNA fragments were amplified from the puc19-690.g5 plasmid construct by cdxp007-cdxp008 and cdxp009-cdxp010 primers, respectively. The two fragments were co-transformed in equal amounts (2.5 and 2.5 μg) into CF-409 fungal protoplasts to obtain gene deleted strains, as described above.

| Primer Name | Sequence (5'-3') |
|---|---|
| cdxp003 | AAGAGTGCAAGAGTGAAGGCAGGC (SEQ ID NO: 186) |
| cdxp004 | CTAGCACAGTCAGACCTCCACATACCATCGTACTCGCAACT GACGCTCGTT (SEQ ID NO: 187) |
| cdxp005 | GCAGTCGCAGCATTTACATCAGGCTGGTATGTGGAGGTCTG ACTGTGCTAG (SEQ ID NO: 188) |
| cdxp006 | GCCCGCTGTCATTCAAGACATTGC (SEQ ID NO: 189) |
| cdxp007 | GCCAAGCTTGCATGCCATCACTGTTGATGACGCTCTCGCT (SEQ ID NO: 190) |
| cdxp008 | TGTTGGCGACCTCGTATTGGGAAT (SEQ ID NO: 191) |
| cdxp009 | TCTCGGAGGGCGAAGAATCTCGTG (SEQ ID NO: 192) |
| cdxp010 | AATTCGAGCTCGGTACTTGTGCATTTACGGTGCTGTGACG (SEQ ID NO: 193) |

Transformation was carried out into UV18#100fΔAlp1Δpyr5Δku70::pyr5 *M. thermophila* strain. The transformants were incubated for 5 days at 35° C. under standard hygromycin-selective conditions known in the art. Colonies were re-streaked and checked for the deletion of the protease using PCR, as described in Example 1, above.

The protease-deleted strain was grown in a fungal growth medium at pH 5.0 and an unmodified strain (control) was grown in the same fungal growth medium at pH 5.0 and pH 6.7. Protein profiles were compared using 2D gel electrophoresis, using standard methods known in the art. Comparison of the 2D gels showed that CBH1a lysis was significantly reduced in the protease-deleted strain.

EXAMPLE 3

Protease Deletion Strain Development and Testing

In this Example, methods used to produce *M. thermophila* strains deficient in protease production are described.

Genomic DNA was isolated from an *M. thermophila* strain ("CF-409") with a deletion of the alp1 gene. The DNA was isolated using standard methods known in the art. To produce knockout of gene 1086.g13 (v4chr4-45825m24; SEQ ID NO:7), the split-marker method was employed, as known in the art. The 3' and 5' homolog arms (i.e., "flanks") of 1086.g13 were amplified from genomic DNA by cdx111006-cdx111007 and cdx111008-cdx111009 primers, respectively, as described below.

| Primer Name | Sequence (5'-3') |
|---|---|
| cdx111006 | CCGTCTCTCCGCATGCCAGAAAGATTCCTTCCCTTGCTCC TTCACACTG (SEQ ID NO: 194) |
| cdx111007 | CCCCTCCCCTACCTATCTTGTGTCT (SEQ ID NO: 195) |
| cdx111008 | GGA TAA GAG TGA ACA ACG ACG AGC (SEQ ID NO: 196) |
| cdx111009 | GTAACACCCAATACGCCGGCCGAACAAAAGCCATTCTTCC TCCGAGAC (SEQ ID NO: 197) |
| cdx10177 | TGTTGGCGACCTCGTATTGGGAAT (SEQ ID NO: 198) |

Primers were designed with 24 bp long adapters (first 24 bp in primers Cdx 111006 and Cdx 111009) complementary to 5' and 3' ends of the HYGRO (i.e., hygromycin B phosphotransferase; "hygromycin gene") selection marker cassette. The 24 bp long adapter part of the Cdx111006 primer is complementary to the promoter region of HYGRO cassette, while the cdx111009 primer carries an adapter complementary to the terminator region of the HYGRO cassette. The whole HYGRO fragment is 2554 bp in length. The overlapping homolog arms of hygromycin gene are indicated herein as "HYG" and "GRO." The 1559 bp long HYG arm (5' arm) was amplified with cdx 10176-cdx 10177 primers. The 1607 bp long GRO arm (3' arm) was amplified with cdx10178-cdx10179 primers. The overlap between the HYG and GRO arms is 612 bp long.

| Primer Name | Primer Sequence | Corresponding Region |
|---|---|---|
| cdx10176 | TCTTTCTGGCATGCGGAGAGACGG (SEQ ID NO: 199) | HYG (5' arm) forward |
| cdx10177 | TGTTGGCGACCTCGTATTGGGAAT (SEQ ID NO: 198) | HYG (5' arm) reverse |
| cdx10178 | TCTCGGAGGGCGAAGAATCTCGTG (SEQ ID NO: 199) | GRO (3' arm) forward |
| cdx10179 | TTCGGCCGGCGTATTGGGTGTTAC (SEQ ID NO: 200) | GRO (3' arm) reverse |

The HYG 5' homolog arm was amplified using the following PCR parameters: denaturation at 95° C. for 2 min, followed by 35 cycles of 95° C. for 20 sec, 60° C. for 20 sec, 72° C. for 1 min, and final extension at 72° C. for 3 min. The 50 μl reaction volume contained 10 μl 5× HERCULASE® II reaction buffer (Agilent Technologies), 0.5 μl 25 mM dNTPs, 1 μl primer Cdx10176 (10 mM), 1 μl primer Cdx10177 (10 mM), 3% DMSO, 1 μl DNA template, HERCULASE® II Fusion Enzyme (Agilent Technologies) with dNTPs Combo (Agilent Technologies), H$_2$O was added to 50 μl final volume.

GRO 3' homolog arm was amplified using the following PCR parameters: denaturation at 95° C. for 2 min, followed by 35 cycles of 95° C. for 20 sec, 60° C. for 20 sec, 72° C. for 1 min, and final extension at 72° C. for 3 min. The 50 μl reaction volume contained 10 μl5× HERCULASE® II reaction buffer (Agilent Technologies), 0.5 μl 25 mM dNTPs, 1 μl primer Cdx10178 (10 mM), 1 μl primer Cdx10179 (10 mM), 3% DMSO, 1 μl DNA template, HERCULASE® II Fusion Enzyme (Agilent Technologies) with dNTPs Combo (Agilent Technologies), H$_2$O was added to 50 μl final volume.

The 943 bp long 1086.g13 3' homolog arm was amplified using the following PCR parameters: denaturation at 98° C. for 30 sec, followed by 35 cycles of 98° C. for 10 sec, 62° C. for 20 sec, and 72° C. for 30 sec, followed by final extension at 72° C. for 5 min. The 50 μl reaction volume contained 10 µl 5× PHUSION® GC buffer, 0.5 µl 25 mM dNTPs, 1 µl Cdx111006 (10 mM), 1 µl primer Cdx111007 (10 mM), 3% DMSO, 1 µl DNA template, 0.5 µl PHUSION® Hot Start High-Fidelity Polymerase (Finnzymes), H₂O was added to 50 µl final volume.

The 852 bp long 1086.g13 5' homolog arm was amplified using the following PCR parameters: denaturation at 95° C. for 2 min, followed by 35 cycles of 95° C. for 20 sec, 62° C. for 20 sec, 72° C. for 30 sec, and final extension at 72° C. for 3 min. The 50 µl reaction volume contained 10 µl 5× HERCULASE® II reaction buffer (Agilent Technologies), 0.5 µl 125 mM dNTPs, 1 µl primer Cdx111008 (10 mM), 1 µl primer Cdx111009 (10 mM), 3% DMSO, 1 µl DNA template, HERCULASE® II Fusion Enzyme (Agilent Technologies) with dNTPs Combo (Agilent Technologies), H₂O was added to 50 µl final volume.

The sizes of the PCR fragments were checked on precast 1.2% EtBr E-gel (Invitrogen). Fragments were spin column purified (QIAQUICK® PCR Purification Kit; Qiagen), and eluted in 50 µl elution buffer.

To attach the 1086.g13 3' homolog arm to HygR fragment, a 50 µl reaction volume containing 10 µl 1 5× HERCULASE® II reaction buffer (Agilent Technologies), 0.5 µl 125 mM dNTPs, 1 µl primer cdx111007 (10 mM), 1 µl primer cdx10177 (10 mM), 3% DMSO, 0.5 µl 13' arm (20 ng), 0.5 µl HYG fragment (20 ng), HERCULASE® II Fusion Enzyme (Agilent Technologies) with dNTPs Combo (Agilent Technologies), with H₂O added to 50 µl final volume. The primers used were Cdx111007 and Cdx10177. The following PCR parameters were used: denaturation at 95° C. for 2 min, followed by 35 cycles of 95° C. for 20 sec, 61° C. for 20 sec, and 72° C. for 1.5 min, followed by final extension at 72° C. for 3 min. The size of the 1086-3'+HYG construct was 2502 bp.

In order to attach the 1086.g13 5' homolog arm to the GRO fragment, a 50 µl reaction volume containing 10 µl 15× HERCULASE® II reaction buffer (Agilent Technologies), 0.5 µl 125 mM dNTPs, 1 µl primer cdx 111008 (10 mM), 1 µl primer cdx10178 (10 mM), 3% DMSO, 0.5 µl 15' arm (20 ng), 0.5 µl GRO fragment (20 ng), HERCULASE® II Fusion Enzyme (Agilent Technologies) with dNTPs Combo (Agilent Technologies), with H₂O added to 50 µl final volume. The PCR parameters used were as follows: denaturation at 95° C. for 2 min, followed by 35 cycles of 95° C. for 20 sec, 58° C. for 20 sec, and 72° C. for 1.5 min, followed by final extension at 72° C. for 3 min. The size of the 1086-5'+GRO construct was 2459 bp.

| Primer name | Sequence (5'-3') |
|---|---|
| cdx111008 | GGATAAGAGTGAACAACGACGAGC (SEQ ID NO: 196) |
| cdx10178 | TCTCGGAGGGCGAAGAATCTCGTG (SEQ ID NO: 200) |

Both constructs (1086-3'+HYG 1086-5' GRO) and were checked on precast 1.2% EtBr E-gel (Invitrogen). They were spin column purified (QIAQUICK® PCR Purification Kit; Qiagen), and eluted in 50 µl elution buffer. The two constructs were co-transformed in equal amounts (2 µg each) into CF-409 fungal protoplasts to obtain gene deleted strains, as described below.

Transformation into *M. thermophila* cells (W1L100LΔAlp1Δchi1Δpyr5Δbgl1::pyr5Δku70::Hyg) was performed as described in Example 1. The transformants were incubated for 5 days at 35° C. under standard hygromycin-selective conditions known in the art. Colonies were re-streaked and checked for the deletion of the protease using PCR, as described in Example 1, above.

The protease-deleted strain was grown in fungal growth medium and incubated at 35° C., 250 rpm, 85% humidity for 2 days. An aliquot (10%) of this culture was then used to inoculate fungal growth medium comprising glucose, CSS (corn stover solids), minerals and incubated at 35° C. at pH=5.0 for 4 days. The clipping of the enzyme CBH1a was determined using 2D gel (Biorad) which showed detectable decrease of the clipping in the protease deleted strain compared to the control.

What is claimed is:

1. An isolated, genetically modified *Myceliophthora* deficient in at least one protease native to said *Myceliophthora*, wherein said protease is capable of degrading *Myceliophthora* cellobiohydrolase enzymes, and comprises an amino acid sequence having at least 98% identity with the polypeptide sequence set forth in SEQ ID NO:12.

2. The *Myceliophthora* of claim 1, wherein said *Myceliophthora* is *Myceliophthora thermophila*.

3. The *Myceliophthora* of claim 1, wherein said *Myceliophthora* produces at least one enzyme.

4. The *Myceliophthora* of claim 3, wherein said at least one enzyme comprises at least one cellulase.

5. The *Myceliophthora* of claim 4, wherein said cellulase is beta-glucosidase.

6. The *Myceliophthora* of claim 5, wherein said cellulase is a recombinant beta-glucosidase.

7. The *Myceliophthora* of claim 4, wherein said *Myceliophthora* further produces at least one non-cellulase enzyme.

8. The *Myceliophthora* of claim 7, wherein said at least one non-cellulase enzyme comprises at least one lipase, amylase, glucoamylase, and/or protease.

9. A composition comprising the *Myceliophthora* of claim 1.

* * * * *

SEQUENCE LISTING

<160> NUMBER OF SEQ ID NOS: 201

<210> SEQ ID NO 1
<211> LENGTH: 1635
<212> TYPE: DNA
<213> ORGANISM: Myceliophthora thermophila

<400> SEQUENCE: 1

```
atgcagctcc ttagtctcgc cgctctcctc ccccttgccc ttgcggcacc ggtgatcaag      60
cctcaggggc tccagctgat tccgggcgac tacatcgtga agctgaagga cggtgcgtcc     120
gagagcactc tccaggacac catccggcac ctccaggcag gcgaggccaa gcatgtctac     180
cgcgcacgcc ggttcaaggg cttcgcggcc aagctgagcc gcaggtggt cgataccctg      240 agcaagctgc ccgaggttcg ttcgtcgtct catgtgtaat tatgtcacaa aaagggatat     300
gtaggatgct aattcagacc cgcaggtcga atacattgag caggacgccg tcgtcaccat     360
ccaggcgctg gtcacccagg aggacgtgcc ctggggtctg gcccgcatct cgcaccacga     420
actgggtccc acgtcgtacg tatacgacga cagcgccggc gagggtacct gcgcctatgt     480
catcgacacg ggcatctatg tggcccactc tgtaagtctg gccgtcaatt cacccactct     540
cccgctgctg ccaccgaatc tctattagta tcttgacgac tttgttgcgg agacaacgac     600
```

```
gctgactctt ttgactccag cagttcgaag gccgcgcgac gtggctggcc aactttatcg    660
acagcagcga tagcgagtca gtttagcatc ccccaccccc tggttgttgc acttgaatga    720
gctgaccttt cataaataaa cagcggcgcg ggccacggca cgcacgtgtc gggcacgatc    780
ggcggcgtga cgtacggcgt ggccaagaag accaagctgt tcgcggtcaa ggtgctcaac    840
gcgagcgggt cggggacggt gtcgtcggtg ctggcggggc tcgagttcgt cgcgtcggac    900
gcgccggcgc gcgtcgcctc gggcgagtgc gccaacggcg cggtcgccaa cctgagcctc    960
ggcggcggcc ggtccaccgc catcaacgcc gccgccgccg ccgccgtcga cgcgggcgtc   1020
ttcgtcgccg tcgcgccgg caacagcaac accgacgccc agtccacctc ccccgccagc   1080
gagcccagcg tctgcaccgt cggcgccacc gacgacagcg acgcccgcgc ctacttctcc   1140
aactacggca gcgtcgtcga cgtctttgct cccggcgtcg acgtcctcag cagctggatc   1200
ggcggtgtcg atgccactgt gagtttttt ttttcctttt cccgtttctt tttgcttctt   1260
gttttctccc cattttgatg ttttacatta ctttccttct tcgttggccg gattcgtttt   1320
catccttttt ttcttctttc ttctgtcaaa aggcgataac aagggatgat gcggaaagag   1380
agaagaggaa taaaaacggg gaaccagaac aagaacatac caggctgact ggaaaacaaa   1440
cagaacacca tctcgggcac ctcgatggcg accccgcata tcgccggcct cggggcctat   1500
ctcctcgctc tgctgggccc caggtcgccc gaggaactgt gcgagtacat caagcagacg   1560
gccaccatcg gcaccatcac cagcctcccc agcggcacca tcaacgccat tgcctacaac   1620
ggtgctacag cctaa                                                     1635

<210> SEQ ID NO 2
<211> LENGTH: 1164
<212> TYPE: DNA
<213> ORGANISM: Myceliophthora thermophila

<400> SEQUENCE: 2
atgcagctcc ttagtctcgc cgctctcctc cccttgccc ttgcggcacc ggtgatcaag     60
cctcaggggc tccagctgat tccgggcgac tacatcgtga agctgaagga cggtgcgtcc    120
gagagcactc tccaggacac catccggcac ctccaggcag gcgaggccaa gcatgtctac    180
cgcgcacgcc ggttcaaggg cttcgcggcc aagctgagcc gcaggtggt cgataccctg    240 agcaagctgc ccgaggtcga atacattgag caggacgccc tcgtcaccat ccaggcgctg    300
gtcacccagg aggacgtgcc ctggggtctg gcccgcatct cgcaccacga actgggtccc    360
acgtcgtacg tatacgacga cagcgccggc gagggtacct gcgcctatgt catcgacacg    420
ggcatctatg tggcccactc tcagttcgaa ggccgcgcga cgtggctggc caactttatc    480
gacagcagcg atagcgacgg cgcgggccac ggcacgcacg tgtcgggcac gatcggcggc    540
gtgacgtacg gcgtggccaa gaagaccaag ctgttcgcgg tcaaggtgct caacgcgagc    600
gggtcgggga cggtgtcgtc ggtgctggcg ggctcgagt cgtcgcgtc ggacgcgccg    660 gcgcgcgtcg cctcgggcga gtgcgccaac ggcgcggtcg ccaacctgag cctcggcggc    720
ggccggtcca ccgccatcaa cgccgccgcc gccgccgccg tcgacgcggg cgtcttcgtc    780
gccgtcgcgg ccggcaacag caacaccgac gcccagtcca cctcccccgc cagcgagccc    840
agcgtctgca ccgtcggcgc caccgacgac agcgacgccc gcgcctactt ctccaactac    900
ggcagcgtcg tcgacgtctt tgctcccggc gtcgacgtcc tcagcagctg gatcggcggt    960
gtcgatgcca ctaacaccat ctcgggcacc tcgatggcga ccccgcatat cgccggcctc   1020
```

```
gggggcctatc tcctcgctct gctgggcccc aggtcgcccg aggaactgtg cgagtacatc    1080
aagcagacgg ccaccatcgg caccatcacc agcctcccca gcggcaccat caacgccatt    1140
gcctacaacg gtgctacagc ctaa                                           1164
```

<210> SEQ ID NO 3
<211> LENGTH: 387
<212> TYPE: PRT
<213> ORGANISM: Myceliophthora thermophila

<400> SEQUENCE: 3

```
Met Gln Leu Leu Ser Leu Ala Ala Leu Leu Pro Leu Ala Leu Ala Ala
1               5                   10                  15

Pro Val Ile Lys Pro Gln Gly Leu Gln Leu Ile Pro Gly Asp Tyr Ile
            20                  25                  30

Val Lys Leu Lys Asp Gly Ala Ser Glu Ser Thr Leu Gln Asp Thr Ile
        35                  40                  45

Arg His Leu Gln Ala Gly Glu Ala Lys His Val Tyr Arg Ala Arg Arg
    50                  55                  60

Phe Lys Gly Phe Ala Ala Lys Leu Ser Pro Gln Val Val Asp Thr Leu
65                  70                  75                  80

Ser Lys Leu Pro Glu Val Glu Tyr Ile Glu Gln Asp Ala Val Val Thr
                85                  90                  95

Ile Gln Ala Leu Val Thr Gln Glu Asp Val Pro Trp Gly Leu Ala Arg
            100                 105                 110

Ile Ser His His Glu Leu Gly Pro Thr Ser Tyr Val Tyr Asp Asp Ser
        115                 120                 125

Ala Gly Glu Gly Thr Cys Ala Tyr Val Ile Asp Thr Gly Ile Tyr Val
    130                 135                 140

Ala His Ser Gln Phe Glu Gly Arg Ala Thr Trp Leu Ala Asn Phe Ile
145                 150                 155                 160

Asp Ser Ser Asp Ser Asp Gly Ala Gly His Gly Thr His Val Ser Gly
                165                 170                 175

Thr Ile Gly Gly Val Thr Tyr Gly Val Ala Lys Lys Thr Lys Leu Phe
            180                 185                 190

Ala Val Lys Val Leu Asn Ala Ser Gly Ser Gly Thr Val Ser Ser Val
        195                 200                 205

Leu Ala Gly Leu Glu Phe Val Ala Ser Asp Ala Pro Ala Arg Val Ala
    210                 215                 220

Ser Gly Glu Cys Ala Asn Gly Ala Val Ala Asn Leu Ser Leu Gly Gly
225                 230                 235                 240

Gly Arg Ser Thr Ala Ile Asn Ala Ala Ala Ala Ala Val Asp Ala
                245                 250                 255

Gly Val Phe Val Ala Val Ala Ala Gly Asn Ser Asn Thr Asp Ala Gln
            260                 265                 270

Ser Thr Ser Pro Ala Ser Glu Pro Ser Val Cys Thr Val Gly Ala Thr
        275                 280                 285

Asp Asp Ser Asp Ala Arg Ala Tyr Phe Ser Asn Tyr Gly Ser Val Val
    290                 295                 300

Asp Val Phe Ala Pro Gly Val Asp Val Leu Ser Ser Trp Ile Gly Gly
305                 310                 315                 320

Val Asp Ala Thr Asn Thr Ile Ser Gly Thr Ser Met Ala Thr Pro His
                325                 330                 335

Ile Ala Gly Leu Gly Ala Tyr Leu Leu Ala Leu Leu Gly Pro Arg Ser
            340                 345                 350
```

Pro Glu Glu Leu Cys Glu Tyr Ile Lys Gln Thr Ala Thr Ile Gly Thr
        355                 360                 365

Ile Thr Ser Leu Pro Ser Gly Thr Ile Asn Ala Ile Ala Tyr Asn Gly
        370                 375                 380

Ala Thr Ala
385

<210> SEQ ID NO 4
<211> LENGTH: 1687
<212> TYPE: DNA
<213> ORGANISM: Myceliophthora thermophila

<400> SEQUENCE: 4

| | |
|---|---:|
| atgaggttac tccgcaccgc gggagcggca actctcttcc tgtcgcccgc cacttttgcg | 60 |
| accaacaacc ctctgacccc aggcaaactt gaggcggaca ttagaaccga agagtatgag | 120 |
| aagacaacag tgccaaacct ttgatccctc tcattcgtta acgaatattg ccaaaccagg | 180 |
| ttgcaaaatg tcctctggaa cctcaatcac attgcgtca cccacggcgg caaccgagcc | 240 |
| tttggcgagc ctgggtacaa agcctcgctc gactttattc tcgagcgcgc ccagacacgc | 300 |
| ttccacaatg agtttgacac tgtcgttcag cccttcaacc acacctacgg caagacgaac | 360 |
| cagatcaagg tgactggacc agagggcgag gatgtctttg tcatcagccc attgtacaat | 420 |
| cccgccacgc cgctgcctga tggtatcacc gctcccttgg tagataccc ggtcgatgac | 480 |
| gagcgcggat cggcgtgctt ccggaccag tgggaggggg tcgatgtgaa ggggaagctg | 540 |
| gtactagtaa agagaggcat tgtgctgtg cagataagt cggcccttgc taaggagcgc | 600 |
| ggggcactgg gtgagctacg tcctggctga cggggaagc aaacgttgac gtcgctctag | 660 |
| gggtgatctt gtataacgaa cagccgggta cgaacatcgt cgtcccgact ctgggtgcag | 720 |
| agagcatcgg caagactgtt cctatcggaa ttattcccct tggaagtagga cagagctgga | 780 |
| agtcccggtt ggcagatggc gaggaggtga ctgtgcacct gctggtcgat ccatatccg | 840 |
| atacgcgcga cgtggaac attattgccg agaccaaaca gggcgacccc gacaaagtta | 900 |
| tcatgctcgg tgcacatctc gacagcgtgc aggcgggagc aggcatcaat gacgacggca | 960 |
| gcggcacggc agctctcctg gagatcttga ccgcggtccg gcgctacgat ggattcccac | 1020 |
| ataagattcg gttcgcctgg tgggcagcag aagagagtgg tctggtcgga tccctctact | 1080 |
| acacctccca cttgaccgag gaggaagccg accgcatcaa gtattacttc aactacgaca | 1140 |
| tgattggctc tccccatccc gactttgaaa ttgcaagcga tggcaacagc ggagtcgggc | 1200 |
| cgcagcttct ggaggaatac ctcgtcgagc aggggaagga gattgtccac gggtaagtag | 1260 |
| atcccactcc agctccacat ctattttgcg tacctggtac ctctatgata tgtgcaggtt | 1320 |
| ccgctgacct tgggatgcaa gcggcttcgg ttctggctcc gattttgtgg gcttcctcga | 1380 |
| gcttggcatc ccgagtaccg cgctacatac cggtgcagga gctccattcg acgaatgcta | 1440 |
| ccaccaggcg tgtgatgacc tcgacaatat caactgggag gcgctgaccg tcaatgccaa | 1500 |
| agcggccgct cgggcggctg cccggctggc caactcgctc gagggcgtgc cgccccgcaa | 1560 |
| gaaaactagc ctgaatcttc acacgcgccg tggagtggtg caaaacttcc gaaagtgggc | 1620 |
| ttcattggcc gaggaagcga gccacgggca cacgtgctcg cacacgggaa agagggtcgt | 1680 |
| agtgtaa | 1687 |

<210> SEQ ID NO 5
<211> LENGTH: 1482

```
<212> TYPE: DNA
<213> ORGANISM: Myceliophthora thermophila

<400> SEQUENCE: 5
atgaggttac tccgcaccgc gggagcggca actctcttcc tgtcgcccgc cacttttgcg      60
accaacaacc ctctgacccc aggcaaactt gaggcggaca ttagaaccga agagttgcaa     120
aatgtcctct ggaacctcaa tcacattgcg gtcacccacg gcggcaaccg agcctttggc     180
gagcctgggt acaaagcctc gctcgacttt attctcgagc gcgcccagac acgcttccac     240
aatgagtttg acactgtcgt tcagcccttc aaccacacct acggcaagac gaaccagatc     300
aaggtgactg gaccagaggg cgaggatgtc tttgtcatca gcccattgta caatcccgcc     360
acgccgctgc ctgatggtat caccgctccc ttggtagata caccggtcga tgacgagcgc     420
ggatcggcgt gctttccgga ccagtgggag gggtcgatg tgaaggggaa gctggtacta      480
gtaaagagag gcatttgtgc tgtggcagat aagtcggccc ttgctaagga gcgcggggca     540 ctggggtgtga tcttgtataa cgaacagccg ggtacgaaca tcgtcgtccc gactctgggt     600
gcagagagca tcggcaagac tgttcctatc ggaattattc ccttggaagt aggacagagc     660
tggaagtccc ggttggcaga tggcgaggag gtgactgtgc acctgctggt cgattccata     720
tccgatacgc gcgagacgtg gaacattatt gccgagacca acagggcga ccccgacaaa      780 gttatcatgc tcggtgcaca tctcgacagc gtgcaggcgg gagcaggcat caatgacgac     840
ggcagcggca cggcagctct cctggagatc ttgaccgcgg tccggcgcta cgatggattc     900
ccacataaga ttcggttcgc ctggtgggca gcagaagaga gtggtctggt cggatccctc     960
tactacacct cccacttgac cgaggaggaa gccgaccgca tcaagtatta cttcaactac    1020
gacatgattg ctctccccca tcccgacttt gaaattgcaa gcgatggcaa cagcggagtc    1080
gggccgcagc ttctggagga ataccctcgtc gagcagggga aggagattgt ccacggcggc    1140
ttcggttctg gctccgattt tgtgggcttc ctcgagcttg gcatcccgag taccgcgcta    1200
cataccggtg caggagctcc attcgacgaa tgctaccacc aggcgtgtga tgacctcgac    1260
aatatcaact gggaggcgct gaccgtcaat gccaaagcgg ccgctcgggc ggctgcccgg    1320
ctggccaact cgctcgaggg cgtgccgccc cgcaagaaaa ctagcctgaa tcttcacacg    1380
cgccgtggag tggtgcaaaa cttccgaaag tgggcttcat tggccgagga agcgagccac    1440
gggcacacgt gctcgcacac gggaaagagg gtcgtagtgt aa                       1482

<210> SEQ ID NO 6
<211> LENGTH: 493
<212> TYPE: PRT
<213> ORGANISM: Myceliophthora thermophila

<400> SEQUENCE: 6

Met Arg Leu Leu Arg Thr Ala Gly Ala Ala Thr Leu Phe Leu Ser Pro
1               5                   10                  15

Ala Thr Phe Ala Thr Asn Asn Pro Leu Thr Pro Gly Lys Leu Glu Ala
            20                  25                  30

Asp Ile Arg Thr Glu Glu Leu Gln Asn Val Leu Trp Asn Leu Asn His
        35                  40                  45

Ile Ala Val Thr His Gly Gly Asn Arg Ala Phe Gly Glu Pro Gly Tyr
    50                  55                  60

Lys Ala Ser Leu Asp Phe Ile Leu Glu Arg Ala Gln Thr Arg Phe His
65                  70                  75                  80

Asn Glu Phe Asp Thr Val Val Gln Pro Phe Asn His Thr Tyr Gly Lys
```

```
            85                  90                  95
Thr Asn Gln Ile Lys Val Thr Gly Pro Glu Gly Glu Asp Val Phe Val
            100                 105                 110

Ile Ser Pro Leu Tyr Asn Pro Ala Thr Pro Leu Pro Asp Gly Ile Thr
            115                 120                 125

Ala Pro Leu Val Asp Thr Pro Val Asp Asp Glu Arg Gly Ser Ala Cys
            130                 135                 140

Phe Pro Asp Gln Trp Glu Gly Val Asp Val Lys Gly Lys Leu Val Leu
145                 150                 155                 160

Val Lys Arg Gly Ile Cys Ala Val Ala Asp Lys Ser Ala Leu Ala Lys
                165                 170                 175

Glu Arg Gly Ala Leu Gly Val Ile Leu Tyr Asn Glu Gln Pro Gly Thr
                180                 185                 190

Asn Ile Val Val Pro Thr Leu Gly Ala Glu Ser Ile Gly Lys Thr Val
                195                 200                 205

Pro Ile Gly Ile Ile Pro Leu Glu Val Gly Gln Ser Trp Lys Ser Arg
                210                 215                 220

Leu Ala Asp Gly Glu Glu Val Thr Val His Leu Leu Val Asp Ser Ile
225                 230                 235                 240

Ser Asp Thr Arg Glu Thr Trp Asn Ile Ile Ala Glu Thr Lys Gln Gly
                245                 250                 255

Asp Pro Asp Lys Val Ile Met Leu Gly Ala His Leu Asp Ser Val Gln
                260                 265                 270

Ala Gly Ala Gly Ile Asn Asp Asp Gly Ser Gly Thr Ala Ala Leu Leu
                275                 280                 285

Glu Ile Leu Thr Ala Val Arg Arg Tyr Asp Gly Phe Pro His Lys Ile
                290                 295                 300

Arg Phe Ala Trp Trp Ala Ala Glu Glu Ser Gly Leu Val Gly Ser Leu
305                 310                 315                 320

Tyr Tyr Thr Ser His Leu Thr Glu Glu Ala Asp Arg Ile Lys Tyr
                325                 330                 335

Tyr Phe Asn Tyr Asp Met Ile Gly Ser Pro His Pro Asp Phe Glu Ile
                340                 345                 350

Ala Ser Asp Gly Asn Ser Gly Val Gly Pro Gln Leu Leu Glu Glu Tyr
                355                 360                 365

Leu Val Glu Gln Gly Lys Glu Ile Val His Gly Phe Gly Ser Gly
                370                 375                 380

Ser Asp Phe Val Gly Phe Leu Glu Leu Gly Ile Pro Ser Thr Ala Leu
385                 390                 395                 400

His Thr Gly Ala Gly Ala Pro Phe Asp Glu Cys Tyr His Gln Ala Cys
                405                 410                 415

Asp Asp Leu Asp Asn Ile Asn Trp Glu Ala Leu Thr Val Asn Ala Lys
                420                 425                 430

Ala Ala Ala Arg Ala Ala Ala Arg Leu Ala Asn Ser Leu Glu Gly Val
                435                 440                 445

Pro Pro Arg Lys Lys Thr Ser Leu Asn Leu His Thr Arg Arg Gly Val
                450                 455                 460

Val Gln Asn Phe Arg Lys Trp Ala Ser Leu Ala Glu Glu Ala Ser His
465                 470                 475                 480

Gly His Thr Cys Ser His Thr Gly Lys Arg Val Val Val
                485                 490

<210> SEQ ID NO 7
```

```
<211> LENGTH: 2479
<212> TYPE: DNA
<213> ORGANISM: Myceliophthora thermophila

<400> SEQUENCE: 7
atgtgttggc tgtgggagcg atcagtggca atattactgg cggccggcgt gatcgccaac      60
ccgctccgcc cgcgccggat ccctggccg gagccggttc cggcatcttc catcgggccc     120
attgactggt cttcaatacc gccttctccc tacaaacacg ccttgcggca gaccaacacc     180
accacgacca gcagcagtag cagcagcagc agcagcaaat atgacaatca agtctactcg     240
gtacaggtct cggatcttc ctcctccccg ccagcatccg tcgactgcg caaccgcgac      300
ggccagaact acatcacgac accgcaggac cagggcgcct gtaacagctg ctgggcgttc     360
gccgtggcgg cgctgatcga gtccatgatg cgcatcgagc acggggtctg gggcaagcgc     420
agcgaggccg acgtgcacga cggggtgggc gcggcgtgcg agagcgtggg caacgccgag     480
gacacgctgg cctgggtggc cgggcagggg cccgaattcg tcgccgaccc gaccggccc     540
gccccgggca tcgccgactg gcctgcgac ccctacgagg cgacgcgca cgcctacgag      600
cactgcgacg accgctccgg cgcacgacg cacattccct actaccaggc cctcggcctg     660
gtcgaggacc agaagcggtg gctggacgag tacgggccca tcatcgccac ctttgtcctc     720
tacgacgact ttggctcgtg aagccgacc gcggccggcg aagcggcgg tgacgtgtac      780
cggtgggacg gcgtttccgg ctcggacggc aaccacctcg ccatcgtgat cggctacgac     840
gacgagaagc aggcctggct tatgaagaac tcatggggat ccggatgggg gacgaggga     900
tttgtctact ttgcgtaagt cagggggttcc actgcttttt ttttttttccc ctccaaaatc    960
gtttgcctct cggtaatttt atccgcatcc agggaactga caacagatac aggtacggcg    1020
aggccaacat cgacaactgg accaagtatg ggctcgtcaa tgtcaacccg gacccgtgga    1080
cacgcaggaa gcaccagagc ggaagcatga tgcaatccgg caacggcgag acgcaccgaa    1140
actttgagct gctcgtcagc gaggccgggg gttccggctt cacgcacgtc tcccgcgatg    1200
ggaacagtac ccaatggagc aaggtgctgg aggtctcggg cagcggcagc ggcagcggcc    1260
tcgtgggcca gctgccatt tcggcacct ccttcaaccg ggacttccac gcggtgagcc    1320
tggatgagaa ccaggtggtc caacagtggg catacagaca gtcggagatg cgctggtccc    1380
gggtctcggc catcgagggc actaagatcg acggcttttcc cggtctcgcc cagagcgacg    1440
gctcaactct ggtcatggtg gtcaagcacg ccgacggcac cctgaacgag gtaagcatat    1500
cttgccggaa gtcataatta cgaaggaag atcttccgta aagaaaagg aaagatgaa    1560
aaaaaaaagg tacacgtgct aacggcggat cgcacaagtg caacaagca cccaacagca    1620
caacctggac cctggccaac tcacccatcg caagcggcat cgcccagagc gggccggcgc    1680
tcgtgcagtc caacgccgga ctcaacctct acgaccggca gcagggcgcc tcgcggggca    1740
acatctacac cgtcgcggtc cgcgaggacg gcaagctgca gctcttctgg cgccccggcg    1800
cggacgcggc cgggtggtcg gccggggagg tgttcggcgg ctccggcgtc gtggacccg    1860
gctcgccgcc cgtcatgatt caggactact cggggacggc caacgagacg agcgtcggcc    1920
ggttccagct ggccgtcgcc gtcggggga cgtccaaca ctgggagcgg ccaacgacg    1980
acctcgaggc cgggcaggcc ccgccgcgg gggcagaagg ggggtccccg gcgggcaggt    2040
gggaactggt cgagacggcg ggcaccgggg tgaagcgcgt ctgggcgctg ctccagggga    2100
gctttggtgg gaggctgcac atgatcacgg agggcacgga cggccggctg tcgtactggg    2160
agcgcgatga gaagtgggtt gaggtcgaga agctgccggc gttgagcgac gccgcttgga    2220
```

```
cgagatcggg cccggtgagt ggtggttgag ggtagtccca agtacctgat tataattata    2280
tgaaagagat gtcccccgaa taattatatg agtgaaccaa cgaccatgaa acatgcggc    2340 tttatcagca taccgacgcg acttgtcctg gttgcatctg ctacgacccc tgattaatta    2400
caacaccgca cagcggcaga gacggggcca gaagctgcac atagaaagaa ggctggacaa    2460
cttccccgag acgctataa                                                 2479
```

<210> SEQ ID NO 8
<211> LENGTH: 2040
<212> TYPE: DNA
<213> ORGANISM: Myceliophthora thermophila

<400> SEQUENCE: 8

```
atgtgttggc tgtgggagcg atcagtggca atattactgg cggccggcgt gatcgccaac      60
ccgctccgcc cgcgccggat cccctggccg gagccggttc cggcatcttc catcgggccc     120
attgactggt cttcaatacc gccttctccc tacaaacacg ccttgcggca gaccaacacc     180
accacgacca gcagcagtag cagcagcagc agcagcaaat atgacaatca agtctactcg     240
gtacaggtct cgggatcttc ctcctccccg ccagcatccg tcgactggcg caaccgcgac     300
ggccagaact acatcacgac accgcaggac cagggcgcct gtaacagctg ctgggcgttc     360
gccgtggcgg cgctgatcga gtccatgatg cgcatcgagc acggggtctg gggcaagcgc     420
agcgaggccg acgtgcacga cggggtgggc gcggcgtgcg agagcgtggg caacgccgag     480
gacacgctgg cctgggtggc cgggcagggg cccgaattcg tcgccgaccc gacccggccc     540
gccccgggca tcgccgactg gcctgcgac ccctacgagg cgacggcgca cgcctacgag     600
cactgcgacg accgctccgg gcgcacgacg cacattccct actaccaggc cctcggcctg     660
gtcgaggacc agaagcggtg gctggacgag tacgggccca tcatcgccac ctttgtcctc     720
tacgacgact ttggctcgtg gaagccgacc gcggccggcg aagcggcgg tgacgtgtac     780 cggtgggacg gcgtttccgg ctcggacggc aaccacctcg ccatcgtgat cggctacgac     840
gacgagaagc aggcctggct tatgaagaac tcatggggat ccggatgggg ggacgaggga     900
tttgtctact ttgcgtacgg cgaggccaac atcgacaact ggaccaagta tgggctcgtc     960
aatgtcaacc cggacccgtg gacacgcagg aagcaccaga gcggaagcat gatgcaatcc    1020
ggcaacggcg agacgcaccg aaactttgag ctgctcgtca gcgaggccgg gggttccggc    1080
ttcacgcacg tctcccgcga tgggaacagt acccaatgga gcaaggtgct ggaggtctcg    1140
ggcagcggca gcgcagcgg cctcgtgggc cagcctgcca ttctcggcac ctccttcaac    1200
cgggacttcc acgcggtgag cctggatgag aaccaggtgg tccaacagtg gcatacagac    1260
agtcggagat cgctggtcc cgggtctcgg ccatcgaggg cactaagatc gacggctttc    1320
ccggtctcgc ccagagcgac ggctcaactc tggtcatggt ggtcaagcac gccgacggca    1380
ccctgaacga gtggcaacaa gcacccaaca gcacaacctg gacccctggcc aactcaccca    1440 tcgcaagcgg catcgcccag agcgggccgg cgctcgtgca gtccaacgcg gactcaacct    1500
ctacgaccgg cagcagggcg cctcgcgggg caacatctac accgtcgcgg tccgcgagga    1560
cggcaagctg cagctcttct ggcgcccgg cgcggacgcg gccgggtggt cggccgggga    1620
ggtgttcggc ggctccggcg tcgtggaccc cggctcgccg cccgtcatga ttcaggacta    1680
ctcggggacg gccaacgaga cgagcgtcgg ccggttccag ctggccgtcg ccgtcggggg    1740
gagcgtccaa cactgggagc gggccaacga cgacctcgag gccgggcagg cccgcccgc    1800
```

```
gggggcagaa gggggggtccc ggcgggcagg tgggaactgg tcgagacggc gggcaccggg    1860
gtgaagcgcg tctgggcgct gctccagggg agctttggtg ggaggctgca catgatcacg    1920
gagggcacgg acgccggct gtcgtactgg gagcgcgatg agaagtgggt tgaggtcgag     1980
aagctgccgg cgttgagcga cgccgcttgg acgagatcgg gcccggtgag tggtggttga    2040
```

<210> SEQ ID NO 9
<211> LENGTH: 680
<212> TYPE: PRT
<213> ORGANISM: Myceliophthora thermophila

<400> SEQUENCE: 9

```
Met Cys Trp Leu Trp Glu Arg Ser Val Ala Ile Leu Leu Ala Ala Gly
1               5                   10                  15

Val Ile Ala Asn Pro Leu Arg Pro Arg Arg Ile Pro Trp Pro Glu Pro
            20                  25                  30

Val Pro Ala Ser Ser Ile Gly Pro Ile Asp Trp Ser Ser Ile Pro Pro
        35                  40                  45

Ser Pro Tyr Lys His Ala Leu Arg Gln Thr Asn Thr Thr Thr Thr Ser
    50                  55                  60

Ser Ser Ser Ser Ser Ser Ser Lys Tyr Asp Asn Gln Val Tyr Ser
65                  70                  75                  80

Val Gln Val Ser Gly Ser Ser Ser Pro Pro Ala Ser Val Asp Trp
                85                  90                  95

Arg Asn Arg Asp Gly Gln Asn Tyr Ile Thr Thr Pro Gln Asp Gln Gly
            100                 105                 110

Ala Cys Asn Ser Cys Trp Ala Phe Ala Val Ala Ala Leu Ile Glu Ser
        115                 120                 125

Met Met Arg Ile Glu His Gly Val Trp Gly Lys Arg Ser Glu Ala Asp
    130                 135                 140

Val His Asp Gly Val Gly Ala Ala Cys Glu Ser Val Gly Asn Ala Glu
145                 150                 155                 160

Asp Thr Leu Ala Trp Val Ala Gly Gln Gly Pro Glu Phe Val Ala Asp
                165                 170                 175

Pro Thr Arg Pro Ala Pro Gly Ile Ala Asp Trp Ala Cys Asp Pro Tyr
            180                 185                 190

Glu Ala Thr Ala His Ala Tyr Glu His Cys Asp Asp Arg Ser Gly Arg
        195                 200                 205

Thr Thr His Ile Pro Tyr Tyr Gln Ala Leu Gly Leu Val Glu Asp Gln
    210                 215                 220

Lys Arg Trp Leu Asp Glu Tyr Gly Pro Ile Ile Ala Thr Phe Val Leu
225                 230                 235                 240

Tyr Asp Asp Phe Gly Ser Trp Lys Pro Thr Ala Ala Gly Gly Ser Gly
                245                 250                 255

Gly Asp Val Tyr Arg Trp Asp Gly Val Ser Gly Ser Asp Gly Asn His
            260                 265                 270

Leu Ala Ile Val Ile Gly Tyr Asp Asp Glu Lys Gln Ala Trp Leu Met
        275                 280                 285

Lys Asn Ser Trp Gly Ser Gly Trp Gly Asp Glu Gly Phe Val Tyr Phe
    290                 295                 300

Ala Tyr Gly Glu Ala Asn Ile Asp Asn Trp Thr Lys Tyr Gly Leu Val
305                 310                 315                 320

Asn Val Asn Pro Asp Pro Trp Thr Arg Arg Lys His Gln Ser Gly Ser
                325                 330                 335
```

Met Met Gln Ser Gly Asn Gly Glu Thr His Arg Asn Phe Glu Leu Leu
              340                 345                 350

Val Ser Glu Ala Gly Gly Ser Gly Phe Thr His Val Ser Arg Asp Gly
          355                 360                 365

Asn Ser Thr Gln Trp Ser Lys Val Leu Glu Val Ser Gly Ser Gly Ser
      370                 375                 380

Gly Ser Gly Leu Val Gly Gln Pro Ala Ile Leu Gly Thr Ser Phe Asn
385                 390                 395                 400

Arg Asp Phe His Ala Val Ser Leu Asp Glu Asn Gln Val Val Gln Gln
                  405                 410                 415

Trp Ala Tyr Arg Gln Ser Glu Met Arg Trp Ser Arg Val Ser Ala Ile
              420                 425                 430

Glu Gly Thr Lys Ile Asp Gly Phe Pro Gly Leu Ala Gln Ser Asp Gly
          435                 440                 445

Ser Thr Leu Val Met Val Val Lys His Ala Asp Gly Thr Leu Asn Glu
      450                 455                 460

Trp Gln Gln Ala Pro Asn Ser Thr Thr Trp Thr Leu Ala Asn Ser Pro
465                 470                 475                 480

Ile Ala Ser Gly Ile Ala Gln Ser Gly Pro Ala Leu Val Gln Ser Asn
                  485                 490                 495

Ala Gly Leu Asn Leu Tyr Asp Arg Gln Gln Gly Ala Ser Arg Gly Asn
              500                 505                 510

Ile Tyr Thr Val Ala Val Arg Glu Asp Gly Lys Leu Gln Leu Phe Trp
          515                 520                 525

Arg Pro Gly Ala Asp Ala Ala Gly Trp Ser Ala Gly Glu Val Phe Gly
      530                 535                 540

Gly Ser Gly Val Val Asp Pro Gly Ser Pro Val Met Ile Gln Asp
545                 550                 555                 560

Tyr Ser Gly Thr Ala Asn Glu Thr Ser Val Gly Arg Phe Gln Leu Ala
                  565                 570                 575

Val Ala Val Gly Gly Ser Val Gln His Trp Glu Arg Ala Asn Asp Asp
              580                 585                 590

Leu Glu Ala Gly Gln Ala Pro Pro Ala Gly Ala Glu Gly Gly Ser Pro
          595                 600                 605

Ala Gly Arg Trp Glu Leu Val Glu Thr Ala Gly Thr Gly Val Lys Arg
      610                 615                 620

Val Trp Ala Leu Leu Gln Gly Ser Phe Gly Gly Arg Leu His Met Ile
625                 630                 635                 640

Thr Glu Gly Thr Asp Gly Arg Leu Ser Tyr Trp Glu Arg Asp Glu Lys
                  645                 650                 655

Trp Val Glu Val Glu Lys Leu Pro Ala Leu Ser Asp Ala Ala Trp Thr
              660                 665                 670

Arg Ser Gly Pro Val Ser Gly Gly
          675                 680

<210> SEQ ID NO 10
<211> LENGTH: 2476
<212> TYPE: DNA
<213> ORGANISM: Myceliophthora thermophila

<400> SEQUENCE: 10
atgtgttggc tgtgggagcg atcagtggca atattactgg cggccggcgt gatcgccaac      60
ccgctccgcc cgcgccggat ccctggccg gagccggttc cggcatcttc catcgggccc      120
attgactggt cttcaatacc gccttctccc tacaaacacg ccttgcggca gaccaacacc      180

```
accacgacca gcagcagtag cagcagcagc agcagcaaat atgacaatca agtctactcg    240
gtacaggtct cgggatcttc ctcctccccg ccagcatccg tcgactggcg caaccgcgac    300
ggccagaact acatcacgac accgcaggac cagggcgcct gtaacagctg ctgggcgttc    360
gccgtggcgg cgctgatcga gtccatgatg cgcatcgagc acggggtctg gggcaagcgc    420
agcgaggccg acgtgcacga cggggtgggc gcggcgtgcg agagcgtggg caacgccgag    480
gacacgctgg cctgggtggc cgggcagggg cccgaattcg tcgccgaccc gacccggccc    540
gccccgggca tcgccgactg ggcctgcgac ccctacgagg cgacggcgca cgcctacgag    600
cactgcgaca accgctccgg gcgcacgacg cacattccct actaccaggc cctcggcctg    660
gtcgaggacc agaagcggtg gctggacgag tacgggccca tcatcgccac ctttgtcctc    720
tacgacgact ttggctcgtg gaagccgacc gcggccggcg gaagcggcgg tgacgtgtac    780
cggtgggacg gcgtttccgg ctcggacggc aaccacctcg ccatcgtgat cggctacgac    840
gacgagaagc aggcctggct tatgaagaac tcatggggat ccggatgggg ggacgaggga    900
tttgtctact ttgcgtaagt caggggttcc actgcttttt ttttttttcc ctccaaaatc    960
gtttgcctct cggtaatttt atccgcatcc agggaactga caacagatac aggtacggcg   1020
aggccaacat cgacaactgg accaagtatg ggctcgtcaa tgtcaacccg gacccgtgga   1080
cacgcaggaa gcaccagagc ggaagcatga tgcaatccgg caacggcgag acgcaccgaa   1140
actttgagct gctcgtcagc gaggccgggg gttccggctt cacgcacgtc tcccgcgatg   1200
ggaacagtac ccaatggagc aaggtgctgg aggtctcggg cagcggcagc ggcagcggcc   1260
tcgtgggcca gcctgccatt ctcggcacct ccttcaaccg ggacttccac gcggtgagcc   1320
tggatgagaa ccaggtggtc caacagtggg catacagaca gtcggagatg cgctggtccc   1380
gggtctcggc catcgagggc actaagatcg acggctttcc cggtctcgcc cagagcgacg   1440
gctcaactct ggtcatggtg gtcaagcacg ccgacggcac cctgaacgag gtaagcatat   1500
cttgccggaa gtcataatta acgaaggaag atcttccgta aaagaaaagg aaaagatgaa   1560
aaaaaaaagg tacacgtgct aacggcggat cgcacaagtg gcaacaagca cccaacagca   1620
caacctggac cctggccaac tcacccatcg caagcggcat cgcccagagc gggccggcgc   1680
tcgtgcagtc caacgccgga ctcaacctct acgaccggca gcagggcgcc tcgcggggca   1740
acatctacac cgtcgcggtc cgcgaggacg gcaagctgca gctcttctgg cgccccggcg   1800
cggacgcggc cgggtggtcg gccggggagg tgttcggcgg ctccggcgtc gtggaccccg   1860
gctcgccgcc cgtcatgatt caggactact cggggacggc caacgagacg agcgtcggcc   1920
ggttccagct ggccgtcgcc gtcgggggga gcgtccaaca ctgggagcgg gccaacgacg   1980
acctcgaggc cgggcaggcc ccgccgcgcg gggcagaagg ggggtccccg gcgggcaggt   2040
gggaactggt cgagacggcg ggcaccgggg tgaagcgcgt ctgggcgctg ctccagggga   2100
gctttggtgg gaggctgcac atgatcacgg agggcacgga cggccggctg tcgtactggg   2160
agcgcgatga gaagtgggtt gaggtcgaga agctgccggc gttgagcgac gccgcttgga   2220
cgagatcggg cccggtgagt ggtggttgag ggtagtccca agtacctgat tataattata   2280
tgaaagagat gtcccccgaa taattatatg agtgaaccaa cgaccatgaa gacatgcggc   2340
tttatcagca taccgacgcg acttgtcctg gttgcatctg ctacgacccc tgattaatta   2400
caacaccgca cagcggcaga gacggggcca gaagctgcac atagaaagaa ggctggacaa   2460
cttccccgag acgcta                                                   2476
```

<210> SEQ ID NO 11
<211> LENGTH: 2042
<212> TYPE: DNA
<213> ORGANISM: Myceliophthora thermophila

<400> SEQUENCE: 11

| | | | | | |
|---|---|---|---|---|---|
| atgtgttggc | tgtgggagcg | atcagtggca | atattactgg | cggccggcgt | gatcgccaac | 60 |
| ccgctccgcc | cgcgccggat | cccctggccg | gagccggttc | cggcatcttc | catcgggccc | 120 |
| attgactggt | cttcaatacc | gccttctccc | tacaaacacg | ccttgcggca | gaccaacacc | 180 |
| accacgacca | gcagcagtag | cagcagcagc | agcagcaaat | atgacaatca | agtctactcg | 240 |
| gtacaggtct | cgggatcttc | ctcctccccg | ccagcatccg | tcgactggcg | caaccgcgac | 300 |
| ggccagaact | acatcacgac | accgcaggac | cagggcgcct | gtaacagctg | ctgggcgttc | 360 |
| gccgtggcgg | cgctgatcga | gtccatgatg | cgcatcgagc | acggggtctg | gggcaagcgc | 420 |
| agcgaggccg | acgtgcacga | cggggtgggc | gcggcgtgcg | agagcgtggg | caacgccgag | 480 |
| gacacgctgg | cctgggtggc | cgggcagggg | cccgaattcg | tcgccgaccc | gacccggccc | 540 |
| gccccgggca | tcgccgactg | ggcctgcgac | ccctacgagg | cgacggcgca | cgcctacgag | 600 |
| cactgcgacg | accgctccgg | gcgcacgacg | cacattccct | actaccaggc | cctcggcctg | 660 |
| gtcgaggacc | agaagcggtg | gctggacgag | tacgggccca | tcatcgccac | ctttgtcctc | 720 |
| tacgacgact | ttggctcgtg | gaagccgacc | gcggccggcg | gaagcggcgg | tgacgtgtac | 780 |
| cggtgggacg | gcgtttccgg | ctcggacggc | aaccacctcg | ccatcgtgat | cggctacgac | 840 |
| gacgagaagc | aggcctggct | tatgaagaac | tcatggggat | ccggatgggg | ggacgaggga | 900 |
| tttgtctact | ttgcgtacgg | cgaggccaac | atcgacaact | ggaccaagta | tgggctcgtc | 960 |
| aatgtcaacc | cggacccgtg | gacacgcagg | aagcaccaga | gcggaagcat | gatgcaatcc | 1020 |
| ggcaacggcg | agacgcaccg | aaactttgag | ctgctcgtca | gcgaggccgg | gggttccggc | 1080 |
| ttcacgcacg | tctcccgcga | tgggaacagt | acccaatgga | gcaaggtgct | ggaggtctcg | 1140 |
| ggcagcggca | gcggcagcgg | cctcgtgggc | cagcctgcca | ttctcggcac | ctccttcaac | 1200 |
| cgggacttcc | acgcggtgag | cctggatgag | aaccaggtgg | tccaacagtg | gcatacagda | 1260 |
| cagtcggaga | tgcgctggtc | ccgggtctcg | gccatcgagg | gcactaagat | cgacggcttt | 1320 |
| cccggtctcg | cccagagcga | cggctcaact | ctggtcatgg | tggtcaagca | cgccgacggc | 1380 |
| accctgaacg | agtggcaaca | agcacccaac | agcacaacct | ggaccctggc | caactcaccc | 1440 |
| atcgcaagcg | gcatcgccca | gagcgggccg | gcgctcgtgc | agtccaacgc | cggactcaac | 1500 |
| ctctacgacc | ggcagcaggg | cgcctcgcgg | ggcaacatct | acaccgtcgc | ggtccgcgag | 1560 |
| gacggcaagc | tgcagctctt | ctggcgcccc | ggcgcggacg | cggccgggtg | gtcggccggg | 1620 |
| gaggtgttcg | gcggctccgg | cgtcgtggac | cccggctcgc | cgcccgtcat | gattcaggac | 1680 |
| tactcgggga | cggccaacga | gacgagcgtc | ggccggttcc | agctggccgt | cgccgtcggg | 1740 |
| gggagcgtcc | aacactggga | gcgggccaac | gacgcctcga | ggccgggcag | gccccgcccg | 1800 |
| cgggggcaga | aggggggtcc | ccggcgggca | ggtgggaact | ggtcgagacg | gcgggcaccg | 1860 |
| gggtgaagcg | cgtctgggcg | ctgctccagg | ggagctttgg | tgggaggctg | cacatgatca | 1920 |
| cggagggcac | ggacggccgg | ctgtcgtact | gggagcgcga | tgagaagtgg | gttgaggtcg | 1980 |
| agaagctgcc | ggcgttgagc | gacgccgctt | ggacgagatc | gggcccggtg | agtggtggtt | 2040 |
| ga | | | | | | 2042 |

```
<210> SEQ ID NO 12
<211> LENGTH: 697
<212> TYPE: PRT
<213> ORGANISM: Myceliophthora thermophila

<400> SEQUENCE: 12

Met Cys Trp Leu Trp Glu Arg Ser Val Ala Ile Leu Leu Ala Ala Gly
1               5                   10                  15

Val Ile Ala Asn Pro Leu Arg Pro Arg Arg Ile Pro Trp Pro Glu Pro
            20                  25                  30

Val Pro Ala Ser Ser Ile Gly Pro Ile Asp Trp Ser Ser Ile Pro Pro
        35                  40                  45

Ser Pro Tyr Lys His Ala Leu Arg Gln Thr Asn Thr Thr Thr Thr Ser
    50                  55                  60

Ser Ser Ser Ser Ser Ser Ser Lys Tyr Asp Asn Gln Val Tyr Ser
65                  70                  75                  80

Val Gln Val Ser Gly Ser Ser Ser Pro Pro Ala Ser Val Asp Trp
            85                  90                  95

Arg Asn Arg Asp Gly Gln Asn Tyr Ile Thr Thr Pro Gln Asp Gln Gly
            100                 105                 110

Ala Cys Asn Ser Cys Trp Ala Phe Ala Val Ala Ala Leu Ile Glu Ser
        115                 120                 125

Met Met Arg Ile Glu His Gly Val Trp Gly Lys Arg Ser Glu Ala Asp
130                 135                 140

Val His Asp Gly Val Gly Ala Ala Cys Glu Ser Val Gly Asn Ala Glu
145                 150                 155                 160

Asp Thr Leu Ala Trp Val Ala Gly Gln Gly Pro Glu Phe Val Ala Asp
            165                 170                 175

Pro Thr Arg Pro Ala Pro Gly Ile Ala Asp Trp Ala Cys Asp Pro Tyr
        180                 185                 190

Glu Ala Thr Ala His Ala Tyr Glu His Cys Asp Asp Arg Ser Gly Arg
    195                 200                 205

Thr Thr His Ile Pro Tyr Tyr Gln Ala Leu Gly Leu Val Glu Asp Gln
210                 215                 220

Lys Arg Trp Leu Asp Glu Tyr Gly Pro Ile Ile Ala Thr Phe Val Leu
225                 230                 235                 240

Tyr Asp Asp Phe Gly Ser Trp Lys Pro Thr Ala Ala Gly Gly Ser Gly
            245                 250                 255

Gly Asp Val Tyr Arg Trp Asp Gly Val Ser Gly Ser Asp Gly Asn His
        260                 265                 270

Leu Ala Ile Val Ile Gly Tyr Asp Asp Glu Lys Gln Ala Trp Leu Met
    275                 280                 285

Lys Asn Ser Trp Gly Ser Gly Trp Gly Asp Gly Phe Val Tyr Phe
290                 295                 300

Ala Tyr Gly Glu Ala Asn Ile Asp Asn Trp Thr Lys Tyr Gly Leu Val
305                 310                 315                 320

Asn Val Asn Pro Asp Pro Trp Thr Arg Arg Lys His Gln Ser Gly Ser
            325                 330                 335

Met Met Gln Ser Gly Asn Gly Glu Thr His Arg Asn Phe Glu Leu Leu
        340                 345                 350

Val Ser Glu Ala Gly Gly Ser Gly Phe Thr His Val Ser Arg Asp Gly
    355                 360                 365

Asn Ser Thr Gln Trp Ser Lys Val Leu Glu Val Ser Gly Ser Gly Ser
370                 375                 380
```

```
Gly Ser Gly Leu Val Gly Gln Pro Ala Ile Leu Gly Thr Ser Phe Asn
385                 390                 395                 400

Arg Asp Phe His Ala Val Ser Leu Asp Glu Asn Gln Val Val Gln Gln
            405                 410                 415

Trp Ala Tyr Arg Gln Ser Glu Met Arg Trp Ser Arg Val Ser Ala Ile
        420                 425                 430

Glu Gly Thr Lys Ile Asp Gly Phe Pro Gly Leu Ala Gln Ser Asp Gly
    435                 440                 445

Ser Thr Leu Val Met Val Val Lys His Ala Asp Gly Thr Leu Asn Glu
450                 455                 460

Trp Gln Gln Ala Pro Asn Ser Thr Thr Trp Thr Leu Ala Asn Ser Pro
465                 470                 475                 480

Ile Ala Ser Gly Ile Ala Gln Ser Gly Pro Ala Leu Val Gln Ser Asn
            485                 490                 495

Ala Gly Leu Asn Leu Tyr Asp Arg Gln Gln Gly Ala Ser Arg Gly Asn
        500                 505                 510

Ile Tyr Thr Val Ala Val Arg Glu Asp Gly Lys Leu Gln Leu Phe Trp
    515                 520                 525

Arg Pro Gly Ala Asp Ala Ala Gly Trp Ser Ala Gly Glu Val Phe Gly
530                 535                 540

Gly Ser Gly Val Val Asp Pro Gly Ser Pro Val Met Ile Gln Asp
545                 550                 555                 560

Tyr Ser Gly Thr Ala Asn Glu Thr Ser Val Gly Arg Phe Gln Leu Ala
            565                 570                 575

Val Ala Val Gly Gly Ser Val Gln His Trp Glu Arg Ala Asn Asp Asp
        580                 585                 590

Leu Glu Ala Gly Gln Ala Pro Pro Ala Gly Ala Glu Gly Gly Ser Pro
    595                 600                 605

Ala Gly Arg Trp Glu Leu Val Glu Thr Ala Gly Thr Gly Val Lys Arg
610                 615                 620

Val Trp Ala Leu Leu Gln Gly Ser Phe Gly Gly Arg Leu His Met Ile
625                 630                 635                 640

Thr Glu Gly Thr Asp Gly Arg Leu Ser Tyr Trp Glu Arg Asp Glu Lys
            645                 650                 655

Trp Val Glu Val Glu Lys Leu Pro Ala Leu Ser Asp Ala Ala Trp Thr
        660                 665                 670

Arg Ser Gly Pro Arg Gln Arg Gly Gln Lys Leu His Ile Glu Arg
    675                 680                 685

Arg Leu Asp Asn Phe Pro Glu Thr Leu
690                 695

<210> SEQ ID NO 13
<211> LENGTH: 1029
<212> TYPE: DNA
<213> ORGANISM: Myceliophthora thermophila

<400> SEQUENCE: 13
atgtccaagg cctctgctct cctcgctggc ctgacgggcg cggccctcgt cgctgcacat    60
ggccacgtca gccacatcgt cgtcaacggc gtctactaca ggaactacga ccccacgaca   120
gactggtacc agcccaaccc gccaacagtc atcggctgga cggcagccga tcaggataat   180
ggcttcgttg aacccaacag ctttggcacg ccagatatca tctgccacaa gagcgccacc   240
cccggcggcg ccacgctac cgttgctgcc ggagacaaga tcaacatcgt ctggaccccc   300
gagtggcccg aatcccacat cggccccgtc attgactacc tagccgcctg caacggtgac   360
```

```
tgcgagaccg tcgacaagtc gtcgctgcgc tggttcaaga ttgacggcgc cggctacgac    420
aaggccgccg gccgctgggc cgccgacgct ctgcgcgcca acggcaacag ctggctcgtc    480
cagatcccgt cggatctcaa ggccggcaac tacgtcctcc gccacgagat catcgccctc    540
cacggtgctc agagccccaa cggcgcccag gcctacccgc agtgcatcaa cctccgcgtc    600
accggcggcg gcagcaacct gcccagcggc gtcgccggca cctcgctgta caaggcgacc    660
gacccgggca tcctcttcaa cccctacgtc tcctccccgg attacaccgt ccccggcccg    720
gccctcattg ccggcgccgc cagctcgatc gcccagagca cgtcggtcgc cactgccacc    780
ggcacggcca ccgttcccgg cggcggcggc gccaacccta ccgccaccac caccgccgcc    840
acctccgccg ccccgagcac caccctgagg acgaccacta cctcggccgc gcagactacc    900
gccccgccct ccggcgatgt gcagaccaag tacggccagt gtggtggcaa cggatggacg    960
ggcccgacgg tgtgcgcccc cggctcgagc tgctccgtcc tcaacgagtg gtactcccag   1020
tgtttgtaa                                                            1029
```

<210> SEQ ID NO 14
<211> LENGTH: 342
<212> TYPE: PRT
<213> ORGANISM: Myceliophthora thermophila

<400> SEQUENCE: 14

```
Met Ser Lys Ala Ser Ala Leu Leu Ala Gly Leu Thr Gly Ala Ala Leu
1               5                   10                  15

Val Ala His Gly His Val Ser His Ile Val Val Asn Gly Val Tyr
            20                  25                  30

Tyr Arg Asn Tyr Asp Pro Thr Thr Asp Trp Tyr Gln Pro Asn Pro Pro
        35                  40                  45

Thr Val Ile Gly Trp Thr Ala Ala Asp Gln Asp Asn Gly Phe Val Glu
    50                  55                  60

Pro Asn Ser Phe Gly Thr Pro Asp Ile Ile Cys His Lys Ser Ala Thr
65                  70                  75                  80

Pro Gly Gly Gly His Ala Thr Val Ala Ala Gly Asp Lys Ile Asn Ile
                85                  90                  95

Val Trp Thr Pro Glu Trp Pro Glu Ser His Ile Gly Pro Val Ile Asp
            100                 105                 110

Tyr Leu Ala Ala Cys Asn Gly Asp Cys Glu Thr Val Asp Lys Ser Ser
        115                 120                 125

Leu Arg Trp Phe Lys Ile Asp Gly Ala Gly Tyr Asp Lys Ala Ala Gly
    130                 135                 140

Arg Trp Ala Ala Asp Ala Leu Arg Ala Asn Gly Asn Ser Trp Leu Val
145                 150                 155                 160

Gln Ile Pro Ser Asp Leu Lys Ala Gly Asn Tyr Val Leu Arg His Glu
                165                 170                 175

Ile Ile Ala Leu His Gly Ala Gln Ser Pro Asn Gly Ala Gln Ala Tyr
            180                 185                 190

Pro Gln Cys Ile Asn Leu Arg Val Thr Gly Gly Gly Ser Asn Leu Pro
        195                 200                 205

Ser Gly Val Ala Gly Thr Ser Leu Tyr Lys Ala Thr Asp Pro Gly Ile
    210                 215                 220

Leu Phe Asn Pro Tyr Val Ser Ser Pro Asp Tyr Thr Val Pro Gly Pro
225                 230                 235                 240

Ala Leu Ile Ala Gly Ala Ala Ser Ser Ile Ala Gln Ser Thr Ser Val
```

```
            245                 250                 255
Ala Thr Ala Thr Gly Thr Ala Thr Val Pro Gly Gly Gly Ala Asn
            260                 265                 270

Pro Thr Ala Thr Thr Thr Ala Ala Thr Ser Ala Ala Pro Ser Thr Thr
            275                 280                 285

Leu Arg Thr Thr Thr Thr Ser Ala Ala Gln Thr Thr Ala Pro Pro Ser
            290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
                325                 330                 335

Trp Tyr Ser Gln Cys Leu
                340

<210> SEQ ID NO 15
<211> LENGTH: 323
<212> TYPE: PRT
<213> ORGANISM: Myceliophthora thermophila

<400> SEQUENCE: 15

His Gly His Val Ser His Ile Val Val Asn Gly Val Tyr Tyr Arg Asn
1               5                   10                  15

Tyr Asp Pro Thr Thr Asp Trp Tyr Gln Pro Asn Pro Thr Val Ile
            20                  25                  30

Gly Trp Thr Ala Ala Asp Gln Asp Asn Gly Phe Val Glu Pro Asn Ser
            35                  40                  45

Phe Gly Thr Pro Asp Ile Ile Cys His Lys Ser Ala Thr Pro Gly Gly
    50                  55                  60

Gly His Ala Thr Val Ala Ala Gly Asp Lys Ile Asn Ile Val Trp Thr
65                  70                  75                  80

Pro Glu Trp Pro Glu Ser His Ile Gly Pro Val Ile Asp Tyr Leu Ala
                85                  90                  95

Ala Cys Asn Gly Asp Cys Glu Thr Val Asp Lys Ser Ser Leu Arg Trp
            100                 105                 110

Phe Lys Ile Asp Gly Ala Gly Tyr Asp Lys Ala Ala Gly Arg Trp Ala
            115                 120                 125

Ala Asp Ala Leu Arg Ala Asn Gly Asn Ser Trp Leu Val Gln Ile Pro
    130                 135                 140

Ser Asp Leu Lys Ala Gly Asn Tyr Val Leu Arg His Glu Ile Ile Ala
145                 150                 155                 160

Leu His Gly Ala Gln Ser Pro Asn Gly Ala Gln Ala Tyr Pro Gln Cys
                165                 170                 175

Ile Asn Leu Arg Val Thr Gly Gly Gly Ser Asn Leu Pro Ser Gly Val
            180                 185                 190

Ala Gly Thr Ser Leu Tyr Lys Ala Thr Asp Pro Gly Ile Leu Phe Asn
            195                 200                 205

Pro Tyr Val Ser Ser Pro Asp Tyr Thr Val Pro Gly Pro Ala Leu Ile
    210                 215                 220

Ala Gly Ala Ala Ser Ser Ile Ala Gln Ser Thr Ser Val Ala Thr Ala
225                 230                 235                 240

Thr Gly Thr Ala Thr Val Pro Gly Gly Gly Ala Asn Pro Thr Ala
                245                 250                 255

Thr Thr Thr Ala Ala Thr Ser Ala Ala Pro Ser Thr Thr Leu Arg Thr
            260                 265                 270
```

Thr Thr Thr Ser Ala Ala Gln Thr Thr Ala Pro Pro Ser Gly Asp Val
            275                 280                 285

Gln Thr Lys Tyr Gly Cys Gly Gly Asn Gly Trp Thr Gly Pro Thr
    290                 295                 300

Val Cys Ala Pro Gly Ser Ser Cys Ser Val Leu Asn Glu Trp Tyr Ser
305                 310                 315                 320

Gln Cys Leu

<210> SEQ ID NO 16
<211> LENGTH: 1029
<212> TYPE: DNA
<213> ORGANISM: Artificial Sequence
<220> FEATURE:
<223> OTHER INFORMATION: Synthetic polynucleotide of M. thermophila
      GH61a "Variant 1"

<400> SEQUENCE: 16

```
atgtccaagg cctctgctct cctcgctggc ctgacgggcg cggccctcgt cgctgcacac      60
ggccacgtca gccacatcgt cgtcaacggc gtctactaca ggggctacga ccccacgaca     120
gactggtacc agcccaaccc gccaacagta tcggctgga cggcagccga tcaggataat     180
ggcttcgttg aacccaacag cttttggcacg ccagatatca tctgccacaa gagcgccacc     240
cccggcggcg ccacgctac cgttgctgcc ggagacaaga tcaacatcgt ctggaccccc     300
gagtggcccc actccacat cggccccgtc attgactacc tagccgcctg caacggtgac     360
tgcgagaccg tcgacaagtc gtcgctgcgc tggttcaaga ttgacggcgc cggctacgac     420
aaggccgccg ccgctgggc cgccgacgct ctgcgcgcca acggcaacag ctggctcgtc     480
cagatcccgt cggatctcaa gcccggcaac tacgtcctcc gccacgagat catcgccctc     540
cacggtgctc agagccccaa cggcgcccag gcgtacccgc agtgcatcaa cctccgcgtc     600
accggcggcg gcagcaacct gccagcggc gtcgccggca cctgctgta caaggcgacc     660
gacccgggca tcctcttcaa cccctacgtc tcctccccgg attacaccgt ccccggcccg     720
gccctcattg ccggcgccgc cagctcgatc gcccagagca cgtcggtcgc cactgccacc     780
ggcacggcca ccgttcccgg cggcggcggc gccaaccca ccgccaccac cacgccgcc     840
acctccgccg ccccgagcac caccctgagg acgaccacta cctcggccgc gcagactacc     900
gccccgccct ccggcgatgt gcagaccaag tacggccagt gtggtggcaa cggatggacg     960
ggcccgacgg tgtgcgcccc cggctcgagc tgctccgtcc tcaacgagtg gtactcccag    1020
tgtttgtaa                                                            1029
```

<210> SEQ ID NO 17
<211> LENGTH: 342
<212> TYPE: PRT
<213> ORGANISM: Artificial Sequence
<220> FEATURE:
<223> OTHER INFORMATION: Synthetic polypeptide of M. thermophila GH61a
      "Variant 1"

<400> SEQUENCE: 17

Met Ser Lys Ala Ser Ala Leu Leu Ala Gly Leu Thr Gly Ala Ala Leu
1               5                  10                  15

Val Ala Ala His Gly His Val Ser His Ile Val Val Asn Gly Val Tyr
            20                  25                  30

Tyr Arg Gly Tyr Asp Pro Thr Thr Asp Trp Tyr Gln Pro Asn Pro Pro
        35                  40                  45

Thr Val Ile Gly Trp Thr Ala Ala Asp Gln Asp Asn Gly Phe Val Glu

Pro Asn Ser Phe Gly Thr Pro Asp Ile Ile Cys His Lys Ser Ala Thr
65                  70                  75                  80

Pro Gly Gly Gly His Ala Thr Val Ala Ala Gly Asp Lys Ile Asn Ile
                85                  90                  95

Val Trp Thr Pro Glu Trp Pro His Ser His Ile Gly Pro Val Ile Asp
            100                 105                 110

Tyr Leu Ala Ala Cys Asn Gly Asp Cys Glu Thr Val Asp Lys Ser Ser
            115                 120                 125

Leu Arg Trp Phe Lys Ile Asp Gly Ala Gly Tyr Asp Lys Ala Ala Gly
            130                 135                 140

Arg Trp Ala Ala Asp Ala Leu Arg Ala Asn Gly Asn Ser Trp Leu Val
145                 150                 155                 160

Gln Ile Pro Ser Asp Leu Lys Pro Gly Asn Tyr Val Leu Arg His Glu
            165                 170                 175

Ile Ile Ala Leu His Gly Ala Gln Ser Pro Asn Gly Ala Gln Ala Tyr
            180                 185                 190

Pro Gln Cys Ile Asn Leu Arg Val Thr Gly Gly Gly Ser Asn Leu Pro
            195                 200                 205

Ser Gly Val Ala Gly Thr Ser Leu Tyr Lys Ala Thr Asp Pro Gly Ile
210                 215                 220

Leu Phe Asn Pro Tyr Val Ser Pro Asp Tyr Thr Val Pro Gly Pro Pro
225                 230                 235                 240

Ala Leu Ile Ala Gly Ala Ala Ser Ser Ile Ala Gln Ser Thr Ser Val
            245                 250                 255

Ala Thr Ala Thr Gly Thr Ala Thr Val Pro Gly Gly Gly Gly Ala Asn
            260                 265                 270

Pro Thr Ala Thr Thr Thr Ala Ala Thr Ser Ala Ala Pro Ser Thr Thr
            275                 280                 285

Leu Arg Thr Thr Thr Thr Ser Ala Ala Gln Thr Thr Ala Pro Pro Ser
            290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
            325                 330                 335

Trp Tyr Ser Gln Cys Leu
            340

<210> SEQ ID NO 18
<211> LENGTH: 323
<212> TYPE: PRT
<213> ORGANISM: Artificial Sequence
<220> FEATURE:
<223> OTHER INFORMATION: Synthetic polypeptide of M. thermophila GH61a
      "Variant 1"

<400> SEQUENCE: 18

His Gly His Val Ser His Ile Val Val Asn Gly Val Tyr Tyr Arg Gly
1               5                   10                  15

Tyr Asp Pro Thr Thr Asp Trp Tyr Gln Pro Asn Pro Thr Val Ile
            20                  25                  30

Gly Trp Thr Ala Ala Asp Gln Asp Asn Gly Phe Val Glu Pro Asn Ser
            35                  40                  45

Phe Gly Thr Pro Asp Ile Ile Cys His Lys Ser Ala Thr Pro Gly Gly
            50                  55                  60

Gly His Ala Thr Val Ala Ala Gly Asp Lys Ile Asn Ile Val Trp Thr
65                  70                  75                  80

Pro Glu Trp Pro His Ser His Ile Gly Pro Val Ile Asp Tyr Leu Ala
                85                  90                  95

Ala Cys Asn Gly Asp Cys Glu Thr Val Asp Lys Ser Ser Leu Arg Trp
            100                 105                 110

Phe Lys Ile Asp Gly Ala Gly Tyr Asp Lys Ala Ala Gly Arg Trp Ala
        115                 120                 125

Ala Asp Ala Leu Arg Ala Asn Gly Asn Ser Trp Leu Val Gln Ile Pro
130                 135                 140

Ser Asp Leu Lys Pro Gly Asn Tyr Val Leu Arg His Glu Ile Ile Ala
145                 150                 155                 160

Leu His Gly Ala Gln Ser Pro Asn Gly Ala Gln Ala Tyr Pro Gln Cys
                165                 170                 175

Ile Asn Leu Arg Val Thr Gly Gly Ser Asn Leu Pro Ser Gly Val
            180                 185                 190

Ala Gly Thr Ser Leu Tyr Lys Ala Thr Asp Pro Gly Ile Leu Phe Asn
        195                 200                 205

Pro Tyr Val Ser Ser Pro Asp Tyr Thr Val Pro Gly Pro Ala Leu Ile
210                 215                 220

Ala Gly Ala Ala Ser Ser Ile Ala Gln Ser Thr Ser Val Ala Thr Ala
225                 230                 235                 240

Thr Gly Thr Ala Thr Val Pro Gly Gly Gly Ala Asn Pro Thr Ala
                245                 250                 255

Thr Thr Thr Ala Ala Thr Ser Ala Ala Pro Ser Thr Thr Leu Arg Thr
        260                 265                 270

Thr Thr Thr Ser Ala Ala Gln Thr Thr Ala Pro Pro Ser Gly Asp Val
        275                 280                 285

Gln Thr Lys Tyr Gly Gln Cys Gly Gly Asn Gly Trp Thr Gly Pro Thr
        290                 295                 300

Val Cys Ala Pro Gly Ser Ser Cys Ser Val Leu Asn Glu Trp Tyr Ser
305                 310                 315                 320

Gln Cys Leu

<210> SEQ ID NO 19
<211> LENGTH: 1035
<212> TYPE: DNA
<213> ORGANISM: Artificial Sequence
<220> FEATURE:
<223> OTHER INFORMATION: Synthetic polynucleotide of M. thermophila
      GH61a "Variant 5"

<400> SEQUENCE: 19
acacaaatgt ccaaggcctc tgctctcctc gctggcctga cgggcgcggc cctcgtcgct    60
gcacacggcc acgtcagcca catcgtcgtc aacggcgtct actacaggaa ctacgacccc   120
acgacagact ggtaccagcc caacccgcca acagtcatcg ctggacggc agccgatcag    180 gataatggct tcgttgaacc caacagcttt ggcacgccag atatcatctg ccacaagagc   240 gccaccccg gcggcggcca cgctaccgtt gctgccggag acaagatcaa catcgtatgg   300
acccccgagt ggccccactc ccacatcggc ccgtcattg actacctagc cgcctgcaac   360
ggtgactgcg agaccgtcga caagtcgtcg ctgcgctggt tcaagattga cggcgccggc   420
tacgacaagg ccgccggccg ctgggccgcc gacgctctgc gcgccaacgg caacagctgg   480
ctcgtccaga tcccgtcgga tctcgcggcc ggcaactacg tcctccgcca cgagatcatc   540

```
gccctccacg gtgctcagag ccccaacggc gcccaggcgt acccgcagtg catcaacctc      600
cgcgtcaccg gcggcggcag caacctgccc agcggcgtcg ccggcacctc gctgtacaag      660
gcgaccgacc cgggcatcct cttcaacccc tacgtctcct ccccggatta caccgtcccc      720
ggcccggccc tcattgccgg cgccgccagc tcgatcgccc agagcacgtc ggtcgccact      780
gccaccggca cggccaccgt tccggcggc ggcggcgcca accctaccgc caccaccacc      840
gccgccacct ccgccgcccc gagcaccacc ctgaggacga ccactacctc ggccgcgcag      900
actaccgccc gccctccgg cgatgtgcag accaagtacg ccagtgtgg tggcaacgga       960 tggacgggcc cgacggtgtg cgcccccggc tcgagctgct ccgtcctcaa cgagtggtac     1020
tcccagtgtt tgtaa                                                      1035
```

<210> SEQ ID NO 20
<211> LENGTH: 342
<212> TYPE: PRT
<213> ORGANISM: Artificial Sequence
<220> FEATURE:
<223> OTHER INFORMATION: Synthetic polypeptide of M. thermophila GH61a
      "Variant 5"

<400> SEQUENCE: 20

```
Met Ser Lys Ala Ser Ala Leu Leu Ala Gly Leu Thr Gly Ala Ala Leu
1               5                   10                  15

Val Ala His Gly His Val Ser His Ile Val Val Asn Gly Val Tyr
            20                  25                  30

Tyr Arg Asn Tyr Asp Pro Thr Thr Asp Trp Tyr Gln Pro Asn Pro
        35                  40                  45

Thr Val Ile Gly Trp Thr Ala Ala Asp Gln Asp Asn Gly Phe Val Glu
    50                  55                  60

Pro Asn Ser Phe Gly Thr Pro Asp Ile Ile Cys His Lys Ser Ala Thr
65                  70                  75                  80

Pro Gly Gly Gly His Ala Thr Val Ala Ala Gly Asp Lys Ile Asn Ile
                85                  90                  95

Val Trp Thr Pro Glu Trp Pro His Ser His Ile Gly Pro Val Ile Asp
            100                 105                 110

Tyr Leu Ala Ala Cys Asn Gly Asp Cys Glu Thr Val Asp Lys Ser Ser
        115                 120                 125

Leu Arg Trp Phe Lys Ile Asp Gly Ala Gly Tyr Asp Lys Ala Ala Gly
    130                 135                 140

Arg Trp Ala Ala Asp Ala Leu Arg Ala Asn Gly Asn Ser Trp Leu Val
145                 150                 155                 160

Gln Ile Pro Ser Asp Leu Ala Ala Gly Asn Tyr Val Leu Arg His Glu
                165                 170                 175

Ile Ile Ala Leu His Gly Ala Gln Ser Pro Asn Gly Ala Gln Ala Tyr
            180                 185                 190

Pro Gln Cys Ile Asn Leu Arg Val Thr Gly Gly Gly Ser Asn Leu Pro
        195                 200                 205

Ser Gly Val Ala Gly Thr Ser Leu Tyr Lys Ala Thr Asp Pro Gly Ile
    210                 215                 220

Leu Phe Asn Pro Tyr Val Ser Ser Pro Asp Tyr Thr Val Pro Gly Pro
225                 230                 235                 240

Ala Leu Ile Ala Gly Ala Ala Ser Ser Ile Ala Gln Ser Thr Ser Val
                245                 250                 255

Ala Thr Ala Thr Gly Thr Ala Thr Val Pro Gly Gly Gly Gly Ala Asn
            260                 265                 270
```

Pro Thr Ala Thr Thr Ala Ala Thr Ser Ala Ala Pro Ser Thr Thr
            275                 280                 285

Leu Arg Thr Thr Thr Ser Ala Ala Gln Thr Thr Ala Pro Pro Ser
    290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
                325                 330                 335

Trp Tyr Ser Gln Cys Leu
            340

<210> SEQ ID NO 21
<211> LENGTH: 323
<212> TYPE: PRT
<213> ORGANISM: Artificial Sequence
<220> FEATURE:
<223> OTHER INFORMATION: Synthetic polypeptide of M. thermophila GH61a
      "Variant 5"

<400> SEQUENCE: 21

His Gly His Val Ser His Ile Val Val Asn Gly Val Tyr Tyr Arg Asn
1               5                   10                  15

Tyr Asp Pro Thr Thr Asp Trp Tyr Gln Pro Asn Pro Thr Val Ile
            20                  25                  30

Gly Trp Thr Ala Ala Asp Gln Asp Asn Gly Phe Val Glu Pro Asn Ser
            35                  40                  45

Phe Gly Thr Pro Asp Ile Ile Cys His Lys Ser Ala Thr Pro Gly Gly
    50                  55                  60

Gly His Ala Thr Val Ala Ala Gly Asp Lys Ile Asn Ile Val Trp Thr
65                  70                  75                  80

Pro Glu Trp Pro His Ser His Ile Gly Pro Val Ile Asp Tyr Leu Ala
                85                  90                  95

Ala Cys Asn Gly Asp Cys Glu Thr Val Asp Lys Ser Ser Leu Arg Trp
            100                 105                 110

Phe Lys Ile Asp Gly Ala Gly Tyr Asp Lys Ala Ala Gly Arg Trp Ala
            115                 120                 125

Ala Asp Ala Leu Arg Ala Asn Gly Asn Ser Trp Leu Val Gln Ile Pro
    130                 135                 140

Ser Asp Leu Ala Ala Gly Asn Tyr Val Leu Arg His Glu Ile Ile Ala
145                 150                 155                 160

Leu His Gly Ala Gln Ser Pro Asn Gly Ala Gln Ala Tyr Pro Gln Cys
                165                 170                 175

Ile Asn Leu Arg Val Thr Gly Gly Ser Asn Leu Pro Ser Gly Val
            180                 185                 190

Ala Gly Thr Ser Leu Tyr Lys Ala Thr Asp Pro Gly Ile Leu Phe Asn
    195                 200                 205

Pro Tyr Val Ser Ser Pro Asp Tyr Thr Val Pro Gly Pro Ala Leu Ile
    210                 215                 220

Ala Gly Ala Ala Ser Ser Ile Ala Gln Ser Thr Ser Val Ala Thr Ala
225                 230                 235                 240

Thr Gly Thr Ala Thr Val Pro Gly Gly Gly Ala Asn Pro Thr Ala
                245                 250                 255

Thr Thr Thr Ala Ala Thr Ser Ala Ala Pro Ser Thr Thr Leu Arg Thr
            260                 265                 270

Thr Thr Thr Ser Ala Ala Gln Thr Thr Ala Pro Pro Ser Gly Asp Val 275                 280                 285
Gln Thr Lys Tyr Gly Gln Cys Gly Gly Asn Gly Trp Thr Gly Pro Thr
            290                 295                 300

Val Cys Ala Pro Gly Ser Ser Cys Ser Val Leu Asn Glu Trp Tyr Ser
305                 310                 315                 320

Gln Cys Leu

<210> SEQ ID NO 22
<211> LENGTH: 1035
<212> TYPE: DNA
<213> ORGANISM: Artificial Sequence
<220> FEATURE:
<223> OTHER INFORMATION: Synthetic polynucleotide of M. thermophila
      GH61a "Variant 9"

<400> SEQUENCE: 22

```
acaaacatgt ccaaggcctc tgctctcctc gctggcctga cgggcgcggc cctcgtcgct      60
gcacatggcc acgtcagcca tcgtcgtc aacggcgtct actacaggaa ctacgacccc      120
acgacagact ggtaccagcc caacccgcca acagtcatcg gctggacggc agccgatcag      180
gataatggct tcgttgaacc caacagcttt ggcacgccag atatcatctg ccacaagagc      240
gccaccccg gcggcggcca cgctaccgtt gctgccggag acaagatcaa catccagtgg      300
accccccgagt ggcccgaatc ccacatcggc ccgtcattg actacctagc cgcctgcaac      360
ggtgactgcg agaccgtcga caagtcgtcg ctgcgctggt tcaagattga cggcgccggc      420
tacgacaagg ccgccggccg ctgggccgcc gacgctctgc gcgccaacgg caacagctgg      480
ctcgtccaga tcccgtcgga tctcaaggcc ggcaactacg tcctccgcca cgagatcatc      540
gccctccacg gtgctcagag ccccaacggg gcccagaact accgcagtg catcaacctc      600
cgcgtcaccg gcggcggcag caacctgccc agcggcgtcg ccggcacctc gctgtacaag      660
gcgaccgacc cgggcatcct cttcaacccc tacgtctcct ccccggatta caccgtcccc      720
ggcccggccc tcattgccgg cgccgccagc tcgatcgccc agagcacgtc ggtcgccact      780
gccaccggca cggccaccgt tcccggcggc ggcggcgcca accctaccgc caccaccacc      840
gccgccacct ccgccgcccc gagcaccacc ctgaggacga ccactacctc ggccgcgcag      900
actaccgccc cgccctccgg cgatgtgcag accaagtacg ccagtgtgg tggcaacgga      960
tggacgggcc cgacggtgtg cgcccccggc tcgagctgct ccgtcctcaa cgagtggtac     1020
tcccagtgtt tgtaa                                                      1035
```

<210> SEQ ID NO 23
<211> LENGTH: 342
<212> TYPE: PRT
<213> ORGANISM: Artificial Sequence
<220> FEATURE:
<223> OTHER INFORMATION: Synthetic polypeptide of M. thermophila GH61a
      "Variant 9"

<400> SEQUENCE: 23

Met Ser Lys Ala Ser Ala Leu Leu Ala Gly Leu Thr Gly Ala Ala Leu
1               5                   10                  15

Val Ala Ala His Gly His Val Ser His Ile Val Asn Gly Val Tyr
            20                  25                  30

Tyr Arg Asn Tyr Asp Pro Thr Thr Asp Trp Tyr Gln Pro Asn Pro Pro
        35                  40                  45

Thr Val Ile Gly Trp Thr Ala Ala Asp Gln Asp Asn Gly Phe Val Glu
    50                  55                  60

```
Pro Asn Ser Phe Gly Thr Pro Asp Ile Ile Cys His Lys Ser Ala Thr
 65                  70                  75                  80

Pro Gly Gly Gly His Ala Thr Val Ala Ala Gly Asp Lys Ile Asn Ile
                 85                  90                  95

Gln Trp Thr Pro Glu Trp Pro Glu Ser His Ile Gly Pro Val Ile Asp
            100                 105                 110

Tyr Leu Ala Ala Cys Asn Gly Asp Cys Glu Thr Val Asp Lys Ser Ser
            115                 120                 125

Leu Arg Trp Phe Lys Ile Asp Gly Ala Gly Tyr Asp Lys Ala Ala Gly
130                 135                 140

Arg Trp Ala Ala Asp Ala Leu Arg Ala Asn Gly Asn Ser Trp Leu Val
145                 150                 155                 160

Gln Ile Pro Ser Asp Leu Lys Ala Gly Asn Tyr Val Leu Arg His Glu
                165                 170                 175

Ile Ile Ala Leu His Gly Ala Gln Ser Pro Asn Gly Ala Gln Asn Tyr
            180                 185                 190

Pro Gln Cys Ile Asn Leu Arg Val Thr Gly Gly Ser Asn Leu Pro
        195                 200                 205

Ser Gly Val Ala Gly Thr Ser Leu Tyr Lys Ala Thr Asp Pro Gly Ile
210                 215                 220

Leu Phe Asn Pro Tyr Val Ser Ser Pro Asp Tyr Thr Val Pro Gly Pro
225                 230                 235                 240

Ala Leu Ile Ala Gly Ala Ala Ser Ser Ile Ala Gln Ser Thr Ser Val
            245                 250                 255

Ala Thr Ala Thr Gly Thr Ala Thr Val Pro Gly Gly Gly Ala Asn
            260                 265                 270

Pro Thr Ala Thr Thr Ala Ala Thr Ser Ala Ala Pro Ser Thr Thr
        275                 280                 285

Leu Arg Thr Thr Thr Thr Ser Ala Ala Gln Thr Ala Pro Pro Ser
290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
                325                 330                 335

Trp Tyr Ser Gln Cys Leu
            340

<210> SEQ ID NO 24
<211> LENGTH: 323
<212> TYPE: PRT
<213> ORGANISM: Artificial Sequence
<220> FEATURE:
<223> OTHER INFORMATION: Synthetic polypeptide of M. thermophila GH61a
      "Variant 9"

<400> SEQUENCE: 24

His Gly His Val Ser His Ile Val Val Asn Gly Val Tyr Tyr Arg Asn
1               5                   10                  15

Tyr Asp Pro Thr Thr Asp Trp Tyr Gln Pro Asn Pro Thr Val Ile
            20                  25                  30

Gly Trp Thr Ala Ala Asp Gln Asp Asn Gly Phe Val Glu Pro Asn Ser
        35                  40                  45

Phe Gly Thr Pro Asp Ile Ile Cys His Lys Ser Ala Thr Pro Gly Gly
50                  55                  60

Gly His Ala Thr Val Ala Ala Gly Asp Lys Ile Asn Ile Gln Trp Thr
```

65                  70                  75                  80
Pro Glu Trp Pro Glu Ser His Ile Gly Pro Val Ile Asp Tyr Leu Ala
                85                  90                  95

Ala Cys Asn Gly Asp Cys Glu Thr Val Asp Lys Ser Ser Leu Arg Trp
            100                 105                 110

Phe Lys Ile Asp Gly Ala Gly Tyr Asp Lys Ala Ala Gly Arg Trp Ala
            115                 120                 125

Ala Asp Ala Leu Arg Ala Asn Gly Asn Ser Trp Leu Val Gln Ile Pro
130                 135                 140

Ser Asp Leu Lys Ala Gly Asn Tyr Val Leu Arg His Glu Ile Ile Ala
145                 150                 155                 160

Leu His Gly Ala Gln Ser Pro Asn Gly Ala Gln Asn Tyr Pro Gln Cys
            165                 170                 175

Ile Asn Leu Arg Val Thr Gly Gly Gly Ser Asn Leu Pro Ser Gly Val
            180                 185                 190

Ala Gly Thr Ser Leu Tyr Lys Ala Thr Asp Pro Gly Ile Leu Phe Asn
            195                 200                 205

Pro Tyr Val Ser Ser Pro Asp Tyr Thr Val Pro Gly Pro Ala Leu Ile
        210                 215                 220

Ala Gly Ala Ala Ser Ser Ile Ala Gln Ser Thr Ser Val Ala Thr Ala
225                 230                 235                 240

Thr Gly Thr Ala Thr Val Pro Gly Gly Gly Ala Asn Pro Thr Ala
            245                 250                 255

Thr Thr Thr Ala Ala Thr Ser Ala Ala Pro Ser Thr Thr Leu Arg Thr
            260                 265                 270

Thr Thr Thr Ser Ala Ala Gln Thr Thr Ala Pro Pro Ser Gly Asp Val
            275                 280                 285

Gln Thr Lys Tyr Gly Gln Cys Gly Gly Asn Gly Trp Thr Gly Pro Thr
            290                 295                 300

Val Cys Ala Pro Gly Ser Ser Cys Ser Val Leu Asn Glu Trp Tyr Ser
305                 310                 315                 320

Gln Cys Leu

<210> SEQ ID NO 25
<211> LENGTH: 738
<212> TYPE: DNA
<213> ORGANISM: Myceliophthora thermophila

<400> SEQUENCE: 25
atgaagctct ccctcttttc cgtcctggcc actgccctca ccgtcgaggg gcatgccatc      60
ttccagaagg tctccgtcaa cggagcggac cagggctccc tcaccggcct ccgcgctccc     120
aacaacaaca ccccgtgca gaatgtcaac agccaggaca tgatctgcgg ccagtcggga     180
tcgacgtcga acactatcat cgaggtcaag gccggcgata ggatcggtgc ctggtatcag     240
catgtcatcg gcggtgccca gttccccaac gacccagaca cccgattgc caagtcgcac     300 aagggccccg tcatggccta cctcgccaag gttgacaatg ccgcaaccgc cagcaagacg     360
ggcctgaagt ggttcaagat tgggaggat acctttaatc ccagcaccaa gacctggggt     420
gtcgacaacc tcatcaacaa caacggctgg gtgtacttca acctcccgca gtgcatcgcc     480
gacggcaact acctcctccg cgtcgaggtc ctcgctctgc actcggccta ctcccagggc     540
caggctcagt tctaccagtc ctgcgcccag atcaacgtat ccggcggcgg ctccttcacg     600
ccggcgtcga ctgtcagctt cccgggtgcc tacagcgcca gcgaccccgg tatcctgatc     660

-continued

```
aacatctacg gcgccaccgg ccagcccgac aacaacggcc agccgtacac tgcccctggg    720
cccgcgccca tctcctgc                                                  738
```

<210> SEQ ID NO 26
<211> LENGTH: 246
<212> TYPE: PRT
<213> ORGANISM: Myceliophthora thermophila

<400> SEQUENCE: 26

```
Met Lys Leu Ser Leu Phe Ser Val Leu Ala Thr Ala Leu Thr Val Glu
1               5                   10                  15

Gly His Ala Ile Phe Gln Lys Val Ser Val Asn Gly Ala Asp Gln Gly
            20                  25                  30

Ser Leu Thr Gly Leu Arg Ala Pro Asn Asn Asn Pro Val Gln Asn
        35                  40                  45

Val Asn Ser Gln Asp Met Ile Cys Gly Gln Ser Gly Ser Thr Ser Asn
    50                  55                  60

Thr Ile Ile Glu Val Lys Ala Gly Asp Arg Ile Gly Ala Trp Tyr Gln
65                  70                  75                  80

His Val Ile Gly Gly Ala Gln Phe Pro Asn Asp Pro Asp Asn Pro Ile
                85                  90                  95

Ala Lys Ser His Lys Gly Pro Val Met Ala Tyr Leu Ala Lys Val Asp
            100                 105                 110

Asn Ala Ala Thr Ala Ser Lys Thr Gly Leu Lys Trp Phe Lys Ile Trp
        115                 120                 125

Glu Asp Thr Phe Asn Pro Ser Thr Lys Thr Trp Gly Val Asp Asn Leu
    130                 135                 140

Ile Asn Asn Gly Trp Val Tyr Phe Asn Leu Pro Gln Cys Ile Ala
145                 150                 155                 160

Asp Gly Asn Tyr Leu Leu Arg Val Glu Val Leu Ala Leu His Ser Ala
                165                 170                 175

Tyr Ser Gln Gly Gln Ala Gln Phe Tyr Gln Ser Cys Ala Gln Ile Asn
            180                 185                 190

Val Ser Gly Gly Gly Ser Phe Thr Pro Ala Ser Thr Val Ser Phe Pro
        195                 200                 205

Gly Ala Tyr Ser Ala Ser Asp Pro Gly Ile Leu Ile Asn Ile Tyr Gly
    210                 215                 220

Ala Thr Gly Gln Pro Asp Asn Asn Gly Gln Pro Tyr Thr Ala Pro Gly
225                 230                 235                 240

Pro Ala Pro Ile Ser Cys
                245
```

<210> SEQ ID NO 27
<211> LENGTH: 227
<212> TYPE: PRT
<213> ORGANISM: Myceliophthora thermophila

<400> SEQUENCE: 27

```
Ile Phe Gln Lys Val Ser Val Asn Gly Ala Asp Gln Gly Ser Leu Thr
1               5                   10                  15

Gly Leu Arg Ala Pro Asn Asn Asn Pro Val Gln Asn Val Asn Ser
            20                  25                  30

Gln Asp Met Ile Cys Gly Gln Ser Gly Ser Thr Ser Asn Thr Ile Ile
        35                  40                  45

Glu Val Lys Ala Gly Asp Arg Ile Gly Ala Trp Tyr Gln His Val Ile
    50                  55                  60
```

Gly Gly Ala Gln Phe Pro Asn Asp Pro Asp Asn Pro Ile Ala Lys Ser
65                  70                  75                  80

His Lys Gly Pro Val Met Ala Tyr Leu Ala Lys Val Asp Asn Ala Ala
            85                  90                  95

Thr Ala Ser Lys Thr Gly Leu Lys Trp Phe Lys Ile Trp Glu Asp Thr
        100                 105                 110

Phe Asn Pro Ser Thr Lys Thr Trp Gly Val Asp Asn Leu Ile Asn Asn
    115                 120                 125

Asn Gly Trp Val Tyr Phe Asn Leu Pro Gln Cys Ile Ala Asp Gly Asn
130                 135                 140

Tyr Leu Leu Arg Val Glu Val Leu Ala Leu His Ser Ala Tyr Ser Gln
145                 150                 155                 160

Gly Gln Ala Gln Phe Tyr Gln Ser Cys Ala Gln Ile Asn Val Ser Gly
                165                 170                 175

Gly Gly Ser Phe Thr Pro Ala Ser Thr Val Ser Phe Pro Gly Ala Tyr
            180                 185                 190

Ser Ala Ser Asp Pro Gly Ile Leu Ile Asn Ile Tyr Gly Ala Thr Gly
        195                 200                 205

Gln Pro Asp Asn Asn Gly Gln Pro Tyr Thr Ala Pro Gly Pro Ala Pro
    210                 215                 220

Ile Ser Cys
225

<210> SEQ ID NO 28
<211> LENGTH: 762
<212> TYPE: DNA
<213> ORGANISM: Myceliophthora thermophila

<400> SEQUENCE: 28
atggccctcc agctcttggc gagcttggcc ctcctctcag tgccggccct tgcccacggt    60
ggcttggcca actacaccgt cggtgatact tggtacagag gctacgaccc aaacctgccg   120
ccggagacgc agctcaacca gacctggatg atccagcggc aatgggccac catcgacccc   180
gtcttcaccg tgtcggagcc gtacctggcc tgcaacaacc cgggcgcgcc gccgccctcg   240
tacatcccca tccgcgccgg tgacaagatc acggccgtgt actggtactg gctgcacgcc   300
atcgggccca tgagcgtctg gctcgcgcgg tgcggcgaca cgcccgcggc cgactgccgc   360
gacgtcgacg tcaaccgggt cggctggttc aagatctggg agggcggcct gctggagggt   420
cccaacctgg ccgaggggct ctggtaccaa aaggacttcc agcgctggga cggctccccg   480
tccctctggc ccgtcacgat ccccaagggg ctcaagagcg ggacctacat catccggcac   540
gagatcctgt cgcttcacgt cgccctcaag ccccagtttt accggagtg tgcgcatctg   600 aatattactg ggggcggaga cttgctgcca cccgaagaga ctctggtgcg gtttccgggg   660
gtttacaaag aggacgatcc ctctatcttc atcgatgtct actcggagga gaacgcgaac   720
cggacagatt atacggttcc gggagggcca atctgggaag gg                     762

<210> SEQ ID NO 29
<211> LENGTH: 254
<212> TYPE: PRT
<213> ORGANISM: Myceliophthora thermophila

<400> SEQUENCE: 29

Met Ala Leu Gln Leu Leu Ala Ser Leu Ala Leu Leu Ser Val Pro Ala
1               5                   10                  15

```
Leu Ala His Gly Gly Leu Ala Asn Tyr Thr Val Gly Asp Thr Trp Tyr
            20                  25                  30

Arg Gly Tyr Asp Pro Asn Leu Pro Pro Glu Thr Gln Leu Asn Gln Thr
        35                  40                  45

Trp Met Ile Gln Arg Gln Trp Ala Thr Ile Asp Pro Val Phe Thr Val
 50                  55                  60

Ser Glu Pro Tyr Leu Ala Cys Asn Asn Pro Gly Ala Pro Pro Ser
65                  70                  75                  80

Tyr Ile Pro Ile Arg Ala Gly Asp Lys Ile Thr Ala Val Tyr Trp Tyr
                85                  90                  95

Trp Leu His Ala Ile Gly Pro Met Ser Val Trp Leu Ala Arg Cys Gly
            100                 105                 110

Asp Thr Pro Ala Ala Asp Cys Arg Asp Val Asp Val Asn Arg Val Gly
        115                 120                 125

Trp Phe Lys Ile Trp Glu Gly Leu Leu Glu Gly Pro Asn Leu Ala
130                 135                 140

Glu Gly Leu Trp Tyr Gln Lys Asp Phe Gln Arg Trp Asp Gly Ser Pro
145                 150                 155                 160

Ser Leu Trp Pro Val Thr Ile Pro Lys Gly Leu Lys Ser Gly Thr Tyr
                165                 170                 175

Ile Ile Arg His Glu Ile Leu Ser Leu His Val Ala Leu Lys Pro Gln
            180                 185                 190

Phe Tyr Pro Glu Cys Ala His Leu Asn Ile Thr Gly Gly Asp Leu
        195                 200                 205

Leu Pro Pro Glu Glu Thr Leu Val Arg Phe Pro Gly Val Tyr Lys Glu
210                 215                 220

Asp Asp Pro Ser Ile Phe Ile Asp Val Tyr Ser Glu Glu Asn Ala Asn
225                 230                 235                 240

Arg Thr Asp Tyr Thr Val Pro Gly Gly Pro Ile Trp Glu Gly
                245                 250

<210> SEQ ID NO 30
<211> LENGTH: 231
<212> TYPE: PRT
<213> ORGANISM: Myceliophthora thermophila

<400> SEQUENCE: 30

Asn Tyr Thr Val Gly Asp Thr Trp Tyr Arg Gly Tyr Asp Pro Asn Leu
1               5                   10                  15

Pro Pro Glu Thr Gln Leu Asn Gln Thr Trp Met Ile Gln Arg Gln Trp
            20                  25                  30

Ala Thr Ile Asp Pro Val Phe Thr Val Ser Glu Pro Tyr Leu Ala Cys
        35                  40                  45

Asn Asn Pro Gly Ala Pro Pro Ser Tyr Ile Pro Ile Arg Ala Gly
 50                  55                  60

Asp Lys Ile Thr Ala Val Tyr Trp Tyr Trp Leu His Ala Ile Gly Pro
65                  70                  75                  80

Met Ser Val Trp Leu Ala Arg Cys Gly Asp Thr Pro Ala Ala Asp Cys
                85                  90                  95

Arg Asp Val Asp Val Asn Arg Val Gly Trp Phe Lys Ile Trp Glu Gly
            100                 105                 110

Gly Leu Leu Glu Gly Pro Asn Leu Ala Glu Gly Leu Trp Tyr Gln Lys
        115                 120                 125

Asp Phe Gln Arg Trp Asp Gly Ser Pro Ser Leu Trp Pro Val Thr Ile
130                 135                 140
```

Pro Lys Gly Leu Lys Ser Gly Thr Tyr Ile Ile Arg His Glu Ile Leu
145                 150                 155                 160

Ser Leu His Val Ala Leu Lys Pro Gln Phe Tyr Pro Glu Cys Ala His
            165                 170                 175

Leu Asn Ile Thr Gly Gly Gly Asp Leu Leu Pro Pro Glu Thr Leu
        180                 185                 190

Val Arg Phe Pro Gly Val Tyr Lys Glu Asp Pro Ser Ile Phe Ile
        195                 200                 205

Asp Val Tyr Ser Glu Glu Asn Ala Asn Arg Thr Asp Tyr Thr Val Pro
    210                 215                 220

Gly Gly Pro Ile Trp Glu Gly
225                 230

<210> SEQ ID NO 31
<211> LENGTH: 705
<212> TYPE: DNA
<213> ORGANISM: Myceliophthora thermophila

<400> SEQUENCE: 31

```
atgaaggccc tctctctcct tgcggctgcc ggggcagtct ctgcgcatac catcttcgtc     60
cagctcgaag cagacggcac gaggtacccg gtttcgtacg ggatccggga cccaacctac    120
gacggcccca tcaccgacgt cacatccaac gacgttgctt gcaacggcgg tccgaacccg    180
acgacccccct ccagcgacgt catcaccgtc accgcgggca ccaccgtcaa ggccatctgg    240
aggcacaccc tccaatccgg cccggacgat gtcatggacg ccagccacaa gggcccgacc    300
ctggcctaca tcaagaaggt cggcgatgcc accaaggact cgggcgtcgg cggtggctgg    360
ttcaagatcc aggaggacgg ttacaacaac ggccagtggg caccagcac cgttatctcc    420
aacggcggcg agcactacat tgacatcccg gcctgcatcc ccgagggtca gtacctcctc    480
cgcgccgaga tgatcgccct ccacgcggcc gggtcccccg gcggcgctca gctctacatg    540
gaatgtgccc agatcaacat cgtcggcggc tccggctcgg tgcccagctc gacggtcagc    600
ttccccggcg cgtatagccc caacgacccg ggtctcctca tcaacatcta ttccatgtcg    660
ccctcgagct cgtacaccat cccgggcccg cccgttttca gtgc                     705
```

<210> SEQ ID NO 32
<211> LENGTH: 235
<212> TYPE: PRT
<213> ORGANISM: Myceliophthora thermophila

<400> SEQUENCE: 32

Met Lys Ala Leu Ser Leu Leu Ala Ala Ala Gly Ala Val Ser Ala His
1               5                   10                  15

Thr Ile Phe Val Gln Leu Glu Ala Asp Gly Thr Arg Tyr Pro Val Ser
            20                  25                  30

Tyr Gly Ile Arg Asp Pro Thr Tyr Asp Gly Pro Ile Thr Asp Val Thr
        35                  40                  45

Ser Asn Asp Val Ala Cys Asn Gly Gly Pro Asn Pro Thr Thr Pro Ser
    50                  55                  60

Ser Asp Val Ile Thr Val Thr Ala Gly Thr Thr Val Lys Ala Ile Trp
65                  70                  75                  80

Arg His Thr Leu Gln Ser Gly Pro Asp Val Met Asp Ala Ser His
                85                  90                  95

Lys Gly Pro Thr Leu Ala Tyr Ile Lys Lys Val Gly Asp Ala Thr Lys
            100                 105                 110

-continued

```
Asp Ser Gly Val Gly Gly Gly Trp Phe Lys Ile Gln Glu Asp Gly Tyr
        115                 120                 125

Asn Asn Gly Gln Trp Gly Thr Ser Thr Val Ile Ser Asn Gly Gly Glu
    130                 135                 140

His Tyr Ile Asp Ile Pro Ala Cys Ile Pro Glu Gly Gln Tyr Leu Leu
145                 150                 155                 160

Arg Ala Glu Met Ile Ala Leu His Ala Ala Gly Ser Pro Gly Gly Ala
                165                 170                 175

Gln Leu Tyr Met Glu Cys Ala Gln Ile Asn Ile Val Gly Gly Ser Gly
            180                 185                 190

Ser Val Pro Ser Ser Thr Val Ser Phe Pro Gly Ala Tyr Ser Pro Asn
        195                 200                 205

Asp Pro Gly Leu Leu Ile Asn Ile Tyr Ser Met Ser Pro Ser Ser Ser
    210                 215                 220

Tyr Thr Ile Pro Gly Pro Pro Val Phe Lys Cys
225                 230                 235

<210> SEQ ID NO 33
<211> LENGTH: 220
<212> TYPE: PRT
<213> ORGANISM: Myceliophthora thermophila

<400> SEQUENCE: 33

His Thr Ile Phe Val Gln Leu Glu Ala Asp Gly Thr Arg Tyr Pro Val
1               5                   10                  15

Ser Tyr Gly Ile Arg Asp Pro Thr Tyr Asp Gly Pro Ile Thr Asp Val
            20                  25                  30

Thr Ser Asn Asp Val Ala Cys Asn Gly Gly Pro Asn Pro Thr Thr Pro
        35                  40                  45

Ser Ser Asp Val Ile Thr Val Thr Ala Gly Thr Thr Val Lys Ala Ile
    50                  55                  60

Trp Arg His Thr Leu Gln Ser Gly Pro Asp Asp Val Met Asp Ala Ser
65                  70                  75                  80

His Lys Gly Pro Thr Leu Ala Tyr Ile Lys Lys Val Gly Asp Ala Thr
                85                  90                  95

Lys Asp Ser Gly Val Gly Gly Gly Trp Phe Lys Ile Gln Glu Asp Gly
            100                 105                 110

Tyr Asn Asn Gly Gln Trp Gly Thr Ser Thr Val Ile Ser Asn Gly Gly
        115                 120                 125

Glu His Tyr Ile Asp Ile Pro Ala Cys Ile Pro Glu Gly Gln Tyr Leu
    130                 135                 140

Leu Arg Ala Glu Met Ile Ala Leu His Ala Ala Gly Ser Pro Gly Gly
145                 150                 155                 160

Ala Gln Leu Tyr Met Glu Cys Ala Gln Ile Asn Ile Val Gly Gly Ser
                165                 170                 175

Gly Ser Val Pro Ser Ser Thr Val Ser Phe Pro Gly Ala Tyr Ser Pro
            180                 185                 190

Asn Asp Pro Gly Leu Leu Ile Asn Ile Tyr Ser Met Ser Pro Ser Ser
        195                 200                 205

Ser Tyr Thr Ile Pro Gly Pro Pro Val Phe Lys Cys
    210                 215                 220

<210> SEQ ID NO 34
<211> LENGTH: 915
<212> TYPE: DNA
```

<213> ORGANISM: Myceliophthora thermophila

<400> SEQUENCE: 34

```
atgaagtcgt ctaccccggc cttgttcgcc gctgggctcc ttgctcagca tgctgcggcc      60
cactccatct tccagcaggc gagcagcggc tcgaccgact tgatacgct gtgcaccgg       120
atgccgccca acaatagccc cgtcactagt gtgaccagcg gcgacatgac ctgcaaagtc     180
ggcggcacca aggggtgtc cggcttctgc gaggtgaacg ccggcgacga gttcacggtt      240
gagatgcacg cgcagcccgg cgaccgctcg tgcgccaacg aggccatcgg cgggaaccac    300
ttcggcccgg tcctcatcta catgagcaag gtcgacgacg cctccaccgc cgacgggtcc    360
ggcgactggt tcaaggtgga cgagttcggc tacgacgcaa gcaccaagac ctggggcacc    420
gacaagctca cgagaactg cggcaagcgc accttcaaca tccccagcca catccccgcg    480
ggcgactatc tcgtccgggc cgaggctatc gcgctacaca ctgccaacca gccaggcggc   540
gcgcagttct acatgagctg ctatcaagtc aggatttccg gcggcgaagg gggccagctg   600
cctgccggag tcaagatccc gggcgcgtac agtgccaacg accccggcat ccttgtcgac   660
atctggggta acgatttcaa cgaccctcca ggacactcgg cccgtcacgc catcatcatc   720
atcagcagca gcagcaacaa cagcggcgcc aagatgacca gaagatcca ggagcccacc   780
atcacatcgg tcacggacct ccccaccgac gaggccaagt ggatcgcgct ccaaaagatc   840
tcgtacgtgg accagacggg cacggcgcgg acatacgagc cggcgtcgcg caagacgcgg  900
tcgccaagag tctag                                                       915
```

<210> SEQ ID NO 35
<211> LENGTH: 304
<212> TYPE: PRT
<213> ORGANISM: Myceliophthora thermophila

<400> SEQUENCE: 35

```
Met Lys Ser Ser Thr Pro Ala Leu Phe Ala Ala Gly Leu Leu Ala Gln
1               5                   10                  15

His Ala Ala His Ser Ile Phe Gln Gln Ala Ser Ser Gly Ser Thr
            20                  25                  30

Asp Phe Asp Thr Leu Cys Thr Arg Met Pro Pro Asn Asn Ser Pro Val
        35                  40                  45

Thr Ser Val Thr Ser Gly Asp Met Thr Cys Lys Val Gly Gly Thr Lys
    50                  55                  60

Gly Val Ser Gly Phe Cys Glu Val Asn Ala Gly Asp Glu Phe Thr Val
65                  70                  75                  80

Glu Met His Ala Gln Pro Gly Asp Arg Ser Cys Ala Asn Glu Ala Ile
                85                  90                  95

Gly Gly Asn His Phe Gly Pro Val Leu Ile Tyr Met Ser Lys Val Asp
            100                 105                 110

Asp Ala Ser Thr Ala Asp Gly Ser Gly Asp Trp Phe Lys Val Asp Glu
        115                 120                 125

Phe Gly Tyr Asp Ala Ser Thr Lys Thr Trp Gly Thr Asp Lys Leu Asn
    130                 135                 140

Glu Asn Cys Gly Lys Arg Thr Phe Asn Ile Pro Ser His Ile Pro Ala
145                 150                 155                 160

Gly Asp Tyr Leu Val Arg Ala Glu Ala Ile Ala Leu His Thr Ala Asn
                165                 170                 175

Gln Pro Gly Gly Ala Gln Phe Tyr Met Ser Cys Tyr Gln Val Arg Ile
            180                 185                 190
```

```
Ser Gly Gly Glu Gly Gly Gln Leu Pro Ala Gly Val Lys Ile Pro Gly
            195                 200                 205

Ala Tyr Ser Ala Asn Asp Pro Gly Ile Leu Val Asp Ile Trp Gly Asn
        210                 215                 220

Asp Phe Asn Asp Pro Pro Gly His Ser Arg His Ala Ile Ile Ile
225                 230                 235                 240

Ile Ser Ser Ser Asn Asn Ser Gly Ala Lys Met Thr Lys Lys Ile
            245                 250                 255

Gln Glu Pro Thr Ile Thr Ser Val Thr Asp Leu Pro Thr Asp Glu Ala
            260                 265                 270

Lys Trp Ile Ala Leu Gln Lys Ile Ser Tyr Val Asp Gln Thr Gly Thr
            275                 280                 285

Ala Arg Thr Tyr Glu Pro Ala Ser Arg Lys Thr Arg Ser Pro Arg Val
        290                 295                 300

<210> SEQ ID NO 36
<211> LENGTH: 284
<212> TYPE: PRT
<213> ORGANISM: Myceliophthora thermophila

<400> SEQUENCE: 36

His Ser Ile Phe Gln Gln Ala Ser Ser Gly Ser Thr Asp Phe Asp Thr
1               5                   10                  15

Leu Cys Thr Arg Met Pro Asn Asn Ser Pro Val Thr Ser Val Thr
            20                  25                  30

Ser Gly Asp Met Thr Cys Lys Val Gly Gly Thr Lys Gly Val Ser Gly
            35                  40                  45

Phe Cys Glu Val Asn Ala Gly Asp Glu Phe Thr Val Glu Met His Ala
        50                  55                  60

Gln Pro Gly Asp Arg Ser Cys Ala Asn Glu Ala Ile Gly Gly Asn His
65                  70                  75                  80

Phe Gly Pro Val Leu Ile Tyr Met Ser Lys Val Asp Asp Ala Ser Thr
                85                  90                  95

Ala Asp Gly Ser Gly Asp Trp Phe Lys Val Asp Glu Phe Gly Tyr Asp
            100                 105                 110

Ala Ser Thr Lys Thr Trp Gly Thr Asp Lys Leu Asn Glu Asn Cys Gly
        115                 120                 125

Lys Arg Thr Phe Asn Ile Pro Ser His Ile Pro Ala Gly Asp Tyr Leu
130                 135                 140

Val Arg Ala Glu Ala Ile Ala Leu His Thr Ala Asn Gln Pro Gly Gly
145                 150                 155                 160

Ala Gln Phe Tyr Met Ser Cys Tyr Gln Val Arg Ile Ser Gly Gly Glu
                165                 170                 175

Gly Gly Gln Leu Pro Ala Gly Val Lys Ile Pro Gly Ala Tyr Ser Ala
            180                 185                 190

Asn Asp Pro Gly Ile Leu Val Asp Ile Trp Gly Asn Asp Phe Asn Asp
        195                 200                 205

Pro Pro Gly His Ser Arg His Ala Ile Ile Ile Ser Ser Ser
            210                 215                 220

Ser Asn Asn Ser Gly Ala Lys Met Thr Lys Lys Ile Gln Glu Pro Thr
225                 230                 235                 240

Ile Thr Ser Val Thr Asp Leu Pro Thr Asp Glu Ala Lys Trp Ile Ala
                245                 250                 255

Leu Gln Lys Ile Ser Tyr Val Asp Gln Thr Gly Thr Ala Arg Thr Tyr
```

```
                260              265            270
Glu Pro Ala Ser Arg Lys Thr Arg Ser Pro Arg Val
            275             280
```

```
<210> SEQ ID NO 37
<211> LENGTH: 726
<212> TYPE: DNA
<213> ORGANISM: Myceliophthora thermophila

<400> SEQUENCE: 37
atgaagtcgt ctaccccggc cttgttcgcc gctgggctcc ttgctcagca tgctgcggcc    60
cactccatct ccagcaggc gagcagcggc tcgaccgact tgatacgct gtgcaccgg     120
atgccgccca acaatagccc cgtcactagt gtgaccagcg gcgacatgac ctgcaacgtc   180
ggcggcacca aggggtgtc gggcttctgc gaggtgaacg ccggcgacga gttcacggtt    240
gagatgcacg cgcagcccgg cgaccgctcg tgcgccaacg aggccatcgg cgggaaccac   300
ttcggcccgg tcctcatcta catgagcaag gtcgacgacg cctccactgc cgacgggtcc   360
ggcgactggt tcaaggtgga cgagttcggc tacgacgcaa gcaccaagac ctggggcacc   420
gacaagctca cgagaactg cggcaagcgc accttcaaca tccccagcca catccccgcg    480
ggcgactatc tcgtccgggc cgaggctatc gcgctacaca ctgccaacca gccaggcggc   540
gcgcagttct acatgagctg ctatcaagtc aggatttccg gcggcgaagg gggccagctg   600
cctgccggag tcaagatccc gggcgcgtac agtgccaacg accccggcat ccttgtcgac   660
atctggggta acgatttcaa cgagtacgtt attccgggcc cccggtcat cgacagcagc    720
tacttc                                                              726

<210> SEQ ID NO 38
<211> LENGTH: 242
<212> TYPE: PRT
<213> ORGANISM: Myceliophthora thermophila

<400> SEQUENCE: 38

Met Lys Ser Ser Thr Pro Ala Leu Phe Ala Ala Gly Leu Leu Ala Gln
  1               5                  10                  15

His Ala Ala Ala His Ser Ile Phe Gln Gln Ala Ser Ser Gly Ser Thr
                 20                  25                  30

Asp Phe Asp Thr Leu Cys Thr Arg Met Pro Pro Asn Asn Ser Pro Val
             35                  40                  45

Thr Ser Val Thr Ser Gly Asp Met Thr Cys Asn Val Gly Gly Thr Lys
 50                  55                  60

Gly Val Ser Gly Phe Cys Glu Val Asn Ala Gly Asp Glu Phe Thr Val
 65                  70                  75                  80

Glu Met His Ala Gln Pro Gly Asp Arg Ser Cys Ala Asn Glu Ala Ile
                 85                  90                  95

Gly Gly Asn His Phe Gly Pro Val Leu Ile Tyr Met Ser Lys Val Asp
                100                 105                 110

Asp Ala Ser Thr Ala Asp Gly Ser Gly Asp Trp Phe Lys Val Asp Glu
            115                 120                 125

Phe Gly Tyr Asp Ala Ser Thr Lys Thr Trp Gly Thr Asp Lys Leu Asn
        130                 135                 140

Glu Asn Cys Gly Lys Arg Thr Phe Asn Ile Pro Ser His Ile Pro Ala
145                 150                 155                 160

Gly Asp Tyr Leu Val Arg Ala Glu Ala Ile Ala Leu His Thr Ala Asn
                165                 170                 175
```

```
Gln Pro Gly Gly Ala Gln Phe Tyr Met Ser Cys Tyr Gln Val Arg Ile
            180                 185                 190

Ser Gly Gly Glu Gly Gly Gln Leu Pro Ala Gly Val Lys Ile Pro Gly
        195                 200                 205

Ala Tyr Ser Ala Asn Asp Pro Gly Ile Leu Val Asp Ile Trp Gly Asn
    210                 215                 220

Asp Phe Asn Glu Tyr Val Ile Pro Gly Pro Val Ile Asp Ser Ser
225                 230                 235                 240

Tyr Phe

<210> SEQ ID NO 39
<211> LENGTH: 222
<212> TYPE: PRT
<213> ORGANISM: Myceliophthora thermophila

<400> SEQUENCE: 39

His Ser Ile Phe Gln Gln Ala Ser Ser Gly Ser Thr Asp Phe Asp Thr
1               5                   10                  15

Leu Cys Thr Arg Met Pro Pro Asn Asn Ser Pro Val Thr Ser Val Thr
            20                  25                  30

Ser Gly Asp Met Thr Cys Asn Val Gly Gly Thr Lys Gly Val Ser Gly
        35                  40                  45

Phe Cys Glu Val Asn Ala Gly Asp Glu Phe Thr Val Glu Met His Ala
    50                  55                  60

Gln Pro Gly Asp Arg Ser Cys Ala Asn Glu Ala Ile Gly Gly Asn His
65                  70                  75                  80

Phe Gly Pro Val Leu Ile Tyr Met Ser Lys Val Asp Asp Ala Ser Thr
                85                  90                  95

Ala Asp Gly Ser Gly Asp Trp Phe Lys Val Asp Glu Phe Gly Tyr Asp
            100                 105                 110

Ala Ser Thr Lys Thr Trp Gly Thr Asp Lys Leu Asn Glu Asn Cys Gly
        115                 120                 125

Lys Arg Thr Phe Asn Ile Pro Ser His Ile Pro Ala Gly Asp Tyr Leu
    130                 135                 140

Val Arg Ala Glu Ala Ile Ala Leu His Thr Ala Asn Gln Pro Gly Gly
145                 150                 155                 160

Ala Gln Phe Tyr Met Ser Cys Tyr Gln Val Arg Ile Ser Gly Gly Glu
                165                 170                 175

Gly Gly Gln Leu Pro Ala Gly Val Lys Ile Pro Gly Ala Tyr Ser Ala
            180                 185                 190

Asn Asp Pro Gly Ile Leu Val Asp Ile Trp Gly Asn Asp Phe Asn Glu
        195                 200                 205

Tyr Val Ile Pro Gly Pro Pro Val Ile Asp Ser Ser Tyr Phe
    210                 215                 220

<210> SEQ ID NO 40
<211> LENGTH: 969
<212> TYPE: DNA
<213> ORGANISM: Myceliophthora thermophila

<400> SEQUENCE: 40
atgaagtcct tcaccctcac cactctggcc gccctggctg gcaacgccgc cgctcacgcg      60
accttccagg ccctctgggt cgacggcgtc gactacggcg cgcagtgtgc ccgtctgccc     120
gcgtccaact cgccggtcac cgacgtgacc tccaacgcga tccgctgcaa cgccaacccc     180
```

```
tcgcccgctc ggggcaagtg cccggtcaag gccggctcga ccgttacggt cgagatgcat      240
cagcaacccg gtgaccgctc gtgcagcagc gaggcgatcg gcggggcgca ctacggcccc      300
gtgatggtgt acatgtccaa ggtgtcggac gcggcgtcgg cggacgggtc gtcgggctgg      360
ttcaaggtgt tcgaggacgg ctgggccaag aacccgtccg gcgggtcggg cgacgacgac      420
tactggggca ccaaggacct gaactcgtgc tgcgggaaga tgaacgtcaa gatccccgcc      480
gacctgccct cgggcgacta cctgctccgg gccgaggccc tcgcgctgca cacggccggc      540
agcgcgggcg gcgcccagtt ctacatgacc tgctaccagc tcaccgtgac cggctccggc      600
agcgccagcc cgcccaccgt ctccttcccg ggcgcctaca aggccaccga cccgggcatc      660
ctcgtcaaca tccacgcccc gctgtccggc tacaccgtgc ccggcccggc cgtctactcg      720
ggcggctcca ccaagaaggc cggcagcgcc tgcaccggct gcgagtccac ttgcgccgtc      780
ggctccggcc ccaccgccac cgtctcccag tcgcccggtt ccaccgccac ctcggccccc      840
ggcggcggcg gcggctgcac cgtccagaag taccagcagt gcggcggcca gggctacacc      900
ggctgcacca actgcgcgtc cggctccacc tgcagcgcgg tctcgccgcc ctactactcg      960
cagtgcgtc                                                              969
```

<210> SEQ ID NO 41
<211> LENGTH: 323
<212> TYPE: PRT
<213> ORGANISM: Myceliophthora thermophila

<400> SEQUENCE: 41

```
Met Lys Ser Phe Thr Leu Thr Thr Leu Ala Ala Leu Ala Gly Asn Ala
1               5                   10                  15

Ala Ala His Ala Thr Phe Gln Ala Leu Trp Val Asp Gly Val Asp Tyr
            20                  25                  30

Gly Ala Gln Cys Ala Arg Leu Pro Ala Ser Asn Ser Pro Val Thr Asp
        35                  40                  45

Val Thr Ser Asn Ala Ile Arg Cys Asn Ala Asn Pro Ser Pro Ala Arg
    50                  55                  60

Gly Lys Cys Pro Val Lys Ala Gly Ser Thr Val Thr Val Glu Met His
65                  70                  75                  80

Gln Gln Pro Gly Asp Arg Ser Cys Ser Ser Glu Ala Ile Gly Ala
                85                  90                  95

His Tyr Gly Pro Val Met Val Tyr Met Ser Lys Val Ser Asp Ala Ala
            100                 105                 110

Ser Ala Asp Gly Ser Ser Gly Trp Phe Lys Val Phe Glu Asp Gly Trp
        115                 120                 125

Ala Lys Asn Pro Ser Gly Gly Ser Gly Asp Asp Asp Tyr Trp Gly Thr
    130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Ala Gln Phe Tyr Met Thr Cys Tyr
            180                 185                 190

Gln Leu Thr Val Thr Gly Ser Gly Ser Ala Ser Pro Pro Thr Val Ser
        195                 200                 205

Phe Pro Gly Ala Tyr Lys Ala Thr Asp Pro Gly Ile Leu Val Asn Ile
    210                 215                 220

His Ala Pro Leu Ser Gly Tyr Thr Val Pro Gly Pro Ala Val Tyr Ser
```

```
                225                 230                 235                 240
Gly Gly Ser Thr Lys Lys Ala Gly Ser Ala Cys Thr Gly Cys Glu Ser
                245                 250                 255

Thr Cys Ala Val Gly Ser Gly Pro Thr Ala Thr Val Ser Gln Ser Pro
                260                 265                 270

Gly Ser Thr Ala Thr Ser Ala Pro Gly Gly Gly Gly Cys Thr Val
                275                 280                 285

Gln Lys Tyr Gln Gln Cys Gly Gly Gln Gly Tyr Thr Gly Cys Thr Asn
        290                 295                 300

Cys Ala Ser Gly Ser Thr Cys Ser Ala Val Ser Pro Pro Tyr Tyr Ser
305                 310                 315                 320

Gln Cys Val

<210> SEQ ID NO 42
<211> LENGTH: 305
<212> TYPE: PRT
<213> ORGANISM: Myceliophthora thermophila

<400> SEQUENCE: 42

His Ala Thr Phe Gln Ala Leu Trp Val Asp Gly Val Asp Tyr Gly Ala
1               5                   10                  15

Gln Cys Ala Arg Leu Pro Ala Ser Asn Ser Pro Val Thr Asp Val Thr
                20                  25                  30

Ser Asn Ala Ile Arg Cys Asn Ala Asn Pro Ser Pro Ala Arg Gly Lys
            35                  40                  45

Cys Pro Val Lys Ala Gly Ser Thr Val Thr Val Glu Met His Gln Gln
50                  55                  60

Pro Gly Asp Arg Ser Cys Ser Ser Glu Ala Ile Gly Gly Ala His Tyr
65                  70                  75                  80

Gly Pro Val Met Val Tyr Met Ser Lys Val Ser Asp Ala Ala Ser Ala
                85                  90                  95

Asp Gly Ser Ser Gly Trp Phe Lys Val Phe Glu Asp Gly Trp Ala Lys
                100                 105                 110

Asn Pro Ser Gly Gly Ser Gly Asp Asp Asp Tyr Trp Gly Thr Lys Asp
            115                 120                 125

Leu Asn Ser Cys Cys Gly Lys Met Asn Val Lys Ile Pro Ala Asp Leu
130                 135                 140

Pro Ser Gly Asp Tyr Leu Leu Arg Ala Glu Ala Leu Ala Leu His Thr
145                 150                 155                 160

Ala Gly Ser Ala Gly Gly Ala Gln Phe Tyr Met Thr Cys Tyr Gln Leu
                165                 170                 175

Thr Val Thr Gly Ser Gly Ser Ala Ser Pro Pro Thr Val Ser Phe Pro
            180                 185                 190

Gly Ala Tyr Lys Ala Thr Asp Pro Gly Ile Leu Val Asn Ile His Ala
        195                 200                 205

Pro Leu Ser Gly Tyr Thr Val Pro Gly Pro Ala Val Tyr Ser Gly Gly
    210                 215                 220

Ser Thr Lys Lys Ala Gly Ser Ala Cys Thr Gly Cys Glu Ser Thr Cys
225                 230                 235                 240

Ala Val Gly Ser Gly Pro Thr Ala Thr Val Ser Gln Ser Pro Gly Ser
                245                 250                 255

Thr Ala Thr Ser Ala Pro Gly Gly Gly Gly Cys Thr Val Gln Lys
            260                 265                 270

Tyr Gln Gln Cys Gly Gly Gln Gly Tyr Thr Gly Cys Thr Asn Cys Ala
```

```
            275                 280                 285
Ser Gly Ser Thr Cys Ser Ala Val Ser Pro Pro Tyr Tyr Ser Gln Cys
        290                 295                 300
Val
305

<210> SEQ ID NO 43
<211> LENGTH: 870
<212> TYPE: DNA
<213> ORGANISM: Myceliophthora thermophila

<400> SEQUENCE: 43 atgaaggac tcctcggcgc cgccgccctc tcgctggccg tcagcgatgt ctcggcccac        60
tacatctttc agcagctgac gacgggcggc gtcaagcacg ctgtgtacca gtacatccgc      120
aagaacacca actataactc gcccgtgacc gatctgacgt ccaacgacct ccgctgcaat      180
gtgggtgcta ccggtgcggg caccgatacc gtcacggtgc gcgccggcga ttcgttcacc      240
ttcacgaccg atacgcccgt ttaccaccag ggcccgacct cgatctacat gtccaaggcc      300
cccggcagcg cgtccgacta cgacggcagc ggcggctggt tcaagatcaa ggactgggct      360
gactacaccg ccacgattcc ggaatgtatt ccccccggcg actacctgct cgcatccag      420 caactcggca tccacaaccc ttggcccgcg gcatccccc agttctacat ctcttgtgcc      480
cagatcaccg tgactggtgg cggcagtgcc aaccccggcc cgaccgtctc catcccaggc      540
gccttcaagg agaccgaccc gggctacact gtcaacatct acaacaactt ccacaactac      600
accgtccctg gccagccgt cttcacctgc aacggtagcg gcggcaacaa cggcggcggc      660
tccaacccag tcaccaccac caccaccacc accaccaggc cgtccaccag caccgcccag      720
tcccagccgt cgtcgagccc gaccagcccc tccagctgca ccgtcgcgaa gtggggccag      780
tgcggaggac agggttacag cggctgcacc gtgtgcgcgg ccgggtcgac ctgccagaag      840
accaacgact actacagcca gtgcttgtag                                      870

<210> SEQ ID NO 44
<211> LENGTH: 289
<212> TYPE: PRT
<213> ORGANISM: Myceliophthora thermophila

<400> SEQUENCE: 44

Met Lys Gly Leu Leu Gly Ala Ala Ala Leu Ser Leu Ala Val Ser Asp
1               5                   10                  15

Val Ser Ala His Tyr Ile Phe Gln Gln Leu Thr Thr Gly Gly Val Lys
            20                  25                  30

His Ala Val Tyr Gln Tyr Ile Arg Lys Asn Thr Asn Tyr Asn Ser Pro
        35                  40                  45

Val Thr Asp Leu Thr Ser Asn Asp Leu Arg Cys Asn Val Gly Ala Thr
    50                  55                  60

Gly Ala Gly Thr Asp Thr Val Thr Val Arg Ala Gly Asp Ser Phe Thr
65                  70                  75                  80

Phe Thr Thr Asp Thr Pro Val Tyr His Gln Gly Pro Thr Ser Ile Tyr
                85                  90                  95

Met Ser Lys Ala Pro Gly Ser Ala Ser Asp Tyr Asp Gly Ser Gly Gly
            100                 105                 110

Trp Phe Lys Ile Lys Asp Trp Ala Asp Tyr Thr Ala Thr Ile Pro Glu
        115                 120                 125

Cys Ile Pro Pro Gly Asp Tyr Leu Leu Arg Ile Gln Gln Leu Gly Ile
```

```
            130                 135                 140
His Asn Pro Trp Pro Ala Gly Ile Pro Gln Phe Tyr Ile Ser Cys Ala
145                 150                 155                 160

Gln Ile Thr Val Thr Gly Gly Ser Ala Asn Pro Gly Pro Thr Val
                165                 170                 175

Ser Ile Pro Gly Ala Phe Lys Glu Thr Asp Pro Gly Tyr Thr Val Asn
                180                 185                 190

Ile Tyr Asn Asn Phe His Asn Tyr Thr Val Pro Gly Pro Ala Val Phe
            195                 200                 205

Thr Cys Asn Gly Ser Gly Gly Asn Asn Gly Gly Ser Asn Pro Val
            210                 215                 220

Thr Thr Thr Thr Thr Thr Thr Arg Pro Ser Thr Ser Thr Ala Gln
225                 230                 235                 240

Ser Gln Pro Ser Ser Pro Thr Ser Pro Ser Ser Cys Thr Val Ala
                245                 250                 255

Lys Trp Gly Gln Cys Gly Gly Gln Gly Tyr Ser Gly Cys Thr Val Cys
                260                 265                 270

Ala Ala Gly Ser Thr Cys Gln Lys Thr Asn Asp Tyr Tyr Ser Gln Cys
            275                 280                 285

Leu

<210> SEQ ID NO 45
<211> LENGTH: 270
<212> TYPE: PRT
<213> ORGANISM: Myceliophthora thermophila

<400> SEQUENCE: 45

His Tyr Ile Phe Gln Gln Leu Thr Thr Gly Gly Val Lys His Ala Val
1               5                   10                  15

Tyr Gln Tyr Ile Arg Lys Asn Thr Asn Tyr Asn Ser Pro Val Thr Asp
                20                  25                  30

Leu Thr Ser Asn Asp Leu Arg Cys Asn Val Gly Ala Thr Gly Ala Gly
            35                  40                  45

Thr Asp Thr Val Thr Val Arg Ala Gly Asp Ser Phe Thr Phe Thr Thr
50                  55                  60

Asp Thr Pro Val Tyr His Gln Gly Pro Thr Ser Ile Tyr Met Ser Lys
65                  70                  75                  80

Ala Pro Gly Ser Ala Ser Asp Tyr Asp Gly Ser Gly Gly Trp Phe Lys
                85                  90                  95

Ile Lys Asp Trp Ala Asp Tyr Thr Ala Thr Ile Pro Glu Cys Ile Pro
            100                 105                 110

Pro Gly Asp Tyr Leu Leu Arg Ile Gln Gln Leu Gly Ile His Asn Pro
            115                 120                 125

Trp Pro Ala Gly Ile Pro Gln Phe Tyr Ile Ser Cys Ala Gln Ile Thr
            130                 135                 140

Val Thr Gly Gly Ser Ala Asn Pro Gly Pro Thr Val Ser Ile Pro
145                 150                 155                 160

Gly Ala Phe Lys Glu Thr Asp Pro Gly Tyr Thr Val Asn Ile Tyr Asn
                165                 170                 175

Asn Phe His Asn Tyr Thr Val Pro Gly Pro Ala Val Phe Thr Cys Asn
            180                 185                 190

Gly Ser Gly Gly Asn Asn Gly Gly Ser Asn Pro Val Thr Thr Thr
            195                 200                 205

Thr Thr Thr Thr Thr Arg Pro Ser Thr Ser Thr Ala Gln Ser Gln Pro
```

| | | | | | | | | | | | | | | |
|---|---|---|---|---|---|---|---|---|---|---|---|---|---|---|
| | | 210 | | | | 215 | | | | 220 | | | | |
| Ser | Ser | Ser | Pro | Thr | Ser | Pro | Ser | Ser | Cys | Thr | Val | Ala | Lys | Trp | Gly |
| 225 | | | | | 230 | | | | | 235 | | | | 240 |
| Gln | Cys | Gly | Gly | Gln | Gly | Tyr | Ser | Gly | Cys | Thr | Val | Cys | Ala | Ala | Gly |
| | | | | 245 | | | | | 250 | | | | | 255 | |
| Ser | Thr | Cys | Gln | Lys | Thr | Asn | Asp | Tyr | Tyr | Ser | Gln | Cys | Leu | | |
| | | 260 | | | | | 265 | | | | | 270 | | | |

<210> SEQ ID NO 46
<211> LENGTH: 834
<212> TYPE: DNA
<213> ORGANISM: Myceliophthora thermophila

<400> SEQUENCE: 46

```
ctgacgacgg gcggcgtcaa gcacgctgtg taccagtaca tccgcaagaa caccaactat      60
aactcgcccg tgaccgatct gacgtccaac gacctccgct gcaatgtggg tgctaccggt     120
gcgggcaccg ataccgtcac ggtgcgcgcc ggcgattcgt tcaccttcac gaccgatacg     180
cccgtttacc accagggccc gacctcgatc tacatgtcca aggcccccgg cagcgcgtcc     240
gactacgacg gcagcggcgg ctggttcaag atcaaggact ggggtgccga ctttagcagc     300
ggccaggcca cctggacctt ggcgtctgac tacaccgcca cgattccgga atgtattccc     360
cccggcgact acctgcttcg catccagcaa ctcggcatcc acaaccctgg ccccgcgggc     420
atcccccagt tctacatctc ttgtgcccag atcaccgtga ctggtggcgg cagtgccaac     480
cccgcccga ccgtctccat cccaggcgcc ttcaaggaga ccgacccggg ctacactgtc     540
aacatctaca caacttcca caactacacc gtccctggcc cagccgtctt cacctgcaac     600
ggtagcggcg gcaacaacgg cggcggctcc aacccagtca ccaccaccac caccaccacc     660
accaggccgt ccaccagcac cgcccagtcc cagccgtcgt cgagcccgac cagcccctcc     720
agctgcaccg tcgcgaagtg gggccagtgc ggaggacagg gttacagcgg ctgcaccgtg     780
tgcgcggccg ggtcgacctg ccagaagacc aacgactact acagccagtg cttg          834
```

<210> SEQ ID NO 47
<211> LENGTH: 303
<212> TYPE: PRT
<213> ORGANISM: Myceliophthora thermophila

<400> SEQUENCE: 47

| | | | | | | | | | | | | | | |
|---|---|---|---|---|---|---|---|---|---|---|---|---|---|---|
| Met | Lys | Gly | Leu | Leu | Gly | Ala | Ala | Ala | Leu | Ser | Leu | Ala | Val | Ser | Asp |
| 1 | | | | 5 | | | | | 10 | | | | | 15 | |
| Val | Ser | Ala | His | Tyr | Ile | Phe | Gln | Gln | Leu | Thr | Thr | Gly | Gly | Val | Lys |
| | | | 20 | | | | | 25 | | | | | 30 | | |
| His | Ala | Val | Tyr | Gln | Tyr | Ile | Arg | Lys | Asn | Thr | Asn | Tyr | Asn | Ser | Pro |
| | | 35 | | | | | 40 | | | | | 45 | | | |
| Val | Thr | Asp | Leu | Thr | Ser | Asn | Asp | Leu | Arg | Cys | Asn | Val | Gly | Ala | Thr |
| | 50 | | | | | 55 | | | | | 60 | | | | |
| Gly | Ala | Gly | Thr | Asp | Thr | Val | Thr | Val | Arg | Ala | Gly | Asp | Ser | Phe | Thr |
| 65 | | | | | 70 | | | | | 75 | | | | | 80 |
| Phe | Thr | Thr | Asp | Thr | Pro | Val | Tyr | His | Gln | Gly | Pro | Thr | Ser | Ile | Tyr |
| | | | | 85 | | | | | 90 | | | | | 95 | |
| Met | Ser | Lys | Ala | Pro | Gly | Ser | Ala | Ser | Asp | Tyr | Asp | Gly | Ser | Gly | Gly |
| | | | 100 | | | | | 105 | | | | | 110 | | |
| Trp | Phe | Lys | Ile | Lys | Asp | Trp | Gly | Ala | Asp | Phe | Ser | Ser | Gly | Gln | Ala |
| | | | 115 | | | | | 120 | | | | | 125 | | |

```
Thr Trp Thr Leu Ala Ser Asp Tyr Thr Ala Thr Ile Pro Glu Cys Ile
        130                 135                 140

Pro Pro Gly Asp Tyr Leu Leu Arg Ile Gln Gln Leu Gly Ile His Asn
145                 150                 155                 160

Pro Trp Pro Ala Gly Ile Pro Gln Phe Tyr Ile Ser Cys Ala Gln Ile
                165                 170                 175

Thr Val Thr Gly Gly Gly Ser Ala Asn Pro Gly Pro Thr Val Ser Ile
                180                 185                 190

Pro Gly Ala Phe Lys Glu Thr Asp Pro Gly Tyr Thr Val Asn Ile Tyr
            195                 200                 205

Asn Asn Phe His Asn Tyr Thr Val Pro Gly Pro Ala Val Phe Thr Cys
210                 215                 220

Asn Gly Ser Gly Gly Asn Asn Gly Gly Ser Asn Pro Val Thr Thr
225                 230                 235                 240

Thr Thr Thr Thr Thr Thr Arg Pro Ser Thr Ser Thr Ala Gln Ser Gln
                245                 250                 255

Pro Ser Ser Ser Pro Thr Ser Pro Ser Ser Cys Thr Val Ala Lys Trp
                260                 265                 270

Gly Gln Cys Gly Gly Gln Gly Tyr Ser Gly Cys Thr Val Cys Ala Ala
                275                 280                 285

Gly Ser Thr Cys Gln Lys Thr Asn Asp Tyr Tyr Ser Gln Cys Leu
            290                 295                 300

<210> SEQ ID NO 48
<211> LENGTH: 284
<212> TYPE: PRT
<213> ORGANISM: Myceliophthora thermophila

<400> SEQUENCE: 48

His Tyr Ile Phe Gln Gln Leu Thr Gly Gly Val Lys His Ala Val
1               5                   10                  15

Tyr Gln Tyr Ile Arg Lys Asn Thr Asn Tyr Asn Ser Pro Val Thr Asp
                20                  25                  30

Leu Thr Ser Asn Asp Leu Arg Cys Asn Val Gly Ala Thr Gly Ala Gly
            35                  40                  45

Thr Asp Thr Val Thr Val Arg Ala Gly Asp Ser Phe Thr Phe Thr Thr
50                  55                  60

Asp Thr Pro Val Tyr His Gln Gly Pro Thr Ser Ile Tyr Met Ser Lys
65                  70                  75                  80

Ala Pro Gly Ser Ala Ser Asp Tyr Asp Gly Ser Gly Gly Trp Phe Lys
                85                  90                  95

Ile Lys Asp Trp Gly Ala Asp Phe Ser Ser Gly Gln Ala Thr Trp Thr
                100                 105                 110

Leu Ala Ser Asp Tyr Thr Ala Thr Ile Pro Glu Cys Ile Pro Pro Gly
            115                 120                 125

Asp Tyr Leu Leu Arg Ile Gln Gln Leu Gly Ile His Asn Pro Trp Pro
130                 135                 140

Ala Gly Ile Pro Gln Phe Tyr Ile Ser Cys Ala Gln Ile Thr Val Thr
145                 150                 155                 160

Gly Gly Gly Ser Ala Asn Pro Gly Pro Thr Val Ser Ile Pro Gly Ala
                165                 170                 175

Phe Lys Glu Thr Asp Pro Gly Tyr Thr Val Asn Ile Tyr Asn Asn Phe
            180                 185                 190

His Asn Tyr Thr Val Pro Gly Pro Ala Val Phe Thr Cys Asn Gly Ser
        195                 200                 205
```

```
Gly Gly Asn Asn Gly Gly Ser Asn Pro Val Thr Thr Thr Thr
        210                 215                 220

Thr Thr Thr Arg Pro Ser Thr Ser Ala Gln Ser Gln Pro Ser Ser
225                 230                 235                 240

Ser Pro Thr Ser Pro Ser Ser Cys Thr Val Ala Lys Trp Gly Gln Cys
                245                 250                 255

Gly Gly Gln Gly Tyr Ser Gly Cys Thr Val Cys Ala Ala Gly Ser Thr
            260                 265                 270

Cys Gln Lys Thr Asn Asp Tyr Tyr Ser Gln Cys Leu
            275                 280
```

<210> SEQ ID NO 49
<211> LENGTH: 1038
<212> TYPE: DNA
<213> ORGANISM: Myceliophthora thermophila

<400> SEQUENCE: 49

```
atgtcttcct tcacctccaa gggtctcctt tccgccctca tgggcgcggc aacggttgcc     60
gcccacggtc acgtcaccaa catcgtcatc aacggcgtct cataccagaa cttcgaccca    120
ttcacgcacc cttatatgca gaaccctccg acggttgtcg gctggaccgc gagcaacacg    180
gacaacggct tcgtcggccc cgagtccttc tctagcccgg acatcatctg ccacaagtcc    240
gccaccaacg ctggcggcca tgccgtcgtc gcggccggcg ataaggtctt catccagtgg    300
gacacctggc ccgagtcgca ccacggtccg gtcatcgact atctcgccga ctgcggcgac    360
gcgggctgcg agaaggtcga caagaccacg ctcaagttct tcaagatcag cgagtccggc    420
ctgctcgacg gcactaacgc ccccggcaag tgggcgtccg acacgctgat cgccaacaac    480
aactcgtggc tggtccagat cccgcccaac atcgccccgg caactacgt cctgcgccac    540
gagatcatcg ccctgcacag cgccggccag cagaacggcg cccagaacta ccctcagtgc    600
ttcaacctgc aggtcaccgg ctccggcact cagaagcccc ccggcgtcct cggcaccgag    660
ctctacaagg ccaccgacgc cggcatcctg gccaacatct acacctcgcc cgtcacctac    720
cagatccccg gccggccat catctcgggc gcctccgccg tccagcagac cacctcgggcc    780
atcaccgcct ctgctagcgc catcaccggc tccgctaccg ccgcgcccac ggctgccacc    840
accaccgccg ccgccgccgc caccactacc accaccgctg gctccggtgc taccgccacg    900
ccctcgaccg gcggctctcc ttcttccgcc cagcctgctc ctaccaccgc tgccgctacc    960
tccagccctg ctcgcccgac ccgctgcgct ggtctgaaga agcgccgtcg ccacgcccgt   1020
gacgtcaagg ttgccctc                                                1038
```

<210> SEQ ID NO 50
<211> LENGTH: 346
<212> TYPE: PRT
<213> ORGANISM: Myceliophthora thermophila

<400> SEQUENCE: 50

```
Met Ser Ser Phe Thr Ser Lys Gly Leu Leu Ser Ala Leu Met Gly Ala
1               5                   10                  15

Ala Thr Val Ala Ala His Gly His Val Thr Asn Ile Val Ile Asn Gly
            20                  25                  30

Val Ser Tyr Gln Asn Phe Asp Pro Phe Thr His Pro Tyr Met Gln Asn
        35                  40                  45

Pro Pro Thr Val Val Gly Trp Thr Ala Ser Asn Thr Asp Asn Gly Phe
    50                  55                  60
```

Val Gly Pro Glu Ser Phe Ser Pro Asp Ile Ile Cys His Lys Ser
 65                  70                  75                  80

Ala Thr Asn Ala Gly Gly His Ala Val Val Ala Ala Gly Asp Lys Val
                 85                  90                  95

Phe Ile Gln Trp Asp Thr Trp Pro Glu Ser His His Gly Pro Val Ile
                100                 105                 110

Asp Tyr Leu Ala Asp Cys Gly Asp Ala Gly Cys Glu Lys Val Asp Lys
                115                 120                 125

Thr Thr Leu Lys Phe Phe Lys Ile Ser Glu Ser Gly Leu Leu Asp Gly
130                 135                 140

Thr Asn Ala Pro Gly Lys Trp Ala Ser Asp Thr Leu Ile Ala Asn Asn
145                 150                 155                 160

Asn Ser Trp Leu Val Gln Ile Pro Pro Asn Ile Ala Pro Gly Asn Tyr
                165                 170                 175

Val Leu Arg His Glu Ile Ile Ala Leu His Ser Ala Gly Gln Gln Asn
                180                 185                 190

Gly Ala Gln Asn Tyr Pro Gln Cys Phe Asn Leu Gln Val Thr Gly Ser
                195                 200                 205

Gly Thr Gln Lys Pro Ser Gly Val Leu Gly Thr Glu Leu Tyr Lys Ala
                210                 215                 220

Thr Asp Ala Gly Ile Leu Ala Asn Ile Tyr Thr Ser Pro Val Thr Tyr
225                 230                 235                 240

Gln Ile Pro Gly Pro Ala Ile Ile Ser Gly Ala Ser Ala Val Gln Gln
                245                 250                 255

Thr Thr Ser Ala Ile Thr Ala Ser Ser Ala Ile Thr Gly Ser Ala
                260                 265                 270

Thr Ala Ala Pro Thr Ala Ala Thr Thr Thr Ala Ala Ala Ala Thr
                275                 280                 285

Thr Thr Thr Thr Ala Gly Ser Gly Ala Thr Ala Thr Pro Ser Thr Gly
                290                 295                 300

Gly Ser Pro Ser Ser Ala Gln Pro Ala Pro Thr Thr Ala Ala Ala Thr
305                 310                 315                 320

Ser Ser Pro Ala Arg Pro Thr Arg Cys Ala Gly Leu Lys Lys Arg Arg
                325                 330                 335

Arg His Ala Arg Asp Val Lys Val Ala Leu
                340                 345

<210> SEQ ID NO 51
<211> LENGTH: 326
<212> TYPE: PRT
<213> ORGANISM: Myceliophthora thermophila

<400> SEQUENCE: 51

Ala His Gly His Val Thr Asn Ile Val Ile Asn Gly Val Ser Tyr Gln
1               5                   10                  15

Asn Phe Asp Pro Phe Thr His Pro Tyr Met Gln Asn Pro Pro Thr Val
                20                  25                  30

Val Gly Trp Thr Ala Ser Asn Thr Asp Asn Gly Phe Val Gly Pro Glu
            35                  40                  45

Ser Phe Ser Ser Pro Asp Ile Ile Cys His Lys Ser Ala Thr Asn Ala
            50                  55                  60

Gly Gly His Ala Val Val Ala Ala Gly Asp Lys Val Phe Ile Gln Trp
65                  70                  75                  80

Asp Thr Trp Pro Glu Ser His His Gly Pro Val Ile Asp Tyr Leu Ala

```
                85                  90                  95
Asp Cys Gly Asp Ala Gly Cys Glu Lys Val Asp Lys Thr Thr Leu Lys
                100                 105                 110

Phe Phe Lys Ile Ser Glu Ser Gly Leu Leu Asp Gly Thr Asn Ala Pro
            115                 120                 125

Gly Lys Trp Ala Ser Asp Thr Leu Ile Ala Asn Asn Ser Trp Leu
        130                 135                 140

Val Gln Ile Pro Pro Asn Ile Ala Pro Gly Asn Tyr Val Leu Arg His
145                 150                 155                 160

Glu Ile Ile Ala Leu His Ser Ala Gly Gln Gln Asn Gly Ala Gln Asn
                165                 170                 175

Tyr Pro Gln Cys Phe Asn Leu Gln Val Thr Gly Ser Gly Thr Gln Lys
            180                 185                 190

Pro Ser Gly Val Leu Gly Thr Glu Leu Tyr Lys Ala Thr Asp Ala Gly
        195                 200                 205

Ile Leu Ala Asn Ile Tyr Thr Ser Pro Val Thr Tyr Gln Ile Pro Gly
    210                 215                 220

Pro Ala Ile Ile Ser Gly Ala Ser Ala Val Gln Gln Thr Thr Ser Ala
225                 230                 235                 240

Ile Thr Ala Ser Ala Ser Ala Ile Thr Gly Ser Ala Thr Ala Ala Pro
                245                 250                 255

Thr Ala Ala Thr Thr Thr Ala Ala Ala Ala Thr Thr Thr Thr Thr
            260                 265                 270

Ala Gly Ser Gly Ala Thr Ala Thr Pro Ser Thr Gly Gly Ser Pro Ser
        275                 280                 285

Ser Ala Gln Pro Ala Pro Thr Thr Ala Ala Thr Ser Ser Pro Ala
290                 295                 300

Arg Pro Thr Arg Cys Ala Gly Leu Lys Lys Arg Arg His Ala Arg
305                 310                 315                 320

Asp Val Lys Val Ala Leu
                325

<210> SEQ ID NO 52
<211> LENGTH: 714
<212> TYPE: DNA
<213> ORGANISM: Myceliophthora thermophila

<400> SEQUENCE: 52
atgaagacgc tcgccgccct cgtggtctcg gccgccctcg tggccgcgca cggctatgtt      60
gaccacgcca cgatcggtgg caaggattat cagttctacc agccgtacca ggacccttac     120
atgggcgaca caagcccga tagggtttcc cgctccatcc cgggcaacgg ccccgtggag      180
gacgtcaact ccatcgacct ccagtgccac gccggtgccg aaccggccaa gctccacgcc     240
cccgccgccg ccggctcgac cgtgacgctc tactggaccc tctggcccga ctcccacgtc     300
ggccccgtca tcacctacat ggctcgctgc ccgacaccg ctgccagga ctggtccccg       360 ggaactaagc ccgtttggtt caagatcaag gaaggcggcc gtgagggcac ctccaatacc     420
ccgctcatga cggccccctc cgcctacacc tacacgatcc cgtcctgcct caagagcggc     480
tactacctcg tccgccacga gatcatcgcc ctgcactcgg cctggcagta ccccggcgcc     540
cagttctacc cgggctgcca ccagctccag gtcaccggcg cgggctccac cgtgccctct     600
accaacctgg tctccttccc cggcgcctac aaggggagcg accccggcat cacctacgac     660
gcttacaagg cgcaacctta caccatccct ggcccggccg tgtttacctg ctga           714
```

<210> SEQ ID NO 53
<211> LENGTH: 237
<212> TYPE: PRT
<213> ORGANISM: Myceliophthora thermophila

<400> SEQUENCE: 53

Met Lys Thr Leu Ala Ala Leu Val Val Ser Ala Ala Leu Val Ala Ala
1               5                   10                  15

His Gly Tyr Val Asp His Ala Thr Ile Gly Gly Lys Asp Tyr Gln Phe
            20                  25                  30

Tyr Gln Pro Tyr Gln Asp Pro Tyr Met Gly Asp Asn Lys Pro Asp Arg
        35                  40                  45

Val Ser Arg Ser Ile Pro Gly Asn Gly Pro Val Glu Asp Val Asn Ser
    50                  55                  60

Ile Asp Leu Gln Cys His Ala Gly Ala Glu Pro Ala Lys Leu His Ala
65                  70                  75                  80

Pro Ala Ala Gly Ser Thr Val Thr Leu Tyr Trp Thr Leu Trp Pro
                85                  90                  95

Asp Ser His Val Gly Pro Val Ile Thr Tyr Met Ala Arg Cys Pro Asp
            100                 105                 110

Thr Gly Cys Gln Asp Trp Ser Pro Gly Thr Lys Pro Val Trp Phe Lys
        115                 120                 125

Ile Lys Glu Gly Gly Arg Glu Gly Thr Ser Asn Thr Pro Leu Met Thr
    130                 135                 140

Ala Pro Ser Ala Tyr Thr Tyr Thr Ile Pro Ser Cys Leu Lys Ser Gly
145                 150                 155                 160

Tyr Tyr Leu Val Arg His Glu Ile Ile Ala Leu His Ser Ala Trp Gln
                165                 170                 175

Tyr Pro Gly Ala Gln Phe Tyr Pro Gly Cys His Gln Leu Gln Val Thr
            180                 185                 190

Gly Gly Gly Ser Thr Val Pro Ser Thr Asn Leu Val Ser Phe Pro Gly
        195                 200                 205

Ala Tyr Lys Gly Ser Asp Pro Gly Ile Thr Tyr Asp Ala Tyr Lys Ala
    210                 215                 220

Gln Pro Tyr Thr Ile Pro Gly Pro Ala Val Phe Thr Cys
225                 230                 235

<210> SEQ ID NO 54
<211> LENGTH: 219
<212> TYPE: PRT
<213> ORGANISM: Myceliophthora thermophila

<400> SEQUENCE: 54

Tyr Val Asp His Ala Thr Ile Gly Gly Lys Asp Tyr Gln Phe Tyr Gln
1               5                   10                  15

Pro Tyr Gln Asp Pro Tyr Met Gly Asp Asn Lys Pro Asp Arg Val Ser
            20                  25                  30

Arg Ser Ile Pro Gly Asn Gly Pro Val Glu Asp Val Asn Ser Ile Asp
        35                  40                  45

Leu Gln Cys His Ala Gly Ala Glu Pro Ala Lys Leu His Ala Pro Ala
    50                  55                  60

Ala Ala Gly Ser Thr Val Thr Leu Tyr Trp Thr Leu Trp Pro Asp Ser
65                  70                  75                  80

His Val Gly Pro Val Ile Thr Tyr Met Ala Arg Cys Pro Asp Thr Gly
                85                  90                  95

| Cys | Gln | Asp | Trp | Ser | Pro | Gly | Thr | Lys | Pro | Val | Trp | Phe | Lys | Ile | Lys |
|---|---|---|---|---|---|---|---|---|---|---|---|---|---|---|---|
| | | | | 100 | | | | | 105 | | | | | 110 | |

Glu Gly Gly Arg Glu Gly Thr Ser Asn Thr Pro Leu Met Thr Ala Pro
              115                 120                 125

Ser Ala Tyr Thr Tyr Thr Ile Pro Ser Cys Leu Lys Ser Gly Tyr Tyr
        130                 135                 140

Leu Val Arg His Glu Ile Ile Ala Leu His Ser Ala Trp Gln Tyr Pro
145                 150                 155                 160

Gly Ala Gln Phe Tyr Pro Gly Cys His Gln Leu Gln Val Thr Gly Gly
                165                 170                 175

Gly Ser Thr Val Pro Ser Thr Asn Leu Val Ser Phe Pro Gly Ala Tyr
            180                 185                 190

Lys Gly Ser Asp Pro Gly Ile Thr Tyr Asp Ala Tyr Lys Ala Gln Pro
                195                 200                 205

Tyr Thr Ile Pro Gly Pro Ala Val Phe Thr Cys
            210                 215

<210> SEQ ID NO 55
<211> LENGTH: 723
<212> TYPE: DNA
<213> ORGANISM: Myceliophthora thermophila

<400> SEQUENCE: 55

```
atgaagacgc tcgccgccct cgtggtctcg gccgccctcg tggccgcgca cggctatgtt      60
gaccacgcca cgatcggtgg caaggattat cagttctacc agccgtacca ggacccttac     120
atgggcgaca caagcccga tagggtttcc cgctccatcc cgggcaacgg ccccgtggag      180
gacgtcaact ccatcgacct ccagtgccac gccggtgccg aaccggccaa gctccacgcc     240
cccgccgccg ccggctcgac cgtgacgctc tactggaccc tctggcccga ctcccacgtc     300
ggccccgtca tcacctacat ggctcgctgc ccgacaccg gctgccagga ctggtccccg      360
ggaactaagc ccgtttggtt caagatcaag gaaggcggcc gtgagggcac ctccaatgtc     420
tgggctgcta cccgctcat gacggccccc tccgcctaca cctacacgat cccgtcctgc     480
ctcaagagcg gctactacct cgtccgccac gagatcatcg ccctgcactc ggcctggcag     540
taccccggcg cccagttcta cccgggctgc caccagctcc aggtcaccgg cggcggctcc     600
accgtgccct ctaccaacct ggtctccttc ccggcgcct acaagggag cgaccccggc       660
atcacctacg acgcttacaa ggcgcaacct tacaccatcc ctggcccggc cgtgtttacc     720
tgc                                                                   723
```

<210> SEQ ID NO 56
<211> LENGTH: 241
<212> TYPE: PRT
<213> ORGANISM: Myceliophthora thermophila

<400> SEQUENCE: 56

Met Lys Thr Leu Ala Ala Leu Val Val Ser Ala Leu Val Ala Ala
1               5                   10                  15

His Gly Tyr Val Asp His Ala Thr Ile Gly Gly Lys Asp Tyr Gln Phe
                20                  25                  30

Tyr Gln Pro Tyr Gln Asp Pro Tyr Met Gly Asp Asn Lys Pro Asp Arg
            35                  40                  45

Val Ser Arg Ser Ile Pro Gly Asn Gly Pro Val Glu Asp Val Asn Ser
        50                  55                  60

Ile Asp Leu Gln Cys His Ala Gly Ala Glu Pro Ala Lys Leu His Ala

```
                65                  70                  75                  80
Pro Ala Ala Ala Gly Ser Thr Val Thr Leu Tyr Trp Thr Leu Trp Pro
                85                  90                  95

Asp Ser His Val Gly Pro Val Ile Thr Tyr Met Ala Arg Cys Pro Asp
                100                 105                 110

Thr Gly Cys Gln Asp Trp Ser Pro Gly Thr Lys Pro Val Trp Phe Lys
                115                 120                 125

Ile Lys Glu Gly Gly Arg Glu Gly Thr Ser Asn Val Trp Ala Ala Thr
    130                 135                 140

Pro Leu Met Thr Ala Pro Ser Ala Tyr Thr Tyr Thr Ile Pro Ser Cys
145                 150                 155                 160

Leu Lys Ser Gly Tyr Tyr Leu Val Arg His Glu Ile Ile Ala Leu His
                165                 170                 175

Ser Ala Trp Gln Tyr Pro Gly Ala Gln Phe Tyr Pro Gly Cys His Gln
                180                 185                 190

Leu Gln Val Thr Gly Gly Gly Ser Thr Val Pro Ser Thr Asn Leu Val
                195                 200                 205

Ser Phe Pro Gly Ala Tyr Lys Gly Ser Asp Pro Gly Ile Thr Tyr Asp
    210                 215                 220

Ala Tyr Lys Ala Gln Pro Tyr Thr Ile Pro Gly Pro Ala Val Phe Thr
225                 230                 235                 240

Cys

<210> SEQ ID NO 57
<211> LENGTH: 223
<212> TYPE: PRT
<213> ORGANISM: Myceliophthora thermophila

<400> SEQUENCE: 57

Tyr Val Asp His Ala Thr Ile Gly Gly Lys Asp Tyr Gln Phe Tyr Gln
1               5                   10                  15

Pro Tyr Gln Asp Pro Tyr Met Gly Asp Asn Lys Pro Asp Arg Val Ser
                20                  25                  30

Arg Ser Ile Pro Gly Asn Gly Pro Val Glu Asp Val Asn Ser Ile Asp
                35                  40                  45

Leu Gln Cys His Ala Gly Ala Glu Pro Ala Lys Leu His Ala Pro Ala
    50                  55                  60

Ala Ala Gly Ser Thr Val Thr Leu Tyr Trp Thr Leu Trp Pro Asp Ser
65                  70                  75                  80

His Val Gly Pro Val Ile Thr Tyr Met Ala Arg Cys Pro Asp Thr Gly
                85                  90                  95

Cys Gln Asp Trp Ser Pro Gly Thr Lys Pro Val Trp Phe Lys Ile Lys
                100                 105                 110

Glu Gly Gly Arg Glu Gly Thr Ser Asn Val Trp Ala Ala Thr Pro Leu
                115                 120                 125

Met Thr Ala Pro Ser Ala Tyr Thr Tyr Thr Ile Pro Ser Cys Leu Lys
    130                 135                 140

Ser Gly Tyr Tyr Leu Val Arg His Glu Ile Ile Ala Leu His Ser Ala
145                 150                 155                 160

Trp Gln Tyr Pro Gly Ala Gln Phe Tyr Pro Gly Cys His Gln Leu Gln
                165                 170                 175

Val Thr Gly Gly Gly Ser Thr Val Pro Ser Thr Asn Leu Val Ser Phe
                180                 185                 190

Pro Gly Ala Tyr Lys Gly Ser Asp Pro Gly Ile Thr Tyr Asp Ala Tyr
```

```
            195                 200                 205
Lys Ala Gln Pro Tyr Thr Ile Pro Gly Pro Ala Val Phe Thr Cys
    210                 215                 220
```

<210> SEQ ID NO 58
<211> LENGTH: 675
<212> TYPE: DNA
<213> ORGANISM: Myceliophthora thermophila

<400> SEQUENCE: 58

```
atgagatact tcctccagct cgctgcggcc gcggcctttg ccgtgaacag cgcggcgggt    60
cactacatct tccagcagtt cgcgacgggc gggtccaagt acccgccctg gaagtacatc   120
cggcgcaaca ccaacccgga ctggctgcag aacgggccgg tgacggacct gtcgtcgacc   180
gacctgcgct gcaacgtggg cgggcaggtc agcaacggga ccgagaccat caccttgaac   240
gccggcgacg agttcagctt catcctcgac acgcccgtct accatgccgg ccccacctcg   300
ctctacatgt ccaaggcgcc cggagctgtg gccgactacg acggcggcgg ggcctggttc   360
aagatctacg actggggtcc gtcggggacg agctggacgt tgagtggcac gtacactcag   420
agaattccca gtgcatccc tgacggcgag tacctcctcc gcatccagca gatcgggctc   480
cacaaccccg cgccgcgcc acagttctac atcagctgcg ctcaagtcaa ggtcgtcgat   540
ggcggcagca ccaatccgac cccgaccgcc cagattccgg gagccttcca cagcaacgac   600
cctggcttga ctgtcaatat ctacaacgac cctctcacca actacgtcgt cccgggacct   660
agagtttcgc actgg                                                    675
```

<210> SEQ ID NO 59
<211> LENGTH: 225
<212> TYPE: PRT
<213> ORGANISM: Myceliophthora thermophila

<400> SEQUENCE: 59

```
Met Arg Tyr Phe Leu Gln Leu Ala Ala Ala Ala Phe Ala Val Asn
1               5                  10                  15

Ser Ala Ala Gly His Tyr Ile Phe Gln Gln Phe Ala Thr Gly Gly Ser
            20                  25                  30

Lys Tyr Pro Pro Trp Lys Tyr Ile Arg Arg Asn Thr Asn Pro Asp Trp
        35                  40                  45

Leu Gln Asn Gly Pro Val Thr Asp Leu Ser Ser Thr Asp Leu Arg Cys
    50                  55                  60

Asn Val Gly Gly Gln Val Ser Asn Gly Thr Glu Thr Ile Thr Leu Asn
65                  70                  75                  80

Ala Gly Asp Glu Phe Ser Phe Ile Leu Asp Thr Pro Val Tyr His Ala
                85                  90                  95

Gly Pro Thr Ser Leu Tyr Met Ser Lys Ala Pro Gly Ala Val Ala Asp
            100                 105                 110

Tyr Asp Gly Gly Gly Ala Trp Phe Lys Ile Tyr Asp Trp Gly Pro Ser
        115                 120                 125

Gly Thr Ser Trp Thr Leu Ser Gly Thr Tyr Thr Gln Arg Ile Pro Lys
    130                 135                 140

Cys Ile Pro Asp Gly Glu Tyr Leu Leu Arg Ile Gln Gln Ile Gly Leu
145                 150                 155                 160

His Asn Pro Gly Ala Ala Pro Gln Phe Tyr Ile Ser Cys Ala Gln Val
                165                 170                 175

Lys Val Val Asp Gly Gly Ser Thr Asn Pro Thr Pro Thr Ala Gln Ile
```

```
                          180                 185                 190
Pro Gly Ala Phe His Ser Asn Asp Pro Gly Leu Thr Val Asn Ile Tyr
            195                 200                 205

Asn Asp Pro Leu Thr Asn Tyr Val Val Pro Gly Pro Arg Val Ser His
            210                 215                 220

Trp
225

<210> SEQ ID NO 60
<211> LENGTH: 205
<212> TYPE: PRT
<213> ORGANISM: Myceliophthora thermophila

<400> SEQUENCE: 60

His Tyr Ile Phe Gln Gln Phe Ala Thr Gly Gly Ser Lys Tyr Pro Pro
1               5                   10                  15

Trp Lys Tyr Ile Arg Arg Asn Thr Asn Pro Asp Trp Leu Gln Asn Gly
            20                  25                  30

Pro Val Thr Asp Leu Ser Ser Thr Asp Leu Arg Cys Asn Val Gly Gly
            35                  40                  45

Gln Val Ser Asn Gly Thr Glu Thr Ile Thr Leu Asn Ala Gly Asp Glu
    50                  55                  60

Phe Ser Phe Ile Leu Asp Thr Pro Val Tyr His Ala Gly Pro Thr Ser
65                  70                  75                  80

Leu Tyr Met Ser Lys Ala Pro Gly Ala Val Ala Asp Tyr Asp Gly Gly
                85                  90                  95

Gly Ala Trp Phe Lys Ile Tyr Asp Trp Gly Pro Ser Gly Thr Ser Trp
            100                 105                 110

Thr Leu Ser Gly Thr Tyr Thr Gln Arg Ile Pro Lys Cys Ile Pro Asp
        115                 120                 125

Gly Glu Tyr Leu Leu Arg Ile Gln Gln Ile Gly Leu His Asn Pro Gly
    130                 135                 140

Ala Ala Pro Gln Phe Tyr Ile Ser Cys Ala Gln Val Lys Val Val Asp
145                 150                 155                 160

Gly Gly Ser Thr Asn Pro Thr Pro Thr Ala Gln Ile Pro Gly Ala Phe
                165                 170                 175

His Ser Asn Asp Pro Gly Leu Thr Val Asn Ile Tyr Asn Asp Pro Leu
            180                 185                 190

Thr Asn Tyr Val Val Pro Gly Pro Arg Val Ser His Trp
        195                 200                 205

<210> SEQ ID NO 61
<211> LENGTH: 1332
<212> TYPE: DNA
<213> ORGANISM: Myceliophthora thermophila

<400> SEQUENCE: 61
atgcacccct cccttctttt cacgcttggg ctggcgagcg tgcttgtccc cctctcgtct     60
gcacacacta ccttcacgac cctcttcgtc aacgatgtca accaaggtga tggtacctgc    120
attcgcatgg cgaagaaggg caatgtcgcc acccatcctc tcgcaggcgg tctcgactcc    180
gaagacatgg cctgtggtcg ggatggtcaa gaacccgtgg catttacgtg tccggcccca    240
gctggtgcca agttgactct cgagtttcgc atgtgggccg atgcttcgca gtccggatcg    300
atcgatccat cccaccttgg cgtcatggcc atctacctca agaaggtttc cgacatgaaa    360
tctgacgcgg ccgctggccc gggctggttc aagatttggg accaaggcta cgacttggcg    420
```

-continued

```
gccaagaagt gggccaccga gaagctcatc gacaacaacg gcctcctgag cgtcaacctt    480
ccaaccggct taccaaccgg ctactacctc gcccgccagg agatcatcac gctccaaaac    540
gttaccaatg acaggccaga gccccagttc tacgtcggct gcgcacagct ctacgtcgag    600
ggcacctcgg actcacccat ccctcggac aagacggtct ccattcccgg ccacatcagc     660
gacccggccg acccgggcct gaccttcaac gtctacacgg cgacgcatc cacctacaag     720
ccgcccggcc ccgaggttta cttccccacc accaccacca ccacctcctc ctcctcctcc    780
ggaagcagcg acaacaaggg agccaggcgc cagcaaaccc ccgacgacaa gcaggccgac    840
ggcctcgttc cagccgactg cctcgtcaag aacgcgaact ggtgcgccgc tgccctgccg    900
ccgtacaccg acgaggccgg ctgctgggcc gccgccgagg actgcaacaa gcagctggac    960
gcgtgctaca ccagcgcacc ccctcgggc agcaaggggt gcaaggtctg ggaggagcag    1020
gtgtgcaccg tcgtctcgca gaagtgcgag gccggggatt tcaaggggcc ccgcagctc    1080
gggaaggagc tcggcgaggg gatcgatgag cctattccgg ggggaaagct gcccccggcg   1140
gtcaacgcgg agagaacgg gaatcatggc ggaggtggtg gtgatgatgg tgatgatgat    1200
aatgatgagg ccggggctgg ggcagcgtcg actccgactt ttgctgctcc tggtgcggcc   1260
aagactcccc aaccaaactc cgagagggcc cggcgccgtg aggcgcattg gcggcgactg   1320
gaatctgctg ag                                                     1332
```

<210> SEQ ID NO 62
<211> LENGTH: 444
<212> TYPE: PRT
<213> ORGANISM: Myceliophthora thermophila

<400> SEQUENCE: 62

```
Met His Pro Ser Leu Leu Phe Thr Leu Gly Leu Ala Ser Val Leu Val
1               5                   10                  15

Pro Leu Ser Ser Ala His Thr Thr Phe Thr Thr Leu Phe Val Asn Asp
                20                  25                  30

Val Asn Gln Gly Asp Gly Thr Cys Ile Arg Met Ala Lys Lys Gly Asn
            35                  40                  45

Val Ala Thr His Pro Leu Ala Gly Gly Leu Asp Ser Glu Asp Met Ala
        50                  55                  60

Cys Gly Arg Asp Gly Gln Glu Pro Val Ala Phe Thr Cys Pro Ala Pro
65                  70                  75                  80

Ala Gly Ala Lys Leu Thr Leu Glu Phe Arg Met Trp Ala Asp Ala Ser
                85                  90                  95

Gln Ser Gly Ser Ile Asp Pro Ser His Leu Gly Val Met Ala Ile Tyr
            100                 105                 110

Leu Lys Lys Val Ser Asp Met Lys Ser Asp Ala Ala Gly Pro Gly
        115                 120                 125

Trp Phe Lys Ile Trp Asp Gln Gly Tyr Asp Leu Ala Ala Lys Lys Trp
    130                 135                 140

Ala Thr Glu Lys Leu Ile Asp Asn Asn Gly Leu Leu Ser Val Asn Leu
145                 150                 155                 160

Pro Thr Gly Leu Pro Thr Gly Tyr Tyr Leu Ala Arg Gln Glu Ile Ile
                165                 170                 175

Thr Leu Gln Asn Val Thr Asn Asp Arg Pro Glu Pro Gln Phe Tyr Val
            180                 185                 190

Gly Cys Ala Gln Leu Tyr Val Glu Gly Thr Ser Asp Ser Pro Ile Pro
        195                 200                 205
```

Ser Asp Lys Thr Val Ser Ile Pro Gly His Ile Ser Asp Pro Ala Asp
210                 215                 220

Pro Gly Leu Thr Phe Asn Val Tyr Thr Gly Asp Ala Ser Thr Tyr Lys
225                 230                 235                 240

Pro Pro Gly Pro Glu Val Tyr Phe Pro Thr Thr Thr Thr Thr Thr Ser
                245                 250                 255

Ser Ser Ser Ser Gly Ser Ser Asp Asn Lys Gly Ala Arg Arg Gln Gln
            260                 265                 270

Thr Pro Asp Asp Lys Gln Ala Asp Gly Leu Val Pro Ala Asp Cys Leu
        275                 280                 285

Val Lys Asn Ala Asn Trp Cys Ala Ala Ala Leu Pro Pro Tyr Thr Asp
290                 295                 300

Glu Ala Gly Cys Trp Ala Ala Ala Glu Asp Cys Asn Lys Gln Leu Asp
305                 310                 315                 320

Ala Cys Tyr Thr Ser Ala Pro Pro Ser Gly Ser Lys Gly Cys Lys Val
                325                 330                 335

Trp Glu Glu Gln Val Cys Thr Val Val Ser Gln Lys Cys Glu Ala Gly
            340                 345                 350

Asp Phe Lys Gly Pro Pro Gln Leu Gly Lys Glu Leu Gly Glu Gly Ile
        355                 360                 365

Asp Glu Pro Ile Pro Gly Gly Lys Leu Pro Ala Val Asn Ala Gly
370                 375                 380

Glu Asn Gly Asn His Gly Gly Gly Gly Asp Asp Gly Asp Asp
385                 390                 395                 400

Asn Asp Glu Ala Gly Ala Gly Ala Ala Ser Thr Pro Thr Phe Ala Ala
                405                 410                 415

Pro Gly Ala Ala Lys Thr Pro Gln Pro Asn Ser Glu Arg Ala Arg Arg
            420                 425                 430

Arg Glu Ala His Trp Arg Arg Leu Glu Ser Ala Glu
            435                 440

<210> SEQ ID NO 63
<211> LENGTH: 423
<212> TYPE: PRT
<213> ORGANISM: Myceliophthora thermophila

<400> SEQUENCE: 63

His Thr Thr Phe Thr Thr Leu Phe Val Asn Asp Val Asn Gln Gly Asp
1               5                   10                  15

Gly Thr Cys Ile Arg Met Ala Lys Lys Gly Asn Val Ala Thr His Pro
                20                  25                  30

Leu Ala Gly Gly Leu Asp Ser Glu Asp Met Ala Cys Gly Arg Asp Gly
            35                  40                  45

Gln Glu Pro Val Ala Phe Thr Cys Pro Ala Pro Ala Gly Ala Lys Leu
    50                  55                  60

Thr Leu Glu Phe Arg Met Trp Ala Asp Ala Ser Gln Ser Gly Ser Ile
65                  70                  75                  80

Asp Pro Ser His Leu Gly Val Met Ala Ile Tyr Leu Lys Lys Val Ser
                85                  90                  95

Asp Met Lys Ser Asp Ala Ala Ala Gly Pro Gly Trp Phe Lys Ile Trp
            100                 105                 110

Asp Gln Gly Tyr Asp Leu Ala Ala Lys Lys Trp Ala Thr Glu Lys Leu
    115                 120                 125

Ile Asp Asn Asn Gly Leu Leu Ser Val Asn Leu Pro Thr Gly Leu Pro

|     |     |     |     |     |     |     |     |     |     |     |
|---|---|---|---|---|---|---|---|---|---|---|
| | | 130 | | | | 135 | | | | 140 |

Thr Gly Tyr Tyr Leu Ala Arg Gln Glu Ile Ile Thr Leu Gln Asn Val
145                    150                    155                    160

Thr Asn Asp Arg Pro Glu Pro Gln Phe Tyr Val Gly Cys Ala Gln Leu
                165                    170                    175

Tyr Val Glu Gly Thr Ser Asp Ser Pro Ile Pro Ser Asp Lys Thr Val
            180                    185                    190

Ser Ile Pro Gly His Ile Ser Asp Pro Ala Asp Pro Gly Leu Thr Phe
        195                    200                    205

Asn Val Tyr Thr Gly Asp Ala Ser Thr Tyr Lys Pro Pro Gly Pro Glu
    210                    215                    220

Val Tyr Phe Pro Thr Thr Thr Thr Thr Ser Ser Ser Ser Ser Ser Gly
225                    230                    235                    240

Ser Ser Asp Asn Lys Gly Ala Arg Arg Gln Gln Thr Pro Asp Asp Lys
            245                    250                    255

Gln Ala Asp Gly Leu Val Pro Ala Asp Cys Leu Val Lys Asn Ala Asn
                260                    265                    270

Trp Cys Ala Ala Ala Leu Pro Pro Tyr Thr Asp Glu Ala Gly Cys Trp
        275                    280                    285

Ala Ala Ala Glu Asp Cys Asn Lys Gln Leu Asp Ala Cys Tyr Thr Ser
    290                    295                    300

Ala Pro Pro Ser Gly Ser Lys Gly Cys Lys Val Trp Glu Glu Gln Val
305                    310                    315                    320

Cys Thr Val Val Ser Gln Lys Cys Glu Ala Gly Asp Phe Lys Gly Pro
            325                    330                    335

Pro Gln Leu Gly Lys Glu Leu Gly Glu Gly Ile Asp Glu Pro Ile Pro
                340                    345                    350

Gly Gly Lys Leu Pro Pro Ala Val Asn Ala Gly Glu Asn Gly Asn His
        355                    360                    365

Gly Gly Gly Gly Gly Asp Asp Gly Asp Asp Asp Asn Asp Glu Ala Gly
    370                    375                    380

Ala Gly Ala Ala Ser Thr Pro Thr Phe Ala Ala Pro Gly Ala Ala Lys
385                    390                    395                    400

Thr Pro Gln Pro Asn Ser Glu Arg Ala Arg Arg Glu Ala His Trp
                405                    410                    415

Arg Arg Leu Glu Ser Ala Glu
        420

```
<210> SEQ ID NO 64
<211> LENGTH: 834
<212> TYPE: DNA
<213> ORGANISM: Myceliophthora thermophila

<400> SEQUENCE: 64
```

| | | |
|---|---|---|
| atgttttctc tcaagttctt tatcttggcc ggtgggcttg ctgtcctcac cgaggctcac | 60 |
| ataagactag tgtcgcccgc ccctttacc aaccctgacc agggcccag cccactccta | 120 |
| gaggctggca gcgactatcc ctgccacaac ggcaatgggg gcggttatca gggaacgcca | 180 |
| acccagatgg caaagggttc taagcagcag ctagccttcc aggggtctgc cgttcatggg | 240 |
| ggtggctcct gccaagtgtc catcacctac gacgaaaacc cgaccgctca gagctccttc | 300 |
| aaggtcattc actcgattca aggtggctgc cccgccaggg ccgagacgat cccggattgc | 360 |
| agcgcacaaa atatcaacgc ctgcaatata aagcccgata tgcccagat ggacaccccg | 420 |
| gataagtatg agttcacgat cccggaggat ctccccagtg gcaaggccac cctcgcctgg | 480 |

```
acatggatca acactatcgg caaccgcgag ttttatatgg catgcgcccc ggttgagatc    540
accggcgacg gcggtagcga gtcggctctg gctgcgctgc ccgacatggt cattgccaac    600
atcccgtcca tcggaggaac ctgcgcgacc gaggagggga agtactacga atatcccaac    660
cccggtaagt cggtcgaaac catcccgggc tggaccgatt tggttcccct gcaaggcgaa    720
tgcggtgctg cctccggtgt ctcgggctcc ggcggaaacg ccagcagtgc taccccctgcc    780 gcagggccg ccccgactcc tgctgtccgc ggccgccgtc ccacctggaa cgcc           834
```

<210> SEQ ID NO 65
<211> LENGTH: 278
<212> TYPE: PRT
<213> ORGANISM: Myceliophthora thermophila

<400> SEQUENCE: 65

```
Met Phe Ser Leu Lys Phe Phe Ile Leu Ala Gly Gly Leu Ala Val Leu
1               5                   10                  15

Thr Glu Ala His Ile Arg Leu Val Ser Pro Ala Pro Phe Thr Asn Pro
            20                  25                  30

Asp Gln Gly Pro Ser Pro Leu Leu Glu Ala Gly Ser Asp Tyr Pro Cys
        35                  40                  45

His Asn Gly Asn Gly Gly Tyr Gln Gly Thr Pro Thr Gln Met Ala
    50                  55                  60

Lys Gly Ser Lys Gln Gln Leu Ala Phe Gln Gly Ser Ala Val His Gly
65                  70                  75                  80

Gly Gly Ser Cys Gln Val Ser Ile Thr Tyr Asp Glu Asn Pro Thr Ala
                85                  90                  95

Gln Ser Ser Phe Lys Val Ile His Ser Ile Gln Gly Gly Cys Pro Ala
            100                 105                 110

Arg Ala Glu Thr Ile Pro Asp Cys Ser Ala Gln Asn Ile Asn Ala Cys
        115                 120                 125

Asn Ile Lys Pro Asp Asn Ala Gln Met Asp Thr Pro Asp Lys Tyr Glu
    130                 135                 140

Phe Thr Ile Pro Glu Asp Leu Pro Ser Gly Lys Ala Thr Leu Ala Trp
145                 150                 155                 160

Thr Trp Ile Asn Thr Ile Gly Asn Arg Glu Phe Tyr Met Ala Cys Ala
                165                 170                 175

Pro Val Glu Ile Thr Gly Asp Gly Gly Ser Glu Ser Ala Leu Ala Ala
            180                 185                 190

Leu Pro Asp Met Val Ile Ala Asn Ile Pro Ser Ile Gly Gly Thr Cys
        195                 200                 205

Ala Thr Glu Glu Gly Lys Tyr Tyr Glu Tyr Pro Asn Pro Gly Lys Ser
    210                 215                 220

Val Glu Thr Ile Pro Gly Trp Thr Asp Leu Val Pro Leu Gln Gly Glu
225                 230                 235                 240

Cys Gly Ala Ala Ser Gly Val Ser Gly Ser Gly Gly Asn Ala Ser Ser
                245                 250                 255

Ala Thr Pro Ala Ala Gly Ala Ala Pro Thr Pro Ala Val Arg Gly Arg
            260                 265                 270

Arg Pro Thr Trp Asn Ala
        275
```

<210> SEQ ID NO 66
<211> LENGTH: 259
<212> TYPE: PRT

<213> ORGANISM: Myceliophthora thermophila

<400> SEQUENCE: 66

| | | | | | | | | | | | | | | | |
|---|---|---|---|---|---|---|---|---|---|---|---|---|---|---|---|
| His | Ile | Arg | Leu | Val | Ser | Pro | Ala | Pro | Phe | Thr | Asn | Pro | Asp | Gln | Gly |
| 1 | | | | 5 | | | | | 10 | | | | | 15 | |
| Pro | Ser | Pro | Leu | Leu | Glu | Ala | Gly | Ser | Asp | Tyr | Pro | Cys | His | Asn | Gly |
| | | | 20 | | | | | 25 | | | | | 30 | | |
| Asn | Gly | Gly | Gly | Tyr | Gln | Gly | Thr | Pro | Thr | Gln | Met | Ala | Lys | Gly | Ser |
| | | 35 | | | | | 40 | | | | | 45 | | | |
| Lys | Gln | Gln | Leu | Ala | Phe | Gln | Gly | Ser | Ala | Val | His | Gly | Gly | Gly | Ser |
| | 50 | | | | | 55 | | | | | 60 | | | | |
| Cys | Gln | Val | Ser | Ile | Thr | Tyr | Asp | Glu | Asn | Pro | Thr | Ala | Gln | Ser | Ser |
| 65 | | | | 70 | | | | | 75 | | | | | 80 | |
| Phe | Lys | Val | Ile | His | Ser | Ile | Gln | Gly | Gly | Cys | Pro | Ala | Arg | Ala | Glu |
| | | | 85 | | | | | 90 | | | | | 95 | | |
| Thr | Ile | Pro | Asp | Cys | Ser | Ala | Gln | Asn | Ile | Asn | Ala | Cys | Asn | Ile | Lys |
| | | | 100 | | | | | 105 | | | | | 110 | | |
| Pro | Asp | Asn | Ala | Gln | Met | Asp | Thr | Pro | Asp | Lys | Tyr | Glu | Phe | Thr | Ile |
| | | | 115 | | | | | 120 | | | | | 125 | | |
| Pro | Glu | Asp | Leu | Pro | Ser | Gly | Lys | Ala | Thr | Leu | Ala | Trp | Thr | Trp | Ile |
| | | 130 | | | | | 135 | | | | | 140 | | | |
| Asn | Thr | Ile | Gly | Asn | Arg | Glu | Phe | Tyr | Met | Ala | Cys | Ala | Pro | Val | Glu |
| 145 | | | | | 150 | | | | | 155 | | | | | 160 |
| Ile | Thr | Gly | Asp | Gly | Ser | Glu | Ser | Ala | Leu | Ala | Ala | Leu | Pro | Asp | |
| | | | 165 | | | | | 170 | | | | | 175 | | |
| Met | Val | Ile | Ala | Asn | Ile | Pro | Ser | Ile | Gly | Thr | Cys | Ala | Thr | Glu | |
| | | | 180 | | | | | 185 | | | | | 190 | | |
| Glu | Gly | Lys | Tyr | Tyr | Glu | Tyr | Pro | Asn | Pro | Gly | Lys | Ser | Val | Glu | Thr |
| | | | 195 | | | | | 200 | | | | | 205 | | |
| Ile | Pro | Gly | Trp | Thr | Asp | Leu | Val | Pro | Leu | Gln | Gly | Glu | Cys | Gly | Ala |
| | | 210 | | | | | 215 | | | | | 220 | | | |
| Ala | Ser | Gly | Val | Ser | Gly | Ser | Gly | Asn | Ala | Ser | Ser | Ala | Thr | Pro | |
| 225 | | | | 230 | | | | | 235 | | | | | 240 | |
| Ala | Ala | Gly | Ala | Ala | Pro | Thr | Pro | Ala | Val | Arg | Gly | Arg | Pro | Thr | |
| | | | 245 | | | | | 250 | | | | | 255 | | |
| Trp | Asn | Ala | | | | | | | | | | | | | |

<210> SEQ ID NO 67
<211> LENGTH: 672
<212> TYPE: DNA
<213> ORGANISM: Myceliophthora thermophila

<400> SEQUENCE: 67

```
atgaagctcg ccacgctcct cgccgccctc accctcgggg tggccgacca gctcagcgtc      60
gggtccagaa agtttggcgt gtacgagcac attcgcaaga acacgaacta caactcgccc     120
gttaccgacc tgtcggacac caacctgcgc tgcaacgtcg gcggggggctc gggcaccagc     180
accaccgtgc tcgacgtcaa ggccggagac tcgttcacct tcttcagcga cgttgccgtc     240
taccaccagg ggcccatctc gctgtgcgtg gaccggacca gtgcagagag catggatgga     300
cgggaaccgg acatgcgctg ccgaactggc tcacaagctg gctacctggc ggtgactgac     360
tacgacgggt ccggtgactg tttcaagatc tatgactggg accgacgtt caacgggggc     420
caggcgtcgt ggccgacgag gaattcgtac gagtacagca tcctcaagtg catcagggac     480
ggcgaatacc tactgcggat tcagtccctg gccatccata acccaggtgc ccttccgcag     540
```

```
ttctacatca gctgcgccca ggtgaatgtg acgggcggag gcaccgtcac cccgagatca    600
aggcgaccga tcctgatcta tttcaacttc cactcgtata tcgtccctgg gccggcagtg    660
ttcaagtgct ag                                                        672
```

<210> SEQ ID NO 68
<211> LENGTH: 223
<212> TYPE: PRT
<213> ORGANISM: Myceliophthora thermophila

<400> SEQUENCE: 68

```
Met Lys Leu Ala Thr Leu Leu Ala Ala Leu Thr Leu Gly Val Ala Asp
1               5                   10                  15

Gln Leu Ser Val Gly Ser Arg Lys Phe Gly Val Tyr Glu His Ile Arg
            20                  25                  30

Lys Asn Thr Asn Tyr Asn Ser Pro Val Thr Asp Leu Ser Asp Thr Asn
        35                  40                  45

Leu Arg Cys Asn Val Gly Gly Gly Ser Gly Thr Ser Thr Thr Val Leu
    50                  55                  60

Asp Val Lys Ala Gly Asp Ser Phe Thr Phe Phe Ser Asp Val Ala Val
65                  70                  75                  80

Tyr His Gln Gly Pro Ile Ser Leu Cys Val Asp Arg Thr Ser Ala Glu
                85                  90                  95

Ser Met Asp Gly Arg Glu Pro Asp Met Arg Cys Arg Thr Gly Ser Gln
            100                 105                 110

Ala Gly Tyr Leu Ala Val Thr Asp Tyr Asp Gly Ser Gly Asp Cys Phe
        115                 120                 125

Lys Ile Tyr Asp Trp Gly Pro Thr Phe Asn Gly Gly Gln Ala Ser Trp
    130                 135                 140

Pro Thr Arg Asn Ser Tyr Glu Tyr Ser Ile Leu Lys Cys Ile Arg Asp
145                 150                 155                 160

Gly Glu Tyr Leu Leu Arg Ile Gln Ser Leu Ala Ile His Asn Pro Gly
                165                 170                 175

Ala Leu Pro Gln Phe Tyr Ile Ser Cys Ala Gln Val Asn Val Thr Gly
            180                 185                 190

Gly Gly Thr Val Thr Pro Arg Ser Arg Arg Pro Ile Leu Ile Tyr Phe
        195                 200                 205

Asn Phe His Ser Tyr Ile Val Pro Gly Pro Ala Val Phe Lys Cys
    210                 215                 220
```

<210> SEQ ID NO 69
<211> LENGTH: 208
<212> TYPE: PRT
<213> ORGANISM: Myceliophthora thermophila

<400> SEQUENCE: 69

```
Asp Gln Leu Ser Val Gly Ser Arg Lys Phe Gly Val Tyr Glu His Ile
1               5                   10                  15

Arg Lys Asn Thr Asn Tyr Asn Ser Pro Val Thr Asp Leu Ser Asp Thr
            20                  25                  30

Asn Leu Arg Cys Asn Val Gly Gly Gly Ser Gly Thr Ser Thr Thr Val
        35                  40                  45

Leu Asp Val Lys Ala Gly Asp Ser Phe Thr Phe Phe Ser Asp Val Ala
    50                  55                  60

Val Tyr His Gln Gly Pro Ile Ser Leu Cys Val Asp Arg Thr Ser Ala
65                  70                  75                  80
```

```
Glu Ser Met Asp Gly Arg Glu Pro Asp Met Arg Cys Arg Thr Gly Ser
                85                  90                  95

Gln Ala Gly Tyr Leu Ala Val Thr Asp Tyr Asp Gly Ser Gly Asp Cys
            100                 105                 110

Phe Lys Ile Tyr Asp Trp Gly Pro Thr Phe Asn Gly Gly Gln Ala Ser
        115                 120                 125

Trp Pro Thr Arg Asn Ser Tyr Glu Tyr Ser Ile Leu Lys Cys Ile Arg
    130                 135                 140

Asp Gly Glu Tyr Leu Leu Arg Ile Gln Ser Leu Ala Ile His Asn Pro
145                 150                 155                 160

Gly Ala Leu Pro Gln Phe Tyr Ile Ser Cys Ala Gln Val Asn Val Thr
                165                 170                 175

Gly Gly Gly Thr Val Thr Pro Arg Ser Arg Arg Pro Ile Leu Ile Tyr
            180                 185                 190

Phe Asn Phe His Ser Tyr Ile Val Pro Gly Pro Ala Val Phe Lys Cys
        195                 200                 205
```

<210> SEQ ID NO 70
<211> LENGTH: 642
<212> TYPE: DNA
<213> ORGANISM: Myceliophthora thermophila

<400> SEQUENCE: 70

```
atgaagctcg ccacgctcct cgccgccctc accctcgggc tcagcgtcgg gtccagaaag    60
tttggcgtgt acgagcacat tcgcaagaac acgaactaca actcgcccgt taccgacctg   120
tcggacacca acctgcgctg caacgtcggc gggggctcgg gcaccagcac caccgtgctc   180
gacgtcaagg ccgagactc gttcaccttc tcagcgacg ttgccgtcta ccaccagggg    240
cccatctcgc tgtgcgtgga ccggaccagt gcagagagca tggatggacg ggaaccggac   300
atgcgctgcc gaactggctc acaagctggc tacctggcgg tgactgtgat gactgtgact   360
gactacgacg gtccggtga ctgttttcaag atctatgact ggggaccgac gttcaacggg   420
ggccaggcgt cgtggccgac gaggaattcg tacgagtaca gcatcctcaa gtgcatcagg   480
gacggcgaat acctactgcg gattcagtcc ctggccatcc ataacccagg tgcccttccg   540
cagttctaca tcagctgcgc ccaggtgaat gtgacgggcg aggcaccat ctatttcaac    600
ttccactcgt atatcgtccc tgggccggca gtgttcaagt gc                      642
```

<210> SEQ ID NO 71
<211> LENGTH: 214
<212> TYPE: PRT
<213> ORGANISM: Myceliophthora thermophila

<400> SEQUENCE: 71

```
Met Lys Leu Ala Thr Leu Leu Ala Ala Leu Thr Leu Gly Leu Ser Val
1               5                   10                  15

Gly Ser Arg Lys Phe Gly Val Tyr Glu His Ile Arg Lys Asn Thr Asn
            20                  25                  30

Tyr Asn Ser Pro Val Thr Asp Leu Ser Asp Thr Asn Leu Arg Cys Asn
        35                  40                  45

Val Gly Gly Gly Ser Gly Thr Ser Thr Thr Val Leu Asp Val Lys Ala
    50                  55                  60

Gly Asp Ser Phe Thr Phe Phe Ser Asp Val Ala Val Tyr His Gln Gly
65                  70                  75                  80

Pro Ile Ser Leu Cys Val Asp Arg Thr Ser Ala Glu Ser Met Asp Gly
```

```
                        85                  90                  95
Arg Glu Pro Asp Met Arg Cys Arg Thr Gly Ser Gln Ala Gly Tyr Leu
            100                 105                 110

Ala Val Thr Val Met Thr Val Thr Asp Tyr Asp Gly Ser Gly Asp Cys
            115                 120                 125

Phe Lys Ile Tyr Asp Trp Gly Pro Thr Phe Asn Gly Gln Ala Ser
            130                 135                 140

Trp Pro Thr Arg Asn Ser Tyr Glu Tyr Ser Ile Leu Lys Cys Ile Arg
145                 150                 155                 160

Asp Gly Glu Tyr Leu Leu Arg Ile Gln Ser Leu Ala Ile His Asn Pro
                165                 170                 175

Gly Ala Leu Pro Gln Phe Tyr Ile Ser Cys Ala Gln Val Asn Val Thr
                180                 185                 190

Gly Gly Gly Thr Ile Tyr Phe Asn Phe His Ser Tyr Ile Val Pro Gly
            195                 200                 205

Pro Ala Val Phe Lys Cys
        210

<210> SEQ ID NO 72
<211> LENGTH: 196
<212> TYPE: PRT
<213> ORGANISM: Myceliophthora thermophila

<400> SEQUENCE: 72

Arg Lys Phe Gly Val Tyr Glu His Ile Arg Lys Asn Thr Asn Tyr Asn
1               5                   10                  15

Ser Pro Val Thr Asp Leu Ser Asp Thr Asn Leu Arg Cys Asn Val Gly
            20                  25                  30

Gly Gly Ser Gly Thr Ser Thr Thr Val Leu Asp Val Lys Ala Gly Asp
        35                  40                  45

Ser Phe Thr Phe Phe Ser Asp Val Ala Val Tyr His Gln Gly Pro Ile
    50                  55                  60

Ser Leu Cys Val Asp Arg Thr Ser Ala Glu Ser Met Asp Gly Arg Glu
65                  70                  75                  80

Pro Asp Met Arg Cys Arg Thr Gly Ser Gln Ala Gly Tyr Leu Ala Val
                85                  90                  95

Thr Val Met Thr Val Thr Asp Tyr Asp Gly Ser Gly Asp Cys Phe Lys
            100                 105                 110

Ile Tyr Asp Trp Gly Pro Thr Phe Asn Gly Gln Ala Ser Trp Pro
            115                 120                 125

Thr Arg Asn Ser Tyr Glu Tyr Ser Ile Leu Lys Cys Ile Arg Asp Gly
        130                 135                 140

Glu Tyr Leu Leu Arg Ile Gln Ser Leu Ala Ile His Asn Pro Gly Ala
145                 150                 155                 160

Leu Pro Gln Phe Tyr Ile Ser Cys Ala Gln Val Asn Val Thr Gly Gly
                165                 170                 175

Gly Thr Ile Tyr Phe Asn Phe His Ser Tyr Ile Val Pro Gly Pro Ala
            180                 185                 190

Val Phe Lys Cys
        195

<210> SEQ ID NO 73
<211> LENGTH: 579
<212> TYPE: DNA
<213> ORGANISM: Myceliophthora thermophila
```

<400> SEQUENCE: 73

```
atgaccaaga atgcgcagag caagcagggc gttgagaacc caacaagcgg cgacatccgc    60
tgctacacct cgcagacggc ggccaacgtc gtgaccgtgc cggccggctc gaccattcac   120
tacatctcga cccagcagat caaccacccc ggcccgactc agtactacct ggccaaggta   180
ccccccggct cgtcggccaa gacctttgac gggtccggcg ccgtctggtt caagatctcg   240
accacgatgc ctaccgtgga cagcaacaag cagatgttct ggccagggca gaacacttat   300
gagacctcaa acaccaccat tcccgccaac accccggacg gcgagtacct ccttcgcgtc   360
aagcagatcg ccctccacat ggcgtctcag cccaacaagg tccagttcta cctcgcctgc   420
acccagatca agatcaccgg tggtcgcaac ggcaccccca gcccgctggt cgcgctgccc   480
ggagcctaca agagcaccga ccccggcatc ctggtcgaca tctactccat gaagcccgaa   540
tcgtaccagc tcccgggcc gcccgtctgg cgcggctaa                           579
```

<210> SEQ ID NO 74
<211> LENGTH: 192
<212> TYPE: PRT
<213> ORGANISM: Myceliophthora thermophila

<400> SEQUENCE: 74

```
Met Thr Lys Asn Ala Gln Ser Lys Gln Gly Val Glu Asn Pro Thr Ser
1               5                   10                  15
Gly Asp Ile Arg Cys Tyr Thr Ser Gln Thr Ala Ala Asn Val Val Thr
                20                  25                  30
Val Pro Ala Gly Ser Thr Ile His Tyr Ile Ser Thr Gln Gln Ile Asn
            35                  40                  45
His Pro Gly Pro Thr Gln Tyr Tyr Leu Ala Lys Val Pro Pro Gly Ser
        50                  55                  60
Ser Ala Lys Thr Phe Asp Gly Ser Gly Ala Val Trp Phe Lys Ile Ser
65                  70                  75                  80
Thr Thr Met Pro Thr Val Asp Ser Asn Lys Gln Met Phe Trp Pro Gly
                85                  90                  95
Gln Asn Thr Tyr Glu Thr Ser Asn Thr Thr Ile Pro Ala Asn Thr Pro
            100                 105                 110
Asp Gly Glu Tyr Leu Leu Arg Val Lys Gln Ile Ala Leu His Met Ala
        115                 120                 125
Ser Gln Pro Asn Lys Val Gln Phe Tyr Leu Ala Cys Thr Gln Ile Lys
    130                 135                 140
Ile Thr Gly Gly Arg Asn Gly Thr Pro Ser Pro Leu Val Ala Leu Pro
145                 150                 155                 160
Gly Ala Tyr Lys Ser Thr Asp Pro Gly Ile Leu Val Asp Ile Tyr Ser
                165                 170                 175
Met Lys Pro Glu Ser Tyr Gln Pro Pro Gly Pro Val Trp Arg Gly
            180                 185                 190
```

<210> SEQ ID NO 75
<211> LENGTH: 672
<212> TYPE: DNA
<213> ORGANISM: Myceliophthora thermophila

<400> SEQUENCE: 75

```
atgaggcttc tcgcaagctt gttgctcgca gctacggctg ttcaagctca ctttgttaac    60
ggacagcccg aagagagtga ctggtcagcc acgcgcatga ccaagaatgc gcagagcaag   120
cagggcgttg agaacccaac aagcggcgac atccgctgct acacctcgca gacggcggcc   180
```

-continued

```
aacgtcgtga ccgtgccggc cggctcgacc attcactaca tctcgaccca gcagatcaac    240 cacccoggcc cgactcagta ctacctggcc aaggtacccc ccggctcgtc ggccaagacc    300
tttgacgggt ccggcgccgt ctggttcaag atctcgacca cgatgcctac cgtggacagc    360
aacaagcaga tgttctggcc agggcagaac acttatgaga cctcaaacac caccattccc    420
gccaacaccc cggacggcga gtacctcctt cgcgtcaagc agatcgccct ccacatggcg    480
tctcagccca caaggtcca gttctacctc gcctgcaccc agatcaagat caccggtggt    540
cgcaacggca ccccagccc gctggtcgcg ctgcccggag cctacaagag caccgacccc    600
ggcatcctgg tcgacatcta ctccatgaag cccgaatcgt accagcctcc cgggccgccc    660
gtctggcgcg gc                                                         672
```

<210> SEQ ID NO 76
<211> LENGTH: 224
<212> TYPE: PRT
<213> ORGANISM: Myceliophthora thermophila

<400> SEQUENCE: 76

```
Met Arg Leu Leu Ala Ser Leu Leu Ala Thr Ala Val Gln Ala
1               5                   10                  15

His Phe Val Asn Gly Gln Pro Glu Glu Ser Asp Trp Ser Ala Thr Arg
                20                  25                  30

Met Thr Lys Asn Ala Gln Ser Lys Gln Gly Val Glu Asn Pro Thr Ser
            35                  40                  45

Gly Asp Ile Arg Cys Tyr Thr Ser Gln Thr Ala Ala Asn Val Val Thr
        50                  55                  60

Val Pro Ala Gly Ser Thr Ile His Tyr Ile Ser Thr Gln Gln Ile Asn
65                  70                  75                  80

His Pro Gly Pro Thr Gln Tyr Tyr Leu Ala Lys Val Pro Pro Gly Ser
                85                  90                  95

Ser Ala Lys Thr Phe Asp Gly Ser Gly Ala Val Trp Phe Lys Ile Ser
            100                 105                 110

Thr Thr Met Pro Thr Val Asp Ser Asn Lys Gln Met Phe Trp Pro Gly
        115                 120                 125

Gln Asn Thr Tyr Glu Thr Ser Asn Thr Thr Ile Pro Ala Asn Thr Pro
    130                 135                 140

Asp Gly Glu Tyr Leu Leu Arg Val Lys Gln Ile Ala Leu His Met Ala
145                 150                 155                 160

Ser Gln Pro Asn Lys Val Gln Phe Tyr Leu Ala Cys Thr Gln Ile Lys
                165                 170                 175

Ile Thr Gly Gly Arg Asn Gly Thr Pro Ser Pro Leu Val Ala Leu Pro
            180                 185                 190

Gly Ala Tyr Lys Ser Thr Asp Pro Gly Ile Leu Val Asp Ile Tyr Ser
        195                 200                 205

Met Lys Pro Glu Ser Tyr Gln Pro Pro Gly Pro Val Trp Arg Gly
    210                 215                 220
```

<210> SEQ ID NO 77
<211> LENGTH: 208
<212> TYPE: PRT
<213> ORGANISM: Myceliophthora thermophila

<400> SEQUENCE: 77

```
His Phe Val Asn Gly Gln Pro Glu Glu Ser Asp Trp Ser Ala Thr Arg
1               5                   10                  15
```

```
Met Thr Lys Asn Ala Gln Ser Lys Gln Gly Val Glu Asn Pro Thr Ser
         20                  25                  30

Gly Asp Ile Arg Cys Tyr Thr Ser Gln Thr Ala Ala Asn Val Val Thr
             35                  40                  45

Val Pro Ala Gly Ser Thr Ile His Tyr Ile Ser Thr Gln Gln Ile Asn
 50                  55                  60

His Pro Gly Pro Thr Gln Tyr Tyr Leu Ala Lys Val Pro Pro Gly Ser
 65                  70                  75                  80

Ser Ala Lys Thr Phe Asp Gly Ser Gly Ala Val Trp Phe Lys Ile Ser
                 85                  90                  95

Thr Thr Met Pro Thr Val Asp Ser Asn Lys Gln Met Phe Trp Pro Gly
            100                 105                 110

Gln Asn Thr Tyr Glu Thr Ser Asn Thr Thr Ile Pro Ala Asn Thr Pro
        115                 120                 125

Asp Gly Glu Tyr Leu Leu Arg Val Lys Gln Ile Ala Leu His Met Ala
130                 135                 140

Ser Gln Pro Asn Lys Val Gln Phe Tyr Leu Ala Cys Thr Gln Ile Lys
145                 150                 155                 160

Ile Thr Gly Gly Arg Asn Gly Thr Pro Ser Pro Leu Val Ala Leu Pro
                165                 170                 175

Gly Ala Tyr Lys Ser Thr Asp Pro Gly Ile Leu Val Asp Ile Tyr Ser
            180                 185                 190

Met Lys Pro Glu Ser Tyr Gln Pro Pro Gly Pro Val Trp Arg Gly
        195                 200                 205
```

<210> SEQ ID NO 78
<211> LENGTH: 849
<212> TYPE: DNA
<213> ORGANISM: Myceliophthora thermophila

<400> SEQUENCE: 78

```
atgaagccct ttagcctcgt cgccctggcg actgccgtga gcggccatgc catcttccag      60
cgggtgtcgg tcaacgggca ggaccagggc cagctcaagg gggtgcgggc gccgtcgagc    120
aactccccga tccagaacgt caacgatgcc aacatggcct gcaacgccaa cattgtgtac    180
cacgacaaca ccatcatcaa ggtgcccgcg ggagcccgcg tcggcgcgtg gtggcagcac    240
gtcatcggcg ggccgcaggg cgccaacgac ccggacaacc cgatcgccgc ctcccacaag    300
ggccccatcc aggtctacct ggccaaggtg acaacgcgg cgacggcgtc gccgtcgggc     360
ctcaagtggt tcaaggtggc cgagcgcggc ctgaacaacg gcgtgtgggc ctacctgatg    420
cgcgtcgagc tgctcgcccct gcacagcgcc tcgagccccg cggcgcccca gttctacatg    480
ggctgtgcac agatcgaagt cactggctcc ggcaccaact cgggctccga ctttgtctcg    540
ttccccggcg cctactcggc caacgacccg gcatcttgc tgagcatcta cgacagctcg     600
ggcaagccca caatggcgg cgctcgtac ccgatccccg cccgcgccc catctcctgc       660
tccggcagcg gcggcggcgg caacaacggc ggcgacggcg cgacgacaa caacggtggt    720
ggcaacaaca acggcggcgg cagcgtcccc ctgtacgggc agtgcggcgg catcggctac    780
acgggcccga ccacctgtgc ccagggaact tgcaaggtgt cgaacgaata ctacagccag    840
tgcctcccc                                                            849
```

<210> SEQ ID NO 79
<211> LENGTH: 283
<212> TYPE: PRT

<213> ORGANISM: Myceliophthora thermophila

<400> SEQUENCE: 79

Met Lys Pro Phe Ser Leu Val Ala Leu Ala Thr Ala Val Ser Gly His
1               5                   10                  15

Ala Ile Phe Gln Arg Val Ser Val Asn Gly Gln Asp Gln Gly Gln Leu
            20                  25                  30

Lys Gly Val Arg Ala Pro Ser Ser Asn Ser Pro Ile Gln Asn Val Asn
        35                  40                  45

Asp Ala Asn Met Ala Cys Asn Ala Asn Ile Val Tyr His Asp Asn Thr
    50                  55                  60

Ile Ile Lys Val Pro Ala Gly Ala Arg Val Gly Ala Trp Trp Gln His
65                  70                  75                  80

Val Ile Gly Gly Pro Gln Gly Ala Asn Asp Pro Asp Asn Pro Ile Ala
                85                  90                  95

Ala Ser His Lys Gly Pro Ile Gln Val Tyr Leu Ala Lys Val Asp Asn
            100                 105                 110

Ala Ala Thr Ala Ser Pro Ser Gly Leu Lys Trp Phe Lys Val Ala Glu
        115                 120                 125

Arg Gly Leu Asn Asn Gly Val Trp Ala Tyr Leu Met Arg Val Glu Leu
    130                 135                 140

Leu Ala Leu His Ser Ala Ser Ser Pro Gly Gly Ala Gln Phe Tyr Met
145                 150                 155                 160

Gly Cys Ala Gln Ile Glu Val Thr Gly Ser Gly Thr Asn Ser Gly Ser
                165                 170                 175

Asp Phe Val Ser Phe Pro Gly Ala Tyr Ser Ala Asn Asp Pro Gly Ile
            180                 185                 190

Leu Leu Ser Ile Tyr Asp Ser Ser Gly Lys Pro Asn Asn Gly Gly Arg
        195                 200                 205

Ser Tyr Pro Ile Pro Gly Pro Arg Pro Ile Ser Cys Ser Gly Ser Gly
    210                 215                 220

Gly Gly Gly Asn Asn Gly Gly Asp Gly Gly Asp Asp Asn Asn Gly Gly
225                 230                 235                 240

Gly Asn Asn Asn Gly Gly Ser Val Pro Leu Tyr Gly Gln Cys Gly
                245                 250                 255

Gly Ile Gly Tyr Thr Gly Pro Thr Thr Cys Ala Gln Gly Thr Cys Lys
            260                 265                 270

Val Ser Asn Glu Tyr Tyr Ser Gln Cys Leu Pro
        275                 280

<210> SEQ ID NO 80
<211> LENGTH: 268
<212> TYPE: PRT
<213> ORGANISM: Myceliophthora thermophila

<400> SEQUENCE: 80

His Ala Ile Phe Gln Arg Val Ser Val Asn Gly Gln Asp Gln Gly Gln
1               5                   10                  15

Leu Lys Gly Val Arg Ala Pro Ser Ser Asn Ser Pro Ile Gln Asn Val
            20                  25                  30

Asn Asp Ala Asn Met Ala Cys Asn Ala Asn Ile Val Tyr His Asp Asn
        35                  40                  45

Thr Ile Ile Lys Val Pro Ala Gly Ala Arg Val Gly Ala Trp Trp Gln
    50                  55                  60

His Val Ile Gly Gly Pro Gln Gly Ala Asn Asp Pro Asp Asn Pro Ile

```
                65                  70                  75                  80
Ala Ala Ser His Lys Gly Pro Ile Gln Val Tyr Leu Ala Lys Val Asp
                    85                  90                  95

Asn Ala Ala Thr Ala Ser Pro Ser Gly Leu Lys Trp Phe Lys Val Ala
                100                 105                 110

Glu Arg Gly Leu Asn Asn Gly Val Trp Ala Tyr Leu Met Arg Val Glu
                115                 120                 125

Leu Leu Ala Leu His Ser Ala Ser Ser Pro Gly Gly Ala Gln Phe Tyr
    130                 135                 140

Met Gly Cys Ala Gln Ile Glu Val Thr Gly Ser Gly Thr Asn Ser Gly
145                 150                 155                 160

Ser Asp Phe Val Ser Phe Pro Gly Ala Tyr Ser Ala Asn Asp Pro Gly
                165                 170                 175

Ile Leu Leu Ser Ile Tyr Asp Ser Ser Gly Lys Pro Asn Asn Gly Gly
                180                 185                 190

Arg Ser Tyr Pro Ile Pro Gly Pro Arg Pro Ile Ser Cys Ser Gly Ser
                195                 200                 205

Gly Gly Gly Gly Asn Asn Gly Gly Asp Gly Gly Asp Asp Asn Asn Gly
        210                 215                 220

Gly Gly Asn Asn Asn Gly Gly Gly Ser Val Pro Leu Tyr Gly Gln Cys
225                 230                 235                 240

Gly Gly Ile Gly Tyr Thr Gly Pro Thr Thr Cys Ala Gln Gly Thr Cys
                245                 250                 255

Lys Val Ser Asn Glu Tyr Tyr Ser Gln Cys Leu Pro
                260                 265

<210> SEQ ID NO 81
<211> LENGTH: 639
<212> TYPE: DNA
<213> ORGANISM: Myceliophthora thermophila

<400> SEQUENCE: 81
atgaagctca cctcgtccct cgctgtcctg gccgctgccg gcgcccaggc tcactatacc     60
ttccctaggg ccggcactgg tggttcgctc tctggcgagt gggaggtggt ccgcatgacc    120
gagaaccatt actcgcacgg cccggtcacc gatgtcacca gccccgagat gacctgctat    180
cagtccggcg tgcagggtgc gccccagacc gtccaggtca aggcgggctc ccaattcacc    240
ttcagcgtgg atccctccat cggccacccc ggccctctcc agttctacat ggctaaggtg    300
ccgtcgggcc agacggccgc cacctttgac ggcacgggag ccgtgtggtt caagatctac    360
caagacggcc cgaacggcct cggcaccgac agcattacct ggcccagcgc cggcaaaacc    420
gaggtctcgg tcaccatccc cagctgcatc gaggatggcg agtacctgct ccgggtcgag    480
cacacccccc tccctacagc gccagcagcg caaaaccgag ctcgctcgtc accatcccca    540
gctgcataca aggccaccga cccgggcatc ctcttccagc tctactggcc catcccgacc    600
gagtacatca cccccggccc ggcccccgtc tcttgctaa                           639

<210> SEQ ID NO 82
<211> LENGTH: 212
<212> TYPE: PRT
<213> ORGANISM: Myceliophthora thermophila

<400> SEQUENCE: 82

Met Lys Leu Thr Ser Ser Leu Ala Val Leu Ala Ala Gly Ala Gln
1               5                   10                  15
```

Ala His Tyr Thr Phe Pro Arg Ala Gly Thr Gly Ser Leu Ser Gly
        20                  25                  30

Glu Trp Glu Val Val Arg Met Thr Glu Asn His Tyr Ser His Gly Pro
        35                  40                  45

Val Thr Asp Val Thr Ser Pro Glu Met Thr Cys Tyr Gln Ser Gly Val
    50                  55                  60

Gln Gly Ala Pro Gln Thr Val Gln Val Lys Ala Gly Ser Gln Phe Thr
65                  70                  75                  80

Phe Ser Val Asp Pro Ser Ile Gly His Pro Gly Pro Leu Gln Phe Tyr
                85                  90                  95

Met Ala Lys Val Pro Ser Gly Gln Thr Ala Ala Thr Phe Asp Gly Thr
            100                 105                 110

Gly Ala Val Trp Phe Lys Ile Tyr Gln Asp Gly Pro Asn Gly Leu Gly
        115                 120                 125

Thr Asp Ser Ile Thr Trp Pro Ser Ala Gly Lys Thr Glu Val Ser Val
    130                 135                 140

Thr Ile Pro Ser Cys Ile Glu Asp Gly Glu Tyr Leu Leu Arg Val Glu
145                 150                 155                 160

His Thr Pro Leu Pro Thr Ala Pro Ala Ala Gln Asn Arg Ala Arg Ser
                165                 170                 175

Ser Pro Ser Pro Ala Ala Tyr Lys Ala Thr Asp Pro Gly Ile Leu Phe
            180                 185                 190

Gln Leu Tyr Trp Pro Ile Pro Thr Glu Tyr Ile Asn Pro Gly Pro Ala
        195                 200                 205

Pro Val Ser Cys
    210

<210> SEQ ID NO 83
<211> LENGTH: 195
<212> TYPE: PRT
<213> ORGANISM: Myceliophthora thermophila

<400> SEQUENCE: 83

His Tyr Thr Phe Pro Arg Ala Gly Thr Gly Ser Leu Ser Gly Glu
1               5                   10                  15

Trp Glu Val Val Arg Met Thr Glu Asn His Tyr Ser His Gly Pro Val
            20                  25                  30

Thr Asp Val Thr Ser Pro Glu Met Thr Cys Tyr Gln Ser Gly Val Gln
        35                  40                  45

Gly Ala Pro Gln Thr Val Gln Val Lys Ala Gly Ser Gln Phe Thr Phe
    50                  55                  60

Ser Val Asp Pro Ser Ile Gly His Pro Gly Pro Leu Gln Phe Tyr Met
65                  70                  75                  80

Ala Lys Val Pro Ser Gly Gln Thr Ala Ala Thr Phe Asp Gly Thr Gly
                85                  90                  95

Ala Val Trp Phe Lys Ile Tyr Gln Asp Gly Pro Asn Gly Leu Gly Thr
            100                 105                 110

Asp Ser Ile Thr Trp Pro Ser Ala Gly Lys Thr Glu Val Ser Val Thr
        115                 120                 125

Ile Pro Ser Cys Ile Glu Asp Gly Glu Tyr Leu Leu Arg Val Glu His
    130                 135                 140

Thr Pro Leu Pro Thr Ala Pro Ala Ala Gln Asn Arg Ala Arg Ser Ser
145                 150                 155                 160

Pro Ser Pro Ala Ala Tyr Lys Ala Thr Asp Pro Gly Ile Leu Phe Gln
                165                 170                 175

Leu Tyr Trp Pro Ile Pro Thr Glu Tyr Ile Asn Pro Gly Pro Ala Pro
            180                 185                 190
Val Ser Cys
        195

<210> SEQ ID NO 84
<211> LENGTH: 695
<212> TYPE: DNA
<213> ORGANISM: Myceliophthora thermophila

<400> SEQUENCE: 84

```
atgaagctca cctcgtccct cgctgtcctg gccgctgccg gcgcccaggc tcactatacc      60
ttccctaggg ccggcactgg tggttcgctc tctggcgagt gggaggtggt ccgcatgacc     120
gagaccatta ctcgcacggc ccggtcaccg atgtcaccag ccccgagatg acctgctatc     180
agtccggcgt gcagggtgcg ccccagaccg tccaggtcaa ggcgggctcc caattcacct     240
tcagcgtgga tcctccatc ggccaccccg gccctctcca gttctacatg gctaaggtgc     300
cgtcgggcca gacggccgcc acctttgacg gcacgggagc cgtgtggttc aagatctacc     360
aagacggccc gaacgccctc ggcaccgaca gcattacctg gccagcgcc ggcaaaaccg      420
aggtctcggt caccatcccc agctgcatcg aggatggcga gtacctgctc cgggtcgagc     480
acatcgcgct ccacagcgcc agcagcgtgg gcggcgccca gttctacatc gcctgcgccc     540
agctctccgt caccggcggc tccggcaccc tcaacacggg ctcgctcgtc tccctgcccg     600
gcgcctacaa ggccaccgac ccgggcatcc tcttccagct ctactggccc atcccgaccg     660
agtacatcaa ccccggcccg gccccgtct cttgc                                  695
```

<210> SEQ ID NO 85
<211> LENGTH: 232
<212> TYPE: PRT
<213> ORGANISM: Myceliophthora thermophila

<400> SEQUENCE: 85

Met Lys Leu Thr Ser Ser Leu Ala Val Leu Ala Ala Gly Ala Gln
1               5                   10                  15

Ala His Tyr Thr Phe Pro Arg Ala Gly Thr Gly Gly Ser Leu Ser Gly
            20                  25                  30

Glu Trp Glu Val Val Arg Met Thr Glu Asn His Tyr Ser His Gly Pro
        35                  40                  45

Val Thr Asp Val Thr Ser Pro Glu Met Thr Cys Tyr Gln Ser Gly Val
    50                  55                  60

Gln Gly Ala Pro Gln Thr Val Gln Val Lys Ala Gly Ser Gln Phe Thr
65                  70                  75                  80

Phe Ser Val Asp Pro Ser Ile Gly His Pro Gly Pro Leu Gln Phe Tyr
                85                  90                  95

Met Ala Lys Val Pro Ser Gly Gln Thr Ala Ala Thr Phe Asp Gly Thr
            100                 105                 110

Gly Ala Val Trp Phe Lys Ile Tyr Gln Asp Gly Pro Asn Gly Leu Gly
        115                 120                 125

Thr Asp Ser Ile Thr Trp Pro Ser Ala Gly Lys Thr Glu Val Ser Val
    130                 135                 140

Thr Ile Pro Ser Cys Ile Glu Asp Gly Glu Tyr Leu Leu Arg Val Glu
145                 150                 155                 160

His Ile Ala Leu His Ser Ala Ser Ser Val Gly Gly Ala Gln Phe Tyr
                165                 170                 175

```
Ile Ala Cys Ala Gln Leu Ser Val Thr Gly Gly Ser Gly Thr Leu Asn
            180                 185                 190

Thr Gly Ser Leu Val Ser Leu Pro Gly Ala Tyr Lys Ala Thr Asp Pro
        195                 200                 205

Gly Ile Leu Phe Gln Leu Tyr Trp Pro Ile Pro Thr Glu Tyr Ile Asn
    210                 215                 220

Pro Gly Pro Ala Pro Val Ser Cys
225                 230

<210> SEQ ID NO 86
<211> LENGTH: 215
<212> TYPE: PRT
<213> ORGANISM: Myceliophthora thermophila

<400> SEQUENCE: 86

His Tyr Thr Phe Pro Arg Ala Gly Thr Gly Gly Ser Leu Ser Gly Glu
1               5                   10                  15

Trp Glu Val Val Arg Met Thr Glu Asn His Tyr Ser His Gly Pro Val
            20                  25                  30

Thr Asp Val Thr Ser Pro Glu Met Thr Cys Tyr Gln Ser Gly Val Gln
        35                  40                  45

Gly Ala Pro Gln Thr Val Gln Val Lys Ala Gly Ser Gln Phe Thr Phe
    50                  55                  60

Ser Val Asp Pro Ser Ile Gly His Pro Gly Pro Leu Gln Phe Tyr Met
65                  70                  75                  80

Ala Lys Val Pro Ser Gly Gln Thr Ala Ala Thr Phe Asp Gly Thr Gly
            85                  90                  95

Ala Val Trp Phe Lys Ile Tyr Gln Asp Gly Pro Asn Gly Leu Gly Thr
            100                 105                 110

Asp Ser Ile Thr Trp Pro Ser Ala Gly Lys Thr Glu Val Ser Val Thr
        115                 120                 125

Ile Pro Ser Cys Ile Glu Asp Gly Glu Tyr Leu Leu Arg Val Glu His
    130                 135                 140

Ile Ala Leu His Ser Ala Ser Ser Val Gly Gly Ala Gln Phe Tyr Ile
145                 150                 155                 160

Ala Cys Ala Gln Leu Ser Val Thr Gly Gly Ser Gly Thr Leu Asn Thr
            165                 170                 175

Gly Ser Leu Val Ser Leu Pro Gly Ala Tyr Lys Ala Thr Asp Pro Gly
        180                 185                 190

Ile Leu Phe Gln Leu Tyr Trp Pro Ile Pro Thr Glu Tyr Ile Asn Pro
    195                 200                 205

Gly Pro Ala Pro Val Ser Cys
    210                 215

<210> SEQ ID NO 87
<211> LENGTH: 447
<212> TYPE: DNA
<213> ORGANISM: Myceliophthora thermophila

<400> SEQUENCE: 87
atgccgccac cacgactgag caccctcctt ccctcctag ccttaatagc ccccaccgcc    60
ctggggcact cccacctcgg gtacatcatc atcaacggcg aggtatacca aggattcgac   120
ccgcggccgg agcaggcgaa ctcgccgttg cgcgtgggct ggtcgacggg ggcaatcgac   180
gacgggttcg tggcgccggc caactactcg tcgcccgaca tcatctgcca catcgagggg   240
```

```
gccagcccgc cggcgcacgc gcccgtccgg gcgggcgacc gggtgcacgt gcaatggaac      300
ggctggccgc tcggacacgt ggggccggtg ctgtcgtacc tggcgccctg cggcgggctg      360
gaggggtccg agagcgggtg cgccggggtg gacaagcggc agctgcggtg gaccaaggtg      420
gacgactcgc tgccggcgat ggagctg                                          447
```

```
<210> SEQ ID NO 88
<211> LENGTH: 149
<212> TYPE: PRT
<213> ORGANISM: Myceliophthora thermophila

<400> SEQUENCE: 88

Met Pro Pro Pro Arg Leu Ser Thr Leu Leu Pro Leu Leu Ala Leu Ile
1               5                   10                  15

Ala Pro Thr Ala Leu Gly His Ser His Leu Gly Tyr Ile Ile Ile Asn
            20                  25                  30

Gly Glu Val Tyr Gln Gly Phe Asp Pro Arg Pro Glu Gln Ala Asn Ser
        35                  40                  45

Pro Leu Arg Val Gly Trp Ser Thr Gly Ala Ile Asp Asp Gly Phe Val
    50                  55                  60

Ala Pro Ala Asn Tyr Ser Ser Pro Asp Ile Ile Cys His Ile Glu Gly
65                  70                  75                  80

Ala Ser Pro Pro Ala His Ala Pro Val Arg Ala Gly Asp Arg Val His
                85                  90                  95

Val Gln Trp Asn Gly Trp Pro Leu Gly His Val Gly Pro Val Leu Ser
            100                 105                 110

Tyr Leu Ala Pro Cys Gly Gly Leu Glu Gly Ser Glu Ser Gly Cys Ala
        115                 120                 125

Gly Val Asp Lys Arg Gln Leu Arg Trp Thr Lys Val Asp Asp Ser Leu
    130                 135                 140

Pro Ala Met Glu Leu
145

<210> SEQ ID NO 89
<211> LENGTH: 127
<212> TYPE: PRT
<213> ORGANISM: Myceliophthora thermophila

<400> SEQUENCE: 89

His Ser His Leu Gly Tyr Ile Ile Ile Asn Gly Glu Val Tyr Gln Gly
1               5                   10                  15

Phe Asp Pro Arg Pro Glu Gln Ala Asn Ser Pro Leu Arg Val Gly Trp
            20                  25                  30

Ser Thr Gly Ala Ile Asp Asp Gly Phe Val Ala Pro Ala Asn Tyr Ser
        35                  40                  45

Ser Pro Asp Ile Ile Cys His Ile Glu Gly Ala Ser Pro Pro Ala His
    50                  55                  60

Ala Pro Val Arg Ala Gly Asp Arg Val His Val Gln Trp Asn Gly Trp
65                  70                  75                  80

Pro Leu Gly His Val Gly Pro Val Leu Ser Tyr Leu Ala Pro Cys Gly
                85                  90                  95

Gly Leu Glu Gly Ser Glu Ser Gly Cys Ala Gly Val Asp Lys Arg Gln
            100                 105                 110

Leu Arg Trp Thr Lys Val Asp Asp Ser Leu Pro Ala Met Glu Leu
        115                 120                 125
```

<210> SEQ ID NO 90
<211> LENGTH: 1176
<212> TYPE: DNA
<213> ORGANISM: Myceliophthora thermophila

<400> SEQUENCE: 90

```
atgccgccac cacgactgag caccctcctt ccctcctag ccttaatagc ccccaccgcc        60
ctggggcact cccacctcgg gtacatcatc atcaacggcg aggtatacca aggattcgac      120
ccgcggccgg agcaggcgaa ctcgccgttg cgcgtgggct ggtcgacggg ggcaatcgac      180
gacgggttcg tggcgccggc caactactcg tcgcccgaca tcatctgcca catcgagggg      240
gccagcccgc cggcgcacgc gcccgtccgg gcgggcgacc gggtgcacgt gcaatggaaa      300
cggctggccg ctcggacacg tggggccggt gctgtcgtac ctggcgccct gcggcgggct      360
ggaggggtcc gagagcgggt ggacgactcg ctgccggcga tggagctggt cggggccgcg      420
gggggcgcgg ggggcgagga cgacggcagc ggcagcgacg gcagcggcag cggcggcagc      480
ggacgcgtcg gcgtgcccgg gcagcgctgg gccaccgacg tgttgatcgc ggccaacaac      540
agctggcagg tcgagatccc gcgcgggctg cgggacgggc cgtacgtgct cgccacgag       600
atcgtcgcgc tgcactacgc ggcccgagccc ggcggcgcgc agaactaccc gctctgcgtc     660
aacctgtggg tcgagggcgg cgacggcagc atggagctgg accacttcga cgccacccag      720
ttctaccggc ccgacgaccc gggcatcctg ctcaacgtga cggccggcct gcgctcatac      780
gccgtgccgg gcccgacgct ggccgcgggg gcgacgccgg tgccgtacgc gcagcagaac      840
atcagctcgg cgagggcgga tggaaccccc gtgattgtca ccaggagcac ggagacggtg      900
cccttcaccg cggcacccac gccagccgag acggcagaag ccaaagggg gaggtatgat       960
gaccaaaccc gaactaaaga cctaaatgaa cgcttctttt atagtagccg gccagaacag     1020
aagaggctga cagcgacctc aagaagggaa ctagttgatc atcgtacccg gtacctctcc     1080
gtagctgtct gcgcagattt cggcgctcat aaggcagcag aaaccaacca cgaagctttg     1140
agaggcggca ataagcacca tggcggtgtt tcagag                              1176
```

<210> SEQ ID NO 91
<211> LENGTH: 392
<212> TYPE: PRT
<213> ORGANISM: Myceliophthora thermophila

<400> SEQUENCE: 91

Met Pro Pro Pro Arg Leu Ser Thr Leu Leu Pro Leu Leu Ala Leu Ile
1               5                   10                  15

Ala Pro Thr Ala Leu Gly His Ser His Leu Gly Tyr Ile Ile Ile Asn
            20                  25                  30

Gly Glu Val Tyr Gln Gly Phe Asp Pro Arg Pro Glu Gln Ala Asn Ser
        35                  40                  45

Pro Leu Arg Val Gly Trp Ser Thr Gly Ala Ile Asp Asp Gly Phe Val
    50                  55                  60

Ala Pro Ala Asn Tyr Ser Ser Pro Asp Ile Ile Cys His Ile Glu Gly
65                  70                  75                  80

Ala Ser Pro Pro Ala His Ala Pro Val Arg Ala Gly Asp Arg Val His
                85                  90                  95

Val Gln Trp Lys Arg Leu Ala Ala Arg Thr Arg Gly Ala Gly Ala Val
            100                 105                 110

Val Pro Gly Ala Leu Arg Arg Ala Gly Gly Val Arg Glu Arg Val Asp
        115                 120                 125

```
Asp Ser Leu Pro Ala Met Glu Leu Val Gly Ala Ala Gly Gly Ala Gly
    130                 135                 140

Gly Glu Asp Asp Gly Ser Gly Ser Asp Gly Ser Gly Ser Gly Gly Ser
145                 150                 155                 160

Gly Arg Val Gly Val Pro Gly Gln Arg Trp Ala Thr Asp Val Leu Ile
                165                 170                 175

Ala Ala Asn Asn Ser Trp Gln Val Glu Ile Pro Arg Gly Leu Arg Asp
                180                 185                 190

Gly Pro Tyr Val Leu Arg His Glu Ile Val Ala Leu His Tyr Ala Ala
            195                 200                 205

Glu Pro Gly Gly Ala Gln Asn Tyr Pro Leu Cys Val Asn Leu Trp Val
210                 215                 220

Glu Gly Gly Asp Gly Ser Met Glu Leu Asp His Phe Asp Ala Thr Gln
225                 230                 235                 240

Phe Tyr Arg Pro Asp Asp Pro Gly Ile Leu Leu Asn Val Thr Ala Gly
                245                 250                 255

Leu Arg Ser Tyr Ala Val Pro Gly Pro Thr Leu Ala Ala Gly Ala Thr
                260                 265                 270

Pro Val Pro Tyr Ala Gln Gln Asn Ile Ser Ser Ala Arg Ala Asp Gly
            275                 280                 285

Thr Pro Val Ile Val Thr Arg Ser Thr Glu Thr Val Pro Phe Thr Ala
290                 295                 300

Ala Pro Thr Pro Ala Glu Thr Ala Glu Ala Lys Gly Gly Arg Tyr Asp
305                 310                 315                 320

Asp Gln Thr Arg Thr Lys Asp Leu Asn Glu Arg Phe Phe Tyr Ser Ser
                325                 330                 335

Arg Pro Glu Gln Lys Arg Leu Thr Ala Thr Ser Arg Arg Glu Leu Val
                340                 345                 350

Asp His Arg Thr Arg Tyr Leu Ser Val Ala Val Cys Ala Asp Phe Gly
            355                 360                 365

Ala His Lys Ala Ala Glu Thr Asn His Glu Ala Leu Arg Gly Gly Asn
370                 375                 380

Lys His His Gly Gly Val Ser Glu
385                 390

<210> SEQ ID NO 92
<211> LENGTH: 370
<212> TYPE: PRT
<213> ORGANISM: Myceliophthora thermophila

<400> SEQUENCE: 92

His Ser His Leu Gly Tyr Ile Ile Ile Asn Gly Glu Val Tyr Gln Gly
1               5                   10                  15

Phe Asp Pro Arg Pro Glu Gln Ala Asn Ser Pro Leu Arg Val Gly Trp
                20                  25                  30

Ser Thr Gly Ala Ile Asp Asp Gly Phe Val Ala Pro Ala Asn Tyr Ser
            35                  40                  45

Ser Pro Asp Ile Ile Cys His Ile Glu Gly Ala Ser Pro Pro Ala His
50                  55                  60

Ala Pro Val Arg Ala Gly Asp Arg Val His Val Gln Trp Lys Arg Leu
65                  70                  75                  80

Ala Ala Arg Thr Arg Gly Ala Gly Ala Val Val Pro Gly Ala Leu Arg
                85                  90                  95

Arg Ala Gly Gly Val Arg Glu Arg Val Asp Asp Ser Leu Pro Ala Met
            100                 105                 110
```

```
Glu Leu Val Gly Ala Ala Gly Ala Gly Gly Glu Asp Asp Gly Ser
        115                 120                 125
Gly Ser Asp Gly Ser Gly Ser Gly Gly Ser Gly Arg Val Gly Val Pro
    130                 135                 140
Gly Gln Arg Trp Ala Thr Asp Val Leu Ile Ala Ala Asn Asn Ser Trp
145                 150                 155                 160
Gln Val Glu Ile Pro Arg Gly Leu Arg Asp Gly Pro Tyr Val Leu Arg
                165                 170                 175
His Glu Ile Val Ala Leu His Tyr Ala Ala Glu Pro Gly Gly Ala Gln
            180                 185                 190
Asn Tyr Pro Leu Cys Val Asn Leu Trp Val Gly Gly Asp Gly Ser
        195                 200                 205
Met Glu Leu Asp His Phe Asp Ala Thr Gln Phe Tyr Arg Pro Asp Asp
    210                 215                 220
Pro Gly Ile Leu Leu Asn Val Thr Ala Gly Leu Arg Ser Tyr Ala Val
225                 230                 235                 240
Pro Gly Pro Thr Leu Ala Ala Gly Ala Thr Pro Val Pro Tyr Ala Gln
                245                 250                 255
Gln Asn Ile Ser Ser Ala Arg Ala Asp Gly Thr Pro Val Ile Val Thr
            260                 265                 270
Arg Ser Thr Glu Thr Val Pro Phe Thr Ala Ala Pro Thr Pro Ala Glu
        275                 280                 285
Thr Ala Glu Ala Lys Gly Gly Arg Tyr Asp Asp Gln Thr Arg Thr Lys
    290                 295                 300
Asp Leu Asn Glu Arg Phe Phe Tyr Ser Ser Arg Pro Glu Gln Lys Arg
305                 310                 315                 320
Leu Thr Ala Thr Ser Arg Arg Glu Leu Val Asp His Arg Thr Arg Tyr
                325                 330                 335
Leu Ser Val Ala Val Cys Ala Asp Phe Gly Ala His Lys Ala Ala Glu
            340                 345                 350
Thr Asn His Glu Ala Leu Arg Gly Gly Asn Lys His His Gly Gly Val
        355                 360                 365
Ser Glu
    370

<210> SEQ ID NO 93
<211> LENGTH: 453
<212> TYPE: DNA
<213> ORGANISM: Myceliophthora thermophila

<400> SEQUENCE: 93
atgaggtcga cattggccgg tgccctggca gccatcgctg ctcagaaagt agccggccac      60
gccacgtttc agcagctctg gcacggctcc tcctgtgtcc gccttccggc tagcaactca     120
cccgtcacca atgtgggaag cagagacttc gtctgcaacg ctggcacccg ccccgtcagt     180
ggcaagtgcc ccgtgaaggc tggcggcacc gtcaccatcg agatgcacca gcaacccggc     240
gaccgcagct gcaacaacga agccatcgga ggggcgcatt ggggccccgt ccaggtgtac     300
ctgaccaagg ttcaggacgc cgcgacggcc gacggctcga cgggctggtt caagatcttc     360
tccgactcgt ggtccaagaa gcccgggggc aacttgggcg acgacgacaa ctggggcacg     420
cgcgacctga acgcctgctg cgggaagatg gac                                  453

<210> SEQ ID NO 94
<211> LENGTH: 151
```

<212> TYPE: PRT
<213> ORGANISM: Myceliophthora thermophila

<400> SEQUENCE: 94

```
Met Arg Ser Thr Leu Ala Gly Ala Leu Ala Ala Ile Ala Ala Gln Lys
1               5                   10                  15

Val Ala Gly His Ala Thr Phe Gln Gln Leu Trp His Gly Ser Ser Cys
            20                  25                  30

Val Arg Leu Pro Ala Ser Asn Ser Pro Val Thr Asn Val Gly Ser Arg
        35                  40                  45

Asp Phe Val Cys Asn Ala Gly Thr Arg Pro Val Ser Gly Lys Cys Pro
    50                  55                  60

Val Lys Ala Gly Gly Thr Val Thr Ile Glu Met His Gln Gln Pro Gly
65                  70                  75                  80

Asp Arg Ser Cys Asn Asn Glu Ala Ile Gly Gly Ala His Trp Gly Pro
                85                  90                  95

Val Gln Val Tyr Leu Thr Lys Val Gln Asp Ala Ala Thr Ala Asp Gly
            100                 105                 110

Ser Thr Gly Trp Phe Lys Ile Phe Ser Asp Ser Trp Ser Lys Lys Pro
        115                 120                 125

Gly Gly Asn Leu Gly Asp Asp Asn Trp Gly Thr Arg Asp Leu Asn
    130                 135                 140

Ala Cys Cys Gly Lys Met Asp
145                 150
```

<210> SEQ ID NO 95
<211> LENGTH: 132
<212> TYPE: PRT
<213> ORGANISM: Myceliophthora thermophila

<400> SEQUENCE: 95

```
His Ala Thr Phe Gln Gln Leu Trp His Gly Ser Ser Cys Val Arg Leu
1               5                   10                  15

Pro Ala Ser Asn Ser Pro Val Thr Asn Val Gly Ser Arg Asp Phe Val
            20                  25                  30

Cys Asn Ala Gly Thr Arg Pro Val Ser Gly Lys Cys Pro Val Lys Ala
        35                  40                  45

Gly Gly Thr Val Thr Ile Glu Met His Gln Gln Pro Gly Asp Arg Ser
    50                  55                  60

Cys Asn Asn Glu Ala Ile Gly Gly Ala His Trp Gly Pro Val Gln Val
65                  70                  75                  80

Tyr Leu Thr Lys Val Gln Asp Ala Ala Thr Ala Asp Gly Ser Thr Gly
                85                  90                  95

Trp Phe Lys Ile Phe Ser Asp Ser Trp Ser Lys Lys Pro Gly Gly Asn
            100                 105                 110

Leu Gly Asp Asp Asp Asn Trp Gly Thr Arg Asp Leu Asn Ala Cys Cys
        115                 120                 125

Gly Lys Met Asp
    130
```

<210> SEQ ID NO 96
<211> LENGTH: 837
<212> TYPE: DNA
<213> ORGANISM: Myceliophthora thermophila

<400> SEQUENCE: 96

```
atgaggtcga cattggccgg tgccctggca gccatcgctg ctcagaaagt agccggccac    60
```

```
gccacgtttc agcagctctg gcacggctcc tcctgtgtcc gccttccggc tagcaactca    120
cccgtcacca atgtgggaag cagagacttc gtctgcaacg ctggcacccg ccccgtcagt    180
ggcaagtgcc ccgtgaaggc tggcggcacc gtcaccatcg agatgcacca gcaacccggc    240
gaccgcagct gcaacaacga agccatcgga ggggcgcatt ggggcccccgt ccaggtgtac    300 ctgaccaagg ttcaggacgc cgcgacggcc gacggctcga cgggctggtt caagatcttc    360
tccgactcgt ggtccaagaa gcccgggggc aactcgggcg acgacgacaa ctggggcacg    420
cgcgacctga acgcctgctg cgggaagatg gacgtggcca tcccggccga catcgcgtcg    480
ggcgactacc tgctgcgggc cgaggcgctg gccctgcaca cggccggaca ggccggcggc    540
gcccagttct acatgagctg ctaccagatg acggtcgagg cggctccgg accgccaac    600 ccgcccaccg tcaagttccc gggcgcctac agcgccaacg acccgggcat cctcgtcaac    660
atccacgccc cctttccag ctacaccgcg cccggcccgg ccgtctacgc gggcggcacc    720
atccgcgagg ccggctccgc ctgcaccggc tgcgcgcaga cctgcaaggt cgggtcgtcc    780
ccgagcgccg ttgcccccgg cagcggcgcg ggcaacggcg gcgggttcca accccga      837
```

<210> SEQ ID NO 97
<211> LENGTH: 279
<212> TYPE: PRT
<213> ORGANISM: Myceliophthora thermophila

<400> SEQUENCE: 97

```
Met Arg Ser Thr Leu Ala Gly Ala Leu Ala Ala Ile Ala Ala Gln Lys
1               5                   10                  15

Val Ala Gly His Ala Thr Phe Gln Gln Leu Trp His Gly Ser Ser Cys
                20                  25                  30

Val Arg Leu Pro Ala Ser Asn Ser Pro Val Thr Asn Val Gly Ser Arg
            35                  40                  45

Asp Phe Val Cys Asn Ala Gly Thr Arg Pro Val Ser Gly Lys Cys Pro
        50                  55                  60

Val Lys Ala Gly Gly Thr Val Thr Ile Glu Met His Gln Gln Pro Gly
65                  70                  75                  80

Asp Arg Ser Cys Asn Asn Glu Ala Ile Gly Ala His Trp Gly Pro
                85                  90                  95

Val Gln Val Tyr Leu Thr Lys Val Gln Asp Ala Ala Thr Ala Asp Gly
                100                 105                 110

Ser Thr Gly Trp Phe Lys Ile Phe Ser Asp Ser Trp Ser Lys Lys Pro
            115                 120                 125

Gly Gly Asn Ser Gly Asp Asp Asp Asn Trp Gly Thr Arg Asp Leu Asn
        130                 135                 140

Ala Cys Cys Gly Lys Met Asp Val Ala Ile Pro Ala Asp Ile Ala Ser
145                 150                 155                 160

Gly Asp Tyr Leu Leu Arg Ala Glu Ala Leu Ala Leu His Thr Ala Gly
                165                 170                 175

Gln Ala Gly Gly Ala Gln Phe Tyr Met Ser Cys Tyr Gln Met Thr Val
            180                 185                 190

Glu Gly Gly Ser Gly Thr Ala Asn Pro Pro Thr Val Lys Phe Pro Gly
        195                 200                 205

Ala Tyr Ser Ala Asn Asp Pro Gly Ile Leu Val Asn Ile His Ala Pro
    210                 215                 220

Leu Ser Ser Tyr Thr Ala Pro Gly Pro Ala Val Tyr Ala Gly Gly Thr
225                 230                 235                 240
```

```
Ile Arg Glu Ala Gly Ser Ala Cys Thr Gly Cys Ala Gln Thr Cys Lys
                245                 250                 255

Val Gly Ser Ser Pro Ser Ala Val Ala Pro Gly Ser Gly Ala Gly Asn
            260                 265                 270

Gly Gly Gly Phe Gln Pro Arg
        275

<210> SEQ ID NO 98
<211> LENGTH: 260
<212> TYPE: PRT
<213> ORGANISM: Myceliophthora thermophila

<400> SEQUENCE: 98

His Ala Thr Phe Gln Gln Leu Trp His Gly Ser Ser Cys Val Arg Leu
1               5                   10                  15

Pro Ala Ser Asn Ser Pro Val Thr Asn Val Gly Ser Arg Asp Phe Val
            20                  25                  30

Cys Asn Ala Gly Thr Arg Pro Val Ser Gly Lys Cys Pro Val Lys Ala
        35                  40                  45

Gly Gly Thr Val Thr Ile Glu Met His Gln Pro Gly Asp Arg Ser
    50                  55                  60

Cys Asn Asn Glu Ala Ile Gly Ala His Trp Gly Pro Val Gln Val
65                  70                  75                  80

Tyr Leu Thr Lys Val Gln Asp Ala Ala Thr Ala Asp Gly Ser Thr Gly
                85                  90                  95

Trp Phe Lys Ile Phe Ser Asp Ser Trp Ser Lys Lys Pro Gly Gly Asn
            100                 105                 110

Ser Gly Asp Asp Asp Asn Trp Gly Thr Arg Asp Leu Asn Ala Cys Cys
        115                 120                 125

Gly Lys Met Asp Val Ala Ile Pro Ala Asp Ile Ala Ser Gly Asp Tyr
    130                 135                 140

Leu Leu Arg Ala Glu Ala Leu Ala Leu His Thr Ala Gly Gln Ala Gly
145                 150                 155                 160

Gly Ala Gln Phe Tyr Met Ser Cys Tyr Gln Met Thr Val Glu Gly Gly
                165                 170                 175

Ser Gly Thr Ala Asn Pro Pro Thr Val Lys Phe Pro Gly Ala Tyr Ser
            180                 185                 190

Ala Asn Asp Pro Gly Ile Leu Val Asn Ile His Ala Pro Leu Ser Ser
        195                 200                 205

Tyr Thr Ala Pro Gly Pro Ala Val Tyr Ala Gly Gly Thr Ile Arg Glu
    210                 215                 220

Ala Gly Ser Ala Cys Thr Gly Cys Ala Gln Thr Cys Lys Val Gly Ser
225                 230                 235                 240

Ser Pro Ser Ala Val Ala Pro Gly Ser Gly Ala Gly Asn Gly Gly Gly
                245                 250                 255

Phe Gln Pro Arg
        260

<210> SEQ ID NO 99
<211> LENGTH: 735
<212> TYPE: DNA
<213> ORGANISM: Myceliophthora thermophila

<400> SEQUENCE: 99
atgctcctcc tcaccctagc cacactcgtc accctcctgg cgcgccacgt ctcggctcac      60
```

-continued

```
gcccggctgt tccgcgtctc tgtcgacggg aaagaccagg gcgacgggct gaacaagtac    120
atccgctcgc cggcgaccaa cgaccccgtg cgcgacctct cgagcgccgc catcgtgtgc    180
aacacccagg ggtccaaggc cgccccggac ttcgtcaggg ccgcggccgg cgacaagctg    240
accttcctct gggcgcacga caaccccgac gacccggtcg actacgtcct cgacccgtcc    300
cacaagggcg ccatcctgac ctacgtcgcc gcctacccct ccggggaccc gaccggcccc    360
atctggagca agcttgccga ggaaggattc accggcgggc agtgggcgac catcaagatg    420
atcgacaacg gcggcaaggt cgacgtgacg ctgcccgagg cccttgcgcc gggaaagtac    480
ctgatccgcc aggagctgct ggccctgcac cgggccgact tgcctgcga cgacccggcc    540 caccccaacc gcggcgccga gtcgtacccc aactgcgtcc aggtggaggt gtcgggcagc    600
ggcgacaaga agccggacca gaactttgac ttcaacaagg gctatacctg cgataacaaa    660
ggactccact ttaagatcta catcggtcag gacagccagt atgtggcccc ggggccgcgg    720
ccttggaatg ggagc                                                    735
```

<210> SEQ ID NO 100
<211> LENGTH: 245
<212> TYPE: PRT
<213> ORGANISM: Myceliophthora thermophila

<400> SEQUENCE: 100

```
Met Leu Leu Leu Thr Leu Ala Thr Leu Val Thr Leu Leu Ala Arg His
1               5                   10                  15

Val Ser Ala His Ala Arg Leu Phe Arg Val Ser Val Asp Gly Lys Asp
                20                  25                  30

Gln Gly Asp Gly Leu Asn Lys Tyr Ile Arg Ser Pro Ala Thr Asn Asp
            35                  40                  45

Pro Val Arg Asp Leu Ser Ser Ala Ala Ile Val Cys Asn Thr Gln Gly
        50                  55                  60

Ser Lys Ala Ala Pro Asp Phe Val Arg Ala Ala Gly Asp Lys Leu
65                  70                  75                  80

Thr Phe Leu Trp Ala His Asp Asn Pro Asp Asp Pro Val Asp Tyr Val
                85                  90                  95

Leu Asp Pro Ser His Lys Gly Ala Ile Leu Thr Tyr Val Ala Ala Tyr
            100                 105                 110

Pro Ser Gly Asp Pro Thr Gly Pro Ile Trp Ser Lys Leu Ala Glu Glu
        115                 120                 125

Gly Phe Thr Gly Gly Gln Trp Ala Thr Ile Lys Met Ile Asp Asn Gly
    130                 135                 140

Gly Lys Val Asp Val Thr Leu Pro Glu Ala Leu Ala Pro Gly Lys Tyr
145                 150                 155                 160

Leu Ile Arg Gln Glu Leu Leu Ala Leu His Arg Ala Asp Phe Ala Cys
                165                 170                 175

Asp Asp Pro Ala His Pro Asn Arg Gly Ala Glu Ser Tyr Pro Asn Cys
            180                 185                 190

Val Gln Val Glu Val Ser Gly Ser Gly Asp Lys Lys Pro Asp Gln Asn
        195                 200                 205

Phe Asp Phe Asn Lys Gly Tyr Thr Cys Asp Asn Lys Gly Leu His Phe
    210                 215                 220

Lys Ile Tyr Ile Gly Gln Asp Ser Gln Tyr Val Ala Pro Gly Pro Arg
225                 230                 235                 240

Pro Trp Asn Gly Ser
                245
```

<210> SEQ ID NO 101
<211> LENGTH: 226
<212> TYPE: PRT
<213> ORGANISM: Myceliophthora thermophila

<400> SEQUENCE: 101

```
His Ala Arg Leu Phe Arg Val Ser Val Asp Gly Lys Asp Gln Gly Asp
1               5                   10                  15

Gly Leu Asn Lys Tyr Ile Arg Ser Pro Ala Thr Asn Asp Pro Val Arg
            20                  25                  30

Asp Leu Ser Ser Ala Ala Ile Val Cys Asn Thr Gln Gly Ser Lys Ala
        35                  40                  45

Ala Pro Asp Phe Val Arg Ala Ala Gly Asp Lys Leu Thr Phe Leu
    50                  55                  60

Trp Ala His Asp Asn Pro Asp Pro Val Asp Tyr Val Leu Asp Pro
65                  70                  75                  80

Ser His Lys Gly Ala Ile Leu Thr Tyr Val Ala Ala Tyr Pro Ser Gly
                85                  90                  95

Asp Pro Thr Gly Pro Ile Trp Ser Lys Leu Ala Glu Glu Gly Phe Thr
            100                 105                 110

Gly Gly Gln Trp Ala Thr Ile Lys Met Ile Asp Asn Gly Gly Lys Val
        115                 120                 125

Asp Val Thr Leu Pro Glu Ala Leu Ala Pro Gly Lys Tyr Leu Ile Arg
    130                 135                 140

Gln Glu Leu Leu Ala Leu His Arg Ala Asp Phe Ala Cys Asp Pro
145                 150                 155                 160

Ala His Pro Asn Arg Gly Ala Glu Ser Tyr Pro Asn Cys Val Gln Val
                165                 170                 175

Glu Val Ser Gly Ser Gly Asp Lys Lys Pro Asp Gln Asn Phe Asp Phe
            180                 185                 190

Asn Lys Gly Tyr Thr Cys Asp Asn Lys Gly Leu His Phe Lys Ile Tyr
        195                 200                 205

Ile Gly Gln Asp Ser Gln Tyr Val Ala Pro Gly Pro Arg Pro Trp Asn
    210                 215                 220

Gly Ser
225
```

<210> SEQ ID NO 102
<211> LENGTH: 600
<212> TYPE: DNA
<213> ORGANISM: Myceliophthora thermophila

<400> SEQUENCE: 102

```
atgttcactt cgctttgcat cacagatcat tggaggactc ttagcagcca ctctgggcca    60
gtcatgaact atctcgccca ttgcaccaat gacgactgca agtctttcaa gggcgacagc   120
ggcaacgtct gggtcaagat cgagcagctc gcgtacaacc cgtcagccaa cccccccttgg   180 gcgtctgacc tcctccgtga gcacggtgcc aagtggaagg tgacgatccc gcccagtctt   240
gtccccggcg aatatctgct gcggcacgag atcctggggt tgcacgtcgc aggaaccgtg   300
atgggcgccc agttctaccc cggctgcacc cagatcaggg tcaccgaagg cgggagcacg   360
cagctgccct cgggtattgc gctcccaggc gcttacggcc acaagacga gggtatcttg   420 gtcgacttgt ggagggttaa ccagggccag gtcaactaca cggcgcctgg aggacccgtt   480
tggagcgaag cgtgggacac cgagtttggc gggtccaaca cgaccgagtg cgccaccatg   540
```

```
ctcgacgacc tgctcgacta catggcggcc aacgacgagt ggatcggctg gacggcctag    600
```

<210> SEQ ID NO 103
<211> LENGTH: 199
<212> TYPE: PRT
<213> ORGANISM: Myceliophthora thermophila

<400> SEQUENCE: 103

```
Met Phe Thr Ser Leu Cys Ile Thr Asp His Trp Arg Thr Leu Ser Ser
1               5                   10                  15

His Ser Gly Pro Val Met Asn Tyr Leu Ala His Cys Thr Asn Asp Asp
            20                  25                  30

Cys Lys Ser Phe Lys Gly Asp Ser Gly Asn Val Trp Val Lys Ile Glu
        35                  40                  45

Gln Leu Ala Tyr Asn Pro Ser Ala Asn Pro Pro Trp Ala Ser Asp Leu
    50                  55                  60

Leu Arg Glu His Gly Ala Lys Trp Lys Val Thr Ile Pro Pro Ser Leu
65                  70                  75                  80

Val Pro Gly Glu Tyr Leu Leu Arg His Glu Ile Leu Gly Leu His Val
                85                  90                  95

Ala Gly Thr Val Met Gly Ala Gln Phe Tyr Pro Gly Cys Thr Gln Ile
            100                 105                 110

Arg Val Thr Glu Gly Gly Ser Thr Gln Leu Pro Ser Gly Ile Ala Leu
        115                 120                 125

Pro Gly Ala Tyr Gly Pro Gln Asp Glu Gly Ile Leu Val Asp Leu Trp
    130                 135                 140

Arg Val Asn Gln Gly Gln Val Asn Tyr Thr Ala Pro Gly Gly Pro Val
145                 150                 155                 160

Trp Ser Glu Ala Trp Asp Thr Glu Phe Gly Gly Ser Asn Thr Thr Glu
                165                 170                 175

Cys Ala Thr Met Leu Asp Asp Leu Leu Asp Tyr Met Ala Ala Asn Asp
            180                 185                 190

Glu Trp Ile Gly Trp Thr Ala
        195
```

<210> SEQ ID NO 104
<211> LENGTH: 693
<212> TYPE: DNA
<213> ORGANISM: Myceliophthora thermophila

<400> SEQUENCE: 104

```
atgaactatc tcgcccattg caccaatgac gactgcaagt ctttcaaggg cgacagcggc     60
aacgtctggg tcaagatcga gcagctcgcg tacaacccgt cagccaaccc ccctgggcg    120 tctgacctcc tccgtgagca cggtgccaag tggaaggtga cgatcccgcc cagtcttgtc    180
cccggcgaat atctgctgcg cacgagatc ctggggttgc acgtcgcagg aaccgtgatg     240 ggcgccagt ctaccccgg ctgcacccag atcagggtca ccgaaggcgg gagcacgcag      300
ctgccctcgg gtattgcgct cccaggcgct tacggcccac aagacgaggg tatcttggtc    360
gacttgtgga gggttaacca gggccaggtc aactacacgg cgcctggagg acccgtttgg    420
agcgaagcgt gggacaccga gtttggcggg tccaacacga ccgagtgcgc caccatgctc    480
gacgacctgc tcgactacat ggcggccaac gacgacccat gctgcaccga ccagaaccag    540
ttcgggagtc tcgagccggg gagcaaggcg gccggcggct cgccgagcct gtacgatacc    600
gtcttggtcc ccgttctcca gaagaaagtg ccgacaaagc tgcagtggag cggaccggcg    660
```
agcgtcaacg gggatgagtt gacagagagg ccc                        693

<210> SEQ ID NO 105
<211> LENGTH: 231
<212> TYPE: PRT
<213> ORGANISM: Myceliophthora thermophila

<400> SEQUENCE: 105

Met Asn Tyr Leu Ala His Cys Thr Asn Asp Asp Cys Lys Ser Phe Lys
1               5                   10                  15

Gly Asp Ser Gly Asn Val Trp Val Lys Ile Glu Gln Leu Ala Tyr Asn
            20                  25                  30

Pro Ser Ala Asn Pro Pro Trp Ala Ser Asp Leu Leu Arg Glu His Gly
        35                  40                  45

Ala Lys Trp Lys Val Thr Ile Pro Pro Ser Leu Val Pro Gly Glu Tyr
    50                  55                  60

Leu Leu Arg His Glu Ile Leu Gly Leu His Val Ala Gly Thr Val Met
65                  70                  75                  80

Gly Ala Gln Phe Tyr Pro Gly Cys Thr Gln Ile Arg Val Thr Glu Gly
                85                  90                  95

Gly Ser Thr Gln Leu Pro Ser Gly Ile Ala Leu Pro Gly Ala Tyr Gly
            100                 105                 110

Pro Gln Asp Glu Gly Ile Leu Val Asp Leu Trp Arg Val Asn Gln Gly
        115                 120                 125

Gln Val Asn Tyr Thr Ala Pro Gly Gly Pro Val Trp Ser Glu Ala Trp
    130                 135                 140

Asp Thr Glu Phe Gly Gly Ser Asn Thr Thr Glu Cys Ala Thr Met Leu
145                 150                 155                 160

Asp Asp Leu Leu Asp Tyr Met Ala Ala Asn Asp Pro Cys Cys Thr
                165                 170                 175

Asp Gln Asn Gln Phe Gly Ser Leu Glu Pro Gly Ser Lys Ala Ala Gly
            180                 185                 190

Gly Ser Pro Ser Leu Tyr Asp Thr Val Leu Val Pro Val Leu Gln Lys
        195                 200                 205

Lys Val Pro Thr Lys Leu Gln Trp Ser Gly Pro Ala Ser Val Asn Gly
    210                 215                 220

Asp Glu Leu Thr Glu Arg Pro
225                 230

<210> SEQ ID NO 106
<211> LENGTH: 681
<212> TYPE: DNA
<213> ORGANISM: Myceliophthora thermophila

<400> SEQUENCE: 106
atgaagctga gcgctgccat cgccgtgctc gcggccgccc ttgccgaggg gcactatacc    60
ttccccagca tcgccaacac ggccgactgg caatatgtgc gcatcacgac caacttccag   120
agcaacggcc ccgtgacgga cgtcaactcg accagatcc ggtgctacga gcgcaacccg   180
ggcaccggcg cccccggcat ctacaacgtc acggccggca aaccatcaa ctacaacgcc   240 aagtcgtcca tctcccaccc gggacccatg gccttctaca ttgccaaggt tcccgccggc   300
cagtcggccg ccacctggga cggtaagggc gccgtctggt ccaagatcca ccaggagatg   360
ccgcactttg gcaccagcct cacctgggac tccaacggcc gcacctccat gcccgtcacc   420 atccccgct gtctgcagga cggcgagtat ctgctgcgtg cagagcacat tgccctccac   480

```
agcgccggca gccccggcgg cgcccagttc tacatttctt gtgcccagct ctcagtcacc    540
ggcggcagcg ggacctggaa ccccaggaac aaggtgtcgt tccccggcgc ctacaaggcc    600
actgacccgg gcatcctgat caacatctac taccccgtcc cgactagcta cactcccgct    660 ggtcccccg tcgacacctg c                                               681
```

```
<210> SEQ ID NO 107
<211> LENGTH: 227
<212> TYPE: PRT
<213> ORGANISM: Myceliophthora thermophila

<400> SEQUENCE: 107
```

Met Lys Leu Ser Ala Ala Ile Ala Val Leu Ala Ala Leu Ala Glu
1               5                   10                  15

Gly His Tyr Thr Phe Pro Ser Ile Ala Asn Thr Ala Asp Trp Gln Tyr
            20                  25                  30

Val Arg Ile Thr Thr Asn Phe Gln Ser Asn Gly Pro Val Thr Asp Val
        35                  40                  45

Asn Ser Asp Gln Ile Arg Cys Tyr Glu Arg Asn Pro Gly Thr Gly Ala
50                  55                  60

Pro Gly Ile Tyr Asn Val Thr Ala Gly Thr Thr Ile Asn Tyr Asn Ala
65                  70                  75                  80

Lys Ser Ser Ile Ser His Pro Gly Pro Met Ala Phe Tyr Ile Ala Lys
                85                  90                  95

Val Pro Ala Gly Gln Ser Ala Ala Thr Trp Asp Gly Lys Gly Ala Val
            100                 105                 110

Trp Ser Lys Ile His Gln Glu Met Pro His Phe Gly Thr Ser Leu Thr
        115                 120                 125

Trp Asp Ser Asn Gly Arg Thr Ser Met Pro Val Thr Ile Pro Arg Cys
130                 135                 140

Leu Gln Asp Gly Glu Tyr Leu Leu Arg Ala Glu His Ile Ala Leu His
145                 150                 155                 160

Ser Ala Gly Ser Pro Gly Gly Ala Gln Phe Tyr Ile Ser Cys Ala Gln
                165                 170                 175

Leu Ser Val Thr Gly Gly Ser Gly Thr Trp Asn Pro Arg Asn Lys Val
            180                 185                 190

Ser Phe Pro Gly Ala Tyr Lys Ala Thr Asp Pro Gly Ile Leu Ile Asn
        195                 200                 205

Ile Tyr Tyr Pro Val Pro Thr Ser Tyr Thr Pro Ala Gly Pro Pro Val
210                 215                 220

Asp Thr Cys
225

```
<210> SEQ ID NO 108
<211> LENGTH: 210
<212> TYPE: PRT
<213> ORGANISM: Myceliophthora thermophila

<400> SEQUENCE: 108
```

His Tyr Thr Phe Pro Ser Ile Ala Asn Thr Ala Asp Trp Gln Tyr Val
1               5                   10                  15

Arg Ile Thr Thr Asn Phe Gln Ser Asn Gly Pro Val Thr Asp Val Asn
            20                  25                  30

Ser Asp Gln Ile Arg Cys Tyr Glu Arg Asn Pro Gly Thr Gly Ala Pro
        35                  40                  45

Gly Ile Tyr Asn Val Thr Ala Gly Thr Thr Ile Asn Tyr Asn Ala Lys
            50                  55                  60

Ser Ser Ile Ser His Pro Gly Pro Met Ala Phe Tyr Ile Ala Lys Val
 65                  70                  75                  80

Pro Ala Gly Gln Ser Ala Ala Thr Trp Asp Gly Lys Gly Ala Val Trp
                 85                  90                  95

Ser Lys Ile His Gln Glu Met Pro His Phe Gly Thr Ser Leu Thr Trp
            100                 105                 110

Asp Ser Asn Gly Arg Thr Ser Met Pro Val Thr Ile Pro Arg Cys Leu
            115                 120                 125

Gln Asp Gly Glu Tyr Leu Leu Arg Ala Glu His Ile Ala Leu His Ser
        130                 135                 140

Ala Gly Ser Pro Gly Gly Ala Gln Phe Tyr Ile Ser Cys Ala Gln Leu
145                 150                 155                 160

Ser Val Thr Gly Gly Ser Gly Thr Trp Asn Pro Arg Asn Lys Val Ser
                165                 170                 175

Phe Pro Gly Ala Tyr Lys Ala Thr Asp Pro Gly Ile Leu Ile Asn Ile
            180                 185                 190

Tyr Tyr Pro Val Pro Thr Ser Tyr Thr Pro Ala Gly Pro Pro Val Asp
        195                 200                 205

Thr Cys
    210

<210> SEQ ID NO 109
<211> LENGTH: 765
<212> TYPE: DNA
<213> ORGANISM: Myceliophthora thermophila

<400> SEQUENCE: 109

```
atgtaccgca cgctcggttc cattgccctg ctcgcggggg gcgctgccgc ccacggcgcc      60
gtgaccagct acaacattgc gggcaaggac taccctggat actcgggctt cgccccctacc    120 ggccaggatg tcatccagtg caatggccc gactataacc ccgtgctgtc cgccagcgac      180
cccaagctcc gctgcaacgg cggcaccggg gcggcgctgt atgccgaggc ggcccccggc     240
gacaccatca cggccacctg ggcccagtgg acgcactccc agggcccgat cctggtgtgg    300
atgtacaagt gccccggcga cttcagctcc tgcgacggct ccggcgcggg ttggttcaag    360
atcgacgagg ccggcttcca cggcgacggc acgaccgtct cctcgacac cgagaccccc     420 tcgggctggg acattgccaa gctggtcggc ggcaacaagt cgtggagcag caagatccct    480
gacggcctcg ccccgggcaa ttacctggtc cgccacgagc tcatcgccct gcaccaggcc    540
aacaacccgc aattctaccc cgagtgcgcc cagatcaagg tcaccggctc tggcaccgcc    600
gagcccgccg cctcctacaa ggccgccatc cccggctact gccagcagag cgaccccaac    660
atttcgttca acatcaacga ccactccctc ccgcaggagt acaagatccc cggtcccccg    720
gtcttcaagg gcaccgcctc cgccaaggct cgcgctttcc aggcc                    765
```

<210> SEQ ID NO 110
<211> LENGTH: 255
<212> TYPE: PRT
<213> ORGANISM: Myceliophthora thermophila

<400> SEQUENCE: 110

Met Tyr Arg Thr Leu Gly Ser Ile Ala Leu Leu Ala Gly Gly Ala Ala
 1               5                  10                  15

Ala His Gly Ala Val Thr Ser Tyr Asn Ile Ala Gly Lys Asp Tyr Pro

```
                20                  25                  30
Gly Tyr Ser Gly Phe Ala Pro Thr Gly Gln Asp Val Ile Gln Trp Gln
             35                  40                  45

Trp Pro Asp Tyr Asn Pro Val Leu Ser Ala Ser Asp Pro Lys Leu Arg
 50                  55                  60

Cys Asn Gly Gly Thr Gly Ala Ala Leu Tyr Ala Glu Ala Ala Pro Gly
 65                  70                  75                  80

Asp Thr Ile Thr Ala Thr Trp Ala Gln Trp Thr His Ser Gln Gly Pro
                 85                  90                  95

Ile Leu Val Trp Met Tyr Lys Cys Pro Gly Asp Phe Ser Ser Cys Asp
                100                 105                 110

Gly Ser Gly Ala Gly Trp Phe Lys Ile Asp Glu Ala Gly Phe His Gly
                115                 120                 125

Asp Gly Thr Thr Val Phe Leu Asp Thr Glu Thr Pro Ser Gly Trp Asp
            130                 135                 140

Ile Ala Lys Leu Val Gly Gly Asn Lys Ser Trp Ser Ser Lys Ile Pro
145                 150                 155                 160

Asp Gly Leu Ala Pro Gly Asn Tyr Leu Val Arg His Glu Leu Ile Ala
                165                 170                 175

Leu His Gln Ala Asn Asn Pro Gln Phe Tyr Pro Glu Cys Ala Gln Ile
                180                 185                 190

Lys Val Thr Gly Ser Gly Thr Ala Glu Pro Ala Ala Ser Tyr Lys Ala
                195                 200                 205

Ala Ile Pro Gly Tyr Cys Gln Gln Ser Asp Pro Asn Ile Ser Phe Asn
            210                 215                 220

Ile Asn Asp His Ser Leu Pro Gln Glu Tyr Lys Ile Pro Gly Pro Pro
225                 230                 235                 240

Val Phe Lys Gly Thr Ala Ser Ala Lys Ala Arg Ala Phe Gln Ala
                245                 250                 255

<210> SEQ ID NO 111
<211> LENGTH: 236
<212> TYPE: PRT
<213> ORGANISM: Myceliophthora thermophila

<400> SEQUENCE: 111

Ala Val Thr Ser Tyr Asn Ile Ala Gly Lys Asp Tyr Pro Gly Tyr Ser
 1               5                  10                  15

Gly Phe Ala Pro Thr Gly Gln Asp Val Ile Gln Trp Gln Trp Pro Asp
                20                  25                  30

Tyr Asn Pro Val Leu Ser Ala Ser Asp Pro Lys Leu Arg Cys Asn Gly
             35                  40                  45

Gly Thr Gly Ala Ala Leu Tyr Ala Glu Ala Ala Pro Gly Asp Thr Ile
 50                  55                  60

Thr Ala Thr Trp Ala Gln Trp Thr His Ser Gln Gly Pro Ile Leu Val
 65                  70                  75                  80

Trp Met Tyr Lys Cys Pro Gly Asp Phe Ser Ser Cys Asp Gly Ser Gly
                 85                  90                  95

Ala Gly Trp Phe Lys Ile Asp Glu Ala Gly Phe His Gly Asp Gly Thr
                100                 105                 110

Thr Val Phe Leu Asp Thr Glu Thr Pro Ser Gly Trp Asp Ile Ala Lys
            115                 120                 125

Leu Val Gly Gly Asn Lys Ser Trp Ser Ser Lys Ile Pro Asp Gly Leu
        130                 135                 140
```

Ala Pro Gly Asn Tyr Leu Val Arg His Glu Leu Ile Ala Leu His Gln
145                 150                 155                 160

Ala Asn Asn Pro Gln Phe Tyr Pro Glu Cys Ala Gln Ile Lys Val Thr
                165                 170                 175

Gly Ser Gly Thr Ala Glu Pro Ala Ala Ser Tyr Lys Ala Ala Ile Pro
            180                 185                 190

Gly Tyr Cys Gln Gln Ser Asp Pro Asn Ile Ser Phe Asn Ile Asn Asp
        195                 200                 205

His Ser Leu Pro Gln Glu Tyr Lys Ile Pro Gly Pro Pro Val Phe Lys
    210                 215                 220

Gly Thr Ala Ser Ala Lys Ala Arg Ala Phe Gln Ala
225                 230                 235

<210> SEQ ID NO 112
<211> LENGTH: 675
<212> TYPE: DNA
<213> ORGANISM: Myceliophthora thermophila

<400> SEQUENCE: 112
atgctgacaa caaccttcgc cctcctgacg gccgctctcg gcgtcagcgc ccattatacc      60
ctccccaggg tcgggaccgg ttccgactgg cagcacgtgc ggcgggctga caactggcaa     120
aacaacggct cgtcggcga cgtcaactcg gagcagatca ggtgcttcca ggcgacccct     180
gccggcgccc aagacgtcta cactgttcag gcgggatcga ccgtgaccta ccacgccaac     240
cccagtatct accaccccgg ccccatgcag ttctacctgg cccgcgttcc ggacggacag     300
gacgtcaagt cgtggaccgg cgagggtgcc gtgtggttca aggtgtacga ggagcagcct     360
caatttggcg cccagctgac ctggcctagc aacggcaaga gctcgttcga ggttcctatc     420
cccagctgca ttcgggcggg caactacctc ctccgcgctg agcacatcgc cctgcacgtt     480
gcccaaagcc agggcggcgc ccagttctac atctcgtgcg cccagctcca ggtcactggt     540
ggcggcagca ccgagccttc tcagaaggtt tccttcccgg gtgcctacaa gtccaccgac     600
cccggcattc ttatcaacat caactacccc gtccctacct cgtaccagaa tccgggtccg     660
gctgtcttcc gttgc                                                      675

<210> SEQ ID NO 113
<211> LENGTH: 225
<212> TYPE: PRT
<213> ORGANISM: Myceliophthora thermophila

<400> SEQUENCE: 113

Met Leu Thr Thr Thr Phe Ala Leu Leu Thr Ala Ala Leu Gly Val Ser
1               5                   10                  15

Ala His Tyr Thr Leu Pro Arg Val Gly Thr Gly Ser Asp Trp Gln His
            20                  25                  30

Val Arg Arg Ala Asp Asn Trp Gln Asn Asn Gly Phe Val Gly Asp Val
        35                  40                  45

Asn Ser Glu Gln Ile Arg Cys Phe Gln Ala Thr Pro Ala Gly Ala Gln
    50                  55                  60

Asp Val Tyr Thr Val Gln Ala Gly Ser Thr Val Thr Tyr His Ala Asn
65                  70                  75                  80

Pro Ser Ile Tyr His Pro Gly Pro Met Gln Phe Tyr Leu Ala Arg Val
                85                  90                  95

Pro Asp Gly Gln Asp Val Lys Ser Trp Thr Gly Glu Gly Ala Val Trp
            100                 105                 110

```
Phe Lys Val Tyr Glu Glu Gln Pro Gln Phe Gly Ala Gln Leu Thr Trp
            115                 120                 125
Pro Ser Asn Gly Lys Ser Ser Phe Glu Val Pro Ile Pro Ser Cys Ile
130                 135                 140
Arg Ala Gly Asn Tyr Leu Leu Arg Ala Glu His Ile Ala Leu His Val
145                 150                 155                 160
Ala Gln Ser Gln Gly Gly Ala Gln Phe Tyr Ile Ser Cys Ala Gln Leu
                165                 170                 175
Gln Val Thr Gly Gly Ser Thr Glu Pro Ser Gln Lys Val Ser Phe
                180                 185                 190
Pro Gly Ala Tyr Lys Ser Thr Asp Pro Gly Ile Leu Ile Asn Ile Asn
            195                 200                 205
Tyr Pro Val Pro Thr Ser Tyr Gln Asn Pro Gly Pro Ala Val Phe Arg
210                 215                 220
Cys
225
```

<210> SEQ ID NO 114
<211> LENGTH: 208
<212> TYPE: PRT
<213> ORGANISM: Myceliophthora thermophila

<400> SEQUENCE: 114

```
His Tyr Thr Leu Pro Arg Val Gly Thr Gly Ser Asp Trp Gln His Val
1               5                   10                  15
Arg Arg Ala Asp Asn Trp Gln Asn Asn Gly Phe Val Gly Asp Val Asn
            20                  25                  30
Ser Glu Gln Ile Arg Cys Phe Gln Ala Thr Pro Ala Gly Ala Gln Asp
        35                  40                  45
Val Tyr Thr Val Gln Ala Gly Ser Thr Val Thr Tyr His Ala Asn Pro
    50                  55                  60
Ser Ile Tyr His Pro Gly Pro Met Gln Phe Tyr Leu Ala Arg Val Pro
65                  70                  75                  80
Asp Gly Gln Asp Val Lys Ser Trp Thr Gly Glu Gly Ala Val Trp Phe
                85                  90                  95
Lys Val Tyr Glu Glu Gln Pro Gln Phe Gly Ala Gln Leu Thr Trp Pro
            100                 105                 110
Ser Asn Gly Lys Ser Ser Phe Glu Val Pro Ile Pro Ser Cys Ile Arg
        115                 120                 125
Ala Gly Asn Tyr Leu Leu Arg Ala Glu His Ile Ala Leu His Val Ala
130                 135                 140
Gln Ser Gln Gly Gly Ala Gln Phe Tyr Ile Ser Cys Ala Gln Leu Gln
145                 150                 155                 160
Val Thr Gly Gly Ser Thr Glu Pro Ser Gln Lys Val Ser Phe Pro
                165                 170                 175
Gly Ala Tyr Lys Ser Thr Asp Pro Gly Ile Leu Ile Asn Ile Asn Tyr
            180                 185                 190
Pro Val Pro Thr Ser Tyr Gln Asn Pro Gly Pro Ala Val Phe Arg Cys
        195                 200                 205
```

<210> SEQ ID NO 115
<211> LENGTH: 711
<212> TYPE: DNA
<213> ORGANISM: Myceliophthora thermophila

<400> SEQUENCE: 115

```
atgaaggttc tcgcgcccct gattctggcc ggtgccgcca gcgcccacac catcttctca    60
tccctcgagg tgggcggcgt caaccagggc atcgggcagg gtgtccgcgt gccgtcgtac   120
aacggtccga tcgaggacgt gacgtccaac tcgatcgcct gcaacgggcc ccccaacccg   180
acgacgccga ccaacaaggt catcacggtc cgggccggcg agacggtgac ggccgtctgg   240
cggtacatgc tgagcaccac cggctcggcc cccaacgaca tcatggacag cagccacaag   300
ggcccgacca tggcctacct caagaaggtc gacaacgcca ccaccgactc gggcgtcggc   360
ggcggctggt tcaagatcca ggaggacggc cttaccaacg gcgtctgggg caccgagcgc   420
gtcatcaacg gccagggccg ccacaacatc aagatcccg agtgcatcgc ccccggccag    480
tacctcctcc gcgccgagat gcttgccctg cacggagctt ccaactaccc cggcgctcag   540
ttctacatgg agtgcgccca gctcaatatc gtcggcggca ccggcagcaa gacgccgtcc   600
accgtcagct tcccgggcgc ttacaagggt accgaccccg gagtcaagat caacatctac   660
tggccccccg tcaccagcta ccagattccc ggccccggcg tgttcacctg c             711
```

<210> SEQ ID NO 116
<211> LENGTH: 237
<212> TYPE: PRT
<213> ORGANISM: Myceliophthora thermophila

<400> SEQUENCE: 116

```
Met Lys Val Leu Ala Pro Leu Ile Leu Ala Gly Ala Ala Ser Ala His
 1               5                  10                  15
Thr Ile Phe Ser Ser Leu Glu Val Gly Gly Val Asn Gln Gly Ile Gly
            20                  25                  30
Gln Gly Val Arg Val Pro Ser Tyr Asn Gly Pro Ile Glu Asp Val Thr
        35                  40                  45
Ser Asn Ser Ile Ala Cys Asn Gly Pro Pro Asn Pro Thr Thr Pro Thr
    50                  55                  60
Asn Lys Val Ile Thr Val Arg Ala Gly Glu Thr Val Thr Ala Val Trp
65                  70                  75                  80
Arg Tyr Met Leu Ser Thr Thr Gly Ser Ala Pro Asn Asp Ile Met Asp
                85                  90                  95
Ser Ser His Lys Gly Pro Thr Met Ala Tyr Leu Lys Lys Val Asp Asn
            100                 105                 110
Ala Thr Asp Ser Gly Val Gly Gly Trp Phe Lys Ile Gln Glu
        115                 120                 125
Asp Gly Leu Thr Asn Gly Val Trp Gly Thr Glu Arg Val Ile Asn Gly
    130                 135                 140
Gln Gly Arg His Asn Ile Lys Ile Pro Glu Cys Ile Ala Pro Gly Gln
145                 150                 155                 160
Tyr Leu Leu Arg Ala Glu Met Leu Ala Leu His Gly Ala Ser Asn Tyr
                165                 170                 175
Pro Gly Ala Gln Phe Tyr Met Glu Cys Ala Gln Leu Asn Ile Val Gly
            180                 185                 190
Gly Thr Gly Ser Lys Thr Pro Ser Thr Val Ser Phe Pro Gly Ala Tyr
        195                 200                 205
Lys Gly Thr Asp Pro Gly Val Lys Ile Asn Ile Tyr Trp Pro Pro Val
    210                 215                 220
Thr Ser Tyr Gln Ile Pro Gly Pro Gly Val Phe Thr Cys
225                 230                 235
```

<210> SEQ ID NO 117

```
<211> LENGTH: 222
<212> TYPE: PRT
<213> ORGANISM: Myceliophthora thermophila

<400> SEQUENCE: 117

His Thr Ile Phe Ser Ser Leu Glu Val Gly Gly Val Asn Gln Gly Ile
1               5                   10                  15

Gly Gln Gly Val Arg Val Pro Ser Tyr Asn Gly Pro Ile Glu Asp Val
            20                  25                  30

Thr Ser Asn Ser Ile Ala Cys Asn Gly Pro Asn Pro Thr Thr Pro
        35                  40                  45

Thr Asn Lys Val Ile Thr Val Arg Ala Gly Glu Thr Val Thr Ala Val
    50                  55                  60

Trp Arg Tyr Met Leu Ser Thr Thr Gly Ser Ala Pro Asn Asp Ile Met
65                  70                  75                  80

Asp Ser Ser His Lys Gly Pro Thr Met Ala Tyr Leu Lys Lys Val Asp
                85                  90                  95

Asn Ala Thr Thr Asp Ser Gly Val Gly Gly Trp Phe Lys Ile Gln
            100                 105                 110

Glu Asp Gly Leu Thr Asn Gly Val Trp Gly Thr Glu Arg Val Ile Asn
        115                 120                 125

Gly Gln Gly Arg His Asn Ile Lys Ile Pro Glu Cys Ile Ala Pro Gly
    130                 135                 140

Gln Tyr Leu Leu Arg Ala Glu Met Leu Ala Leu His Gly Ala Ser Asn
145                 150                 155                 160

Tyr Pro Gly Ala Gln Phe Tyr Met Glu Cys Ala Gln Leu Asn Ile Val
                165                 170                 175

Gly Gly Thr Gly Ser Lys Thr Pro Ser Thr Val Ser Phe Pro Gly Ala
            180                 185                 190

Tyr Lys Gly Thr Asp Pro Gly Val Lys Ile Asn Ile Tyr Trp Pro Pro
        195                 200                 205

Val Thr Ser Tyr Gln Ile Pro Gly Pro Gly Val Phe Thr Cys
    210                 215                 220

<210> SEQ ID NO 118
<211> LENGTH: 225
<212> TYPE: DNA
<213> ORGANISM: Myceliophthora thermophila

<400> SEQUENCE: 118
atgatcgaca acctccctga tgactcccta caacccgcct gcctccgccc gggccactac      60
ctcgtccgcc acgagatcat cgcgctgcac tcggcctggg ccgagggcga ggcccagttc     120
taccccttcc cctttttcc tttttttccc tcccttcttt tgtccggtaa ctacacgatt      180
cccggtcccg cgatctggaa gtgcccagag gcacagcaga acgag                     225

<210> SEQ ID NO 119
<211> LENGTH: 75
<212> TYPE: PRT
<213> ORGANISM: Myceliophthora thermophila

<400> SEQUENCE: 119

Met Ile Asp Asn Leu Pro Asp Asp Ser Leu Gln Pro Ala Cys Leu Arg
1               5                   10                  15

Pro Gly His Tyr Leu Val Arg His Glu Ile Ile Ala Leu His Ser Ala
            20                  25                  30

Trp Ala Glu Gly Glu Ala Gln Phe Tyr Pro Phe Pro Leu Phe Pro Phe
```

```
                35                  40                  45
Phe Pro Ser Leu Leu Leu Ser Gly Asn Tyr Thr Ile Pro Gly Pro Ala
     50                  55                  60

Ile Trp Lys Cys Pro Glu Ala Gln Gln Asn Glu
65                  70                  75
```

<210> SEQ ID NO 120
<211> LENGTH: 57
<212> TYPE: PRT
<213> ORGANISM: Myceliophthora thermophila

<400> SEQUENCE: 120

```
His Tyr Leu Val Arg His Glu Ile Ile Ala Leu His Ser Ala Trp Ala
1               5                   10                  15

Glu Gly Glu Ala Gln Phe Tyr Pro Phe Pro Leu Phe Pro Phe Phe Pro
            20                  25                  30

Ser Leu Leu Leu Ser Gly Asn Tyr Thr Ile Pro Gly Pro Ala Ile Trp
        35                  40                  45

Lys Cys Pro Glu Ala Gln Gln Asn Glu
    50                  55
```

<210> SEQ ID NO 121
<211> LENGTH: 1395
<212> TYPE: DNA
<213> ORGANISM: Myceliophthora thermophila

<400> SEQUENCE: 121

```
atggggcaga agactctcca ggggctggtg gcggcggcgg cactggcagc ctcggtggcg      60
aacgcgcagc aaccgggcac cttcacgccc gaggtgcatc cgacgctgcc gacgtggaag     120
tgcacgacga gcggcgggtg cgtccagcag acacgtcgg tggtgctcga ctggaactac      180
cgctggttcc acaccgagga cggtagcaag tcgtgcatca cctctagcgg cgtcgaccgg     240
accctgtgcc cggacgaggc gacgtgcgcc aagaactgct cgtcgagggg cgtcaactac     300
acgagcagcg gggtcgagac gtccggcagc tccctcaccc tccgccagtt cttcaagggc     360
tccgacggcg ccatcaacag cgtctccccg cgcgtctacc tgctcggggg agacggcaac     420
tatgtcgtgc tcaagctcct cggccaggag ctgagcttcg acgtggacgt atcgtcgctc     480
ccgtgcggcg agaacgcggc cctgtacctg tccgagatgg acgcgacggg aggacggaac     540
gagtacaaca cgggcggggc cgagtacggg tcgggctact gtgacgccca gtgccccgtg     600
cagaactgga caacgggac gctcaacacg ggccgggtgg ctcgtgctg caacgagatg      660
gacatcctcg aggccaactc caaggccgag gccttcacgc cgcaccctg catcggcaac     720
tcgtgcgaca gagcgggtg cggcttcaac gcgtacgcgc gcggttacca caactactgg     780
gcccccggcg gcacgctcga cacgtcccgg cctttcacca tgatcacccg cttcgtcacc     840
gacgacggca ccacctcggg caagctcgcc cgcatcgagc gcgtctacgt ccaggacggc     900
aagaaggtgc ccagcgcggc gcccgggggg gacgtcatca cggccgacgg tgcacctcc     960
gcgcagccct acggcggcct ttccggcatg ggcgacgccc tcggccgcgg catggtcctg    1020
gccctgagca tctggaacga cgcgtccggg tacatgaact ggctcgacgc cggcagcaac    1080
ggcccctgca gcgacaccga gggtaacccg tccaacatcc tggccaacca cccggacgcc    1140
cacgtcgtgc tctccaacat ccgctggggc gacatcggct ccaccgtcga caccggcgat    1200
ggcgacaaca acggcggcgg ccccaacccg tcatccacca ccaccggctac cgctaccacc    1260
acctcctccg gcccggccga gctacccag acccactacg ccagtgtgg agggaaagga     1320
```

```
tggacgggcc ctacccgctg cgagacgccc tacacctgca agtaccagaa cgactggtac    1380
tcgcagtgcc tgtag                                                      1395
```

<210> SEQ ID NO 122
<211> LENGTH: 464
<212> TYPE: PRT
<213> ORGANISM: Myceliophthora thermophila

<400> SEQUENCE: 122

```
Met Gly Gln Lys Thr Leu Gln Gly Leu Val Ala Ala Ala Leu Ala
1               5                   10                  15

Ala Ser Val Ala Asn Ala Gln Gln Pro Gly Thr Phe Thr Pro Glu Val
            20                  25                  30

His Pro Thr Leu Pro Thr Trp Lys Cys Thr Thr Ser Gly Gly Cys Val
            35                  40                  45

Gln Gln Asp Thr Ser Val Val Leu Asp Trp Asn Tyr Arg Trp Phe His
        50                  55                  60

Thr Glu Asp Gly Ser Lys Ser Cys Ile Thr Ser Ser Gly Val Asp Arg
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Glu Thr Ser Gly Ser Ser Leu
            100                 105                 110

Thr Leu Arg Gln Phe Phe Lys Gly Ser Asp Gly Ala Ile Asn Ser Val
        115                 120                 125

Ser Pro Arg Val Tyr Leu Leu Gly Gly Asp Gly Asn Tyr Val Val Leu
    130                 135                 140

Lys Leu Leu Gly Gln Glu Leu Ser Phe Asp Val Asp Val Ser Ser Leu
145                 150                 155                 160

Pro Cys Gly Glu Asn Ala Ala Leu Tyr Leu Ser Glu Met Asp Ala Thr
                165                 170                 175

Gly Gly Arg Asn Glu Tyr Asn Thr Gly Gly Ala Glu Tyr Gly Ser Gly
            180                 185                 190

Tyr Cys Asp Ala Gln Cys Pro Val Gln Asn Trp Asn Asn Gly Thr Leu
        195                 200                 205

Asn Thr Gly Arg Val Gly Ser Cys Cys Asn Glu Met Asp Ile Leu Glu
    210                 215                 220

Ala Asn Ser Lys Ala Glu Ala Phe Thr Pro His Pro Cys Ile Gly Asn
225                 230                 235                 240

Ser Cys Asp Lys Ser Gly Cys Gly Phe Asn Ala Tyr Ala Arg Gly Tyr
                245                 250                 255

His Asn Tyr Trp Ala Pro Gly Gly Thr Leu Asp Thr Ser Arg Pro Phe
            260                 265                 270

Thr Met Ile Thr Arg Phe Val Thr Asp Asp Gly Thr Thr Ser Gly Lys
        275                 280                 285

Leu Ala Arg Ile Glu Arg Val Tyr Val Gln Asp Gly Lys Lys Val Pro
    290                 295                 300

Ser Ala Ala Pro Gly Gly Asp Val Ile Thr Ala Asp Gly Cys Thr Ser
305                 310                 315                 320

Ala Gln Pro Tyr Gly Gly Leu Ser Gly Met Gly Asp Ala Leu Gly Arg
                325                 330                 335

Gly Met Val Leu Ala Leu Ser Ile Trp Asn Asp Ala Ser Gly Tyr Met
            340                 345                 350
```

```
Asn Trp Leu Asp Ala Gly Ser Asn Gly Pro Cys Ser Asp Thr Glu Gly
            355                 360                 365

Asn Pro Ser Asn Ile Leu Ala Asn His Pro Asp Ala His Val Val Leu
        370                 375                 380

Ser Asn Ile Arg Trp Gly Asp Ile Gly Ser Thr Val Asp Thr Gly Asp
385                 390                 395                 400

Gly Asp Asn Asn Gly Gly Pro Asn Pro Ser Ser Thr Thr Thr Ala
                405                 410                 415

Thr Ala Thr Thr Thr Ser Ser Gly Pro Ala Glu Pro Thr Gln Thr His
                420                 425                 430

Tyr Gly Gln Cys Gly Gly Lys Gly Trp Thr Gly Pro Thr Arg Cys Glu
            435                 440                 445

Thr Pro Tyr Thr Cys Lys Tyr Gln Asn Asp Trp Tyr Ser Gln Cys Leu
        450                 455                 460

<210> SEQ ID NO 123
<211> LENGTH: 442
<212> TYPE: PRT
<213> ORGANISM: Myceliophthora thermophila

<400> SEQUENCE: 123

Gln Gln Pro Gly Thr Phe Thr Pro Glu Val His Pro Thr Leu Pro Thr
1               5                   10                  15

Trp Lys Cys Thr Thr Ser Gly Gly Cys Val Gln Gln Asp Thr Ser Val
            20                  25                  30

Val Leu Asp Trp Asn Tyr Arg Trp Phe His Thr Glu Asp Gly Ser Lys
        35                  40                  45

Ser Cys Ile Thr Ser Ser Gly Val Asp Arg Thr Leu Cys Pro Asp Glu
    50                  55                  60

Ala Thr Cys Ala Lys Asn Cys Phe Val Glu Gly Val Asn Tyr Thr Ser
65                  70                  75                  80

Ser Gly Val Glu Thr Ser Gly Ser Ser Leu Thr Leu Arg Gln Phe Phe
                85                  90                  95

Lys Gly Ser Asp Gly Ala Ile Asn Ser Val Ser Pro Arg Val Tyr Leu
            100                 105                 110

Leu Gly Gly Asp Gly Asn Tyr Val Val Leu Lys Leu Leu Gly Gln Glu
        115                 120                 125

Leu Ser Phe Asp Val Asp Val Ser Ser Leu Pro Cys Gly Glu Asn Ala
    130                 135                 140

Ala Leu Tyr Leu Ser Glu Met Asp Ala Thr Gly Gly Arg Asn Glu Tyr
145                 150                 155                 160

Asn Thr Gly Gly Ala Glu Tyr Gly Ser Gly Tyr Cys Asp Ala Gln Cys
                165                 170                 175

Pro Val Gln Asn Trp Asn Asn Gly Thr Leu Asn Thr Gly Arg Val Gly
            180                 185                 190

Ser Cys Cys Asn Glu Met Asp Ile Leu Glu Ala Asn Ser Lys Ala Glu
        195                 200                 205

Ala Phe Thr Pro His Pro Cys Ile Gly Asn Ser Cys Asp Lys Ser Gly
    210                 215                 220

Cys Gly Phe Asn Ala Tyr Ala Arg Gly Tyr His Asn Tyr Trp Ala Pro
225                 230                 235                 240

Gly Gly Thr Leu Asp Thr Ser Arg Pro Phe Thr Met Ile Thr Arg Phe
                245                 250                 255

Val Thr Asp Asp Gly Thr Thr Ser Gly Lys Leu Ala Arg Ile Glu Arg
            260                 265                 270
```

```
Val Tyr Val Gln Asp Gly Lys Lys Val Pro Ser Ala Ala Pro Gly Gly
        275                 280                 285

Asp Val Ile Thr Ala Asp Gly Cys Thr Ser Ala Gln Pro Tyr Gly Gly
        290                 295                 300

Leu Ser Gly Met Gly Asp Ala Leu Gly Arg Gly Met Val Leu Ala Leu
305                 310                 315                 320

Ser Ile Trp Asn Asp Ala Ser Gly Tyr Met Asn Trp Leu Asp Ala Gly
                325                 330                 335

Ser Asn Gly Pro Cys Ser Asp Thr Glu Gly Asn Pro Ser Asn Ile Leu
                340                 345                 350

Ala Asn His Pro Asp Ala His Val Val Leu Ser Asn Ile Arg Trp Gly
                355                 360                 365

Asp Ile Gly Ser Thr Val Asp Thr Gly Asp Gly Asp Asn Asn Gly Gly
        370                 375                 380

Gly Pro Asn Pro Ser Ser Thr Thr Thr Ala Thr Ala Thr Thr Thr Ser
385                 390                 395                 400

Ser Gly Pro Ala Glu Pro Thr Gln Thr His Tyr Gly Gln Cys Gly Gly
                405                 410                 415

Lys Gly Trp Thr Gly Pro Thr Arg Cys Glu Thr Pro Tyr Thr Cys Lys
                420                 425                 430

Tyr Gln Asn Asp Trp Tyr Ser Gln Cys Leu
        435                 440

<210> SEQ ID NO 124
<211> LENGTH: 1170
<212> TYPE: DNA
<213> ORGANISM: Myceliophthora thermophila

<400> SEQUENCE: 124
atgaagtcct ccatcctcgc cagcgtcttc gccacgggcg ccgtggctca aagtggtccg      60
tggcagcaat gtggtggcat cggatggcaa ggatcgaccg actgtgtgtc gggttaccac     120
tgcgtctacc agaacgattg gtacagccag tgcgtgcctg gcgcggcgtc gacaacgctc     180
cagacatcta ccacgtccag gcccaccgcc accagcaccg ccctccgtc gtccaccacc     240
tcgcctagca agggcaagct caagtggctc ggcagcaacg agtcgggcgc cgagttcggg     300
gagggcaact accccggcct ctggggcaag cacttcatct cccgtcgac ttcggcgatt     360
cagacgctca tcaatgatgg atacaacatc ttccggatcg acttctcgat ggagcgtctg     420
gtgcccaacc agttgacgtc gtccttcgac gagggctacc tccgcaacct gaccgaggtg     480
gtcaacttcg tgacgaacgc gggcaagtac gccgtcctgg acccgcacaa ctacggccgg     540
tactacggca acgtcatcac ggacacgaac gcgttccgga ccttctggac caacctggcc     600
aagcagttcg cctccaactc gctcgtcatc ttcgacacca caacgagta caacacgatg     660
gaccagaccc tggtgctcaa cctcaaccag gccgccatcg acggcatccg ggccgccggc     720
gcgacctcgc agtacatctt cgtcgagggc aacgcgtgga gcggggcctg gagctggaac     780
acgaccaaca ccaacatggc cgccctgacg gacccgcaga acaagatcgt gtacgagatg     840
caccagtacc tcgactcgga cagctcgggc acccacgccg agtgcgtcag cagcaacatc     900
ggcgcccagc gcgtcgtcgg agccacccag tggctccgcg ccaacggcaa gctcggcgtc     960
ctcggcgagt cgccggcgg cgccaacgcc gtctgccagc aggccgtcac cggcctcctc    1020
gaccacctcc aggacaacag cgacgtctgg ctgggtgccc tctggtgggc cgccggtccc    1080
tggtggggcg actacatgta ctcgttcgag cctccttcgg gcaccggcta tgtcaactac    1140
```
aactcgatcc taaagaagta cttgccgtaa                                                1170

<210> SEQ ID NO 125
<211> LENGTH: 389
<212> TYPE: PRT
<213> ORGANISM: Myceliophthora thermophila

<400> SEQUENCE: 125

Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Glu Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Val Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Ser Trp Asn Thr Thr Asn Thr Asn Met Ala Ala Leu Thr Asp Pro
            260                 265                 270

Gln Asn Lys Ile Val Tyr Glu Met His Gln Tyr Leu Asp Ser Asp Ser
        275                 280                 285

Ser Gly Thr His Ala Glu Cys Val Ser Ser Asn Ile Gly Ala Gln Arg
    290                 295                 300

Val Val Gly Ala Thr Gln Trp Leu Arg Ala Asn Gly Lys Leu Gly Val
305                 310                 315                 320

Leu Gly Glu Phe Ala Gly Ala Asn Ala Val Cys Gln Gln Ala Val
                325                 330                 335

Thr Gly Leu Leu Asp His Leu Gln Asp Asn Ser Glu Val Trp Leu Gly
            340                 345                 350

Ala Leu Trp Trp Ala Ala Gly Pro Trp Trp Gly Asp Tyr Met Tyr Ser
        355                 360                 365

Phe Glu Pro Pro Ser Gly Thr Gly Tyr Val Asn Tyr Asn Ser Ile Leu
            370                 375                 380

Lys Lys Tyr Leu Pro
385

<210> SEQ ID NO 126
<211> LENGTH: 373
<212> TYPE: PRT
<213> ORGANISM: Myceliophthora thermophila

<400> SEQUENCE: 126

Gln Ser Gly Pro Trp Gln Gln Cys Gly Ile Gly Trp Gln Gly Ser
1               5                   10                  15

Thr Asp Cys Val Ser Gly Tyr His Cys Val Tyr Gln Asn Asp Trp Tyr
            20                  25                  30

Ser Gln Cys Val Pro Gly Ala Ala Ser Thr Thr Leu Gln Thr Ser Thr
            35                  40                  45

Thr Ser Arg Pro Thr Ala Thr Ser Thr Ala Pro Pro Ser Ser Thr Thr
50                      55                  60

Ser Pro Ser Lys Gly Lys Leu Lys Trp Leu Gly Ser Asn Glu Ser Gly
65                      70                  75                  80

Ala Glu Phe Gly Glu Gly Asn Tyr Pro Gly Leu Trp Gly Lys His Phe
                85                  90                  95

Ile Phe Pro Ser Thr Ser Ala Ile Gln Thr Leu Ile Asn Asp Gly Tyr
            100                 105                 110

Asn Ile Phe Arg Ile Asp Phe Ser Met Glu Arg Leu Val Pro Asn Gln
            115                 120                 125

Leu Thr Ser Ser Phe Asp Glu Gly Tyr Leu Arg Asn Leu Thr Glu Val
            130                 135                 140

Val Asn Phe Val Thr Asn Ala Gly Lys Tyr Ala Val Leu Asp Pro His
145                 150                 155                 160

Asn Tyr Gly Arg Tyr Tyr Gly Asn Val Ile Thr Asp Thr Asn Ala Phe
                165                 170                 175

Arg Thr Phe Trp Thr Asn Leu Ala Lys Gln Phe Ala Ser Asn Ser Leu
            180                 185                 190

Val Ile Phe Asp Thr Asn Asn Glu Tyr Asn Thr Met Asp Gln Thr Leu
            195                 200                 205

Val Leu Asn Leu Asn Gln Ala Ala Ile Asp Gly Ile Arg Ala Ala Gly
            210                 215                 220

Ala Thr Ser Gln Tyr Ile Phe Val Glu Gly Asn Ala Trp Ser Gly Ala
225                 230                 235                 240

Trp Ser Trp Asn Thr Thr Asn Thr Asn Met Ala Ala Leu Thr Asp Pro
                245                 250                 255

Gln Asn Lys Ile Val Tyr Glu Met His Gln Tyr Leu Asp Ser Asp Ser
            260                 265                 270

Ser Gly Thr His Ala Glu Cys Val Ser Ser Asn Ile Gly Ala Gln Arg
            275                 280                 285

Val Val Gly Ala Thr Gln Trp Leu Arg Ala Asn Gly Lys Leu Gly Val
            290                 295                 300

Leu Gly Glu Phe Ala Gly Gly Ala Asn Ala Val Cys Gln Gln Ala Val
305                 310                 315                 320

Thr Gly Leu Leu Asp His Leu Gln Asp Asn Ser Glu Val Trp Leu Gly
                325                 330                 335

Ala Leu Trp Trp Ala Ala Gly Pro Trp Trp Gly Asp Tyr Met Tyr Ser

```
                     340                 345                 350
Phe Glu Pro Pro Ser Gly Thr Gly Tyr Val Asn Tyr Asn Ser Ile Leu
            355                 360                 365
Lys Lys Tyr Leu Pro
        370

<210> SEQ ID NO 127
<211> LENGTH: 2613
<212> TYPE: DNA
<213> ORGANISM: Myceliophthora thermophila

<400> SEQUENCE: 127
atgaaggctg ctgcgctttc ctgcctcttc ggcagtaccc ttgccgttgc aggcgccatt      60
gaatcgagaa aggttcacca gaagcccctc gcgagatctg aaccttttta cccgtcgcca     120
tggatgaatc ccaacgccga cggctgggcg gaggcctatg cccaggccaa gtcctttgtc     180
tcccaaatga ctctgctaga aaggtcaac ttgaccacgg gagtcggctg ggggctgag      240 cagtgcgtcg gccaagtggg cgcgatccct cgccttggac ttcgcagtct gtgcatgcat     300
gactcccctc tcggcatccg aggagccgac tacaactcag cgttcccctc tggccagacc     360
gttgctgcta cctgggatcg cggtctgatg taccgtcgcg gctacgcaat gggccaggag     420
gccaaaggca agggcatcaa tgtccttctc ggaccagtcg ccggccccct ggccgcatg      480 cccgagggcg gtcgtaactg ggaaggcttc gctccggatc ccgtccttac cggcatcggc     540
atgtccgaga cgatcaaggg cattcaggat gctggcgtca tcgcttgtgc gaagcacttt     600
attggaaacg agcaggagca cttcagacag gtgccagaag cccagggata cggttacaac     660
atcagcgaaa ccctctcctc caacattgac gacaagacca tgcacgagct ctacctttgg     720
ccgtttgccg atgccgtccg ggccggcgtc ggctctgtca tgtgctcgta ccagcaggtc     780
aacaactcgt acgcctgcca gaactcgaag ctgctgaacg acctcctcaa gaacgagctt     840
gggtttcagg gcttcgtcat gagcgactgg caggcacagc acactggcgc agcaagcgcc     900
gtggctggtc tcgatatgtc catgccgggc gacacccagt tcaacactgg cgtcagtttc     960
tggggcgcca atctcacccc tcgccgtcct caacggcacag tccctgccta ccgtctcgac    1020
gacatggcca tgcgcatcat ggccgccctc ttcaaggtca ccaagaccac cgacctggaa    1080
ccgatcaact tctccttctg gaccgacgac acttatggcc cgatccactg gccgccaag     1140 cagggctacc aggagattaa ttcccacgtt gacgtccgcg ccgaccacgg caacctcatc    1200
cgggagattg ccgccaaggg tacggtgctg ctgaagaata ccggctctct accctgaac     1260 aagccaaagt tcgtggccgt catcggcgag gatgctgggt cgagcccaa cgggcccaac     1320 ggctgcagcg accgcggctg taacgaaggc acgctcgcca tgggctgggg atccggcaca    1380
gccaactatc cgtacctcgt tccccccgac gccgcgctcc aggcccgggc catccaggac    1440
ggcacgaggt acgagagcgt cctgtccaac tacgccgagg aaaagacaaa ggctctggtc    1500
tcgcaggcca atgcaaccgc catcgtcttc gtcaatgccg actcaggcga gggctacatc    1560
aacgtggacg gtaacgaggg cgaccgtaag aacctgactc tctggaacaa cggtgatact    1620
ctggtcaaga acgtctcgag ctggtgcagc aacaccatcg tcgtcatcca ctcggtcggc    1680
ccggtcctcc tgaccgattg gtacgacaac cccaacatca cggccattct ctgggctggt    1740
cttccgggcc aggagtcggg caactccatc accgacgtgc tttacggcaa ggtcaacccc    1800
gccgcccgct cgccctttac ttggggcaag acccgcgaaa gctatggcgc ggacgtcctg    1860
tacaagccga ataatggcaa tggtgcgccc caacaggact tcaccgaggg cgtcttcatc    1920
```

```
gactaccgct acttcgacaa ggttgacgat gactcggtca tctacgagtt cggccacggc    1980
ctgagctaca ccaccttcga gtacagcaac atccgcgtcg tcaagtccaa cgtcagcgag    2040
taccggccca cgacgggcac cacggcccag gccccgacgt ttggcaactt ctccaccgac    2100
ctcgaggact atctcttccc caaggacgag ttcccctaca tctaccagta catctacccg    2160
tacctcaaca cgaccgaccc ccggagggcc tcggccgatc ccactacgg ccagaccgcc     2220 gaggagttcc tcccgcccca cgccaccgat gacgaccccc agccgctcct ccggtcctcg    2280
ggcggaaact ccccggcgg caaccgccag ctgtacgaca ttgtctacac aatcacggcc     2340
gacatcacga atacgggctc cgttgtaggc gaggaggtac cgcagctcta cgtctcgctg    2400
ggcggtcccg aggatcccaa ggtgcagctg cgcgactttg acaggatgcg gatcgaaccc    2460
ggcgagacga ggcagttcac cggccgcctg acgcgcagag atctgagcaa ctgggacgtc    2520
acggtgcagg actgggtcat cagcaggtat cccaagacgg catatgttgg gaggagcagc    2580
cggaagttgg atctcaagat tgagcttcct tga                                 2613
```

<210> SEQ ID NO 128
<211> LENGTH: 870
<212> TYPE: PRT
<213> ORGANISM: Myceliophthora thermophila

<400> SEQUENCE: 128

```
Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
```

-continued

```
                245                 250                 255
Tyr Gln Gln Val Asn Asn Ser Tyr Ala Cys Gln Asn Ser Lys Leu Leu
            260                 265                 270
Asn Asp Leu Leu Lys Asn Glu Leu Gly Phe Gln Gly Phe Val Met Ser
            275                 280             285
Asp Trp Gln Ala Gln His Thr Gly Ala Ala Ser Ala Val Ala Gly Leu
        290                 295                 300
Asp Met Ser Met Pro Gly Asp Thr Gln Phe Asn Thr Gly Val Ser Phe
305                 310                 315                 320
Trp Gly Ala Asn Leu Thr Leu Ala Val Leu Asn Gly Thr Val Pro Ala
                325                 330                 335
Tyr Arg Leu Asp Asp Met Ala Met Arg Ile Met Ala Ala Leu Phe Lys
            340                 345                 350
Val Thr Lys Thr Thr Asp Leu Glu Pro Ile Asn Phe Ser Phe Trp Thr
            355                 360                 365
Asp Asp Thr Tyr Gly Pro Ile His Trp Ala Ala Lys Gln Gly Tyr Gln
        370                 375                 380
Glu Ile Asn Ser His Val Asp Val Arg Ala Asp His Gly Asn Leu Ile
385                 390                 395                 400
Arg Glu Ile Ala Ala Lys Gly Thr Val Leu Leu Lys Asn Thr Gly Ser
                405                 410                 415
Leu Pro Leu Asn Lys Pro Lys Phe Val Ala Val Ile Gly Glu Asp Ala
            420                 425                 430
Gly Ser Ser Pro Asn Gly Pro Asn Gly Cys Ser Asp Arg Gly Cys Asn
            435                 440                 445
Glu Gly Thr Leu Ala Met Gly Trp Gly Ser Gly Thr Ala Asn Tyr Pro
        450                 455                 460
Tyr Leu Val Ser Pro Asp Ala Ala Leu Gln Ala Arg Ala Ile Gln Asp
465                 470                 475                 480
Gly Thr Arg Tyr Glu Ser Val Leu Ser Asn Tyr Ala Glu Glu Lys Thr
                485                 490                 495
Lys Ala Leu Val Ser Gln Ala Asn Ala Thr Ala Ile Val Phe Val Asn
            500                 505                 510
Ala Asp Ser Gly Glu Gly Tyr Ile Asn Val Asp Gly Asn Glu Gly Asp
            515                 520                 525
Arg Lys Asn Leu Thr Leu Trp Asn Asn Gly Asp Thr Leu Val Lys Asn
        530                 535                 540
Val Ser Ser Trp Cys Ser Asn Thr Ile Val Ile His Ser Val Gly
545                 550                 555                 560
Pro Val Leu Leu Thr Asp Trp Tyr Asp Asn Pro Asn Ile Thr Ala Ile
                565                 570                 575
Leu Trp Ala Gly Leu Pro Gly Gln Glu Ser Gly Asn Ser Ile Thr Asp
            580                 585                 590
Val Leu Tyr Gly Lys Val Asn Pro Ala Ala Arg Ser Pro Phe Thr Trp
            595                 600                 605
Gly Lys Thr Arg Glu Ser Tyr Gly Ala Asp Val Leu Tyr Lys Pro Asn
        610                 615                 620
Asn Gly Asn Gly Ala Pro Gln Gln Asp Phe Thr Glu Gly Val Phe Ile
625                 630                 635                 640
Asp Tyr Arg Tyr Phe Asp Lys Val Asp Asp Ser Val Ile Tyr Glu
                645                 650                 655
Phe Gly His Gly Leu Ser Tyr Thr Thr Phe Glu Tyr Ser Asn Ile Arg
            660                 665                 670
```

```
Val Val Lys Ser Asn Val Ser Glu Tyr Arg Pro Thr Thr Gly Thr Thr
            675                 680                 685

Ala Gln Ala Pro Thr Phe Gly Asn Phe Ser Thr Asp Leu Glu Asp Tyr
690                 695                 700

Leu Phe Pro Lys Asp Glu Phe Pro Tyr Ile Tyr Gln Tyr Ile Tyr Pro
705                 710                 715                 720

Tyr Leu Asn Thr Thr Asp Pro Arg Arg Ala Ser Ala Asp Pro His Tyr
                725                 730                 735

Gly Gln Thr Ala Glu Glu Phe Leu Pro Pro His Ala Thr Asp Asp Asp
            740                 745                 750

Pro Gln Pro Leu Leu Arg Ser Ser Gly Gly Asn Ser Pro Gly Gly Asn
                755                 760                 765

Arg Gln Leu Tyr Asp Ile Val Tyr Thr Ile Thr Ala Asp Ile Thr Asn
            770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
            820                 825                 830

Arg Asp Leu Ser Asn Trp Asp Val Thr Val Gln Asp Trp Val Ile Ser
                835                 840                 845

Arg Tyr Pro Lys Thr Ala Tyr Val Gly Arg Ser Ser Arg Lys Leu Asp
            850                 855                 860

Leu Lys Ile Glu Leu Pro
865                 870

<210> SEQ ID NO 129
<211> LENGTH: 851
<212> TYPE: PRT
<213> ORGANISM: Myceliophthora thermophila

<400> SEQUENCE: 129

Ile Glu Ser Arg Lys Val His Gln Lys Pro Leu Ala Arg Ser Glu Pro
1               5                   10                  15

Phe Tyr Pro Ser Pro Trp Met Asn Pro Asn Ala Asp Gly Trp Ala Glu
            20                  25                  30

Ala Tyr Ala Gln Ala Lys Ser Phe Val Ser Gln Met Thr Leu Leu Glu
        35                  40                  45

Lys Val Asn Leu Thr Thr Gly Val Gly Trp Gly Ala Glu Gln Cys Val
50                  55                  60

Gly Gln Val Gly Ala Ile Pro Arg Leu Gly Leu Arg Ser Leu Cys Met
65                  70                  75                  80

His Asp Ser Pro Leu Gly Ile Arg Gly Ala Asp Tyr Asn Ser Ala Phe
                85                  90                  95

Pro Ser Gly Gln Thr Val Ala Ala Thr Trp Asp Arg Gly Leu Met Tyr
            100                 105                 110

Arg Arg Gly Tyr Ala Met Gly Gln Glu Ala Lys Gly Lys Gly Ile Asn
        115                 120                 125

Val Leu Leu Gly Pro Val Ala Gly Pro Leu Gly Arg Met Pro Glu Gly
130                 135                 140

Gly Arg Asn Trp Glu Gly Phe Ala Pro Asp Pro Val Leu Thr Gly Ile
145                 150                 155                 160

Gly Met Ser Glu Thr Ile Lys Gly Ile Gln Asp Ala Gly Val Ile Ala
```

```
               165                 170                 175
Cys Ala Lys His Phe Ile Gly Asn Glu Gln Glu His Phe Arg Gln Val
            180                 185                 190

Pro Glu Ala Gln Gly Tyr Gly Tyr Asn Ile Ser Glu Thr Leu Ser Ser
        195                 200                 205

Asn Ile Asp Asp Lys Thr Met His Glu Leu Tyr Leu Trp Pro Phe Ala
210                 215                 220

Asp Ala Val Arg Ala Gly Val Gly Ser Val Met Cys Ser Tyr Gln Gln
225                 230                 235                 240

Val Asn Asn Ser Tyr Ala Cys Gln Asn Ser Lys Leu Leu Asn Asp Leu
                245                 250                 255

Leu Lys Asn Glu Leu Gly Phe Gln Gly Phe Val Met Ser Asp Trp Gln
            260                 265                 270

Ala Gln His Thr Gly Ala Ala Ser Ala Val Ala Gly Leu Asp Met Ser
        275                 280                 285

Met Pro Gly Asp Thr Gln Phe Asn Thr Gly Val Ser Phe Trp Gly Ala
290                 295                 300

Asn Leu Thr Leu Ala Val Leu Asn Gly Thr Val Pro Ala Tyr Arg Leu
305                 310                 315                 320

Asp Asp Met Ala Met Arg Ile Met Ala Ala Leu Phe Lys Val Thr Lys
                325                 330                 335

Thr Thr Asp Leu Glu Pro Ile Asn Phe Ser Phe Trp Thr Asp Asp Thr
            340                 345                 350

Tyr Gly Pro Ile His Trp Ala Ala Lys Gln Gly Tyr Gln Glu Ile Asn
        355                 360                 365

Ser His Val Asp Val Arg Ala Asp His Gly Asn Leu Ile Arg Glu Ile
370                 375                 380

Ala Ala Lys Gly Thr Val Leu Leu Lys Asn Thr Gly Ser Leu Pro Leu
385                 390                 395                 400

Asn Lys Pro Lys Phe Val Ala Val Ile Gly Glu Asp Ala Gly Ser Ser
                405                 410                 415

Pro Asn Gly Pro Asn Gly Cys Ser Asp Arg Gly Cys Asn Glu Gly Thr
            420                 425                 430

Leu Ala Met Gly Trp Gly Ser Gly Thr Ala Asn Tyr Pro Tyr Leu Val
        435                 440                 445

Ser Pro Asp Ala Ala Leu Gln Ala Arg Ala Ile Gln Asp Gly Thr Arg
450                 455                 460

Tyr Glu Ser Val Leu Ser Asn Tyr Ala Glu Glu Lys Thr Lys Ala Leu
465                 470                 475                 480

Val Ser Gln Ala Asn Ala Thr Ala Ile Val Phe Val Asn Ala Asp Ser
                485                 490                 495

Gly Glu Gly Tyr Ile Asn Val Asp Gly Asn Glu Gly Asp Arg Lys Asn
            500                 505                 510

Leu Thr Leu Trp Asn Asn Gly Asp Thr Leu Val Lys Asn Val Ser Ser
        515                 520                 525

Trp Cys Ser Asn Thr Ile Val Val Ile His Ser Val Gly Pro Val Leu
530                 535                 540

Leu Thr Asp Trp Tyr Asp Asn Pro Asn Ile Thr Ala Ile Leu Trp Ala
545                 550                 555                 560

Gly Leu Pro Gly Gln Glu Ser Gly Asn Ser Ile Thr Asp Val Leu Tyr
                565                 570                 575

Gly Lys Val Asn Pro Ala Ala Arg Ser Pro Phe Thr Trp Gly Lys Thr
            580                 585                 590
```

Arg Glu Ser Tyr Gly Ala Asp Val Leu Tyr Lys Pro Asn Asn Gly Asn
         595                 600                 605

Gly Ala Pro Gln Gln Asp Phe Thr Glu Gly Val Phe Ile Asp Tyr Arg
         610                 615                 620

Tyr Phe Asp Lys Val Asp Asp Ser Val Ile Tyr Glu Phe Gly His
625                 630                 635                 640

Gly Leu Ser Tyr Thr Thr Phe Glu Tyr Ser Asn Ile Arg Val Lys
             645                 650                 655

Ser Asn Val Ser Glu Tyr Arg Pro Thr Thr Gly Thr Thr Ala Gln Ala
         660                 665                 670

Pro Thr Phe Gly Asn Phe Ser Thr Asp Leu Glu Asp Tyr Leu Phe Pro
         675                 680                 685

Lys Asp Glu Phe Pro Tyr Ile Tyr Gln Tyr Ile Tyr Pro Tyr Leu Asn
         690                 695                 700

Thr Thr Asp Pro Arg Arg Ala Ser Ala Asp Pro His Tyr Gly Gln Thr
705                 710                 715                 720

Ala Glu Glu Phe Leu Pro Pro His Ala Thr Asp Asp Pro Gln Pro
                 725                 730                 735

Leu Leu Arg Ser Ser Gly Gly Asn Ser Pro Gly Gly Asn Arg Gln Leu
             740                 745                 750

Tyr Asp Ile Val Tyr Thr Ile Thr Ala Asp Ile Thr Asn Thr Gly Ser
         755                 760                 765

Val Val Gly Glu Glu Val Pro Gln Leu Tyr Val Ser Leu Gly Gly Pro
         770                 775                 780

Glu Asp Pro Lys Val Gln Leu Arg Asp Phe Asp Arg Met Arg Ile Glu
785                 790                 795                 800

Pro Gly Glu Thr Arg Gln Phe Thr Gly Arg Leu Thr Arg Asp Leu
                 805                 810                 815

Ser Asn Trp Asp Val Thr Val Gln Asp Trp Val Ile Ser Arg Tyr Pro
             820                 825                 830

Lys Thr Ala Tyr Val Gly Arg Ser Ser Arg Lys Leu Asp Leu Lys Ile
         835                 840                 845

Glu Leu Pro
    850

<210> SEQ ID NO 130
<211> LENGTH: 2613
<212> TYPE: DNA
<213> ORGANISM: Artificial Sequence
<220> FEATURE:
<223> OTHER INFORMATION: Synthetic polynucleotide of BGL "Variant 883"

<400> SEQUENCE: 130
atgaaggctg ctgcgctttc ctgcctcttc ggcagtaccc ttgccgttgc aggcgccatt      60
gaatcgagaa aggttcacca gaagcccctc gcgagatctg aaccttttta cccgtcgcca     120
tggatgaatc ccaacgccga cggctgggcg gaggcctatg cccaggccaa gtcctttgtc     180
tcccaaatga ctctgctaga aaggtcaac ttgaccacgg gagtcggctg ggggctgag      240 cagtgcgtcg ccaagtgggc gcgatccct cgccttggac ttcgcagtct gtgcatgcat     300 gactccccctc tcggcatccg aggagccgac tacaactcag cgttcccctc tggccagacc     360
gttgctgcta cctgggatcg cggtctgatg taccgtcgcg gctacgcaat gggccaggag     420
gccaaaggca aggcatcaa tgtccttctc ggaccagtcg ccggcccct tggccgcatg     480 cccgagggcg gtcgtaactg ggaaggcttc gctccggatc ccgtccttac cggcatcggc     540

```
atgtccgaga cgatcaaggg cattcaggat gctggcgtca tcgcttgtgc gaagcacttt      600
attggaaacg agcaggagca cttcagacag gtgccagaag cccagggata cggttacaac      660
atcagcgaaa ccctctcctc caacattgac gacaagacca tgcacgagct ctacctttgg      720
ccgtttgccg atgccgtccg ggccggcgtc ggctctgtca tgtgctcgta caaccaggtc      780
aacaactcgt acgcctgcca gaactcgaag ctgctgaacg acctcctcaa gaacgagctt      840
gggtttcagg gcttcgtcat gagcgactgg tgggcacagc acactggcgc agcaagcgcc      900
gtggctggtc tcgatatgtc catgccgggc gacaccatgt tcaacactgg cgtcagtttc      960
tggggcgcca atctcaccct cgccgtcctc aacggcacag tccctgccta ccgtctcgac     1020
gacatggcca tgcgcatcat ggccgccctc ttcaaggtca ccaagaccac cgacctggaa     1080
ccgatcaact tctccttctg gacccgcgac acttatggcc cgatccactg ggccgccaag     1140
cagggctacc aggagattaa ttcccacgtt gacgtccgcg ccgaccacgg caacctcatc     1200
cggaacattg ccgccaaggg tacggtgctg ctgaagaata ccggctctct accccctgaac    1260 aagccaaagt tcgtggccgt catcggcgag gatgctgggc cgagccccaa cgggcccaac     1320
ggctgcagcg accgcggctg taacgaaggc acgctcgcca tgggctgggg atccggcaca     1380
gccaactatc cgtacctcgt tttcccccgac gccgcgctcc agttgcgggc catccaggac    1440
ggcacgaggt acgagagcgt cctgtccaac tacgccgagg aaaatacaaa ggctctggtc     1500
tcgcaggcca atgcaaccgc catcgtcttc gtcaatgccg actcaggcga gggctacatc     1560
aacgtggacg gtaacgaggg cgaccgtaag aacctgactc tctggaacaa cggtgatact     1620
ctggtcaaga acgtctcgag ctggtgcagc aacaccatcg tcgtcatcca ctcggtcggc     1680
ccggtcctcc tgaccgattg gtacgacaac cccaacatca cggccattct ctgggctggt     1740
cttccgggcc aggagtcggg caactccatc accgacgtgc tttacggcaa ggtcaacccc     1800
gccgcccgct cgcccttcac ttggggcaag acccgcgaaa gctatggcgc ggacgtcctg     1860
tacaagccga ataatggcaa ttgggcgccc caacaggact tcaccgaggg cgtcttcatc     1920
gactaccgct acttcgacaa ggttgacgat gactcggtca tctacgagtt cggccacggc     1980
ctgagctaca ccaccttcga gtacagcaac atccgcgtcg tcaagtccaa cgtcagcgag     2040
taccggccca cgacgggcac cacgattcag gccccgacgt tggcaacttc tccaccgac     2100 ctcgaggact atctcttccc caaggacgag ttccctaca tcccgcagta catctacccg       2160
tacctcaaca cgaccgaccc ccggagggcc tcggccgatc cccactacgg ccagaccgcc      2220
gaggagttcc tcccgcccca cgccaccgat gacgaccccc agccgctcct ccggtcctcg      2280
ggcggaaact cccccggcgg caaccgccag ctgtacgaca ttgtctacac aatcacggcc      2340
gacatcacga atacgggctc cgttgtaggc gaggaggtac cgcagctcta cgtctcgctg     2400
ggcggtcccg aggatcccaa ggtgcagctg cgcgactttg acaggatgcg gatcgaaccc     2460
ggcgagacga ggcagttcac cggccgcctg acgcgcagag atctgagcaa ctgggacgtc     2520
acggtgcagg actgggtcat cagcaggtat cccaagacgg catatgttgg gaggagcagc     2580
cggaagttgg atctcaagat tgagcttcct tga                                   2613
```

<210> SEQ ID NO 131
<211> LENGTH: 870
<212> TYPE: PRT
<213> ORGANISM: Artificial Sequence
<220> FEATURE:
<223> OTHER INFORMATION: Synthetic polypeptide of BGL "Variant 883"

```
<400> SEQUENCE: 131

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Asn Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Trp Ala Gln His Thr Gly Ala Ala Ser Ala Val Ala Gly Leu
    290                 295                 300

Asp Met Ser Met Pro Gly Asp Thr Met Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Arg Asp Thr Tyr Gly Pro Ile His Trp Ala Ala Lys Gln Gly Tyr Gln
    370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415
```

-continued

```
Leu Pro Leu Asn Lys Pro Lys Phe Val Ala Val Ile Gly Glu Asp Ala
        420                 425                 430

Gly Pro Ser Pro Asn Gly Pro Asn Gly Cys Ser Asp Arg Gly Cys Asn
        435                 440                 445

Glu Gly Thr Leu Ala Met Gly Trp Gly Ser Gly Thr Ala Asn Tyr Pro
        450                 455                 460

Tyr Leu Val Ser Pro Asp Ala Ala Leu Gln Leu Arg Ala Ile Gln Asp
465                 470                 475                 480

Gly Thr Arg Tyr Glu Ser Val Leu Ser Asn Tyr Ala Glu Asn Thr
                485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
        515                 520                 525

Arg Lys Asn Leu Thr Leu Trp Asn Asn Gly Asp Thr Leu Val Lys Asn
        530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
            580                 585                 590

Val Leu Tyr Gly Lys Val Asn Pro Ala Ala Arg Ser Pro Phe Thr Trp
        595                 600                 605

Gly Lys Thr Arg Glu Ser Tyr Gly Ala Asp Val Leu Tyr Lys Pro Asn
        610                 615                 620

Asn Gly Asn Trp Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
            660                 665                 670

Val Val Lys Ser Asn Val Ser Glu Tyr Arg Pro Thr Thr Gly Thr Thr
        675                 680                 685

Ile Gln Ala Pro Thr Phe Gly Asn Phe Ser Thr Asp Leu Glu Asp Tyr
        690                 695                 700

Leu Phe Pro Lys Asp Glu Phe Pro Tyr Ile Pro Gln Tyr Ile Tyr Pro
705                 710                 715                 720

Tyr Leu Asn Thr Thr Asp Pro Arg Arg Ala Ser Ala Asp Pro His Tyr
                725                 730                 735

Gly Gln Thr Ala Glu Glu Phe Leu Pro Pro His Ala Thr Asp Asp Asp
            740                 745                 750

Pro Gln Pro Leu Leu Arg Ser Ser Gly Gly Asn Ser Pro Gly Gly Asn
        755                 760                 765

Arg Gln Leu Tyr Asp Ile Val Tyr Thr Ile Thr Ala Asp Ile Thr Asn
        770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Gly Thr Arg Gln Phe Thr Gly Arg Leu Thr Arg
            820                 825                 830
```

Arg Asp Leu Ser Asn Trp Asp Val Thr Val Gln Asp Trp Val Ile Ser
            835                 840                 845

Arg Tyr Pro Lys Thr Ala Tyr Val Gly Arg Ser Arg Lys Leu Asp
    850                 855                 860

Leu Lys Ile Glu Leu Pro
865                 870

<210> SEQ ID NO 132
<211> LENGTH: 851
<212> TYPE: PRT
<213> ORGANISM: Artificial Sequence
<220> FEATURE:
<223> OTHER INFORMATION: Synthetic polypeptide of BGL "Variant 883"

<400> SEQUENCE: 132

Ile Glu Ser Arg Lys Val His Gln Lys Pro Leu Ala Arg Ser Glu Pro
1               5                   10                  15

Phe Tyr Pro Ser Pro Trp Met Asn Pro Asn Ala Asp Gly Trp Ala Glu
            20                  25                  30

Ala Tyr Ala Gln Ala Lys Ser Phe Val Ser Gln Met Thr Leu Leu Glu
        35                  40                  45

Lys Val Asn Leu Thr Thr Gly Val Gly Trp Ala Glu Gln Cys Val
50                  55                  60

Gly Gln Val Gly Ala Ile Pro Arg Leu Gly Leu Arg Ser Leu Cys Met
65                  70                  75                  80

His Asp Ser Pro Leu Gly Ile Arg Gly Ala Asp Tyr Asn Ser Ala Phe
                85                  90                  95

Pro Ser Gly Gln Thr Val Ala Ala Thr Trp Asp Arg Gly Leu Met Tyr
            100                 105                 110

Arg Arg Gly Tyr Ala Met Gly Gln Glu Ala Lys Gly Lys Gly Ile Asn
        115                 120                 125

Val Leu Leu Gly Pro Val Ala Gly Pro Leu Gly Arg Met Pro Glu Gly
130                 135                 140

Gly Arg Asn Trp Glu Gly Phe Ala Pro Asp Pro Val Leu Thr Gly Ile
145                 150                 155                 160

Gly Met Ser Glu Thr Ile Lys Gly Ile Gln Asp Ala Gly Val Ile Ala
                165                 170                 175

Cys Ala Lys His Phe Ile Gly Asn Glu Gln Glu His Phe Arg Gln Val
            180                 185                 190

Pro Glu Ala Gln Gly Tyr Gly Tyr Asn Ile Ser Glu Thr Leu Ser Ser
        195                 200                 205

Asn Ile Asp Asp Lys Thr Met His Glu Leu Tyr Leu Trp Pro Phe Ala
210                 215                 220

Asp Ala Val Arg Ala Gly Val Gly Ser Val Met Cys Ser Tyr Asn Gln
225                 230                 235                 240

Val Asn Asn Ser Tyr Ala Cys Gln Asn Ser Lys Leu Leu Asn Asp Leu
                245                 250                 255

Leu Lys Asn Glu Leu Gly Phe Gln Gly Phe Val Met Ser Asp Trp Trp
            260                 265                 270

Ala Gln His Thr Gly Ala Ala Ser Ala Val Ala Gly Leu Asp Met Ser
        275                 280                 285

Met Pro Gly Asp Thr Met Phe Asn Thr Gly Val Ser Phe Trp Gly Ala
    290                 295                 300

Asn Leu Thr Leu Ala Val Leu Asn Gly Thr Val Pro Ala Tyr Arg Leu
305                 310                 315                 320

```
Asp Asp Met Ala Met Arg Ile Met Ala Ala Leu Phe Lys Val Thr Lys
                    325                 330                 335

Thr Thr Asp Leu Glu Pro Ile Asn Phe Ser Phe Trp Thr Arg Asp Thr
            340                 345                 350

Tyr Gly Pro Ile His Trp Ala Ala Lys Gln Gly Tyr Gln Glu Ile Asn
        355                 360                 365

Ser His Val Asp Val Arg Ala Asp His Gly Asn Leu Ile Arg Asn Ile
    370                 375                 380

Ala Ala Lys Gly Thr Val Leu Leu Lys Asn Thr Gly Ser Leu Pro Leu
385                 390                 395                 400

Asn Lys Pro Lys Phe Val Ala Val Ile Gly Glu Asp Ala Gly Pro Ser
                405                 410                 415

Pro Asn Gly Pro Asn Gly Cys Ser Asp Arg Gly Cys Asn Glu Gly Thr
            420                 425                 430

Leu Ala Met Gly Trp Gly Ser Gly Thr Ala Asn Tyr Pro Tyr Leu Val
        435                 440                 445

Ser Pro Asp Ala Ala Leu Gln Leu Arg Ala Ile Gln Asp Gly Thr Arg
    450                 455                 460

Tyr Glu Ser Val Leu Ser Asn Tyr Ala Glu Glu Asn Thr Lys Ala Leu
465                 470                 475                 480

Val Ser Gln Ala Asn Ala Thr Ala Ile Val Phe Val Asn Ala Asp Ser
                485                 490                 495

Gly Glu Gly Tyr Ile Asn Val Asp Gly Asn Glu Gly Asp Arg Lys Asn
            500                 505                 510

Leu Thr Leu Trp Asn Asn Gly Asp Thr Leu Val Lys Asn Val Ser Ser
        515                 520                 525

Trp Cys Ser Asn Thr Ile Val Val Ile His Ser Val Gly Pro Val Leu
    530                 535                 540

Leu Thr Asp Trp Tyr Asp Asn Pro Asn Ile Thr Ala Ile Leu Trp Ala
545                 550                 555                 560

Gly Leu Pro Gly Gln Glu Ser Gly Asn Ser Ile Thr Asp Val Leu Tyr
                565                 570                 575

Gly Lys Val Asn Pro Ala Ala Arg Ser Pro Phe Thr Trp Gly Lys Thr
            580                 585                 590

Arg Glu Ser Tyr Gly Ala Asp Val Leu Tyr Lys Pro Asn Asn Gly Asn
        595                 600                 605

Trp Ala Pro Gln Gln Asp Phe Thr Glu Gly Val Phe Ile Asp Tyr Arg
    610                 615                 620

Tyr Phe Asp Lys Val Asp Asp Ser Val Ile Tyr Glu Phe Gly His Gly
625                 630                 635                 640

Gly Leu Ser Tyr Thr Thr Phe Glu Tyr Ser Asn Ile Arg Val Val Lys
                645                 650                 655

Ser Asn Val Ser Glu Tyr Arg Pro Thr Thr Gly Thr Thr Ile Gln Ala
            660                 665                 670

Pro Thr Phe Gly Asn Phe Ser Thr Asp Leu Glu Asp Tyr Leu Phe Pro
        675                 680                 685

Lys Asp Glu Phe Pro Tyr Ile Pro Gln Tyr Ile Tyr Pro Tyr Leu Asn
    690                 695                 700

Thr Thr Asp Pro Arg Arg Ala Ser Ala Asp Pro His Tyr Gly Gln Thr
705                 710                 715                 720

Ala Glu Glu Phe Leu Pro Pro His Ala Thr Asp Asp Pro Gln Pro
                725                 730                 735

Leu Leu Arg Ser Ser Gly Gly Asn Ser Pro Gly Gly Asn Arg Gln Leu
```

```
              740                 745                 750
Tyr Asp Ile Val Tyr Thr Ile Thr Ala Asp Ile Thr Asn Thr Gly Ser
            755                 760                 765

Val Val Gly Glu Glu Val Pro Gln Leu Tyr Val Ser Leu Gly Gly Pro
    770                 775                 780

Glu Asp Pro Lys Val Gln Leu Arg Asp Phe Asp Arg Met Arg Ile Glu
785                 790                 795                 800

Pro Gly Glu Thr Arg Gln Phe Thr Gly Arg Leu Thr Arg Arg Asp Leu
                805                 810                 815

Ser Asn Trp Asp Val Thr Val Gln Asp Trp Val Ile Ser Arg Tyr Pro
            820                 825                 830

Lys Thr Ala Tyr Val Gly Arg Ser Ser Arg Lys Leu Asp Leu Lys Ile
        835                 840                 845

Glu Leu Pro
    850

<210> SEQ ID NO 133
<211> LENGTH: 2613
<212> TYPE: DNA
<213> ORGANISM: Artificial Sequence
<220> FEATURE:
<223> OTHER INFORMATION: Synthetic polynucleotide of BGL "Variant 900"

<400> SEQUENCE: 133
atgaaggctg ctgcgctttc ctgcctcttc ggcagtaccc ttgccgttgc aggcgccatt     60
gaatcgagaa aggttcacca gaagcccctc gcgagatctg aaccttttta cccgtcgcca    120
tggatgaatc ccaacgccat cggctgggcg gaggcctatg cccaggccaa gtcctttgtc    180
tcccaaatga ctctgctaga aaggtcaac ttgaccacgg gagtcggctg ggggaggag      240 cagtgcgtcg gcaacgtggg cgcgatccct cgccttggac ttcgcagtct gtgcatgcat    300
gactcccctc tcggcgtgcg aggaaccgac tacaactcag cgttcccctc tggccagacc    360
gttgctgcta cctgggatcg cggtctgatg taccgtcgcg gctacgcaat gggccaggag    420
gccaaaggca agggcatcaa tgtccttctc ggaccagtcg ccggccccct tggccgcatg    480
cccgagggcg gtcgtaactg ggaaggcttc gctccggatc ccgtccttac cggcatcggc    540
atgtccgaga cgatcaaggg cattcaggat gctggcgtca tcgcttgtgc gaagcacttt    600
attggaaacg agcaggagca cttcagacag gtgccagaag cccagggata cggttacaac    660
atcagcgaaa ccctctcctc caacattgac gacaagacca tgcacgagct ctaccttttgg    720 ccgtttgccg atgccgtccg ggccggcgtc ggctctgtca tgtgctcgta caaccagggc    780
aacaactcgt acgcctgcca gaactcgaag ctgctgaacg acctcctcaa gaacgagctt    840
gggtttcagg gcttcgtcat gagcgactgg tgggcacagc acactggcgc agcaagcgcc    900
gtggctggtc tcgatatgtc catgccgggc gacaccatgg tcaacactgg cgtcagtttc    960
tggggcgcca atctcaccct cgccgtcctc aacggcacag tccctgccta ccgtctcgac   1020
gacatgtgca tgcgcatcat ggccgccctc ttcaaggtca ccaagaccac cgacctggaa   1080
ccgatcaact ctcctcttctg gacccgcgac acttatggcc cgatccactg gccgccaag    1140 cagggctacc aggagattaa ttcccacgtt gacgtccgcg ccgaccacgg caacctcatc   1200
cggaacattg ccgccaaggg tacggtgctg ctgaagaata ccggctctct acccctgaac   1260
aagccaaagt tcgtggccgt catcggcgag gatgctgggc cgagcccaa cgggcccaac    1320 ggctgcagcg accgcggctg taacgaaggc acgctcgcca tgggctgggg atccggcaca   1380
```

```
gccaactatc cgtacctcgt ttcccccgac gccgcgctcc aggcgcgggc catccaggac      1440
ggcacgaggt acgagagcgt cctgtccaac tacgccgagg aaaatacaaa ggctctggtc      1500
tcgcaggcca atgcaaccgc catcgtcttc gtcaatgccg actcaggcga gggctacatc      1560
aacgtggacg gtaacgaggg cgaccgtaag aacctgactc tctggaacaa cggtgatact      1620
ctggtcaaga acgtctcgag ctggtgcagc aacaccatcg tcgtcatcca ctcggtcggc      1680
ccggtcctcc tgaccgattg gtacgacaac cccaacatca cggccattct ctgggctggt      1740
cttccgggcc aggagtcggg caactccatc accgacgtgc tttacggcaa ggtcaacccc      1800
gccgcccgct cgcccttcac ttggggcaag accgcgaaa gctatggcgc ggacgtcctg      1860
tacaagccga ataatggcaa ttgggcgccc caacaggact tcaccgaggg cgtcttcatc      1920
gactaccgct acttcgacaa ggttgacgat gactcggtca tctacgagtt cggccacggc      1980
ctgagctaca ccaccttcga gtacagcaac atccgcgtcg tcaagtccaa cgtcagcgag      2040
taccggccca cgacgggcac cacgattcag gccccgacgt ttggcaactt ctccaccgac      2100
ctcgaggact atctcttccc caaggacgag ttccctaca tcccgcagta catctacccg      2160
tacctcaaca cgaccgaccc cggagggcc tcgggcgatc cccactacgg ccagaccgcc      2220
gaggagttcc tcccgcccca cgccaccgat gacgacccc agccgctcct ccggtcctcg      2280
ggcggaaact cccccggcgg caaccgccag ctgtacgaca ttgtctacac aatcacggcc      2340
gacatcacga atacgggctc cgttgtaggc gaggaggtac cgcagctcta cgtctcgctg      2400
ggcggtcccg aggatcccaa ggtgcagctg cgcgactttg acaggatgcg gatcgaaccc      2460
ggcgagacga ggcagttcac cggccgcctg acgcgcagag atctgagcaa ctgggacgtc      2520
acggtgcagg actgggtcat cagcaggtat cccaagacgg catatgttgg gaggagcagc      2580
cggaagttgg atctcaagat tgagcttcct tga                                  2613
```

<210> SEQ ID NO 134
<211> LENGTH: 870
<212> TYPE: PRT
<213> ORGANISM: Artificial Sequence
<220> FEATURE:
<223> OTHER INFORMATION: Synthetic polypeptide of BGL "Variant 900"

<400> SEQUENCE: 134

```
Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Ile Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Glu Glu
65                  70                  75                  80

Gln Cys Val Gly Asn Val Gly Ala Ile Pro Arg Leu Gly Leu Arg Ser
                85                  90                  95

Leu Cys Met His Asp Ser Pro Leu Gly Val Arg Gly Thr Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140
```

-continued

```
Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
            165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
            195                 200                 205

Arg Gln Val Pro Glu Ala Gln Gly Tyr Gly Tyr Asn Ile Ser Glu Thr
            210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
            245                 250                 255

Tyr Asn Gln Gly Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
            275                 280                 285

Asp Trp Trp Ala Gln His Thr Gly Ala Ala Ser Ala Val Ala Gly Leu
            290                 295                 300

Asp Met Ser Met Pro Gly Asp Thr Met Val Asn Thr Gly Val Ser Phe
305                 310                 315                 320

Trp Gly Ala Asn Leu Thr Leu Ala Val Leu Asn Gly Thr Val Pro Ala
            325                 330                 335

Tyr Arg Leu Asp Asp Met Cys Met Arg Ile Met Ala Ala Leu Phe Lys
            340                 345                 350

Val Thr Lys Thr Thr Asp Leu Glu Pro Ile Asn Phe Ser Phe Trp Thr
            355                 360                 365

Arg Asp Thr Tyr Gly Pro Ile His Trp Ala Ala Lys Gln Gly Tyr Gln
            370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
            405                 410                 415

Leu Pro Leu Asn Lys Pro Lys Phe Val Ala Val Ile Gly Glu Asp Ala
            420                 425                 430

Gly Pro Ser Pro Asn Gly Pro Asn Gly Cys Ser Asp Arg Gly Cys Asn
            435                 440                 445

Glu Gly Thr Leu Ala Met Gly Trp Gly Ser Gly Thr Ala Asn Tyr Pro
450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Asn Thr
            485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
            515                 520                 525

Arg Lys Asn Leu Thr Leu Trp Asn Asn Gly Asp Thr Leu Val Lys Asn
            530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
```

565                 570                 575

Leu Trp Ala Gly Leu Pro Gly Gln Glu Ser Gly Asn Ser Ile Thr Asp
                580                 585                 590

Val Leu Tyr Gly Lys Val Asn Pro Ala Ala Arg Ser Pro Phe Thr Trp
                595                 600                 605

Gly Lys Thr Arg Glu Ser Tyr Gly Ala Asp Val Leu Tyr Lys Pro Asn
        610                 615                 620

Asn Gly Asn Trp Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
                660                 665                 670

Val Val Lys Ser Asn Val Ser Glu Tyr Arg Pro Thr Thr Gly Thr Thr
            675                 680                 685

Ile Gln Ala Pro Thr Phe Gly Asn Phe Ser Thr Asp Leu Glu Asp Tyr
        690                 695                 700

Leu Phe Pro Lys Asp Glu Phe Pro Tyr Ile Pro Gln Tyr Ile Tyr Pro
705                 710                 715                 720

Tyr Leu Asn Thr Thr Asp Pro Arg Arg Ala Ser Gly Asp Pro His Tyr
                725                 730                 735

Gly Gln Thr Ala Glu Glu Phe Leu Pro Pro His Ala Thr Asp Asp Asp
                740                 745                 750

Pro Gln Pro Leu Leu Arg Ser Ser Gly Gly Asn Ser Pro Gly Gly Asn
                755                 760                 765

Arg Gln Leu Tyr Asp Ile Val Tyr Thr Ile Thr Ala Asp Ile Thr Asn
        770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
            820                 825                 830

Arg Asp Leu Ser Asn Trp Asp Val Thr Val Gln Asp Trp Val Ile Ser
        835                 840                 845

Arg Tyr Pro Lys Thr Ala Tyr Val Gly Arg Ser Ser Arg Lys Leu Asp
    850                 855                 860

Leu Lys Ile Glu Leu Pro
865                 870

<210> SEQ ID NO 135
<211> LENGTH: 851
<212> TYPE: PRT
<213> ORGANISM: Artificial Sequence
<220> FEATURE:
<223> OTHER INFORMATION: Synthetic polypeptide of BGL "Variant 900"

<400> SEQUENCE: 135

Ile Glu Ser Arg Lys Val His Gln Lys Pro Leu Ala Arg Ser Glu Pro
1               5                   10                  15

Phe Tyr Pro Ser Pro Trp Met Asn Pro Asn Ala Ile Gly Trp Ala Glu
                20                  25                  30

Ala Tyr Ala Gln Ala Lys Ser Phe Val Ser Gln Met Thr Leu Leu Glu
            35                  40                  45

Lys Val Asn Leu Thr Thr Gly Val Gly Trp Gly Glu Glu Gln Cys Val

```
            50                  55                  60
Gly Asn Val Gly Ala Ile Pro Arg Leu Gly Leu Arg Ser Leu Cys Met
 65                  70                  75                  80

His Asp Ser Pro Leu Gly Val Arg Gly Thr Asp Tyr Asn Ser Ala Phe
                     85                  90                  95

Pro Ser Gly Gln Thr Val Ala Ala Thr Trp Asp Arg Gly Leu Met Tyr
                100                 105                 110

Arg Arg Gly Tyr Ala Met Gly Gln Glu Ala Lys Gly Lys Gly Ile Asn
            115                 120                 125

Val Leu Leu Gly Pro Val Ala Gly Pro Leu Gly Arg Met Pro Glu Gly
        130                 135                 140

Gly Arg Asn Trp Glu Gly Phe Ala Pro Asp Pro Val Leu Thr Gly Ile
145                 150                 155                 160

Gly Met Ser Glu Thr Ile Lys Gly Ile Gln Asp Ala Gly Val Ile Ala
                165                 170                 175

Cys Ala Lys His Phe Ile Gly Asn Glu Gln Glu His Phe Arg Gln Val
                180                 185                 190

Pro Glu Ala Gln Gly Tyr Gly Tyr Asn Ile Ser Glu Thr Leu Ser Ser
            195                 200                 205

Asn Ile Asp Asp Lys Thr Met His Glu Leu Tyr Leu Trp Pro Phe Ala
210                 215                 220

Asp Ala Val Arg Ala Gly Val Gly Ser Val Met Cys Ser Tyr Asn Gln
225                 230                 235                 240

Gly Asn Asn Ser Tyr Ala Cys Gln Asn Ser Lys Leu Leu Asn Asp Leu
                245                 250                 255

Leu Lys Asn Glu Leu Gly Phe Gln Gly Phe Val Met Ser Asp Trp Trp
            260                 265                 270

Ala Gln His Thr Gly Ala Ala Ser Ala Val Ala Gly Leu Asp Met Ser
        275                 280                 285

Met Pro Gly Asp Thr Met Val Asn Thr Gly Val Ser Phe Trp Gly Ala
290                 295                 300

Asn Leu Thr Leu Ala Val Leu Asn Gly Thr Val Pro Ala Tyr Arg Leu
305                 310                 315                 320

Asp Asp Met Cys Met Arg Ile Met Ala Ala Leu Phe Lys Val Thr Lys
                325                 330                 335

Thr Thr Asp Leu Glu Pro Ile Asn Phe Ser Phe Trp Thr Arg Asp Thr
                340                 345                 350

Tyr Gly Pro Ile His Trp Ala Ala Lys Gln Gly Tyr Gln Glu Ile Asn
            355                 360                 365

Ser His Val Asp Val Arg Ala Asp His Gly Asn Leu Ile Arg Asn Ile
        370                 375                 380

Ala Ala Lys Gly Thr Val Leu Leu Lys Asn Thr Gly Ser Leu Pro Leu
385                 390                 395                 400

Asn Lys Pro Lys Phe Val Ala Val Ile Gly Glu Asp Ala Gly Pro Ser
                405                 410                 415

Pro Asn Gly Pro Asn Gly Cys Ser Asp Arg Gly Cys Asn Glu Gly Thr
                420                 425                 430

Leu Ala Met Gly Trp Gly Ser Gly Thr Ala Asn Tyr Pro Tyr Leu Val
            435                 440                 445

Ser Pro Asp Ala Ala Leu Gln Ala Arg Ala Ile Gln Asp Gly Thr Arg
        450                 455                 460

Tyr Glu Ser Val Leu Ser Asn Tyr Ala Glu Glu Asn Thr Lys Ala Leu
465                 470                 475                 480
```

```
Val Ser Gln Ala Asn Ala Thr Ala Ile Val Phe Val Asn Ala Asp Ser
                485                 490                 495

Gly Glu Gly Tyr Ile Asn Val Asp Gly Asn Glu Gly Asp Arg Lys Asn
            500                 505                 510

Leu Thr Leu Trp Asn Asn Gly Asp Thr Leu Val Lys Asn Val Ser Ser
            515                 520                 525

Trp Cys Ser Asn Thr Ile Val Ile His Ser Val Gly Pro Val Leu
    530                 535                 540

Leu Thr Asp Trp Tyr Asp Asn Pro Asn Ile Thr Ala Ile Leu Trp Ala
545                 550                 555                 560

Gly Leu Pro Gly Gln Glu Ser Gly Asn Ser Ile Thr Asp Val Leu Tyr
                565                 570                 575

Gly Lys Val Asn Pro Ala Ala Arg Ser Pro Phe Thr Trp Gly Lys Thr
            580                 585                 590

Arg Glu Ser Tyr Gly Ala Asp Val Leu Tyr Lys Pro Asn Asn Gly Asn
            595                 600                 605

Trp Ala Pro Gln Gln Asp Phe Thr Glu Gly Val Phe Ile Asp Tyr Arg
    610                 615                 620

Tyr Phe Asp Lys Val Asp Asp Ser Val Ile Tyr Glu Phe Gly His
625                 630                 635                 640

Gly Leu Ser Tyr Thr Thr Phe Glu Tyr Ser Asn Ile Arg Val Val Lys
                645                 650                 655

Ser Asn Val Ser Glu Tyr Arg Pro Thr Thr Gly Thr Thr Ile Gln Ala
            660                 665                 670

Pro Thr Phe Gly Asn Phe Ser Thr Asp Leu Glu Asp Tyr Leu Phe Pro
    675                 680                 685

Lys Asp Glu Phe Pro Tyr Ile Pro Gln Tyr Ile Tyr Pro Tyr Leu Asn
690                 695                 700

Thr Thr Asp Pro Arg Arg Ala Ser Gly Asp Pro His Tyr Gly Gln Thr
705                 710                 715                 720

Ala Glu Glu Phe Leu Pro Pro His Ala Thr Asp Asp Pro Gln Pro
                725                 730                 735

Leu Leu Arg Ser Ser Gly Gly Asn Ser Pro Gly Gly Asn Arg Gln Leu
            740                 745                 750

Tyr Asp Ile Val Tyr Thr Ile Thr Ala Asp Ile Thr Asn Thr Gly Ser
            755                 760                 765

Val Val Gly Glu Glu Val Pro Gln Leu Tyr Val Ser Leu Gly Gly Pro
770                 775                 780

Glu Asp Pro Lys Val Gln Leu Arg Asp Phe Asp Arg Met Arg Ile Glu
785                 790                 795                 800

Pro Gly Glu Thr Arg Gln Phe Thr Gly Arg Leu Thr Arg Arg Asp Leu
                805                 810                 815

Ser Asn Trp Asp Val Thr Val Gln Asp Trp Val Ile Ser Arg Tyr Pro
            820                 825                 830

Lys Thr Ala Tyr Val Gly Arg Ser Ser Arg Lys Leu Asp Leu Lys Ile
            835                 840                 845

Glu Leu Pro
    850

<210> SEQ ID NO 136
<211> LENGTH: 1368
<212> TYPE: DNA
<213> ORGANISM: Talaromyces emersonii
```

<400> SEQUENCE: 136

```
atgcttcgac gggctcttct tctatcctct tccgccatcc ttgctgtcaa ggcacagcag      60
gccggcacgg cgacggcaga gaaccacccg cccctgacat ggcaggaatg caccgcccct     120
gggagctgca ccacccagaa cggggcggtc gttcttgatg cgaactggcg ttgggtgcac     180
gatgtgaacg gatacaccaa ctgctacacg gcaatacct gggaccccac gtactgccct      240
gacgacgaaa cctgcgccca gaactgtgcg ctggacggcg cggattacga gggcacctac     300
ggcgtgactt cgtcgggcag ctccttgaaa ctcaatttcg tcaccgggtc gaacgtcgga     360
tcccgtctct acctgctgca ggacgactcg acctatcaga tcttcaagct tctgaaccgc     420
gagttcagct ttgacgtcga tgtctccaat cttccgtgcg gattgaacgg cgctctgtac     480
tttgtcgcca tggacgccga cggcggcgtg tccaagtacc gaacaacaa ggctggtgcc      540
aagtacggaa ccgggtattg cgactcccaa tgcccacggg acctcaagtt catcgacggc     600
gaggccaacg tcgagggctg gcagccgtct tcgaacaacg ccaacaccgg aattggcgac     660
cacggctcct gctgtgcgga gatggatgtc tgggaagcaa acagcatctc caatgcggtc     720
actccgcacc cgtgcgacac gccaggccag acgatgtgct ctggagatga ctgcggtggc     780
acatactcta cgatcgcta cgcgggaacc tgcgatcctg acggctgtga cttcaaccct     840
taccgcatgg gcaacacttc tttctacggg cctggcaaga tcatcgatac caccaagccc     900
ttcactgtcg tgacgcagtt cctcactgat gatggtacgg atactggaac tctcagcgag     960
atcaagcgct tctacatcca gaacagcaac gtcattccgc agcccaactc ggacatcagt    1020
ggcgtgaccg gcaactcgat cacgacggag ttctgcactg ctcagaagca ggcctttggc    1080
gacacggacg acttctctca gcacggtggc ctggccaaga tgggagcggc catgcagcag    1140
ggtatggtcc tggtgatgag tttgtgggac gactacgccg cgcagatgct gtggttggat    1200
tccgactacc cgacggatgc ggaccccacg acccctggta ttgcccgtgg aacgtgtccg    1260
acggactcgg cgctcccatc ggatgtcgag tcgcagagcc ccaactccta cgtgacctac    1320
tcgaacatta gtttggtcc gatcaactcg accttcaccg cttcgtga                  1368
```

<210> SEQ ID NO 137
<211> LENGTH: 455
<212> TYPE: PRT
<213> ORGANISM: Talaromyces emersonii

<400> SEQUENCE: 137

```
Met Leu Arg Arg Ala Leu Leu Ser Ser Ala Ile Leu Ala Val
1               5                   10                  15

Lys Ala Gln Gln Ala Gly Thr Ala Thr Ala Glu Asn His Pro Pro Leu
                20                  25                  30

Thr Trp Gln Glu Cys Thr Ala Pro Gly Ser Cys Thr Thr Gln Asn Gly
            35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
                100                 105                 110

Phe Val Thr Gly Ser Asn Val Gly Ser Arg Leu Tyr Leu Leu Gln Asp
            115                 120                 125
```

Asp Ser Thr Tyr Gln Ile Phe Lys Leu Leu Asn Arg Glu Phe Ser Phe
        130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
                180                 185                 190

Arg Asp Leu Lys Phe Ile Asp Gly Glu Ala Asn Val Glu Gly Trp Gln
                195                 200                 205

Pro Ser Ser Asn Asn Ala Asn Thr Gly Ile Gly Asp His Gly Ser Cys
210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
                260                 265                 270

Pro Asp Gly Cys Asp Phe Asn Pro Tyr Arg Met Gly Asn Thr Ser Phe
                275                 280                 285

Tyr Gly Pro Gly Lys Ile Ile Asp Thr Thr Lys Pro Phe Thr Val Val
290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
                340                 345                 350

Thr Ala Gln Lys Gln Ala Phe Gly Asp Thr Asp Phe Ser Gln His
                355                 360                 365

Gly Gly Leu Ala Lys Met Gly Ala Ala Met Gln Gln Gly Met Val Leu
                370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
                420                 425                 430

Ser Pro Asn Ser Tyr Val Thr Tyr Ser Asn Ile Lys Phe Gly Pro Ile
                435                 440                 445

Asn Ser Thr Phe Thr Ala Ser
        450                 455

<210> SEQ ID NO 138
<211> LENGTH: 437
<212> TYPE: PRT
<213> ORGANISM: Talaromyces emersonii

<400> SEQUENCE: 138

Gln Gln Ala Gly Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
                20                  25                  30

Val Leu Asp Ala Asn Trp Arg Trp Val His Asp Val Asn Gly Tyr Thr

```
            35                  40                  45
Asn Cys Tyr Thr Gly Asn Thr Trp Asp Pro Thr Tyr Cys Pro Asp Asp
 50                  55                  60

Glu Thr Cys Ala Gln Asn Cys Ala Leu Asp Gly Ala Asp Tyr Glu Gly
 65                  70                  75                  80

Thr Tyr Gly Val Thr Ser Ser Gly Ser Ser Leu Lys Leu Asn Phe Val
                 85                  90                  95

Thr Gly Ser Asn Val Gly Ser Arg Leu Tyr Leu Leu Gln Asp Asp Ser
                100                 105                 110

Thr Tyr Gln Ile Phe Lys Leu Leu Asn Arg Glu Phe Ser Phe Asp Val
            115                 120                 125

Asp Val Ser Asn Leu Pro Cys Gly Leu Asn Gly Ala Leu Tyr Phe Val
        130                 135                 140

Ala Met Asp Ala Asp Gly Gly Val Ser Lys Tyr Pro Asn Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asp Gly Glu Ala Asn Val Glu Gly Trp Gln Pro Ser
                180                 185                 190

Ser Asn Asn Ala Asn Thr Gly Ile Gly Asp His Gly Ser Cys Cys Ala
            195                 200                 205

Glu Met Asp Val Trp Glu Ala Asn Ser Ile Ser Asn Ala Val Thr Pro
210                 215                 220

His Pro Cys Asp Thr Pro Gly Gln Thr Met Cys Ser Gly Asp Asp Cys
225                 230                 235                 240

Gly Gly Thr Tyr Ser Asn Asp Arg Tyr Ala Gly Thr Cys Asp Pro Asp
                245                 250                 255

Gly Cys Asp Phe Asn Pro Tyr Arg Met Gly Asn Thr Ser Phe Tyr Gly
                260                 265                 270

Pro Gly Lys Ile Ile Asp Thr Thr Lys Pro Phe Thr Val Val Thr Gln
            275                 280                 285

Phe Leu Thr Asp Asp Gly Thr Asp Thr Gly Thr Leu Ser Glu Ile Lys
        290                 295                 300

Arg Phe Tyr Ile Gln Asn Ser Asn Val Ile Pro Gln Pro Asn Ser Asp
305                 310                 315                 320

Ile Ser Gly Val Thr Gly Asn Ser Ile Thr Thr Glu Phe Cys Thr Ala
                325                 330                 335

Gln Lys Gln Ala Phe Gly Asp Thr Asp Asp Phe Ser Gln His Gly Gly
                340                 345                 350

Leu Ala Lys Met Gly Ala Ala Met Gln Gln Gly Met Val Leu Val Met
            355                 360                 365

Ser Leu Trp Asp Asp Tyr Ala Ala Gln Met Leu Trp Leu Asp Ser Asp
        370                 375                 380

Tyr Pro Thr Asp Ala Asp Pro Thr Thr Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Tyr Ser Asn Ile Lys Phe Gly Pro Ile Asn Ser
                420                 425                 430

Thr Phe Thr Ala Ser
            435

<210> SEQ ID NO 139
```

<211> LENGTH: 1581
<212> TYPE: DNA
<213> ORGANISM: Myceliophthora thermophila

<400> SEQUENCE: 139

```
atgtacgcca agttcgcgac cctcgccgcc cttgtggctg gcgccgctgc tcagaacgcc      60
tgcactctga ccgctgagaa ccacccctcg ctgacgtggt ccaagtgcac gtctggcggc     120
agctgcacca cgcgtccagg gttccatcac catcgacgcc actggcggtg gactcaccgg     180
accgatagcg ccaccaactg ctacgagggc aacaagtggg atacttcgta ctgcagcgat     240
ggtccttctt gcgcctccaa gtgctgcatc gacggcgctg actactcgag cacctatggc     300
atcaccacga gcggtaactc cctgaacctc aagttcgtca ccaagggcca gtactcgacc     360
aacatcggct cgcgtaccta cctgatggag agcgacacca gtaccagat gttccagctc     420
ctcggcaacg agttcacctt cgatgtcgac gtctccaacc tcggctgcgg cctcaatggc     480
gccctctact tcgtgtccat ggatgccgat ggtggcatgt ccaagtactc gggcaacaag     540
gcaggtgcca agtacggtac cggctactgt gattctcagt gccccgcga cctcaagttc     600
atcaacggcg aggccaacgt agagaactgg cagagctcga ccaacgatgc caacgccggc     660
acgggcaagt acgcagctg ctgctccgag atggacgtct gggaggccaa caacatggcc     720
gccgccttca ctccccaccc ttgcaccgtg atcggccagt cgcgctgcga gggcgactcg     780
tgcggcggta cctacagcac cgaccgctat gccggcatct cgaccccga cggatgcgac     840
ttcaactcgt accgccaggg caacaagacc ttctacggca agggcatgac ggtcgacacg     900
accaagaaga tcacggtcgt cacccagttc ctcaagaact cggccggcga gctctccgag     960
atcaagcggt tctacgtcca gaacggcaag gtcatcccca ctccgagtc caccatcccg    1020
ggcgtcgagg gcaactccat cacccaggac tggtgcgacc gccagaaggc cgccttcggc    1080
gacgtgaccg acttccagga caagggcggc atggtccaga tgggcaaggc cctcgcgggg    1140
cccatggtcc tcgtcatgtc catctgggac gaccacgccg tcaacatgct ctggctcgac    1200
tccacctggc ccatcgacgg cgccggcaag ccgggcgccg agcgcggtgc ctgccccacc    1260
acctcgggcg tccccgctga ggtcgaggcc gaggccccca actccaacgt catcttctcc    1320
aacatccgct tcggccccat cggctccacc gtctccggcc tgcccgacgg cggcagcggc    1380
aaccccaacc cgcccgtcag ctcgtccacc ccggtcccct cctcgtccac cacatcctcc    1440
ggttcctccg gcccgactgg cggcacgggt gtcgctaagc actatgagca atgcggagga    1500
atcgggttca ctggccctac ccagtgcgag agcccctaca cttgcaccaa gctgaatgac    1560
tggtactcgc agtgcctgta a                                              1581
```

<210> SEQ ID NO 140
<211> LENGTH: 526
<212> TYPE: PRT
<213> ORGANISM: Myceliophthora thermophila

<400> SEQUENCE: 140

```
Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Ser Leu Thr
            20                  25                  30

Tyr Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60
```

```
Thr Asn Cys Tyr Glu Gly Asn Lys Trp Asp Thr Ser Trp Cys Ser Asp
 65                  70                  75                  80

Gly Pro Ser Cys Ala Ser Lys Cys Cys Ile Asp Gly Ala Asp Tyr Ser
                 85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
            115                 120                 125

Met Glu Ser Asp Thr Lys Tyr Gln Met Phe Gln Leu Leu Gly Asn Glu
            130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
            195                 200                 205

Asn Trp Gln Ser Ser Thr Asn Asp Ala Asn Ala Gly Thr Gly Lys Tyr
            210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
            275                 280                 285

Lys Thr Phe Tyr Gly Lys Gly Met Thr Val Asp Thr Thr Lys Lys Ile
            290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
            340                 345                 350

Asp Arg Gln Lys Ala Ala Phe Gly Asp Val Thr Asp Phe Gln Asp Lys
            355                 360                 365

Gly Gly Met Val Gln Met Gly Lys Ala Leu Ala Gly Pro Met Val Leu
            370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
            435                 440                 445

Ser Thr Val Ser Gly Leu Pro Asp Gly Gly Ser Gly Asn Pro Asn Pro
            450                 455                 460

Pro Val Ser Ser Ser Thr Pro Val Pro Ser Ser Ser Thr Ser Ser Ser
465                 470                 475                 480
```

-continued

```
Gly Ser Ser Gly Pro Thr Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525

<210> SEQ ID NO 141
<211> LENGTH: 509
<212> TYPE: PRT
<213> ORGANISM: Myceliophthora thermophila

<400> SEQUENCE: 141

Gln Asn Ala Cys Thr Leu Thr Ala Glu Asn His Pro Ser Leu Thr Tyr
1               5                   10                  15

Ser Lys Cys Thr Ser Gly Gly Ser Cys Thr Ser Val Gln Gly Ser Ile
            20                  25                  30

Thr Ile Asp Ala Asn Trp Arg Trp Thr His Arg Thr Asp Ser Ala Thr
        35                  40                  45

Asn Cys Tyr Glu Gly Asn Lys Trp Asp Thr Ser Trp Cys Ser Asp Gly
50                  55                  60

Pro Ser Cys Ala Ser Lys Cys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
            85                  90                  95

Thr Lys Gly Gln Tyr Ser Thr Asn Ile Gly Ser Arg Thr Tyr Leu Met
            100                 105                 110

Glu Ser Asp Thr Lys Tyr Gln Met Phe Gln Leu Leu Gly Asn Glu Phe
        115                 120                 125

Thr Phe Asp Val Asp Val Ser Asn Leu Gly Cys Gly Leu Asn Gly Ala
    130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
            165                 170                 175

Cys Pro Arg Asp Leu Lys Phe Ile Asn Gly Glu Ala Asn Val Glu Asn
        180                 185                 190

Trp Gln Ser Ser Thr Asn Asp Ala Asn Ala Gly Thr Gly Lys Tyr Gly
        195                 200                 205

Ser Cys Cys Ser Glu Met Asp Val Trp Glu Ala Asn Asn Met Ala Ala
    210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
            245                 250                 255

Cys Asp Pro Asp Gly Cys Asp Phe Asn Ser Tyr Arg Gln Gly Asn Lys
        260                 265                 270

Thr Phe Tyr Gly Lys Gly Met Thr Val Asp Thr Thr Lys Lys Ile Thr
    275                 280                 285

Val Val Thr Gln Phe Leu Lys Asn Ser Ala Gly Glu Leu Ser Glu Ile
    290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Asp Trp Cys Asp
            325                 330                 335
```

```
Arg Gln Lys Ala Ala Phe Gly Asp Val Thr Asp Phe Gln Asp Lys Gly
                340                 345                 350

Gly Met Val Gln Met Gly Lys Ala Leu Ala Gly Pro Met Val Leu Val
            355                 360                 365

Met Ser Ile Trp Asp Asp His Ala Val Asn Met Leu Trp Leu Asp Ser
370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Ala Glu Ala Pro
                405                 410                 415

Asn Ser Asn Val Ile Phe Ser Asn Ile Arg Phe Gly Pro Ile Gly Ser
            420                 425                 430

Thr Val Ser Gly Leu Pro Asp Gly Gly Ser Gly Asn Pro Asn Pro Pro
        435                 440                 445

Val Ser Ser Ser Thr Pro Val Pro Ser Ser Ser Thr Thr Ser Ser Gly
    450                 455                 460

Ser Ser Gly Pro Thr Gly Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
                485                 490                 495

Thr Cys Thr Lys Leu Asn Asp Trp Tyr Ser Gln Cys Leu
                500                 505

<210> SEQ ID NO 142
<211> LENGTH: 1581
<212> TYPE: DNA
<213> ORGANISM: Artificial Sequence
<220> FEATURE:
<223> OTHER INFORMATION: Synthetic polynucleotide of M. thermophila
      CBH1a "Variant 145"

<400> SEQUENCE: 142
atgtacgcca agttcgcgac cctcgccgcc cttgtggctg gcgccgctgc tcagaacgcc      60
tgcactctga ccgctgagaa ccaccccctcg ctgacgtggt ccaagtgcac gtctggcggc     120
agctgcacca gcgtccaggg ttccatcacc atcgacgcca actggcggtg gactcaccgg     180
accgatagcg ccaccaactg ctacgagggc aacaagtggg atacttcgtg gtgcagcgat     240
ggtccttctt cgcctccaa gtgctgcatc gacggcgctg actactcgag cacctatggc     300
atcaccacga gcggtaactc cctgaacctc aagttcgtca ccaagggcca gtactcgacc     360
aacatcggct cgcgtaccta cctgatggag agcgacacca gtaccagat gttccagctc     420 ctcggcaacg agttcacctt cgatgtcgac gtctccaacc tcggctgcgg cctcaatggc     480
gccctctact cgtgtccat ggatgccgat ggtggcatgt ccaagtactc gggcaacaag     540
gcaggtgcca agtacggtac cggctactgt gattctcagt gccccgcga cctcaagttc     600 atcaacggcg aggccaacgt agagaactgg cagagctcga ccaacgatgc caacgccggc     660
acgggcaagt acggcagctg ctgctccgag atggacgtct gggaggccaa caacatggcc     720
gccgccttca ctccccaccc ttgcaccgtg atcggccagt cgcgctgcga gggcgactcg     780
tgcggcggta cctacagcac cgaccgctat gccggcatct cgacccccga cggatgcgac     840
ttcaactcgt accgccaggg caacaagacc ttctacggca agggcatgac ggtcgacacg     900
accaagaaga tcacggtcgt cacccagttc ctcaagaact cggccggcga gctctccgag     960
atcaagcggt tctacgtcca gaacggcaag gtcatcccca ctccgagtc caccatcccg    1020
```

```
ggcgtcgagg gcaactccat cacccaggac tggtgcgacc gccagaaggc cgccttcggc   1080
gacgtgaccg acttccagga caagggcggc atggtccaga tgggcaaggc cctcgcgggg   1140
cccatggtcc tcgtcatgtc catctgggac gaccacgccg tcaacatgct ctggctcgac   1200
tccacctggc ccatcgacgg cgccggcaag cggggcgccg agcgcggtgc ctgccccacc   1260
acctcgggcg tccccgctga ggtcgaggcc gaggccccca actccaacgt catcttctcc   1320
aacatccgct tcggcccat cggctccacc gtctccggcc tgcccgacgg cggcagcggc   1380
aaccccaacc cgcccgtcag ctcgtccacc ccggtcccct cctcgtccac cacatcctcc   1440
ggttcctccg gcccgactgg cggcacgggt gtcgctaagc actatgagca atgcggagga   1500
atcgggttca ctggccctac ccagtgcgag agcccctaca cttgcaccaa gctgaatgac   1560
tggtactcgc agtgcctgta a                                              1581
```

<210> SEQ ID NO 143
<211> LENGTH: 526
<212> TYPE: PRT
<213> ORGANISM: Artificial Sequence
<220> FEATURE:
<223> OTHER INFORMATION: Synthetic polypeptide of M. thermophila CBH1a "Variant 145"

<400> SEQUENCE: 143

```
Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Ser Leu Thr
                20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Trp Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Ser Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255
```

-continued

```
Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
            340                 345                 350

Asp Arg Gln Lys Ala Ala Phe Gly Asp Val Thr Asp Phe Gln Asp Lys
        355                 360                 365

Gly Gly Met Val Gln Met Gly Lys Ala Leu Ala Gly Pro Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Thr Pro Val Pro Ser Ser Thr Thr Ser Ser
465                 470                 475                 480

Gly Ser Ser Gly Pro Thr Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525

<210> SEQ ID NO 144
<211> LENGTH: 509
<212> TYPE: PRT
<213> ORGANISM: Artificial Sequence
<220> FEATURE:
<223> OTHER INFORMATION: Synthetic polypeptide of M. thermophila CBH1a
      "Variant 145"

<400> SEQUENCE: 144

Gln Asn Ala Cys Thr Leu Thr Ala Glu Asn His Pro Ser Leu Thr Trp
1               5                   10                  15

Ser Lys Cys Thr Ser Gly Gly Ser Cys Thr Ser Val Gln Gly Ser Ile
            20                  25                  30

Thr Ile Asp Ala Asn Trp Arg Trp Thr His Arg Thr Asp Ser Ala Thr
        35                  40                  45

Asn Cys Tyr Glu Gly Asn Lys Trp Asp Thr Ser Trp Cys Ser Asp Gly
    50                  55                  60

Pro Ser Cys Ala Ser Lys Cys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
                85                  90                  95
```

```
Thr Lys Gly Gln Tyr Ser Thr Asn Ile Gly Ser Arg Thr Tyr Leu Met
            100                 105                 110

Glu Ser Asp Thr Lys Tyr Gln Met Phe Gln Leu Leu Gly Asn Glu Phe
            115                 120                 125

Thr Phe Asp Val Asp Val Ser Asn Leu Gly Cys Gly Leu Asn Gly Ala
            130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Glu Ala Asn Val Glu Asn
            180                 185                 190

Trp Gln Ser Ser Thr Asn Asp Ala Asn Ala Gly Thr Gly Lys Tyr Gly
            195                 200                 205

Ser Cys Cys Ser Glu Met Asp Val Trp Glu Ala Asn Asn Met Ala Ala
210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
            245                 250                 255

Cys Asp Pro Asp Gly Cys Asp Phe Asn Ser Tyr Arg Gln Gly Asn Lys
            260                 265                 270

Thr Phe Tyr Gly Lys Gly Met Thr Val Asp Thr Thr Lys Lys Ile Thr
            275                 280                 285

Val Val Thr Gln Phe Leu Lys Asn Ser Ala Gly Glu Leu Ser Glu Ile
            290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Asp Trp Cys Asp
            325                 330                 335

Arg Gln Lys Ala Ala Phe Gly Asp Val Thr Asp Phe Gln Asp Lys Gly
            340                 345                 350

Gly Met Val Gln Met Gly Lys Ala Leu Ala Gly Pro Met Val Leu Val
            355                 360                 365

Met Ser Ile Trp Asp Asp His Ala Val Asn Met Leu Trp Leu Asp Ser
370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Glu Ala Glu Ala Pro
            405                 410                 415

Asn Ser Asn Val Ile Phe Ser Asn Ile Arg Phe Gly Pro Ile Gly Ser
            420                 425                 430

Thr Val Ser Gly Leu Pro Asp Gly Gly Ser Gly Asn Pro Asn Pro Pro
            435                 440                 445

Val Ser Ser Ser Thr Pro Val Pro Ser Ser Thr Thr Ser Ser Gly
            450                 455                 460

Ser Ser Gly Pro Thr Gly Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
            485                 490                 495

Thr Cys Thr Lys Leu Asn Asp Trp Tyr Ser Gln Cys Leu
            500                 505
```

<210> SEQ ID NO 145
<211> LENGTH: 1581
<212> TYPE: DNA
<213> ORGANISM: Artificial Sequence
<220> FEATURE:
<223> OTHER INFORMATION: Synthetic polynucleotide of M. thermophila
      CBH1a "Variant 983"

<400> SEQUENCE: 145

```
atgtacgcca agttcgcgac cctcgccgcc cttgtggctg gcgccgctgc tcagaacgcc      60
tgcactctga acgctgagaa ccaccctcg ctgacgtggt ccaagtgcac gtctggcggc     120
agctgcacca gcgtccaggg ttccatcacc atcgacgcca actggcggtg gactcaccgg     180
accgatagcg ccaccaactg ctacgagggc aacaagtggg atacttcgta ctgcagcgat     240
ggtccttctt gcgcctccaa gtgctgcatc gacggcgctg actactcgag cacctatggc     300
atcaccacga gcggtaactc cctgaacctc aagttcgtca ccaagggcca gtactcgacc     360
aacatcggct cgcgtaccta cctgatggag agcgacacca gtaccagat gttccagctc     420 ctcggcaacg agttcacctt cgatgtcgac gtctccaacc tcggctgcgg cctcaatggc     480
gccctctact tcgtgtccat ggatgccgat ggtggcatgt ccaagtactc gggcaacaag     540
gcaggtgcca agtacggtac cggctactgt gattctcagt gccccgcga cctcaagttc     600 atcaacggcg aggccaacgt agagaactgg cagagctcga ccaacgatgc caacgccggc     660
acgggcaagt acggcagctg ctgctccgag atggacgtct gggaggccaa caacatggcc     720
gccgccttca ctcccacc ttgcaccgtg atcggccagt cgcgctgcga gggcgactcg     780
tgcggcggta cctacagcac cgaccgctat gccggcatct gcgaccccga cggatgcgac     840
ttcaactcgt accgccaggg caacaagacc ttctacggca agggcatgac ggtcgacacg     900
accaagaaga tcacggtcgt cacccagttc ctcaagaact cggccggcga gctctccgag     960
atcaagcggt tctacgtcca gaacggcaag gtcatcccca ctccgagtc caccatcccg    1020 ggcgtcgagg gcaactccat cacccaggag tactgcgacc gccagaaggc cgccttcggc    1080
gacgtgaccg acttccagga caagggcggc atggtccaga tgggcaaggc cctcgcgggg    1140
cccatggtcc tcgtcatgtc catctgggac gaccacgccg acaacatgct ctggctcgac    1200
tccacctggc ccatcgacgg cgccggcaag ccgggcgccg agcgcggtgc ctgccccacc    1260
acctcgggcg tccccgctga ggtcgaggcc gaggccccca ctccaacgt catcttctcc    1320 aacatccgct tcggcccat cggctccacc gtctccggcc tgcccgacgg cggcagcggc    1380
aaccccaacc cgcccgtcag ctcgtccacc ccggtcccct cctcgtccac cacatcctcc    1440
ggttcctccg gcccgactgg cggcacgggt gtcgctaagc actatgagca atgcggagga    1500
atcgggttca ctggccctac ccagtgcgag agcccctaca cttgcaccaa gctgaatgac    1560
tggtactcgc agtgcctgta a                                              1581
```

<210> SEQ ID NO 146
<211> LENGTH: 526
<212> TYPE: PRT
<213> ORGANISM: Artificial Sequence
<220> FEATURE:
<223> OTHER INFORMATION: Synthetic polypeptide of M. thermophila CBH1a
      "Variant 983"

<400> SEQUENCE: 146

Met Tyr Ala Lys Phe Ala Thr Leu Ala Ala Leu Val Ala Gly Ala Ala
1               5                   10                  15

```
Ala Gln Asn Ala Cys Thr Leu Asn Ala Glu Asn His Pro Ser Leu Thr
            20                  25                  30
Trp Ser Lys Cys Thr Ser Gly Gly Ser Cys Thr Ser Val Gln Gly Ser
        35                  40                  45
Ile Thr Ile Asp Ala Asn Trp Arg Trp Thr His Arg Thr Asp Ser Ala
    50                  55                  60
Thr Asn Cys Tyr Glu Gly Asn Lys Trp Asp Thr Ser Tyr Cys Ser Asp
65                  70                  75                  80
Gly Pro Ser Cys Ala Ser Lys Cys Cys Ile Asp Gly Ala Asp Tyr Ser
                85                  90                  95
Ser Thr Tyr Gly Ile Thr Thr Ser Gly Asn Ser Leu Asn Leu Lys Phe
            100                 105                 110
Val Thr Lys Gly Gln Tyr Ser Thr Asn Ile Gly Ser Arg Thr Tyr Leu
        115                 120                 125
Met Glu Ser Asp Thr Lys Tyr Gln Met Phe Gln Leu Leu Gly Asn Glu
    130                 135                 140
Phe Thr Phe Asp Val Asp Val Ser Asn Leu Gly Cys Gly Leu Asn Gly
145                 150                 155                 160
Ala Leu Tyr Phe Val Ser Met Asp Ala Asp Gly Gly Met Ser Lys Tyr
                165                 170                 175
Ser Gly Asn Lys Ala Gly Ala Lys Tyr Gly Thr Gly Tyr Cys Asp Ser
            180                 185                 190
Gln Cys Pro Arg Asp Leu Lys Phe Ile Asn Gly Glu Ala Asn Val Glu
        195                 200                 205
Asn Trp Gln Ser Ser Thr Asn Asp Ala Asn Ala Gly Thr Gly Lys Tyr
    210                 215                 220
Gly Ser Cys Cys Ser Glu Met Asp Val Trp Glu Ala Asn Asn Met Ala
225                 230                 235                 240
Ala Ala Phe Thr Pro His Pro Cys Thr Val Ile Gly Gln Ser Arg Cys
                245                 250                 255
Glu Gly Asp Ser Cys Gly Gly Thr Tyr Ser Thr Asp Arg Tyr Ala Gly
            260                 265                 270
Ile Cys Asp Pro Asp Gly Cys Asp Phe Asn Ser Tyr Arg Gln Gly Asn
        275                 280                 285
Lys Thr Phe Tyr Gly Lys Gly Met Thr Val Asp Thr Thr Lys Lys Ile
    290                 295                 300
Thr Val Val Thr Gln Phe Leu Lys Asn Ser Ala Gly Glu Leu Ser Glu
305                 310                 315                 320
Ile Lys Arg Phe Tyr Val Gln Asn Gly Lys Val Ile Pro Asn Ser Glu
                325                 330                 335
Ser Thr Ile Pro Gly Val Glu Gly Asn Ser Ile Thr Gln Glu Tyr Cys
            340                 345                 350
Asp Arg Gln Lys Ala Ala Phe Gly Asp Val Thr Asp Phe Gln Asp Lys
        355                 360                 365
Gly Gly Met Val Gln Met Gly Lys Ala Leu Ala Gly Pro Met Val Leu
    370                 375                 380
Val Met Ser Ile Trp Asp Asp His Ala Asp Asn Met Leu Trp Leu Asp
385                 390                 395                 400
Ser Thr Trp Pro Ile Asp Gly Ala Gly Lys Pro Gly Ala Glu Arg Gly
                405                 410                 415
Ala Cys Pro Thr Thr Ser Gly Val Pro Ala Glu Val Glu Ala Glu Ala
            420                 425                 430
Pro Asn Ser Asn Val Ile Phe Ser Asn Ile Arg Phe Gly Pro Ile Gly
```

|     |     |     |     |     |     |     |     |     |     |     |     |
|---|---|---|---|---|---|---|---|---|---|---|---|
|     |     |     | 435 |     |     |     | 440 |     |     |     | 445 |

Ser Thr Val Ser Gly Leu Pro Asp Gly Gly Ser Gly Asn Pro Asn Pro
450                 455                 460

Pro Val Ser Ser Thr Pro Val Pro Ser Ser Thr Thr Ser Ser
465                 470                 475                 480

Gly Ser Ser Gly Pro Thr Gly Thr Gly Val Ala Lys His Tyr Glu
                485                 490                 495

Gln Cys Gly Gly Ile Gly Phe Thr Gly Pro Thr Gln Cys Glu Ser Pro
                500                 505                 510

Tyr Thr Cys Thr Lys Leu Asn Asp Trp Tyr Ser Gln Cys Leu
            515                 520                 525

<210> SEQ ID NO 147
<211> LENGTH: 509
<212> TYPE: PRT
<213> ORGANISM: Artificial Sequence
<220> FEATURE:
<223> OTHER INFORMATION: Synthetic polypeptide of M. thermophila CBH1a
      "Variant 983"

<400> SEQUENCE: 147

Gln Asn Ala Cys Thr Leu Asn Ala Glu Asn His Pro Ser Leu Thr Trp
1               5                   10                  15

Ser Lys Cys Thr Ser Gly Gly Ser Cys Thr Ser Val Gln Gly Ser Ile
            20                  25                  30

Thr Ile Asp Ala Asn Trp Arg Trp Thr His Arg Thr Asp Ser Ala Thr
        35                  40                  45

Asn Cys Tyr Glu Gly Asn Lys Trp Asp Thr Ser Tyr Cys Ser Asp Gly
50                  55                  60

Pro Ser Cys Ala Ser Lys Cys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
                85                  90                  95

Thr Lys Gly Gln Tyr Ser Thr Asn Ile Gly Ser Arg Thr Tyr Leu Met
            100                 105                 110

Glu Ser Asp Thr Lys Tyr Gln Met Phe Gln Leu Leu Gly Asn Glu Phe
        115                 120                 125

Thr Phe Asp Val Asp Val Ser Asn Leu Gly Cys Gly Leu Asn Gly Ala
130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Glu Ala Asn Val Glu Asn
            180                 185                 190

Trp Gln Ser Ser Thr Asn Asp Ala Asn Ala Gly Thr Gly Lys Tyr Gly
        195                 200                 205

Ser Cys Cys Ser Glu Met Asp Val Trp Glu Ala Asn Asn Met Ala Ala
210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
                245                 250                 255

Cys Asp Pro Asp Gly Cys Asp Phe Asn Ser Tyr Arg Gln Gly Asn Lys
            260                 265                 270

```
Thr Phe Tyr Gly Lys Gly Met Thr Val Asp Thr Thr Lys Lys Ile Thr
            275                 280                 285

Val Val Thr Gln Phe Leu Lys Asn Ser Ala Gly Glu Leu Ser Glu Ile
        290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Glu Tyr Cys Asp
                325                 330                 335

Arg Gln Lys Ala Ala Phe Gly Asp Val Thr Asp Phe Gln Asp Lys Gly
            340                 345                 350

Gly Met Val Gln Met Gly Lys Ala Leu Ala Gly Pro Met Val Leu Val
        355                 360                 365

Met Ser Ile Trp Asp Asp His Ala Asp Asn Met Leu Trp Leu Asp Ser
    370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Ile Phe Ser Asn Ile Arg Phe Gly Pro Ile Gly Ser
            420                 425                 430

Thr Val Ser Gly Leu Pro Asp Gly Gly Ser Gly Asn Pro Asn Pro Pro
        435                 440                 445

Val Ser Ser Ser Thr Pro Val Pro Ser Ser Ser Thr Thr Ser Ser Gly
    450                 455                 460

Ser Ser Gly Pro Thr Gly Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
                485                 490                 495

Thr Cys Thr Lys Leu Asn Asp Trp Tyr Ser Gln Cys Leu
            500                 505

<210> SEQ ID NO 148
<211> LENGTH: 1449
<212> TYPE: DNA
<213> ORGANISM: Myceliophthora thermophila

<400> SEQUENCE: 148
atggccaaga agcttttcat caccgccgcg cttgcggctg ccgtgttggc ggccccgtc      60 attgaggagc gccagaactg cggcgctgtg tggactcaat gcggcggtaa cgggtggcaa    120
ggtcccacat gctgcgcctc gggctcgacc tgcgttgcgc agaacgagtg gtactctcag    180
tgcctgccca acagccaggt gacgagttcc accactccgt cgtcgacttc cacctcgcag    240
cgcagcacca gcacctccag cagcaccacc aggagcggca gctcctcctc ctcctccacc    300 acgccccgc ccgtctccag ccccgtgacc agcattcccg gcggtgcgac tccacggcg      360 agctactctg caacccctt ctcgggcgtc cggctcttcg ccaacgacta ctacaggtcc     420
gaggtccaca atctcgccat tcctagcatg actggtactc tggcggccaa ggcttccgcc    480
gtcgccgaag tccctagctt ccagtggctc gaccggaacg tcaccatcga caccctgatg    540
gtccagactc tgtcccaggt ccgggctctc aataaggccg tgccaatcc tccctatgct     600 gcccaactcg tcgtctacga cctccccgac cgtgactgtg ccgccgctgc gtccaacggc    660
gagttttcga ttgcaaacgg cggcgccgcc aactacagga gctacatcga cgctatccgc    720
aagcacatca ttgagtactc ggacatccgg atcatcctgg ttatcgagcc cgactcgatg    780
```

```
gccaacatgg tgaccaacat gaacgtggcc aagtgcagca acgccgcgtc gacgtaccac    840
gagttgaccg tgtacgcgct caagcagctg aacctgccca acgtcgccat gtatctcgac    900
gccggccacg ccggctggct cggctggccc gccaacatcc agcccgccgc cgagctgttt    960
gccggcatct acaatgatgc cggcaagccg gctgccgtcc gcggcctggc cactaacgtc   1020
gccaactaca acgcctggag catcgcttcg gccccgtcgt acacgtcgcc taaccctaac   1080
tacgacgaga agcactacat cgaggccttc agcccgctct tgaactcggc cggcttcccc   1140
gcacgcttca ttgtcgacac tggccgcaac ggcaaacaac ctaccggcca acaacagtgg   1200
ggtgactggt gcaatgtcaa gggcaccggc tttggcgtgc cccgacggc caacacgggc    1260 cacgagctgg tcgatgcctt tgtctgggtc aagcccggcg cgagtccga cggcacaagc    1320 gacaccagcg ccgcccgcta cgactaccac tgcggcctgt ccgatgccct gcagcctgcc   1380
cccgaggctg gacagtggtt ccaggcctac ttcgagcagc tgctcaccaa cgccaacccg   1440
cccttctaa                                                           1449
```

<210> SEQ ID NO 149
<211> LENGTH: 482
<212> TYPE: PRT
<213> ORGANISM: Myceliophthora thermophila

<400> SEQUENCE: 149

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80

Arg Ser Thr Ser Thr Ser Ser Ser Thr Thr Arg Ser Gly Ser Ser Ser
                85                  90                  95

Ser Ser Ser Thr Thr Pro Pro Val Ser Ser Pro Val Thr Ser Ile
            100                 105                 110

Pro Gly Gly Ala Thr Ser Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255
```

Pro Asp Ser Met Ala Asn Met Val Thr Asn Met Asn Val Ala Lys Cys
                260                 265                 270

Ser Asn Ala Ala Ser Thr Tyr His Glu Leu Thr Val Tyr Ala Leu Lys
            275                 280                 285

Gln Leu Asn Leu Pro Asn Val Ala Met Tyr Leu Asp Ala Gly His Ala
        290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ser Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro Phe

<210> SEQ ID NO 150
<211> LENGTH: 465
<212> TYPE: PRT
<213> ORGANISM: Myceliophthora thermophila

<400> SEQUENCE: 150

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
            20                  25                  30

Thr Cys Val Ala Gln Asn Glu Trp Tyr Ser Gln Cys Leu Pro Asn Ser
        35                  40                  45

Gln Val Thr Ser Ser Thr Pro Ser Ser Thr Ser Thr Ser Gln Arg
    50                  55                  60

Ser Thr Ser Thr Ser Ser Ser Thr Thr Arg Ser Gly Ser Ser Ser Ser
65                  70                  75                  80

Ser Ser Thr Thr Pro Pro Pro Val Ser Ser Pro Val Thr Ser Ile Pro
                85                  90                  95

Gly Gly Ala Thr Ser Thr Ala Ser Tyr Ser Gly Asn Pro Phe Ser Gly
            100                 105                 110

Val Arg Leu Phe Ala Asn Asp Tyr Tyr Arg Ser Glu Val His Asn Leu
        115                 120                 125

Ala Ile Pro Ser Met Thr Gly Thr Leu Ala Ala Lys Ala Ser Ala Val
    130                 135                 140

Ala Glu Val Pro Ser Phe Gln Trp Leu Asp Arg Asn Val Thr Ile Asp
145                 150                 155                 160

Thr Leu Met Val Gln Thr Leu Ser Gln Val Arg Ala Leu Asn Lys Ala
                165                 170                 175

Gly Ala Asn Pro Pro Tyr Ala Ala Gln Leu Val Val Tyr Asp Leu Pro
            180                 185                 190

Asp Arg Asp Cys Ala Ala Ala Ser Asn Gly Glu Phe Ser Ile Ala
        195                 200                 205

Asn Gly Gly Ala Ala Asn Tyr Arg Ser Tyr Ile Asp Ala Ile Arg Lys
        210                 215                 220

His Ile Ile Glu Tyr Ser Asp Ile Arg Ile Ile Leu Val Ile Glu Pro
225                 230                 235                 240

Asp Ser Met Ala Asn Met Val Thr Asn Met Asn Val Ala Lys Cys Ser
                245                 250                 255

Asn Ala Ala Ser Thr Tyr His Glu Leu Thr Val Tyr Ala Leu Lys Gln
            260                 265                 270

Leu Asn Leu Pro Asn Val Ala Met Tyr Leu Asp Ala Gly His Ala Gly
        275                 280                 285

Trp Leu Gly Trp Pro Ala Asn Ile Gln Pro Ala Ala Glu Leu Phe Ala
        290                 295                 300

Gly Ile Tyr Asn Asp Ala Gly Lys Pro Ala Ala Val Arg Gly Leu Ala
305                 310                 315                 320

Thr Asn Val Ala Asn Tyr Asn Ala Trp Ser Ile Ala Ser Ala Pro Ser
                325                 330                 335

Tyr Thr Ser Pro Asn Pro Asn Tyr Asp Glu Lys His Tyr Ile Glu Ala
            340                 345                 350

Phe Ser Pro Leu Leu Asn Ser Ala Gly Phe Pro Ala Arg Phe Ile Val
        355                 360                 365

Asp Thr Gly Arg Asn Gly Lys Gln Pro Thr Gly Gln Gln Gln Trp Gly
        370                 375                 380

Asp Trp Cys Asn Val Lys Gly Thr Gly Phe Gly Val Arg Pro Thr Ala
385                 390                 395                 400

Asn Thr Gly His Glu Leu Val Asp Ala Phe Val Trp Val Lys Pro Gly
                405                 410                 415

Gly Glu Ser Asp Gly Thr Ser Asp Thr Ser Ala Ala Arg Tyr Asp Tyr
            420                 425                 430

His Cys Gly Leu Ser Asp Ala Leu Gln Pro Ala Pro Glu Ala Gly Gln
        435                 440                 445

Trp Phe Gln Ala Tyr Phe Glu Gln Leu Leu Thr Asn Ala Asn Pro Pro
        450                 455                 460

Phe
465

<210> SEQ ID NO 151
<211> LENGTH: 1449
<212> TYPE: DNA
<213> ORGANISM: Artificial Sequence
<220> FEATURE:
<223> OTHER INFORMATION: Synthetic polynucleotide of M. thermophila
      CBH2b "Variant 196"

<400> SEQUENCE: 151
atggccaaga agcttttcat caccgccgcg cttgcggctg ccgtgttggc ggccccgtc    60 attgaggagc gccagaactg cggcgctgtg tggactcaat gcggcggtaa cgggtggcaa   120

```
ggtcccacat gctgcgcctc gggctcgacc tgcgttgcgc agaacgagtg gtactctcag    180
tgcctgccca acagccaggt gacgagttcc accactccgt cgtcgacttc cacctcgcag    240
cgcagcacca gcacctccag cagcaccacc aggagcggca gctcctcctc ctcctccacc    300
acgcccaccc ccgtctccag ccccgtgacc agcattcccg gcggtgcgac ctccacggcg    360
agctactctg gcaacccctt ctcgggcgtc cggctcttcg ccaacgacta ctacaggtcc    420
gaggtccaca atctcgccat tcctagcatg actggtactc tggcggccaa ggcttccgcc    480
gtcgccgaag tccctagctt ccagtggctc gaccggaacg tcaccatcga caccctgatg    540
gtcccgactc tgtcccgcgt ccgggctctc aataaggccg gtgccaatcc tccctatgct    600
gcccaactcg tcgtctacga cctccccgac cgtgactgtg ccgccgctgc gtccaacggc    660
gagttttcga ttgcaaacgg cggcgccgcc aactacagga gctacatcga cgctatccgc    720
aagcacatca ttgagtactc ggacatccgg atcatcctgg ttatcgagcc cgactcgatg    780
gccaacatgg tgaccaacat gaacgtggcc aagtgcagca acgccgcgtc gacgtaccac    840
gagttgaccg tgtacgcgct caagcagctg aacctgccca acgtcgccat gtatctcgac    900
gccggccacg ccggctggct cggctggccc gccaacatcc agcccgccgc cgagctgttt    960
gccggcatct acaatgatgc cggcaagccg gctgccgtcc gcggcctggc cactaacgtc   1020
gccaactaca acgcctggag catcgcttcg gccccgtcgt acacgtcgcc taaccctaac   1080
tacgacgaga agcactacat cgaggccttc agcccgctct tgaactcggc cggcttcccc   1140
gcacgcttca ttgtcgacac tggccgcaac ggcaaacaac ctaccggcca acaacagtgg   1200
ggtgactggt gcaatgtcaa gggcaccggc tttggcgtgc cccgacggc caacacgggc   1260 cacgagctgg tcgatgcctt tgtctgggtc aagcccggcg gcgagtccga cggcacaagc   1320
gacaccagcg ccgcccgcta cgactaccac tgccgcctgt ccgatgccct gcagcctgcc   1380
cccgaggctg acagtggttt ccaggcctac ttcgagcagc tgctcaccaa cgccaacccg   1440
cccttctaa                                                            1449
```

<210> SEQ ID NO 152
<211> LENGTH: 482
<212> TYPE: PRT
<213> ORGANISM: Artificial Sequence
<220> FEATURE:
<223> OTHER INFORMATION: Synthetic polypeptide of M. thermophila CBH2b
      "Variant 196"

<400> SEQUENCE: 152

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80

Arg Ser Thr Ser Thr Ser Ser Ser Thr Thr Arg Ser Gly Ser Ser Ser
                85                  90                  95

Ser Ser Ser Thr Thr Pro Thr Pro Val Ser Ser Pro Val Thr Ser Ile
            100                 105                 110

Pro Gly Gly Ala Thr Ser Thr Ala Ser Tyr Ser Gly Asn Pro Phe Ser
```

```
            115                 120                 125
Gly Val Arg Leu Phe Ala Asn Asp Tyr Tyr Arg Ser Glu Val His Asn
    130                 135                 140
Leu Ala Ile Pro Ser Met Thr Gly Thr Leu Ala Ala Lys Ala Ser Ala
145                 150                 155                 160
Val Ala Glu Val Pro Ser Phe Gln Trp Leu Asp Arg Asn Val Thr Ile
                165                 170                 175
Asp Thr Leu Met Val Pro Thr Leu Ser Arg Val Arg Ala Leu Asn Lys
            180                 185                 190
Ala Gly Ala Asn Pro Pro Tyr Ala Ala Gln Leu Val Val Tyr Asp Leu
        195                 200                 205
Pro Asp Arg Asp Cys Ala Ala Ala Ser Asn Gly Glu Phe Ser Ile
    210                 215                 220
Ala Asn Gly Gly Ala Ala Asn Tyr Arg Ser Tyr Ile Asp Ala Ile Arg
225                 230                 235                 240
Lys His Ile Ile Glu Tyr Ser Asp Ile Arg Ile Ile Leu Val Ile Glu
                245                 250                 255
Pro Asp Ser Met Ala Asn Met Val Thr Asn Met Asn Val Ala Lys Cys
            260                 265                 270
Ser Asn Ala Ala Ser Thr Tyr His Glu Leu Thr Val Tyr Ala Leu Lys
        275                 280                 285
Gln Leu Asn Leu Pro Asn Val Ala Met Tyr Leu Asp Ala Gly His Ala
    290                 295                 300
Gly Trp Leu Gly Trp Pro Ala Asn Ile Gln Pro Ala Ala Glu Leu Phe
305                 310                 315                 320
Ala Gly Ile Tyr Asn Asp Ala Gly Lys Pro Ala Ala Val Arg Gly Leu
                325                 330                 335
Ala Thr Asn Val Ala Asn Tyr Asn Ala Trp Ser Ile Ala Ser Ala Pro
            340                 345                 350
Ser Tyr Thr Ser Pro Asn Pro Asn Tyr Asp Glu Lys His Tyr Ile Glu
        355                 360                 365
Ala Phe Ser Pro Leu Leu Asn Ser Ala Gly Phe Pro Ala Arg Phe Ile
    370                 375                 380
Val Asp Thr Gly Arg Asn Gly Lys Gln Pro Thr Gly Gln Gln Gln Trp
385                 390                 395                 400
Gly Asp Trp Cys Asn Val Lys Gly Thr Gly Phe Gly Val Arg Pro Thr
                405                 410                 415
Ala Asn Thr Gly His Glu Leu Val Asp Ala Phe Val Trp Val Lys Pro
            420                 425                 430
Gly Gly Glu Ser Asp Gly Thr Ser Asp Thr Ser Ala Ala Arg Tyr Asp
        435                 440                 445
Tyr His Cys Gly Leu Ser Asp Ala Leu Gln Pro Ala Pro Glu Ala Gly
    450                 455                 460
Gln Trp Phe Gln Ala Tyr Phe Glu Gln Leu Leu Thr Asn Ala Asn Pro
465                 470                 475                 480
Pro Phe

<210> SEQ ID NO 153
<211> LENGTH: 465
<212> TYPE: PRT
<213> ORGANISM: Artificial Sequence
<220> FEATURE:
<223> OTHER INFORMATION: Synthetic polypeptide of M. thermophila CBH2b
      "Variant 196"
```

<400> SEQUENCE: 153

```
Ala Pro Val Ile Glu Glu Arg Gln Asn Cys Gly Ala Val Trp Thr Gln
 1               5                  10                  15
Cys Gly Gly Asn Gly Trp Gln Gly Pro Thr Cys Cys Ala Ser Gly Ser
             20                  25                  30
Thr Cys Val Ala Gln Asn Glu Trp Tyr Ser Gln Cys Leu Pro Asn Ser
         35                  40                  45
Gln Val Thr Ser Ser Thr Thr Pro Ser Ser Thr Ser Thr Ser Gln Arg
     50                  55                  60
Ser Thr Ser Thr Ser Ser Thr Thr Arg Ser Gly Ser Ser Ser Ser Ser
 65                  70                  75                  80
Ser Ser Thr Thr Pro Thr Pro Val Ser Ser Pro Val Thr Ser Ile Pro
                 85                  90                  95
Gly Gly Ala Thr Ser Thr Ala Ser Tyr Ser Gly Asn Pro Phe Ser Gly
            100                 105                 110
Val Arg Leu Phe Ala Asn Asp Tyr Tyr Arg Ser Glu Val His Asn Leu
        115                 120                 125
Ala Ile Pro Ser Met Thr Gly Thr Leu Ala Ala Lys Ala Ser Ala Val
    130                 135                 140
Ala Glu Val Pro Ser Phe Gln Trp Leu Asp Arg Asn Val Thr Ile Asp
145                 150                 155                 160
Thr Leu Met Val Pro Thr Leu Ser Arg Val Arg Ala Leu Asn Lys Ala
                165                 170                 175
Gly Ala Asn Pro Pro Tyr Ala Ala Gln Leu Val Val Tyr Asp Leu Pro
            180                 185                 190
Asp Arg Asp Cys Ala Ala Ala Ser Asn Gly Glu Phe Ser Ile Ala
        195                 200                 205
Asn Gly Gly Ala Ala Asn Tyr Arg Ser Tyr Ile Asp Ala Ile Arg Lys
    210                 215                 220
His Ile Ile Glu Tyr Ser Asp Ile Arg Ile Ile Leu Val Ile Glu Pro
225                 230                 235                 240
Asp Ser Met Ala Asn Met Val Thr Asn Met Asn Val Ala Lys Cys Ser
                245                 250                 255
Asn Ala Ala Ser Thr Tyr His Glu Leu Thr Val Tyr Ala Leu Lys Gln
            260                 265                 270
Leu Asn Leu Pro Asn Val Ala Met Tyr Leu Asp Ala Gly His Ala Gly
        275                 280                 285
Trp Leu Gly Trp Pro Ala Asn Ile Gln Pro Ala Ala Glu Leu Phe Ala
    290                 295                 300
Gly Ile Tyr Asn Asp Ala Gly Lys Pro Ala Ala Val Arg Gly Leu Ala
305                 310                 315                 320
Thr Asn Val Ala Asn Tyr Asn Ala Trp Ser Ile Ala Ser Ala Pro Ser
                325                 330                 335
Tyr Thr Ser Pro Asn Pro Asn Tyr Asp Glu Lys His Tyr Ile Glu Ala
            340                 345                 350
Phe Ser Pro Leu Leu Asn Ser Ala Gly Phe Pro Ala Arg Phe Ile Val
        355                 360                 365
Asp Thr Gly Arg Asn Gly Lys Gln Pro Thr Gly Gln Gln Gln Trp Gly
    370                 375                 380
Asp Trp Cys Asn Val Lys Gly Thr Gly Phe Gly Val Arg Pro Thr Ala
385                 390                 395                 400
Asn Thr Gly His Glu Leu Val Asp Ala Phe Val Trp Val Lys Pro Gly
                405                 410                 415
```

Gly Glu Ser Asp Gly Thr Ser Asp Thr Ser Ala Ala Arg Tyr Asp Tyr
            420                 425                 430

His Cys Gly Leu Ser Asp Ala Leu Gln Pro Ala Pro Glu Ala Gly Gln
        435                 440                 445

Trp Phe Gln Ala Tyr Phe Glu Gln Leu Leu Thr Asn Ala Asn Pro Pro
    450                 455                 460

Phe
465

<210> SEQ ID NO 154
<211> LENGTH: 1449
<212> TYPE: DNA
<213> ORGANISM: Artificial Sequence
<220> FEATURE:
<223> OTHER INFORMATION: Synthetic polynucleotide of M. thermophila
      CBH2b "Variant 287"

<400> SEQUENCE: 154

```
atggccaaga agcttttcat caccgccgcg cttgcggctg ccgtgttggc ggcccccgtc     60
attgaggagc gccagaactg cggcgctgtg tggactcaat gcggcggtaa cgggtggcaa    120
ggtcccacat gctgcgcctc gggctcgacc tgcgttgcgc agaacgagtg gtactctcag    180
tgcctgccca acagccaggt gacgagttcc accactccgt cgtcgacttc cacctcgcag    240
cgcagcacca gcacctccag cagcaccacc aggagcggca gctcctcctc ctcctccacc    300
acgccccgc ccgtctccag ccccgtgacc agcattccg cggtgcgac tccacggcg      360
agctactctg gcaaccccctt ctcgggcgtc cggctcttcg ccaacgacta ctacaggtcc    420
gaggtccaca atctcgccat tcctagcatg actggtactc tggcggccaa ggcttccgcc    480
gtcgccgaag tccctagctt ccagtggctc gaccggaacg tcaccatcga caccctgatg    540
gtcccgactc tgtcccgcgt ccgggctctc aataaggccg gtgccaatcc tcctctatgct   600
gcccaactcg tcgtctacga cctccccgac cgtgactgtg ccgccgctgc gtccaacggc    660
gagttttcga ttgcaaacgg cggcgccgcc aactacagga gctacatcga cgctatccgc    720
aagcacatca aggagtactc ggacatccgg atcatcctgg ttatcgagcc cgactcgatg    780
gccaacatgg tgaccaacat gaacgtggcc aagtgcagca acgccgcgtc gacgtaccac    840
gagttgaccg tgtacgcgct caagcagctg aacctgccca acgtcgccat gtatctcgac    900
gccggccacg ccggctggct cggctggccc gccaacatcc agcccgccgc cgagctgttt    960
gccggcatct acaatgatgc cggcaagccg gctgccgtcc gcggcctggc cactaacgtc   1020
gccaactaca acgcctggag catcgcttcg gccccgtcgt acacgtcgcc taaccctaac   1080
tacgacgaga agcactacat cgaggccttc agcccgctct tgaacgacgc cggcttcccc   1140
gcacgcttca ttgtcgacac tggccgcaac ggcaaacaac ctaccggcca acaacagtgg   1200
ggtgactggt gcaatgtcaa gggcaccggc tttggcgtgc cccgacggc caacacgggc   1260
cacgagctgg tcgatgcctt tgtctgggtc aagcccggcg gcgagtccga cggcacaagc   1320
gacaccagcg ccgcccgcta cgactaccac tgcggcctgt ccgatgccct gcagcctgcc   1380
cccgaggctg gacagtggtt ccaggcctac ttcgagcagc tgctcaccaa cgccaacccg   1440
cccttctaa                                                           1449
```

<210> SEQ ID NO 155
<211> LENGTH: 482
<212> TYPE: PRT
<213> ORGANISM: Artificial Sequence
<220> FEATURE:
<223> OTHER INFORMATION: Synthetic polypeptide of M. thermophila CBH2b "Variant 287"

<400> SEQUENCE: 155

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Thr Thr Pro Ser Ser Thr Ser Thr Ser Gln
65                  70                  75                  80

Arg Ser Thr Ser Thr Ser Ser Thr Thr Arg Ser Gly Ser Ser Ser
                85                  90                  95

Ser Ser Ser Thr Thr Pro Pro Val Ser Ser Pro Thr Ser Ile
                100                 105                 110

Pro Gly Gly Ala Thr Ser Thr Ala Ser Tyr Ser Gly Asn Pro Phe Ser
            115                 120                 125

Gly Val Arg Leu Phe Ala Asn Asp Tyr Tyr Arg Ser Glu Val His Asn
        130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Pro Thr Leu Ser Arg Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Lys Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Asp Ala Gly Phe Pro Ala Arg Phe Ile
    370                 375                 380

Val Asp Thr Gly Arg Asn Gly Lys Gln Pro Thr Gly Gln Gln Gln Trp
```

```
                385                 390                 395                 400
Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
                420                 425                 430

Gly Gly Glu Ser Asp Gly Thr Ser Asp Thr Ser Ala Ala Arg Tyr Asp
                435                 440                 445

Tyr His Cys Gly Leu Ser Asp Ala Leu Gln Pro Ala Pro Glu Ala Gly
                450                 455                 460

Gln Trp Phe Gln Ala Tyr Phe Glu Gln Leu Leu Thr Asn Ala Asn Pro
465                 470                 475                 480

Pro Phe

<210> SEQ ID NO 156
<211> LENGTH: 465
<212> TYPE: PRT
<213> ORGANISM: Artificial Sequence
<220> FEATURE:
<223> OTHER INFORMATION: Synthetic polypeptide of M. thermophila CBH2b
      "Variant 287"

<400> SEQUENCE: 156

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
                20                  25                  30

Thr Cys Val Ala Gln Asn Glu Trp Tyr Ser Gln Cys Leu Pro Asn Ser
                35                  40                  45

Gln Val Thr Ser Ser Thr Thr Pro Ser Ser Thr Ser Thr Ser Gln Arg
            50                  55                  60

Ser Thr Ser Thr Ser Ser Ser Thr Thr Arg Ser Gly Ser Ser Ser Ser
65                  70                  75                  80

Ser Ser Thr Thr Pro Pro Pro Val Ser Ser Pro Val Thr Ser Ile Pro
                85                  90                  95

Gly Gly Ala Thr Ser Thr Ala Ser Tyr Ser Gly Asn Pro Phe Ser Gly
                100                 105                 110

Val Arg Leu Phe Ala Asn Asp Tyr Tyr Arg Ser Glu Val His Asn Leu
                115                 120                 125

Ala Ile Pro Ser Met Thr Gly Thr Leu Ala Ala Lys Ala Ser Ala Val
                130                 135                 140

Ala Glu Val Pro Ser Phe Gln Trp Leu Asp Arg Asn Val Thr Ile Asp
145                 150                 155                 160

Thr Leu Met Val Pro Thr Leu Ser Arg Val Arg Ala Leu Asn Lys Ala
                165                 170                 175

Gly Ala Asn Pro Pro Tyr Ala Ala Gln Leu Val Val Tyr Asp Leu Pro
                180                 185                 190

Asp Arg Asp Cys Ala Ala Ala Ser Asn Gly Glu Phe Ser Ile Ala
                195                 200                 205

Asn Gly Gly Ala Ala Asn Tyr Arg Ser Tyr Ile Asp Ala Ile Arg Lys
                210                 215                 220

His Ile Lys Glu Tyr Ser Asp Ile Arg Ile Leu Val Ile Glu Pro
225                 230                 235                 240

Asp Ser Met Ala Asn Met Val Thr Asn Met Asn Val Ala Lys Cys Ser
                245                 250                 255

Asn Ala Ala Ser Thr Tyr His Glu Leu Thr Val Tyr Ala Leu Lys Gln
```

```
                260              265              270
Leu Asn Leu Pro Asn Val Ala Met Tyr Leu Asp Ala Gly His Ala Gly
            275              280              285
Trp Leu Gly Trp Pro Ala Asn Ile Gln Pro Ala Ala Glu Leu Phe Ala
            290              295              300
Gly Ile Tyr Asn Asp Ala Gly Lys Pro Ala Ala Val Arg Gly Leu Ala
305              310              315              320
Thr Asn Val Ala Asn Tyr Asn Ala Trp Ser Ile Ala Ser Ala Pro Ser
                325              330              335
Tyr Thr Ser Pro Asn Pro Asn Tyr Asp Glu Lys His Tyr Ile Glu Ala
            340              345              350
Phe Ser Pro Leu Leu Asn Asp Ala Gly Phe Pro Ala Arg Phe Ile Val
            355              360              365
Asp Thr Gly Arg Asn Gly Lys Gln Pro Thr Gly Gln Gln Gln Trp Gly
            370              375              380
Asp Trp Cys Asn Val Lys Gly Thr Gly Phe Gly Val Arg Pro Thr Ala
385              390              395              400
Asn Thr Gly His Glu Leu Val Asp Ala Phe Val Trp Val Lys Pro Gly
                405              410              415
Gly Glu Ser Asp Gly Thr Ser Asp Thr Ser Ala Ala Arg Tyr Asp Tyr
                420              425              430
His Cys Gly Leu Ser Asp Ala Leu Gln Pro Ala Pro Glu Ala Gly Gln
            435              440              445
Trp Phe Gln Ala Tyr Phe Glu Gln Leu Leu Thr Asn Ala Asn Pro Pro
            450              455              460
Phe
465

<210> SEQ ID NO 157
<211> LENGTH: 1449
<212> TYPE: DNA
<213> ORGANISM: Artificial Sequence
<220> FEATURE:
<223> OTHER INFORMATION: Synthetic polynucleotide of M. thermophila
      CBH2b "Variant 962"

<400> SEQUENCE: 157
atggccaaga agcttttcat caccgccgcg cttgcggctg ccgtgttggc ggcccccgtc      60
attgaggagc gccagaactg cggcgctgtg tggactcaat gcggcggtaa cgggtggcaa     120
ggtcccacat gctgcgcctc gggctcgacc tgcgttgcgc agaacgagtg gtactctcag     180
tgcctgccca acagccaggt gacgagttcc accactccgt cgtcgacttc cacctcgcag     240
cgcagcacca gcacctccag cagcaccacc aggagcggca gctcctcctc ctcctccacc     300
acgcccaccc ccgtctccag ccccgtgacc agcattcccg gcggtgcgac ctccacggcg     360
agctactctg gcaaccccct tcgggcgtc cggctcttcg ccaacgacta ctacaggtcc     420
gaggtcatga atctcgccat tcctagcatg actggtactc tggcggccaa ggcttccgcc     480
gtcgccgaag tccctagctt ccagtggctc gaccggaacg tcaccatcga caccctgatg     540
gtcaccactc tgtcccaggt ccgggctctc aataaggccg gtgccaatcc tccctatgct     600
gcccaactcg tcgtctacga cctccccgac cgtgactgtg ccgccgctgc gtccaacggc     660
gagttttcga ttgcaaacgg cggcagcgcc aactacagga gctacatcga cgctatccgc     720
aagcacatca ttgagtactc ggacatccgg atcatcctgg ttatcgagcc cgactcgatg     780
gccaacatgg tgaccaacat gaacgtggcc aagtgcagca acgccgcgtc gacgtaccac     840
```

-continued

```
gagttgaccg tgtacgcgct caagcagctg aacctgccca acgtcgccat gtatctcgac    900
gccggccacg ccggctggct cggctggccc gccaacatcc agcccgccgc cgagctgttt    960
gccggcatct acaatgatgc cggcaagccg gctgccgtcc gcggcctggc cactaacgtc   1020
gccaactaca acgcctggag catcgcttcg gccccgtcgt acacgcagcc taaccctaac   1080
tacgacgaga agcactacat cgaggccttc agcccgctct tgaactcggc cggcttcccc   1140
gcacgcttca ttgtcgacac tggccgcaac ggcaaacaac ctaccggcca acaacagtgg   1200
ggtgactggt gcaatgtcaa gggcaccggc tttggcgtgc ccccgacggc caacacgggc   1260
cacgagctgg tcgatgcctt tgtctgggtc aagcccggcg cgagtccga cggcacaagc    1320 gacaccagcg ccgcccgcta cgactaccac tgcggcctgt ccgatgccct gcagcctgcc   1380
cccgaggctg acagtggtt ccaggcctac ttcgagcagc tgctcaccaa cgccaacccg    1440
cccttctaa                                                          1449
```

<210> SEQ ID NO 158
<211> LENGTH: 482
<212> TYPE: PRT
<213> ORGANISM: Artificial Sequence
<220> FEATURE:
<223> OTHER INFORMATION: Synthetic polypeptide of M. thermophila CBH2b "Variant 962"

<400> SEQUENCE: 158

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80

Arg Ser Thr Ser Thr Ser Ser Thr Thr Arg Ser Gly Ser Ser Ser
                85                  90                  95

Ser Ser Ser Thr Thr Pro Thr Pro Val Ser Ser Pro Val Thr Ser Ile
            100                 105                 110

Pro Gly Gly Ala Thr Ser Thr Ala Ser Tyr Ser Gly Asn Pro Phe Ser
        115                 120                 125

Gly Val Arg Leu Phe Ala Asn Asp Tyr Tyr Arg Ser Glu Val Met Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Thr Thr Leu Ser Gln Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ser Asn Gly Glu Phe Ser Ile
    210                 215                 220

Ala Asn Gly Gly Ser Ala Asn Tyr Arg Ser Tyr Ile Asp Ala Ile Arg
225                 230                 235                 240
```

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Gln Pro Asn Pro Asn Tyr Asp Glu Lys His Tyr Ile Glu
        355                 360                 365

Ala Phe Ser Pro Leu Leu Asn Ser Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro Phe

<210> SEQ ID NO 159
<211> LENGTH: 464
<212> TYPE: PRT
<213> ORGANISM: Artificial Sequence
<220> FEATURE:
<223> OTHER INFORMATION: Synthetic polypeptide of M. thermophila CBH2b
    "Variant 962"

<400> SEQUENCE: 159

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
            20                  25                  30

Thr Cys Val Ala Gln Asn Glu Trp Tyr Ser Gln Cys Leu Pro Asn Ser
        35                  40                  45

Gln Val Thr Ser Ser Thr Thr Pro Ser Ser Thr Ser Thr Ser Gln Arg
    50                  55                  60

Ser Thr Ser Thr Ser Ser Ser Thr Thr Arg Ser Gly Ser Ser Ser Ser
65                  70                  75                  80

Ser Ser Thr Thr Pro Thr Pro Val Ser Ser Pro Val Thr Ser Ile Pro
                85                  90                  95

Gly Gly Ala Thr Ser Thr Ala Ser Tyr Ser Gly Asn Pro Phe Ser Gly
            100                 105                 110

Val Arg Leu Phe Ala Asn Asp Tyr Tyr Arg Ser Glu Val Met Asn Leu
        115                 120                 125
Ala Ile Pro Ser Met Thr Gly Thr Leu Ala Ala Lys Ala Ser Ala Val
130                 135                 140
Ala Glu Val Pro Ser Phe Gln Trp Leu Asp Arg Asn Val Thr Ile Asp
145                 150                 155                 160
Thr Leu Met Val Thr Thr Leu Ser Gln Val Arg Ala Leu Asn Lys Ala
                165                 170                 175
Gly Ala Asn Pro Pro Tyr Ala Ala Gln Leu Val Val Tyr Asp Leu Pro
            180                 185                 190
Asp Arg Asp Cys Ala Ala Ala Ser Asn Gly Glu Phe Ser Ile Ala
        195                 200                 205
Asn Gly Gly Ser Ala Asn Tyr Arg Ser Tyr Ile Asp Ala Ile Arg Lys
    210                 215                 220
His Ile Ile Glu Tyr Ser Asp Ile Arg Ile Ile Leu Val Ile Glu Pro
225                 230                 235                 240
Asp Ser Met Ala Asn Met Val Thr Asn Met Asn Val Ala Lys Cys Ser
                245                 250                 255
Asn Ala Ala Ser Thr Tyr His Glu Leu Thr Val Tyr Ala Leu Lys Gln
            260                 265                 270
Leu Asn Leu Pro Asn Val Ala Met Tyr Leu Asp Ala Gly His Ala Gly
        275                 280                 285
Trp Leu Gly Trp Pro Ala Asn Ile Gln Pro Ala Ala Glu Leu Phe Ala
    290                 295                 300
Gly Ile Tyr Asn Asp Gly Lys Pro Ala Ala Val Arg Gly Leu Ala Thr
305                 310                 315                 320
Asn Val Ala Asn Tyr Asn Ala Trp Ser Ile Ala Ser Ala Pro Ser Tyr
                325                 330                 335
Thr Gln Pro Asn Pro Asn Tyr Asp Glu Lys His Tyr Ile Glu Ala Phe
            340                 345                 350
Ser Pro Leu Leu Asn Ser Ala Gly Phe Pro Ala Arg Phe Ile Val Asp
        355                 360                 365
Thr Gly Arg Asn Gly Lys Gln Pro Thr Gly Gln Gln Gln Trp Gly Asp
    370                 375                 380
Trp Cys Asn Val Lys Gly Thr Gly Phe Gly Val Arg Pro Thr Ala Asn
385                 390                 395                 400
Thr Gly His Glu Leu Val Asp Ala Phe Val Trp Val Lys Pro Gly Gly
                405                 410                 415
Glu Ser Asp Gly Thr Ser Asp Ser Ala Ala Arg Tyr Asp Tyr His
            420                 425                 430
Cys Gly Leu Ser Asp Ala Leu Gln Pro Ala Pro Glu Ala Gly Gln Trp
        435                 440                 445
Phe Gln Ala Tyr Phe Glu Gln Leu Leu Thr Asn Ala Asn Pro Pro Phe
    450                 455                 460

<210> SEQ ID NO 160
<211> LENGTH: 1239
<212> TYPE: DNA
<213> ORGANISM: Myceliophthora thermophila

<400> SEQUENCE: 160
atgcactcca aagctttctt ggcagcgctt cttgcgcctg ccgtctcagg gcaactgaac     60
gacctcgccg tcagggctgg actcaagtac tttggtactg ctcttagcga gagcgtcatc    120
aacagtgata ctcggtatgc tgccatcctc agcgacaaga gcatgttcgg ccagctcgtc    180

```
cccgagaatg gcatgaagtg ggatgctact gagccgtccc gtggccagtt caactacgcc    240
tcgggcgaca tcacggccaa cacggccaag aagaatggcc agggcatgcg ttgccacacc    300
atggtctggt acagccagct cccgagctgg gtctcctcgg gctcgtggac cagggactcg    360
ctcacctcgg tcatcgagac gcacatgaac aacgtcatgg ccactacaa gggccaatgc     420 tacgcctggg atgtcatcaa cgaggccatc aatgacgacg gcaactcctg cgcgacaac     480 gtctttctcc ggaccttttgg gaccgactac ttcgccctgt ccttcaacct agccaagaag    540
gccgatcccg ataccaagct gtactacaac gactacaacc tcgagtacaa ccaggccaag    600
acggaccgcg ctgttgagct cgtcaagatg gtccaggccg ccggcgcgcc catcgacggt    660
gtcggcttcc agggccacct cattgtcggc tcgaccccga cgcgctcgca gctggccacc    720
gccctccagc gcttcaccgc gctcggcctc gaggtcgcct acaccgagct cgacatccgc    780
cactcgagcc tgccggcctc ttcgtcggcg ctcgcgaccc agggcaacga cttcgccaac    840
gtggtcggct cttgcctcga caccgccggc tgcgtcggcg tcaccgtctg gggcttcacc    900
gatgcgcact cgtggatccc gaacacgttc cccggccagg gcgacgccct gatctacgac    960
agcaactaca acaagaagcc cgcgtggacc tcgatctcgt ccgtcctggc cgccaaggcc   1020
accggcgccc cgcccgcctc gtcctccacc accctcgtca ccatcaccac ccctccgccg   1080
gcatccacca ccgcctcctc ctcctccagt gccacgccca cgagcgtccc gacgcagacg   1140
aggtggggac agtgcggcgg catcggatgg acggggccga cccagtgcga gagcccatgg   1200
acctgccaga agctgaacga ctggtactgg cagtgcctg                           1239
```

<210> SEQ ID NO 161
<211> LENGTH: 413
<212> TYPE: PRT
<213> ORGANISM: Myceliophthora thermophila

<400> SEQUENCE: 161

```
Met His Ser Lys Ala Phe Leu Ala Ala Leu Leu Ala Pro Ala Val Ser
1               5                   10                  15

Gly Gln Leu Asn Asp Leu Ala Val Arg Ala Gly Leu Lys Tyr Phe Gly
                20                  25                  30

Thr Ala Leu Ser Glu Ser Val Ile Asn Ser Asp Thr Arg Tyr Ala Ala
            35                  40                  45

Ile Leu Ser Asp Lys Ser Met Phe Gly Gln Leu Val Pro Glu Asn Gly
        50                  55                  60

Met Lys Trp Asp Ala Thr Glu Pro Ser Arg Gly Gln Phe Asn Tyr Ala
65                  70                  75                  80

Ser Gly Asp Ile Thr Ala Asn Thr Ala Lys Lys Asn Gly Gln Gly Met
                85                  90                  95

Arg Cys His Thr Met Val Trp Tyr Ser Gln Leu Pro Ser Trp Val Ser
                100                 105                 110

Ser Gly Ser Trp Thr Arg Asp Ser Leu Thr Ser Val Ile Glu Thr His
            115                 120                 125

Met Asn Asn Val Met Gly His Tyr Lys Gly Gln Cys Tyr Ala Trp Asp
        130                 135                 140

Val Ile Asn Glu Ala Ile Asn Asp Asp Gly Asn Ser Trp Arg Asp Asn
145                 150                 155                 160

Val Phe Leu Arg Thr Phe Gly Thr Asp Tyr Phe Ala Leu Ser Phe Asn
                165                 170                 175

Leu Ala Lys Lys Ala Asp Pro Asp Thr Lys Leu Tyr Tyr Asn Asp Tyr
```

```
                180                 185                 190
Asn Leu Glu Tyr Asn Gln Ala Lys Thr Asp Arg Ala Val Glu Leu Val
                195                 200                 205
Lys Met Val Gln Ala Ala Gly Ala Pro Ile Asp Gly Val Gly Phe Gln
                210                 215                 220
Gly His Leu Ile Val Gly Ser Thr Pro Thr Arg Ser Gln Leu Ala Thr
225                 230                 235                 240
Ala Leu Gln Arg Phe Thr Ala Leu Gly Leu Glu Val Ala Tyr Thr Glu
                245                 250                 255
Leu Asp Ile Arg His Ser Ser Leu Pro Ala Ser Ser Ala Leu Ala
                260                 265                 270
Thr Gln Gly Asn Asp Phe Ala Asn Val Val Gly Ser Cys Leu Asp Thr
                275                 280                 285
Ala Gly Cys Val Gly Val Thr Val Trp Gly Phe Thr Asp Ala His Ser
290                 295                 300
Trp Ile Pro Asn Thr Phe Pro Gly Gln Gly Asp Ala Leu Ile Tyr Asp
305                 310                 315                 320
Ser Asn Tyr Asn Lys Lys Pro Ala Trp Thr Ser Ile Ser Ser Val Leu
                325                 330                 335
Ala Ala Lys Ala Thr Gly Ala Pro Pro Ala Ser Ser Thr Thr Leu
                340                 345                 350
Val Thr Ile Thr Thr Pro Pro Ala Ser Thr Ala Ser Ser Ser
                355                 360                 365
Ser Ser Ala Thr Pro Thr Ser Val Pro Thr Gln Thr Arg Trp Gly Gln
                370                 375                 380
Cys Gly Gly Ile Gly Trp Thr Gly Pro Thr Gln Cys Glu Ser Pro Trp
385                 390                 395                 400
Thr Cys Gln Lys Leu Asn Asp Trp Tyr Trp Gln Cys Leu
                405                 410

<210> SEQ ID NO 162
<211> LENGTH: 396
<212> TYPE: PRT
<213> ORGANISM: Myceliophthora thermophila

<400> SEQUENCE: 162

Gln Leu Asn Asp Leu Ala Val Arg Ala Gly Leu Lys Tyr Phe Gly Thr
1               5                   10                  15
Ala Leu Ser Glu Ser Val Ile Asn Ser Asp Thr Arg Tyr Ala Ala Ile
                20                  25                  30
Leu Ser Asp Lys Ser Met Phe Gly Gln Leu Val Pro Glu Asn Gly Met
                35                  40                  45
Lys Trp Asp Ala Thr Glu Pro Ser Arg Gly Gln Phe Asn Tyr Ala Ser
                50                  55                  60
Gly Asp Ile Thr Ala Asn Thr Ala Lys Lys Asn Gly Gln Gly Met Arg
65                  70                  75                  80
Cys His Thr Met Val Trp Tyr Ser Gln Leu Pro Ser Trp Val Ser Ser
                85                  90                  95
Gly Ser Trp Thr Arg Asp Ser Leu Thr Ser Val Ile Glu Thr His Met
                100                 105                 110
Asn Asn Val Met Gly His Tyr Lys Gly Gln Cys Tyr Ala Trp Asp Val
                115                 120                 125
Ile Asn Glu Ala Ile Asn Asp Asp Gly Asn Ser Trp Arg Asp Asn Val
                130                 135                 140
```

```
Phe Leu Arg Thr Phe Gly Thr Asp Tyr Phe Ala Leu Ser Phe Asn Leu
145                 150                 155                 160

Ala Lys Lys Ala Asp Pro Asp Thr Lys Leu Tyr Tyr Asn Asp Tyr Asn
            165                 170                 175

Leu Glu Tyr Asn Gln Ala Lys Thr Asp Arg Ala Val Glu Leu Val Lys
        180                 185                 190

Met Val Gln Ala Ala Gly Ala Pro Ile Asp Gly Val Gly Phe Gln Gly
        195                 200                 205

His Leu Ile Val Gly Ser Thr Pro Thr Arg Ser Gln Leu Ala Thr Ala
        210                 215                 220

Leu Gln Arg Phe Thr Ala Leu Gly Leu Glu Val Ala Tyr Thr Glu Leu
225                 230                 235                 240

Asp Ile Arg His Ser Ser Leu Pro Ala Ser Ser Ala Leu Ala Thr
                245                 250                 255

Gln Gly Asn Asp Phe Ala Asn Val Val Gly Ser Cys Leu Asp Thr Ala
        260                 265                 270

Gly Cys Val Gly Val Thr Val Trp Gly Phe Thr Asp Ala His Ser Trp
        275                 280                 285

Ile Pro Asn Thr Phe Pro Gly Gln Gly Asp Ala Leu Ile Tyr Asp Ser
290                 295                 300

Asn Tyr Asn Lys Lys Pro Ala Trp Thr Ser Ile Ser Ser Val Leu Ala
305                 310                 315                 320

Ala Lys Ala Thr Gly Ala Pro Pro Ala Ser Ser Thr Thr Leu Val
                325                 330                 335

Thr Ile Thr Thr Pro Pro Pro Ala Ser Thr Thr Ala Ser Ser Ser Ser
                340                 345                 350

Ser Ala Thr Pro Thr Ser Val Pro Thr Gln Thr Arg Trp Gly Gln Cys
        355                 360                 365

Gly Gly Ile Gly Trp Thr Gly Pro Thr Gln Cys Glu Ser Pro Trp Thr
        370                 375                 380

Cys Gln Lys Leu Asn Asp Trp Tyr Trp Gln Cys Leu
385                 390                 395

<210> SEQ ID NO 163
<211> LENGTH: 654
<212> TYPE: DNA
<213> ORGANISM: Myceliophthora thermophila

<400> SEQUENCE: 163
atggtctcgt tcactctcct cctcacggtc atcgccgctg cggtgacgac ggccagccct      60
ctcgaggtgg tcaagcgcgg catccagccg ggcacgggca cccacgaggg gtacttctac     120
tcgttctgga ccgacggccg tggctcggtc gacttcaacc ccgggccccg cggctcgtac     180
agcgtcacct ggaacaacgt caacaactgg gttggcggca agggctggaa cccgggcccg     240
ccgcgcaaga ttgcgtacaa cggcacctgg aacaactaca acgtgaacag ctacctcgcc     300
ctgtacggct ggactcgcaa cccgctggtc gagtattaca tcgtggaggc atacggcacg     360
tacaacccct cgtcgggcac ggcgcggctg ggcaccatcg aggacgacgg cggcgtgtac     420
gacatctaca agacgacgcg gtacaaccag ccgtccatcg aggggacctc caccttcgac     480
cagtactggt ccgtccgccg ccagaagcgc gtcggcggca ctatcgacac gggcaagcac     540
tttgacgagt ggaagcgcca gggcaacctc cagctcggca cctggaacta catgatcatg     600
gccaccgagg gctaccagag ctctggttcg gccactatcg aggtccggga ggcc           654
```

<210> SEQ ID NO 164
<211> LENGTH: 218
<212> TYPE: PRT
<213> ORGANISM: Myceliophthora thermophila

<400> SEQUENCE: 164

Met Val Ser Phe Thr Leu Leu Leu Thr Val Ile Ala Ala Ala Val Thr
1               5                   10                  15

Thr Ala Ser Pro Leu Glu Val Val Lys Arg Gly Ile Gln Pro Gly Thr
            20                  25                  30

Gly Thr His Glu Gly Tyr Phe Tyr Ser Phe Trp Thr Asp Gly Arg Gly
        35                  40                  45

Ser Val Asp Phe Asn Pro Gly Pro Arg Gly Ser Tyr Ser Val Thr Trp
    50                  55                  60

Asn Asn Val Asn Asn Trp Val Gly Gly Lys Gly Trp Asn Pro Gly Pro
65                  70                  75                  80

Pro Arg Lys Ile Ala Tyr Asn Gly Thr Trp Asn Asn Tyr Asn Val Asn
                85                  90                  95

Ser Tyr Leu Ala Leu Tyr Gly Trp Thr Arg Asn Pro Leu Val Glu Tyr
            100                 105                 110

Tyr Ile Val Glu Ala Tyr Gly Thr Tyr Asn Pro Ser Ser Gly Thr Ala
        115                 120                 125

Arg Leu Gly Thr Ile Glu Asp Asp Gly Gly Val Tyr Asp Ile Tyr Lys
    130                 135                 140

Thr Thr Arg Tyr Asn Gln Pro Ser Ile Glu Gly Thr Ser Thr Phe Asp
145                 150                 155                 160

Gln Tyr Trp Ser Val Arg Arg Gln Lys Arg Val Gly Gly Thr Ile Asp
                165                 170                 175

Thr Gly Lys His Phe Asp Glu Trp Lys Arg Gln Gly Asn Leu Gln Leu
            180                 185                 190

Gly Thr Trp Asn Tyr Met Ile Met Ala Thr Glu Gly Tyr Gln Ser Ser
        195                 200                 205

Gly Ser Ala Thr Ile Glu Val Arg Glu Ala
    210                 215

<210> SEQ ID NO 165
<211> LENGTH: 200
<212> TYPE: PRT
<213> ORGANISM: Myceliophthora thermophila

<400> SEQUENCE: 165

Ser Pro Leu Glu Val Val Lys Arg Gly Ile Gln Pro Gly Thr Gly Thr
1               5                   10                  15

His Glu Gly Tyr Phe Tyr Ser Phe Trp Thr Asp Gly Arg Gly Ser Val
            20                  25                  30

Asp Phe Asn Pro Gly Pro Arg Gly Ser Tyr Ser Val Thr Trp Asn Asn
        35                  40                  45

Val Asn Asn Trp Val Gly Gly Lys Gly Trp Asn Pro Gly Pro Pro Arg
    50                  55                  60

Lys Ile Ala Tyr Asn Gly Thr Trp Asn Asn Tyr Asn Val Asn Ser Tyr
65                  70                  75                  80

Leu Ala Leu Tyr Gly Trp Thr Arg Asn Pro Leu Val Glu Tyr Tyr Ile
                85                  90                  95

Val Glu Ala Tyr Gly Thr Tyr Asn Pro Ser Ser Gly Thr Ala Arg Leu
            100                 105                 110

Gly Thr Ile Glu Asp Asp Gly Gly Val Tyr Asp Ile Tyr Lys Thr Thr

```
                 115                 120                 125
Arg Tyr Asn Gln Pro Ser Ile Glu Gly Thr Ser Thr Phe Asp Gln Tyr
        130                 135                 140

Trp Ser Val Arg Arg Gln Lys Arg Val Gly Gly Thr Ile Asp Thr Gly
145                 150                 155                 160

Lys His Phe Asp Glu Trp Lys Arg Gln Gly Asn Leu Gln Leu Gly Thr
                165                 170                 175

Trp Asn Tyr Met Ile Met Ala Thr Glu Gly Tyr Gln Ser Ser Gly Ser
            180                 185                 190

Ala Thr Ile Glu Val Arg Glu Ala
        195                 200

<210> SEQ ID NO 166
<211> LENGTH: 1155
<212> TYPE: DNA
<213> ORGANISM: Myceliophthora thermophila

<400> SEQUENCE: 166
atgcgtactc ttacgttcgt gctggcagcc gccccggtgg ctgtgcttgc ccaatctcct        60
ctgtggggcc agtgcggcgg tcaaggctgg acaggtccca cgacctgcgt ttctggcgca       120
gtatgccaat tcgtcaatga ctggtactcc aatgcgtgcc ccggatcgag caaccctcct       180
acgggcacca ccagcagcac cactggaagc accccggctc ctactggcgg cggcggcagc       240
ggaaccggcc tccacgacaa attcaaggcc aagggcaagc tctacttcgg aaccgagatc       300
gatcactacc atctcaacaa caatgccttg accaacattg tcaagaaaga ctttggtcaa       360
gtcactcacg agaacagctt gaagtgggat gctactgagc cgagccgcaa tcaattcaac       420
tttgccaacg ccgacgcggt tgtcaacttt gcccaggcca acggcaagct catccgcggc       480
cacaccctcc tctggcactc tcagctgccg cagtgggtgc agaacatcaa cgaccgcaac       540
accttgaccc aggtcatcga gaaccacgtc accaccttg tcactcgcta caagggcaag       600
atcctccact gggacgtcgt taacgagatc tttgccgagg acggctcgct ccgcgacagc       660
gtcttcagcc gcgtcctcgg cgaggacttt gtcggcatcg ccttccgcgc cgcccgcgcc       720
gccgatccca cgccaagct ctacatcaac gactacaacc tcgacattgc caactacgcc       780
aaggtgaccc ggggcatggt cgagaaggtc aacaagtgga tcgcccaggg catcccgatc       840
gacggcatcg gcacccagtg ccacctggcc gggcccggcg gtggaacac ggccgccggc       900 gtccccgacg ccctcaaggc cctcgccgcg ccaacgtca aggagatcgc catcaccgag       960
ctcgacatcg ccggcgcctc cgccaacgac tacctcaccg tcatgaacgc ctgcctccag      1020
gtctccaagt gcgtcggcat caccgtctgg ggcgtctctg acaaggacag ctggaggtcg      1080
agcagcaacc cgctcctctt cgacagcaac taccagccaa aggcggcata caatgctctg      1140
attaatgcct tgtaa                                                       1155

<210> SEQ ID NO 167
<211> LENGTH: 384
<212> TYPE: PRT
<213> ORGANISM: Myceliophthora thermophila

<400> SEQUENCE: 167

Met Arg Thr Leu Thr Phe Val Leu Ala Ala Ala Pro Val Ala Val Leu
1               5                   10                  15

Ala Gln Ser Pro Leu Trp Gly Gln Cys Gly Gly Gln Gly Trp Thr Gly
            20                  25                  30
```

Pro Thr Thr Cys Val Ser Gly Ala Val Cys Gln Phe Val Asn Asp Trp
                35                  40                  45

Tyr Ser Gln Cys Val Pro Gly Ser Ser Asn Pro Thr Gly Thr Thr
 50                  55                  60

Ser Ser Thr Thr Gly Ser Thr Pro Ala Pro Thr Gly Gly Gly Ser
 65                  70                  75                  80

Gly Thr Gly Leu His Asp Lys Phe Lys Ala Lys Gly Lys Leu Tyr Phe
                 85                  90                  95

Gly Thr Glu Ile Asp His Tyr His Leu Asn Asn Ala Leu Thr Asn
                100                 105                 110

Ile Val Lys Lys Asp Phe Gly Gln Val Thr His Glu Asn Ser Leu Lys
                115                 120                 125

Trp Asp Ala Thr Glu Pro Ser Arg Asn Gln Phe Asn Phe Ala Asn Ala
130                 135                 140

Asp Ala Val Val Asn Phe Ala Gln Ala Asn Gly Lys Leu Ile Arg Gly
145                 150                 155                 160

His Thr Leu Leu Trp His Ser Gln Leu Pro Gln Trp Val Gln Asn Ile
                165                 170                 175

Asn Asp Arg Asn Thr Leu Thr Gln Val Ile Glu Asn His Val Thr Thr
                180                 185                 190

Leu Val Thr Arg Tyr Lys Gly Lys Ile Leu His Trp Asp Val Val Asn
                195                 200                 205

Glu Ile Phe Ala Glu Asp Gly Ser Leu Arg Asp Ser Val Phe Ser Arg
                210                 215                 220

Val Leu Gly Glu Asp Phe Val Gly Ile Ala Phe Arg Ala Ala Arg Ala
225                 230                 235                 240

Ala Asp Pro Asn Ala Lys Leu Tyr Ile Asn Asp Tyr Asn Leu Asp Ile
                245                 250                 255

Ala Asn Tyr Ala Lys Val Thr Arg Gly Met Val Glu Lys Val Asn Lys
                260                 265                 270

Trp Ile Ala Gln Gly Ile Pro Ile Asp Gly Ile Gly Thr Gln Cys His
                275                 280                 285

Leu Ala Gly Pro Gly Gly Trp Asn Thr Ala Ala Gly Val Pro Asp Ala
290                 295                 300

Leu Lys Ala Leu Ala Ala Asn Val Lys Glu Ile Ala Ile Thr Glu
305                 310                 315                 320

Leu Asp Ile Ala Gly Ala Ser Ala Asn Asp Tyr Leu Thr Val Met Asn
                325                 330                 335

Ala Cys Leu Gln Val Ser Lys Cys Val Gly Ile Thr Val Trp Gly Val
                340                 345                 350

Ser Asp Lys Asp Ser Trp Arg Ser Ser Ser Asn Pro Leu Leu Phe Asp
                355                 360                 365

Ser Asn Tyr Gln Pro Lys Ala Ala Tyr Asn Ala Leu Ile Asn Ala Leu
                370                 375                 380

<210> SEQ ID NO 168
<211> LENGTH: 367
<212> TYPE: PRT
<213> ORGANISM: Myceliophthora thermophila

<400> SEQUENCE: 168

Gln Ser Pro Leu Trp Gly Gln Cys Gly Gly Gln Gly Trp Thr Gly Pro
1               5                   10                  15

Thr Thr Cys Val Ser Gly Ala Val Cys Gln Phe Val Asn Asp Trp Tyr
                20                  25                  30

```
Ser Gln Cys Val Pro Gly Ser Ser Asn Pro Pro Thr Gly Thr Thr Ser
        35                  40                  45
Ser Thr Thr Gly Ser Thr Pro Ala Pro Thr Gly Gly Gly Ser Gly
 50                  55                  60
Thr Gly Leu His Asp Lys Phe Lys Ala Lys Gly Lys Leu Tyr Phe Gly
 65                  70                  75                  80
Thr Glu Ile Asp His Tyr His Leu Asn Asn Ala Leu Thr Asn Ile
                85                  90                  95
Val Lys Lys Asp Phe Gly Gln Val Thr His Glu Asn Ser Leu Lys Trp
                100                 105                 110
Asp Ala Thr Glu Pro Ser Arg Asn Gln Phe Asn Phe Ala Asn Ala Asp
                115                 120                 125
Ala Val Val Asn Phe Ala Gln Ala Asn Gly Lys Leu Ile Arg Gly His
                130                 135                 140
Thr Leu Leu Trp His Ser Gln Leu Pro Gln Trp Val Gln Asn Ile Asn
145                 150                 155                 160
Asp Arg Asn Thr Leu Thr Gln Val Ile Glu Asn His Val Thr Thr Leu
                165                 170                 175
Val Thr Arg Tyr Lys Gly Lys Ile Leu His Trp Asp Val Asn Glu
                180                 185                 190
Ile Phe Ala Glu Asp Gly Ser Leu Arg Asp Ser Val Phe Ser Arg Val
                195                 200                 205
Leu Gly Glu Asp Phe Val Gly Ile Ala Phe Arg Ala Ala Arg Ala Ala
                210                 215                 220
Asp Pro Asn Ala Lys Leu Tyr Ile Asn Asp Tyr Asn Leu Asp Ile Ala
225                 230                 235                 240
Asn Tyr Ala Lys Val Thr Arg Gly Met Val Glu Lys Val Asn Lys Trp
                245                 250                 255
Ile Ala Gln Gly Ile Pro Ile Asp Gly Ile Gly Thr Gln Cys His Leu
                260                 265                 270
Ala Gly Pro Gly Gly Trp Asn Thr Ala Ala Gly Val Pro Asp Ala Leu
                275                 280                 285
Lys Ala Leu Ala Ala Ala Asn Val Lys Glu Ile Ala Ile Thr Glu Leu
                290                 295                 300
Asp Ile Ala Gly Ala Ser Ala Asn Asp Tyr Leu Thr Val Met Asn Ala
305                 310                 315                 320
Cys Leu Gln Val Ser Lys Cys Val Gly Ile Thr Val Trp Gly Val Ser
                325                 330                 335
Asp Lys Asp Ser Trp Arg Ser Ser Asn Pro Leu Leu Phe Asp Ser
                340                 345                 350
Asn Tyr Gln Pro Lys Ala Ala Tyr Asn Ala Leu Ile Asn Ala Leu
                355                 360                 365

<210> SEQ ID NO 169
<211> LENGTH: 687
<212> TYPE: DNA
<213> ORGANISM: Myceliophthora thermophila

<400> SEQUENCE: 169
atggtctcgc tcaagtccct cctcctcgcc gcggcggcga cgttgacggc ggtgacggcg      60
cgcccgttcg actttgacga cggcaactcg accgaggcgc tggccaagcg ccaggtcacg     120 ccaacgcgc agggctacca ctcgggctac ttctactcgt ggtggtccga cggcggcggc     180
caggccacct tcaccctgct cgagggcagc cactaccagg tcaactggag gaacacgggc     240
```

```
aactttgtcg gtggcaaggg ctggaacccg ggtaccggcc ggaccatcaa ctacggcggc    300
tcgttcaacc cgagcggcaa cggctacctg gccgtctacg gctggacgca caacccgctg    360
atcgagtact acgtggtcga gtcgtacggg acctacaacc cgggcagcca ggcccagtac    420
aagggcagct tccagagcga cggcggcacc tacaacatct acgtctcgac ccgctacaac    480
gcgccctcga tcgagggcac ccgcaccttc agcagtact ggtccatccg cacctccaag    540
cgcgtcggcg ctccgtcac catgcagaac cacttcaacg cctgggccca gcacggcatg    600
cccctcggct cccacgacta ccagatcgtc gccaccgagg gctaccagag cagcggctcc    660
tccgacatct acgtccagac tcactag                                         687
```

```
<210> SEQ ID NO 170
<211> LENGTH: 228
<212> TYPE: PRT
<213> ORGANISM: Myceliophthora thermophila

<400> SEQUENCE: 170

Met Val Ser Leu Lys Ser Leu Leu Ala Ala Ala Thr Leu Thr
 1               5                  10                  15

Ala Val Thr Ala Arg Pro Phe Asp Phe Asp Asp Gly Asn Ser Thr Glu
            20                  25                  30

Ala Leu Ala Lys Arg Gln Val Thr Pro Asn Ala Gln Gly Tyr His Ser
        35                  40                  45

Gly Tyr Phe Tyr Ser Trp Trp Ser Asp Gly Gly Gln Ala Thr Phe
    50                  55                  60

Thr Leu Leu Glu Gly Ser His Tyr Gln Val Asn Trp Arg Asn Thr Gly
65                  70                  75                  80

Asn Phe Val Gly Gly Lys Gly Trp Asn Pro Gly Thr Gly Arg Thr Ile
                85                  90                  95

Asn Tyr Gly Gly Ser Phe Asn Pro Ser Gly Asn Gly Tyr Leu Ala Val
            100                 105                 110

Tyr Gly Trp Thr His Asn Pro Leu Ile Glu Tyr Tyr Val Val Glu Ser
        115                 120                 125

Tyr Gly Tyr Asn Pro Gly Ser Gln Ala Gln Tyr Lys Gly Ser Phe
    130                 135                 140

Gln Ser Asp Gly Gly Thr Tyr Asn Ile Tyr Val Ser Thr Arg Tyr Asn
145                 150                 155                 160

Ala Pro Ser Ile Glu Gly Thr Arg Thr Phe Gln Gln Tyr Trp Ser Ile
                165                 170                 175

Arg Thr Ser Lys Arg Val Gly Gly Ser Val Thr Met Gln Asn His Phe
            180                 185                 190

Asn Ala Trp Ala Gln His Gly Met Pro Leu Gly Ser His Asp Tyr Gln
        195                 200                 205

Ile Val Ala Thr Glu Gly Tyr Gln Ser Ser Gly Ser Ser Asp Ile Tyr
    210                 215                 220

Val Gln Thr His
225
```

```
<210> SEQ ID NO 171
<211> LENGTH: 208
<212> TYPE: PRT
<213> ORGANISM: Myceliophthora thermophila

<400> SEQUENCE: 171

Arg Pro Phe Asp Phe Asp Asp Gly Asn Ser Thr Glu Ala Leu Ala Lys
```

```
1               5                   10                  15
Arg Gln Val Thr Pro Asn Ala Gln Gly Tyr His Ser Gly Tyr Phe Tyr
                    20                  25                  30

Ser Trp Trp Ser Asp Gly Gly Gln Ala Thr Phe Thr Leu Leu Glu
            35                  40                  45

Gly Ser His Tyr Gln Val Asn Trp Arg Asn Thr Gly Asn Phe Val Gly
        50                  55                  60

Gly Lys Gly Trp Asn Pro Gly Thr Gly Arg Thr Ile Asn Tyr Gly Gly
65                  70                  75                  80

Ser Phe Asn Pro Ser Gly Asn Gly Tyr Leu Ala Val Tyr Gly Trp Thr
                85                  90                  95

His Asn Pro Leu Ile Glu Tyr Val Val Glu Ser Tyr Gly Thr Tyr
                100                 105                 110

Asn Pro Gly Ser Gln Ala Gln Tyr Lys Gly Ser Phe Gln Ser Asp Gly
            115                 120                 125

Gly Thr Tyr Asn Ile Tyr Val Ser Thr Arg Tyr Asn Ala Pro Ser Ile
        130                 135                 140

Glu Gly Thr Arg Thr Phe Gln Gln Tyr Trp Ser Ile Arg Thr Ser Lys
145                 150                 155                 160

Arg Val Gly Gly Ser Val Thr Met Gln Asn His Phe Asn Ala Trp Ala
                165                 170                 175

Gln His Gly Met Pro Leu Gly Ser His Asp Tyr Gln Ile Val Ala Thr
            180                 185                 190

Glu Gly Tyr Gln Ser Ser Gly Ser Ser Asp Ile Tyr Val Gln Thr His
        195                 200                 205

<210> SEQ ID NO 172
<211> LENGTH: 681
<212> TYPE: DNA
<213> ORGANISM: Myceliophthora thermophila

<400> SEQUENCE: 172
atggttaccc tcactcgcct ggcggtcgcc gcggcggcca tgatctccag cactggcctg      60
gctgccccga cgcccgaagc tggccccgac cttcccgact ttgagctcgg ggtcaacaac     120
ctcgcccgcc gcgcgctgga ctacaaccag aactacagga ccagcggcaa cgtcaactac     180
tcgcccaccg acaacggcta ctcggtcagc ttctccaacg cgggagattt tgtcgtcggg     240
aagggctgga ggacgggagc caccagaaac atcaccttct cgggatcgac acagcatacc     300
tcgggcaccg tgctcgtctc cgtctacggc tggacccgga accgctgat cgagtactac      360 gtgcaggagt acacgtccaa cggggccggc tccgctcagg gcgagaagct gggcacggtc     420
gagagcgacg ggggcacgta cgagatctgg cggcaccagc aggtcaacca gccgtcgatc     480
gagggcacct cgaccttctg gcagtacatc tcgaaccgcg tgtccggcca gcggcccaac     540
ggcggcaccg tcaccctcgc caaccacttc gccgcctggc agaagctcgg cctgaacctg     600
ggccagcacg actaccaggt cctggccacc gagggctggg caacgccgg cggcagctcc      660 cagtacaccg tcagcggctg a                                               681

<210> SEQ ID NO 173
<211> LENGTH: 226
<212> TYPE: PRT
<213> ORGANISM: Myceliophthora thermophila

<400> SEQUENCE: 173

Met Val Thr Leu Thr Arg Leu Ala Val Ala Ala Ala Ala Met Ile Ser
```

```
  1               5                  10                 15
Ser Thr Gly Leu Ala Ala Pro Thr Pro Glu Ala Gly Pro Asp Leu Pro
                 20                 25                 30

Asp Phe Glu Leu Gly Val Asn Asn Leu Ala Arg Arg Ala Leu Asp Tyr
                 35                 40                 45

Asn Gln Asn Tyr Arg Thr Ser Gly Asn Val Asn Tyr Ser Pro Thr Asp
 50                 55                 60

Asn Gly Tyr Ser Val Ser Phe Ser Asn Ala Gly Asp Phe Val Val Gly
 65                 70                 75                 80

Lys Gly Trp Arg Thr Gly Ala Thr Arg Asn Ile Thr Phe Ser Gly Ser
                 85                 90                 95

Thr Gln His Thr Ser Gly Thr Val Leu Val Ser Val Tyr Gly Trp Thr
                100                105                110

Arg Asn Pro Leu Ile Glu Tyr Tyr Val Gln Glu Tyr Thr Ser Asn Gly
                115                120                125

Ala Gly Ser Ala Gln Gly Glu Lys Leu Gly Thr Val Glu Ser Asp Gly
130                135                140

Gly Thr Tyr Glu Ile Trp Arg His Gln Gln Val Asn Gln Pro Ser Ile
145                150                155                160

Glu Gly Thr Ser Thr Phe Trp Gln Tyr Ile Ser Asn Arg Val Ser Gly
                165                170                175

Gln Arg Pro Asn Gly Gly Thr Val Thr Leu Ala Asn His Phe Ala Ala
                180                185                190

Trp Gln Lys Leu Gly Leu Asn Leu Gly Gln His Asp Tyr Gln Val Leu
                195                200                205

Ala Thr Glu Gly Trp Gly Asn Ala Gly Gly Ser Ser Gln Tyr Thr Val
                210                215                220

Ser Gly
225

<210> SEQ ID NO 174
<211> LENGTH: 205
<212> TYPE: PRT
<213> ORGANISM: Myceliophthora thermophila

<400> SEQUENCE: 174

Ala Pro Thr Pro Glu Ala Gly Pro Asp Leu Pro Asp Phe Glu Leu Gly
 1               5                  10                 15

Val Asn Asn Leu Ala Arg Arg Ala Leu Asp Tyr Asn Gln Asn Tyr Arg
                 20                 25                 30

Thr Ser Gly Asn Val Asn Tyr Ser Pro Thr Asp Asn Gly Tyr Ser Val
                 35                 40                 45

Ser Phe Ser Asn Ala Gly Asp Phe Val Val Gly Lys Gly Trp Arg Thr
 50                 55                 60

Gly Ala Thr Arg Asn Ile Thr Phe Ser Gly Ser Thr Gln His Thr Ser
 65                 70                 75                 80

Gly Thr Val Leu Val Ser Val Tyr Gly Trp Thr Arg Asn Pro Leu Ile
                 85                 90                 95

Glu Tyr Tyr Val Gln Glu Tyr Thr Ser Asn Gly Ala Gly Ser Ala Gln
                100                105                110

Gly Glu Lys Leu Gly Thr Val Glu Ser Asp Gly Gly Thr Tyr Glu Ile
                115                120                125

Trp Arg His Gln Gln Val Asn Gln Pro Ser Ile Glu Gly Thr Ser Thr
130                135                140
```

```
Phe Trp Gln Tyr Ile Ser Asn Arg Val Ser Gly Gln Arg Pro Asn Gly
145                 150                 155                 160

Gly Thr Val Thr Leu Ala Asn His Phe Ala Ala Trp Gln Lys Leu Gly
                165                 170                 175

Leu Asn Leu Gly Gln His Asp Tyr Gln Val Leu Ala Thr Glu Gly Trp
            180                 185                 190

Gly Asn Ala Gly Gly Ser Ser Gln Tyr Thr Val Ser Gly
            195                 200                 205

<210> SEQ ID NO 175
<211> LENGTH: 1833
<212> TYPE: DNA
<213> ORGANISM: Myceliophthora thermophila

<400> SEQUENCE: 175
```

| | | | | | |
|---|---|---|---|---|---|
| atgttcttcg | cttctctgct | gctcggtctc | ctggcgggcg | tgtccgcttc | accgggacac | 60 |
| gggcggaatt | ccaccttcta | caaccccatc | ttccccggct | tctacccga | tccgagctgc | 120 |
| atctacgtgc | ccgagcgtga | ccacaccttc | ttctgtgcct | cgtcgagctt | caacgccttc | 180 |
| ccgggcatcc | cgattcatgc | cagcaaggac | ctgcagaact | ggaagttgat | cggccatgtg | 240 |
| ctgaatcgca | aggaacagct | tccccggctc | gctgagacca | ccggtcgac | cagcggcatc | 300 |
| tgggcaccca | ccctccggtt | ccatgacgac | accttctggt | tggtcaccac | actagtggac | 360 |
| gacgaccggc | gcaggagga | cgcttccaga | tgggacaata | ttatcttcaa | ggcaaagaat | 420 |
| ccgtatgatc | cgaggtcctg | gtccaaggcc | gtccacttca | acttcactgg | ctacgacacg | 480 |
| gagcctttct | gggacgaaga | tggaaaggtg | tacatcaccg | cgcccatgc | ttggcatgtt | 540 |
| ggcccataca | tccagcaggc | cgaagtcgat | ctcgacacgg | gggccgtcgg | cgagtggcgc | 600 |
| atcatctgga | acggaacggg | cggcatggct | cctgaagggc | gcacacatcta | ccgcaaagat | 660 |
| gggtggtact | acttgctggc | tgctgaaggg | gggaccggca | tcgaccatat | ggtgaccatg | 720 |
| gcccggtcga | gaaaaatctc | cagtccttac | gagtccaacc | caaacaaccc | cgtgttgacc | 780 |
| aacgccaaca | cgaccagtta | ctttcaaacc | gtcgggcatt | cagacctgtt | ccatgacaga | 840 |
| catgggaact | ggtgggcagt | cgccctctcc | acccgctccg | gtccagaata | tcttcactac | 900 |
| cccatgggcc | gcgagaccgt | catgacagcc | gtgagctggc | cgaaggacga | gtggccaacc | 960 |
| ttcacccca | tatctggcaa | gatgagcggc | tggccgatgc | ctccttcgca | gaaggacatt | 1020 |
| cgcggagtcg | gcccctacgt | caactccccc | gacccggaac | cctgaccttt | ccccgctcg | 1080 |
| gcgcccctgc | cggcccacct | cacctactgg | cgataccga | accgtcctc | ctacacgccg | 1140 |
| tccccgcccg | ggcaccccaa | caccctccgc | ctgacccgt | cccgcctgaa | cctgaccgcc | 1200 |
| ctcaacggca | actacgcggg | ggccgaccag | accttcgtct | cgcgccggca | gcagcacacc | 1260 |
| ctcttcacct | acagcgtcac | gctcgactac | gcgccgcgga | ccgccgggga | ggaggccggc | 1320 |
| gtgaccgcct | tcctgacgca | gaaccaccac | ctcgacctgg | gcgtcgtcct | gctccctcgc | 1380 |
| ggctccgcca | ccgcgccctc | gctgccgggc | ctgagtagta | gtacaactac | tactagtagt | 1440 |
| agtagtagtc | gtccggacga | ggaggaggag | cgcgaggcgg | gcgaagagga | agaagagggc | 1500 |
| ggacaagact | tgatgatccc | gcatgtgcgg | ttcaggggcg | agtcgtacgt | gcccgtcccg | 1560 |
| gcgcccgtcg | tgtacccgat | accccgggcc | tggagaggcg | ggaagcttgt | gttagagatc | 1620 |
| cgggcttgta | attcgactca | cttctcgttc | cgtgtcgggc | cggacgggag | acggtctgag | 1680 |
| cggacggtgg | tcatggaggc | ttcgaacgag | gccgttagct | ggggctttac | tggaacgctg | 1740 |
| ctgggcatct | atgcgaccag | taatggtggc | aacggaacca | cgccggcgta | tttttcggat | 1800 | tggaggtaca caccattgga gcagtttagg gat                                      1833

<210> SEQ ID NO 176
<211> LENGTH: 611
<212> TYPE: PRT
<213> ORGANISM: Myceliophthora thermophila

<400> SEQUENCE: 176

Met Phe Phe Ala Ser Leu Leu Gly Leu Ala Gly Val Ser Ala
1               5                   10                  15

Ser Pro Gly His Gly Arg Asn Ser Thr Phe Tyr Asn Pro Ile Phe Pro
            20                  25                  30

Gly Phe Tyr Pro Asp Pro Ser Cys Ile Tyr Val Pro Glu Arg Asp His
        35                  40                  45

Thr Phe Phe Cys Ala Ser Ser Phe Asn Ala Phe Pro Gly Ile Pro
    50                  55                  60

Ile His Ala Ser Lys Asp Leu Gln Asn Trp Lys Leu Ile Gly His Val
65                  70                  75                  80

Leu Asn Arg Lys Glu Gln Leu Pro Arg Leu Ala Glu Thr Asn Arg Ser
                85                  90                  95

Thr Ser Gly Ile Trp Ala Pro Thr Leu Arg Phe His Asp Asp Thr Phe
            100                 105                 110

Trp Leu Val Thr Thr Leu Val Asp Asp Arg Pro Gln Glu Asp Ala
        115                 120                 125

Ser Arg Trp Asp Asn Ile Ile Phe Lys Ala Lys Asn Pro Tyr Asp Pro
    130                 135                 140

Arg Ser Trp Ser Lys Ala Val His Phe Asn Phe Thr Gly Tyr Asp Thr
145                 150                 155                 160

Glu Pro Phe Trp Asp Glu Asp Gly Lys Val Tyr Ile Thr Gly Ala His
                165                 170                 175

Ala Trp His Val Gly Pro Tyr Ile Gln Gln Ala Glu Val Asp Leu Asp
            180                 185                 190

Thr Gly Ala Val Gly Glu Trp Arg Ile Ile Trp Asn Gly Thr Gly Gly
        195                 200                 205

Met Ala Pro Glu Gly Pro His Ile Tyr Arg Lys Asp Gly Trp Tyr Tyr
    210                 215                 220

Leu Leu Ala Ala Glu Gly Gly Thr Gly Ile Asp His Met Val Thr Met
225                 230                 235                 240

Ala Arg Ser Arg Lys Ile Ser Ser Pro Tyr Glu Ser Asn Pro Asn Asn
                245                 250                 255

Pro Val Leu Thr Asn Ala Asn Thr Thr Ser Tyr Phe Gln Thr Val Gly
            260                 265                 270

His Ser Asp Leu Phe His Asp Arg His Gly Asn Trp Trp Ala Val Ala
        275                 280                 285

Leu Ser Thr Arg Ser Gly Pro Glu Tyr Leu His Tyr Pro Met Gly Arg
    290                 295                 300

Glu Thr Val Met Thr Ala Val Ser Trp Pro Lys Asp Glu Trp Pro Thr
305                 310                 315                 320

Phe Thr Pro Ile Ser Gly Lys Met Ser Gly Trp Pro Met Pro Pro Ser
                325                 330                 335

Gln Lys Asp Ile Arg Gly Val Gly Pro Tyr Val Asn Ser Pro Asp Pro
            340                 345                 350

Glu His Leu Thr Phe Pro Arg Ser Ala Pro Leu Pro Ala His Leu Thr
        355                 360                 365

```
Tyr Trp Arg Tyr Pro Asn Pro Ser Ser Tyr Thr Pro Ser Pro Pro Gly
        370                 375                 380

His Pro Asn Thr Leu Arg Leu Thr Pro Ser Arg Leu Asn Leu Thr Ala
385                 390                 395                 400

Leu Asn Gly Asn Tyr Ala Gly Ala Asp Gln Thr Phe Val Ser Arg Arg
                405                 410                 415

Gln Gln His Thr Leu Phe Thr Tyr Ser Val Thr Leu Asp Tyr Ala Pro
            420                 425                 430

Arg Thr Ala Gly Glu Glu Ala Gly Val Thr Ala Phe Leu Thr Gln Asn
            435                 440                 445

His His Leu Asp Leu Gly Val Val Leu Leu Pro Arg Gly Ser Ala Thr
450                 455                 460

Ala Pro Ser Leu Pro Gly Leu Ser Ser Ser Thr Thr Thr Thr Ser Ser
465                 470                 475                 480

Ser Ser Ser Arg Pro Asp Glu Glu Glu Arg Glu Ala Gly Glu Glu
                485                 490                 495

Glu Glu Glu Gly Gly Gln Asp Leu Met Ile Pro His Val Arg Phe Arg
            500                 505                 510

Gly Glu Ser Tyr Val Pro Val Pro Ala Pro Val Tyr Pro Ile Pro
        515                 520                 525

Arg Ala Trp Arg Gly Gly Lys Leu Val Leu Glu Ile Arg Ala Cys Asn
530                 535                 540

Ser Thr His Phe Ser Phe Arg Val Gly Pro Asp Gly Arg Arg Ser Glu
545                 550                 555                 560

Arg Thr Val Val Met Glu Ala Ser Asn Glu Ala Val Ser Trp Gly Phe
                565                 570                 575

Thr Gly Thr Leu Leu Gly Ile Tyr Ala Thr Ser Asn Gly Gly Asn Gly
            580                 585                 590

Thr Thr Pro Ala Tyr Phe Ser Asp Trp Arg Tyr Thr Pro Leu Glu Gln
            595                 600                 605

Phe Arg Asp
    610

<210> SEQ ID NO 177
<211> LENGTH: 595
<212> TYPE: PRT
<213> ORGANISM: Myceliophthora thermophila

<400> SEQUENCE: 177

Ser Pro Gly His Gly Arg Asn Ser Thr Phe Tyr Asn Pro Ile Phe Pro
1               5                   10                  15

Gly Phe Tyr Pro Asp Pro Ser Cys Ile Tyr Val Pro Glu Arg Asp His
                20                  25                  30

Thr Phe Phe Cys Ala Ser Ser Phe Asn Ala Phe Pro Gly Ile Pro
            35                  40                  45

Ile His Ala Ser Lys Asp Leu Gln Asn Trp Lys Leu Ile Gly His Val
        50                  55                  60

Leu Asn Arg Lys Glu Gln Leu Pro Arg Leu Ala Glu Thr Asn Arg Ser
65                  70                  75                  80

Thr Ser Gly Ile Trp Ala Pro Thr Leu Arg Phe His Asp Asp Thr Phe
                85                  90                  95

Trp Leu Val Thr Thr Leu Val Asp Asp Arg Pro Gln Glu Asp Ala
            100                 105                 110

Ser Arg Trp Asp Asn Ile Ile Phe Lys Ala Lys Asn Pro Tyr Asp Pro
```

```
            115                 120                 125
Arg Ser Trp Ser Lys Ala Val His Phe Asn Phe Thr Gly Tyr Asp Thr
            130                 135                 140
Glu Pro Phe Trp Asp Glu Asp Gly Lys Val Tyr Ile Thr Gly Ala His
145                 150                 155                 160
Ala Trp His Val Gly Pro Tyr Ile Gln Gln Ala Glu Val Asp Leu Asp
                165                 170                 175
Thr Gly Ala Val Gly Glu Trp Arg Ile Ile Trp Asn Gly Thr Gly Gly
            180                 185                 190
Met Ala Pro Glu Gly Pro His Ile Tyr Arg Lys Asp Gly Trp Tyr Tyr
            195                 200                 205
Leu Leu Ala Ala Glu Gly Gly Thr Gly Ile Asp His Met Val Thr Met
210                 215                 220
Ala Arg Ser Arg Lys Ile Ser Ser Pro Tyr Glu Ser Asn Pro Asn Asn
225                 230                 235                 240
Pro Val Leu Thr Asn Ala Asn Thr Thr Ser Tyr Phe Gln Thr Val Gly
                245                 250                 255
His Ser Asp Leu Phe His Asp Arg His Gly Asn Trp Trp Ala Val Ala
                260                 265                 270
Leu Ser Thr Arg Ser Gly Pro Glu Tyr Leu His Tyr Pro Met Gly Arg
            275                 280                 285
Glu Thr Val Met Thr Ala Val Ser Trp Pro Lys Asp Glu Trp Pro Thr
290                 295                 300
Phe Thr Pro Ile Ser Gly Lys Met Ser Gly Trp Pro Met Pro Pro Ser
305                 310                 315                 320
Gln Lys Asp Ile Arg Gly Val Gly Pro Tyr Val Asn Ser Pro Asp Pro
                325                 330                 335
Glu His Leu Thr Phe Pro Arg Ser Ala Pro Leu Pro Ala His Leu Thr
                340                 345                 350
Tyr Trp Arg Tyr Pro Asn Pro Ser Ser Tyr Thr Pro Ser Pro Pro Gly
            355                 360                 365
His Pro Asn Thr Leu Arg Leu Thr Pro Ser Arg Leu Asn Leu Thr Ala
            370                 375                 380
Leu Asn Gly Asn Tyr Ala Gly Ala Asp Gln Thr Phe Val Ser Arg Arg
385                 390                 395                 400
Gln Gln His Thr Leu Phe Thr Tyr Ser Val Thr Leu Asp Tyr Ala Pro
                405                 410                 415
Arg Thr Ala Gly Glu Glu Ala Gly Val Thr Ala Phe Leu Thr Gln Asn
                420                 425                 430
His His Leu Asp Leu Gly Val Val Leu Leu Pro Arg Gly Ser Ala Thr
            435                 440                 445
Ala Pro Ser Leu Pro Gly Leu Ser Ser Ser Thr Thr Thr Ser Ser
            450                 455                 460
Ser Ser Ser Arg Pro Asp Glu Glu Glu Arg Glu Ala Gly Glu Glu
465                 470                 475                 480
Glu Glu Glu Gly Gly Gln Asp Leu Met Ile Pro His Val Arg Phe Arg
                485                 490                 495
Gly Glu Ser Tyr Val Pro Val Pro Ala Pro Val Tyr Pro Ile Pro
            500                 505                 510
Arg Ala Trp Arg Gly Gly Lys Leu Val Leu Glu Ile Arg Ala Cys Asn
            515                 520                 525
Ser Thr His Phe Ser Phe Arg Val Gly Pro Asp Gly Arg Arg Ser Glu
            530                 535                 540
```

Arg Thr Val Val Met Glu Ala Ser Asn Glu Ala Val Ser Trp Gly Phe
545                 550                 555                 560

Thr Gly Thr Leu Leu Gly Ile Tyr Ala Thr Ser Asn Gly Gly Asn Gly
            565                 570                 575

Thr Thr Pro Ala Tyr Phe Ser Asp Trp Arg Tyr Thr Pro Leu Glu Gln
        580                 585                 590

Phe Arg Asp
        595

<210> SEQ ID NO 178
<211> LENGTH: 942
<212> TYPE: DNA
<213> ORGANISM: Myceliophthora thermophila

<400> SEQUENCE: 178

```
atgaagctcc tgggcaaact ctcggcggca ctcgccctcg cgggcagcag gctggctgcc      60
gcgcacccgg tcttcgacga gctgatgcgc cgacggcgc cgctggtgcg cccgcgggcg     120
gccctgcagc aggtgaccaa ctttggcagc aacccgtcca cacgaagat gttcatctac     180
gtgcccgaca gctggcccc caacccgccc atcatagtgg ccatccacta ctgcaccggc     240
accgcccagg cctactactc gggctcccct tacgcccgcc tcgccgacca gaagggcttc     300
atcgtcatct accggagtc ccctacagc ggcacctgtt gggacgtctc gtcgcgcgcc     360
gccctgaccc acaacggcgg cggcgacagc aactcgatcg ccaacatggt cacctacacc     420
ctcgaaaagt acaatggcga cgccagcaag gtctttgtca ccggctcctc gtccggcgcc     480
atgatgacga acgtgatggc cgccgcgtac ccggaactgt tcgcggcagg aatcgcctac     540
tcgggcgtgc cgccggctg cttctacagc cagtccggag caccaacgc gtggaacagc     600
tcgtgcgcca acgggcagat caactcgacg ccccaggtgt gggccaagat ggtcttcgac     660
atgtacccgg aatacgacgg cccgcgcccc aagatgcaga tctaccacgg ctcggccgac     720
ggcacgctca gacccagcaa ctacaacgag accatcaagc agtggtgcgg cgtcttcggc     780
ttcgactaca cccgcccga caccaccag gccaactccc cgcaggccgg ctacaccacc     840
tacacctggg gcgagcagca gctcgtcggc atctacgccc agggcgtcgg acacacggtc     900
cccatccgcg cagcgacga catggccttc tttggcctgt ga                        942
```

<210> SEQ ID NO 179
<211> LENGTH: 313
<212> TYPE: PRT
<213> ORGANISM: Myceliophthora thermophila

<400> SEQUENCE: 179

Met Lys Leu Leu Gly Lys Leu Ser Ala Ala Leu Ala Leu Ala Gly Ser
1               5                   10                  15

Arg Leu Ala Ala Ala His Pro Val Phe Asp Glu Leu Met Arg Pro Thr
            20                  25                  30

Ala Pro Leu Val Arg Pro Arg Ala Leu Gln Gln Val Thr Asn Phe
        35                  40                  45

Gly Ser Asn Pro Ser Asn Thr Lys Met Phe Ile Tyr Val Pro Asp Lys
    50                  55                  60

Leu Ala Pro Asn Pro Pro Ile Ile Val Ala Ile His Tyr Cys Thr Gly
65                  70                  75                  80

Thr Ala Gln Ala Tyr Tyr Ser Gly Ser Pro Tyr Ala Arg Leu Ala Asp
                85                  90                  95

```
Gln Lys Gly Phe Ile Val Ile Tyr Pro Glu Ser Pro Tyr Ser Gly Thr
                100                 105                 110

Cys Trp Asp Val Ser Ser Arg Ala Ala Leu Thr His Asn Gly Gly Gly
        115                 120                 125

Asp Ser Asn Ser Ile Ala Asn Met Val Thr Tyr Thr Leu Glu Lys Tyr
    130                 135                 140

Asn Gly Asp Ala Ser Lys Val Phe Val Thr Gly Ser Ser Ser Gly Ala
145                 150                 155                 160

Met Met Thr Asn Val Met Ala Ala Tyr Pro Glu Leu Phe Ala Ala
                165                 170                 175

Gly Ile Ala Tyr Ser Gly Val Pro Ala Gly Cys Phe Tyr Ser Gln Ser
            180                 185                 190

Gly Gly Thr Asn Ala Trp Asn Ser Ser Cys Ala Asn Gly Gln Ile Asn
        195                 200                 205

Ser Thr Pro Gln Val Trp Ala Lys Met Val Phe Asp Met Tyr Pro Glu
    210                 215                 220

Tyr Asp Gly Pro Arg Pro Lys Met Gln Ile Tyr His Gly Ser Ala Asp
225                 230                 235                 240

Gly Thr Leu Arg Pro Ser Asn Tyr Asn Glu Thr Ile Lys Gln Trp Cys
                245                 250                 255

Gly Val Phe Gly Phe Asp Tyr Thr Arg Pro Asp Thr Gln Ala Asn
            260                 265                 270

Ser Pro Gln Ala Gly Tyr Thr Thr Tyr Thr Trp Gly Glu Gln Gln Leu
        275                 280                 285

Val Gly Ile Tyr Ala Gln Gly Val Gly His Thr Val Pro Ile Arg Gly
    290                 295                 300

Ser Asp Asp Met Ala Phe Phe Gly Leu
305                 310

<210> SEQ ID NO 180
<211> LENGTH: 292
<212> TYPE: PRT
<213> ORGANISM: Myceliophthora thermophila

<400> SEQUENCE: 180

His Pro Val Phe Asp Glu Leu Met Arg Pro Thr Ala Pro Leu Val Arg
1               5                   10                  15

Pro Arg Ala Ala Leu Gln Gln Val Thr Asn Phe Gly Ser Asn Pro Ser
            20                  25                  30

Asn Thr Lys Met Phe Ile Tyr Val Pro Asp Lys Leu Ala Pro Asn Pro
        35                  40                  45

Pro Ile Ile Val Ala Ile His Tyr Cys Thr Gly Thr Ala Gln Ala Tyr
    50                  55                  60

Tyr Ser Gly Ser Pro Tyr Ala Arg Leu Ala Asp Gln Lys Gly Phe Ile
65                  70                  75                  80

Val Ile Tyr Pro Glu Ser Pro Tyr Ser Gly Thr Cys Trp Asp Val Ser
                85                  90                  95

Ser Arg Ala Ala Leu Thr His Asn Gly Gly Gly Asp Ser Asn Ser Ile
            100                 105                 110

Ala Asn Met Val Thr Tyr Thr Leu Glu Lys Tyr Asn Gly Asp Ala Ser
        115                 120                 125

Lys Val Phe Val Thr Gly Ser Ser Ser Gly Ala Met Met Thr Asn Val
    130                 135                 140

Met Ala Ala Ala Tyr Pro Glu Leu Phe Ala Ala Gly Ile Ala Tyr Ser
145                 150                 155                 160
```

```
Gly Val Pro Ala Gly Cys Phe Tyr Ser Gln Ser Gly Thr Asn Ala
                165                 170                 175

Trp Asn Ser Ser Cys Ala Asn Gly Gln Ile Asn Ser Thr Pro Gln Val
            180                 185                 190

Trp Ala Lys Met Val Phe Asp Met Tyr Pro Glu Tyr Asp Gly Pro Arg
        195                 200                 205

Pro Lys Met Gln Ile Tyr His Gly Ser Ala Asp Gly Thr Leu Arg Pro
    210                 215                 220

Ser Asn Tyr Asn Glu Thr Ile Lys Gln Trp Cys Gly Val Phe Gly Phe
225                 230                 235                 240

Asp Tyr Thr Arg Pro Asp Thr Thr Gln Ala Asn Ser Pro Gln Ala Gly
                245                 250                 255

Tyr Thr Thr Tyr Thr Trp Gly Glu Gln Leu Val Gly Ile Tyr Ala
                260                 265                 270

Gln Gly Val Gly His Thr Val Pro Ile Arg Gly Ser Asp Asp Met Ala
            275                 280                 285

Phe Phe Gly Leu
        290

<210> SEQ ID NO 181
<211> LENGTH: 840
<212> TYPE: DNA
<213> ORGANISM: Myceliophthora thermophila

<400> SEQUENCE: 181
atgatctcgg ttcctgctct cgctctggcc cttctggccg ccgtccaggt cgtcgagtct    60
gcctcggctg gctgtggcaa ggcgccccct tcctcgggca ccaagtcgat gacggtcaac   120
ggcaagcagc gccagtacat tctccagctg cccaacaact acgacgccaa caaggcccac   180
agggtggtga tcgggtacca ctggcgcgac ggatccatga cgacgtggc caacggcggc   240
ttctacgatc tgcggtcccg ggcgggcgac agcaccatct tcgttgcccc caacggcctc   300
aatgccggat gggccaacgt gggcggcgag gacatcacct ttacggacca gatcgtagac   360
atgctcaaga cgaccctctg cgtggacgag acccagttct ttgctacggg ctggagctat   420
ggcggtgcca tgagccatag cgtggcttgt tctcggccag acgtcttcaa ggccgtcgcg   480
gtcatcgccg gggcccagct gtccggctgc gccggcggca cgacgcccgt ggcgtaccta   540
ggcatccacg gagccgccga caacgtcctg cccatcgacc tcggccgcca gctgcgcgac   600
aagtggctgc agaccaacgg ctgcaactac cagggcgccc aggaccccgc gccgggccag   660
caggcccaca tcaagaccac ctacagctgc tcccgcgcgc ccgtcacctg gatcggccac   720
ggggcggcc acgtccccga ccccacgggc aacaacggcg tcaagtttgc gccccaggag   780
acctgggact tctttgatgc cgccgtcgga gcggccggcg cgcagagccc gatgacataa   840

<210> SEQ ID NO 182
<211> LENGTH: 279
<212> TYPE: PRT
<213> ORGANISM: Myceliophthora thermophila

<400> SEQUENCE: 182

Met Ile Ser Val Pro Ala Leu Ala Leu Ala Leu Leu Ala Ala Val Gln
1               5                   10                  15

Val Val Glu Ser Ala Ser Ala Gly Cys Gly Lys Ala Pro Pro Ser Ser
            20                  25                  30

Gly Thr Lys Ser Met Thr Val Asn Gly Lys Gln Arg Gln Tyr Ile Leu
```

```
                35                  40                  45
Gln Leu Pro Asn Asn Tyr Asp Ala Asn Lys Ala His Arg Val Val Ile
 50                  55                  60

Gly Tyr His Trp Arg Asp Gly Ser Met Asn Asp Val Ala Asn Gly Gly
 65                  70                  75                  80

Phe Tyr Asp Leu Arg Ser Arg Ala Gly Asp Ser Thr Ile Phe Val Ala
                 85                  90                  95

Pro Asn Gly Leu Asn Ala Gly Trp Ala Asn Val Gly Gly Glu Asp Ile
                100                 105                 110

Thr Phe Thr Asp Gln Ile Val Asp Met Leu Lys Asn Asp Leu Cys Val
                115                 120                 125

Asp Glu Thr Gln Phe Phe Ala Thr Gly Trp Ser Tyr Gly Gly Ala Met
130                 135                 140

Ser His Ser Val Ala Cys Ser Arg Pro Asp Val Phe Lys Ala Val Ala
145                 150                 155                 160

Val Ile Ala Gly Ala Gln Leu Ser Gly Cys Ala Gly Gly Thr Thr Pro
                165                 170                 175

Val Ala Tyr Leu Gly Ile His Gly Ala Ala Asp Asn Val Leu Pro Ile
                180                 185                 190

Asp Leu Gly Arg Gln Leu Arg Asp Lys Trp Leu Gln Thr Asn Gly Cys
                195                 200                 205

Asn Tyr Gln Gly Ala Gln Asp Pro Ala Pro Gly Gln Gln Ala His Ile
210                 215                 220

Lys Thr Thr Tyr Ser Cys Ser Arg Ala Pro Val Thr Trp Ile Gly His
225                 230                 235                 240

Gly Gly Gly His Val Pro Asp Pro Thr Gly Asn Asn Gly Val Lys Phe
                245                 250                 255

Ala Pro Gln Glu Thr Trp Asp Phe Phe Asp Ala Ala Val Gly Ala Ala
                260                 265                 270

Gly Ala Gln Ser Pro Met Thr
                275

<210> SEQ ID NO 183
<211> LENGTH: 259
<212> TYPE: PRT
<213> ORGANISM: Myceliophthora thermophila

<400> SEQUENCE: 183

Ala Ser Ala Gly Cys Gly Lys Ala Pro Pro Ser Ser Gly Thr Lys Ser
 1                   5                  10                  15

Met Thr Val Asn Gly Lys Gln Arg Gln Tyr Ile Leu Gln Leu Pro Asn
                 20                  25                  30

Asn Tyr Asp Ala Asn Lys Ala His Arg Val Val Ile Gly Tyr His Trp
                 35                  40                  45

Arg Asp Gly Ser Met Asn Asp Val Ala Asn Gly Gly Phe Tyr Asp Leu
 50                  55                  60

Arg Ser Arg Ala Gly Asp Ser Thr Ile Phe Val Ala Pro Asn Gly Leu
 65                  70                  75                  80

Asn Ala Gly Trp Ala Asn Val Gly Gly Glu Asp Ile Thr Phe Thr Asp
                 85                  90                  95

Gln Ile Val Asp Met Leu Lys Asn Asp Leu Cys Val Asp Glu Thr Gln
                100                 105                 110

Phe Phe Ala Thr Gly Trp Ser Tyr Gly Gly Ala Met Ser His Ser Val
                115                 120                 125
```

```
Ala Cys Ser Arg Pro Asp Val Phe Lys Ala Val Ala Val Ile Ala Gly
    130                 135                 140

Ala Gln Leu Ser Gly Cys Ala Gly Gly Thr Thr Pro Val Ala Tyr Leu
145                 150                 155                 160

Gly Ile His Gly Ala Ala Asp Asn Val Leu Pro Ile Asp Leu Gly Arg
                165                 170                 175

Gln Leu Arg Asp Lys Trp Leu Gln Thr Asn Gly Cys Asn Tyr Gln Gly
            180                 185                 190

Ala Gln Asp Pro Ala Pro Gly Gln Gln Ala His Ile Lys Thr Thr Tyr
        195                 200                 205

Ser Cys Ser Arg Ala Pro Val Thr Trp Ile Gly His Gly Gly His
210                 215                 220

Val Pro Asp Pro Thr Gly Asn Asn Gly Val Lys Phe Ala Pro Gln Glu
225                 230                 235                 240

Thr Trp Asp Phe Phe Asp Ala Ala Val Gly Ala Ala Gly Ala Gln Ser
                245                 250                 255

Pro Met Thr

<210> SEQ ID NO 184
<211> LENGTH: 39
<212> TYPE: DNA
<213> ORGANISM: Artificial Sequence
<220> FEATURE:
<223> OTHER INFORMATION: Synthetic polynucleotide primer cdxp001

<400> SEQUENCE: 184
accgcggtgg cggccaggtt cgttcgtcgt ctcatgtgt                       39

<210> SEQ ID NO 185
<211> LENGTH: 39
<212> TYPE: DNA
<213> ORGANISM: Artificial Sequence
<220> FEATURE:
<223> OTHER INFORMATION: Synthetic polynucleotide primer cdxp002

<400> SEQUENCE: 185
caatagacat cagcatccgg ccaacgaaga aggaaagta                       39

<210> SEQ ID NO 186
<211> LENGTH: 24
<212> TYPE: DNA
<213> ORGANISM: Artificial Sequence
<220> FEATURE:
<223> OTHER INFORMATION: Synthetic polynucleotide primer cdxp003

<400> SEQUENCE: 186
aagagtgcaa gagtgaaggc aggc                                       24

<210> SEQ ID NO 187
<211> LENGTH: 51
<212> TYPE: DNA
<213> ORGANISM: Artificial Sequence
<220> FEATURE:
<223> OTHER INFORMATION: Synthetic polynucleotide primer cdxp004

<400> SEQUENCE: 187
ctagcacagt cagacctcca cataccatcg tactcgcaac tgacgctcgt t         51

<210> SEQ ID NO 188
<211> LENGTH: 51
<212> TYPE: DNA
<213> ORGANISM: Artificial Sequence
```

-continued

```
<220> FEATURE:
<223> OTHER INFORMATION: Synthetic polynucleotide primer cdxp005

<400> SEQUENCE: 188
gcagtcgcag catttacatc aggctggtat gtggaggtct gactgtgcta g        51

<210> SEQ ID NO 189
<211> LENGTH: 24
<212> TYPE: DNA
<213> ORGANISM: Artificial Sequence
<220> FEATURE:
<223> OTHER INFORMATION: Synthetic polynucleotide primer cdxp006

<400> SEQUENCE: 189
gcccgctgtc attcaagaca ttgc                                      24

<210> SEQ ID NO 190
<211> LENGTH: 40
<212> TYPE: DNA
<213> ORGANISM: Artificial Sequence
<220> FEATURE:
<223> OTHER INFORMATION: Synthetic polynucleotide primer cdxp007

<400> SEQUENCE: 190
gccaagcttg catgccatca ctgttgatga cgctctcgct                     40

<210> SEQ ID NO 191
<211> LENGTH: 24
<212> TYPE: DNA
<213> ORGANISM: Artificial Sequence
<220> FEATURE:
<223> OTHER INFORMATION: Synthetic polynucleotide primer cdxp008

<400> SEQUENCE: 191
tgttggcgac ctcgtattgg gaat                                      24

<210> SEQ ID NO 192
<211> LENGTH: 24
<212> TYPE: DNA
<213> ORGANISM: Artificial Sequence
<220> FEATURE:
<223> OTHER INFORMATION: Synthetic polynucleotide primer cdxp009

<400> SEQUENCE: 192
tctcggaggg cgaagaatct cgtg                                      24

<210> SEQ ID NO 193
<211> LENGTH: 40
<212> TYPE: DNA
<213> ORGANISM: Artificial Sequence
<220> FEATURE:
<223> OTHER INFORMATION: Synthetic polynucleotide primer cdxp010

<400> SEQUENCE: 193
aattcgagct cggtacttgt gcatttacgg tgctgtgacg                     40

<210> SEQ ID NO 194
<211> LENGTH: 49
<212> TYPE: DNA
<213> ORGANISM: Artificial Sequence
<220> FEATURE:
<223> OTHER INFORMATION: Synthetic polynucleotide primer cdx111006

<400> SEQUENCE: 194
ccgtctctcc gcatgccaga aagattcctt cccttgctcc ttcacactg           49
```

<210> SEQ ID NO 195
<211> LENGTH: 25
<212> TYPE: DNA
<213> ORGANISM: Artificial Sequence
<220> FEATURE:
<223> OTHER INFORMATION: Synthetic polynucleotide primer cdx111007

<400> SEQUENCE: 195
cccctcccct acctatcttg tgtct                                          25

<210> SEQ ID NO 196
<211> LENGTH: 24
<212> TYPE: DNA
<213> ORGANISM: Artificial Sequence
<220> FEATURE:
<223> OTHER INFORMATION: Synthetic polynucleotide primer cdx111008

<400> SEQUENCE: 196
ggataagagt gaacaacgac gagc                                           24

<210> SEQ ID NO 197
<211> LENGTH: 48
<212> TYPE: DNA
<213> ORGANISM: Artificial Sequence
<220> FEATURE:
<223> OTHER INFORMATION: Synthetic polynucleotide primer cdx111009

<400> SEQUENCE: 197
gtaacaccca atacgccggc cgaacaaaag ccattcttcc tccgagac                 48

<210> SEQ ID NO 198
<211> LENGTH: 24
<212> TYPE: DNA
<213> ORGANISM: Artificial Sequence
<220> FEATURE:
<223> OTHER INFORMATION: Synthetic polynucleotide primer cdx10177

<400> SEQUENCE: 198
tgttggcgac ctcgtattgg gaat                                           24

<210> SEQ ID NO 199
<211> LENGTH: 24
<212> TYPE: DNA
<213> ORGANISM: Artificial Sequence
<220> FEATURE:
<223> OTHER INFORMATION: Synthetic polynucleotide primer cdx10176

<400> SEQUENCE: 199
tctttctggc atgcggagag acgg                                           24

<210> SEQ ID NO 200
<211> LENGTH: 24
<212> TYPE: DNA
<213> ORGANISM: Artificial Sequence
<220> FEATURE:
<223> OTHER INFORMATION: Synthetic polynucleotide primer cdx10178

<400> SEQUENCE: 200
tctcggaggg cgaagaatct cgtg                                           24

<210> SEQ ID NO 201
<211> LENGTH: 24
<212> TYPE: DNA
<213> ORGANISM: Artificial Sequence
<220> FEATURE:
<223> OTHER INFORMATION: Synthetic polynucleotide primer cdx10179

-continued

```
<400> SEQUENCE: 201
ttcggccggc gtattgggtg ttac                                              24
```